US012780932B1

(12) United States Patent
Hilbert et al.

(10) Patent No.: US 12,780,932 B1
(45) Date of Patent: Nov. 3, 2026

(54) MULTIFUNCTIONAL IMMUNE CELL THERAPIES

(71) Applicant: Arcellx, Inc., Redwood City, CA (US)

(72) Inventors: David M. Hilbert, Bethesda, MD (US); Jeffrey S. Swers, Bethesda, MD (US); David William Lafleur, Washington, DC (US)

(73) Assignee: Arcellx, Inc., Redwood City, CA (US)

(*) Notice: Subject to any disclaimer, the term of this patent is extended or adjusted under 35 U.S.C. 154(b) by 0 days.

(21) Appl. No.: 19/029,591

(22) Filed: Jan. 17, 2025

Related U.S. Application Data

(60) Continuation of application No. 18/815,117, filed on Aug. 26, 2024, which is a continuation of application (Continued)

(51) Int. Cl.
*C07K 16/28* (2006.01)
*A61K 38/17* (2006.01)
(Continued)

(52) U.S. Cl.
CPC ........ *C07K 16/289* (2013.01); *A61K 38/1774* (2013.01); *A61K 40/11* (2025.01); *A61K 40/31* (2025.01); *A61K 40/4205* (2025.01); *A61K 40/4215* (2025.01); *A61K 40/4217* (2025.01); *A61K 40/4252* (2025.01); *A61K 40/4265* (2025.01); *A61P 35/00* (2018.01); *C07K 14/7051* (2013.01); *C07K 16/2866* (2013.01); *C07K 16/2878* (2013.01); *C07K 16/32* (2013.01); *C12N 5/0636* (2013.01); (Continued)

(58) Field of Classification Search
None
See application file for complete search history.

(56) References Cited

U.S. PATENT DOCUMENTS 6,534,628 B1 3/2003 Nilsson et al.
7,208,576 B2 4/2007 Mulroy et al.
(Continued)

FOREIGN PATENT DOCUMENTS

BR 112019008975 A2 7/2019
CN 107254447 A 10/2017
(Continued)

OTHER PUBLICATIONS

Jacobson et al., Blood (2011) 118 (18): 4761-4762 (Year: 2011).*
(Continued)

*Primary Examiner* — Karl J Puttlitz
(74) *Attorney, Agent, or Firm* — Sheppard Mullin Richter & Hampton LLP

(57) ABSTRACT

Provided herein are multi-functional chimeric antigen receptor (CAR)-based compositions and their use in directing immune responses to target cells. The compositions have uses that include treating hyperproliferative disorders such as cancer. The provided methods generally include the use of a CAR cell in combination with an Adapter. The Adapter confers the ability to modulate, alter, and/or redirect CAR cell-mediated immune response in vitro and in vivo. In some embodiments, the CAR cell comprises a genetic modification to reduce or eliminate the expression of a targeted antigenic determinant.

26 Claims, 21 Drawing Sheets

Specification includes a Sequence Listing.

Related U.S. Application Data

No. 18/342,898, filed on Jun. 28, 2023, which is a division of application No. 16/763,776, filed as application No. PCT/US2018/060902 on Nov. 14, 2018, now Pat. No. 11,730,763.

(60) Provisional application No. 62/717,165, filed on Aug. 10, 2018, provisional application No. 62/585,770, filed on Nov. 14, 2017.

(51) Int. Cl.

| | |
|---|---|
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 16/32*** | (2006.01) |
| ***C12N 5/0783*** | (2010.01) |

(52) U.S. Cl.

CPC ...... *A61K 2239/24* (2023.05); *A61K 2239/28* (2023.05); *C07K 2317/622* (2013.01); *C07K 2317/73* (2013.01); *C07K 2317/92* (2013.01); *C07K 2319/33* (2013.01)

(56) References Cited

U.S. PATENT DOCUMENTS

| | | | |
|---|---|---|---|
| 7,314,974 | B2 | 1/2008 | Cao et al. |
| 8,268,756 | B2 | 9/2012 | Logtenberg et al. |
| 8,383,117 | B2 | 2/2013 | Glover et al. |
| 9,045,545 | B1 | 6/2015 | Clube |
| 9,233,125 | B2 | 1/2016 | Davila et al. |
| 9,902,758 | B2 | 2/2018 | Shin et al. |
| 10,647,775 | B2 | 5/2020 | Lafleur et al. |
| 10,662,248 | B2 | 5/2020 | Lafleur et al. |
| 11,008,397 | B2 | 5/2021 | Lafleur et al. |
| 11,318,165 | B2 | 5/2022 | Hilbert et al. |
| 11,377,482 | B2 | 7/2022 | Hilbert et al. |
| 11,464,803 | B2 | 10/2022 | Hilbert et al. |
| 11,730,763 | B2 | 8/2023 | Hilbert et al. |
| 11,827,716 | B2 | 11/2023 | LaFleur et al. |
| 12,338,294 | B2 | 6/2025 | LaFleur et al. |
| 12,358,995 | B2 | 7/2025 | Lafleur et al. |
| 12,421,291 | B2 | 9/2025 | Hilbert et al. |
| 2011/0293579 | A1 | 12/2011 | Nielsen et al. |
| 2012/0195882 | A1 | 8/2012 | Doms et al. |
| 2013/0158232 | A1 | 6/2013 | Timmerman et al. |
| 2013/0190221 | A1 | 7/2013 | Burrows et al. |
| 2014/0271582 | A1 | 9/2014 | Forman et al. |
| 2016/0311878 | A1 | 10/2016 | Shin et al. |
| 2017/0296623 | A1* | 10/2017 | Juillerat ............. A61K 40/4221 |
| 2017/0360910 | A1 | 12/2017 | Wang et al. |
| 2018/0209983 | A1 | 7/2018 | Lafleur |
| 2020/0362046 | A1 | 11/2020 | Lafleur |
| 2021/0002381 | A1 | 1/2021 | Lafleur et al. |
| 2021/0230288 | A1 | 7/2021 | Lafleur et al. |
| 2023/0125550 | A1 | 4/2023 | Hilbert et al. |
| 2024/0043550 | A1 | 2/2024 | Lafleur |
| 2024/0124605 | A1 | 4/2024 | LaFleur et al. |
| 2024/0156866 | A1 | 5/2024 | Hilbert et al. |
| 2024/0307439 | A1 | 9/2024 | Hilbert |
| 2025/0026849 | A1 | 1/2025 | Hilbert et al. |

FOREIGN PATENT DOCUMENTS

| | | | | |
|---|---|---|---|---|
| EP | 3025719 | A1 | 6/2016 | |
| JP | 2007503838 | A | 3/2007 | |
| JP | 7470840 | B2 | 4/2024 | |
| WO | WO-2004013180 | A2 | 2/2004 | |
| WO | WO-2005024044 | A2 | 3/2005 | |
| WO | WO-2007019376 | A2 | 2/2007 | |
| WO | WO-2008052043 | A2 | 5/2008 | |
| WO | WO-2010124829 | A1 | 11/2010 | |
| WO | WO-2011034947 | A2 | 3/2011 | |
| WO | WO-2012167109 | A2 | 12/2012 | |
| WO | WO-2013154760 | A1 | 10/2013 | |
| WO | WO-2014138805 | A1 | 9/2014 | |
| WO | WO-2014167350 | A1 | 10/2014 | |
| WO | WO-2015168666 | A2 | 11/2015 | |
| WO | WO-2016154621 | A1 * | 9/2016 | ........... A61K 48/005 |
| WO | WO-2016164305 | A1 | 10/2016 | |
| WO | WO-2016164308 | A1 * | 10/2016 | ........... C07K 14/435 |
| WO | WO-2016164369 | A2 | 10/2016 | |
| WO | WO-2017083511 | A1 | 5/2017 | |
| WO | WO-2018083071 | A1 | 5/2018 | |
| WO | WO-2019099433 | A2 | 5/2019 | |
| WO | WO-2019099440 | A1 | 5/2019 | |
| WO | WO-2022204340 | A1 | 9/2022 | |
| WO | WO-2024118651 | A2 | 6/2024 | |
| WO | WO-2024118651 | A3 | 7/2024 | |

OTHER PUBLICATIONS

Li et al., Epub May 14, 2021 (Year: 2021).*

Ali et al., "T cells expressing an anti-B-cell maturation antigen chimeric antigen receptor cause remissions of multiple myeloma," Blood, 128(13):1688-1700 (2016).

Attwood, "The babel of bioinformatics," Science 290(5491):471-473 (2000).

Baker, et al. Protein structure prediction and structural genomics. Science294.5540 (2001): 93-96.

Bowie, James U. et al. Deciphering the message in protein sequences: tolerance to amino acid substitutions. Science 247(4948):1306-1310 (1990).

Buonato, Janine et al., "Novel CAR-T Cell Therapy that can be Activated, Silenced, and Reprogrammed In Vivo with Soluble Protein Adapters in a Dose Dependent Manner", Arcellx, Inc., presented at the American Society of Gene & Cell Therapy Virtual Annual Meeting, May 12-15, 2020, Abstract 788, 1 page.

Burgess, Wilson H. et al. Possible dissociation of the heparin-binding and mitogenic activities of heparin-binding (acidic fibroblast) growth factor-1 from its receptor-binding activities by site-directed mutagenesis of a single lysine residue. The Journal of Cell Biology 111(5):2129-2138 (1990).

Cangelosi et al., "A de novodesigned metalloenzyme for the hydration of CO2," Angew Chem. Int. Ed Engl., 53(30)7900-7903 (2014).

Carpenter R.O. et al., B-cell maturation antigen is a promising target for adoptive T-cell therapy of multiple myeloma. Clin Cancer Res, Jan. 23, 2013, vol. 19, No. 8, pp. 2048-2060.

Chakraborty et al., "Realization of a Designed Three-Helix Bundle Capable of Binding Heavy Metals in a Tris (Cysteine) Environment," Angew Chem. Int. Ed Engl., 50(9):2049-2053 (2011).

Co-pending U.S. Appl. No. 19/030,139, inventors Hilbert; David M. et al., filed Jan. 17, 2025.

Dudich, Igor. et al. Isolation and Structural and Functional Characterization of Two Stable Peptic Fragments of Human alpha-Fetoprotein. Biochemistry 38(32):10406-10414 (1999).

EP18878722.0 Extended European Search Report dated Jan. 4, 2022.

EP18878722.0 Partial Supplementary European Search Report dated Oct. 4, 2021.

EP18879073.7 Extended European Search Report dated Sep. 24, 2021.

EP18879073.7 Partial Supplementary European Search Report dated Jul. 8, 2021.

Frankel et al. Characterization of diphtheria fusion proteins targeted to the human interleukin-3 receptor. Protein Engineering 13(8):575-581 (2000).

Gilbreth et al., "Structural insights for engineering binding proteins based on non-antibody scaffolds," Current opinion in structural biology, 22:413-420 (2012).

Hey, Thomas, et al. Artificial, Non-Antibody Binding Proteins for Pharmaceutical and Industrial Applications. Trends in Biotechnology. vol. No. 23, Issue No. 10 (2005): pp. 514-522.

(56) References Cited

OTHER PUBLICATIONS

International Search Report and Written Opinion of the International Searching Authority for PCT/US2018/060887, filed on Nov. 14, 2018; mail date Apr. 1, 2019.
International Search Report and Written Opinion of the International Searching Authority for PCT/US2018/060902, filed on Nov. 14, 2018; mail date Mar. 27, 2019.
International Search Report for PCT/US2016/025868, filed on Apr. 4, 2016; mail date Sep. 2, 2016.
International Search Report for PCT/US2016/025880, filed on Apr. 4, 2016; mail date Jul. 26, 2016.
International Search Report for PCT/US2016/026054, filed on Apr. 5, 2016; mail date Sep. 21, 2016.
Kuchar et al., "Human interleukin-23 receptor antagonists derived from an albumin-binding domain scaffold inhibit IL-23-dependent ex vivo expansion of IL-17-producing T-cells," 82:975-989 (2013).
Lafleur, David. et al. Monoclonal antibody therapeutics with up to five specificities: functional enhancement through fusion of target-specific peptides. MAbs 5(2):208-218 (2013).
Lafleur, David W., et al., "Chimeric Antigen Receptors Incorporating Novel (non-scFv) Binding Domains Targeting CD123 Direct Potent Antitumor Activity of T Cells: Correlation Between Affinity and Activity", Arcellx, Inc., presented at the American Association for Cancer Research 2020 Virtual Annual Meeting II, Jun. 22-24, 2020, Abstract 3243,1 page.
Lazar et al., "Transforming Growth Factor α; Mutation of Aspartic Acid 47 and Leucine 48 Results in Different Biological Activities," Molecular and Cellular Biology, 8(3):1247-1252 (1988).
Liu, et al. Targeting Alpha-fetoprotein (AFP)-MHC Complex With Car T-Cell Therapy for Liver Cancer. Clinical Cancer Research 23(2):478-488 (2017).
Lofblom et al. Affibody molecules: engineered proteins for therapeutic, diagnostic and biotechnological applications. FEBS Letters 584(12):2670-2680 (2010).
Lonial et al., "Elotuzumaab Therapy for Relapsed or Refractory Multiple Myeloma," N Engl J Med., 373:621-31 (2015).
Mardiros et al. "T cells expressing CD123-specific chimeric antigen receptors exhibit specific cytolytic effector functions and antitumor effects against human acute myeloid leukemia" Blood 122(18). 3138-48 (2013).
Michael C. Gundry et al., "Highly Efficient Genome Editing of Murine and Human Hematopoietic Progenitor Cells by CRISPR/Cas9", Cell Reports, vol. 17, No. 5, Oct. 25, 2016, pp. 1453-1461, XP055485683.
Mouratou et al., "Artificial Affinity Proteins as Ligands of Immunoglobulins," Biomolecules, 5:60-75 (2015).
Ngo et al., "Computational Complexity, Protein Structure Prediction, and the Levinthal Paradox," The Protein Folding Problem and Tertiary Structure Prediction, pp. 433 and 492-495 (1994).
Noad et al., "Virus-like particles as immunogens" Trends in Microbiology vol. 11. No. 9 pp. 438-444, Sep. 1, 2003.
Nygren, Per-Ake et al. Alternative Binding Proteins: Affibody Binding Proteins Developed From a Small Three-helix Bundle Scaffold. The FEBS Journal 275(11):2668-2676 (2008).
Pakula et al. Genetic Analysis of Protein Stability and Function. Annu. Rev. Genet. 23:289-310 (1989).
Park et al., "Limitations of yeast surface display in engineering proteins of high thermostability," Protein Engineering, Design & Selection, 19(5):211-217 (2006).
Pluckthun, Andreas. et al. Designed Ankyrin Repeat Proteins (DARPins): Binding Proteins for Research, Diagnostics, and Therapy. Annual Review of Pharmacology and Toxicology 55(1):489-511 (2015).
Qin et al. Chimeric Antigen Receptors Incorporating D Domains Targeting CD123 Direct Potent Mono- and Bi-specific Antitumor Activity of T Cells. Molecular Therapy, vol. 27, No. 7, pp. 1262-1274 (Jul. 2019). With Supplemental Information. 18 pages.
Ronnmark et al. Human immunoglobulin A (IgA)-specific ligands from combinatorial engineering of protein A. Eur. J Biochem., 269:2647-2655 (2002).
Tamada, et al. Redirecting Gene-Modified T Cells Toward Various Cancer Types Using Tagged Antibodies. Clinical Cancer Research 18(23):6436-6445 (2012).
Traxlmayr, et al., "Directed evolution of proteins for increased stability and expression using yeast display," Archives of Biochemistry Biophysics, 526:174-180 (2012).
Unknown; Coiled-coil domain-containing protein 70, UniProtKB database accession No. T2MC19 , accessed at https://www.uniprot.org/uniprot/T2MC19 on May 20, 2019.
Unknown; Cytoplasmic dynein 2 heavy chain 1, UniProtKB database accession No. Q9SMH5, secondary accession No. Q9ZSS7, accessed at https://www.uniprot.org/uniprot/Q9SMH5 on May 20, 2019.
Unknown; Lipoprotein, UniProtKB database accession No. F2UEQ6, accessed at https://www.uniprot.org/uniprot/F2UEQ6 on May 20, 2019.
Unknown; Protein-disulfide isomerase, UniProtKB database accession No. S9SHI3, accessed at https://www.uniprot.org/uniprot/S9SHI3 on May 20, 2019.
Unknown, UniProtKB Accession No. A0A0V0I7C1 "Putative poly(U)-specific endoribonuclease-B-like" Apr. 7, 2021 [online]. [Retrieved on Mar. 18, 2023]. Retrieved from the internet: URL: https://rest.uniprot.org/unisave/A0A0V0I7C1?format=txt&versions=11.
U.S. Appl. No. 16/763,776 Notice of Allowance dated Apr. 20, 2023.
U.S. Appl. No. 16/763,776 Notice of Allowance dated Mar. 29, 2023.
U.S. Appl. No. 16/763,784 Notice of Allowance dated Mar. 16, 2022.
U.S. Appl. No. 17/471,206 Office Action dated Jan. 25, 2022.
U.S. Appl. No. 17/471,271 Notice of Allowance dated Feb. 18, 2022.
Van Der Kuip, Heiko et al., "Short term culture of breast tissues to study the activity of the anticancer drug taxol in an intact tumor environment," BMC Cancer, 6:86, 11 pages (2006).
Walker et al., "Targeting high-risk pediatric solid tumors with CART cells directed against ALK (anaplastic lymphoma kinase, CD246);" J Immunother. Cancer, 2(Suppl 3):P40 (2014).
Walsh, Scott T R, et al. Solution Structure and Dynamics of a De Novo Designed Three-helix Bundle Protein. Proceedings of the National Academy of Sciences of the United States of America. vol. No. 96, Issue No. 10 (1999): pp. 5486-5491.
Written Opinion of the International Searching Authority for PCT/US2016/025868, filed on Apr. 4, 2016; mail date Sep. 2, 2016.
Written Opinion of the International Searching Authority for PCT/US2016/025880, filed on Apr. 4, 2016; mail date Jul. 26, 2016.
Written Opinion of the International Searching Authority for PCT/US2016/026054, filed on Apr. 5, 2016; mail date Sep. 21, 2016.
Zhao, Yangbing. et al. A herceptin-based chimeric antigen receptor with modified signaling domains leads to enhanced survival of transduced T lymphocytes and antitumor activity. Journal of immunology 183(9):5563-5574 (2009).
Antibody. Wikipedia, the free encyclopedia, 2025 ;[retrieved on Sep. 10, 2025]. Available at URL: https://en.wikipedia.org/wiki/Antibody pp. 1-34.
Carpenter et al. B-cell maturation antigen is a promising target for adoptive T-cell therapy of multiple myeloma. Clin Cancer Res 19(8):2048-2060 (2013).
Complementarity-determining region. Wikipedia, the free encyclopedia, [retrieved on Sep. 10, 2025]. Available at URL: https://en.wikipedia.org/wiki/Complementarity-determining_region pp. 1-3.
Co-pending U.S. Appl. No. 19/417,732, inventors Lafleur; David William et al., filed Dec. 12, 2025.
EP25178325.4 Extended European Search Report dated Sep. 16, 2025.
Mizejewski, G J. Alpha-fetoprotein binding proteins: implications for transmembrane passage and subcellular localization. Life sciences 56(1):1-9 (1995). (Abstract only).
Mizejewski, Gerald J. Alpha-fetoprotein structure and function: relevance to isoforms, epitopes, and conformational variants. Experimental biology and medicine 226(5):377-408 (2001).

(56) References Cited

OTHER PUBLICATIONS

Ramadoss, Nitya S. et al. An Anti-B Cell Maturation Antigen Bispecific Antibody for Multiple Myeloma. Journal of the American Chemical Society 137(16):5288-5291 (2015).
Rosenzweig, Michael. et al. Preclinical data support leveraging CS1 chimeric antigen receptor T-cell therapy for systemic light chain amyloidosis. Cytotherapy 19(7):861-866 (2017).
Tai, Yu-Tzu et al. Targeting B-cell maturation antigen in multiple myeloma. Immunotherapy 7(11):1187-1199 (2015).
Tomasi Jr, Thomas B. Structure and function of alpha-fetoprotein. Annual review of medicine 28:453-465 (1977).
U.S. Appl. No. 18/342,898 Office Action dated Sep. 8, 2025.
U.S. Appl. No. 19/030,139 Office Action dated Aug. 18, 2025.
Co-pending U.S. Appl. No. 19/047,185, inventors Hilbert; David M. et al., filed Feb. 6, 2025.
Co-pending U.S. Appl. No. 19/216,526, inventors Lafleur; David et al., filed May 22, 2025.
Co-pending U.S. Appl. No. 19/220,959, inventor Buonato; Janine, filed May 28, 2025.
Co-pending U.S. Appl. No. 19/231,210, inventors Lafleur; David William et al., filed Jun. 6, 2025.
U.S. Appl. No. 17/936,023 Notice of Allowance dated Jun. 23, 2025.
U.S. Appl. No. 19/030,139 Office Action dated Apr. 17, 2025.

* cited by examiner

IL-2 (ng/ml)
0.0
0.5
1.0
1.5
-2
-1
0
1
Log10 (Concentration, µg/ml)

IFN (ng/ml)
0
1
2
3
4
5
-2
-1
0
1
Log10 (Concentration, µg/ml)
cg05-AFP (p26) Adapter
cg05-AFP (p26) Adapter + MOLM13
cg06-AFP (p26) Adapter
cg06-AFP (p26) Adapter + MOLM13
AFP-p26 specific (Af03) CAR T-cells
AFP-p26 specific (Af05) CAR T-cells
Adapter
Binding Domain Specificity
Antigenic Determinant
HIS-tag
CD123 (cg05)
AFP

SEQ ID NO: Adapter Design

1161 α3D(Q19E).3xGS.p26.3xGS.eb08.HIS

1162 α3D(Q19E).3xGS.p26.3xGS.eb09.HIS

1163 α3D(Q19E).3xGS.p26.3xGS.eb10.HIS

MULTIFUNCTIONAL IMMUNE CELL THERAPIES

CROSS-REFERENCE TO RELATED APPLICATIONS

This application is a continuation of U.S. patent application Ser. No. 18/815,117, filed Aug. 26, 2024, which is a continuation of U.S. patent application Ser. No. 18/342,898, filed Jun. 28, 2023, which is a divisional of U.S. patent application Ser. No. 16/763,776, 371 (c) date May 13, 2020, which is a U.S. National Phase of PCT Application No. PCT/US2018/060902, filed Nov. 14, 2018, which claims the benefit of U.S. Provisional Patent Application No. 62/585,770, filed Nov. 14, 2017, and also claims the benefit of U.S. Provisional Patent Application No. 62/717,165, filed Aug. 10, 2018, each of which is incorporated herein by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Jul. 1, 2026, is named 441329.xml and is 1,600,842 bytes in size.

BACKGROUND

The adoptive transfer of genetically modified T cells is a rapidly evolving innovative treatment for cancer. Chimeric antigen receptor (CAR) engineered T cells are renewable drugs with the capacity to provide sustained functional immunity. Clinical efficacy has been demonstrated with CD19 CAR T in a range of hematological cancers and encouraging early clinical data has been reported for other genetically modified CAR T in solid tumors. However, significant challenges must be met before CAR technology can more fully realize its substantial potential.

Current clinical trials with CAR T cells observe a high incidence of relapse in one year or less due to the inability of CAR T cells to address antigen escape and the inherent heterogeneity in the cancer or tumor phenotype. Moreover, current CAR technologies are not adaptive to such changes in cancer or tumor phenotype. In solid tumors, for example, current CAR technologies exhibit limited efficacy due to tumor target heterogeneity and the inability to reprogram CAR T cells to recognize an expanded set of antigenic targets expressed over time. In addition to improving the durability and sustainability of clinical responses, other key impediments to the use of current CAR cell-based technologies include the time required to generate CAR T cells, and the suboptimal specificity, efficacy, and safety of CAR cells for use in cancers beyond leukemia. Accordingly, there is a need for CAR cell-based technology that provides simultaneous and/or sequential target multispecificity and the ability to modulate, alter, or redirect CAR cell-mediated immune responses in vivo.

Bone marrow transplantation (BMT) and hematopoietic stem cell transplantation (HSCT) hold the promise of correcting any blood or immune disease. Czechowicz et al., Blood 128 (22): 493 (2016). Despite their tremendous potential, the clinical use of BMT and HSCT remain fairly limited in part due to the severe safety and toxicity risks associated with current high dose chemotherapy/irradiation conditioning regimens to prepare patients for transplant and subsequent donor HSC engraftment. The most common toxicities experienced by patients include neutropenia, infections, anemia, mucositis, infertility, organ damage particularly in the bone marrow compartment and secondary malignancies. Complete elimination of these toxic conditioning regimens would dramatically improve the safety profile of BMT and HSCT and expand the potential applications to include many more non-malignant hematologic disorders, a wide variety of autoimmune disorders, as well as facilitate solid organ transplant. Accordingly, there is a need for the development of improved conditioning regimens that limit or eliminate toxicities associated with current high dose chemotherapy/irradiation while also effectively treating the underlying disease state.

BRIEF SUMMARY

Provided herein are multi-functional chimeric antigen receptor (CAR)-based compositions and their use in directing immune responses to target cells. The compositions have uses that include treating hyperproliferative disorders such as cancer. The provided methods generally include the use of a CAR cell in combination with an Adapter. The Adapter confers the ability to modulate, alter, and/or redirect CAR cell-mediated immune response in vitro and in vivo.

The present disclosure relates to compositions comprising: (a) a cell expressing a chimeric antigen receptor (CAR), wherein the CAR comprises an antigenic determinant binding domain (ADBD), and (b) a soluble protein (an "Adapter") which comprises (i) an antigenic determinant (AD) and (ii) and an ADBD. The present disclosure also provides methods of killing a target cell with the compositions provided herein, including therapeutic applications of the compositions provided herein.

In some embodiments, the disclosure provides a composition comprising: (a) a cell expressing a CAR, wherein the CAR comprises an (i) an ADBD that binds to a first AD on a target cell, (ii) a transmembrane domain, and (iii) an intracellular domain; and (b) an Adapter which comprises (i) said first AD and (ii) an ADBD that binds to a second AD on said target cell.

In some embodiments, the disclosure provides a composition comprising: (a) a cell expressing a CAR, wherein the CAR comprises (i) an ADBD that binds to a first AD on a target cell, (ii) a transmembrane domain, and (iii) an intracellular domain; and (b) an Adapter which comprises (i) said first AD and (ii) an ADBD that binds to a second AD on a second target cell.

In some embodiments, the disclosure provides a composition comprising: (a) a cell expressing a CAR, wherein the CAR comprises (i) an ADBD that is an alternative scaffold binding domain (ASBD) that binds to a first AD, (ii) a transmembrane domain, and (iii) an intracellular domain; and (b) an Adapter which comprises (i) said first AD and (ii) an ADBD that binds to a second AD on a target cell.

In some embodiments, the disclosure provides a composition comprising: (a) a cell expressing a CAR, wherein the CAR comprises (i) an ADBD that binds to a first AD, (ii) a transmembrane domain, and (iii) an intracellular domain; and (b) an Adapter which comprises (i) said first AD and (ii) an ADBD comprising an ASBD that binds to a second AD on a target cell.

In some embodiments, the disclosure provides a composition comprising: (a) a cell expressing a CAR, wherein the CAR comprises (i) an ADBD that binds to a first AD, (ii) a transmembrane domain, and (iii) an intracellular domain;

and (b) an Adapter which comprises (i) said first AD and (ii) a D domain that binds to a second AD on a target cell.

In some embodiments, the disclosure provides a composition comprising: (a) a cell expressing a CAR, wherein the CAR comprises (i) a D domain that binds to a first AD, (ii) a transmembrane domain, and (iii) an intracellular domain; and (b) an Adapter which comprises (i) said first AD and (ii) an ADBD that binds to a second AD on a target cell.

In some embodiments, the disclosure provides a composition comprising: (a) a cell expressing a CAR, wherein the CAR comprises (i) a first D domain that binds to a first AD, (ii) a transmembrane domain, and (iii) an intracellular domain; and (b) an Adapter which comprises (i) said first AD and (ii) a second D domain that binds to a second AD on a target cell.

In some embodiments, the disclosure provides a method of killing a target cell comprising contacting a composition comprising a target cell with an Adapter, wherein (a) the composition comprising the target cell further comprises a cell expressing a CAR, wherein the CAR comprises (i) an ADBD that binds to a first AD on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of killing one or more target cells comprising contacting a composition comprising a first target cell with an Adapter, wherein (a) the composition comprising the target cell further comprises a cell expressing a CAR, wherein the CAR comprises (i) an ADBD that binds to a first AD on said first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of killing a target cell comprising contacting a composition comprising a target cell with an Adapter, wherein (a) the composition comprising the target cell further comprises a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of killing a target cell comprising contacting a composition comprising a target cell with an Adapter, wherein (a) the composition comprising the target cell further comprises a cell expressing a CAR, wherein the CAR comprises (i) an ADBD that binds to a first AD, (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of killing a target cell comprising contacting a composition comprising a target cell with a cell expressing a CAR, wherein (a) a first AD is present on the target cell; (b) the composition comprising the first target cell further comprises an Adapter comprising (i) said first AD and (ii) an ADBD that binds to a second AD on the target cell; and (c) the CAR comprises (i) an ADBD that binds to said first AD on the target cell or the Adapter, (ii) a transmembrane domain, and (iii) an intracellular domain.

In some embodiments, the disclosure provides a method of killing one or more target cells comprising contacting a composition comprising a target cell with a cell expressing a CAR, wherein (a) a first AD is present on the first target cell; (b) the composition comprising the first target cell further comprises a second target cell and an Adapter comprising (i) said first AD and (ii) an ADBD that binds to a second AD on a second target cell; and (c) the CAR comprises (i) an ADBD that binds to said first AD on the first target cell or the Adapter, (ii) a transmembrane domain, and (iii) an intracellular domain.

In some embodiments, the disclosure provides a method of killing a target cell comprising contacting a composition comprising a target cell with a cell expressing a CAR, wherein (a) a first AD is present on the target cell; (b) the composition comprising the target cell further comprises an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides a method of killing a target cell comprising contacting a composition comprising a target cell with a cell expressing a CAR, wherein (a) a first AD is present on the target cell; (b) the composition comprising the target cell further comprises an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of delivering an immune response to a target cell comprising contacting a composition comprising a target cell with an Adapter, wherein (a) the composition comprising the target cell further comprises a cell expressing a CAR, wherein the CAR comprises (i) an ADBD that binds to a first AD on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of delivering an immune response to one or more target cells comprising contacting a composition comprising a first target cell with an Adapter, wherein (a) the composition comprising the target cell further comprises a cell expressing a CAR, wherein the CAR comprises (i) an ADBD that binds to a first AD on said first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of delivering an immune response to a target cell comprising contacting a composition comprising a target cell with an Adapter, wherein (a) the composition comprising the target cell further comprises a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of delivering an immune response to a target cell comprising contacting a composition comprising a target cell with an Adapter, wherein (a) the composition comprising the target cell further comprises a cell expressing a CAR, wherein the CAR comprises (i) an ADBD that binds to a first AD, (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of delivering an immune response to a target cell comprising contacting a composition comprising a target cell with a CAR, wherein (a) a first AD is present on the target cell; (b) the composition comprising the first target cell further comprises an Adapter comprising (i) said first AD and (ii) an ADBD that binds to a second AD on the target cell; and (c) the CAR comprises (i) an ADBD that binds to said first AD on the target cell or the Adapter, (ii) a transmembrane domain, and (iii) an intracellular domain.

In some embodiments, the disclosure provides a method of delivering an immune response to one or more target cells comprising contacting a composition comprising a target cell with a cell expressing a CAR, wherein (a) a first AD is present on the first target cell; (b) the composition comprising the first target cell further comprises a second target cell and an Adapter comprising (i) said first AD and (ii) an ADBD that binds to a second AD on a second target cell; and (c) the CAR comprises (i) an ADBD that binds to said first AD on the first target cell or the Adapter, (ii) a transmembrane domain, and (iii) an intracellular domain.

In some embodiments, the disclosure provides a method of delivering an immune response to a target cell comprising contacting a composition comprising a target cell with a CAR, wherein (a) a first AD is present on the target cell; (b) the composition comprising the target cell further comprises an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides a method of delivering an immune response to a target cell comprising contacting a composition comprising a target cell with a CAR, wherein (a) a first antigenic determinant (AD) is present on the target cell; (b) the composition comprising the target cell further comprises an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of killing a target cell in a patient comprising administering an Adapter to the patient, wherein (a) the patient has been treated with a cell expressing a CAR, wherein the CAR comprises (i) an ADBD that binds to a first AD on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of redirecting target cell killing in a patient comprising administering an Adapter to the patient, wherein (a) the patient has been treated with a cell expressing a CAR, wherein the CAR comprises (i) an ADBD that binds to a first AD on a first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of killing a target cell in a patient comprising administering an Adapter to the patient, wherein (a) the patient has been treated with a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of killing a target cell in a patient comprising administering an Adapter to the patient, wherein (a) the patient has been treated with a cell expressing a CAR, wherein the CAR comprises (i) an ADBD that binds to a first AD, (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of killing a target cell in a patient comprising administering a cell expressing a CAR to the patient, wherein (a) a first AD and a second AD is present on the target cell; (b) the patient has been treated with an Adapter comprising (i) said first AD and (ii) an ADBD that binds to said second AD on said target cell; and (c) the CAR comprises (i) an ADBD that binds to said first AD on the target cell or the Adapter, (ii) a transmembrane domain, and (iii) an intracellular domain.

In some embodiments, the disclosure provides a method of directing target cell killing in a patient comprising administering a cell expressing a CAR to the patient, wherein (a) the patient has been treated with an Adapter comprising (i) a first AD and (ii) an ADBD that binds to a second AD on the target cell; and (b) the CAR comprises (i) an ADBD that binds to said first AD on the Adapter, (ii) a transmembrane domain, and (iii) an intracellular domain.

In some embodiments, the disclosure provides a method of killing a target cell in a patient comprising administering a cell expressing a CAR to the patient, wherein (a) a first AD is present on the target cell; (b) the patient has been treated with an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides a method of killing a target cell in a patient comprising administering a cell expressing a CAR to the patient, wherein (a) a first AD is present on the target cell; (b) the patient has been treated with an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of delivering an immune response to a target cell in a patient comprising administering an Adapter to the patient, wherein (a) the patient has been treated with a cell expressing a CAR, wherein the CAR comprises (i) an ADBD that binds to a first AD on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of redirecting an immune response to a target cell in a patient comprising administering an Adapter to the patient, wherein (a) the patient has been treated with a cell expressing a CAR, wherein the CAR comprises (i) an ADBD that binds to a first AD on a first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of delivering an immune response to a target cell in a patient comprising administering an Adapter to the patient, wherein (a) the patient has been treated with a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of delivering an immune response to a target cell in a patient comprising administering an Adapter to the patient, wherein (a) the patient has been treated with a cell expressing a CAR, wherein the CAR comprises (i) an ADBD that binds to a first AD, (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of delivering an immune response to a target cell in a patient comprising administering a cell expressing a CAR to the patient, wherein (a) a first AD and a second AD is present on the target cell; (b) the patient has been treated with an Adapter comprising (i) said first AD and (ii) an ADBD that binds to said second AD on said target cell; and (c) the CAR comprises (i) an ADBD that binds to said first AD on the target cell or the Adapter, (ii) a transmembrane domain, and (iii) an intracellular domain.

In some embodiments, the disclosure provides a method of directing an immune response to a target cell in a patient comprising administering a cell expressing a CAR to the patient, wherein (a) the patient has been treated with an Adapter comprising (i) a first AD and (ii) an ADBD that binds to a second AD on the target cell; and (b) the CAR comprises (i) an ADBD that binds to said first AD on the Adapter, (ii) a transmembrane domain, and (iii) an intracellular domain.

In some embodiments, the disclosure provides a method of delivering an immune response to a target cell in a patient comprising administering a cell expressing a CAR to the patient, wherein (a) a first AD is present on the target cell; (b) the patient has been treated with an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides a method of delivering an immune response to a target cell in a patient comprising administering a cell expressing a CAR to the patient, wherein (a) a first AD is present on the target cell; (b) the patient has been treated with a an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of treating proliferative disorder, cancer, autoimmune disease, infection, or allograft rejection comprising contacting a composition comprising a target cell with a cell expressing a CAR, wherein (a) a first AD is present on the target cell; (b) the composition comprising the target cell further comprises an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of treating proliferative disorder, cancer, autoimmune disease, infection, or allograft rejection comprising administering an Adapter to the patient, wherein (a) the patient has been treated with a cell expressing a CAR, wherein the CAR comprises (i) an ADBD that binds to a first AD on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of redirecting treatment of a proliferative disorder, cancer, autoimmune disease, infection, or allograft rejection comprising administering an Adapter to the patient, wherein (a) the patient has been treated with a cell expressing a CAR, wherein the CAR comprises (i) an ADBD that binds to a first AD on a first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of treating proliferative disorder, cancer, autoimmune disease, infection, or allograft rejection comprising administering an Adapter to the patient, wherein (a) the patient has been treated with a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of treating proliferative disorder, cancer, autoimmune disease, infection, or allograft rejection comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of treating proliferative disorder, cancer, autoimmune disease, infection, or allograft rejection comprising administering a cell expressing a CAR to the patient, wherein (a) a first AD and a second AD is present on the target cell; (b) the patient has been treated with an Adapter comprising (i) said first AD and (ii) an ADBD that binds to said second AD on said target cell; and (c) the CAR comprises (i) an ADBD that binds to said first AD on the target cell or the Adapter, (ii) a transmembrane domain, and (iii) an intracellular domain.

In some embodiments, the disclosure provides a method of directing treatment of a proliferative disorder, cancer, autoimmune disease, infection, or allograft rejection comprising administering a cell expressing a CAR to the patient, wherein (a) the patient has been treated with an Adapter comprising (i) a first AD and (ii) an ADBD that binds to a second AD on the target cell; and (b) the CAR comprises (i) an ADBD that binds to said first AD on the Adapter, (ii) a transmembrane domain, and (iii) an intracellular domain.

In some embodiments, the disclosure provides a method of treating proliferative disorder, cancer, autoimmune disease, infection, or allograft rejection comprising administering a cell expressing a CAR to the patient, wherein (a) a first AD is present on the target cell; (b) the patient has been treated with an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides a method of treating a proliferative disorder, cancer, autoimmune disease, infection, or allograft rejection comprising administering a cell expressing a CAR to the patient, wherein (a) a first AD is present on the target cell; (b) the patient has been treated with a an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of treating hematological cancer comprising contacting a composition comprising a target cell with a cell expressing a CAR, wherein (a) a first AD is present on the target cell; (b) the composition comprising the target cell further comprises an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides a method of treating hematological cancer comprising administering an Adapter to the patient, wherein (a) the patient has been treated with a cell expressing a CAR, wherein the CAR comprises (i) an ADBD that binds to a first antigenic determinant (AD) on said target cell, (ii) a transmembrane domain, and (iii) an intracellular domain; and (b) the Adapter comprises (i) said first AD and (ii) an ADBD that binds to a second AD on said target cell.

In some embodiments, the disclosure provides a method of redirecting treatment of a hematological cancer comprising administering an Adapter to the patient, wherein (a) the patient has been treated with a cell expressing a CAR, wherein the CAR comprises (i) an ADBD that binds to a first AD on a first target cell, (ii) a transmembrane domain, and (iii) an intracellular domain; and (b) the Adapter comprises (i) said first AD and (ii) an ADBD that binds to a second AD on a second target cell.

In some embodiments, the disclosure provides a method of treating hematological cancer comprising administering an Adapter to the patient, wherein (a) the patient has been treated with a cell expressing a CAR, wherein the CAR comprises (i) an ADBD that is an ASBD that binds to a first AD, (ii) a transmembrane domain, and (iii) an intracellular domain; and (b) the Adapter comprises (i) said first AD and (ii) an ADBD that binds to a second AD on said target cell.

In some embodiments, the disclosure provides a method of treating hematological cancer comprising administering an Adapter to the patient, wherein (a) the patient has been treated with a cell expressing a CAR, wherein the CAR comprises (i) an ADBD that binds to a first AD, (ii) a transmembrane domain, and (iii) an intracellular domain; and (b) the Adapter comprises (i) said first AD and (ii) an ADBD that is an ASBD that binds to a second AD on said target cell.

In some embodiments, the disclosure provides a method of treating hematological cancer comprising administering a cell expressing a CAR to the patient, wherein (a) a first AD and a second AD is present on the target cell; (b) the patient has been treated with an Adapter comprising (i) said first AD and (ii) an ADBD that binds to said second AD on said target cell; and (c) the CAR comprises (i) an ADBD that binds to said first AD on the target cell or the Adapter, (ii) a transmembrane domain, and (iii) an intracellular domain.

In some embodiments, the disclosure provides a method of directing treatment of a hematological cancer comprising administering a cell expressing a CAR to the patient, wherein (a) the patient has been treated with an Adapter comprising (i) a first AD and (ii) an ADBD that binds to a second AD on the target cell; and (b) the CAR comprises (i) an ADBD that binds to said first AD on the Adapter, (ii) a transmembrane domain, and (iii) an intracellular domain.

In some embodiments, the disclosure provides a method of treating hematological cancer comprising administering a cell expressing a CAR to the patient, wherein (a) a first AD is present on the target cell; (b) the patient has been treated with an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In some embodiments, the disclosure provides method of treating hematological cancer comprising administering a cell expressing a CAR to the patient, wherein (a) a first AD is present on the target cell; (b) the patient has been treated with a an Adapter comprising (i) an ADBD that is an ASBD that binds to said first AD on said target cell and (ii) a second AD; and (c) the CAR comprises (i) an ADBD that binds to said second AD, (ii) a transmembrane domain, and (iii) an intracellular domain.

In some embodiments, the disclosure provides an engineered human immune effector cell comprising (a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (b) a genetic modification that eliminates the expression of the human CD45 AD on the engineered cell, wherein the engineered cell is capable of directing an immune response to a CD45 AD expressing cell in an in vitro assay, and wherein the engineered cell does not express the CD45 AD.

In some embodiments, the disclosure provides a method of killing a human CD45 expressing target cell comprising contacting the target cell with an engineered human immune effector cell, wherein the engineered human immune effector cell comprises (a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (b) a genetic modification that eliminates the expression of the human CD45 AD on the engineered cell.

In some embodiments, the disclosure provides a method of delivering an immune response to a human CD45 expressing target cell comprising contacting the target cell with an engineered human immune effector cell, wherein the engineered human immune effector cell comprises (a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (b) a genetic modification that eliminates the expression of the human CD45 AD on the engineered cell.

In some embodiments, the disclosure provides a method of treating a proliferative disorder, cancer, autoimmune disease, infection, or allograft rejection in a subject comprising administering to the subject in need thereof a therapeutically effective amount of an engineered human immune effector cell, wherein the engineered human immune effector cell comprises (a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (b) a genetic modification that eliminates the expression of the human CD45 AD on the engineered cell.

In some embodiments, the disclosure provides an engineered human immune effector cell comprising (a) a chimeric antigen receptor (CAR) comprising (1) a first antigenic determinant binding domain (ADBD) that specifically binds to a first antigenic determinant (AD), (2) a transmembrane domain, and (3) an intracellular domain; and (b) a genetic modification that eliminates the expression of at least one human CD45 AD on the engineered cell, wherein the first AD is not the at least one human CD45 AD, wherein the engineered cell used in combination with an Adapter is capable of directing an immune response to a CD45 expressing cell in an in vitro assay, wherein the Adapter comprises the first AD and a second ADBD that specifically binds to the at least one human CD45 AD, and wherein the engineered cell does not express the at least one human CD45 AD.

In some embodiments, the disclosure provides a method of killing a target cell comprising contacting the target cell with an engineered human immune effector cell and an Adapter, wherein the target cell expresses CD45, wherein the engineered human immune effector cell comprises (a) a chimeric antigen receptor (CAR) comprising (1) a first antigenic determinant binding domain (ADBD) that specifically binds to a first antigenic determinant (AD), (2) a transmembrane domain, and (3) an intracellular domain; and (b) a genetic modification that eliminates the expression of at least one human CD45 AD on the engineered cell, and wherein the Adapter comprises the first AD and a second ADBD that specifically binds to a human CD45 AD.

In some embodiments, the disclosure provides a method of delivering an immune response to a target cell comprising contacting the target cell with an engineered human immune effector cell and an Adapter, wherein the target cell expresses CD45, wherein the engineered human immune effector cell comprises (a) a chimeric antigen receptor (CAR) comprising (1) a first antigenic determinant binding domain (ADBD) that specifically binds to a first antigenic determinant (AD), (2) a transmembrane domain, and (3) an intracellular domain; and (b) a genetic modification that eliminates the expression of at least one human CD45 AD on the engineered cell, and wherein the Adapter comprises the first AD and a second ADBD that specifically binds to a human CD45 AD.

In some embodiments, the disclosure provides a method of directing an immune response to a CD45 expressing target cell in a subject comprising (a) administering to the subject in need thereof a therapeutically effective amount of an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell; and (b) administering to the subject a therapeutically effective amount of an Adapter comprising the first AD and a second ADBD that specifically binds to a human CD45 AD.

In some embodiments, the disclosure provides a method of directing an immune response to a CD45 expressing target cell in a subject comprising administering to the subject in need thereof a therapeutically effective amount of an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell, wherein the subject has been administered an Adapter comprising the first AD and a second ADBD that specifically binds to a human CD45 AD.

In some embodiments, the disclosure provides a method of directing an immune response to a CD45 expressing target cell in a subject comprising administering to the subject in need thereof a therapeutically effective amount of an Adapter comprising the first AD and a second ADBD that specifically binds to a human CD45 AD, wherein the subject has been administered an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell.

In some embodiments, the disclosure provides a method of treating a proliferative disorder, cancer, autoimmune disease, infection, or allograft rejection in a subject comprising (a) administering to the subject in need thereof a therapeutically effective amount of an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell; and (b) administering to the subject a therapeutically effective amount of an Adapter comprising the first AD and a second ADBD that specifically binds to a human CD45 AD.

In some embodiments, the disclosure provides a method of treating a proliferative disorder, cancer, autoimmune disease, infection, or allograft rejection in a subject comprising administering to the subject in need thereof a therapeutically effective amount of an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell, wherein the subject has been administered an Adapter comprising the first AD and a second ADBD that specifically binds to a human CD45 AD.

In some embodiments, the disclosure provides a method of treating a proliferative disorder, cancer, autoimmune disease, infection, or allograft rejection in a subject comprising administering to a subject in need thereof a therapeutically effective amount of an Adapter comprising the first AD and a second ADBD that specifically binds to a human CD45 AD, wherein the subject has been administered an engineered human immune effector cell comprising (i) a chimeric antigen receptor (CAR) comprising (1) a first antigenic determinant binding domain (ADBD) that specifically binds to a first antigenic determinant (AD), (2) a transmembrane domain, and (3) an intracellular domain; and (ii) a genetic modification that eliminates the expression of at least one human CD45 AD on the engineered cell.

In some embodiments, the disclosure provides an engineered human immune effector cell comprising (a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and (b) a genetic modification that eliminates the expression of the first AD on the engineered cell, wherein the engineered cell does not express the first AD.

In some embodiments, the disclosure provides a method of killing a target cell comprising contacting the target cell with an engineered cell engineered human immune effector cell comprising (a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and (b) a genetic modification that eliminates the expression of the first AD on the engineered cell.

In some embodiments, the disclosure provides a method of directing an immune response to a target cell in a subject comprising administering to the subject in need thereof a therapeutically effective amount of an engineered cell engineered human immune effector cell comprising (a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and (b) a genetic modification that eliminates the expression of the first AD on the engineered cell.

In some embodiments, the disclosure provides a method of treating a proliferative disorder, cancer, autoimmune disease, infection, or allograft rejection in a subject comprising administering to the subject in need thereof a therapeutically effective amount of an engineered human immune effector cell comprising (a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and (b) a genetic modification that eliminates the expression of the first AD on the engineered cell.

In some embodiments, the disclosure provides a method of directing an immune response to a target cell in a subject comprising (a) administering to the subject in need thereof a therapeutically effective amount of an engineered human immune effector cell comprising (i) a chimeric antigen receptor (CAR), wherein the CAR comprises (1) two or more antigenic determinant binding domains (ADBD) comprising a first ADBD that bind to a first antigenic determinants (AD), (2) a transmembrane domain, and (3) an intracellular domain; and (ii) a genetic modification that eliminates the expression of the first AD on the engineered cell; and (b) administering to the subject a therapeutically effective amount of an Adapter comprising an AD recognized by the CAR and a second ADBD that is capable of binding a second AD on the target cell.

In some embodiments, the disclosure provides a engineered human immune effector cell comprising (a) a chimeric antigen receptor (CAR), wherein the CAR comprises (i) a first antigenic determinant binding domain (ADBD) that specifically binds to a first antigenic determinant (AD), (ii) a transmembrane domain, and (iii) an intracellular domain; and (b) a genetic modification that eliminates the expression of a second AD on the engineered cell, wherein the engineered cell used in combination with an Adapter is capable of directing an immune response to a cell expressing the second AD in an in vitro assay, wherein the Adapter comprises the first AD and a second ADBD that specifically binds to the second AD, and wherein the engineered cell does not express the second AD.

In some embodiments, the disclosure provides a method of directing an immune response to a target cell in a subject comprising (a) administering to the subject in need thereof a therapeutically effective amount of an engineered human immune effector cell comprising (i) a chimeric antigen receptor (CAR), wherein the CAR comprises (1) a first antigenic determinant binding domain (ADBD) that specifically binds to a first antigenic determinant (AD), (2) a transmembrane domain, and (3) an intracellular domain; and (ii) a genetic modification that eliminates the expression of a second AD on the engineered cell; and (b) administering to the subject a therapeutically effective amount of an Adapter comprising the first AD recognized by the CAR and a second ADBD that is capable of binding the second AD, wherein the second AD is expressed on the target cell.

In some embodiments, the disclosure provides an engineered human immune effector cell comprising (a) a chimeric antigen receptor (CAR), wherein the CAR comprises (i) two or more antigenic determinant binding domains (ADBD) comprising a first ADBD that specifically binds to a first antigenic determinants (AD), (ii) a transmembrane domain, and (iii) an intracellular domain; and (b) a genetic modification that eliminates the expression of a second AD on the engineered cell, wherein the engineered cell used in combination with an Adapter is capable of directing an immune response to a cell expressing the second AD in an in vitro assay, wherein the Adapter comprises the first AD and a second ADBD that specifically binds to the second AD, and wherein the engineered cell does not express the second AD.

In some embodiments, the disclosure provides a method of directing an immune response to a target cell in a subject comprising (a) administering to the subject in need thereof a therapeutically effective amount of an engineered human immune effector cell comprising (i) a chimeric antigen receptor (CAR), wherein the CAR comprises (1) two or more antigenic determinant binding domains (ADBD) comprising a first ADBD that specifically binds to a first antigenic determinants (AD), (2) a transmembrane domain, and (3) an intracellular domain; and (ii) a genetic modification that eliminates the expression of a second AD on the engineered cell; and (b) administering to the subject a therapeutically effective amount of an Adapter comprising the first AD recognized by the CAR and a second ADBD that is capable of binding the second AD, wherein the second AD is expressed on the target cell.

In some embodiments, the disclosure provides:

[1.] A composition comprising:

(a) a cell expressing a chimeric antigen receptor (CAR), wherein the CAR comprises (i) an antigenic determinant binding domain (ADBD) that binds to a first antigenic determinant (AD) on a target cell, (ii) a transmembrane domain, and (iii) an intracellular domain; and (b) an Adapter which comprises (i) said first AD and (ii) an ADBD that binds to a second AD on said target cell;

[2.] a composition comprising:

(a) a cell expressing a chimeric antigen receptor (CAR), wherein the CAR comprises (i) an antigenic determinant binding domain (ADBD) that binds to a first antigenic determinant (AD) on a target cell, (ii) a transmembrane domain, and (iii) an intracellular domain; and (b) an Adapter which comprises (i) said first AD and (ii) an ADBD that binds to a second AD on a second target cell;

[3.] a composition comprising:

(a) a cell expressing a chimeric antigen receptor (CAR), wherein the CAR comprises (i) an antigenic determinant binding domain (ADBD) that is an alternative scaffold binding domain (ASBD) that binds to a first antigenic determinant (AD), (ii) a transmembrane domain, and (iii) an intracellular domain; and (b) an Adapter which comprises (i) said first AD and (ii) an ADBD that binds to a second AD on a target cell;

[4.] a composition comprising:

(a) a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) an Adapter which comprises (i) said first AD and (ii) an ADBD comprising an ASBD that binds to a second AD on a target cell;

[5.] a composition comprising:

(a) a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) an Adapter which comprises (i) said first AD and (ii) a D domain that binds to a second AD on a target cell;

[6.] a composition comprising:

(a) a cell expressing a chimeric antigen receptor (CAR), wherein the CAR comprises (i) a D domain that binds to a first antigenic determinant (AD), (ii) a transmembrane domain, and (iii) an intracellular domain; and (b) an Adapter which comprises (i) said first AD and (ii) an ADBD that binds to a second AD on a target cell;

[7.] a composition comprising:

(a) a cell expressing a chimeric antigen receptor (CAR), wherein the CAR comprises (i) a first D domain that binds to a first antigenic determinant (AD), (ii) a transmembrane domain, and (iii) an intracellular domain; and (b) an Adapter which comprises (i) said first AD and (ii) a second D domain that binds to a second AD on a target cell;

[8.] the composition of any of [1]-[7], wherein CAR comprises a single-chain variable fragment (scFv) ADBD;

[9.] the composition of any of [1]-[7], wherein the CAR comprises an alternative scaffold binding domain (ASBD) ADBD;

[10.] the composition of [9], wherein the CAR comprises a D domain, and optionally wherein the CAR comprises a sequence selected from the group: SEQ ID NO: 17-26, and 27 or SEQ ID NO: 44-1078, and 1079;

[11.] the composition of any one of [1]-[10], wherein the CAR comprises 2 ADBDs;

[12.] the composition of [11], wherein the CAR comprises an ASBD and a scFv;

[13.] the composition of [11], wherein the CAR comprises a D domain and a scFv;

[14.] the composition of [11], wherein the CAR comprises 2 ASBDs;

[15.] the composition of [11], wherein the CAR comprises 2 D domains;

[16.] the composition of any of [1]-[15], wherein the CAR intracellular domain is a signaling domain;

[17.] the composition of [16], wherein the CAR intracellular domain comprises a primary signaling domain;

[18.] the composition of [16], wherein the CAR intracellular domain comprises a CD3ζ primary signaling domain;

[19.] the composition of [17] or [18], wherein the CAR intracellular domain further comprises a costimulatory signaling domain;

[20.] the composition of [19], wherein the CAR intracellular domain comprises a costimulatory signaling domain selected from: CD28, 41BB, CD27, and CD134;

[21.] the composition of [20], wherein the CAR intracellular domain comprises a 41BB costimulatory signaling domain;

[22.] the composition of any of [1]-[21], wherein the CAR binds to an antigen selected from: CD19, CD22, CD123, BCMA, CS1, HER2, TACI, BAFFR, and PDL1;

[23.] the composition of [22], wherein the CAR binds to BCMA, and optionally wherein the CAR comprises a sequence selected from the group: SEQ ID NO: 44-338, and 339;

[24.] the composition of [22], wherein the CAR binds to CD123, and optionally wherein the CAR comprises a sequence selected from the group: SEQ ID NO: 340-77 and 773;

[25.] the composition of [22], wherein the CAR binds to CD19, and optionally wherein the CAR comprises a sequence selected from the group: SEQ ID NO: 1030-1058, and 1059;

[26.] the composition of [22], wherein the CAR binds to CD22, and optionally wherein the CAR comprises a sequence selected from the group: SEQ ID NO: 1060-1068, and 1069;

[27.] the composition of [22], wherein the CAR binds to CS1, and optionally wherein the CAR comprises a sequence selected from the group: SEQ ID NO: 780-794, and 795;

[28.] the composition of [22], wherein the CAR binds to HER2, optionally wherein the CAR comprises a sequence selected from the group: SEQ ID NO: 800-839, and 840;

[29.] the composition of [22], wherein the CAR binds to PDL1, and optionally wherein the CAR comprises a sequence selected from the group: SEQ ID NO: 1010-1016, 1074-1078, and 1079;

[30.] the composition of any of [1]-[21], wherein the CAR binds to AFP p26, and optionally wherein the CAR comprises a sequence selected from the group: SEQ ID NO: 841-983, and 984;

[31.] the composition of any of [1]-[30], wherein the CAR comprises 2 ADBDs that bind to separate targets;

[32.] the composition of [31], wherein the CAR binds to CD19 and CD123;

[33.] the composition of [31], wherein the CAR binds to BCMA and CS1;

[34.] the composition of [31], wherein the CAR binds to CD22 and CD123;

[35.] the composition of [31], wherein the CAR binds to PDL1 and CD123;

[36.] the composition of [32], wherein the CAR comprises a first ASBD that binds to CD19 and a second ASBD that binds to CD123;

[37.] the composition [36] of wherein the CAR comprises a first D domain that binds to CD19 and a second D domain that binds to CD123;

[38.] the composition of [32], wherein the CAR comprises a D domain that binds to CD19 and a scFv that binds to CD123;

[39.] the composition of [33], wherein the CAR comprises a first ASBD that binds to BCMA and a second ASBD that binds to CS1;

[40.] the composition [39] of wherein the CAR comprises a first D domain that binds to BCMA and a second D domain that binds to CS1;

[41.] the composition of [33], wherein the CAR comprises a D domain that binds to CS1 and a scFv that binds to BCMA;

[42.] the composition of [39], wherein the CAR comprises a D domain that binds to BCMA and a scFv that binds to CS1;

[43.] the composition of [34], wherein the CAR comprises a first ASBD that binds to CD22 and a second ASBD that binds to CD123;

[44.] the composition of [43], wherein the CAR comprises a first D domain that binds to CD22 and a second D domain that binds to CD123;

[45.] the composition of [34], wherein the CAR comprises a D domain that binds to CD22 and a scFv that binds to CD123;

[46.] the composition of [35], wherein the CAR comprises a first ASBD that binds to PDL1 and a second ASBD that binds to CD123;

[47.] the composition of [46], wherein the CAR comprises a first D domain that binds to PDL1 and a second D domain that binds to CD123;

[48.] the composition of [35], wherein the CAR comprises a D domain that binds to PDL1 and a scFv that binds to CD123;

[49.] the composition of [32], wherein the CAR comprises an ASBD that binds to CD19 and a scFv that binds to CD123;

[50.] the composition of any of [1]-[49], wherein the Adapter comprises an AD of a tumor antigen, optionally wherein the tumor antigen is selected from the group: BCMA, CD123, CD19, CD22, CS1, HER2, TACI, BAFFR, and PDL1;

[51.] the composition of [1]-[50], wherein the Adapter comprises an AD that is an epitope of AFP p26 or AFP, and optionally comprises the amino acid residues of SEQ ID NO: 16 or 1117-1123;

[52.] the composition of any of [1]-[51] wherein the Adapter comprises an ADBD that is a scFv;

[53.] the composition of any of [1]-[51], wherein the Adapter comprises an ADBD that is an ASBD;

[54.] the composition of [53], wherein the Adapter comprises a D domain, and optionally wherein the Adapter comprises a sequence selected from the group: SEQ ID NO: 17-26, and 27, or SEQ ID NO: 44-1078, and 1079;

[55.] the composition of any one of [1]-[54], wherein the Adapter comprises two ADBDs;

[56.] the composition of [55], wherein the two ADBDs (a) are the same, (b) bind to the same antigenic determinant, (c) bind to different ADs of the same antigen, or (d) bind to different antigens on the same cell, or (e) bind to different antigens on different cells;

[57.] the composition of [55] or [56], wherein the Adapter comprises two ASBDs;

[58.] the composition of any one of [55]-[57], wherein the Adapter comprises two D domains, and optionally wherein the Adapter comprises an amino acid sequence selected from the group: SEQ ID NO: 44-1079;

[59.] the composition of any one of [55] or [56], wherein the Adapter comprises an ADBD that is a scFv and an ADBD that is an ASBD;

[60.] the composition of [59], wherein the Adapter comprises an ADBD that is a scFv and an ADBD that is a D domain;

[61.] the composition of any of [1]-[60], wherein the Adapter comprises an ADBD that binds to a member selected from: BCMA, CD123, CD19, CD22, CS1, HER2, TACI, BAFFR, and PDL1;

[62.] the composition of [61], wherein the Adapter comprises an ADBD that binds to BCMA, and optionally wherein the ADBD comprises a sequence selected from the group: SEQ ID NO: 44-338, and 339;

[63.] the composition of [61], wherein the Adapter comprises an ADBD that binds to CS1, and optionally wherein the ADBD comprises a sequence selected from the group: SEQ ID NO: 780-794, and 795;

[64.] the composition of [61], wherein the Adapter comprises an ADBD that binds to CD123, and optionally wherein the ADBD comprises a sequence selected from the group: SEQ ID NO: 340-772 and 773;

[65.] the composition of [61], wherein the Adapter comprises an ADBD that binds to CD19, and optionally wherein the ADBD comprises a sequence selected from the group: SEQ ID NO: 1030-1058, and 1059;

[66.] the composition of [61], wherein the Adapter comprises an ADBD that binds to binds to CD22, and optionally wherein the ADBD comprises a sequence selected from the group: SEQ ID NO: 1060-1068, and 1069;

[67.] the composition of [61], wherein the Adapter comprises an ADBD that binds to binds to binds to HER2, and optionally wherein the ADBD comprises a sequence selected from the group: SEQ ID NO: 800-839, and 840;

[68.] the composition of [61], wherein the Adapter comprises an ADBD that binds to TACI or BAFFR;

[69.] the composition of [61], wherein the Adapter comprises an ADBD that binds to PDL1, and optionally wherein the ADBD comprises a sequence selected from the group: SEQ ID NO: 1010-1016, 1074-1078, and 1079;

[70.] the composition of any of [1]-[69], wherein the Adapter is bispecific;

[71.] the composition of [70], wherein the Adapter comprises an ADBD that binds to CD19 and an ADBD that binds to CD123;

[72.] the composition of [70], wherein the Adapter comprises an ADBD that binds to BCMA and an ADBD that binds to CS1;

[73.] the composition of [70], wherein the Adapter comprises an ADBD that binds to CD22 and an ADBD that binds to CD123;

[74.] the composition of [70], wherein the Adapter comprises an ADBD that binds to PDL1 and an ADBD that binds to CD123;

[75.] the composition of any of [1]-[74], wherein the target cell is a tumor cell;

[76.] the composition of [75], wherein the tumor cell is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, myelodysplasia, breast cancer, and ovarian cancer;

[77.] the composition of [75], wherein the tumor cell is multiple myeloma;

[78.] the composition of [75], wherein at least one target cell is a tumor cell;

[79.] the composition of [75], wherein the first and second target cells are tumor cells;

[80.] the composition of [79], wherein the first and second tumor cells are of the same type;

[81.] the composition of [79], wherein the first and second tumor cells are of a different type;

[82.] the composition of [80] or [81], wherein the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, myelodysplasia, breast cancer, and ovarian cancer;

[83.] the composition of [82], wherein the tumor cells are multiple myeloma;

[84.] the composition of any of [1]-[83], wherein the cell expressing the CAR is an immune effector cell;

[85.] the composition of [84], wherein the immune effector cell is a T cell;

[86.] the composition of [84], wherein the immune effector cell is an NK cell;

[87.] the composition of any of [1]-[86], wherein the cell expressing the CAR kills the target cell;

[88.] the composition of any of [1]-[87], wherein binding of the Adapter to an antigenic determinant blocks the activity of the antigen comprising the AD;

[89.] a method of killing a target cell comprising contacting the target cell with the composition of any one of [1]-[88];

[90.] a method of killing a target cell comprising contacting a composition comprising a target cell with an Adapter, wherein
(a) the composition comprising the target cell further comprises a cell expressing a CAR], wherein the CAR comprises (i) an antigenic determinant binding domain (ADBD) that binds to a first AD on said target cell, (ii) a transmembrane domain, and (iii) an intracellular domain; and
(b) the Adapter comprises (i) said first AD and (ii) an ADBD that binds to a second AD on said target cell;

[91.] a method of killing one or more target cells comprising contacting a composition comprising a first target cell with an Adapter, wherein
(a) the composition comprising the target cell further comprises a cell expressing a chimeric antigen receptor (CAR), wherein the CAR comprises (i) an antigenic determinant binding domain (ADBD) that binds to a first AD on said first target cell, (ii) a transmembrane domain, and (iii) an intracellular domain; and
(b) the Adapter comprises (i) said first AD and (ii) an ADBD that binds to a second AD on a second target cell;

[92.] a method of killing a target cell comprising contacting a composition comprising a target cell with an Adapter, wherein
(a) the composition comprising the target cell further comprises a cell expressing a chimeric antigen receptor (CAR), wherein the CAR comprises (i) an antigenic determinant binding domain (ADBD) that is an ASBD that binds to a first AD, (ii) a transmembrane domain, and (iii) an intracellular domain; and
(b) the Adapter comprises (i) said first AD and (ii) an ADBD that binds to a second AD on said target cell;

[93.] a method of killing a target cell comprising contacting a composition comprising a target cell with an Adapter, wherein
(a) the composition comprising the target cell further comprises a cell expressing a chimeric antigen receptor (CAR), wherein the CAR comprises (i) an antigenic determinant binding domain (ADBD) that binds to a first AD, (ii) a transmembrane domain, and (iii) an intracellular domain; and
(b) the Adapter comprises (i) said first AD and (ii) an ADBD that is an ASBD that binds to a second AD on said target cell;

[94.] a method of killing a target cell comprising contacting a composition comprising a target cell with a cell expressing a chimeric antigen receptor (CAR), wherein
(a) a first antigenic determinant (AD) is present on the target cell;
(b) the composition comprising the first target cell further comprises an Adapter comprising (i) said first AD and (ii) an antigenic determinant binding domain (ADBD) that binds to a second AD on the target cell; and
(c) the CAR comprises (i) an ADBD that binds to said first AD on the target cell or the Adapter, (ii) a transmembrane domain, and (iii) an intracellular domain;

[95.] a method of killing one or more target cells comprising contacting a composition comprising a target cell with a cell expressing a chimeric antigen receptor (CAR), wherein
(a) a first AD is present on the first target cell;
(b) the composition comprising the first target cell further comprises a second target cell and an Adapter comprising (i) said first AD and (ii) an antigenic determinant binding domain (ADBD) that binds to a second AD on a second target cell; and
(c) the CAR comprises (i) an ADBD that binds to said first AD on the first target cell or the Adapter, (ii) a transmembrane domain, and (iii) an intracellular domain;

[96.] a method of killing a target cell comprising contacting a composition comprising a target cell with a cell expressing a chimeric antigen receptor (CAR), wherein
(a) a first antigenic determinant (AD) is present on the target cell;
(b) the composition comprising the target cell further comprises an Adapter comprising (i) an antigenic determinant binding domain (ADBD) that binds to said first AD on said target cell and (ii) a second AD; and
(c) the CAR comprises (i) an ADBD that is an ASBD that binds to said second AD, (ii) a transmembrane domain, and (iii) an intracellular domain;

[97.] a method of killing a target cell comprising contacting a composition comprising a target cell with a cell expressing a chimeric antigen receptor (CAR), wherein
(a) a first antigenic determinant (AD) is present on the target cell;
(b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[98.] a method of delivering an immune response to a target cell comprising contacting a composition comprising a target cell with an Adapter, wherein (a) the composition comprising the target cell further comprises a cell expressing a CAR], wherein the CAR comprises (i) an antigenic determinant binding domain (ADBD) that binds to a first AD on said target cell, (ii) a transmembrane domain, and (iii) an intracellular domain; and (b) the Adapter comprises (i) said first AD and (ii) an ADBD that binds to a second AD on said target cell;

[99.] a method of delivering an immune response to one or more target cells comprising contacting a composition comprising a first target cell with an Adapter, wherein (a) the composition comprising the target cell further comprises a cell expressing a chimeric antigen receptor (CAR), wherein the CAR comprises (i) an antigenic determinant binding domain (ADBD) that binds to a first AD on said first target cell, (ii) a transmembrane domain, and (iii) an intracellular domain; and (b) the Adapter comprises (i) said first AD and (ii) an ADBD that binds to a second AD on a second target cell;

[100.] a method of delivering an immune response to a target cell comprising contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that is an ASBD that binds to a first AD, (ii) a transmembrane domain, and (iii) an intracellular domain; and (b) the Adapter comprises (i) said first AD and (ii) an ADBD that binds to a second AD on said target cell;

[101.] a method of delivering an immune response to a target cell comprising contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that binds to a first AD, (ii) a transmembrane domain, and (iii) an intracellular domain; and (b) the Adapter comprises (i) said first AD and (ii) an ADBD that is an ASBD that binds to a second AD on said target cell;

[102.] a method of delivering an immune response to a target cell comprising contacting a composition comprising a target cell with a cell expressing a chimeric antigen receptor (CAR), wherein (a) a first antigenic determinant (AD) is present on the target cell;

(b) the composition comprising the first target cell further comprises an Adapter comprising (i) said first AD and (ii) an antigenic determinant binding domain (ADBD) that binds to a second AD on the target cell; and (c) the CAR comprises (i) an ADBD that binds to said first AD on the target cell or the Adapter, (ii) a transmembrane domain, and (iii) an intracellular domain.

[103.] a method of delivering an immune response to one or more target cells comprising contacting a composition comprising a target cell with a cell expressing a chimeric antigen receptor (CAR), wherein (a) a first AD is present on the first target cell;

(b) the composition comprising the first target cell further comprises a second target cell and an Adapter comprising (i) said first AD and (ii) an antigenic determinant binding domain (ADBD) that binds to a second AD on a second target cell; and (c) the CAR comprises (i) an ADBD that binds to said first AD on the first target cell or the Adapter, (ii) a transmembrane domain, and (iii) an intracellular domain;

[104.] a method of delivering an immune response to a target cell comprising contacting a composition comprising a target cell with a cell expressing a chimeric antigen receptor (CAR), wherein (a) a first antigenic determinant (AD) is present on the target cell;

(b) the composition comprising the target cell further comprises an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain;

[105.] a method of delivering an immune response to a target cell comprising contacting a composition comprising a target cell with a cell expressing a chimeric antigen receptor (CAR), wherein (a) a first antigenic determinant (AD) is present on the target cell;

(b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[106.] a method of killing a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and (b) the Adapter comprises (i) said first AD and (ii) an ADBD that binds to a second AD on said target cell;

[107.] a method of redirecting target cell killing in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on a first target cell, (ii) a transmembrane domain, and (iii) an intracellular domain; and (b) the Adapter comprises (i) said first AD and (ii) an ADBD that binds to a second AD on a second target cell;

[108.] a method of killing a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and (b) the Adapter comprises (i) said first AD and (ii) an ADBD that binds to a second AD on said target cell;

[109.] a method of killing a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) the Adapter comprises (i) said first AD and (ii) an ADBD that is an ASBD that binds to a second AD on said target cell;

[110.] a method of killing a target cell in a patient comprising administering a cell expressing a chimeric antigen receptor (CAR) to the patient, wherein (a) a first antigenic determinant (AD) and a second AD is present on the target cell;

(b) the patient has been treated with an Adapter comprising (i) said first AD and (ii) an antigenic determinant binding domain (ADBD) that binds to said second AD on said target cell; and (c) the CAR comprises (i) an ADBD that binds to said first AD on the target cell or the Adapter, (ii) a transmembrane domain, and (iii) an intracellular domain;

[111.] a method of directing target cell killing in a patient comprising administering a cell expressing a chimeric antigen receptor (CAR) to the patient, wherein (a) the patient has been treated with an Adapter comprising (i) a first antigenic determinant (AD) and (ii) an antigenic determinant binding domain (ADBD) that binds to a second AD on the target cell; and (b) the CAR comprises (i) an ADBD that binds to said first AD on the Adapter, (ii) a transmembrane domain, and (iii) an intracellular domain;

[112.] a method of killing a target cell in a patient comprising administering a cell expressing a chimeric antigen receptor (CAR) to the patient, wherein (a) a first antigenic determinant (AD) is present on the target cell;

(b) the patient has been treated with an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain;

[113.] a method of killing a target cell in a patient comprising administering a cell expressing a chimeric antigen receptor (CAR) to the patient, wherein (a) a first antigenic determinant (AD) is present on the target cell;

(b) the patient has been treated with a an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[114.] a method of delivering an immune response to a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and (b) the Adapter comprises (i) said first AD and (ii) an ADBD that binds to a second AD on said target cell;

[115.] a method of redirecting an immune response to a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on a first target cell, (ii) a transmembrane domain, and (iii) an intracellular domain; and (b) the Adapter comprises (i) said first AD and (ii) an ADBD that binds to a second AD on a second target cell;

[116.] a method of delivering an immune response to a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and (b) the Adapter comprises (i) said first AD and (ii) an ADBD that binds to a second AD on said target cell;

[117.] a method of delivering an immune response to a target cell in a patient comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) the Adapter comprises (i) said first AD and (ii) an ADBD that is an ASBD that binds to a second AD on said target cell;

[118.] a method of delivering an immune response to a target cell in a patient comprising administering a cell expressing a chimeric antigen receptor (CAR) to the patient, wherein (a) a first antigenic determinant (AD) and a second AD is present on the target cell;

(b) the patient has been treated with an Adapter comprising (i) said first AD and (ii) an antigenic determinant binding domain (ADBD) that binds to said second AD on said target cell; and (c) the CAR comprises (i) an ADBD that binds to said first AD on the target cell or the Adapter, (ii) a transmembrane domain, and (iii) an intracellular domain;

[119.] a method of directing an immune response to a target cell in a patient comprising administering a cell expressing a chimeric antigen receptor (CAR) to the patient, wherein (a) the patient has been treated with an Adapter comprising (i) a first antigenic determinant (AD) and (ii) an antigenic determinant binding domain (ADBD) that binds to a second AD on the target cell; and (b) the CAR comprises (i) an ADBD that binds to said first AD on the Adapter, (ii) a transmembrane domain, and (iii) an intracellular domain;

[120.] a method of delivering an immune response to a target cell in a patient comprising administering a cell expressing a chimeric antigen receptor (CAR) to the patient, wherein (a) a first antigenic determinant (AD) is present on the target cell;

(b) the patient has been treated with an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain;

[121.] a method of delivering an immune response to a target cell in a patient comprising administering a cell expressing a chimeric antigen receptor (CAR) to the patient, wherein (a) a first antigenic determinant (AD) is present on the target cell;

(b) the patient has been treated with a an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[122.] a method of treating proliferative disorder, cancer, autoimmune disease, infection, or allograft rejection comprising contacting a composition comprising a target cell with a cell expressing a chimeric antigen receptor (CAR), wherein (a) a first antigenic determinant (AD) is present on the target cell;

(b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[123.] a method of treating proliferative disorder, cancer, autoimmune disease, infection, or allograft rejection comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and (b) the Adapter comprises (i) said first AD and (ii) an ADBD that binds to a second AD on said target cell;

[124.] a method of redirecting treatment of a proliferative disorder, cancer, autoimmune disease, infection, or allograft rejection comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on a first target cell, (ii) a transmembrane domain, and (iii) an intracellular domain; and (b) the Adapter comprises (i) said first AD and (ii) an ADBD that binds to a second AD on a second target cell;

[125.] a method of treating proliferative disorder, cancer, autoimmune disease, infection, or allograft rejection comprising administering an Adapter to the patient, wherein (a) the patient has been treated with a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and (b) the Adapter comprises (i) said first AD and (ii) an ADBD that binds to a second AD on said target cell;

[126.] a method of treating proliferative disorder, cancer, autoimmune disease, infection, or allograft rejection comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) the Adapter comprises (i) said first AD and (ii) an ADBD that is an ASBD that binds to a second AD on said target cell;

[127.] a method of treating proliferative disorder, cancer, autoimmune disease, infection, or allograft rejection comprising administering a cell expressing a chimeric antigen receptor (CAR) to the patient, wherein (a) a first antigenic determinant (AD) and a second AD is present on the target cell;

(b) the patient has been treated with an Adapter comprising (i) said first AD and (ii) an antigenic determinant binding domain (ADBD) that binds to said second AD on said target cell; and (c) the CAR comprises (i) an ADBD that binds to said first AD on the target cell or the Adapter, (ii) a transmembrane domain, and (iii) an intracellular domain;

[128.] a method of directing treatment of a proliferative disorder, cancer, autoimmune disease, infection, or allograft rejection comprising administering a cell expressing a chimeric antigen receptor (CAR) to the patient, wherein (a) the patient has been treated with an Adapter comprising (i) a first antigenic determinant (AD) and (ii) an antigenic determinant binding domain (ADBD) that binds to a second AD on the target cell; and (b) the CAR comprises (i) an ADBD that binds to said first AD on the Adapter, (ii) a transmembrane domain, and (iii) an intracellular domain;

[129.] a method of treating proliferative disorder, cancer, autoimmune disease, infection, or allograft rejection comprising administering a cell expressing a chimeric antigen receptor (CAR) to the patient, wherein (a) a first antigenic determinant (AD) is present on the target cell;

(b) the patient has been treated with an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain;

[130.] a method of treating a proliferative disorder, cancer, autoimmune disease, infection, or allograft rejection comprising administering a cell expressing a chimeric antigen receptor (CAR) to the patient, wherein (a) a first antigenic determinant (AD) is present on the target cell;

(b) the patient has been treated with a an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[131.] the method of any one of [122]-[130], wherein the proliferative disorder or cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, myelodysplasia, breast cancer, and ovarian cancer;

[132.] the method of any one of [122]-[130], wherein the proliferative disorder or cancer is multiple myeloma;

[133.] a method of treating hematological cancer comprising contacting a composition comprising a target cell with a cell expressing a chimeric antigen receptor (CAR), wherein (a) a first antigenic determinant (AD) is present on the target cell;

(b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[134.] a method of treating hematological cancer comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and (b) the Adapter comprises (i) said first AD and (ii) an ADBD that binds to a second AD on said target cell;

[135.] a method of redirecting treatment of a hematological cancer comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD) on a first target cell, (ii) a transmembrane domain, and (iii) an intracellular domain; and (b) the Adapter comprises (i) said first AD and (ii) an ADBD that binds to a second AD on a second target cell;

[136.] a method of treating hematological cancer comprising administering an Adapter to the patient, wherein (a) the patient has been treated with a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and (b) the Adapter comprises (i) said first AD and (ii) an ADBD that binds to a second AD on said target cell;

[137.] a method of treating hematological cancer comprising administering an Adapter to the patient, wherein (a) the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) the Adapter comprises (i) said first AD and (ii) an ADBD that is an ASBD that binds to a second AD on said target cell;

[138.] a method of treating hematological cancer comprising administering a cell expressing a chimeric antigen receptor (CAR) to the patient, wherein (a) a first antigenic determinant (AD) and a second AD is present on the target cell;

(b) the patient has been treated with an Adapter comprising (i) said first AD and (ii) an antigenic determinant binding domain (ADBD) that binds to said second AD on said target cell; and (c) the CAR comprises (i) an ADBD that binds to said first AD on the target cell or the Adapter, (ii) a transmembrane domain, and (iii) an intracellular domain;

[139.] a method of directing treatment of a hematological cancer comprising administering a cell expressing a chimeric antigen receptor (CAR) to the patient, wherein (a) the patient has been treated with an Adapter comprising (i) a first antigenic determinant (AD) and (ii) an antigenic determinant binding domain (ADBD) that binds to a second AD on the target cell; and (b) the CAR comprises (i) an ADBD that binds to said first AD on the Adapter, (ii) a transmembrane domain, and (iii) an intracellular domain;

[140.] a method of treating hematological cancer comprising administering a cell expressing a chimeric antigen receptor (CAR) to the patient, wherein (a) a first antigenic determinant (AD) is present on the target cell;

(b) the patient has been treated with an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain;

[141.] a method of treating hematological cancer comprising administering a cell expressing a chimeric antigen receptor (CAR) to the patient, wherein (a) a first antigenic determinant (AD) is present on the target cell;

(b) the patient has been treated with a an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain;

[142.] the method of any one of [133]-[141], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[143.] the method of any one of [133]-[141], wherein the hematological cancer is multiple myeloma;

[144.] the method of any of [90]-[131], wherein CAR comprises a single-chain variable fragment (scFv) ADBD;

[145.] the method of any of [90]-[143], wherein the CAR comprises an alternative scaffold binding domain (ASBD) ADBD;

[146.] the method of [145], wherein the CAR comprises a D domain, and optionally wherein the CAR comprises a sequence selected from the group: SEQ ID NO: 17-26, and 27 or SEQ ID NO: 44-1078, and 1079;

[147.] the method of any one of [90]-[146], wherein the CAR comprises 2 ADBDs;

[148.] the method of [147], wherein the CAR comprises an ASBD and a scFv;

[149.] the method of [147], wherein the CAR comprises a D domain and a scFv;

[150.] the method of [147], wherein the CAR comprises 2 ASBDs;

[151.] the method of [147], wherein the CAR comprises 2 D domains;

[152.] the method of any one of [90]-[151], wherein the CAR intracellular domain is a signaling domain;

[153.] the method of [152], wherein the CAR intracellular domain comprises a primary signaling domain;

[154.] the method of [152], wherein the CAR intracellular domain comprises a CD3ζ primary signaling domain;

[155.] the method of [153] or [154], wherein the CAR intracellular domain further comprises a costimulatory signaling domain;

[156.] the method of [155], wherein the CAR intracellular domain comprises a costimulatory signaling domain selected from: CD28, 41BB, CD27, and CD134;

[157.] the method of [156], wherein the CAR intracellular domain comprises a 41BB costimulatory signaling domain;

[158.] the method of any one of [90]-[157], wherein the CAR binds to an antigen selected from: CD19, CD22, CD123, BCMA, CS1, HER2, TACI, BAFFR, and PDL1;

[159.] the method of [158], wherein the CAR binds to BCMA, and optionally wherein the CAR comprises a sequence selected from the group: SEQ ID NO: SEQ ID NO: 44-338, and 339;

[160.] the method of [158], wherein the CAR binds to CS1, and optionally wherein the CAR comprises a sequence selected from the group: SEQ ID NO: 780-794, and 795;

[161.] the method of [158], wherein the CAR binds to CD123, and optionally wherein the CAR comprises a sequence selected from the group: SEQ ID NO: 340-772 and 773;

[162.] the method of [158], wherein the CAR binds to CD19, and optionally wherein the CAR comprises a sequence selected from the group: SEQ ID NO: 1030-1058, and 1059;

[163.] the method of [158], wherein the CAR binds to CD22, and optionally wherein the CAR comprises a sequence selected from the group: SEQ ID NO: 1060-1068, and 1069;

[164.] the method of [158], wherein the CAR binds to binds to HER2, and optionally wherein the CAR comprises a sequence selected from the group: SEQ ID NO: 800-839, and 840;

[165.] the method of [158], wherein the CAR binds to PDL1, and optionally wherein the CAR comprises a sequence selected from the group: SEQ ID NO: 1010-1016, 1074-1078, and 1079;

[166.] the method of any one of [90]-[157], wherein the CAR binds to AFP p26, and optionally wherein the CAR comprises a sequence selected from the group: SEQ ID NO: 841-983, and 984;

[167.] the method of any one of [90]-[166], wherein the CAR comprises 2 ADBDs that bind to separate targets;

[168.] the method of [167], wherein the CAR binds to CD19 and CD123;

[169.] the method of [167], wherein the CAR binds to CD22 and CD123; [170.] the method of [167], wherein the CAR binds to PDL1 and CD123;

[171.] the method of [167], wherein the CAR binds to CS1 and BCMA;

[172.] the method of [168], wherein the CAR comprises a first ASBD that binds to CD19 and a second ASBD that binds to C123;

[173.] the method of [172], wherein the CAR comprises a first D domain that binds to CD19 and a second D domain that binds to CD123;

[174.] the method of [168], wherein the CAR comprises a D domain that binds to CD19 and a scFv that binds to CD123;

[175.] the method of [169], wherein the CAR comprises a first ASBD that binds to CD22 and a second ASBD that binds to CD123;

[176.] the method of [175], wherein the CAR comprises a first D domain that binds to CD22 and a second D domain that binds to CD123;

[177.] the method of [169], wherein the CAR comprises a D domain that binds to CD22 and a scFv that binds to CD123;

[178.] the method of [170], wherein the CAR comprises a first ASBD that binds to PDL1 and a second ASBD that binds to CD123;

[179.] the method of [178], wherein the CAR comprises a first D domain that binds to PDL1 and a second D domain that binds to CD123;

[180.] the method of [170], wherein the CAR comprises a D domain that binds to PDL1 and a scFv that binds to CD123;

[181.] the method of [168], wherein the CAR comprises an ASBD that binds to CD19 and a scFv that binds to CD123;

[182.] the method of [171], wherein the CAR comprises a first ASBD that binds to BCMA and a second ASBD that binds to CS1;

[183.] the method of [182], wherein the CAR comprises a first D domain that binds to BCMA and a second D domain that binds to CS1;

[184.] the method of [171], wherein the CAR comprises a D domain that binds to BCMA and a scFv that binds to CS1;

[185.] the method of [171], wherein the CAR comprises a D domain that binds to CS1 and a scFv that binds to BCMA;

[186.] the method of any one of [90]-[185], wherein the Adapter comprises an AD of a tumor antigen, optionally wherein the tumor antigen is selected from the group: BCMA, CD123, CD19, CD22, CS1, HER2, TACI, BAFFR, and PDL1;

[187.] the method of [90]-[186], wherein the Adapter comprises an AD that is an epitope of AFP p26 or AFP, and optionally comprises the amino acid residues of SEQ ID NO: 16 or 1117-1123;

[188.] the method of any one of [90]-[187], wherein the Adapter comprises an ADBD that is a scFv;

[189.] the method of any one of [90]-[187], wherein the Adapter comprises an ADBD that is an ASBD;

[190.] the method of [189], wherein the Adapter comprises a D domain, and optionally wherein the Adapter comprises a sequence selected from the group: SEQ ID NO: 17-26, and 27, or SEQ ID NO: 44-1078, and 1079;

[191.] the method of any one of [90]-[190], wherein the Adapter comprises two ADBDs;

[192.] the method of [191], wherein the two ADBDs (a) are the same, (b) bind to the same antigenic determinant, (c) bind to different ADs of the same antigen, or (d) bind to different antigens on the same cell, or (e) bind to different antigens on different cells;

[193.] the method of [191] or [192], wherein the Adapter comprises two ASBDs;

[194.] the method of any one of [191], [192], or [193], wherein the Adapter comprises two D domains, and optionally wherein the Adapter comprises an amino acid sequence selected from the group: SEQ ID NO: 44-1079;

[195.] the method of [191] or [192], wherein the Adapter comprises an ADBD that is a scFv and an ADBD that is an ASBD;

[196.] the method of [195], wherein the Adapter comprises an ADBD that is a scFv and an ADBD that is a D domain;

[197.] the method of any one of [90]-[196], wherein the Adapter comprises an ADBD that binds to a member selected from: BCMA, CS1, HER2, CD123, CD19, CD22, TACI, BAFFR, and PDL1;

[198.] the method of [197], wherein the Adapter comprises an ADBD that binds to BCMA, and optionally wherein the ADBD comprises a sequence selected from the group: SEQ ID NO: 44-338, and 339;

[199.] the method of [197], wherein the Adapter comprises an ADBD that binds to CS1, and optionally wherein the ADBD comprises a sequence selected from the group: SEQ ID NO: 780-794, and 795;

[200.] the method of [197], wherein the Adapter comprises an ADBD that binds to CD123, and optionally wherein the ADBD comprises a sequence selected from the group: SEQ ID NO: 340-772, and 773;

[201.] the method of [197], wherein the Adapter comprises an ADBD that binds to CD19, and optionally wherein the ADBD comprises a sequence selected from the group: SEQ ID NO: 1030-1058, and 1059;

[202.] the method of [197], wherein the Adapter comprises an ADBD that binds to binds to CD22, and optionally wherein the ADBD comprises a sequence selected from the group: SEQ ID NO: 1060-1068, and 1069;

[203.] the method of [197], wherein the Adapter comprises an ADBD that binds to binds to HER2, and optionally wherein the ADBD comprises a sequence selected from the group: SEQ ID NO: 800-839, and 840;

[204.] the method of [197], wherein the Adapter comprises an ADBD that binds to TACI or BAFFR;

[205.] the method of [197], wherein the Adapter comprises an ADBD that binds to PDL1, and optionally wherein the ADBD comprises a sequence selected from the group: SEQ ID NO: 1010-1016, 1074-1078, and 1079;

[206.] the method of any one of [90]-[205], wherein the Adapter is bispecific;

[207.] the method of [206], wherein the Adapter comprises an ADBD that binds to BCMA and an ADBD that binds to CS1;

[208.] the method of [206], wherein the Adapter comprises an ADBD that binds to CD19 and an ADBD that binds to CD123;

[209.] the method of [206], wherein the Adapter comprises an ADBD that binds to CD22 and an ADBD that binds to CD123;

[210.] the method of [206], wherein the Adapter comprises an ADBD that binds to PDL1 and an ADBD that binds to CD123;

[211.] the method of any one of [90]-[210], wherein the target cell is a tumor cell;

[212.] the method of [211], wherein the tumor cell is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, myelodysplasia, breast cancer, and ovarian cancer;

[213.] the method of [211], wherein the tumor cell is multiple myeloma;

[214.] the method of [211], wherein at least one target cell is a tumor cell;

[215.] the method of [211], wherein the first and second target cells are tumor cells;

[216.] the method of [215], wherein the first and second tumor cells are of the same type;

[217.] the method of [215], wherein the first and second tumor cells are of a different type;

[218.] the method of [214] or [215], wherein the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, myelodysplasia, breast cancer, and ovarian cancer;

[219.] the method of [214] or [215], wherein the tumor cells are multiple myeloma;

[220.] the method of any one of [90]-[219], wherein the cell expressing the CAR is an immune effector cell;

[221.] the method of [220], wherein the immune effector cell is a T cell;

[222.] the method of [220], wherein the immune effector cell is an NK cell;

[223.] the method of any one of [90]-[222], wherein the cell expressing the CAR kills the target cell;

[224.] An engineered human immune effector cell comprising (a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (b) a genetic modification that eliminates the expression of the human CD45 AD on the engineered cell, wherein the engineered cell is capable of directing an immune response to a CD45 AD expressing cell in an in vitro assay, and wherein the engineered cell does not express the CD45 AD;

[225.] a method of killing a target cell comprising contacting the engineered cell according to [224] with the target cell], wherein the target cell expresses human CD45;

[226.] a method of delivering an immune response to a target cell comprising contacting the engineered cell according to [224] with the target cell], wherein the target cell expresses human CD45;

[227.] a method of directing an immune response to a target cell in a subject comprising administering to the subject in need thereof a therapeutically effective amount of the engineered cell according to [224];

[228.] a method of treating a proliferative disorder, cancer, autoimmune disease, infection, or allograft rejection in a subject comprising administering to the subject in need thereof a therapeutically effective amount of the engineered cell according to [224];

[229.] a method of depleting lymphocytes comprising administering to a subject in need thereof an effective amount of the engineered cell according to [224];

[230.] a method of depleting memory T cell comprising administering to a subject in need thereof an effective amount of the engineered cell according to [224];

[231.] a method of treating an autoimmune disease or disorder comprising administering to a subject in need thereof a therapeutically effective amount of the engineered cell according to [224];

[232.] a method of conditioning a subject for transplantation comprising administering to the subject in need thereof an effective amount of the engineered cell according to [224];

[233.] a method of treating a hematological cancer comprising administering to a subject in need thereof a therapeutically effective amount of the engineered cell according to [224];

[234.] An engineered human immune effector cell comprising (a) a chimeric antigen receptor (CAR) comprising (1) a first antigenic determinant binding domain (ADBD) that specifically binds to a first antigenic determinant (AD), (2) a transmembrane domain, and (3) an intracellular domain; and (b) a genetic modification that eliminates the expression of at least one human CD45 AD on the engineered cell, wherein the first AD is not the at least one human CD45 AD], wherein the engineered cell used in combination with an Adapter is capable of directing an immune response to a CD45 AD expressing cell in an in vitro assay], wherein the Adapter comprises the first AD and a second ADBD that specifically binds to the at least one human CD45 AD, and wherein the engineered cell does not express the at least one human CD45 AD;

[235.] a method of killing a target cell comprising contacting the engineered cell according to [234] with an Adapter and the target cell], wherein the target cell expresses CD45, and wherein the Adapter comprises the first AD and a second ADBD that specifically binds to a human CD45 AD;

[236.] a method of delivering an immune response to a target cell comprising contacting the engineered cell according to [234] with an Adapter and the target cell], wherein the target cell expresses CD45, and wherein the Adapter comprises the first AD and a second ADBD that specifically binds to a human CD45 AD;

[237.] a method of treating hematological cancer comprising contacting the engineered cell according to [234] with an Adapter and a cancer cell], wherein the cancer cell expresses CD45, and wherein the Adapter comprises the first AD and a second ADBD that specifically binds to a human CD45 AD;

[238.] a method of directing an immune response to a target cell in a subject comprising (a) administering to the subject in need thereof a therapeutically effective amount of the engineered cell according to [234]; and (b) administering to the subject a therapeutically effective amount of an Adapter comprising the first AD and a second ADBD that specifically binds to a human CD45 AD;

[239.] a method of directing an immune response to a target cell in a subject comprising administering to the subject in need thereof a therapeutically effective amount of the engineered cell according to [234], wherein the subject has been administered an Adapter comprising the first AD and a second ADBD that specifically binds to a human CD45 AD;

[240.] a method of directing an immune response to a target cell in a subject comprising administering to a subject in need thereof a therapeutically effective amount of an Adapter comprising the first AD and a second ADBD that specifically binds to a human CD45 AD], wherein the subject has been administered the engineered cell according to [234];

[241.] a method of treating a proliferative disorder, cancer, autoimmune disease, infection, or allograft rejection in a subject comprising (a) administering to the subject in need thereof a therapeutically effective amount of the engineered cell according to [234]; and (b) administering to the subject a therapeutically effective amount of an Adapter comprising the first AD and a second ADBD that specifically binds to a human CD45 AD;

[242.] a method of treating a proliferative disorder, cancer, autoimmune disease, infection, or allograft rejection in a subject comprising administering to the subject in need thereof a therapeutically effective amount of the engineered cell according to [234], wherein the subject has been administered an Adapter comprising the first AD and a second ADBD that specifically binds to a human CD45 AD;

[243.] a method of treating a proliferative disorder, cancer, autoimmune disease, infection, or allograft rejection in a subject comprising administering to a subject in need thereof a therapeutically effective amount of an Adapter comprising the first AD and a second ADBD that specifically binds to a human CD45 AD], wherein the subject has been administered the engineered cell according to [234];

[244.] a method of depleting lymphocytes comprising (a) administering to a subject in need thereof a therapeutically effective amount of the engineered cell according to [234]; and (b) administering to the subject a therapeutically effective amount of an Adapter comprising the first AD and a second ADBD that specifically binds to a human CD45 AD;

[245.] a method of depleting lymphocytes comprising administering to a subject in need thereof a therapeutically effective amount of the engineered cell according to [234], wherein the subject has been administered an Adapter comprising the first AD and a second ADBD that specifically binds to a human CD45 AD;

[246.] a method of depleting lymphocytes comprising administering to a subject in need thereof a therapeutically effective amount of an Adapter comprising the first AD and a second ADBD that specifically binds to a human CD45 AD], wherein the subject has been administered the engineered cell according to [234];

[247.] a method of depleting memory T cell comprising
(a) administering to a subject in need thereof a therapeutically effective amount of the engineered cell according to [234]; and
(b) administering to the subject a therapeutically effective amount of an Adapter comprising the first AD and a second ADBD that specifically binds to a human CD45 AD;

[248.] a method of depleting memory T cell comprising administering to a subject in need thereof a therapeutically effective amount of an Adapter comprising the first AD and a second ADBD that specifically binds to a human CD45 AD], wherein the subject has been administered the engineered cell according to [234];

[249.] a method of depleting memory T cell comprising administering to a subject in need thereof a therapeutically effective amount of an Adapter comprising the first AD and a second ADBD that specifically binds to a human CD45 AD], wherein the subject has been administered the engineered cell according to [234];

[250.] a method of treating an autoimmune disease or disorder comprising
(a) administering to a subject in need thereof a therapeutically effective amount of the engineered cell according to [234]; and
(b) administering to the subject a therapeutically effective amount of an Adapter comprising the first AD and a second ADBD that specifically binds to a human CD45 AD;

[251.] a method of treating an autoimmune disease or disorder comprising administering to a subject in need thereof a therapeutically effective amount of an Adapter comprising the first AD and a second ADBD that specifically binds to a human CD45 AD], wherein the subject has been administered the engineered cell according to [234];

[252.] a method of treating an autoimmune disease or disorder comprising administering to a subject in need thereof a therapeutically effective amount of an Adapter comprising the first AD and a second ADBD that specifically binds to a human CD45 AD], wherein the subject has been administered the engineered cell according to [234];

[253.] a method of conditioning a subject for transplantation comprising
(a) administering to a subject in need thereof a therapeutically effective amount of the engineered cell according to [234]; and
(b) administering to the subject a therapeutically effective amount of an Adapter comprising the first AD and a second ADBD that specifically binds to a human CD45 AD;

[254.] a method of conditioning a subject for transplantation comprising administering to a subject in need thereof a therapeutically effective amount of the engineered cell according to [234], wherein the subject has been administered an Adapter comprising the first AD and a second ADBD that specifically binds to a human CD45 AD;

[255.] a method of conditioning a subject for transplantation comprising administering to a subject in need thereof a therapeutically effective amount of an Adapter comprising the first AD and a second ADBD that specifically binds to a human CD45 AD], wherein the subject has been administered the engineered cell according to [234];

[256.] a method of treating a hematological cancer comprising
(a) administering to a subject in need thereof a therapeutically effective amount of the engineered cell according to [234]; and
(b) administering to the subject a therapeutically effective amount of an Adapter comprising the first AD and a second ADBD that specifically binds to a human CD45 AD;

[257.] a method of treating a hematological cancer comprising administering to a subject in need thereof a therapeutically effective amount of the engineered cell according to [234], wherein the subject has been administered an Adapter comprising the first AD and a second ADBD that specifically binds to a human CD45 AD;

[258.] a method of treating a hematological cancer comprising administering to a subject in need thereof a therapeutically effective amount of an Adapter comprising the first AD and a second ADBD that specifically binds to a human CD45 AD], wherein the subject has been administered the engineered cell according to [234];

[259.] An engineered human immune effector cell comprising:
(a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and
(b) a genetic modification that eliminates the expression of the first AD on the engineered cell, wherein the engineered cell does not express the first AD;

[260.] a method of killing a target cell comprising contacting the engineered cell according to [259] with the target cell;

[261.] a method of delivering an immune response to a target cell comprising contacting the engineered cell according to [259] with the target cell;

[262.] a method of directing an immune response to a target cell in a subject comprising administering to the subject in need thereof a therapeutically effective amount of the engineered cell according to [259];

[263.] a method of treating a proliferative disorder, cancer, autoimmune disease, infection, or allograft rejection in a subject comprising administering to the subject in need thereof a therapeutically effective amount of the engineered cell according to [259];

[264.] a method of depleting lymphocytes comprising administering to a subject in need thereof an effective amount of the engineered cell according to [259];

[265.] a method of conditioning a subject for transplantation comprising administering to the subject in need thereof an effective amount of the engineered cell according to [259];

[266.] a method of treating a hematological cancer comprising administering to a subject in need thereof a therapeutically effective amount of the engineered cell according to [259];

[267.] a method of killing a target cell comprising contacting the engineered cell according to [259] with an Adapter and the target cell], wherein the Adapter comprises an AD recognized by the CAR and a second ADBD;

[268.] a method of delivering an immune response to a target cell comprising contacting the engineered cell according to [259] with an Adapter and the target cell, and wherein the Adapter comprises an AD recognized by the CAR and a second ADBD that is capable of binding a second AD on the target cell;

[269.] a method of treating hematological cancer comprising contacting the engineered cell according to [259] with an Adapter and a cancer cell], wherein the Adapter comprises an AD recognized by the CAR and a second ADBD that is capable of binding a second AD on the cancer cell;

[270.] a method of directing an immune response to a target cell in a subject comprising
- (a) administering to the subject in need thereof a therapeutically effective amount of the engineered cell according to [259]; and
- (b) administering to the subject a therapeutically effective amount of an Adapter comprising an AD recognized by the CAR and a second ADBD that is capable of binding a second AD on the target cell;

[271.] a method of directing an immune response to a target cell in a subject comprising administering to the subject in need thereof a therapeutically effective amount of the engineered cell according to [259], wherein the subject has been administered an Adapter comprising an AD recognized by the CAR and a second ADBD that is capable of binding a second AD on the target cell;

[272.] a method of directing an immune response to a target cell in a subject comprising administering to a subject in need thereof a therapeutically effective amount of an Adapter comprising an AD recognized by the CAR and a second ADBD that is capable of binding a second AD on the target cell], wherein the subject has been administered the engineered cell according to [259];

[273.] a method of treating a proliferative disorder, cancer, autoimmune disease, infection, or allograft rejection in a subject comprising
- (a) administering to the subject in need thereof a therapeutically effective amount of the engineered cell according to [259]; and
- (b) administering to the subject a therapeutically effective amount of an Adapter comprising an AD recognized by the CAR and a second ADBD that is capable of binding a second AD on a target cell;

[274.] a method of treating a proliferative disorder, cancer, autoimmune disease, infection, or allograft rejection in a subject comprising administering to the subject in need thereof a therapeutically effective amount of the engineered cell according to [259], wherein the subject has been administered an Adapter comprising an AD recognized by the CAR and a second ADBD that is capable of binding a second AD on a target cell;

[275.] a method of treating a proliferative disorder, cancer, autoimmune disease, infection, or allograft rejection in a subject comprising administering to a subject in need thereof a therapeutically effective amount of an Adapter comprising an AD recognized by the CAR and a second ADBD that is capable of binding a second AD on a target cell], wherein the subject has been administered the engineered cell according to [259];

[276.] a method of depleting lymphocytes comprising
- (a) administering to a subject in need thereof a therapeutically effective amount of the engineered cell according to [259]; and
- (b) administering to the subject a therapeutically effective amount of an Adapter comprising an AD recognized by the CAR and a second ADBD that is capable of binding a second AD on a target cell;

[277.] a method of depleting lymphocytes comprising administering to a subject in need thereof a therapeutically effective amount of the engineered cell according to [259], wherein the subject has been administered an Adapter comprising an AD recognized by the CAR and a second ADBD that is capable of binding a second AD on a target cell;

[278.] a method of depleting lymphocytes comprising administering to a subject in need thereof a therapeutically effective amount of an Adapter comprising an AD recognized by the CAR and a second ADBD that is capable of binding a second AD on a target cell], wherein the subject has been administered the engineered cell according to [259];

[279.] a method of conditioning a subject for transplantation comprising
- (a) administering to a subject in need thereof a therapeutically effective amount of the engineered cell according to [259]; and
- (b) administering to the subject a therapeutically effective amount of an Adapter comprising an AD recognized by the CAR and a second ADBD that is capable of binding a second AD on a target cell;

[280.] a method of conditioning a subject for transplantation comprising administering to a subject in need thereof a therapeutically effective amount of the engineered cell according to [259], wherein the subject has been administered an Adapter comprising an AD recognized by the CAR and a second ADBD that is capable of binding a second AD on a target cell;

[281.] a method of conditioning a subject for transplantation comprising administering to a subject in need thereof a therapeutically effective amount of an Adapter comprising an AD recognized by the CAR and a second ADBD that is capable of binding a second AD on a target cell], wherein the subject has been administered the engineered cell according to [259];

[282.] a method of treating a hematological cancer comprising
- (a) administering to a subject in need thereof a therapeutically effective amount of the engineered cell according to [259]; and
- (b) administering to the subject a therapeutically effective amount of an Adapter comprising an AD recognized by the CAR and a second ADBD that is capable of binding a second AD on a target cell;

[283.] a method of treating a hematological cancer comprising administering to a subject in need thereof a therapeutically effective amount of the engineered cell according to [259], wherein the subject has been administered an Adapter comprising an AD recognized by the CAR and a second ADBD that is capable of binding a second AD on a target cell;

[284.] a method of treating a hematological cancer comprising administering to a subject in need thereof a therapeutically effective amount of an Adapter comprising an AD recognized by the CAR and a second ADBD that is capable of binding a second AD on a target cell], wherein the subject has been administered the engineered cell according to [259];

[285.] An engineered human immune effector cell comprising:

(a) a chimeric antigen receptor (CAR), wherein the CAR comprises (i) a first antigenic determinant binding domain (ADBD) that specifically binds to a first antigenic determinant (AD), (ii) a transmembrane domain, and (iii) an intracellular domain; and (b) a genetic modification that eliminates the expression of a second AD on the engineered cell, wherein the engineered cell used in combination with an Adapter is capable of directing an immune response to a cell expressing the second AD in an in vitro assay], wherein the Adapter comprises the first AD and a second ADBD that specifically binds to the second AD, and wherein the engineered cell does not express the second AD;

[286.] An engineered human immune effector cell comprising:

(a) a chimeric antigen receptor (CAR), wherein the CAR comprises (i) two or more antigenic determinant binding domains (ADBD) comprising a first ADBD that specifically binds to a first antigenic determinants (AD), (ii) a transmembrane domain, and (iii) an intracellular domain; and (b) a genetic modification that eliminates the expression of a second AD on the engineered cell, wherein the engineered cell used in combination with an Adapter is capable of directing an immune response to a cell expressing the second AD in an in vitro assay], wherein the Adapter comprises the first AD and a second ADBD that specifically binds to the second AD, and wherein the engineered cell does not express the second AD;

[287.] a method of directing an immune response to a target cell in a subject comprising administering to the subject in need thereof a therapeutically effective amount of the engineered cell according to or [286];

[288.] a method of treating a proliferative disorder, cancer, autoimmune disease, infection, or allograft rejection in a subject comprising administering to the subject in need thereof a therapeutically effective amount of the engineered cell according to [285] or [286];

[289.] a method of depleting lymphocytes comprising administering to a subject in need thereof an effective amount of the engineered cell according to [285] or [286];

[290.] a method of conditioning a subject for transplantation comprising administering to the subject in need thereof an effective amount of the engineered cell according to [285] or [286];

[291.] a method of treating a hematological cancer comprising administering to a subject in need thereof a therapeutically effective amount of the engineered cell according to [285] or [286];

[292.] a method of killing a target cell comprising contacting the engineered cell according to [285] or [286] with an Adapter and the target cell], wherein the Adapter comprises the first AD and a second ADBD that specifically binds to the second AD, and wherein the second AD is expressed on the target cell;

[293.] a method of delivering an immune response to a target cell comprising contacting the engineered cell according to [285] or [286] with an Adapter and the target cell], wherein the Adapter comprises the first AD and a second ADBD that specifically binds to the second AD, and wherein the second AD is expressed on the target cell;

[294.] a method of treating hematological cancer comprising contacting the engineered cell according to [285] or [286] with an Adapter and a cancer cell], wherein the Adapter comprises the first AD and a second ADBD that specifically binds to the second AD, and wherein the second AD is expressed on the cancer cell;

[295.] a method of directing an immune response to a target cell in a subject comprising (a) administering to the subject in need thereof a therapeutically effective amount of the engineered cell according to [285] or [286]; and (b) administering to the subject a therapeutically effective amount of an Adapter comprising the first AD and a second ADBD that specifically binds to the second AD], wherein the second AD is expressed on the target cell;

[296.] a method of directing an immune response to a target cell in a subject comprising administering to the subject in need thereof a therapeutically effective amount of the engineered cell according to [285] or [286]], wherein the subject has been administered an Adapter comprising the first AD and a second ADBD that specifically binds to the second AD, and wherein the second AD is expressed on the target cell;

[297.] a method of directing an immune response to a target cell in a subject comprising administering to a subject in need thereof a therapeutically effective amount of an Adapter comprising the first AD and a second ADBD that specifically binds to the second AD], wherein the subject has been administered the engineered cell according to [285] or [286], and wherein the second AD is expressed on the target cell;

[298.] a method of treating a proliferative disorder, cancer, autoimmune disease, infection, or allograft rejection in a subject comprising (a) administering to the subject in need thereof a therapeutically effective amount of the engineered cell according to [285] or [286]; and (b) administering to the subject a therapeutically effective amount of an Adapter comprising the first AD and a second ADBD that specifically binds to the second AD], wherein the second AD is expressed on a target cell associated with the proliferative disorder, cancer, autoimmune disease, infection, or allograft rejection;

[299.] a method of treating a proliferative disorder, cancer, autoimmune disease, infection, or allograft rejection in a subject comprising administering to the subject in need thereof a therapeutically effective amount of the engineered cell according to [285] or [286]], wherein the subject has been administered an Adapter comprising the first AD and a second ADBD that specifically binds to the second AD, and wherein the second AD is expressed on a target cell associated with the proliferative disorder, cancer, autoimmune disease, infection, or allograft rejection;

[300.] a method of treating a proliferative disorder, cancer, autoimmune disease, infection, or allograft rejection in a subject comprising administering to a subject in need thereof a therapeutically effective amount of an Adapter comprising the first AD and a second ADBD that specifically binds to the second AD], wherein the subject has been administered the engineered cell according to [285] or [286], and wherein the second AD is expressed on a target cell associated with the proliferative disorder, cancer, autoimmune disease, infection, or allograft rejection;

[301.] a method of depleting lymphocytes comprising
- (a) administering to a subject in need thereof a therapeutically effective amount of the engineered cell according to [285] or [286]; and
- (b) administering to the subject a therapeutically effective amount of an Adapter comprising the first AD and a second ADBD that specifically binds to the second AD], wherein the second AD is expressed on a lymphocyte target cell;

[302.] a method of depleting lymphocytes comprising administering to a subject in need thereof a therapeutically effective amount of the engineered cell according to [285] or [286]], wherein the subject has been administered an Adapter comprising the first AD and a second ADBD that specifically binds to the second AD, and wherein the second AD is expressed on a lymphocyte target cell;

[303.] a method of depleting lymphocytes comprising administering to a subject in need thereof a therapeutically effective amount of an Adapter comprising the first AD and a second ADBD that specifically binds to the second AD], wherein the subject has been administered the engineered cell according to [285] or [286], and wherein the second AD is expressed on a lymphocyte target cell;

[304.] a method of conditioning a subject for transplantation comprising
- (a) administering to a subject in need thereof a therapeutically effective amount of the engineered cell according to [285] or [286]; and
- (b) administering to the subject a therapeutically effective amount of an Adapter comprising the first AD and a second ADBD that specifically binds to the second AD], wherein the second AD is expressed on a target cell associated with the transplantation;

[305.] a method of conditioning a subject for transplantation comprising administering to a subject in need thereof a therapeutically effective amount of the engineered cell according to [285] or [286], wherein the subject has been administered an Adapter comprising the first AD and a second ADBD that specifically binds to the second AD, and wherein the second AD is expressed on a target cell associated with the transplantation;

[306.] a method of conditioning a subject for transplantation comprising administering to a subject in need thereof a therapeutically effective amount of an Adapter comprising the first AD and a second ADBD that specifically binds to the second AD], wherein the subject has been administered the engineered cell according to [285] or [286], and wherein the second AD is expressed on a target cell associated with the transplantation;

[307.] a method of treating a hematological cancer comprising
- (a) administering to a subject in need thereof a therapeutically effective amount of the engineered cell according to [285] or [286]; and
- (b) administering to the subject a therapeutically effective amount of an Adapter comprising the first AD and a second ADBD that specifically binds to the second AD], wherein the second AD is expressed on a target cell associated with the hematological cancer;

[308.] a method of treating a hematological cancer comprising administering to a subject in need thereof a therapeutically effective amount of the engineered cell according to [285] or [286]], wherein the subject has been administered an Adapter comprising the first AD and a second ADBD that specifically binds to the second AD, and wherein the second AD is expressed on a target cell associated with the hematological cancer;

[309.] a method of treating a hematological cancer comprising administering to a subject in need thereof a therapeutically effective amount of an Adapter comprising the first AD and a second ADBD that specifically binds to the second AD], wherein the subject has been administered the engineered cell according to [285] or [286], and wherein the second AD is expressed on a target cell associated with the hematological cancer;

[310.] an isolated Adapter polypeptide comprising (1) an antigenic determinant (AD) and (b) one or more antigenic determinant binding domain (ADBD),
wherein at least one ADBD specifically binds to a human CD45 AD, and wherein contacting the Adaptor with a CD45 AD expressing target cell in the presence of an engineered cell according to [234] is capable of directing an immune response by the engineered cell to the target cell in an in vitro assay.

BRIEF DESCRIPTION OF THE DRAWINGS/FIGURES

FIG. 1A-1D: The cytolytic activity of CD123-specific (cg06) and BCMA-specific (bc-40) CARs were compared to a CAR with no known target-specificity (α3D) on a panel of tumors using effector cell to target cell ratios ranging from 1:4 to 1:64. Briefly, 20,000 T cells expressing the bc40, cg06, or α3D CAR were incubated with increasing numbers of a CD123+/BCMA tumor target (MOLM13) (FIG. 1A); a $CD123^{-}/BCMA^{+}$ tumor target (H929) (FIG. 1B); a $CD123^{-}$ tumor target (RAJI) (FIG. 1C); or a $CD123^{+}/BCMA^{-}$ tumor target (MOLM13) (FIG. 1D). After 16 hours, cells were washed and luciferase activity was assessed.

FIGS. 2A-2B: Adapter binding associates with the Adapter and CAR binding specificity. Jurkat NFAT-Luciferase reporter cells were transduced with a negative control CAR (α3D), an AFP (p26)-binding CAR (af03), or a BCMA-binding CAR (bc40). In FIG. 2A, CAR transduced Jurkat cells were incubated with 0.5 μg of Adapter protein (4° C. for 20 minutes), washed, and then stained with anti-HIS PE (clone J095G46, 4° C. for 20 minutes). FIG. 2B shows CAR expression based on FLAG staining (clone L5) versus mock transduced Jurkat cells.

FIGS. 3A-3C show that the Adapter binding of matching CAR: Adapter and Target: Adapter specificity drives lysis of target cells. In FIG. 3A, 40,000 $CD123^{+}BCMA^{-}$ MOLM13-GFP/Luciferase cells were incubated with various Adapters in the presence or absence of 20,000 T cells (E:T ratio of 1:2, donor D14-053017, Day 7) transduced with BCMA-binding CAR (bc40) for 16 hours. After 16 hours, cells were washed and luciferase activity was assessed. Percent lysis was assessed based on wells of MOLM13-GFP/Luciferase cultured in the absence of T cells or Adapter protein. A control of CD123-specific CAR T cells (cg06) cultured at the same ratio was used as a positive control for lysis. In FIG. 3B, 40,000 $CD123^{+}BCMA^{-}$ MOLM13-GFP/Luciferase cells were incubated with CD123 (cg06)-AFP (p26) Adapter in the presence or absence of 20,000 T cells (E:T ratio of 1:2, donor D16-061317, Day 7) transduced with AFP-binding CARs (Af03 or Af05) for 16 hours. After 16 hours, cells were washed and luciferase activity was assessed. Percent lysis was assessed based on wells of MOLM13-GFP/Luciferase cultured in the absence of T cells or Adapter protein. A control of CD123-specific CAR T cells (cg06) cultured at the same ratio was used as a positive control for lysis. In FIG. 3C, 40,000 $BCMA^{+}$ NCI H929-GFP/Luciferase cells were incubated with bc40-AFP (p26) Adapter in the presence or absence of 10,000 T cells (E:T ratio of 1:4, donor D15-062017, Day 8) mock transduced or transduced with AFP-binding CARs (Af03 or Af05) for 16 hours. After 16 hours, cells were washed and luciferase activity was assessed. Percent lysis was assessed based on wells of NCI-H929-GFP/Luciferase cultured in the absence of T cells or Adapter protein.

FIGS. 4A-4D show that Adapter binding of matching CAR: Adapter and Target: Adapter specificity drives cytokine production by CAR T cells. In FIGS. 4A and 4B, donor D14-053017 T cells transduced with BCMA-binding CAR (bc40) were cultured overnight with various Adapters in the presence or absence of $CD123^{+}BCMA^{-}$ MOLM13 cells (25,000 T cells and target cells). Cultured supernatants were collected and assessed for the production of IL-2 (FIG. 4A) and IFN-γ (FIG. 4B). In FIGS. 4C and 4D, donor D15-062017 T cells transduced with AFP-binding CARs (Af03 and Af05) were cultured overnight with cg06-AFP (p26) Adapter in the presence or absence of $CD123^{+}BCMA^{-}$ MOLM13 cells (25,000 T cells and target cells). Cultured supernatants were collected and assessed for the production of IL-2 (FIG. 4C) and IFN-γ (FIG. 4D).

FIG. 5: Adapter binding of matching CAR: Adapter and Target: Adapter specificity drives proliferation of CAR T cells. Donor D16-062717 cells transduced with AFP-binding CAR (Af03) were CFSE labeled (10 minutes at 0.5 μM), then cultured (25,000) in the presence of CD123-specific Adapter or BCMA-specific Adapter in the presence or absence of mitomycin-C treated $CD123^{-}$ $BCMA^{+}$ NCI-H929 cells (25,000) for 72 hours. At 72 hours, cells were stained for CD3, then analyzed for absolute numbers of CD3+ cells via flow cytometry.

FIGS. 6A and 6B show that Adapter binding of matching CAR: Adapter and Target: Adapter drives signaling by CAR-expressing Jurkat NFAT-Luciferase reporter cells. In FIG. 6A, 50,000 reporter cells previously transduced with a BCMA-binding CAR (bc40) were cultured for 5 hours in the presence of various Adapter proteins in the presence or absence of 50,000 $CD123^{+}BCMA^{-}$ MOLM14 cells, then assessed for luciferase activity. In FIG. 6B, 50,000 reporter cells previously transduced with an AFP (p26)-binding CAR (af03) were cultured for 5 hours in the presence of the aspecific α3D-Adapter or the BCMA-specific Bc40-Adapter protein in the presence or absence of 50,000 $BCMA^{+}$ NCI-H929 cells, then assessed for luciferase activity.

FIGS. 7A and 7B show that the CD123-specific Adapter with a BCMA antigenic determinant can function with either a BCMA-specific D domain CAR (bc40) or a BCMA-specific scFv CAR (c11D5-3). In FIG. 7A, 40,000 $CD123^{+}$ $BCMA^{-}$ MOLM13-GFP/Luciferase cells were incubated with the Cg06-BCMA Adapter in the presence or absence of 20,000 T cells (E:T ratio of 1:2, donor D14-062717, Day 9) transduced with a non-specific CAR (α3D), the BCMA-binding D domain CAR (bc40), or the BCMA-binding scFv CAR (c11D5-3) for 16 hours. After 16 hours, cells were washed and luciferase activity was assessed. Percent lysis was assessed based on wells of MOLM13-GFP/Luciferase cultured in the absence of T cells or Adapter protein. Solid lines indicate calculated 3-parameter non-linear curves, while the dashed line for c11D5-3 is present for illustrative purposes only. In FIG. 7B, $CD123^{+}BCMA^{-}$MOLM13-GFP/Luciferase cells were cultured in the same experiment as in FIG. 7A with transduced T cells in the absence of Adapter protein.

FIGS. 8A and 8B show that AFP-specific CARs can simultaneously have CD123 and BCMA-binding capacity via incubation with multiple Adapter proteins. $10^{5}$ Jurkat NFAT-Luciferase transduced with an AFP (p26)-binding CAR (af03) were incubated with a total of 0.5 μg of Adapter proteins at various ratios of the BCMA- to CD123-specific Adapters (4° C. for 20 minutes), washed, and then incubated with CD123-Fc and biotinylated BCMA (0.5 μg of each) (4° C. for 20 minutes), washed, then binding detected with Anti-Fc A488 and Streptavidin-PE. FIG. 8A presents a flow cytometric analysis of CD123-binding and BCMA-binding to their respective target proteins, FIG. 8B provides a comparison of mean fluorescence intensity (MFI) of A488 MFI (CD123-binding, left axis) and PE MFI (BCMA-binding, right axis) flow cytometric data presented in FIG. 8A.

FIGS. 9A and 9B show that dual-binding domain adaptor proteins drive enhanced signaling by CAR-expressing Jurkat NFAT-Luciferase reporter cells over single-binding domain adaptor proteins. In FIG. 9A, 50,000 reporter cells previously transduced with an AFP (p26 domain)-binding CAR (af03) were cultured for 5 hours in the presence of the CD123-specific Cg06-adaptor (Cg06-p26) or the Cg06-dual adaptor protein (Cg06-p26-Cg06 in the presence of 50,000 $CD123^{+}$ MOLM13 or CD123-deficient MOLM13 cells, then assessed for luciferase activity. CD123 deficient cells were generated using CRISPR/Cas9 genetic engineering technology. In FIG. 9B, 50,000 reporter cells previously transduced with an AFP (p26 domain)-binding CAR (af03) were cultured for 5 hours in the presence of the BCMA-specific Bc40-adaptor (Bc40-p26) or the Bc40-dual adaptor protein (Bc40-p26-Bc40) in the presence or absence of 50,000 $BCMA^{+}$ U266 cells, then assessed for luciferase activity.

FIG. 10 shows that binding of truncated and full length p26 to human FcRn is pH dependent.

FIGS. 11A-11D show that adapters comprising CS1 (SLAMF7, CRACC, CD319) specific ADBD modulate intracellular signaling and killing of CS1 positive tumors. In FIG. 11A, the cc02 and cc08 ADBD displayed the most potent NFAT signaling when cultured in the presence of af59-CAR expressing JNL10 cells (FIG. 11A) and the CS1 positive tumor cell line, MM.1S. FIG. 11B shows that the bispecific bc98-p26-cc02 adapter capable of binding both CS1 and BCMA was more potent in its ability to signal than were the monospecific BCMA-binding bc98-p26-α3DQ19E adapter and the monospecific CS1-binding α3DQ19E-p26-cc02 adapter. FIGS. 11C and 11D indicate the bispecific bc98-p26-cc02 is an effective adapter in killing HT929 (high expression of both BCMA and CS1; FIG. 11C) and MM.1S (high BCMA, low CS1; FIG. 11D).

FIG. 12A shows that the adapter comprising eb08 HER2-binding ABDB was the most potent stimulator in this assay.

FIG. 12B shows that the NFAT signaling in JNL10 cells mediated by the adapter comprising eb08 is greater than that of mediated by the adapter comprising zHERs: 4, comparable to that of mediated by the adapter comprising 9.29, and less than that of G3 and zHER2:342. FIG. 12C demonstrates that adapters comprising the HER2-binding eb08 or eb04 modulate tumor lysis in a dose-dependent manner.

DETAILED DESCRIPTION

I. Definitions

Figures 1A, 1B, 1C, 1D:
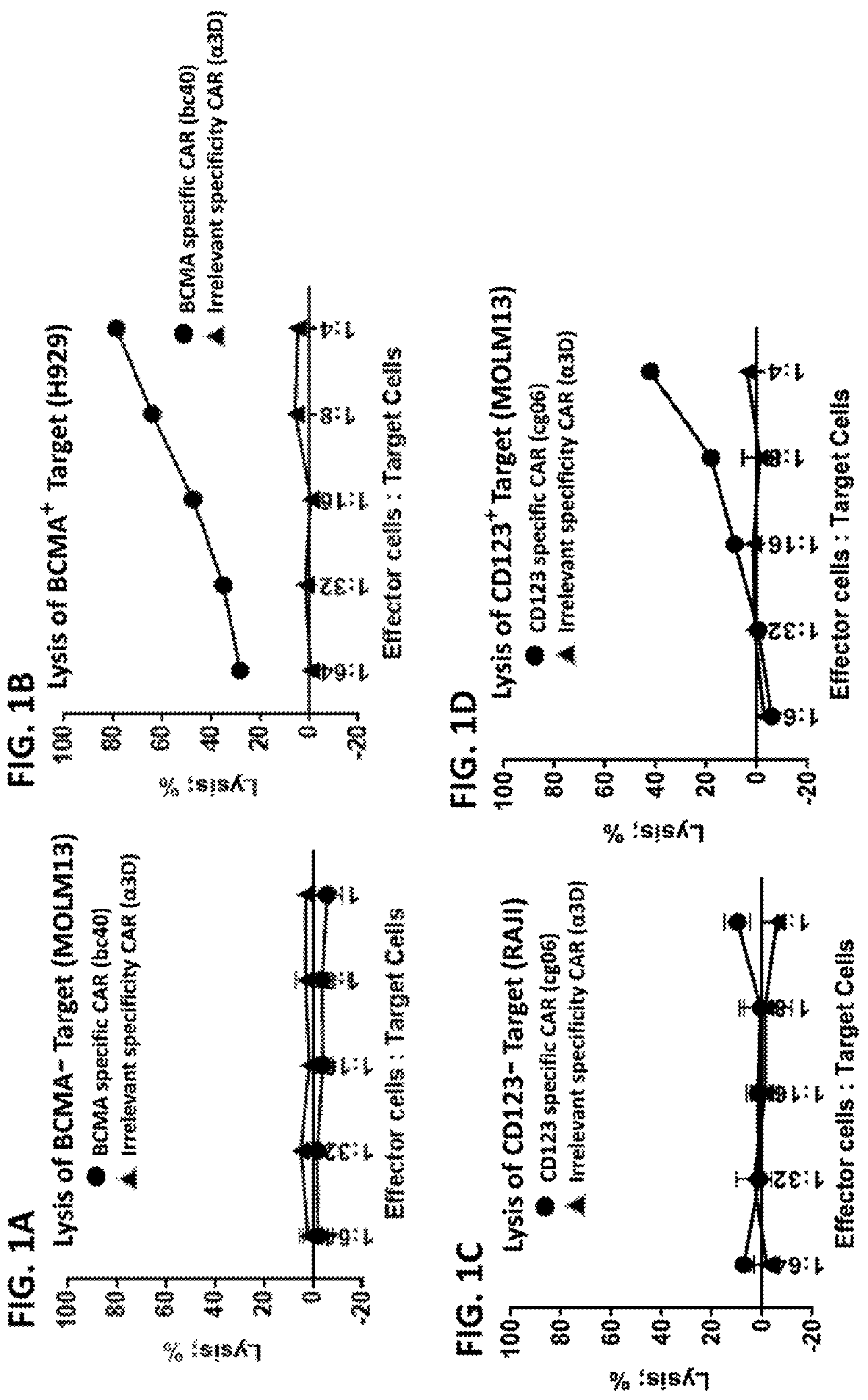

Unless defined otherwise, all technical and scientific terms used herein have the same meaning as commonly understood by one of ordinary skill in the art to which the disclosure pertains.

It is understood that wherever embodiments are described herein with the language "comprising" otherwise analogous embodiments described in terms of "consisting of" and/or "consisting essentially of" are also provided. However, when used in the claims as transitional phrases, each should be interpreted separately and in the appropriate legal and factual context (e.g., "comprising" is considered more of an open-ended phrase while "consisting of" is more exclusive and "consisting essentially of" achieves a middle ground).

As used herein, the singular form "a", "an", and "the" includes plural references unless indicated otherwise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

"About" as the term is used herein, when referring to a measurable value such as an amount, a temporal duration, and other measurable values known in the art, is meant to encompass variations of ±20% or in some embodiments±10%, or in some embodiments±5%, or in some embodiments±1%, or in some embodiments±0.1% from the specified value, as such variations are appropriate to perform the disclosed methods.

The terms "protein" and "polypeptide" are used interchangeably herein to refer to a biological polymer comprising units derived from amino acids linked via peptide bonds; a protein can be composed of two or more polypeptide chains.

"Cell surface receptor" refers to molecules and complexes of molecules capable of receiving a signal and the transmission of such a signal across the plasma membrane of a cell. An example of a cell surface receptor provided herein is an activated integrin receptor, for example, an activated αvβ3 integrin receptor on a metastatic cell. As used herein, "cell surface receptor" also includes a molecule expressed on a cell surface that contains a CAR capable of binding an antigenic determinant target of interest. The term "receptor" denotes a cell-associated protein that binds to, or otherwise interacts with, a molecule (e.g., a ligand) and mediates the effect of the ligand on the cell. In several embodiments, the molecule that interacts with a receptor is a bioactive molecule. Membrane-bound cell-surface receptors are characterized by a multi-domain structure comprising an extracellular ligand-binding domain, a membrane spanning domain, and an intracellular effector domain that is typically involved in signal transduction.

The term "Chimeric antigen receptor" or "CAR" or "CARs" as used herein refers to an engineered chimeric polypeptide that grafts an antigen or target specificity onto a cell such as an immune cell (e.g., a T cell such as a naive T cell, central memory T cell, effector memory T cell, NK cell, NKT cell, or a plurality or combination thereof). CARs may also be referred to herein as artificial T cell receptors, chimeric T cell receptors or chimeric immunoreceptors. The CARs share structural or functional properties with a cell immune-function receptor or Adapter molecule. Upon binding to cognate antigen, a CAR can activate or inactivate the cytotoxic cell in which it is disposed, or modulate the cell's antitumor activity or otherwise modulate the cells immune response. In some embodiments, CARs comprise one or more element (e.g., domain) from a T cell receptor (TCR, e.g., the zeta chain associated with the T cell receptor complex) or a natural killer cell receptor (NKR). In some embodiments, CARs comprise (1) an antigenic determinant binding domain (ADBD) that specifically binds to antigenic determinant (AD), (2) a transmembrane domain, and (3) an intracellular domain. In some embodiments, CARs comprise more than one antigenic determinant binding domains. In some embodiments, CARs comprise more than one antigenic determinant binding domains that bind to different antigenic determinants of the same antigen, different antigenic determinants on different antigens, or antigenic determinants expressed by different target cells.

The term "immune cell" as used herein refers to the cells of the mammalian immune system including but not limited to antigen presenting cells, B-cells, basophils, cytotoxic T cells, dendritic cells, eosinophils, granulocytes, helper T cells, leukocytes, lymphocytes, macrophages, mast cells, memory cells, monocytes, natural killer cells, neutrophils, phagocytes, plasma cells and T cells.

The terms "T cell" and "T-lymphocyte" are interchangeable and used synonymously herein. Examples include but are not limited to naive T cells, central memory T cells, effector memory T cells or combinations thereof.

"Autologous" as the term is used herein refers to any material derived from the same individual to whom it is later to be re-introduced.

"Allogeneic" as the term is used herein refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "effector cells" are leukocytes which express one or more FcRs and perform effector functions. Preferably, the cells express at least FcRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred in certain embodiments. The effector cells can be isolated from native source thereof, e.g., from blood or PBMCs as described herein or otherwise known in the art. In a specific embodiment, the effector cells are human effector cells.

The term "effector function" refers to the specialized immune function of a differentiated cell. Effector function of a T cell, for example, may be cytolytic activity or helper activity including the secretion of cytokines.

The term "immune response" as used herein refers to immunities including but not limited to innate immunity, humoral immunity, cellular immunity, immunity, inflammatory response, acquired (adaptive) immunity, autoimmunity and/or overactive immunity. Indicators of an immune response may include secretion of cytokines by immune cells, expansion of immune cell populations, production of antibodies, degranulation of cytotoxic cells, and killing of target cells. Such indicators may routinely be measured using readily available assays, e.g., ELISA or ELISpot, known in the art.

The term "Adapter" as used herein refers to a multi-domain soluble protein that comprises an antigenic determinant (AD) and an antigenic determinant binding domain (ADBD), wherein the ADBD binds to a second AD. In addition to the AD and the ADBD, an Adapter can comprise additional AD, additional ADBD, and/or other additional domains.

The terms "antibody" or "immunoglobulin," as used interchangeably herein, includes whole antibodies. A whole antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, C1. The VH and VL regions can be further subdivided into regions of hypervariability, termed Complementarity Determining Regions (CDRs), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The terms "antibody fragments" and the like as used herein, include any functional domain of an antibody such as an antigen-binding fragment or single chains thereof, an effector domain, salvage receptor binding epitope, or portion thereof. The antibody fragments described herein may exist in a variety of forms. Examples of antibody fragments include, but are not limited to, Fab, Fab', F(ab') 2, and Fv fragments, an disulfide-linked Fv (sdFv), a Fd fragment consisting of VH and CH1 domains, an scFv, a minibody, a BiTE, a Tandab, a diabody ($(VL-VH)_2$ or $(VH-VL)_2$), a single domain antibody (e.g., an sdAb such as a nanobody (either VL or VH)), and a camelid VHH domain), and multi-specific antibodies formed from antibody fragments. In some embodiments, an "antibody fragment" corresponds to an antigen-binding site or epitope binding site of an antibody. In other embodiments, an "antibody fragment" corresponds to other functional regions of an antibody such as, an effector domain or portion thereof, or a salvage receptor binding epitope, or portion thereof.

The terms "single chain variable fragment(s)," or "scFv" antibodies as used herein refer to forms of antibodies (e.g., antibody fragments) comprising the variable regions of only the heavy and light chains, connected by a linker peptide. The scFv may comprise VL-linker-VH or may comprise VH-linker-VL. ScFv antibodies are generally 220-250 amino acids in length and contain linkers 10-25 amino acids in length.

As used herein, the term, "Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise (1) a CH1 domain, a CH2 domain, and a CH3 domain, (2) a CH1 domain and a CH2 domain, (3) a CH1 domain and a CH3 domain, (4) a CH2 domain and a CH3 domain, or (5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044, each of which is incorporated by reference herein, in their entirety. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM. Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole, J. Immunol. 159:3613 (1997)).

"Antibody-dependent cell-mediated cytotoxicity" or "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis (or other cytotoxic effects) of the target cell. To assess ADCC activity of a molecule of interest, any in vitro ADCC assay known in the art can be used, such as that described in U.S. Pat. Nos. 5,500,362 or 5,821,337. Useful effector cells for such assays include, but are not limited to, peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al., PNAS 95:652-656 (1998).

The term "antigenic determinant binding domain" or "ADBD" as the term is used herein, refers to a sequence of a polypeptide (e.g., an Adapter or CAR) that is sufficient to confer recognition and specific binding to a target antigenic determinant (AD). In some embodiments, the ADBD is an antigen-binding antibody fragment, a scFv, or an antigen-binding peptide that is not based on an antibody or antibody fragment sequence (e.g., a D domain or an affibody). In some embodiments, the ADBD comprises a non antibody-based binding scaffold (e.g., a D domain, affibody, fibronectin domain, nanobody, lipocalin domain ankyrin domain, maxybody, Protein A domain, or affilin domain). In some embodiments the ADBD is a D domain. In some embodiments, the ADBD is an antibody-based binding sequence. In some embodiments the ADBD is a scFv or a domain antibody (dAb). In some embodiments, the ADBD has the ability to bind to a target antigen on the surface of a cell. In some embodiments, the ADBD has the ability to bind to a target antigen on the surface of an immune effector cell. In some embodiments, the ADBD has the ability to bind a growth factor receptor or a hormone receptor.

In particular embodiments, the ADBD is a non antibody-scaffold based polypeptide sequence that is sufficient to confer recognition and specific binding to a target antigenic determinant. In some embodiments, non-antibody based ADBD is a polypeptide that has the ability to bind to target antigen on the surface of a cell. In some embodiments, the non-antibody based ADBD has the ability to bind a growth factor receptor or a hormone receptor. In some embodiments, the ADBD is a D domain-based polypeptide. In particular embodiments, the ADBD is a D domain-based polypeptide that is sufficient to confer recognition and specific binding to a target antigenic determinant. In some embodiments, the ADBD is a D domain-based polypeptide that has the ability to bind to target antigen on the surface of a cell. In some embodiments, the ADBD is a D domain-based polypeptide that has the ability to bind a growth factor receptor or a hormone receptor. In some embodiments, the ADBD is a D domain-based polypeptide that has the ability to bind a target antigen on a serum protein.

The terms "specifically binds" or "having selective affinity for" mean that a binding agent such as an Adapter or CAR, reacts or associates more frequently, more rapidly, with greater duration, with greater affinity, or with some combination of the above to the epitope, protein, or target molecule than with alternative substances, including proteins unrelated to the target epitope. Because of the sequence identity between homologous proteins in different species, specific binding can, in several embodiments, include a binding agent that recognizes a protein or target in more than one species. Likewise, because of homology within certain regions of polypeptide sequences of different proteins, specific binding can include a binding agent that recognizes more than one protein or target. It is understood that, in certain embodiments, a binding agent that specifically binds a first target may or may not specifically bind a second target. As such, "specific binding" does not necessarily require (although it can include) exclusive binding, e.g., binding to a single target. Thus, a binding agent may, in certain embodiments, specifically bind more than one target. In certain embodiments, multiple targets may be bound by the same antigen-binding site on the binding agent.

The terms "linker," "spacer," and "hinge" are used interchangeably herein to refer to a peptide or other chemical linkage located between two or more otherwise independent functional domains of an Adapter or CAR. For example, a linker may be located between an antigenic determinant domain and an antigenic determinant binding domain of an Adapter. Similarly, a linker may be located between two antigenic determinant binding domains or an antigenic binding domain and a transmembrane domain of a CAR. Suitable linkers for coupling the two or more domains of an Adapter are described herein and/or will otherwise be clear to a person skilled in the art.

The term "operably linked," as used herein, indicates that two molecules are attached so as to each retain at least some level of functional activity that each molecule had alone (assuming that each molecule had a function activity). In embodiments when one molecule was without functional activity, it is operably linked with another molecule if the other molecule retains at least some level of its functional activity. Operably linked can also refer to linkage of two non-function molecules. Two molecules can be "operably linked" whether they are attached directly or indirectly (e.g., via a linker).

"Target" refers to any molecule or combination of molecules that can be bound by an Adapter or CAR, or a component of the Adapter or CAR such as antigenic determinant binding domain.

The term "target cell" as used herein refers to cells which are involved in a disease and can be targeted by a CAR, an Adapter, and/or CAR/Adapter composition provided herein. Target cells include any cell in a subject (e.g., a human or animal) that can be targeted by a CAR, an Adapter, and/or CAR/Adapter composition. The target cell can be a cell expressing or overexpressing a target specifically bound by a CAR, Adapter, and/or CAR/Adapter composition.

Expressions like "binding affinity for a target", "binding to a target" and analogous expressions known in the art refer to a property of a polypeptide which may be directly measured through the determination of the affinity constants, e.g., the amount of Adapter that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a Biacore® instrument). These methods are well-known to the skilled person and are described, for example, in Neri et al., Tibtech 14:465-470 (1996), and Jansson et al., J. Biol. Chem. 272:8189-8197 (1997).

"The terms "antigenic determinant" and "epitope" are used interchangeably herein and refer to that portion of any molecule (e.g., a target of interest, or an Adapter) capable of being recognized and specifically bound by a particular binding agent (e.g., an Adapter or CAR). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3 amino acids, and more usually, at least 5 or 8-10 amino acids in a unique spatial conformation.

"Derived from" as that term is used herein, indicates a relationship between a first and a second molecule. It generally refers to structural similarity between the first molecule and a second molecule and does not connote or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The term "naturally occurring" when used in connection with biological materials such as a nucleic acid molecules, polypeptides, antigenic determinants, and host cells, refers to those which are found in nature and not modified by a human being. Conversely, "non-natural" or "synthetic" when used in connection with biological materials refers to those which are not found in nature and have been modified by a human being.

As used herein "modifications" with respect to a sequence of reference includes substitutions, deletions insertions and/ or additions of a sequence when compared to the corresponding amino acid position(s) of the reference sequence.

A "substitution" with respect to a sequence of reference refers to a replacement of a particular amino acid residue with a different amino acid residue at a corresponding amino acid position of the reference sequence.

A "conservative" amino acid substitution is one in which one amino acid residue is replaced with another amino acid residue having a similar side chain. Families of amino acid residues having similar side chains have been defined in the art, including basic side chains (e.g., lysine (K), arginine (R), histidine (H)), acidic side chains (e.g., aspartic acid (D), glutamic acid (E)), uncharged polar side chains (e.g., glycine (G), asparagine (N), glutamine (Q), serine(S), threonine (T), tyrosine (Y), cysteine (C)), nonpolar side chains (e.g., alanine (A), valine (V), leucine (L), isoleucine (I), proline (P), phenylalanine (F), methionine (M), tryptophan (W), beta-branched side chains (e.g., threonine (T), valine (V), isoleucine (I)) and aromatic side chains (e.g., tyrosine (Y), phenylalanine (F), tryptophan (W), histidine (H)). For example, substitution of a phenylalanine for a tyrosine is a conservative substitution. In one embodiment, conservative substitutions in the sequences of the Adapter or CAR results in a retained specific binding of the Adapter or CAR containing the substitution to the target of interest to which it binds. Methods of identifying nucleotide and amino acid conservative substitutions and non-conservative substitutions which confer, alter or maintain selective binding affinity are known in the art (see, e.g., Brummell, Biochem. 32:1180-1187 (1993); Kobayashi, Protein Eng. 12 (10): 879-884 (1999); and Burks, PNAS 94:412-417 (1997)).

A "non-conservative" amino acid substitution is one in which one amino acid residue is replaced with another amino acid residue having a dissimilar side chain. In one embodiment, non-conservative substitutions in the sequences of the Adapter or CAR result in a retained specific binding of the Adapter or CAR containing the substitution to the target of interest to which it binds.

"Non natural amino acids," "amino acid analogs" and "non-standard amino acid residues" are used interchangeably herein. Non-natural amino acids that can be substituted in an Adapter as provided herein are known in the art. In one embodiment the non-natural amino acid is 4-hydroxyproline which can be substituted for proline; 5-hydroxylysine which can be substituted for lysine; 3-methylhistidine which can be substituted for histidine; homoserine which can be substituted for serine; and ornithine which can be substituted for lysine. Additional examples of non-natural amino acids that can be substituted in an Adapter include, but are not limited to molecules such as: D-isomers of the common amino acids, 2,4-diaminobutyric acid, alpha-amino isobutyric acid, A-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, lanthionine, dehydroalanine, γ-aminobutyric acid, selenocysteine and pyrrolysine fluoro-amino acids, designer amino acids such as beta-methyl amino acids, C alpha-methyl amino acids, and N alpha-methyl amino acids, or combinations of non-natural amino acids. Still additional non-natural amino acids can include 4-amino butyric acid, 4-amino-3-hydroxy-5-phenylpentanoic acid, 4-amino-3-hydroxy-6-methylheptanoic acid, 2-thienyl alanine, and/or D-isomers of amino acids. As discussed herein, in several embodiments non-natural amino acids or amino acid analogs can include deletion of one or more amino acids from a sequence.

The terms "polynucleotide" and "nucleic acid," used interchangeably herein, refer to a polymeric form of nucleotides of any length, either ribonucleotides or deoxyribonucleotides. These terms include, but are not limited to, DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA. In some embodiments, an isolated polynucleotide is a modified mRNA comprising non-naturally occurring nucleosides or nucleotides. In some embodiments, a modified mRNA comprises 2-thiouridine, pseudouridine, or 1-methylpseudouridine.

The term "naked DNA" as used herein refers to DNA (e.g., histone free DNA) encoding a protein, such as an Adapter or a CAR, that is cloned in a suitable expression vector in proper orientation for expression (e.g., a plasmid). Viral vectors which may be used include but are not limited to SIN lentiviral vectors, retroviral vectors, foamy virus vectors, adenovirus vectors, adeno-associated virus (AAV) vectors, hybrid vectors and/or plasmid transposons (for example sleeping beauty transposon system) or integrase based vector systems. Other vectors that can be used in connection with making and using Adapters and CARs are described herein or otherwise known in the art.

The terms "vector", "cloning vector" and "expression vector" as used herein refer to the vehicle by which a nucleic acid sequence (e.g., an Adapter or CAR coding sequence) can be maintained or amplified in a host cell (e.g., cloning vector) or introduced into a host cell, so as to transform the host and promote expression (e.g., transcription and translation) of the introduced sequence. Vectors include plasmids, phages, viruses, etc.

A "host cell" includes an individual cell or cell culture which can be or has been a recipient of nucleic acids encoding an Adapter or CAR. Host cells include but are not limited to viral particles, phagemids, bacteria, yeast, plant, animal, and mammalian cells. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo, in vitro, or ex vivo with nucleic acids encoding an Adapter or CAR. In some examples, the host cell is capable of expressing an Adapter. In some examples, the host cell is capable of expressing and secreting an Adapter. In some examples, the host cell is capable of expressing a CAR. In some examples, the host cell is capable of expressing and displaying a CAR on its surface. "Expression" includes transcription and/or translation.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and other therapeutically prohibitive undesirable physiological effects known in the art.

"Parenteral" administration of an immunogenic composition includes, e.g., subcutaneous (s.c.), intravenous (i.v.), intramuscular (i.m.), or intrasternal injection, or infusion techniques.

The term "stimulate" or "stimulation" refers to a primary response induced by binding of a stimulatory molecule with its cognate ligand thereby mediating a signal transduction event, such as, but not limited to, signal transduction via the appropriate receptor, e.g., T or NK receptor.

"Modulate" or "modulation" means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity). In several embodiments, modulation in a positive or negative direction is referenced as compared to the cell, tissue, or organ function prior to administration of a therapeutic. In additional embodiments, modulation in a positive or negative direction is referenced with respect to a normal, healthy cell, tissue or organ.

An "effective amount" of a CAR cell, Adapter, and/or CAR cell/Adapter composition as provided herein is an amount sufficient to carry out a specifically stated purpose such as to bring about an observable change in the level of one or more biological activities related to the target to which the CAR cell and/or Adapter binds. In certain embodiments, the change increases the level of target activity. In other embodiments, the change decreases the level of target activity. An "effective amount" can be determined empirically and in a routine manner, in relation to the stated purpose. The term "therapeutically effective amount" refers to an amount of a CAR cell and/or Adapter, or other therapeutic agent effective to "treat" (e.g., reduce symptoms of) a disease or disorder in a subject (mammal). A "prophylactically effective amount" refers to an amount effective, at dosages and for periods of time necessary, to achieve the desired prophylactic result.

"Patient," "subject," "animal" and "mammal" are used interchangeably and refer to mammals such as human patients and non-human primates, as well as experimental animals such as rabbits, rats, and mice, and other animals. Animals include all vertebrates, e.g., mammals and non-mammals, such as chickens, amphibians, and reptiles. "Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and other members of the class Mammalia known in the art. In a particular embodiment, the patient is a human. The term does not denote a particular age or sex. Thus, adult and newborn subjects, as well as embryos and fetuses, whether male or female, are intended to be included within the scope of this term.

The terms "treat," "treatment," and "treating," as used herein refer to both therapeutic treatment and prophylactic or preventative measures, wherein the object is to prevent or slow down (lessen or delay) the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Treatment can be with a CAR cell, Adapter, and/or CAR cell/Adapter composition, alone or in combination with an additional therapeutic agent. In some embodiments, the terms "treat," "treatment," and "treating," are used herein to refer to therapeutic treatment and prophylactic or preventative measures, wherein the object is to prevent or slow down (lessen or delay) the symptoms, complications, or biochemical indicia of a proliferative disorder, or the amelioration of one or more symptoms (preferably, one or more discernible symptoms) of a proliferative disorder. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size, tumor cell proliferation or survival, or cancerous cell count.

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. Cancers that can be treated using a CAR cell, Adapter, and/or CAR cell/Adapter composition provided herein include without limitation, breast, lung, brain, cervical, skin, bone, liver, pancreatic, colorectal, renal, head and neck, ovarian, hematopoietic (e.g., leukemia), and prostate cancer, and lymphoma. Other types of cancer and tumors that may be treated using a CAR cell, Adapter, and/or CAR cell/Adapter composition are described herein or otherwise known in the art. A reference to cancers, tumors, or tumor cells of a particular "type" is understood to mean cancer, tumors, or tumor cells characterized by a specific disease. For example, in some embodiments a first and second cancer of the same type is mixed cellularity Hodgkin's lymphoma and lymphocyte rich Hodgkin's lymphoma. In other embodiments a first and second cancer of the same type is precursor B cell acute lymphoblastic leukemia (ALL) and mature B cell ALL. Examples of a first and second cancer of a different type include, for example, Hodgkin's lymphoma and ALL.

The term "tumor antigen" refers to an antigen that is common to a specific hyperproliferative disorder such as cancer. The terms "tumor antigen" or "cancer antigen" are used interchangeably herein. In certain aspects, antigens are derived from cancers including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer, mesothelioma, and adenocarcinomas such as breast cancer, prostate cancer, ovarian cancer, pancreatic cancer, colon cancer and other cancers known in the art. In some embodiments, the cancer is B-cell acute lymphoid leukemia ("BALL"), T cell acute lymphoid leukemia ("TALL"), acute lymphoid leukemia (ALL), acute myelogenous leukemia (AML); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia.

Tumor and cancer antigens may be further defined as "tumor-specific antigens (TSA)", "cancer-specific antigens (CSA)", "tumor-associated antigens (TAA)", or "cancer-associated antigens (CAA)". A TSA is an antigen that is unique to tumor cells and does not occur on other cells in the body. A TAA is an antigen that is found on both tumor and some normal cells. A TAA may be expressed on normal cells under conditions that fail to induce a state of immunologic tolerance to the antigen. The expression of the TAAs on the tumor may occur under conditions that enable the immune system to respond to the antigen. TAAs may be expressed on normal cells during fetal development when the immune system is immature and unable to respond or may be normally present at extremely low levels on normal cells but which are expressed at much higher levels on tumor cells. Because of the dynamic nature of tumors, in some instances, tumor cells may express unique antigens at certain stages, and at others also express antigens that are also expressed on non-tumor cells. Thus, inclusion of a certain marker as a TAA does not preclude it being considered a TSA. In some embodiments, the TAA and/or TSA that contains an antigenic determinant specifically bound by a CAR cell, Adapter, and/or CAR cell/Adapter composition provided herein, is selected from: BCMA, CD19, CD20, CD22, CD30, CD33/IL3Ra, CD70, CD123, CD171 (L1-CAM), CS1, EGFRvIII, GD2, $Lewis^{Y}$, ROR 1, mesothelin, IL13Ra2, cMet, PSMA, folate receptor alpha (FR-alpha), CEA, ErbB2 (HER-2/neu); EGFR (HER), PSCA, PSA, MUC1, MUC16, CD44v6, CD44v6/7, CD44v7/8, CD55, IL11Ra, EphA2, EGP40, TAG72, CAIX, HMW-MAA (CSPG4), MAGEA4, NKG2D ligands, beta-HCG, Glycolipid F77, HLA-A2 (NY-ESO-1), HMW-MAA, GD3, TCR, MAGE A3, MARTI, WT1, thyroglobulin, gp100 (Pmel 17), tyrosinase, TRP1, TRP2, HLA-A1, MAGE1, MAGE3, BAGE, GAGE1, GAGE2, pi5, p53, Ras, BCR-ABL, E2A-PRL, H4-RET, IGH-IGK, MYL-RAR; VEGFR2, FAP, FAR, EBVA, HPV antigen E6, HPV antigen E7, TSP-180, MAGE4, MAGE5, MAGE6, RAGE, p185erbB2, p180erbB3, nm-23H1, CA 19-9, CA72-4, CAM 17.1, NuMa, K-ras, beta-Catenin, CDK4, Mum-1, p15, p16, 43-9F, alpha-fetoprotein, BCA225, BTAA, CA125, CA 15-3, CA 27.29 (BCAA), CA195, CA242, CA50, CAM43, CD68, CO-029, FGF5, G250, HTgp-175, M344, MA50, MG7-Ag, NB/70K, NY-CO-1, RCAS1, SDCCAG16, M2BP, TAAL6, TLP, and TPS.

The term "CS1" as used herein refers to an NK cell receptor regulating immune functions that is also expressed on B cells, T cells, dendritic cells, NK-T cells, and monocytes. CS1 is overexpressed in multiple myeloma and has been successfully targeted for immunotherapy multiple myeloma. Malaer & Mathew, Am J Cancer Res. 7 (8): 1637-1641 (2017). CS1 is also known as SLAM7, protein 19A, CRACC, and CD319. The term "CS1" includes variants, isoforms, homologues, orthologs and paralogs. CS1 is a transmembrane protein with various differentially spliced isoforms. In some embodiments, the amino acid sequence of human CS1, comprising a 22 amino acid residue N-terminal signal sequence (MAGSPTCLTLIYILWQLTGSAA, SEQ ID NO: 1137) and an extracellular domain comprising the 226 N-terminal residues (SEQ ID NO: 1138), has Genbank Accession No. NP_067004 (SEQ ID NO: 1139). In some embodiments, the amino acid sequence of human CS1 has Genbank Accession No. NP_001269517, NP_001269518, NP_001269519, NP_001269520, NP 001269521, NP_001269522, NP_001269523, NP_001269524, or NP_001269525.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "transduction" as used herein refers to the introduction of a foreign nucleic acid into a cell using a viral vector. "Transfection" as used herein refers to the introduction of a foreign nucleic acid into a cell using recombinant DNA technology. The term "transformation" means the introduction of a "foreign" (e.g., extrinsic, extracellular, or otherwise non-endogenous) nucleic acid (DNA or RNA) sequence to a host cell, so that the host cell will express the introduced nucleic acid to produce a desired substance, such as a protein or enzyme coded by the introduced coding sequence. The introduced nucleic acid sequence can also be called a "cloned" or "foreign" gene or sequence, can include regulatory or control sequences, such as start, stop, promoter, signal, secretion, or other sequences used by a cell's genetic machinery. The nucleic acid sequence can include nonfunctional sequences or sequences with no known function. A host cell that receives and expresses introduced nucleic acid (e.g., DNA or RNA) has been "transformed" and is a "transformant" or a "clone." The DNA or RNA introduced to a host cell can come from any source, including cells of the same genus or species as the host cell, or cells of a different genus or species or may be non-naturally occurring.

The term "D domain" refers to a target binding polypeptide sharing certain sequence and certain structural features of the reference scaffold sequence: MGSWAEFKQRLAAIK TRLQALGGSEAELAAFEKEIAAFESELQAYKGKG-NPEVEALRK EAAAIRDELQAYRHN (SEQ ID NO: 1) (see WO 2016/164305 and WO 2016/164308, each of which is incorporated by reference herein in its entirety). The reference scaffold is a variant of a non-naturally occurring and targetless antiparallel three helical bundle reference polypeptide originally engineered as an exercise in protein folding (see, Walsh et al., PNAS 96:5486-5491 (1999)

incorporated by reference herein in its entirety). It has been discovered that polypeptides containing modifications of the targetless reference scaffold having the amino acid sequence of SEQ ID NO: 1 are able to specifically bind targets of interest. Thus, a D domain, or a molecule comprising a D domain, can specifically (non-randomly) bind to a target molecule. While not wishing to be bound by theory, it is believed that in designing the D domain, the structural constraints of surface-exposed residues (that can be modified) confer the ability of the surface exposed residues to specifically bind a target of interest.

"Co-express" as used herein refers to expression of two or more protein coding sequences by the same cell or cell population. The coding sequences may be for example, nucleic acids that each encode a single protein or a chimeric protein as a single polypeptide chain.

"Antigen loss escape variants" as used herein refer to cells which exhibit reduced or loss of expression of the target antigen, which antigenic determinants are targeted by an Adapter or CAR provided herein.

II. Antigenic Determinants (ADs)

Antigenic determinants (ADs) are epitopes that are capable of being recognized and specifically bound by an antigenic determinant binding regions (ADBDs) (e.g., antigen-binding fragments of an antibody or alternative scaffold binding domains (ASBDs) (e.g., D domains)). The ADs in the Adapters and on the target cells provided herein can be bound by the CARs discussed below.

In some embodiments, the AD (e.g., in an Adapter and/or on a target cell) is an AD that is present in a naturally occurring protein or other molecule. In some embodiments, the AD is an AD that is endogenous to humans.

In some embodiments, the AD in the Adapter is an AD that is present on a target cell.

In some embodiments, the AD (e.g., in an Adapter and/or on a target cell) is an AD that is present in a transmembrane protein, e.g., an AD that is present in the extracellular portion of a transmembrane protein. In some embodiments, the AD is a tumor antigen. In some embodiments, the AD is a tumor-associated antigen. In some embodiments, the AD is a tumor-specific antigen.

In some embodiments, the AD (e.g., in an Adapter and/or on a target cell) is a cancer antigen. In some embodiments, the AD is a cancer-associated antigen. In some embodiments, the AD is a cancer-specific antigen.

In some embodiments, the AD (e.g., in an Adapter and/or on a target cell) is an epitope of BCMA. In further embodiments, the AD comprises 5-25, 5-50, 5-75, 5-100, 5-125, or 5-150 amino acid residues, more than 150 amino acid residues, or all of the amino acid residues of SEQ ID NO: 5.

In some embodiments, the AD is an epitope of CD19. In further embodiments, the AD comprises 5-25, 5-50, 5-75, 5-100, 5-125, or 5-150 amino acid residues, more than 150 amino acid residues, or all of the amino acid residues of SEQ ID NO: 3.

In some embodiments, the AD is an epitope of CD20. In further embodiments, the AD comprises 5-25, 5-50, 5-75, 5-100, 5-125, or 5-150 amino acid residues, more than 150 amino acid residues, or all of the amino acid residues of SEQ ID NO: 6-9, or 10.

In some embodiments, the AD is an epitope of CD22. In further embodiments, the AD comprises 5-25, 5-50, 5-75, 5-100, 5-125, or 5-150 amino acid residues, more than 150 amino acid residues, or all of the amino acid residues of SEQ ID NO: 41.

In some embodiments, the AD is an epitope of CD123. In further embodiments, the AD comprises 5-25, 5-50, 5-75, 5-100, 5-125, or 5-150 amino acid residues, more than 150 amino acid residues, or all of the amino acid residues of SEQ ID NO: 11.

In some embodiments, the AD is an epitope of CD37. In further embodiments, the AD comprises 5-25, 5-50, 5-75, 5-100, 5-125, or 5-150 amino acid residues, more than 150 amino acid residues, or all of the amino acid residues of SEQ ID NO: 12 or 13.

In some embodiments, the AD is an epitope of CS1. In further embodiments, the AD comprises 5-25, 5-50, 5-75, 5-100, 5-125, or 5-150 amino acid residues, more than 150 amino acid residues, or all of the amino acid residues of SEQ ID NO: 1139. In further embodiments, the AD is an epitope of CS1 that is bound by elotuzumab.

In some embodiments, the AD is an epitope of HER2. In further embodiments, the AD comprises 5-25, 5-50, 5-75, 5-100, 5-125, or 5-150 amino acid residues, more than 150 amino acid residues, or all of the amino acid residues of SEQ ID NO: 42.

In some embodiments, the AD is an epitope of AFP. In further embodiments, the AD comprises 5-25, 5-50, 5-75, 5-100, 5-125, or 5-150 amino acid residues, more than 150 amino acid residues, or all of the amino acid residues of SEQ ID NO: 15.

In some embodiments, the AD is an epitope of AFP p26. In further embodiments, the AD comprises 5-25, 5-50, 5-75, 5-100, 5-125, or 5-150 amino acid residues, more than 150 amino acid residues, or all of the amino acid residues of SEQ ID NO: 16. In further embodiments, the AD comprises 5-25, 5-50, 5-75, 5-100, 5-125, or 5-150 amino acid residues, more than 150 amino acid residues, or all of the amino acid residues of SEQ ID NO: 1117. In further embodiments, the AD comprises the amino acid residues of SEQ ID NO: 16, 1117, 1118, 1119, 1120, 1121, 1122, or 1123.

In some embodiments, the AD (e.g., in an Adapter and/or on a target cell) is expressed on the surface of an immune effector cell.

In some embodiments, the AD is an epitope of the extracellular domain (ECD) of human CD45. In further embodiments, the AD comprises 5-25, 5-50, 5-75, 5-100, 5-125, or 5-150 amino acid residues, more than 150 amino acid residues, or all of the amino acid residues of residues 29-766 of SEQ ID NO: 1106.

In some embodiments, the AD is an epitope of human CD45 that is bound by the UCHL-1, A6, or ODP4 antibody. In some embodiments, the AD is an epitope of human CD45 that is bound by the 4KB5, MB1, KiB3, 2H4, or MT2 antibody.

In some embodiments, the AD is an epitope of CD26. In further embodiments, the AD comprises 5-25, 5-50, 5-75, 5-100, 5-125, or 5-150 amino acid residues, more than 150 amino acid residues, or all of the amino acid residues of residues 29-766 of SEQ ID NO: 1113.

In some embodiments, the AD is an epitope of CD30. In further embodiments, the AD comprises 5-25, 5-50, 5-75, 5-100, 5-125, or 5-150 amino acid residues, more than 150 amino acid residues, or all of the amino acid residues of residues 19-379 of SEQ ID NO: 1114.

In some embodiments, the AD is an epitope of CD33. In further embodiments, the AD comprises 5-25, 5-50, 5-75, 5-100, 5-125, or 5-150 amino acid residues, more than 150 amino acid residues, or all of the amino acid residues of residues 18-259 of SEQ ID NO: 1115.

In some embodiments, the AD is an epitope of CD38. In further embodiments, the AD comprises 5-25, 5-50, 5-75, 5-100, 5-125, or 5-150 amino acid residues, more than 150 amino acid residues, or all of the amino acid residues of residues 43-300 of SEQ ID NO: 1116.

In some embodiments, the AD is an epitope of a human intracellular protein. In further embodiments, the AD is an epitope of an intracellular portion of a membrane associated receptor protein selected from the group: cytokine receptor, chemokine receptor, T cell receptor, B cell receptor, NK cell receptor, myeloid cell receptor, endothelial cell receptor, and epithelial cell receptor. In some embodiments, the AD is an epitope of the intracellular portion of CD3, CD137, CD279, CD223, CD152, CD28, and VEGFR-2. In some embodiments, the AD is an epitope of a human nuclear protein.

In some embodiments, the AD (e.g., in an Adapter and/or on a target cell) is an epitope of a tumor antigen associated with a malignant tumor. In some embodiments, the AD is an epitope of a tissue-specific antigen from a melanoma. In some embodiments, the AD is an epitope of a tissue-specific melanoma antigen selected from: MART-1, tyrosinase, and GP 100. In some embodiments, the AD is an epitope of a tissue-specific antigen from a prostate cancer. In some embodiments, the tissue-specific prostate cancer antigen is selected from: prostatic acid phosphatase (PAP) and prostate-specific antigen (PSA). In some embodiments, the AD is an epitope of a transformation-related molecule. In further embodiments, the AD is an epitope of ErbB2 (HER2). In some embodiments, the AD is an epitope of an onco-fetal antigen. In some embodiments, the AD is an epitope of carcinoembryonic antigen (CEA). In some embodiments, the AD is an epitope of a B-cell lymphoma-specific idiotype immunoglobulin. In some embodiments, the AD is an epitope of a B-cell differentiation antigen. In some embodiments, the AD is an epitope of a B-cell differentiation antigen selected from: CD19, CD20, and CD37. In some embodiments, the AD is an epitope of an antigen on myeloid cells. In some embodiments, the AD is an epitope of a myeloid cell antigen selected from: TSLPR and IL-7R. In some embodiments, the AD is an epitope of a cancer testis (CT) antigen. In some embodiments, the AD is an epitope of a cancer testis (CT) selected from: NY-ESO-1 and LAGE-1a. In some embodiments, the AD is an epitope of an antigen selected from: CS1, CD38, CD138, MUC1, HM1.24, CYP1B1, SP17, PRAME, Wilms' tumor 1 (WT1), and heat shock protein gp96 on multiple myeloma cells.

In some embodiments, the AD (e.g., in an Adapter and/or on a target cell) is an epitope of a TSA or TAA. In some embodiments, the AD is an epitope of a tumor differentiation antigen. In some embodiments, the AD is an epitope of a tumor differentiation antigen selected from: MART1/MelanA, gp100 (Pmel 17), tyrosinase, TRP1, and TRP2. In some embodiments, the AD is an epitope of a tumor-specific multilineage antigen. In some embodiments, the AD is an epitope of a tumor-specific multilineage antigen selected from: MAGE1, MAGE3, BAGE, GAGE1, GAGE2, and p15. In some embodiments, the AD is an epitope of an overexpressed embryonic antigen. In some embodiments, the AD is an epitope of CEA. In some embodiments, the AD is an epitope of an overexpressed oncogene or mutated tumor-suppressor gene product. In some embodiments, the AD is an epitope of an overexpressed oncogene or mutated tumor-suppressor gene product selected from: p53, Ras, and HER2/neu. In some embodiments, the AD is an epitope of a unique tumor antigen resulting from chromosomal translocations. In some embodiments, the AD is an epitope of a unique tumor antigen resulting from a chromosomal translocation selected from: BCR-ABL, E2A-PRL, H4-RET, IGH-IGK, and MYL-RAR. In some embodiments, the AD is an epitope of a viral antigen. In some embodiments, the AD is an epitope of the Epstein Barr virus antigen EBVA. In other embodiments, the AD is an epitope of the human papillomavirus (HPV) antigen E6 or E7. In some embodiments, the AD is an epitope of a large, protein-based antigen.

In some embodiments, the AD (e.g., in an Adapter and/or on a target cell) is an epitope of a hematological tumor antigen. In some embodiments, the AD is an epitope of an antigen selected from: BCMA, CD19, CD20, CD22, CD30, CD138, CD33, CD38, CD123, CS1, ROR1, Lewis$^{Y}$, Ig kappa light chain, TCR, BCMA, TACI, BAFFR (CD268), and a NKG2DL ligand.

In some embodiments, the AD (e.g., in an Adapter and/or on a target cell) is an epitope of a solid tumor antigen. In some embodiments, the AD is an epitope of an antigen selected from: disialoganglioside (GD2), o-acetyl GD2, EGFRvIII, HER2 (ErbB2), VEGFR2, FAP, mesothelin, IL13Ra2 (glioma), cMET, PSMA, folate receptor alpha, L1CAM, carcinoembryonic antigen (CEA), and EGFR.

In some embodiments, the AD (e.g., in an Adapter and/or on a target cell) is an epitope of an antigen selected from the group: CD137, PDL1, CTLA4, CD47, KIR, TNFRSF10B (DR5), TIM3, PD1, cMet, Glycolipid F77, EGFRVIII, HLAA2 (NY-ESO-1), LAG3, CD134 (OX40), HVEM, BTLA, TNFRSF25 (DR3), CD133, MAGE A3, PSCA, MUC1, CD44v6, CD44v6/7, CD44v7/8, IL11Ra, ephA2, CAIX, MNCAIX, CSPG4, MUC16, EPCAM (EGP2), TAG72, EGP40, ErbB receptor family, ErbB2 (HER2), ErbB3/4, RAGE1, GD3, FAR, Lewis$^{Y}$, NCAM, HLAA1/MAGE1, MAGEA1, MAGEA3, MAGE-A4, B7H3, WT1, MelanA (MART1), HPV E6, HPV E7, thyroglobulin, tyrosinase, PSA, CLL1GD3, Tn Ag, FLT3, KIT, PRSS21, CD24, PDGFR-beta, SSEA4, prostase, PAP, ELF2M, ephB2, IGF1, IGFII, IGFI receptor, LMP2, gp100, bcr-abl, Fucosyl GM1, sLe, GM3, TGS5, folate receptor beta, TEM1 (CD248), TEM7R, CLDN6, TSHR, GPRC5D, CXORF61, CD97, CD7a, HLE, CD179a, ALK, Plysialic acid, PLAC1, GloboH, NY-BR-1, UPK2, HAVCR, ADRB3, PANX3, GPR20, LY6K, OR51E2, TARP, LAGE1a, legumain, E7, ETV6-AML, sperm protein 17, XAGE1, Tie 2, MAD-CT1, MAD-CT2, Fos-related antigen 1, p53, p53 mutant, prostein, survivin, telomerase, PCTA1 (Galectin 8), Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP2, CYP1B1, BORIS, SART3, PAX5, OY-TESI, LCK, AKAP4, SSX2, reverse transcriptase, RU1, RU2, intestinal carboxyl esterase, neutrophil elastase, mut hsp70-2, CD79a, CD79b, CD72, LAIR1, FCAR, LILRA2, CD300LF, CLEC12A, BST2, EMR2, LY75, GPC3, FCRLS, IGLL1, TSP-180, MAGE4, MAGE5, MAGE6, VEGFR1, IGF1R, hepatocyte growth factor receptor, p185ErbB2, p180ErbB-3, nm-23H1, CA 19-9, CA 72-4, CAM 17.1, NuMa, K-ras, beta-Catenin, CDK4, Mum1, p15, p16, 43-9F, 5T4, 791Tgp72, β-human chorionic gonadotropin, BCA225, BTAA, CA125, CA15-3, CA 27.29 (BCAA), CA195, CA242, CA-50, CAM43, CD68, CO-029, FGF5, G250, HTgp-175, M344, MA50, MG7-Ag, MOV18, NB/70K, NY-CO1, RCAS1, SDCCAG16, M2BP, TAAL6, TLP, and TPS, glioma-associated antigen, alpha-fetoprotein (AFP), a p26 fragment of AFP, or variants thereof, lectin-reactive AFP, and TLR4.

In some embodiments, the AD (e.g., in an Adapter and/or on a target cell) is an epitope of a TSA or TAA. In some embodiments the AD is an epitope of an antigen selected from: PTGER4, ITGA4, CD37, CD52, CD62L (L-selectin), CXCR4, CD69, EVI2B (CD361), SLC39A8, MICB, LRRC70, CLELC2B, HMHA1, LST1, and CMTM6 (CK-LFSF6). In some embodiments the AD is an epitope of BCMA. In some embodiments the AD is an epitope of CS1.

In some embodiments, the AD (e.g., in an Adapter and/or on a target cell) is an epitope of an antigen selected from: PDGFRA, VEGFR1, VEGFR3, neuropilin 1 (NRP1), neuropilin 2 (NRP2), betacellulin, PLGF, RET (rearranged during transfection), TIE1, TIE2 (TEK), CA125, CD3, CD4, CD7, CD10, CD13, CD25 CD32, CD32b, CD44 (e.g., CD44v6), CD47, CD49e (integrin alpha 5), CD54 (ICAM), CD55, CD64, CD74, CD80, CD90, CD200, CD147, CD166, CD200, ESA, SHH, DHH, IHH, patched 1 (PTCH1), smoothened (SMO), WNT1, WNT2B, WNT3A, WNT4, WNT4A, WNT5A, WNT5B, WNT7B, WNT8A, WNT10A, WNT10B, WNT16B, LKP5, LRP5, LRP6, FZD1, FZD2, FZD4, FZD5, FZD6, FZD7, FZD8, Notch, Notch1, Notch3, Notch4, DLL4, Jagged, Jagged1, Jagged2, Jagged3, TNFRSF1A (TNFR1, p55, p60), TNFRSF1B (TNFR2), TNFRSF6 (Fas, CD95), TNFRSF6B (DcR3), TNFRSF7 (CD27), TNFSF9 (41BB Ligand), TNFRSF8 (CD30), TNFRSF10A (TRAILR1, DR4), TNFRSF11A (RANK), TNFRSF12 (TWEAKR), TNFRSF19L (KELT), TNFRSF19 (TROY), TNFRSF21 (DR6), ILIR1, ILIR2, IL2R, IL5R, IL6R, IL8R, IL10R, IL12R, IL13R, IL15R, IL18R, IL19R, IL21R, IL23R, XAG1, XAG3, REGIV, FGFR1, FGFR2, FGFR3, ALK, ALK1, ALK7, ALCAM, Axl, TGFb, TGFb2, TGFb3, TGFBR1, IGFIIR, BMPRI, N-cadherin, E-cadherin, VE-cadherin, ganglioside GM2, ganglioside GD3, PSGR, DCC, CDCP1, CXCR2, CXCR7, CCR3, CCR4, CCR5, CCR7, CCR10, Claudin1, Claudin2, Claudin3, Claudin4, TMEFF2, neuregulin, MCSF, CSF, CSFR (fms), GCSF, GCSFR, BCAM, BRCA1, BRCA2, HLA-DR, ABCC3, ABCB5, HM 1.24, LFA1, LYNX, S100A8, S100A9, SCF, Von Willebrand factor, Lewis Y6 receptor, CA G250 (CA9), CRYPTO, VLA5, HLADR, MUC18, mucin CanAg, EGFL7, integrin avb3, integrin α5β activin B1 alpha, leukotriene B4 receptor (LTB4R), neurotensin NT receptor (NTR), 5T4 oncofetal antigen, Tenascin C, MMP, MMP2, MMP7, MMP9, MMP12, MMP14, MMP26, cathepsin G, SULF1, SULF2, MET, CA9, TM4SF1, syndecan (SDCl), Ephrin B4, TEM1, TGFbeta 1, and TGFBRII.

In some embodiments, the AD (e.g., in an Adapter and/or on a target cell) is an epitope of an antigen associated with an autoimmune disorder, associated with an inflammatory or other disorder of the immune system, or is associated with regulating an immune response.

In some embodiments, the AD (e.g., in an Adapter and/or on a target cell) is an epitope of an immunoinhibitory target. In another embodiment, the AD is an epitope of an immunoinhibitory target selected from: IL1Ra, IL6R, CD26L, CD28, CD80, FcGamma RIIB. In another embodiment, the AD in the Adapter is an epitope of an immunostimulatory target selected from: CD25, CD28, CTLA4, PD1, B7H1 (PDL1), B7H4 TGFbeta, TNFRSF4 (OX40), TNFRSF5 (CD40), TNFRSF9 (41BB, CD137), TNFRSF14 (HVEM), TNFRSF25 (DR3), and TNFRSF18 (GITR).

In some embodiments, the AD (e.g., in an Adapter and/or on a target cell) is an epitope of a target selected from: IL1Rb, C3AR, C5AR, CXCR1, CXCR2, CCR1, CCR3, CCR7, CCR8, CCR9, CCR10, ChemR23, MPL, GP130, TLR2, TLR3, TLR4, TLR5, TLR7, TLR8, TLR9, TREM1, TREM2, CD49a (integrin alpha 1), integrin a5b3, alpha4 integrin subunit, A4B7 integrin, cathepsin G, TNFRSF3 (LTBR), TNFRSF6 (Fas, CD95), TNFRSF6B (DcR3), TNFRSF8 (CD30), TNFRSF11A (RANK), TNFRSF16 (NGFR), TNFRSF19L (RELT), TNFRSF19 (TROY), TNFRSF21 (DR6), CD14, CD23, CD36, CD36L, CD39, CD91, CD153, CD164, CD200, CD200R, B71 (CD80), B72 (CD86), B7h, B7DC (PDL2), ICOS, ICOSL, MHC, CD, B7H2, B7H3, B7x, SLAM, KIM1, SLAMF2, SLAMF3, SLAMF4, SLAMF5, SLAMF6, SLAMF7, TNFRSF1A (TNFR1, p55, p60), TNFRSF1B (TNFR2), TNFRSF7 (CD27), TNFRSF12 (TWEAKR), TNFRSF5 (CD40), IL1R, IL2R, IL4Ra, IL5R, IL6RIL15R, IL17R, IL17Rb, IL17RC, IL22RA, IL23R, TSLPR, B7RP1, cKit, GMCSF, GMCSFR, CD2, CD4, CD11a, CD18, CD30, CD40, CD86, CXCR3, CCR2, CCR4, CCR5, CCR8, RhD, IgE, and Rh.

In some embodiments, the AD (e.g., in an Adapter and/or on a target cell) is an epitope of an antigen associated with a neurological disorder.

In some embodiments, the AD (e.g., in an Adapter and/or on a target cell) is an epitope of a target selected from: amyloid beta (Abeta), beta amyloid, PLP, ROBO4, ROBO, LINGO, gpIIB, gpIIIa, integrin a2bB3, AOC3, TNFRSF19L (RELT), TNFRSF19 (TROY), and sclerostin.

The above targets and those otherwise described herein are intended to be illustrative and not limiting.

In some embodiments, the AD (e.g., in an Adapter and/or on a target cell) is bound by a chimeric antigen receptor (CAR). In some embodiments, the AD is bound by a cell expressing a chimeric antigen receptor. In some embodiments, the AD is bound by a scFv. In some embodiments, the AD is bound by an alternative scaffold binding domain (ASBD). In some embodiments, the AD is bound by a D domain. In some embodiments, the AD is bound by an antibody or an antigen-binding fragment thereof.

III. Antigenic Determinant Binding Domains (ADBDs)

A protein domain that binds to an antigenic determinant (AD) (e.g., as described in Section II and Section XI) is referred to herein as an "antigenic-determinant binding domain" or "ADBD." In some embodiments, the ADBD is sufficient to confer recognition and specific binding to a target of interest. The ADBD described herein can be present in an Adapter (e.g., as described in Section V and Section XI) and/or in a chimeric antigen receptor (CAR) (e.g., as described in Section VI and Section XI).

The target of interest specifically bound by the ADBD (e.g., of an Adapter and/or CAR) can be any molecule for which it is desirable for an Adapter and/or CAR to bind, e.g., any of the ADs described herein (e.g., as described in Section II and Section XI). In some embodiments, the target(s) specifically bound by the ADBD can be any target of purification, manufacturing, formulation, therapeutic, diagnostic, or prognostic relevance or value. In some embodiments, the target of the ADBD can be naturally occurring or synthetic. In some embodiments, the target of the ADBD can be an extracellular component, an intracellular component, a soluble factor (e.g., an enzyme, hormone, cytokine, growth factor, toxin, venom, pollutant, etc.), or a transmembrane protein (e.g., a cell surface receptor).

In some embodiment, the ADBD (e.g., of an Adapter and/or CAR) specifically binds a target of interest on the surface of a target cell. In some embodiments, the ADBD specifically binds a cell surface receptor. In some embodiments, the ADBD specifically binds a target of interest that is a member of a family selected from: a phosphatase receptor, growth factor receptor, a tyrosine kinase receptor, a TNF family receptor, a G-protein-coupled receptor, and a chemokine receptor. In some embodiments, the ADBD binds multiple members of the same family (e.g., the TNF receptors TRAILR1 and TRAILR2). In some embodiments, the ADBD binds members from different families. Thus, for example, in some embodiments, the ADBD can bind to a growth factor receptor and a TNF receptor or a G-protein-coupled receptor and a chemokine receptor.

In some embodiments, the ADBD (e.g., of an Adapter and/or CAR) binds to a tumor antigen. In some embodiments, the ADBD binds to a tumor-associated antigen. In some embodiments, the ADBD binds to a tumor-specific antigen.

In some embodiments, the ADBD (e.g., of an Adapter and/or CAR) binds a cancer antigen. In some embodiments, the ADBD binds to a cancer-associated antigen. In some embodiments, the ADBD binds to a cancer-specific antigen.

In some embodiments, the ADBD (e.g., of an Adapter and/or CAR) binds an antigen expressed on the surface of an immune effector cell.

In some embodiments, a target of interest bound by the ADBD (e.g., of an Adapter and/or CAR) is a human protein. In one embodiment, the ADBD binds a human protein target of interest and its monkey (e.g., cynomolgous monkey), mouse, rabbit, hamster and/or a rabbit ortholog.

In another embodiment, the ADBD (e.g., of an Adapter and/or CAR) binds a peptide tag present on a target of interest. Such peptide tags provide a useful means by which to detect, monitor, and/or attach one or more additional moieties to the Adapter. In one embodiment, the ADBD specifically binds a peptide tag selected from: a hexahistidyl (His6) tag, a myc tag, and a FLAG tag. Other peptide tags are described herein or otherwise known in the art.

Affinity requirements for a given ADBD binding event are contingent on a variety of factors including, but not limited to: the composition and complexity of the binding matrix, the valency and density of both the ADBD and target molecules, and the functional application of the ADBD. In one embodiment, the ADBD binds a target of interest with a dissociation constant (KD) of less than or equal to $5\times10^{-3}$ M, $10^{-3}$ M, $5\times10^{-4}$ M, $10^{-4}$ M, $5\times10^{-5}$ M, or $10^{-5}$ M. In an additional embodiment, the ADBD binds a target of interest with a KD of less than or equal to $5\times10^{-6}$ M, $10^{-6}$ M, $5\times10^{-7}$ M, $10^{-7}$M, $5\times10^{-8}$ M, or $10^{-8}$ M. In additional embodiments, a the ADBD binds a target of interest with a KD less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In several embodiments, the ADBD generated by the methods disclosed herein have a dissociation constant selected from the group: between $10^{-4}$ M and $10^{-5}$ M, between $10^{-5}$ M and $10^{-6}$ M, between $10^{-6}$ M and $10^{-7}$ M, between $10^{-7}$ M and $10^{-8}$ M, between $10^{-8}$ M and $10^{-9}$ M, between $10^{-9}$ M and $10^{-10}$ M, between $10^{-10}$ M and $10^{-11}$ M and between $10^{-11}$ M and $10^{-12}$ M.

In one embodiment the ADBD binds a target of interest in active form. In one embodiment the ADBD reversibly binds a target of interest in active form and also releases the bound target in active form. In one embodiment the ADBD binds a target of interest in the native form. In specific embodiments, the ADBD bind targets of interest with off-rates or Koff of greater than or equal to $10^{-10}$ $sec^{-1}$, $5\times10^{-9}$ $sec^{-1}$, $10^{-9}$ $sec^{-1}$, $5\times10^{-8}$ $sec^{-1}$, $10^{-8}$ $sec^{-1}$, $5\times10^{-7}$ $sec^{-1}$, $10^{-7}$ $sec^{-1}$, $5\times10^{-6}$ $sec^{-1}$, $10^{-6}$ $sec^{-1}$, $5\times10^{-5}$ $sec^{-1}$, $10^{-5}$ $sec^{-1}$, $5\times10^{-4}$ $sec^{-1}$, $10^{-4}$ $sec^{-1}$, $5\times10^{-3}$ $sec^{-1}$, $10^{-3}$ $sec^{-1}$, $5\times10^{-2}$ $sec^{-1}$, $10^{-2}$ $sec^{-1}$, $5\times10^{-1}$ $sec^{-1}$, or $10^{-1}$ $sec^{-1}$.

Binding experiments to determine KD and off-rates can be performed in a number of conditions including, but not limited to, [pH 6.0, 0.01% Tween 20], [pH 6.0, 0.1% gelatin], [pH5.0, 0.01% Tween 20], [pH9.0, 0.1% Tween 20], [pH6.0, 15% ethylene glycol, 0.01% Tween 20], [pH5.0, 15% ethylene glycol, 0.01% Tween 20], and [pH9.0, 15% ethylene glycol, 0.01% Tween 20]. The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine KD and off-rates for the purpose of determining, for example, optimal pH and/or salt concentrations.

In one embodiment, the ADBD specifically binds a target of interest with a KOff ranging from 0.1 to $10^{-7}$ $sec^{-1}$, $10^{-2}$ to $10^{-7}$ $sec^{-1}$, or $0.5\times10^{-2}$ to $10^{-7}$ $sec^{-1}$. In a specific embodiment, the ADBD binds a target of interest with an off rate (KOff) of less than $5\times10^{-2}$ $sec^{-1}$, $10^{-2}$ $sec^{-1}$, $5\times10^{-3}$ $sec^{-1}$, or $10^{-3}$ $sec^{-1}$. In an additional embodiment, the ADBD binds a target of interest with an off rate (Koff) of less than $5\times10^{-4}$ $sec^{-1}$, $10^{-4}$ $sec^{-1}$, $5\times10^{5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$, or $10^{-7}$ $sec^{-1}$.

In one embodiment, the ADBD specifically binds a target of interest with a KOn ranging from $10^{3}$ to $10^{7}$ $M^{-1}$ $sec^{-1}$, $10^{3}$ to $10^{6}$ $M^{-1}$ $sec^{-1}$, or $10^{3}$ to $10^{5}$ $M^{-1}$ $sec^{-1}$. In other specific embodiments, the ADBD binds the target of interest its target of interest with an on rate (KOn) of greater than $10^{3}$ $M^{-1}$ $sec^{-1}$, $5\times10^{3}$ $M^{-1}$ $sec^{-1}$, $10^{4}$ $M^{-1}$ $sec^{-1}$, or $5\times10^{4}$ $M^{-1}$ $sec^{-1}$. In an additional embodiment, the ADBD binds a target of interest with a KOn of greater than $10^{5}$ $M^{-1}$ $sec^{-1}$, $5\times10^{5}$ $M^{-1}$ $sec^{-1}$, $10^{6}$ $M^{-1}$ $sec^{-1}$, or $5\times10^{6}$ $M^{-1}$ $sec^{-1}$, or $10^{7}$ $M^{-1}$ $sec^{-1}$.

In some embodiments, the ADBD (e.g., of an Adapter and/or CAR) is an antibody or an antigen-binding fragment thereof. In some embodiments, the ADBD is a scFv. In some embodiments, the ADBD is an alternative scaffold binding domain. In some embodiments, the ADBD is a D domain.

IIIa. Antibody-Derived Antigenic Determinant Binding Domains (ADBD)

In some embodiments, one or more ADBDs (e.g., of an Adapter and/or CAR) can be derived from an antibody molecule, e.g., one or more of monoclonal antibodies, polyclonal antibodies, recombinant antibodies, human antibodies, humanized antibodies, single-domain antibodies e.g., a heavy chain variable domain (VH), a light chain variable domain (VL) and a variable domain (VHH) from, e.g., human or camelid origin. In some embodiments, the ADBD is derived from the same species in which the Adapter or CAR will ultimately be used, e.g., for use in humans. It may be beneficial for Adapter and/or CAR to comprise a human or a humanized ADBD. Compositions and techniques for routinely generating such ADBDs are known in the art.

In some embodiments, the ADBD (e.g., of an Adapter and/or CAR) comprises a fragment of an antibody that is sufficient to confer recognition and specific binding to the target antigen. Examples of an antibody fragment include, but are not limited to, an Fab, Fab', $F(ab')_2$, or Fv fragment, an scFv antibody fragment, a linear antibody, single domain antibody such as an sdAb (either VL or VH), a camelid VHH domain, and multi-specific antibodies formed from antibody fragments.

In some embodiments, the ADBD (e.g., of an Adapter and/or CAR) is a "scFv," which can comprise a fusion protein comprising a VL chain and a VH chain of an antibody, wherein the VH and VL are, e.g., linked via a short flexible polypeptide linker, e.g., a linker described herein. scFvs can routinely be prepared according to methods known in the art (see, e.g., Bird et al., Science 242:423-426 (1988) and Huston et al., Proc. Natl. Acad. Sci. USA 85:5879-5883 (1988)).

In some embodiments, the ADBD (e.g., of an Adapter and/or CAR) is a single domain antigen binding (SDAB) molecule. A SDAB molecule includes molecules containing complementary determining regions that are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules can be derived from any species including, but not limited to mouse, human, camel, llama, fish, shark, goat, rabbit, and bovine. This term also includes naturally occurring single domain antibody molecules from species other than Camelidae and sharks.

In some embodiments, the ADBD (e.g., of an Adapter and/or CAR) comprises a human antibody or a fragment thereof. In some embodiments, the ADBD (e.g., of an Adapter and/or CAR) comprises a humanized antibody or a fragment thereof.

Humanization of antibodies is well-known in the art and can essentially be performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody, i.e., CDR-grafting (EP 239,400; Intl. Appl. Publ. No. WO 91/09967; and U.S. Pat. Nos. 4,816,567; 6,331,415; 5,225,539; 5,530,101; 5,585,089; and 6,548,640; the contents of which are incorporated herein by reference herein in their entirety). Humanization of antibodies can also be achieved by veneering or resurfacing (EP 592,106; EP 519,596; Padlan, 1991, Molecular Immunology, 28 (4/5): 489-498; Studnicka et al., Protein Engineering 7 (6): 805-814 (1994); and Roguska et al., PNAS 91:969-973 (1994)) or chain shuffling (U.S. Pat. No. 5,565,332), the contents of which are incorporated herein by reference herein in their entirety.

IIIb. Alternative Scaffold Binding Domains

In some embodiments, the ADBD(s) (e.g., of an Adapter and/or CAR) is an alternative scaffold binding domain (ASBD). An "alternative scaffold binding domain" or "ASBD" as used herein, is an antigen determinant binding domain that is derived from, or corresponds to, a non-antibody-based binding scaffold.

In some embodiments, the disclosure provides a CAR comprising an ADBD that is an ASBD. In some embodiments, the disclosure provides a cell comprising a CAR that comprises an ADBD that is an ASBD. In further embodiments, an immune effector cell that comprises a CAR comprising and ASBD is provided. In some embodiments, the disclosure provides an Adapter comprising an ADBD that is an ASBD.

In further embodiments, the disclosure provides a composition comprising an Adapter and a CAR that each comprise an ASBD.

In some embodiments, the binding of the ASBD (e.g., of an Adapter and/or CAR) to the target AD is mediated by secondary structures of the binding scaffold, such as alpha helices or beta sheets. In some embodiments, the ASBD is a three-helix bundle-based binding domain. In some embodiments, the ASBD is a D domain-based binding domain. In other embodiments, the ASBD is a Z-domain (Affibody)-based binding domain.

In some embodiments, the ASBD (e.g., of an Adapter and/or CAR) is a D domain (de novo binding domain)-based AD binding domain. The D domain scaffold-based binding domain generally consists of 70-75 amino acid residues in which substitutions of up to 20 positions corresponding to structurally constrained surface-exposed residues in a non-naturally occurring antiparallel three helical bundle reference scaffold (SEQ ID NO: 1) confer target recognition and binding specificity for the target (AD) of interest. D domain scaffold-based binding domains are further disclosed in Intl. Appl. Publ. No. WO2016164308, the contents of which are herein incorporated by reference in their entirety. In one embodiment, the D domain comprises an amino acid sequence that differs (e.g., due to amino acid modifications) from that of a reference scaffold having the sequence of SEQ ID NO: 1 by up to 20 substitutions. In some embodiments, the D domain comprises a sequence selected from the group: SEQ ID NO: 17, 18, and 19. In some embodiments, the D domain comprises a sequence selected from the group: SEQ ID NO: 20-26, and 27. In further embodiments, the D domain comprises a sequence selected from the group: SEQ ID NO: 44-1078 and 1079.

In some embodiments the ASBD (e.g., of an Adapter and/or CAR) is a Z-domain scaffold (Affibody)-based AD binding domain. Z-domain scaffold-based binding domains generally consist of 58 amino acid residues in which substitutions of up to 13 positions located in the first and second of three alpha helices, confer binding confer target (AD) recognition and binding specificity for the target (AD) of interest. In further embodiments, the Z-domain ASBD comprises a sequence selected from SEQ ID NO: 28 and 29. Z-domain (Affibody) scaffold-based binding domains are further described in U.S. Pat. No. 5,831,012, the entire contents of which are herein incorporated by reference in their entirety.

Additional examples of ASBDs that display secondary structure-mediated target binding include DARPins, affilins, and armadillo repeat-based binding scaffolds.

In some embodiments, the ASBD (e.g., of an Adapter and/or CAR) is a DARPin-based AD binding domain. DARPin-based binding domains generally contain 2-3 repeats of the sequence of SEQ ID NO: 30 positioned between N- and C-terminal capping repeats (e.g., the sequence MRGSHHHHHHGSDLGKKLLEAARAGQDDEVRILMANGA DVNAX$_{33}$ (SEQ ID NO: 31) and the sequence QDKFGKTAFDISIDNGNEDLAEILQ (SEQ ID NO: 32), respectively, wherein the first Gln corresponds to consensus repeat position X$_{33}$ of the preceding repeat). Each internal repeat consists of 27 framework residues and up to 6 substituted non-framework residues that that form a β-turn followed by two antiparallel helices and a loop that connects to the β-turn of the next repeat. The collective substitutions and structure of the DARPin confers target (AD) recognition and binding specificity.

TABLE 1

| Exemplary secondary structure-based ASBD Sequences | |
|---|---|
| ADBD | Sequence |
| D-domain | MGSWX$_5$X$_6$FKX$_9$X$_{10}$LAX$_{13}$IKX$_{16}$X$_{17}$LEALGGSEAELAX$_{30}$FE |
| F1 | X$_{33}$X$_{34}$IAX$_{37}$FEX$_{40}$X$_{41}$LQX$_{44}$YKGKGNPEVEALRKEAAAI-RD ELQAYRHN (SEQ ID NO: 17) |

TABLE 1-continued

Exemplary secondary structure-based ASBD Sequences

| ADBD | Sequence |
|---|---|
| D-domain F2 | MGSWAEFKQRLAAIKTRLEALGGSEAELAAF$X_{32}X_{33}$EI$X_{36}$AF$X_{39}X_{40}$EL$X_{43}$AYKGKGNPEVEAL$X_{57}X_{58}$EA$X_{61}$AI$X_{64}X_{65}$EL$X_{68}$AYRHN (SEQ ID NO: 18) |
| D-domain F3 | MGSW$X_5$EF$X_8X_9$RL$X_{12}$AI$X_{15}X_{16}$RL$X_{19}$ALGGSEAELAAFEKEIAAFESELQAYKGKGNPEVE$X_{55}$LR$X_{58}X_{59}$AA$X_{62}$IR$X_{65}X_{66}$LQAYRHN (SEQ ID NO: 19) |
| D-domain C1 | MGSW$X_5X_6$FK$X_9X_{10}$LA$X_{13}$IK$X_{16}X_{17}$LEALGGSEAELAAF$X_{32}X_{33}$EI$X_{36}$AF$X_{39}X_{40}$EL$X_{43}$AYKGKGNPEVE$X_{55}$LR$X_{58}X_{59}$AA$X_{62}$IR$X_{65}X_{66}$LQAYRHN (SEQ ID NO: 20) |
| D-domain C2 | MGSW$X_5$EF$X_8X_9$RL$X_{12}$AI$X_{15}X_{16}$RL$X_{19}$ALGGSEAELA$X_{30}$FE$X_{33}X_{34}$IA$X_{37}$FE$X_{40}X_{41}$LQ$X_{44}$YKGKGNPEVEAL$X_{57}X_{58}$EA$X_{61}$AI$X_{64}X_{65}$EL$X_{68}$AYRHN (SEQ ID NO: 21) |
| D-domain F1Lp$_x$ | MGSW$X_5X_6$FK$X_9X_{10}$LA$X_{13}$IK$X_{16}X_{17}$LEAL$Z_1$EAELA$X_{28}$FE$X_{31}X_{32}$IA$X_{35}$PE$X_{38}X_{39}$LQ$X_{42}$Y$Z_2$NPEVEALRKEAAAIRDELQAYRHN (SEQ ID NO: 22) |
| D-domain F2Lp$_x$ | MGSWAEFKQRLAAIKTRLEAL$Z_1$EAELAAF$X_{30}X_{31}$EI$X_{34}$AF$X_{37}X_{38}$EL$X_{41}$AY$Z_2$NPEVEAL$X_{52}X_{53}$EA$X_{56}$AI$X_{59}X_{60}$EL$X_{63}$AYRHN (SEQ ID NO: 23) |
| D-domain F3Lp$_x$ | MGSW$X_5$EF$X_8X_9$RL$X_{12}$AI$X_{15}X_{16}$RL$X_{19}$AL$Z_1$EAELAAFEKEIAAFESELQAY$Z_2$NPEVE$X_{50}$LR$X_{53}X_{54}$AA$X_{57}$IR$X_{60}X_{61}$LQAYRHN (SEQ ID NO: 24) |
| D-domain C1Lp$_x$ | MGSW$X_5X_6$FK$X_9X_{10}$LA$X_{13}$IK$X_{16}X_{17}$LEAL$Z_1$EAELAAF$X_{30}X_{31}$EI$X_{34}$AF$X_{37}X_{38}$EL$X_{41}$AY$Z_2$NPEVE$X_{50}$LR$X_{53}X_{54}$AA$X_{57}$IR$X_{60}X_{61}$LQAYRHN (SEQ ID NO: 25) |
| D-domain C2Lp$_x$ | MGSW$X_5$EF$X_8X_9$RL$X_{12}$AI$X_{15}X_{16}$RL$X_{19}$AL$Z_1$EAELA$X_{28}$FE$X_{31}X_{32}$IA$X_{35}$PE$X_{38}X_{39}$LQ$X_{42}$Y$Z_2$NPEVEAL$X_{52}X_{53}$EA$X_{56}$AI$X_{59}X_{60}$EL$X_{63}$AYRHN (SEQ ID NO: 26) |
| D-domain DD-WTF | MGSW$X_5$EF$X_8X_9$RL$X_{12}X_{13}$I$X_{15}X_{16}$RL$X_{19}$ALGGSEAELAAFEKEI$X_{36}$AF$X_{39}X_{40}$EL$X_{43}$AYKGKGNPEVEALR$X_{58}$EA$X_{61}X_{62}$IR$X_{65}$EL$X_{68}X_{69}$YR$X_{72}X_{73}$ (SEQ ID NO: 27) |
| Z-Domain AFFa | VDNKFNKE$X_9X_{10}X_{11}$A$X_{13}X_{14}$EI$X_{17}X_{18}$LPNLN$X_{24}X_{25}$Q$X_{27}X_{28}$AFI$X_{32}$SL$X_{35}$DDPSQSANLLAEAKKLNDAQAPK (SEQ ID NO: 28) |
| Z-Domain AFFb | NKE$X_4X_5X_6$A$X_8X_9$EI$X_{12}X_{13}$LPNLN$X_{19}X_{20}$Q$X_{22}X_{23}$AFI$X_{27}$SL$X_{30}$DDP (SEQ ID NO: 29) |
| DARPin | D$X_2X_3$G$X_5$TPLHLAA$X_{13}X_{14}$GHLEIVEVLLK$Z_{26}$GADVNA$X_{33}$ (SEQ ID NO: 30) wherein X is any amino acid but C, R or P and Z is H, N, or Y. |

X = all amino acid residues, including natural and non-natural amino acids

Z = amino acid sequence corresponding to loop1 ($Z_1$) or loop2 ($Z_2$) as described herein, comprising between about 2 to about 30 natural or non-natural amino acids In some embodiments, the binding specificity of the ASBD (e.g., of an Adapter and/or CAR) to the target AD is mediated by amino acids in exposed loops on the ASBD.

Examples of scaffolds having these binding properties include, adnectins, lipocalins, avimers, knottins, fynomers, atrimers, kunitz domain-based binders, and CTLA4-based binding scaffolds.

In some embodiments, the ASBD is an adnectin-based AD binding domain. The adnectin-based binding domain is derived from the tenth domain of fibronectin type III (10Fn3). This ADBD is generally a 94 amino acid binding domain that adopts a beta sandwich fold containing seven strands that are connected by six loops. Substitutions in three surface-exposed loops on one side of the adnectin domain generate target (AD) specific binding moieties.

In some embodiments, the ASBD (e.g., of an Adapter and/or CAR) is a lipocalin-, affilin-, or anticalin-based AD-binding domain. The anticalin scaffold displays a conserved β-barrel structure made up of eight anti-parallel β-strands and generally consists of 160-180 amino acids. The ligand binding pocket of the anticallin-based binding scaffold is composed of four loops, each containing up to 24 substitutions, that collectively confer target (AD) recognition and binding specificity.

In some embodiments, the ASBD (e.g., of an Adapter and/or CAR) is an Avimer scaffold-based AD-binding domain. Avimer scaffold-based binding domains are derived from the A-domain of cell surface receptors and are generally 35 amino acids in length. The structure of the Avimer-based binding domain is maintained by 12 conserved amino acids. Substitutions of up to all of the remaining 23 residues of the binding domain confer target (AD) recognition and binding specificity. In some embodiments, the Avimer scaffold-based binding domain comprises the sequence EF$X_3$C$X_5$NG$X_8$CIP$X_{12}X_{13}$W$X_{15}$CDG$X_{19}$DDCGD$X_{25}$SDE, wherein X is any amino acid (SEQ ID NO: 33). Avimer scaffold-based binding domains are further described in U.S. Appl. Publ. Nos. 20040175756, 20050053973, 20050048512, and 20060008844, the entire contents of each of which are herein incorporated by reference in their entireties.

In some embodiments, the ASBD (e.g., of an Adapter and/or CAR) is a fynomer scaffold-based AD binding domain. The fynomer binding domain is generally 60-75 amino acids in length and is composed of a pair of anti-parallel beta sheets joined by two flexible loops. Substitutions/insertions in the loops confer AD target recognition and binding specificity. In some embodiments, the fynomer-based AD binding domain comprises the sequence GVTLFVALYDY$X_{12}X_{13}X_{14}X_{15}X_{16}X_{17}X_{18}X_{19}$ $X_{20}X_{21}$ $X_{22}$LSFHKGEKFQILSTHEYE$X_{41}X_{42}X_{43}X_{44}X_{45}$ $X_{46}X_{47}X_{48}$WEARSLTTGETG$X_{61}$IPSNYVAPVDSIQ, wherein X is any amino acid residue and $X_{13}$-$X_{21}$ and $X_{42}$-$X_{46}$, are optionally absent (SEQ ID NO: 34). In some embodiments, the fynomer-based AD binding domain comprises the sequence GVTLFVALYDY$X_{12}X_{13}X_{14}X_{15}X_{16}X_{17}X_{18}X_{19}$ $X_{20}X_{21}X_{22}$ LSFHKGEKFQILSTHEYEDWWEARSLTTGETGYIPSNYVAPVDSIQ, wherein X is any amino acid residue and $X_{16}$-$X_{21}$ and are optionally absent (SEQ ID NO: 35).

In some embodiments the ASBD (e.g., of an Adapter and/or CAR) is a knottin scaffold-based AD binding domain. Knottin scaffold-based binding domains correspond to a 30-amino-acid protein fold composed of three anti-parallel β-strands connected by loops of variable length and multiple disulfide bonds.

In some embodiments the ASBD (e.g., of an Adapter and/or CAR) is a Kunitz domain-based AD binding domain. Kunitz domain-based binding domains are derived from the active motif of Kunitz-type protease inhibitors and are generally about 60 amino acids in length. The hydrophobic core of this ADBD is composed of a twisted two-stranded antiparallel β-sheet and two α-helices stabilized by three pairs of disulfide bonds. Substitutions and insertions in the three loops confer AD target recognition and binding specificity. In some embodiments, the Kunitz domain-based AD binding domain comprises the sequence MHSFCA FKADX$_{11}$GX$_{13}$C X$_{15}$ X$_{16}$X$_{17}$X$_{18}$X$_{19}$RFFFNIFTRQC-EEFX$_{34}$ YGGCX$_{39}$X$_{40}$NQNRFESLEECKKMCTRDGA (SEQ ID NO: 36) sequence that is at least 85% identical to at positions other than X; X$_{11}$ is one of: A, D, E, F, G, H, I, K, L, M, N, P, Q, R, S, T, V, W, Y; X$_{13}$ is one of: A, D, E, F, G, H, I, K, L, M, N, P, Q, R, S, T, V, W, Y; X$_{15}$ is one of: A, D, E, F, G, H, I, K, L, M, N, Q, R, S, T, V, W, Y; X$_{16}$ is one of: A, G, E, D, H, T; X$_{17}$ is one of: A, D, E, F, G, H, I, K, L, M, N, Q, R, S, T, V, W, Y; X$_{18}$ is one of: A, D, E, F, G, H, I, K, L, M, N, Q, R, S, T, V, W, Y; X$_{19}$ is one of: A, D, E, F, G, H, I, K, L, M, N, P, Q, R, S, T, V, W, Y; X$_{34}$ is one of: A, C, D, E, F, G, H, I, K, L, M, N, P, Q, R, S, T, V, W, Y; X$_{39}$ is one of: A, C, D, E, F, G, H, I, K, L, M, N, P, Q, R, S, T, V, W, Y; and X$_{40}$ is one of: G, and A. Kunitz scaffold-based binding domains are further described in Intl. Appl. Publ. No. WO 2004063337, the entire contents of which are herein incorporated by reference in their entirety.

In some embodiments the ASBD (e.g., of an Adapter and/or CAR) is a WW domain-based AD-binding domain. WW domain-based binding scaffolds are generally 30-35 amino acids in length. In some embodiments, the WW domain-based AD binding scaffold comprises the sequence KLPPGWX$_7$KX$_9$WSX$_{12}$X$_{13}$X$_{14}$GRVX$_{18}$YX$_{20}$NX$_{22}$ITX$_{25}$ AX$_{27}$QWERP (SEQ ID NO: 37), wherein X$_7$, X$_9$, X$_{12}$, X$_{13}$, X$_{14}$, X$_{18}$, X$_{20}$, X$_{22}$, X$_{25}$, and X$_{27}$ represent any amino acid, and X$_{14}$ is optionally absent.

In some embodiments, the WW domain-based AD binding scaffold comprises the sequence KLPPGWX$_7$KX$_9$ WSX$_{12}$X$_{13}$GRVX$_{17}$YX$_{19}$NX$_{21}$ITX$_{24}$AX$_{26}$QWERP (SEQ ID NO: 38), wherein X$_7$, X$_9$, X$_{12}$, X$_{13}$, X$_{17}$, X$_{19}$, X$_{21}$, X$_{24}$, and X$_{26}$ represent any amino acid, and X$_{14}$ is optionally absent.

TABLE 2

Exemplary loop-based ASBDs

| ASBD | Sequence |
|---|---|
| Avimer1 | EFX$_3$CX$_5$NGX$_8$CIPX$_{12}$X$_{13}$WX$_{15}$C DGX$_{19}$DDCGDX$_{25}$SDE (SEQ ID NO: 33) |
| Fynomer1 | GVTLFVALYDYX$_{12}$X$_{13}$X$_{14}$X$_{15}$X$_{16}$X$_{17}$X$_{18}$X$_{19}$X$_{20}$X$_{21}$X$_{22}$LSFH KGEK FQILSTHEYEX$_{41}$X$_{42}$X$_{43}$X$_{44}$X$_{45}$X$_{46}$X$_{47}$X$_{48}$WEARSLTT GETGX$_{61}$IPSNY VAPVDSIQ<br>wherein X = any amino acid residue and X$_{13}$-X$_{21}$ and X$_{42}$-X$_{46}$, are optionally absent<br>(SEQ ID NO: 34) |
| Fynomer2 | GVTLFVALYDYX$_{12}$X$_{13}$X$_{14}$X$_{15}$X$_{16}$X$_{17}$X$_{18}$X$_{19}$X$_{20}$X$_{21}$X$_{22}$LSFH KGEKFQILSTHEYEDWWEARSLTTGETGYIPSNYVAPVDS IQ<br>wherein X$_{16}$-X$_{21}$ are optionally absent<br>(SEQ ID NO: 35) |
| Kunitz1 | MHSFCAFKADX$_{11}$GX$_{13}$CX$_{15}$X$_{16}$X$_{17}$X$_{18}$X$_{19}$RFFFNIFTRQCE EFX$_{34}$ YGGCX$_{39}$X$_{40}$NQNRFESLEEC KKMCTRDGA<br>(SEQ ID NO: 36) |
| WW1 | KLPPGWX$_7$KX$_9$WSX$_{12}$X$_{13}$X$_{14}$GRVX$_{18}$ YX$_{20}$NX$_{22}$ITX$_{25}$AX$_{27}$QW ERP<br>(SEQ ID NO: 37) |
| WW2 | KLPPGWX$_7$KX$_9$WSX$_{12}$X$_{13}$GRVX$_{17}$ YX$_{19}$NX$_{21}$ITX$_{24}$AX$_{26}$QWERP<br>(SEQ ID NO: 38) |

X = all amino acid residues

IV. Linkers

Linkers are peptide or other chemical linkages located between two or more otherwise independent functional domains of the Adapter or CAR.

Suitable linkers for operably linking two or more functional domains of the Adapter in a single-chain amino acid sequence include but are not limited to, polypeptide linkers such as glycine linkers, serine linkers, mixed glycine/serine linkers, glycine- and serine-rich linkers or linkers composed of largely polar polypeptide fragments.

In one embodiment, the linker is made up of a majority of amino acids selected from glycine, alanine, proline, asparagine, glutamine, and lysine. In one embodiment, one or more linkers in the Adapter or CAR is made up of a majority of amino acids selected from glycine, alanine, proline, asparagine, aspartic acid, threonine, glutamine, and lysine. In one embodiment, one or more linkers in the Adapter or CAR is made up of one or more amino acids selected from glycine, alanine, proline, asparagine, aspartic acid, threonine, glutamine, and lysine. In another embodiment, one or more linkers in the Adapter or CAR is made up of a majority of amino acids that are sterically unhindered. In another embodiment, a linker in which the majority of amino acids are glycine, serine, and/or alanine. In some embodiments, one or more linkers in an Adapter or CAR linker comprises polyglycines (such as (Gly)$_5$ (SEQ ID NO: 1099), and (Gly)$_8$ (SEQ ID NO:1100), poly(Gly-Ala), and polyalanines. In some embodiments, the peptide linker contains the sequence of Gly-Gly-Gly-Gly-Thr-Gly-Gly-Gly-Gly-Ser (SEQ ID NO: 39). In some embodiments, one or more linkers in the Adapter or CAR comprises the sequence of Gly-Gly-Gly-Gly-Asp-Gly-Gly-Gly-Gly-Ser (SEQ ID NO: 40).

In one embodiment, the Adapter or CAR comprises an ADBD directly attached (i.e., without a linker) to another component of the Adapter or CAR, respectively. In one embodiment, the Adapter or CAR contains at least 2, at least 3, at least 4, or at least 5 ADBDs directly attached to another domain of the Adapter or CAR, respectively.

In another embodiment, an ADBD can be operably linked to another component of the Adapter or CAR through a linker. Adapters or CARs can contain a single linker, multiple linkers, or no linkers. In one embodiment, the Adapter or CAR comprises an ADBD operably linked to another component of the Adapter or CAR, respectively, through a linker peptide. In one embodiment, the Adapter or CAR contains at least 2, at least 3, at least 4, or at least 5 ADBDs operably linked to another domain of the Adapter or CAR, respectively, through the same or different linkers.

Linkers can be of any size or composition so long as they are able to operably link a functional domain of the Adapter or CAR in a manner that enables the functional domain to function (e.g., the ability of an antigenic determinant binding domain to bind a target of interest). In some embodiments, linker(s) are about 1 to about 100 amino acids, about 1 to 50 amino acids, about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. It should be clear that the length, the degree of flexibility and/or other properties of the linker(s) may have some influence on the properties of the final polypeptide of the invention, including but not limited to the affinity, specificity or avidity for a target of interest, or for one or more other target proteins of interest. When two or more linkers are used in the Adapter or CAR, these linkers may be the same or different. In the context and disclosure provided herein, a person skilled in the art will be able to routinely determine the optimal linker composition and length for the purpose of operably linking the functional domains of an Adapter or CAR.

The linker can also be a non-peptide linker such as an alkyl linker, or a PEG linker. For example, alkyl linkers such as —NH—(CH2)s-C(O)—, wherein s=2-20 can be used. These alkyl linkers may further be substituted by any non-sterically hindering group such as lower alkyl e.g., C1-C6) lower acyl, halogen (e.g., CI, Br), CN, NH2, phenyl, etc. An exemplary non-peptide linker is a PEG linker. In certain embodiments, the PEG linker has a molecular weight of about 100 to 5000 kDa, or about 100 to 500 kDa.

Suitable linkers for coupling Adapter or CAR functional domains by chemical cross-linking include, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidylpropionate) (DSP) and dithiobis (sulfosuccini-midylpropionate) (DTSSP). Examples of suitable linkers for coupling Adapter or CAR functional domains include but are not limited to cross-linkers with one amine-reactive end and a sulfhydryl-reactive moiety at the other end, or with a NHS ester at one end and an SH-reactive group (e.g., a maleimide or pyridyl).

In additional embodiments, one or more of the linkers in the Adapter or CAR is cleavable. Examples of cleavable linkers include, include but are not limited to a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments.

In some embodiments, the linker is a "cleavable linker" that facilitates the release of an Adapter functional domain or cytotoxic agent in a cell or at the cell surface. For example, an acid-labile linker (e.g., hydrazone), protease-sensitive (e.g., peptidase-sensitive) linker, photolabile linker, dimethyl linker or disulfide-containing linker (see, e.g., Chari, Can. Res. 52:127-131 (1992); U.S. Pat. No. 5,208,020; and U.S. Appl. Pub. No. 20090110753; the contents of each of which is herein incorporated by reference in its entirety) can be used wherein it is desirable that the covalent attachment between an Adapter or a cytotoxic agent is intracellularly cleaved when the composition is internalized into the cell. The terms "intracellularly cleaved" and "intracellular cleavage" refer to a metabolic process or reaction inside a cell on an Adapter drug conjugate whereby the covalent attachment, i.e., linked via a linker between the Adapter and cytotoxic agent is broken, resulting in the free Adapter and/or cytotoxic agent dissociated inside the cell.

In additional embodiments, one or more of the linkers in the CAR is cleavable. Examples of cleavable linkers include, include but are not limited to a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments.

In some embodiments, a short oligo- or polypeptide linker, from about 1 to 100 amino acids in length, is used to link together any of the domains of a CAR. Linkers can be composed of flexible residues like glycine and serine (or any other amino acid) so that the adjacent protein domains are free to move relative to one another. The amino acids sequence composition of the linker may be selected to minimize potential immunogenicity of the CAR. Longer linkers can be used when it is desirable to ensure that two adjacent domains do not sterically interfere with one another.

In some embodiments, preferably between 2 and 10 amino acids in length forms the linkage between the transmembrane domain and the cytoplasmic signaling domain of the CAR. In further embodiments, the linker is between 10 and 15 amino acids in length, or between 15 and 20, or between 20 and 30, or between 30 and 60, or between 60 and 100 amino acids in length (or any range in between those listed). In further embodiments, the linker is a glycine-serine doublet sequence. In some embodiments, the ESD corresponds to the human T cell surface glycoprotein CD8 alpha-chain ESD region (e.g., amino acid residues 138 to 182 CD8 alpha chain; Swiss-Prot Acc. No. P01732). In some embodiments, the ESD corresponds to the CD8 ESD region that has been further modified, through amino acid substitution, to improve expression function or immunogenicity. In further embodiments, the ESD corresponds to the CD28 ESD or sequences containing modifications of the CD28 ESD that confer improved expression function or immunogenicity.

Linker optimization can be evaluated using techniques described herein and/or otherwise known in the art. In some embodiments, linkers do not disrupt the ability of an Adapter or CAR to bind a target antigenic determinant and/or another Adapter or CAR functional domain to function appropriately (e.g., the ability of an effector functional domain in the Adapter to elicit an effector function or the ability of an FcRn binding domain in the Adapter to bind FcRn).

V. Adapters-Soluble Proteins

Provided herein are multi-domain soluble Adapter proteins. The Adapter comprises an antigenic determinant (AD) (e.g., as described in Section II and Section XI) and an antigenic determinant binding domain (ADBD) (e.g., as described in Section III and Section XI). The Adapter can further comprise additional ADs, additional ADBDs, and/or other additional domains.

In an Adapter provided herein, the AD can be N-terminal to ADBD. Alternatively, the ADBD can be N-terminal to the AD. In some embodiments, the AD and ADBD are directly fused. In some embodiments, the AD and the ADBD are fused via a linker (a protein linker or chemical linker) or another protein domain (e.g., a functional domain).

In some embodiments, the Adapter comprises a linker located between an ADBD and another functional domain of the Adapter. In some embodiments, the linker is located between two ADBDs of the Adapter. In some embodiments, the linker is located between the AD and an ADBD of the Adapter. Suitable linkers for coupling the two or more functional domains of the Adapter will be clear to persons skilled in the art and may generally be any linker used in the art to link peptides, proteins or other organic molecules. Exemplary linkers are provided in Section IV. In particular embodiments, the linker(s) is suitable for constructing proteins or polypeptides that are intended for pharmaceutical use.

In addition to the AD (or multiple ADs) and the ADBD (or multiple ADBDs), an Adapter provided herein can further comprise an additional domain or additional domains, e.g., a domain that confers an extended half-life.

In some embodiments, the Adapter, or the ADBD in the Adapter, is deimmunized.

The Adapters provided herein have uses that include but are not limited to diagnostic, analytic, and therapeutic applications. In particular embodiments, the Adapters are used in combination with chimeric antigen receptors (CARs) (e.g., as described in Section VI and Section XI) expressed on the surface of cells (e.g., as described in Section VII and Section XI), e.g., to kill a target cell.

Va. Antigenic Determinants (ADs)

An Adapter provided herein comprises at least one antigenic determinant (AD). In some embodiments, the Adapter comprises a single AD. In some embodiments, the Adapter comprises two or more ADs. Where an Adapter comprises two or more ADs, the ADs can be the same or different.

In an Adapter provided herein, the AD can be any AD or combination of ADs (e.g., as described in Section II and Section XI).

In some embodiments, the Adapter comprises the extracellular domain of BCMA (e.g., a polypeptide comprising the sequence of SEQ ID NO: 5. In some embodiments, the Adapter comprises 5-25, 5-50, 5-75, 5-100, 5-125, or 5-150 amino acid residues, more than 150 amino acid residues, or all of the amino acid residues of SEQ ID NO: 5.

In some embodiments, Adapter comprises the extracellular domain of CD123 (e.g., a polypeptide comprising the sequence of SEQ ID NO: 11. In some embodiments, the Adapter comprises 5-25, 5-50, 5-75, 5-100, 5-125, or 5-150 amino acid residues, more than 150 amino acid residues, or all of the amino acid residues of SEQ ID NO: 11.

In some embodiments, the Adapter comprises the extracellular domain of CD19 (e.g., a polypeptide comprising the sequence of SEQ ID NO: 2 or 3. In some embodiments, the Adapter comprises 5-25, 5-50, 5-75, 5-100, 5-125, or 5-150 amino acid residues, more than 150 amino acid residues, or all of the amino acid residues of SEQ ID NO: 2 or 3.

In some embodiments, the Adapter comprises the extracellular domain of CD20. In some embodiments, the Adapter comprises 5-25, 5-50, 5-75, 5-100, 5-125, or 5-150 amino acid residues, more than 150 amino acid residues, or all of the amino acid residues of SEQ ID NO: 6-9, or 10.

In some embodiments, the Adapter comprises the extracellular domain of CD22 (e.g., a polypeptide comprising the sequence of SEQ ID NO: 41). In some embodiments, the Adapter comprises 5-25, 5-50, 5-75, 5-100, 5-125, or 5-150 amino acid residues, more than 150 amino acid residues, or all of the amino acid residues of SEQ ID NO: 41.

In some embodiments, the Adapter comprises the extracellular domain of CD37 (e.g., a polypeptide comprising the sequence of SEQ ID NO: 12 or 13). In some embodiments, the Adapter comprises 5-25, 5-50, 5-75, 5-100, 5-125, or 5-150 amino acid residues, more than 150 amino acid residues, or all of the amino acid residues of SEQ ID NO: 12 or 13.

In some embodiments, the Adapter comprises the extracellular domain of CS1 (e.g., a polypeptide comprising the sequence of SEQ ID NO: 1138). In some embodiments, the Adapter comprises 5-25, 5-50, 5-75, 5-100, 5-125, or 5-150 amino acid residues, more than 150 amino acid residues, or all of the amino acid residues of SEQ ID NO: 1138.

In some embodiments, the Adapter comprises the extracellular domain of HER2 (e.g., a polypeptide comprising the sequence of SEQ ID NO: 42). In some embodiments, the Adapter comprises 5-25, 5-50, 5-75, 5-100, 5-125, or 5-150 amino acid residues, more than 150 amino acid residues, or all of the amino acid residues of SEQ ID NO: 42.

In some embodiments, the Adapter comprises the extracellular domain of CD45 (e.g., a polypeptide comprising the sequence of residues 29-766 of SEQ ID NO: 1106). In some embodiments, the Adapter comprises 5-25, 5-50, 5-75, 5-100, 5-125, or 5-150 amino acid residues, more than 150 amino acid residues, or all of the amino acid residues of residues 29-766 of SEQ ID NO: 1106.

In some embodiments, the Adapter comprises the extracellular domain of CD26, CD30, CD33, or CD38. In some embodiments, the Adapter comprises 5-25, 5-50, 5-75, 5-100, 5-125, or 5-150 amino acid residues, more than 150 amino acid residues, or all of the amino acid residues of the extracellular domain of CD26, CD30, CD33, or CD38.

In some embodiments, the AD is an epitope of AFP. In further embodiments, the AD comprises 5-25, 5-50, 5-75, 5-100, 5-125, or 5-150 amino acid residues, more than 150 amino acid residues, or all of the amino acid residues of SEQ ID NO: 15.

In some embodiments, the AD is an epitope of AFP p26. In further embodiments, the AD comprises 5-25, 5-50, 5-75, 5-100, 5-125, or 5-150 amino acid residues, more than 150 amino acid residues, or all of the amino acid residues of SEQ ID NO: 16. In further embodiments, the AD comprises 5-25, 5-50, 5-75, 5-100, 5-125, or 5-150 amino acid residues, more than 150 amino acid residues, or all of the amino acid residues of SEQ ID NO: 1117. In further embodiments, the AD comprises the amino acid residues of SEQ ID NO: 16, 1117, 1118, 1119, 1120, 1121, 1122, or 1123.

In some embodiments, Adapter comprises a p26 protein (e.g., having the sequence of SEQ ID NO: 16, 1117, 1118, 1119, 1120, 1121, 1122, or 1123). Such fusion proteins containing p26 sequences have been discovered herein to have surprisingly long serum half-life. In some embodiments, the Adapter has a plasma half-life in vivo of at least 1 hour, at least 2 hours, at least 4 hours, at least 8 hours, at least 16 hours, at least 32 hours, at least 64 hours, or more. In some embodiments, the Adapter has an in vivo plasma half-life of at least 1 hour, at least 2 hours, at least 4 hours, at least 8 hours, at least 16 hours, at least 32 hours, at least 64 hours, or more hours 65 hours, or 1-10 hours, 2-10 hours, 4-10 hours, 6-10 hours, or 6-9 hours in a mouse. In some embodiments, the Adapter has an in vivo plasma half-life of at least 1 hour, at least 2 hours, at least 4 hours, at least 8 hours, at least 16 hours, at least 32 hours, at least 64 hours, or more hours 65 hours, or 1-10 hours, 2-10 hours, 4-10 hours, 6-10 hours, or 6-9 hours, in a human.

In some embodiments, the disclosure provides a method for modifying the in vivo half-life (e.g., in a mouse or human) of an Adapter comprising a p26 protein (e.g., having the sequence of SEQ ID NO: 16, 1117, 1118, 1119, 1120, 1121, 1122, or 1123). In some embodiments, the Adapter comprises one or more target-binding DDpp. In some embodiments, the half-life of the Adapter is increased or decreased by substituting or deleting one or more amino acid residues normally found in the human p26 protein, or by inserting one or more amino acid residues not normally found in the human p26 protein. In another embodiment, the p26 sequence of the Adapter is modified through 1, 2, 3, 5, 5, 10, or 1-20, 1-10, 3-10, or 3-5, amino acid substitutions (conservative and/or nonconservative substitutions), deletions, and/or insertions so as to increase or decrease the in vivo half-life of the Adapter. In a particular embodiment, the amino acid residue corresponding to the glutamine (Gln, Q) at position 217 of p26 (SEQ ID NO: 16) is substituted with another amino acid residues. In a further embodiment, the substitution is Gln217Pro. In another embodiment, the p26 sequence of the Adapter is modified through deletion of 1-150, 1-100, 1-50, 1-25 or 1-10 amino acid residues so as to increase or decrease the in vivo half-life of the Adapter. In additional embodiments, the p26 sequence of the Adapter is modified through 1, 2, 3, 5, 5, 10 or 1-20, 1-10, 3-10, or 3-5, amino acid substitutions (conservative and/or nonconservative substitutions), deletions, and/or insertions so as to increase or decrease the interaction of the Adapter with FcRn.

In some embodiments, the AD (e.g., in an Adapter and/or on a target cell) is an AD that is present in a naturally occurring protein or other molecule. In some embodiments, the AD is an AD that is endogenous to humans.

In some embodiments, the AD is an epitope of a human intracellular protein. In further embodiments, the AD is an epitope of a human intracellular protein selected from: elastinTyk2, Jak1, Jak2, Jak3, LCK, ZAP-70, and GRB2. In further embodiments, the AD comprises 5-25, 5-50, 5-75, 5-100, 5-125, or 5-150 amino acid residues, more than 150 amino acid residues, or all of the amino acid residues of the intracellular protein.

In some embodiments, the target of interest specifically bound by the ADBD of an Adapter is itself an AD of another Adapter, having a different sequence.

Vb. Antigenic Determinant Binding Domains (ADBDs)

An Adapter provided herein comprises at least one antigenic determinant binding domain (ADBD). In some embodiments, the Adapter contains one ADBD. In some embodiments, the Adapter contains at least 2, 3, 4, or 5, or more than 5 ADBDs. In some embodiments, the Adapter contains 1-3, 1-4, 1-5, or more than 5 different ADBDs. In some embodiments, the Adapter contains at least 2, 3, 4, or 5, or more than 5 different ADBDs. Thus, an Adapter can comprise a monomeric ADBD (i.e., containing one antigenic determinant binding domain) or multimeric ADBDs (i.e., containing more than one antigenic determinant binding domains in tandem optionally operably connected by a linker). In some embodiments, the use of a multimeric Adapter provides enhanced (e.g., synergistic) target binding. In additional embodiments, the use of a multimeric Adapter allows for targeting of more than one target using a single Adapter construct (e.g., bi-, trispecific, etc.).

The multimeric Adapter is homo-multimeric (i.e., containing more than one of the same ADBD optionally connected by linker(s) (e.g., homodimers, homotrimers, homotetramers etc.) or Adapter hetero-multimeric (i.e., containing two or more antigenic determinant binding domains in which there are at least two different antigenic determinant binding domains). The number of ADBDs included in any particular Adapter may vary, depending on the embodiment, and may be defined, at least in part, by the expression system in which the Adapter is produced. In several embodiments, however, the fusion proteins may comprise multimers of about 5 to about 10 ADBDs, about 10 to about 15 ADBDs, about 15 to about 20 ADBDs, about 20 to about 25 ADBDs, or about 25 to about 30 ADBDs (including numbers in between those listed as well as endpoints). Moreover, multiple domains of an Adapter can contain the same or different ADBD(s). In some embodiments, 2, 3, 4, 5, or more than 5 domains are in tandem.

In one embodiment, the Adapter comprises two or more ADBDs that are operably linked. In one embodiment, the Adapter comprises two ADBDs that bind to the same or different ADs on a target antigen. The linkage of two or more identical ADBDs that bind to the same target antigen results in a multivalent molecule that provides distinct advantages (e.g., increased binding avidity, target clustering and receptor activation) over compositions that only contain one ADBD for a target antigen. In another embodiment the Adapter comprises two ADBDs that bind to different antigens. In some embodiments the Adapter comprises two ADBDs that bind to different antigens on the same cell. In some embodiments the Adapter comprises two ADBDs that bind to different antigens on different cells. The linkage of two or more ADBDs results in a multivalent and multispecific Adapter that has the potential to bind more than one target antigen, either independently or simultaneously. In some embodiments, the multivalent Adapter is able to bind the same target antigen simultaneously. In some embodiments, the multivalent Adapter is able to bind different target antigens simultaneously. In some embodiments, the Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by an AFP P26 Antigenic Determinant. In further embodiments, the Adapter comprises two or more operably linked ADBDs that are separated by a CD45 Antigenic Determinant. In further embodiments, the Adapter comprises two or more operably linked ADBDs that are separated by a CD26, CD30, CD33, or CD38 Antigenic Determinant.

An ADBD in the Adapter provided herein can bind to any AD (e.g., as described in Section II and Section XI). In some embodiments, the ADBD binds to BCMA (e.g., a polypeptide comprising the sequence of SEQ ID NO: 5). In some embodiments, the ADBD binds to CD123 (e.g., a polypeptide comprising the sequence of SEQ ID NO: 11). In some embodiments, the ADBD binds to CD22 (e.g., a polypeptide comprising the sequence of SEQ ID NO: 41). In some embodiments, the ADBD binds to CD19 (e.g., a polypeptide comprising the sequence of SEQ ID NO: 3). In some embodiments, the ADBD binds to CD20 (e.g., a polypeptide comprising the sequence of SEQ ID NO: 6-9 or 10). In some embodiments, the ADBD binds to CD37 (e.g., a polypeptide comprising the sequence of SEQ ID NO: 12 or 13). In some embodiments, the ADBD binds to CS1 (e.g., a polypeptide comprising the sequence of SEQ ID NO: 1138). In some embodiments, the ADBD binds to HER2 (e.g., a polypeptide comprising the sequence of SEQ ID NO: 42). In some embodiments, the ABDB binds to CD45. In some embodiments, the ABDB in the Adapter provided herein specifically binds to an AD of human CD26, CD30, CD33, or CD38. An Adapter can be "monospecific" or "multi-specific." An Adapter that is "multi-specific" (e.g., bispecific, trispecific or of greater multi-specificity) recognizes and binds to two or more different epitopes present on one or more different molecules.

In some embodiments, the Adapter comprises a domain (e.g., the extracellular domain) of BCMA (e.g., a polypeptide comprising the sequence of SEQ ID NO 4). In some embodiments, Adapter comprises a domain (e.g., the extracellular domain) of CD123 (e.g., a polypeptide comprising the sequence of SEQ ID NO: 11). In some embodiments, the Adapter comprises a domain (e.g., the extracellular domain) of CD22 (e.g., a polypeptide comprising the sequence of SEQ ID NO: 24). In some embodiments, the Adapter comprises a domain (e.g., the extracellular domain) of CD19 (e.g., a polypeptide comprising the sequence of SEQ ID NO: 3). In some embodiments, the Adapter comprises a domain (e.g., the extracellular domain) of CS1 (e.g., a polypeptide comprising the sequence of SEQ ID NO: 1138). In some embodiments, the Adapter comprises a domain (e.g., the extracellular domain) of HER2 (e.g., a polypeptide comprising the sequence of SEQ ID NO: 42). In some embodiments, the Adapter comprises a domain (e.g., the extracellular domain) of CD45. In some embodiments, the Adapter comprises a domain (e.g., the extracellular domain) of CD26, CD30, CD33, or CD38. In some embodiments, the Adapter comprises a fragment of a domain. In further embodiments, the Adapter comprises a fragment of a domain having an amino acid sequence selected from the group: SEQ ID NO: 4 or 5, SEQ ID NO: 11, SEQ ID NO: 24, and SEQ ID NO: 3. In some embodiments, the Adapter comprises a fragment of a domain that is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150, amino acids in length.

In some embodiments, the Adapter contains at least two ADBDs that bind and cross-link one or more target antigens bound by the ADBDs and/or complexes containing the target antigen(s). In some embodiments, the cross-linked antigen(s) is on the same cell. In some embodiments, the cross-linked antigen(s) is on different cells. In some embodiments, the Adapter comprises two or more operably linked ADBDs that are separated by an Antigenic Determinant (e.g., a domain described above). In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by a CD45 Antigenic Determinant. In further embodiments, the Adapter comprises two or more operably linked ADBDs that are separated by a CD26, CD30, CD33, or CD38 Antigenic Determinant. In further embodiments, the Adapter comprises two or more operably linked ADBDs that are separated by an AFP P26 Antigenic Determinant.

In some embodiments, the Adapter contains at least two of the same ADBDs (i.e., is multivalent). In some embodiments, the multivalent Adapter is able to bind two or more of the same target antigens simultaneously. In some embodiments, the Adapter is multivalent and is able to bind the same target antigen simultaneously. In some embodiments, the multi-multivalent Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the multivalent Adapter comprises two or more operably linked ADBDs that are separated by a BCMA Antigenic Determinant. In further embodiments, the multivalent Adapter comprises two or more operably linked ADBDs that are separated by a CD45 Antigenic Determinant. In further embodiments, the multivalent Adapter comprises two or more operably linked ADBDs that are separated by an AFP P26 Antigenic Determinant.

In some embodiments, the Adapter contains at least two ADBDs that bind to different antigens (i.e., is multispecific). In some embodiments, the multi-specific Adapter is able to bind the different target antigens simultaneously. In some embodiments, the Adapter is also multivalent and is able to bind the same target antigen simultaneously. In some embodiments, the multi-specific Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by a CD45 Antigenic Determinant. In further embodiments, the Adapter comprises two or more operably linked ADBDs that are separated by an AFP P26 Antigenic Determinant.

In one embodiment, a multi-specific Adapter contains at least two ADBDs that bind to at least two different epitopes on a single target of interest (i.e., is multiepitotic for the same target antigen). In additional embodiments, a multi-specific Adapter comprises at least one ADBD that specifically binds one epitope on a target of interest and at least one other ADBD that specifically binds to a different epitope on the same target antigen. In one embodiment, a multi-specific Adapter comprises at least one ADBD that specifically binds to an epitope on a first target antigen and at least one ADBD that specifically binds to an epitope on a second antigen. In some embodiments, the Adapter comprises at least one ADBD that specifically binds to an epitope on a first target antigen on a cell and at least one ADBD that specifically binds to an epitope on a second antigen on the same cell. In some embodiments, the Adapter comprises at least one ADBD that specifically binds to an epitope on a first target antigen on a cell and at least one ADBD that specifically binds to an epitope on a second antigen on a different cell.

In a further embodiment, the Adapter comprises 2 or more ADBDs that are operably linked with other heterologous proteins (or their subdomains) and in so doing, impart the multivalent, multi-specific, and/or functional properties (e.g., pharmacokinetics such as increased half-life) of the fusion partner to the Adapter fusion protein. Examples of fusion partners of an Adapter include but are not limited to, antibodies, antibody subdomains (e.g., scFv or Fc domains), serum albumin, serum albumin subdomains, cell surface receptors, an alpha chain of a T cell receptor (TCR), a beta chain of a T cell receptor, cell surface receptor subdomains, peptides, peptide tags (e.g., FLAG or myc). The number and location of ADBDs and their respective positions within the Adapter can vary. For example, ADBDs can be located at one or all termini of a fusion partner and/or interspersed within heterologous subunits within the Adapter fusion partner. In some embodiments the Adapter comprises 2 or more ADBDs that are separated by a heterologous protein (e.g., Antigenic Determinant). In some embodiments, the heterologous protein is at least 50, 75, 100, 150, 200, 250, 300, 350, 400, 450, or 500 amino acids in length. In some embodiments, the heterologous protein is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length.

In one embodiment, the Adapter is bispecific and contains ADBDs that specifically bind to two different target antigens. In further embodiments, the bispecific Adapter specifically binds to two different target antigens expressed on the surface of two different cell types. In further embodiments, the bispecific Adapter specifically binds to two different target antigens expressed on the surface of a tumor cell. In further embodiments, the bispecific Adapter specifically binds to two different target antigens expressed on the surface of a multiple myeloma cell (e.g., BCMA and CS1). In one embodiment, the bispecific Adapter binds to target antigens expressed on different cells. In a further embodiment, the bispecific Adapter binds to target antigens expressed on different cells of a tumor. In another embodiment, the bispecific Adapter binds to target antigens expressed on different cells within a tumor vasculature or tumor microenvironment. In one embodiment, the bispecific Adapter specifically binds to a cancer cell target and an immune effector cell target. In one embodiment the bispecific Adapter specifically binds a target expressed on a cancer cell (e.g. CD19) and a target expressed on the surface of a T lymphocyte (e.g., CD3 or CD45).). In some embodiments, the bispecific Adapter is able to bind the different target antigens simultaneously. In some embodiments, the bispecific Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by a CD45 Antigenic Determinant. In further embodiments, the Adapter comprises two or more operably linked ADBDs that are separated by an AFP P26 Antigenic Determinant.

In some embodiments where the Adapter comprises more than one ADBD, the ADBD can be any of the types of ADBD discussed herein (e.g., any ADBD described in Section III above and in and Section XI). For example, an ADBD can be an antibody, an antigen-binding fragment thereof, a ScFv, an alternative scaffold binding domain, a D domain, a T cell receptor, or an antigen-binding fragment thereof.

In some embodiments, where an Adapter comprises more than one ADBD, those ADBD can be the same types of antigen-binding molecules or can be different. For example, an Adapter can comprise two ADBD that are D domains. The two ADBD that are D domains can be the same or different. An Adapter can also comprise an ADBD that is a D domain and an ADBD that is a scFv. An Adapter can also comprise an ADBD that is a T cell receptor or antigen-binding fragment thereof and an ADBD that is a scFv. In some embodiments, the Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by a CD45 Antigenic Determinant. In further embodiments, the Adapter comprises two or more operably linked ADBDs that are separated by an AFP P26 Antigenic Determinant.

In some embodiments, the ADBD of the Adapter is deimmunized.

In some embodiments, the Adapter comprises an ABDB that binds to an antigen target containing an AD of interest, and has no discernable impact on the function of the target. Alternatively, in some embodiments, the Adapter comprises an ADBD that binds to an antigen target containing an AD of interest and completely or partially inhibits, antagonizes, agonizes, blocks, increases, stimulates, or interferes with the biological activity of the target. Binding can be identified as agonistic or antagonistic and determined using or routinely modifying assays, bioassays, and/or animal models known in the art for evaluating such activity.

An Adapter agonist refers to an Adapter that in some way increases or enhances the biological activity of the Adapter target or has biological activity comparable to a known agonist of the Adapter target. In another embodiment, the Adapter is an antagonist of the target it binds. An Adapter antagonist refers to an Adapter that completely or partially blocks or in some way interferes with the biological activity of the Adapter target or has biological activity comparable to a known antagonist or inhibitor of the Adapter target.

In one embodiment an Adapter specifically binds a target of interest that is a serum protein. In one embodiment, an Adapter specifically binds a serum protein selected from: serum albumin (e.g., human serum albumin (HSA)), thyroxin-binding protein, transferrin, fibrinogen, and an immunoglobulin (e.g., IgG, IgE and IgM). Without being bound by theory, the binding of an Adapter to a carrier protein is believed to confer upon the Adapter an improved pharmacodynamic profile that includes, but is not limited to, improved tumor targeting, tumor penetration, diffusion within the tumor, and enhanced therapeutic activity compared to the Adapter in which the carrier protein binding sequence is missing (see, e.g., WO 01/45746, the contents of which are herein incorporated by reference in its entirety).

In one embodiment the target of interest specifically bound by an Adapter is a disease-related antigen. The antigen can be an antigen characteristic of a cancer, and/or of a particular cell type (e.g., a hyperproliferative cell), and/or of a pathogen (e.g., a bacterial cell (e.g., tuberculosis, smallpox, and anthrax), a virus (e.g., HIV and H), a parasite (e.g., malaria and leishmaniosis), a fungal infection, a mold, a mycoplasm, a prion antigen, or an antigen associated with a disorder of the immune system.

In an additional embodiment, the target of interest bound by an Adapter (is a bacterial antigen, a viral antigen, a fungal antigen, a mycoplasm antigen, a prion antigen, or a parasite antigen (e.g., one infecting a mammal). In one embodiment, the target of an Adapter is human papillomavirus anthrax, hepatitis b, rabies, Nipah virus, west Nile virus, a meningitis virus, or CMV. In an additional embodiment, an Adapter specifically binds a pathogen.

Vc. Adapter Functional Domain(s)

In some embodiments, the Adapter comprises a first antigenic determinant (an AD), a domain that binds to a second antigenic determinant (an ADBD), and further comprises a functional domain that confers one or more additional desirable properties (e.g., improved manufacturing) and/or pharmacokinetic properties (e.g., improved half-life). The functional domain of the Adapter can be located between the AD and the ADBD. The Adapter can also be located N-terminal to both the AD and ADBD or C-terminal to both the AD and ADBD. In some embodiments, where the Adapter comprises two or more ADs, the functional domain of the Adapter can be located between two or more ADs, N-terminal to two or more ADs, or C-terminal to two or more ADs. In some embodiments, where the Adapter comprises two or more ADBDs, the functional domain of the Adapter can be located between two or more ADBDs, N-terminal to two or more ADBDs, or C-terminal to two or more ADBDs.

In some embodiments, the Adapter comprises a functional domain selected from: an Fc or variant Fc (e.g., a human Fc or variant Fc domain) or a fragment thereof, a serum protein (e.g., human serum albumin) or a fragment thereof; an FcRn binding domain; a serum protein binding domain; a cytokine, growth factor, hormone, or enzyme; an imaging agent; a labeling agent; and a peptide tag.

The functional domain(s) of the Adapter can be naturally derived or the result of recombinant engineering (e.g., phage display, xenomouse, or synthetic). In certain embodiments, the functional domain of the Adapter enhances half-life, increases or decreases antibody dependent cellular cytotoxicity (ADCC), and/or increases or decreases complement dependent cytotoxicity (CDC) activity.

In some embodiments, the Adapter comprises a functional domain selected from: an Fc or variant Fc (e.g., a human Fc or variant human Fc domain) or a fragment or derivative thereof, a serum protein (e.g., human serum albumin) or a fragment or derivative thereof (e.g., a serum protein binding domain); an FcRn binding domain; and a serum protein binding domain.

In one embodiment, an Adapter comprises a functional domain that comprises an antibody effector domain or derivative of an antibody effector domain that confers one or more effector functions to the Adapter, such as the ability to bind to one or more Fc receptors. In some embodiments, the functional domain comprises one or more CH2 and or CH3 domains of an antibody having effector function provided by the CH2 and CH3 domains. In some embodiments, the functional domain comprises one or more derivatives of CH2 and/or CH3 domains of an antibody having effector function provided by the CH2 and CH3 domains. Other sequences that can be included in the Adapter to provide an effector function and that are encompassed by the invention will be clear to those skilled in the art and can routinely be chosen and designed into an Adapter encompassed herein on the basis of the desired effector function(s).

In one embodiment, the Adapter comprises a functional domain that increases the antibody dependent cellular cytotoxicity (ADCC) conferred by the Adapter (see, e.g., Bruhns et al., Blood 113:3716-3725 (2009); Shields et al., J. Biol. Chem. 276:6591-6604 (2001); Lazar et al., PNAS 103:4005-4010 (2006); Stavenhagen et al., Cancer Res. 67:8882-8890 (2007); Horton et al., Cancer Res. 68:8049-8057 (2008); Zalevsky et al., Blood 113:3735-3743 (2009); Bruckheimer, Neoplasia 11:509-517 (2009); WO2006/020114; Strohl, Curr. Op. Biotechnol. 20:685-691 (2009); and WO2004/074455, each of which is herein incorporated by reference in its entirety). Examples of fragment engineering modifications of effector function conferring portions of an Fc contained in the functional domain of an Adapter that increases ADCC include one or more modifications corresponding to: IgG1-S298A, E333A, K334A; IgG1-S239D, 1332E; IgG1-S239D, A330L, 1332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index of Kabat et al. (Kabat et al., Sequences of proteins of Immunological Interest, 1991 Fifth edition).

Accordingly, in some embodiments, the Adapter comprises a functional domain that comprises an antibody fragment that confers upon the Adapter a biological or biochemical characteristic of an immunoglobulin. In some embodiments, the antibody fragment confers a characteristic selected from: the ability to non-covalently dimerize, the ability to localize at the site of a tumor, and an increased serum half-life when compared to an Adapter without the antibody fragment. In certain embodiments, the Adapter is at least as stable as the corresponding antibody fragment without the Adapter. In certain embodiments, the Adapter is more stable than the corresponding antibody fragment without the Adapter. Adapter protein stability can be measured using established methods, including, for example, ELISA techniques. In some embodiments, the Adapter is stable in whole blood (in vivo or ex vivo) at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours (including any time between those listed). In one embodiment, the Adapter contains an immunoglobulin effector domain or half-life influencing domain that corresponds to an immunoglobulin domain or fragment in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an immunoglobulin fragment having the corresponding unaltered immunoglobulin sequence. These alterations of the constant region domains can be amino acid substitutions, insertions, or deletions.

In one embodiment, the Adapter comprises a functional domain that comprises an amino acid sequence of an immunoglobulin effector domain or a derivative of an immunoglobulin effector domain that confers antibody dependent cellular cytotoxicity (ADCC) to the Adapter. In additional embodiments, the Adapter comprises a sequence of an immunoglobulin effector domain that has been modified to increase ADCC (see, e.g., Bruhns, Blood 113:3716-3725 (2009); Shields, J. Biol. Chem. 276:6591-6604 (2001); Lazar, PNAS 103:4005-4010 (2006); Stavenhagen, Cancer Res. 67:8882-8890 (2007); Horton, Cancer Res. 68:8049-8057 (2008); Zalevsky, Blood 113:3735-3743 (2009); Bruckheimer, Neoplasia 11:509-517 (2009); WO 06/020114; Strohl, Curr. Op. Biotechnol. 20:685-691 (2009); and WO 04/074455, the contents of each of which is herein incorporated by reference in its entirety). Examples of immunoglobulin fragment engineering modifications contained in an amino acid sequence in the Adapter that increases ADCC include immunoglobulin effector domain sequences having one or more modifications corresponding to: IgG1-S298A, E333A, K334A; IgG1-S239D, 1332E; IgG1-S239D, A330L, 1332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index of Kabat et al. (Kabat et al., Sequences of proteins of Immunological Interest, 1991 Fifth edition, herein incorporated by reference).

In additional embodiments, the Adapter comprises a functional domain that comprises the amino acid sequence of an immunoglobulin effector domain, or a derivative of an immunoglobulin effector domain, that confers antibody-dependent cell phagocytosis (ADCP) to the Adapter. In additional embodiments, the Adapter comprises a sequence of an immunoglobulin effector domain that has been modified to increase antibody-dependent cell phagocytosis (ADCP); (see, e.g., Shields et al., J. Biol. Chem. 276:6591-6604 (2001); Lazar et al., PNAS 103:4005-4010 (2006); Stavenhagen et al., Cancer Res. 67:8882-8890 (2007); Richards et al., Mol. Cancer Ther. 7:2517-2527 (2008); Horton et al., Cancer Res. 68:8049-8057 (2008), Zalevsky et al., Blood 113:3735-3743 (2009); Bruckheimer et al., Neoplasia 11:509-517 (2009); WO 06/020114; Strohl, Curr. Op. Biotechnol. 20:685-691 (2009); and WO 04/074455, the contents of each of which is herein incorporated by reference in its entirety). Examples of immunoglobulin fragment engineering modifications contained in an amino acid sequence in the Adapter that increases ADCP include immunoglobulin effector domain sequences having one or more modifications corresponding to: IgG1-S298A, E333A, K334A; IgG1-S239D, 1332E; IgG1-S239D, A330L, 1332E; IgG1-P247I, A339D or Q; IgG1-D280H, K290S with or without S298D or V; IgG1-F243L, R292P, Y300L; IgG1-F243L, R292P, Y300L, P396L; IgG1-F243L, R292P, Y300L, V305I, P396L; and IgG1-G236A, S239D, 1332E; wherein the numbering of the residues is that of the EU index of Kabat et al. (Kabat et al., Sequences of proteins of Immunological Interest, 1991 Fifth edition, herein incorporated by reference).

In additional embodiments, the Adapter comprises a functional domain that comprises an amino acid sequence of an immunoglobulin effector domain, or a derivative of an immunoglobulin effector domain, that confers complement-dependent cytotoxicity (CDC) to the Adapter. In additional embodiments, the Adapter comprises a sequence of an immunoglobulin effector domain that has been modified to increase complement-dependent cytotoxicity (CDC) (see, e.g., Idusogie et al., J. Immunol. 166:2571-2575 (2001); Strohl, Curr. Op. Biotechnol. 20:685-691 (2009); and Natsume et al., Cancer Res. 68:3863-3872 (2008), the contents of each of which is herein incorporated by reference in its entirety). By way of example, Adapters can contain an antibody fragment or domain that contains one or more of the following modifications that increase CDC: IgG1-K326A, E333A; IgG1-K326W, E333S, IgG2-E333S; wherein the numbering of the residues is that of the EU index of Kabat et al. (Sequences of proteins of Immunological Interest, 1991 Fifth edition, herein incorporated by reference).

In additional embodiments, the Adapter comprises a functional domain that comprises an amino acid sequence of an immunoglobulin effector domain, or a derivative of an immunoglobulin effector domain, that confers the ability to bind FcgammaRIIb receptor to the Adapter. In additional embodiments, the Adapter comprises a sequence of an immunoglobulin effector domain that has been modified to increase inhibitory binding to FcgammaRIIb receptor (see, e.g., Chu et al., Mol. Immunol. 45:3926-3933 (2008)). An example of an immunoglobulin fragment engineering modification contained in an amino acid sequence in the Adapter that increases binding to inhibitory FcgammaRIIb receptor is IgG1-S267E, L328F.

The half-life of an IgG is mediated by its pH-dependent binding to the neonatal receptor FcRn. In certain embodiments the Adapter contains a functional domain that comprises an amino acid sequence of an immunoglobulin effector domain, or a derivative of an immunoglobulin effector domain, that confers the ability to bind neonatal receptor FcRn to the Adapter. In certain embodiments the Adapter contains a functional domain that comprises a sequence of an immunoglobulin FcRn binding domain that has been modified to enhance binding to FcRn (see, e.g., Petkova et al., Int. Immunol. 18:1759-1769 (2006); Dall'Acqua et al., J. Immunol. 169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176:346-356 (2006); Datta-Mannan et al., Drug Metab. Dispos. 35:86-94 (2007); Datta-Mannan et al., J. Biol. Chem. 282:1709-1717 (2007); WO 06/130834; Strohl, Curr. Op. Biotechnol. 20:685-691 (2009); and Yeung et al., J. Immunol. 182:7663-7671 (2009), the contents of each of which is herein incorporated by reference in its entirety).

In additional embodiments, the Adapter comprises a functional domain that comprises a sequence of an immunoglobulin effector domain that has been modified to have a selective affinity for FcRn at pH 6.0, but not pH 7.4. By way of example, the Adapter functional domain can contain an antibody fragment or domain that contains one or more of the following modifications that increase half-life: IgG1-M252Y, S254T, T256E; IgG1-T250Q, M428L; IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, herein incorporated by reference).

According to another embodiment, the Adapter comprises a functional domain that comprises an amino acid sequence corresponding to a immunoglobulin effector domain that has been modified to contain at least one substitution in its sequence corresponding to the Fc region (e.g., Fc gamma) position selected from: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438, and 439, wherein the numbering of the residues in the Fc region is according to the EU numbering system; of Kabat et al. (Sequences of proteins of Immunological Interest, 1991 Fifth edition, herein incorporated by reference). In a specific embodiment, the Adapter contains a functional domain that comprises a sequence of an immunoglobulin effector domain derivative wherein at least one residue corresponding to position 434 is a residue selected from: A, W, Y, F and H. According to another embodiment, the Adapter comprises a sequence of an immunoglobulin effector fragment derivative having the following respective substitutions S298A/E333A/K334A. In an additional embodiment, the Adapter comprises an immunoglobulin effector domain derivative having a substitution corresponding to K322A. In another embodiment, the Adapter comprises a sequence of an immunoglobulin effector domain derivative having one or any combination of the following substitutions K246H, H268D, E283L, S324G, S239D and I332E. According to yet another embodiment, the Adapter comprises a sequence of an immunoglobulin effector domain derivative having substitutions corresponding to D265A/N297A.

In certain embodiments, the Adapter comprises a functional domain that comprises a sequence of an immunoglobulin effector domain that has been glycoengineered or mutated to increase effector function using techniques known in the art. For example, the inactivation (through point mutations or other means) of a constant region domain sequence contained in the Adapter may reduce Fc receptor binding of the circulating Adapter thereby increasing tumor localization. In other cases it may be that constant region modifications consistent with certain embodiments of the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

Adapter as Chemical Conjugates

Adapter that promote specific binding to targets of interest can be chemically conjugated with a variety of compound such as fluorescent dyes, radioisotopes, chromatography compositions (e.g., beads, resins, gels, etc.) and chemotherapeutic agents. Adapter conjugates have uses that include but are not limited to purification, diagnostic, analytic, manufacturing and therapeutic applications.

The inherent lack of cysteines in the Adapter sequence provides the opportunity for introduction of unique cysteines for purposes of site-specific conjugation.

In some embodiments, the Adapter contains at least one reactive residue. Reactive residues are useful, for example, as sites for the attachment of conjugates such as chemotherapeutic drugs. The reactive residue can be, for example, a cysteine, a lysine, or another reactive residue. Thus, a cysteine can be added to an Adapter at either the N- or C-terminus, or within the Adapter sequence. A cysteine can be substituted for another amino acid in the sequence of an Adapter. In addition, a lysine can be added to an Adapter at either end or within the Adapter sequence and/or a lysine can be substituted for another amino acid in the sequence of an Adapter. In one embodiment, a reactive residue (e.g., cysteine, lysine, etc.,) is located in a loop sequence of an ADBD (e.g., Z1 and Z2 of SEQ ID NOS: 22-25, or 26). In one embodiment, a reactive residue is located between components of an Adapter, e.g., in a linker located between an ADBD and other component of an Adapter fusion protein. The reactive residue (e.g., cysteine, lysine, etc.) can also be located within the sequence of an Adapter. In one embodiment, an Adapter comprises at least one, at least two, at least three reactive residues. In one embodiment, an Adapter comprises at least one, at least two, or at least three, cysteine residues.

Vd. Production of Adapters

The production of the Adapter, useful in practicing the provided methods, may be carried out using a variety of standard techniques for chemical synthesis, semi-synthetic methods, and recombinant DNA methodologies known in the art. Also provided is a method for producing the Adapter, individually or as part of multi-domain fusion protein, as soluble agents and cell associated proteins.

In several embodiments, the overall production scheme for the Adapter comprises obtaining a reference protein scaffold and identifying a plurality of residues within the scaffold for modification. Depending on the embodiment, the reference scaffold may comprise a protein structure with one or more alpha-helical regions, or other tertiary structure. Once identified, the plurality of residues can be modified, for example by substitution of an amino acid. In some embodiments substitution is conservative, while in other embodiments non-conservative substitutions are made. In some embodiments a natural amino acid (e.g., one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine) is substituted into the reference scaffold at the targeted position for modification. In certain embodiments, the modifications do not include substituting in either a cysteine or a proline. After modifications have been made at all the identified positions desired in a particular embodiment, the resulting modified polypeptides (e.g., candidate Adapter) can be recombinantly expressed, for example in a plasmid, bacteria, phage, or other vector (e.g. to increase the number of each of the modified polypeptides). The modified polypeptides can then be purified and screened to identify those modified polypeptides that have specific binding to a particular target of interest. In several embodiments, certain modified polypeptides will show enhanced binding specificity for a target of interest vis-à-vis the reference scaffold, which in some embodiments may exhibit little or no binding to a given target of interest. In additional embodiments, depending on the target of interest the reference scaffold may show some interaction (e.g. nonspecific interaction) with a target of interest, while certain modified polypeptides will exhibit at least about two fold, at least about five fold, at least about 10 fold, at least about 20 fold, at least about 50 fold, or at least about 100 fold (or more) increased binding specificity for the target of interest. Optionally, the reference sequence and/or the modified polypeptides (e.g., Adapter) can be de-immunized. For example, residues or motifs that are potentially immunogenic can be identified and modified in order to reduce or eliminate potential immune responses to the Adapter. Additional details regarding various embodiments of the production, selection, and isolation of Adapter are provided in more detail below.

Ve. Recombinant Expression of Adapters

In some embodiments, the Adapter is "recombinantly produced," (i.e., produced using recombinant DNA technology). Exemplary recombinant methods available for synthesizing Adapter fusion proteins, include, but are not limited to polymerase chain reaction (PCR) based synthesis, concatemerization, seamless cloning, and recursive directional ligation (RDL) (see, e.g., Meyer et al., Biomacromolecules 3:357-367 (2002), Kurihara et al., Biotechnol. Lett. 27:665-670 (2005), Haider et al., Mol. Pharm. 2:139-150 (2005); and McMillan et al., 32:3643-3646 (1999), the contents of each of which is herein incorporated by reference in its entirety).

Nucleic acids comprising a polynucleotide sequence encoding the Adapter are also provided. Such polynucleotides optionally further comprise, one or more expression control elements. For example, the polynucleotide can comprise one or more promoters or transcriptional enhancers, ribosomal binding sites, transcription termination signals, and polyadenylation signals, as expression control elements. The polynucleotide can be inserted within any suitable vector, which can be contained within any suitable host cell for expression.

The expression of nucleic acids encoding the Adapter is typically achieved by operably linking a nucleic acid encoding the Adapter to a promoter in an expression vector. Typical expression vectors contain transcription and translation terminators, initiation sequences, and promoters useful for regulation of the expression of the desired nucleic acid sequence. Methods known in the art can be used to routinely construct expression vectors containing the nucleic acid sequence encoding an Adapter along with appropriate transcriptional/translational control signals. These methods include, but are not limited to in vitro recombinant DNA techniques, synthetic techniques and in vivo recombination/genetic recombination. The expression of the polynucleotide can be performed in any suitable expression host known in the art including, but not limited to bacterial cells, yeast cells, insect cells, plant cells or mammalian cells. In one embodiment, a nucleic acid sequence encoding the Adapter is operably linked to a suitable promoter sequence such that the nucleic acid sequence is transcribed and/or translated into the Adapter in a host. Promoters useful for expression in *E. coli*, include but are not limited to, the T7 promoter.

In one embodiment, a vector comprising the Adapter encoding nucleic acid is introduced into a host cell (e.g., phagemid) for expression of the Adapter. The vector can remain episomal or become chromosomally integrated, as long as the insert encoding therapeutic agent can be transcribed. Vectors can be constructed by standard recombinant DNA technology. Vectors can be plasmids, phages, cosmids, phagemids, viruses, or any other types known in the art, which are used for replication and expression in prokaryotic or eukaryotic cells. It will be appreciated by one of skill in the art that a wide variety of components known in the art (such as expression control elements) can be included in such vectors, including a wide variety of transcription signals, such as promoters and other sequences that regulate the binding of RNA polymerase onto the promoter. Any promoter known or demonstrated to be effective in the cells in which the vector will be expressed can be used to initiate expression of the Adapter. Suitable promoters can be inducible (e.g., regulated) or constitutive. Non-limiting examples of suitable promoters include the SV40 early promoter region, the promoter contained in the 3' long terminal repeat of Rous sarcoma virus, the HSV-1 (herpes simplex virus-1) thymidine kinase promoter, the regulatory sequences of the metallothionein gene, etc., as well as the following animal transcriptional control regions, which exhibit tissue specificity and have been utilized in transgenic animals: elastase I gene control region which is active in pancreatic acinar cells; insulin gene control region which is active in pancreatic beta cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus. In a particular embodiment, the promoter is an immunoglobulin gene control region which is active in lymphoid cells.

In one embodiment, one or several nucleic acids encoding the Adapter is expressed under the control of a constitutive promoter or, alternately, a regulated expression system. Suitable regulated expression systems include, but are not limited to, a tetracycline-regulated expression system, an ecdysone inducible expression system, a lac-switch expression system, a glucocorticoid-inducible expression system, a temperature-inducible promoter system, and a metallothionein metal-inducible expression system. If several different nucleic acids encoding the Adapter are contained within the host cell system, some of the nucleic acids may be expressed under the control of a constitutive promoter, while others may be expressed under the control of a regulated promoter. Expression levels may be determined by methods known in the art, including Western blot analysis and Northern blot analysis.

A variety of host-expression vector systems can be utilized to express a nucleic acid encoding the Adapter. Vectors containing the nucleic acids encoding the Adapter or portions or fragments thereof, include plasmid vectors, a single and double-stranded phage vectors, as well as single and double-stranded RNA or DNA viral vectors. Phage and viral vectors may also be introduced into host cells in the form of packaged or encapsulated virus using known techniques for infection and transduction. Moreover, viral vectors may be replication competent or alternatively, replication defective. Alternatively, cell-free translation systems may also be used to produce the protein using RNAs derived from the DNA expression constructs (see, e.g., WO86/05807 and WO89/01036; and U.S. Pat. No. 5,122,464, each incorporated in its entirety by reference herein).

Generally, any type of cells or cultured cell line can be used to express the Adapter provided herein. In some embodiments the background cell line used to generate an engineered host cells is a phage, a bacterial cell, a yeast cell or a mammalian cell. A variety of host-expression vector systems may be used to express the coding sequence of the Adapter. Mammalian cells can be used as host cell systems transfected with recombinant plasmid DNA or cosmid DNA expression vectors containing the coding sequence of the target of interest and the coding sequence of the Adapter.

The cells can be primary isolates from organisms (including human), cultures, or cell lines of transformed or transgenic nature. In some embodiments the host cell is a human cell. In some embodiments, the host cell is human T cell. In some embodiments, the host cell is derived from a human patient.

Useful host cells include but are not limited to microorganisms such as, bacteria (e.g., *E. coli* and *B. subtilis*) transformed with recombinant bacteriophage DNA, plasmid DNA or cosmid DNA expression vectors containing Adapter coding sequences; yeast (e.g., *Saccharomyces, Pichia*) transformed with recombinant yeast expression vectors containing Adapter coding sequences; insect cell systems infected with recombinant virus expression vectors (e.g., Baculovirus) containing Adapter coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Adapter coding sequences. In particular embodiments, the mammalian cell systems are used to produce the Adapter. Mammalian cell systems typically utilize recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in producing the Adapter, include gram negative or gram positive organisms such as, *E. coli* and *B. subtilis*. Expression vectors for use in prokaryotic host cells generally contain one or more phenotypic selectable marker genes (e.g., genes encoding proteins that confer antibiotic resistance or that supply an autotrophic requirement). Examples of useful prokaryotic host expression vectors include the pKK223-3 (Pharmacia, Uppsala, Sweden), pGEM1 (Promega, Wis., USA), pET (Novagen, Wis., USA) and pRSET (Invitrogen, Calif., USA) series of vectors (see, e.g., Studier, J. Mol. Biol. 219:37 (1991) and Schoepfer, Gene 124:83 (1993)). Exemplary promoter sequences frequently used in prokaryotic host cell expression vectors include T7, (Rosenberg et al., Gene 56:125-135 (1987)), beta-lactamase (penicillinase), lactose promoter system (Chang et al., Nature 275:615 (1978)); and Goeddel et al., Nature 281:544 (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.).

In one embodiment, a eukaryotic host cell systems is used, including yeast cells transformed with recombinant yeast expression vectors containing the coding sequence of an Adapter, such as, the expression systems taught in U.S. Appl. No. 60/344,169 and WO03/056914 (methods for producing humanlike glycoprotein in a non-human eukaryotic host cell) (the contents of each of which are incorporated by reference in their entirety). Exemplary yeast that can be used to produce compositions of the invention, such as, DBD, include yeast from the genus *Saccharomyces, Pichia*, Actinomycetes and *Kluyveromyces*. Yeast vectors typically contain an origin of replication sequence from a 2mu yeast plasmid, an autonomously replicating sequence (ARS), a promoter region, sequences for polyadenylation, sequences for transcription termination, and a selectable marker gene. Examples of promoter sequences in yeast expression constructs include, promoters from metallothionein, 3-phosphoglycerate kinase (Hitzeman, J. Biol. Chem. 255:2073 (1980)) and other glycolytic enzymes, such as, enolase, glyceraldehyde-3-phosphate dehydrogenase, hexokinase, pyruvate decarboxylase, phosphofructokinase, glucose-6-phosphate isomerase, 3-phospho glycerate mutase, pyruvate kinase, triosephosphate isomerase, phosphoglucose isomerase, and glucokinase. Additional suitable vectors and promoters for use in yeast expression as well as yeast transformation protocols are known in the art. See, e.g., Fleer, Gene 107:285-195 (1991) and Hinnen, PNAS 75:1929 (1978).

Insect and plant host cell culture systems are also useful for producing the compositions of the invention. Such host cell systems include for example, insect cell systems infected with recombinant virus expression vectors (e.g., baculovirus) containing the coding sequence of a DBD; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of a DBD, including, but not limited to, the expression systems taught in U.S. Pat. No. 6,815,184; U.S. Publ. Nos. 60/365,769, and 60/368,047; and WO2004/057002, WO2004/024927, and WO2003/078614, the contents of each of which is herein incorporated by reference in its entirety.

In an additional embodiment the host cell systems may be used, including animal cell systems infected with recombinant virus expression vectors (e.g., adenoviruses, retroviruses, adeno-associated viruses, herpes viruses, lentiviruses) including cell lines engineered to contain multiple copies of the DNA encoding an Adapter either stably amplified (CHO/dhfr) or unstably amplified in double-minute chromosomes (e.g., murine cell lines). In one embodiment, the vector comprising the polynucleotide(s) encoding the Adapter is polycistronic. Exemplary mammalian cells useful for producing these compositions include 293 cells (e.g., 293T and 293F), CHO cells, BHK cells, NS0 cells, SP2/0 cells, YO myeloma cells, P3X63 mouse myeloma cells, PER cells, PER.C6 (Crucell, Netherlands) cells VERY, Hela cells, COS cells, MDCK cells, 3T3 cells, W138 cells, BT483 cells, Hs578T cells, HTB2 cells, BT20 cells, T47D cells, CRL7030 cells, HsS78Bst cells, hybridoma cells, and other mammalian cells. Additional exemplary mammalian host cells that are useful in practicing the invention include but are not limited, to T cells. Some examples of expression systems and selection methods are described in the following references and references cited therein: Borth et al., Biotechnol. Bioen. 71 (4): 266-73 (2000), in Werner et al., Arzneimittelforschung/Drug Res. 48 (8): 870-80 (1998), Andersen et al., Curr. Op. Biotechnol. 13:117-123 (2002), Chadd et al., Curr. Op. Biotechnol. 12:188-194 (2001), and Giddings, Curr. Op. Biotechnol. 12:450-454 (2001). Additional examples of expression systems and selection methods are described in Logan et al., PNAS 81:355-359 (1984), Birtner et al. Methods Enzymol. 153:51-544 (1987)). Transcriptional and translational control sequences for mammalian host cell expression vectors are frequently derived from viral genomes. Commonly used promoter sequences and enhancer sequences in mammalian expression vectors include, sequences derived from Polyoma virus, Adenovirus 2, Simian Virus 40 (SV40), and human cytomegalovirus (CMV). Exemplary commercially available expression vectors for use in mammalian host cells include pCEP4 (Invitrogen) and pcDNA3 (Invitrogen).

Physical methods for introducing a nucleic acid into a host cell (e.g., a mammalian host cell) include calcium phosphate precipitation, lipofection, particle bombardment, microinjection, electroporation, and other methods known in the art. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian (e.g., human) cells. Other viral vectors can be derived from lentivirus, poxviruses, herpes simplex virus I, adenoviruses and adeno-associated viruses, and other viral vectors known in the art. See, for example, U.S. Pat. Nos. 5,350,674 and 5,585,362, the contents of each of which is herein incorporated by reference in its entirety.

Methods for introducing a DNA and RNA polynucleotides of interest into a host cell include electroporation of cells, in which an electrical field is applied to cells in order to increase the permeability of the cell membrane, allowing chemicals, drugs, or polynucleotides to be introduced into the cell. Adapter encoding DNA or RNA constructs may be introduced into mammalian or prokaryotic cells using electroporation.

In a preferred embodiment, electroporation of cells results in the expression of a CAR on the surface of T cells, NK cells, NKT cells. Such expression may be transient or stable over the life of the cell. Electroporation may be accomplished with methods known in the art including MaxCyte GT® and STX® Transfection Systems (MaxCyte, Gaithersburg, MD, USA).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristoyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristoyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5:505-510 (1991)). However, compositions that have different structures in solution than the normal vesicular structure are also encompassed. For example, the lipids can assume a micellar structure or merely exist as non-uniform aggregates of lipid molecules. Also contemplated are lipofectamine-nucleic acid complexes.

Regardless of the method used to introduce exogenous nucleic acids into a host cell, or the presence of the recombinant nucleic acid sequence in the host cell can routinely be confirmed through a variety of assays known in the art. Such assays include, for example, "molecular biological" assays known in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Reporter genes are used for identifying potentially transfected cells and for evaluating the functionality of regulatory sequences. In general, a reporter gene is a gene that is not present in or expressed by the recipient organism, tissue, or cell and that encodes a polypeptide whose expression is manifested by some easily detectable property, e.g., enzymatic activity. Expression of the reporter gene is assayed at a suitable time after the DNA has been introduced into the recipient cells. A non-limiting list of suitable reporter genes can include genes encoding luciferase, beta-galactosidase, chloramphenicol acetyl transferase, secreted alkaline phosphatase, or the green fluorescent protein gene (e.g., Ui-Tei et al., FEBS Lett. 479:79-82 (2000)). Suitable expression systems are known in the art and can be prepared using known techniques or obtained commercially. In general, the construct with the minimal 5' flanking region showing the highest level of expression of reporter gene is identified as the promoter. Such promoter regions can routinely be linked to a reporter gene and used to evaluate agents for the ability to modulate promoter-driven transcription.

A number of selection systems can be used in mammalian host-vector expression systems, including, but not limited to, the herpes simplex virus thymidine kinase, hypoxanthine-guanine phosphoribosyltransferase and adenine phosphoribosyltransferase (Lowy et al., Cell 22:817 (1980)) genes, which can be employed in tk, hgprt or aprt cells, respectively. Additionally, antimetabolite resistance can be used as the basis of selection for e.g., dhfr, gpt, neo, hygro, trpB, hisD, ODC (ornithine decarboxylase), and the glutamine synthase system.

Vf. Adapter Purification

Once an Adapter has been produced by recombinant expression, it can be purified by any method known in the art for purification of a recombinant protein, for example, by chromatography (e.g., ion exchange, affinity, and sizing column chromatography), centrifugation, differential solubility, or by any other standard technique for the purification of proteins. In additional embodiments, the Adapter is optionally fused to a heterologous polypeptide sequences described herein or otherwise known in the art to facilitate purification. More particularly, it is envisioned that ligands (e.g., antibodies and other affinity matrices) for Adapter affinity columns for affinity purification and that optionally, the Adapter or other components of the Adapter fusion composition that are bound by these ligands are removed from the composition prior to final preparation of the Adapter using techniques known in the art.

Vg. Chemical Synthesis of Adapters

In addition to recombinant methods, Adapter production may also be carried out using organic chemical synthesis of the desired polypeptide using a variety of liquid and solid phase chemical processes known in the art. Various automatic synthesizers are commercially available and can be used in accordance with known protocols. See, for example, Tam et al., J. Am. Chem. Soc. 105:6442 (1983); Merrifield, Science 232:341-347 (1986); Barany and Merrifield, The Peptides, Gross and Meienhofer, eds, Academic Press, New York, 1-284; Barany et al., Int. J. Pep. Protein Res. 30:705-

739 (1987); Kelley et al. in Genetic Engineering Principles and Methods, Setlow, J. K., ed. Plenum Press, NY. 1990, vol. 12, pp. 1-19; Stewart et al., Solid-Phase Peptide Synthesis, W.H. Freeman Co., San Francisco, 1989. One advantage of these methodologies is that they allow for the incorporation of non-natural amino acid residues into the sequence of the Adapter.

The Adapters that are used in the methods of the present invention may be modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (see, e.g., Creighton, Proteins: Structures and Molecular Properties, 2d Ed. (W.H. Freeman and Co., N.Y., 1992); Postranslational Covalent Modification of Proteins, Johnson, ed. (Academic Press, New York, 1983), pp. 1-12; Seifter, Meth. Enzymol. 182:626-646 (1990); Rattan, Ann. NY Acad. Sci. 663:48-62 (1992).) In specific embodiments, the peptides are acetylated at the N-terminus and/or amidated at the C-terminus.

Any of numerous chemical modifications may be carried out by known techniques, including, but not limited to acetylation, formylation, etc. Additionally, the derivative may contain one or more non-classical amino acids.

VI. Chimeric Antigen Receptors

As provided herein, chimeric antigen receptors (CARs) are multi-domain proteins that comprise an extracellular domain comprising an ADBD, a transmembrane domain, and an intracellular signaling domain. Such CARs can be expressed on the surface of cells (e.g., as described in Section VII and Section XI) and used in combination with Adapters (e.g., as described in Section V and Section XI), for example, to kill a target cell. In several embodiments, the ADBD is made up of, at least in part, a target-binding polypeptide as disclosed herein. In several embodiments, the intracellular signaling domain is selected from the group: a human CD3 zeta domain, 41BB domain, a CD28 domain and any combination thereof. Depending on the embodiment, the costimulatory signaling region comprises the intracellular domain of a costimulatory molecule selected from the group: CD27, CD28, 41BB, OX40, CD30, CD40, PD1, lymphocyte function-associated antigen-1 (LFA1), CD2, CD7, LIGHT, NKG2C, B7H3, a ligand that specifically binds with CD83, and any combination thereof. In several embodiments, the CAR comprises a fusion protein that includes an additional target-binding polypeptide. Also provided for are isolated nucleic acid sequences encoding CARs that include the target-binding polypeptides as part (or all) of the targeting region.

In some embodiments, the ADBD of a CAR comprises at least one alternative scaffold binding domain (e.g., a D domain or affibody) designed to impart binding specificity to a membrane bound CAR. A receptor comprising an alternative scaffold binding domain may be expressed by any cell type.

In one embodiment, the CAR is composed of the following elements: an extracellular domain, a transmembrane domain and a cytoplasmic domain wherein the cytoplasmic domain comprises the signaling domain. In another embodiment the CAR is composed of an extracellular domain and a transmembrane domain. In a further embodiment the CAR is comprised of an extracellular domain composed of one or more ADBDs with the same or different specificities. In one embodiment, the intracellular domain (e.g., the cytoplasmic domain) of the CAR comprises the intracellular domain of CD3 zeta chain. In another embodiment the intracellular signaling domain of the CAR is comprised of part of the intracellular domain of CD3 zeta chain. In a further embodiment, the intracellular domain of the CAR comprises the intracellular domain of CD3 zeta chain and a costimulatory signaling region. The costimulatory signaling region refers to a portion of the CAR comprising all or part of the intracellular domain of a costimulatory molecule. Costimulatory molecules and portions of these molecules that are able to confer costimulatory properties to a CAR are known in the art and can routinely be incorporated into the CAR. In addition, truncations or mutation to these intracellular signaling and costimulatory domains may be incorporated to further enhance or reduce receptor signaling. In preferred embodiments, a T cell is genetically modified to stably express a CAR. In such embodiments the cytoplasmic domain of the CAR can be designed to comprise the CD28 and/or 41BB signaling domain by itself or be combined with any other desired cytoplasmic domain(s) useful in the context of the invention. In one embodiment, the cytoplasmic domain of the CAR can be designed to further comprise the signaling domain of CD3-zeta. In one embodiment, the CAR comprises an extracellular domain, an extracellular protein linker with a transmembrane domain that passes through the cellular membrane (such as found in T cells or NK cells), and a cytoplasmic domain, optionally comprising multiple signaling modules. In several embodiments, the CAR may also comprise an epitope tag. In several embodiments, the cytoplasmic domain of the CAR can include but is not limited to CD3-zeta, 41BB and CD28 signaling modules and combinations thereof.

VIa. CAR Extracellular Antigenic Determinant Binding Domain

The CARs provided herein comprise one or more antigenic determinant binding domains (ADBDs). The ADBD of the CAR can be any ADBD described herein (e.g., as described in Section III and Section XI). An exemplary ADBD comprises a polypeptide, e.g., an antibody molecule (which includes an antibody, and antigen binding fragments thereof, e.g., an immunoglobulin, single domain antibody (sdAb), and a scFv), or a non-antibody scaffold (e.g., a D domain, or affibody).

Depending on the desired antigen(s) to be targeted, the extracellular domain of the CAR can be engineered to include one or more antigenic determinant binding domains (ADBDs) that specifically bind the desired antigen target(s). For example, in one embodiment, the CAR is engineered to target CD19 and a CD19-binding ADBD is incorporated into the extracellular domain of the CAR. Alternatively, an extracellular domain of a CAR may include more than one ADBD, thereby imparting multi-specificity or multi-valency to the CAR.

The choice of ADBDs in the extracellular domain of the CAR depends upon the identity of the cell or cells to be targeted. For example, the extracellular domain of the CAR may be engineered to specifically bind to cell surface proteins, such as a receptor, on the same cell or another cell. In other embodiments, the extracellular domain of the CAR is engineered to specifically bind to a soluble molecule, such as an immunoglobulin. In other embodiments the targets of interest bound by the CAR include those associated with viral, bacterial and parasitic infections, diseases and disorders of the immune system (e.g., autoimmune disease).

In other embodiments, the extracellular domain of the CAR contains one or more ADBDs that bind a ligand that acts as a cell surface marker on target cells associated with a cancer. In some embodiments, ADBD(s) target and bind a tumor or cancer antigen (e.g., a TAA, TSA, CAA, CSA or other tumor antigen described herein or otherwise known in the art). Accordingly, provided herein are methods for creating CAR, their use in creating chimeric cells such as, human T cells and natural killer cells, and the use of these chimeric T and NK cells in adoptive immunotherapy.

The choice of an ADBD can depend upon the type and number of ligands or receptors that define the surface of a target cell. For example, the ADBD may be chosen to recognize a ligand or receptor that acts as a cell surface marker on target cells associated with a particular disease state. Examples of cell surface markers that may act as ligands or receptors include a cell surface marker associated with a particular disease state, e.g., cell surface makers for viral diseases, bacterial diseases parasitic infections, autoimmune diseases and disorders associated with unwanted cell proliferation, e.g., a cancer, such as, a cancer described herein.

The target of interest specifically bound by the ADBD of the CAR can be any molecule for which it is desirable for a CAR or an Adapter to bind, e.g., any of the ADs described in Section IIa and Section XI. In some embodiments, the ADBD binds to a target listed in Table 4. In further embodiments, the ADBD comprises 1, 2, 3, 4, 5, 1-5, 1-10, or more than 10, D domain sequences listed in Table 3 (e.g., SEQ ID NO: 44-1078, or 1079). In some embodiments, the ADBD comprises 1, 2, 3, 4, 5, 1-5, 1-10, or more than 10, different D domain sequences listed in Table 3.

In some embodiments, the ADBD binds to BCMA (e.g., a polypeptide comprising the sequence of SEQ ID NO: 5). In some embodiments, the ADBD comprises a DD sequence selected from the group: SEQ ID NO: 44-338, and 339.

In some embodiments, the ADBD binds to CS1 (e.g., a polypeptide comprising the sequence of SEQ ID NO: 1138). In some embodiments, the ADBD comprises a DD sequence selected from the group: SEQ ID NO: 780-794, and 795

In some embodiments, the ADBD binds to HER2 (e.g., a polypeptide comprising the sequence of SEQ ID NO: 42). In some embodiments, the ADBD comprises a DD sequence selected from the group: SEQ ID NO: 800-839, and 840

In some embodiments, the ADBD binds to CD123 (e.g., a polypeptide comprising the sequence of SEQ ID NO: 11). In some embodiments, the ADBD comprises a DD sequence selected from the group: SEQ ID NO: 340-772 and 773.

In some embodiments, the ADBD binds to AFP (e.g., a polypeptide comprising the sequence of SEQ ID NO: 14 or 15). In some embodiments, the ADBD binds to AFP p26 (e.g., a polypeptide comprising the sequence of SEQ ID NO: 16, 1117, 1118, 1119, 1120, 1121, 1122, or 1123). In some embodiments, the ADBD comprises a DD sequence selected from the group: SEQ ID NO: 841-983 and 984.

In some embodiments, the ADBD binds to CD137 (e.g., a polypeptide comprising the sequence of SEQ ID NO: 1081). In further embodiments, the ADBD comprises a DD sequence selected from the group: SEQ ID NO: 985-990 and 991.

In some embodiments, the ADBD binds to CD47. In further embodiments, the ADBD comprises a DD sequence selected from the group: SEQ ID NO: 992-995 and 996.

In some embodiments, the ADBD binds to CTLA4. In further embodiments, the ADBD comprises a DD sequence of SEQ ID NO: 997.

In some embodiments, the ADBD binds to DR5. In further embodiments, the ADBD comprises a DD sequence selected from the group: SEQ ID NO: 998-1006, 1070-1072, and 1073.

In some embodiments, the ADBD binds to KIR. In further embodiments, the ADBD comprises a DD sequence selected from the group: SEQ ID NO: 1007, 1008, and 1009.

In some embodiments, the ADBD binds to PDL1. In further embodiments, the ADBD comprises a DD sequence selected from the group: SEQ ID NO: 1010-1016, 1074-1078, and 1079.

In some embodiments, the ADBD binds to TIM3. In further embodiments, the ADBD comprises the DD sequence of SEQ ID NO: 1017.

In some embodiments, the ADBD binds to PD1. In further embodiments, the ADBD comprises a DD sequence selected from the group: SEQ ID NO: 1018, 1019, and 1020.

In some embodiments, the ADBD binds to CD137. In further embodiments, the ADBD comprises a DD sequence selected from the group: SEQ ID NO: 985-990 and 991.

In some embodiments, the ADBD binds to CD19 (e.g., a polypeptide comprising the sequence of SEQ ID NO: 3). In some embodiments, the ADBD binds to CD20 (e.g., a polypeptide comprising the sequence of SEQ ID NO: 6-9 or 10). In further embodiments, the ADBD comprises a DD sequence selected from the group: SEQ ID NO: 1030-1058, and 1059.

In some embodiments, the ADBD binds to CD22 (e.g., a polypeptide comprising the sequence of SEQ ID NO: 41). In further embodiments, the ADBD comprises a DD sequence selected from the group: SEQ ID NO: 1060-1068, and 1069.

In some embodiments, the ADBD binds an intracellular protein. In further embodiments, the ADBD comprises a DD sequence that binds an intracellular protein selected from the group: elastin, Tyk2, Jak1, Jak2, Jak3, LCK, ZAP-70, and GRB2.

In some embodiments, the ADBD binds to the extracellular domain (ECD) of human CD45 (e.g., residues 29-766 of SEQ ID NO: 1106).

In some embodiments, the ADBD binds to CD26 (e.g., residues 29-766 of SEQ ID NO: 1113).

In some embodiments, the ADBD binds to CD30 (e.g., residues 19-379 of SEQ ID NO: 1114).

In some embodiments, the ADBD binds to CD33 (e.g., residues 18-259 of SEQ ID NO: 1115).

In some embodiments, the ADBD binds to CD38 (e.g., residues 43-300 of SEQ ID NO: 1116).

In some embodiments, the ADBD binds a tumor antigen or cancer antigen that comprises one or more antigenic cancer epitopes immunologically recognized by tumor infiltrating lymphocytes (TIL) derived from a cancer or tumor of a mammal.

In some embodiments, the ADBD binds an AD expressed on the surface of an immune effectore cell.

In some embodiments, the CAR binds to an AD (e.g., in an Adapter and/or on a target cell) that is present in a naturally occurring protein or other molecule. In some embodiments, the CAR binds to an AD that is endogenous to humans.

In some embodiments, a CAR provided herein comprises an ADBD (e.g., an antibody fragment or ASBD) that binds to a MHC presented-peptide. Normally, peptides derived from endogenous proteins fill the pocket of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigenic determinants in the context of human leukocyte antigen (HLA)-A1 or HLA-A2 have been described (see, e.g., Sastry et al., J. Virol. 85 (5): 1935-1942 (2011); Sergeeva et al., Blood 117 (16): 4262-4272 (2011); Verma et al., J. Immunol. 184 (4): 2156-2165 (2010); Willemsen et al., Gene Ther. 8 (21): 1601-1608 (2001); Dao et al., Sci. Transl. Med. 5 (176): 176ra33 (2013); Tassev et al., Cancer Gene Ther. 19 (2): 84-100 (2012)). For example, TCR-like antibody can be identified from screening a library, such as a human scFv phage displayed library. Accordingly, in some embodiments, the disclosure provides a CAR that comprises an ADBD that binds to a MHC presented peptide of a molecule selected from any tumor antigen described above that is expressed intracellularly, e.g., p53, BCR-Ab1, Ras, K-ras, NY-ESO-1, and c-met.

In some embodiments, the CAR comprises an ADBD that is an antibody or an antigen-binding fragment thereof. In some embodiments, the CAR comprises an ADBD that is a scFv. In some embodiments, the CAR comprises an ADBD that is an alternative scaffold binding domain. In some embodiments, the CAR comprises an ADBD that is a D domain. In some embodiments, the CAR comprises a T cell receptor, or an antigen-binding fragment thereof.

Also provided herein are CAR wherein the CAR comprises a plurality of ADBDs. In some embodiments, the CAR comprises a plurality of the same ADBD. In some embodiments, the CAR comprises a plurality of different ADBDs. In some embodiments, the CAR comprises a plurality of ADBDs that bind the same antigenic determinant. In some embodiments, the CAR comprises a plurality of ADBDs, wherein the binding domains bind to different ADs. In some embodiments, the CAR comprises a plurality of ADBDs, wherein the binding domains bind to different ADs on the same cell. In some embodiments, the CAR comprises a plurality of ADBDs, wherein the binding domains bind to different ADs on different cells.

In some embodiments, a CAR comprises a plurality of, e.g., 2, 3, 4, 5, or more than 5, ADBDs (e.g., D domains, affibodies, or scFvs), wherein each ADBD(s) are able to bind to a target antigen. In one embodiment, two or more of the ADBDs of a CAR can bind to different ADs. In an additional embodiment, two or more of the ADBDs of the CAR can bind to the same antigen, e.g., the same or different epitopes on the same antigen. In one embodiment, a plurality of ADBDs of the CAR are linked to each other, e.g., the C-terminus of a first ADBD is linked to the N-terminus of a second ADBD. In an embodiment, the C-terminus of a first ADBD is linked to the N-terminus of a second ADBD by a covalent bond, e.g., a peptide bond.

In some embodiments, a linker or hinge region is contained between one or more of the ADBDs, e.g., a linker or hinge region is located between the C-terminus of a first ADBD and the N-terminus of a second ADBD. By way of example, an antigen binding member comprising two ADBDs (e.g., $ADBD_1$ and $ADBD_2$) can be arranged in the following configuration: [$ADBD_1$]-[linker/hinge]-[$ADBD_2$]. Additional ADBDs can be added in a similar manner, optionally with linker or hinge regions located between the C-terminus of an ADBD and the N-terminus of the next ADBD. Linkers or hinge regions suitable for use in linking a plurality of antigen binding members are flexible, non-cleavable, and allow near-free motion of each ADBD independent from the other ADBDs to encourage binding with multiple target ADs simultaneously. Any flexible linker or hinge region known in the art can be used. Examples of linkers include peptide linkers comprising glycine and serine residues, e.g., (GGGGS)n, where n is a positive integer equal to or greater than 1, e.g., n=1, 2, 3, 4, 5, 6, 7, 8, 9, or 10 (SEQ ID NO: 43).

VIb. Extracellular Spacer Domain

In some embodiments, the CARs comprise an extracellular spacer domain. As used herein, the term "extracellular spacer domain" or "ESD" refers to a polypeptide sequence of a CAR disposed between the ADBD and the transmembrane domain. In an embodiment the extracellular spacer domain allows sufficient distance from the outer surface of the cell and the ADBD as well as flexibility to minimize steric hindrance between the cell and the ADBD.

In particular embodiments, the extracellular spacer domain is sufficiently short or flexible that it does not interfere with engagement of the cell that includes the CAR with a cell bearing an AD, e.g., a target cell. In an embodiment, the extracellular spacer domain is from 2 to 20, 5 to 15, 7 to 12, or 8 to 10 amino acids in length. In some embodiments, the ESD domain includes at least 50, 20, or 10 residues. In some embodiments the ESD is 10 to 300, 10 to 250, or 10 to 200 residues in length.

In some embodiments the distance from which the ESD extends from the cell is sufficiently short that the hinge does not hinder engagement of the CAR ADBD with the surface of a target cell. In some embodiment the ESD extends less than 20, 15, or 10 nanometers from the surface of the cytotoxic cell. Thus, suitability for an ESD can be influenced by both linear length, the number of amino acid residues and flexibility of the ESD. By way of example, an IgG4 ESD can be as long as 200 amino acids in length, but the distance it extends from the surface of the cytotoxic cell is smaller due to Ig-domain folding. A CD8 alpha ESD, which is ~43 amino acids at ~8 nm in length. In contrast, the IgG4 C2 & C3 ESD is ~ 200 amino acids in length, but has a distance from the cytotoxic cell surface that is comparable to that of the CD8 alpha ESD. While not wishing to be bound by theory, the similarity in extension is influenced by flexibility.

In some embodiments, the extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof. Additional examples of extracellular spacer domains include but are not limited to CD8a hinge, and artificial spacers made of polypeptides which may be as small as, for example, Gly3 or CH1 and CH3 domains of IgGs (such as human IgG4). In some embodiments, the extracellular spacer domain is any one or more of (i) a hinge, CH2 and CH3 regions of IgG4, (ii) a hinge region of IgG4, (iii) a hinge and CH2 of IgG4, (iv) a hinge region of CD8a, (v) a hinge, CH2 and CH3 regions of IgG1, (vi) a hinge region of IgG1 or (vi) a hinge and CH2 region of IgG1. Other extracellular spacer domains will be apparent to those of skill in the art and may be used in connection with alternate embodiments provided herein.

In some embodiments, the ESD is a naturally occurring sequence. In some embodiments, the ESD of the CAR corresponds to an ESD from a human protein, a fragment thereof, or a short oligo- or polypeptide linker. In some embodiments, the CAR ESD corresponds to a human Ig (immunoglobulin) ESD (hinge), or fragment thereof. In one embodiment, the ESD comprises (e.g., consists of) the amino acid sequence of the IgG4 ESD. In one embodiment, for example, the hinge comprises (e.g., consists of) the amino acid sequence of the IgD hinge. In some embodiments, the hinge can be a human CD8 hinge, or fragment thereof. In one embodiment, for example, the hinge comprises (e.g., consists of) the amino acid sequence of the CD8 hinge.

In some embodiments, the ESD is an artificial sequence. In one embodiment, the ESD is a short oligopeptide linker comprising a glycine-serine doublet.

In some embodiments, the CARs do not contain an extracellular spacer domain.

VIc. Transmembrane Domain

The term "transmembrane domain" (TMD) as used herein refers to the region of a cell surface expressed protein, such as a CAR, which spans the plasma membrane. In some embodiments, the TMD links an extracellular sequence, e.g., an extracellular ADBD, and an intracellular sequence, such as an intracellular signaling domain. In some embodiments, the transmembrane domain of the CAR is the transmembrane region of a transmembrane protein (for example Type I transmembrane proteins), an artificial hydrophobic sequence or a combination thereof. Other transmembrane domains will be apparent to those of skill in the art and may be used in connection with alternate embodiments of the invention.

The CAR can be designed to contain a transmembrane domain that is fused to the extracellular domain of the receptor. As described above, the fusion of the extracellular and transmembrane domains can be accomplished with or without a linker. In one embodiment, the transmembrane domain that is naturally associated with one of the domains in the CAR is used. In a specific embodiment, the transmembrane domain in the CAR is the CD8 transmembrane domain. In some instances, the transmembrane domain of the CAR comprises the CD8 hinge domain. In some embodiments, the transmembrane domain is selected or modified by amino acid substitution to promote or inhibit association with other surface membrane proteins.

The transmembrane domain can be derived either from a natural or from a synthetic source. Where the source is natural, the domain can be derived from any membrane-bound or transmembrane protein. Transmembrane regions of particular use for the purposes herein may be derived from (i.e., comprise at least the transmembrane region(s) of) a member selected from the group: the alpha, beta or zeta chain of the T cell receptor; CD28, CD3 epsilon, CD45, CD4, CD5, CD8, CD9, CD16, CD22, CD33, CD37, CD64, CD80, CD86, CD134, CD137, and CD154. In some embodiments, the transmembrane domain is derived from the transmembrane region(s) of a NKR. In further embodiments, the transmembrane domain is derived from the transmembrane region of a molecule selected from the group consisting of, KIRDS2, OX40, TNFR2, LFA1 (CD11a, CD18), ICOS, 41BB, GITR, LTBR, BAFFR, HVEM, NKp80 (KLRF1), IL2R beta, IL2R gamma, IL7R α, ITGA1, ITGA4, ITGA6, ITGAD, ITGAE, ITGAL, ITGAM, ITGB7, VLA1, VLA6, IA4, ITGAX, CD11c, ITGB1 CD27, CD29, ITGB2, CD2, CD11a, CD11b, CD11d, CD18, CD19, CD40, CD49a, CD49d, CD49f, CD84, CD96, CD100, CD103, CD160, CD162, CD226, CD229, CEACAM1, CRTAM, PSGL1, SLAM (SLAMF1), SLAMF4, SLAMF6 (NTB-A, Ly108), SLAMF7, SLAMF8, SELPLG, and PAG/Cbp. Alternatively, the transmembrane domain can be synthetic, and preferably predominantly comprises hydrophobic residues such as leucine and valine. In further embodiments, the transmembrane domain comprises the triplet of FWV (phenylalanine, tryptophan and valine) at each end of the transmembrane domain.

Exemplary NKR domains, e.g., transmembrane, hinge or stem, or intracellular (e.g., cytoplasmic) domains (identified by the NKR from which the domain is derived) Killer immunoglobulin KIR2DL1 receptors (KIRs) include KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3, KIR2DP1, KIR2DP1, NCRs, NKp30, NKp44, NKp46, SLAM; Receptors SLAM, CD48, CD229, 2B4, CD84, NTB-A, CRACC, BLAME, CD2F-10, SLAMF6, SLAMF7; Fc-binding Receptors CD16, FcgRIII, CD64, Ly49; Receptors Ly49, Lectin-related NK Ly49A cell receptor, Ly49C; other NK receptors NKG2D, CD160 (TM containing splice variant(s)) DNAM1, CRTAM, CD27, PSGL1, CD96, CD100, NKp80, CEACAM1, and CD244.

VId. Intracellular Signaling Domain

Described herein are intracellular signaling domains that can be used in a chimeric antigen receptor (CAR) according to the present invention.

"Intracellular signaling domain" (ISD) or "cytoplasmic domain" as used herein refer to the portion of the CAR which transduces the effector function signal and directs the cell to perform its specialized function (e.g., cytolytic activity and helper activity, including cytokine secretion).

The cytoplasmic domain (i.e., intracellular signaling domain) of a CAR is responsible for activation of at least one of the normal effector functions of an immune cell engineered to express a CAR. The term "effector function" refers to a specialized function of a cell. The effector function of a T cell, for example, includes cytolytic activity and helper activity including the secretion of cytokines. Thus the term "intracellular signaling domain" refers to the portion of a CAR protein which transduces the effector function signal and directs the cell to perform a specialized function. While typically the entire intracellular signaling domain corresponding to a naturally occurring receptor can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In one embodiment, an intracellular signaling domain in the CAR includes the cytoplasmic sequences of the T cell receptor (TCR) and also the sequence of co-receptors that act in concert to initiate signal transduction following antigen receptor engagement, or any derivative or variant of these sequences that has functional capability. Examples of domains that transduce an effector function signal include but are not limited to the ζ chain of the T cell receptor complex or any of its homologues (e.g., η chain, FcsRly and β chains, MB 1 (Iga) chain, B29 (Ig) chain, etc.), human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T cell transduction, such as CD2, CD5 and CD28.

In some embodiments, the intracellular signaling domain of the CAR produces an intracellular signal when an extracellular domain (e.g., an ADBD) to which it is fused, binds a cognate AD. The Intracellular signaling domains of the CAR can include primary intracellular signaling domains and costimulatory signaling domains. In one embodiment, the CAR is constructed for expression in an immune cell (e.g., a T or NK cell), such that the expressed CAR comprises a domain such as a primary intracellular signaling domain and/or costimulatory signaling domain, that is derived from a polypeptide typically associated with the immune cell. For example, in some embodiments, the CAR is for expression in a T cell and comprises a 41BB domain and a CD3 zeta domain. In another embodiment, the CAR molecule is constructed for expression in an immune cell such that the expressed CAR comprises a domain that is derived from a polypeptide that is not typically associated with the immune cell. For example, in some embodiments the CAR for expression in a T cell comprises a KIR domain derived from a NK cell. In an alternative embodiment, the CAR for expression in an NK cell comprises a 41BB domain and a CD3 zeta domain derived from a T cell (See e.g. WO2013/033626, incorporated herein by reference).

The intracellular signaling domain of the CAR comprises sufficient primary stimulatory molecule sequence to produce an intracellular signal, e.g., when an ADBD to which it is fused binds a cognate AD. In particular embodiments, the intracellular signal of the CAR mediates a T cell response selected from the group: proliferation, cytokine secretion, killing, activation, and differentiation.

In one embodiment, the intracellular signaling region of the CAR comprises a domain that contains an immunoreceptor tyrosine-based activation motif (ITAM). In a further embodiment, the CAR intracellular signaling region comprises ITAM containing domain from a molecule selected from: TCR zeta (CD3 zeta), FcR gamma (FCER1G), Fc gamma RIIa, FcR beta (FCER1B), CD3 gamma, CD3 delta, CD3 epsilon, CD3 gamma, CD5, CD22, CD79a, CD79b, DAP10, DAP12, CD32 (Fc gamma RIIa), CD79a, and CD79b. In a specific embodiment, the intracellular signaling domain of the CAR comprises a CD3 zeta signaling domain. In another specific embodiment, the intracellular signaling domain of the CAR comprises a DAP12 signaling domain. In some embodiments, the ITAM containing signaling domain has at least 70, 75, 80, 85, 90, 95, 98, or 99% sequence identity with, or differs by no more than 30, 25, 20, 15, 10, 5, 4, 3, 2, or 1 amino acid residues from the corresponding residues of a naturally occurring ITAM containing domain.

Examples of ITAM containing primary cytoplasmic signaling sequences that are of particular use in the invention include those derived from TCR zeta, FcR gamma, FcR beta, CD3 gamma, CD3 delta, CD3 epsilon, CD22, CD79a, CD79b, and CD66d. It is particularly preferred that a cytoplasmic signaling molecule in the CAR comprises a cytoplasmic signaling sequence derived from CD3 zeta.

In a preferred embodiment, the cytoplasmic domain of the CAR comprises the CD3-zeta signaling domain by itself or combined with any other desired cytoplasmic domain(s) useful in the context of the CAR. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 41BB (CD 137), OX40, CD30, CD40, PD1, ICOS, lymphocyte function-associated antigen-1 (LFA1), CD2, CD7, LIGHT, NKG2C, B7H3, TIM1, and LAG3.

"Co-stimulatory domain" (CSD) as used herein refers to the portion of the CAR which enhances the proliferation, survival and/or development of memory cells. The CAR may comprise one or more co-stimulatory domains. Each co-stimulatory domain comprises the costimulatory domain of any one or more of, for example, a member of the TNFR superfamily, selected from CD28, CD137 (41BB), CD134 (OX40), Dap10, CD27, CD2, CD5, ICAM1, LFA1 (CD1 1a/CD18), Lck, TNFRI, TNFRII, Fas, CD30, and CD40 or a combination thereof. Other co-stimulatory domains (e.g., from other proteins) will be apparent to those of skill in the art and may be used in connection with alternate embodiments of the invention.

In some embodiments, the intracellular domain of the CAR comprises an ITAM containing domain and a costimulatory signaling domain that comprises a functional fragment or analog of a costimulatory molecule that is sufficient to produce an intracellular signal when an extracellular ADBD to which it is fused, binds cognate ligand. In some embodiments, the CAR comprises a costimulatory signaling domain corresponding to that found in a molecule selected from: CD137 (41BB), OX40, LIGHT, TNFR2, TRANCE/RANKL, GITR, BAFFR, HVEM, B7H3, CDS, IL2R beta, IL2R gamma, IL7R alpha, ITGA4, ITGA6, ITGAD, ITGAE, ITGAL, ITGAM, ITGAX, ITGB1, ITGB2, ITGB7, VLA1, VLA6, C49f, IA4, LFA1, CD2, CD4, CD7, CD8 alpha, CD8 beta, CD11A, CD11B, CD11C, CD11D, CD18, CD19, CD27, CD28, CD29, CD30, CD40, CD49A, CD49D, CD69, CD84, CD96, CD100, CD103, CD150, CD160, CD162, CD226, CD229, CD278, ICAM1, CEACAM1, CRTAM, PSGL1, SLAMF1, SLAMF4, SLAMF6, SLAMF7, SLAMF8, LTBR, LAT, GADS, PAG/Cbp, SLP76, NKG2C, NKp30, NKp44, NKp46 and NKp80.

In some embodiments, the CAR comprises a costimulatory domain corresponding to that found in a molecule selected from the group consisting 41BB, CD28, CD27, ICOS, and OX40.

In some embodiments, the CAR comprises a plurality of costimulatory domains. In particular embodiments, the CAR comprises the following costimulatory signaling domains, from the extracellular to intracellular direction: 41BB-CD27, CD27-41BB, 41BB-CD28, CD28-41BB, OX40-CD28, CD28-OX40, CD28-41BB; or 41BB-CD28.

In some embodiments the costimulatory signaling domain of the CAR has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring costimulatory domain.

Polypeptide linkers may be positioned between adjacent elements of the CAR. For example linkers may be positioned between adjacent ADBDs or between an ADBD and the transmembrane domain or between the transmembrane domain and the cytoplasmic domain or between adjacent cytoplasmic domains. The cytoplasmic signaling sequences within the cytoplasmic signaling portion of the CAR may be linked to each other in a random or specified order. Optionally, a short linker, preferably between 2 and 10 amino acids in length may form the linkage. A glycine-serine doublet provides a particularly suitable linker.

VIe. Expression of CARs

CARs are intentionally cell associated and used in the context of the cell in which they are expressed. One particular embodiment relates to a strategy of adoptive cell transfer of T cells which have been transduced to express a CAR. Preferably, the cell can be genetically modified to stably express a CAR on its surface, conferring novel target specificity that is MHC independent.

A variety of viral-derived vectors can be used in applications in which viruses are used for transfection and integration into a mammalian cell genome. Viruses, which are useful as vectors include, but are not limited to, retroviruses, adenoviruses, adeno-associated viruses, herpes viruses, and lentiviruses. Lentiviral vectors are particularly suitable to achieving long-term gene transfer (e.g., adoptive T cell immune therapy) since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, a suitable vector contains an origin of replication functional in at least one organism, a promoter sequence, convenient restriction endonuclease sites, and one or more selectable markers, (e.g., Intl. Appl. Publ. Nos. WO 01/96584 and WO 01/29058; and U.S. Pat. No. 6,326,193). Several vector promoter sequences are available for expression of the transgenes. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is EF-1a. However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters include, but are not limited to a metallothionein promoter, a glucocorticoid promoter, a progesterone promoter, and a tetracycline promoter.

In order to assess the expression of a CAR polypeptide or portions thereof, the expression vector introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and are otherwise known in the art.

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments provided herein, any number of T cell lines available in the art, may be used.

A full discussion of T cell isolation, culturing, activation and expansion methods may be found in WO 2012079000, the contents of which is herein incorporated by reference in its entirety.

Additionally provided is a host cell comprising nucleic acids encoding a CAR described herein. Further provided is a composition comprising a nucleic acid sequence encoding the CAR.

VII. Chimeric Antigen Receptor Cells

The disclosure provides compositions and methods to regulate the specificity and activity of cells modified to express one or more different CAR(s).

In some embodiments, cells are engineered to express one or more of the CARs described herein. Such CAR-containing cells, referred to as "CAR cells" have uses in monotherapy and in combination therapies that include other therapeutic agents, such as the Adapters described herein, for example, to kill a target cell.

In some embodiments, a CAR cell comprises a nucleic acid sequence encoding a CAR, wherein the CAR comprises an extracellular domain made up of, at least in part, an ADBD that binds a target of interest, a transmembrane domain, and a signaling domain. In several embodiments, the encoded CAR polypeptide binds specifically to a tumor antigen (and thus functions to deliver the cell expressing the CAR to the tumor). In several embodiments, the tumor antigen bound by the CAR is associated with a hematologic malignancy. In additional embodiments, tumor antigen bound by the CAR is associated with a solid tumor. In further embodiments the CAR is engineered to bind both solid and hematologic tumors. Depending on the embodiment, the cell expressing the CAR can be an immune effector cell (e.g., a T cell or a natural killer (NK) cell) or another cell type. In several embodiments, the cell (whether T cell, NK cell or other cell type) exhibits an anti-tumor immunity when the antigen-binding domain of the CAR binds to its targeted tumor antigen(s).

In some embodiments, prior to expansion and genetic modification or other modification, a source of cells (e.g., T cells or natural killer cells), can routinely be obtained from a subject using techniques known in the art. The term "subject" is intended to include living organisms in which an immune response can be elicited (e.g., mammals). T cells can be obtained from sources, including but not limited to peripheral blood mononuclear cells, bone marrow, lymph node tissue, cord blood, thymus tissue, tissue from a site of infection, ascites, pleural effusion, spleen tissue, and tumors.

In some embodiments, the CAR cell is capable of killing a target cell, e.g., when the ADBD of the CAR interacts with an AD, which can be present on the surface of a target cell and/or in an Adapter. In some embodiments, the CAR cell is capable of degranulating, e.g., when the ADBD of the CAR interacts with an AD, which can be present on the surface of a target cell and/or in an Adapter. In some embodiments, the CAR cell is capable of secreting a cytokine or cytokines, e.g., when the ADBD of the CAR interacts with an AD, which can be present on the surface of a target cell and/or in an Adapter.

In some embodiments, the CAR-containing cell is an immune cell. In some embodiments, the CAR-containing cell is an immune effector cell. In further embodiments, the CAR-containing immune cell is a cytotoxic cell. In further embodiments, the cytotoxic cell is selected from a T cell, NK cell, or a cultured NK cell (e.g., a NK92 cell).

In certain embodiments, an immune effector cell comprises a cell surface receptor for an immunoglobulin or other peptide binding molecule, such as a receptor for an immunoglobulin constant region and including the class of receptors commonly referred to as "Fc receptors" ("FcR" s). A number of FcRs have been structurally and/or functionally characterized and are known in the art, including FcR having specific abilities to interact with a restricted subset of immunoglobulin heavy chain isotypes, or that interact with Fc domains with varying affinities, and/or which may be expressed on restricted subsets of immune effector cells under certain conditions (e.g., Kijimoto-Ochichai et al., Cell Mol. Life. Sci. 59:648 (2002); Davis et al., Curr. Top. Microbiol. Immunol. 266:85 (2002); Pawankar, Curr. Opin. Allerg. Clin. Immunol. 1:3 (2001); Radaev et al., Mol.

Immunol. 38:1073 (2002); Wurzburg et al., Mol. Immunol. 38:1063 (2002); Sulica et al., Int. Rev. Immunol. 20:371 (2001); Underhill et al., Ann. Rev. Immunol. 20:825 (2002); Coggeshall, Curr. Dir. Autoimm. 5:1 (2002); Mimura et al., Adv. Exp. Med. Biol. 495:49 (2001); Baumann et al., Adv. Exp. Med. Biol. 495:219 (2001); Santoso et al., Ital. Heart J. 2:811 (2001); Novak et al., Curr. Opin. Immunol. 13:721 (2001); Fossati et al., Eur. J. Clin. Invest. 31:821 (2001)), the contents of each of which is herein incorporated by reference in its entirety.

Cells that are capable of mediating ADCC are examples of immune effector cells. Other immune effector cells include Natural Killer cells, tumor-infiltrating T lymphocytes (TILs), cytotoxic T lymphocytes, and granulocytic cells such as cells that comprise allergic response mechanisms. Immune effector cells thus include, but are not limited to, cells of hematopoietic origin including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), as well as quiescent, activated, and mature forms of such cells. Other immune effector cells may include cells of non-hematopoietic origin that are capable of mediating immune functions, for example, endothelial cells, keratinocytes, fibroblasts, osteoclasts, epithelial cells, and other cells. Immune effector cells can also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

In some embodiments, the CAR-containing cell is a T cell. In some embodiments, the CAR-containing cell is a NK cell. In additional embodiments, the CAR-containing cell is a B cell. Other immune cells, and/or combinations of different immune cell types can optionally be used. In some embodiments, combinations of cell types (e.g., NK cells and T cells) are advantageous because they act synergistically to treat a disease or condition (e.g., a hyperproliferative disease such as cancer). When combinations are used, the various cell types can target the same, different, or overlapping tumor antigenic determinants.

In some embodiments, the CAR-containing immune cell is a T cell, and the binding of the ADBD of the CAR to a cognate ligand (i.e., target of interest) stimulates the T cell to initiate intracellular signaling. In further embodiments, binding of the ADBD of the CAR to a cognate ligand stimulates the T cell to produce cytokines and degranulate, leading to the cytotoxic effects on the cell expressing the target of interest on its surface (e.g., a cancer cell). In additional embodiments, the CAR-containing T cell proliferates in response to binding the target of interest. In some embodiments, the activity of the CAR-containing T cell does not result in the T cells exhibiting a phenotype associated with T cell exhaustion. In some embodiments where the CAR cell is a T cell, the transmembrane domain of the CAR comprises 41BB or CD28, and the cytoplasmic domain comprises a T cell receptor alpha, beta, or zeta chain.

In some embodiments, the CAR-containing immune cell is a NK cell, the transmembrane domain comprises CD28, and the cytoplasmic domain comprises a zeta chain of a T cell receptor.

In some embodiments, the CAR-containing immune cell has been engineered to bind to a target of interest expressed by a cancer cell. In further embodiments the CAR-containing cell binds a tumor antigen selected from the group: CD137, PDL1, CD123, CTLA4, CD47, KIR, DR5, TIM3, PD1, EGFR, TCR, CD19, CD20, CD22, ROR1, mesothelin, CD33, IL3Ra, cMet, PSMA, Glycolipid F77, EGFRVIII, GD2, NY-ESO-1, and MAGE A3. In further embodiments the CAR-containing cell binds 2, 3, 4, 5 or more of the above tumor antigens.

In some embodiments, the CAR of the CAR cell binds two or more targets of interest. In further embodiments, the CAR further comprises a second polypeptide comprising the amino acid of SEQ ID NO: 17-26, or 27, the polypeptide being able to specifically bind a second target of interest expressed by a cancer cell, and wherein the second polypeptide's specific binding the second target of interest is greater than binding of a polypeptide according to SEQ ID NO: 1 to the second target of interest.

In some embodiments, the CAR cell is engineered to express an Adapter disclosed herein (e.g., as described in Section V and Section XI).

In additional embodiments, the CAR cell is engineered to express a second CAR. In some embodiments, the second CAR comprises an extracellular domain comprising an ADBD, a transmembrane domain, and an intracellular signaling domain. In an additional embodiment the second CAR is comprised of an extracellular domain composed of one or more ADBDs (e.g., as described in Section VI herein and in Section XI) with the same or different specificities. In some embodiments, the second CAR is able to transduce an effector function signal upon binding a target of interest. In further embodiments, the second CAR comprises an extracellular domain comprising an ADBD, and transmembrane or other cell-surface associating domain, but is unable to signal upon binding a target of interest.

In some embodiments the CAR cell is engineered such that the CAR coding sequence is site specifically introduced into a locus of a gene highly expressed in the corresponding host cell. In some embodiments the CAR coding sequence is introduced into a T cell receptor locus. In further embodiments, the CAR coding sequence is introduced into the T cell receptor a constant (TRAC) of the cell. Modified cells that lack expression of a functional TCR and/or HLA can routinely be obtained using any suitable means known in the art, including for example, siRNA, shRNA, CRISPR, TALEN, and/or ZFN.

In some embodiments, the immune effector cell can be an allogeneic immune effector cell, e.g., T cell or NK cell.

VIIa. Genetic Modifications of CAR Cells

To avoid or reduce the possibility that CAR cells disclosed herein target an immune response (e.g., kill) to themselves, a CAR cell can be genetically modified to reduce or eliminate the expression of one or more AD targeted by the CAR cell directly by a CAR provided herein or indirectly through an Adaptor provided herein. For example, a CAR cell provided herein with an ADBD that specifically binds to an AD of human CD45 or a CAR cell provided herein suited to be used in combination with an Adapter comprising an ADBD that specifically binds to an AD of human CD45 can be engineered to reduce or eliminate the expression of the human CD45 AD recognized by the ADBD. In some embodiments, the CAR cell is a human immune effector cell.

In some embodiments, the CAR cell comprises a genetic modification that reduces or eliminates the expression of one AD bound by a CAR or Adapter provided herein. In some embodiments, the CAR cell comprises a genetic modification that reduces or eliminates the expression of more than one AD bound by a CAR or Adapter provided herein. In some embodiments, the CAR cell comprises more than one genetic modification that reduces or eliminates the expression of more than one AD bound by a CAR or Adapter provided herein. In some embodiments, the more then one AD is comprised by a single antigen. In some embodiments, the AD is a human CD45 AD. In some embodiments, the the AD is a human CD26, CD30, CD33, or CD38 AD. In some embodiments, the CAR cell is a human immune effector cell.

In some embodiments, the genetic modification reduces expression of the AD by about 50%, about 60%, about 70%, about 80%, about 90%, about 95% compared to a reference cell without the genetic modification. In some embodiments, the genetic modification eliminates expression of the AD.

In some embodiments, the genetic modification reduces expression of the polypeptide comprising the AD by about 50%, about 60%, about 70%, about 80%, about 90%, about 95% compared to a reference cell without the genetic modification. In some embodiments, the genetic modification eliminates expression of the polyeptide comprising the AD. In some embodiments, the AD is a human CD45 AD. In some embodiments, the AD is a human CD26, CD30, CD33, or CD38 AD.

In some embodiments, the genetic modification is a deletion, insertion, or substitution in a gene or fragment thereof encoding the AD. In some embodiments, the genetic modification is a deletion, insertion, or substitution in a gene or fragment thereof encoding the AD that eliminates expression of the AD. In some embodiments, the AD is a human CD45 AD. In some embodiments, the AD is a human CD26, CD30, CD33, or CD38 AD.

In some embodiments, the genetic modification is a substitution of a gene or fragment thereof encoding a polypeptide comprising the AD with a nucleotide sequence encoding a homologue, variant, or derivative of the polypeptide comprising the AD, wherein the encoded homologue, variant, or derivative does not comprise the AD. In some embodiments, the homologue is a non-human primate homologue. In some embodiments, the homologue is derived from rhesus macaque. In some embodiments, the homologue is derived from cynomolgus monkey. In some embodiments, the variant is a naturally occurring variant. In some embodiments, the variant is a splice variant. In some embodiments, the variant ihas altered glycosylation pattern. In some embodiments, the variant or derivative is capable of signaling. In some embodiments, the AD is a human CD45 AD. In some embodiments, the AD is a human CD26, CD30, CD33, or CD38 AD.

The genetic modification can reduce or eliminate the expression of any AD for which it is desirable for a CAR or an Adapter to bind, e.g., any of the ADs described in Section IIa and in Section XI.

The production of CAR cells comprising a genetic modification useful in practicing the provided methods may be carried out using a variety of standard techniques for recombinant DNA methodologies, genetic manipulation, and genome editing known in the art. Genetically modified CAR cells described herein that lack expression of an AD can routinely be obtained using any suitable means known in the art, including for example, siRNA, shRNA, CRISPR, TALEN, and/or ZFN. Methods for genetic manipulation of CAR cells is described, for example, in U.S. Patent Appl. Pub. 20170204372, which is encorporated herein by reference in its entirety.

In some embodiments the CAR cell is engineered to eliminate or reduce the expression of a functional T cell receptor (TCR) and/or human leukocyte antigen (HLA), e.g., HLA class I and/or HLA class II. Modified cells that lack expression of a functional TCR and/or HLA can routinely be obtained using any suitable means known in the art, including for example, siRNA, shRNA, CRISPR, TALEN, and/or ZFN.

In some embodiments, the CAR cell is engineered to eliminate or reduce the expression of a molecule that may decrease the ability of a CAR cell to mount an immune effector response. In further embodiments, the CAR cell is engineered to eliminate or reduce the expression of a molecule selected from: PD1, PDL1, CTLA4, TIM3, LAG3, VISTA, BTLA, TIGIT, LAIR1, CD160, 2B4 and TGFR beta. In some embodiments, the CAR cell has been engineered to eliminate or reduce the expression of 2, 3, 4, 5 or more of the above molecules. Modified cells that lack expression of one or more of the above molecules can routinely be obtained using any suitable means known in the art, including for example, siRNA, shRNA, CRISPR, TALEN, and/or ZFN.

In further embodiments, the CAR cell is engineered to eliminate or reduce the expression of one or more of (a) a functional TCR and an HLA; and (b) a molecule selected from: PD1, PDL1, CTLA4, TIM3, LAG3, VISTA, BTLA, TIGIT, LAIR1, CD160, 2B4 and TGFR beta. In further embodiments, the CAR cell has been engineered to eliminate or reduce the expression of 2, 3, 4, 5, 6 or more of the above molecules.

VIII. Compositions

Described herein are compositions comprising a CAR cell (e.g., as described in Section VII and Section XI) and an Adapter (e.g., as described in Section V and Section XI).

For example, in one embodiment a composition comprises (a) a cell expressing a chimeric antigen receptor (CAR), wherein the CAR comprises (i) an antigenic determinant binding domain (ADBD) that binds to a first antigenic determinant (AD) on a target cell, (ii) a transmembrane domain, and (iii) an intracellular domain; and (b) an Adapter which comprises (i) said first AD and (ii) an ADBD that binds to a second AD on said target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In one embodiment, a composition comprises (a) a cell expressing a chimeric antigen receptor (CAR), wherein the CAR comprises (i) an antigenic determinant binding domain (ADBD) that binds to a first antigenic determinant (AD) on a target cell, (ii) a transmembrane domain, and (iii) an intracellular domain; and (b) an Adapter which comprises (i) said first AD and (ii) an ADBD that binds to a second AD on a second target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In one embodiment, a composition comprises (a) a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) an Adapter which comprises (i) said first AD and (ii) an ADBD that binds to a second AD on a target cell. The CAR cell can be any CAR cell described herein (e.g., as described in Section VII and Section XI) and/or the Adapter can be any Adapter described herein (e.g., as described in Section V and Section XI). In some embodiments, the binding of the Adapter cross-links the second AD on the target cell or complexes containing the second AD. In some embodiments, the Adapter contains an ADBD that is derived from a non-naturally occurring scaffold. In some embodiments, the Adapter contains an AD that is not expressed by the target cell. In some embodiments the Adapter contains an AD is on a secreted protein. In some embodiments the Adapter contains an alfafetoprotein AD. In some embodiments, the AD of the Adapter is not a nuclear protein. In some embodiments, the CAR cell comprises a genetic modification that eliminates the expression of the first or second AD.

In one embodiment, a composition comprises (a) a cell expressing a chimeric antigen receptor (CAR), wherein the CAR comprises (i) an antigenic determinant binding domain (ADBD) that is an alternative scaffold binding domain (ASBD) that binds to a first antigenic determinant (AD), (ii) a transmembrane domain, and (iii) an intracellular domain; and (b) an Adapter which comprises (i) said first AD and (ii) an ADBD that binds to a second AD on a target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In one embodiment, a composition comprises (a) a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and (b) an Adapter which comprises (i) said first AD and (ii) an ADBD comprising an ASBD that binds to a second AD on a target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In one embodiment a composition comprises (a) a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; (b) an Adapter which comprises (i) said first AD and (ii) a D domain that binds to a second AD on a target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In one embodiment, the composition comprises (a) a cell expressing a chimeric antigen receptor (CAR), wherein the CAR comprises (i) a D domain that binds to a first antigenic determinant (AD), (ii) a transmembrane domain, and (iii) an intracellular domain; and (b) an Adapter which comprises (i) said first AD and (ii) an ADBD that binds to a second AD on a target cell. The CAR cell can be any CAR cell described herein (e.g., as described in Section VII and Section XI) and/or the Adapter can be any Adapter described in Section V and Section XI. In some embodiments, the CAR cell comprises a genetic modification that eliminates the expression of the first or second AD.

In one embodiment, a composition comprises (a) a cell expressing a chimeric antigen receptor (CAR), wherein the CAR comprises (i) a first D domain that binds to a first antigenic determinant (AD), (ii) a transmembrane domain, and (iii) an intracellular domain; and (b) an Adapter which comprises (i) said first AD and (ii) a second D domain that binds to a second AD on a target cell. The CAR cell can be any CAR cell described herein (e.g., as described in Section VII and Section XI) and/or the Adapter can be any Adapter described herein (e.g., as described in Section V and Section XI). In some embodiments, the CAR cell comprises a genetic modification that eliminates the expression of the first or second AD.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3ζ primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain.

In some embodiments, the CAR binds to an antigen selected from: CD45, CD26, CD30, CD33, and CD38. In some embodiments, the CAR binds to CD26. In some embodiments, the CAR binds to CD30. In some embodiments, the CAR binds to CD33. In some embodiments, the CAR binds to CD38. In further embodiments, the CAR binds to CD45.

In some embodiments, the CAR binds to an antigen selected from: CD19, CD22, CD123, BCMA, CS1, HER2, TACI, BAFFR, and PDL1. In further embodiments, the CAR binds to BCMA. In further embodiments, the CAR binds to CS1. In other embodiments, the CAR binds to CD123. In other embodiments, the CAR binds to CD19. In other embodiments, the CAR binds to CD22. In other embodiments, the CAR binds to TACI. In other embodiments, the CAR binds to BAFFR. In other embodiments, the CAR binds to PDL1. In other embodiments, the CAR binds to HER2.

In some embodiments, the CAR comprises 2 ADBDs that bind to separate targets. In further embodiments, the CAR binds to BCMA and CS1. In further embodiments, the CAR binds to CD19 and CD123. In other embodiments, the CAR binds to CD22 and CD123. In other embodiments, the CAR binds to PDL1 and CD123. In some embodiments, the CAR binds to CD45 and a second target. In certain embodiments, the CAR comprises a first ASBD that binds to BCMA and a second ASBD that binds to CS1. In other embodiments, the CAR comprises a first D domain that binds to BCMA and a second D domain that binds to CS1. In other embodiments, the CAR comprises a D domain that binds to BCMA and a scFv that binds to CS1. In other embodiments, the CAR comprises a D domain that binds to CS1 and a scFv that binds to BCMA. In certain embodiments, the CAR comprises a first ASBD that binds to CD19 and a second ASBD that binds to CD123. In other embodiments, the CAR comprises a first D domain that binds to CD19 and a second D domain that binds to CD123. In some embodiments, the CAR comprises a first D domain that binds to a CD45 AD and a second D domain that binds to a second AD. In other embodiments, the CAR comprises a D domain that binds to CD19 and a scFv that binds to CD123. In other embodiments, the CAR comprises a first ASBD that binds to CD22 and a second ASBD that binds to CD123. In other embodiments, the CAR comprises a first D domain that binds to CD22 and a second D domain that binds to CD123. In other embodiments, the CAR comprises a D domain that binds to CD22 and a scFv that binds to CD123. In some embodiments, the CAR comprises a first ASBD that binds to PDL1 and a second ASBD that binds to CD123. In some embodiments, the CAR comprises a first D domain that binds to PDL1 and a second D domain that binds to CD123. In some embodiments, the CAR comprises a D domain that binds to PDL1 and a scFv that binds to CD123. In some embodiments, the CAR comprises an ASBD that binds to CD19 and a scFv that binds to CD123.

In some embodiments, the Adapter comprises an AD of a tumor antigen. In further embodiments, the tumor antigen is selected from the group: BCMA, CD123, CD19, CD22, CS1, TACI, BAFFR, and PDL1. In further embodiments, the tumor antigen is HER2.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (d) bind to different antigens on different cells. In further embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD45. In other embodiments, the Adapter comprises an ADBD that binds to CD26. In some embodiments, the Adapter comprises an ADBD that binds to CD30. In other embodiments, the Adapter comprises an ADBD that binds to CD33. In other embodiments, the Adapter comprises an ADBD that binds to CD38. In some embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to HER2. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD19 and an ADBD that binds to CD123. In other embodiments, the Adapter comprises an ADBD that binds to BCMA and an ADBD that binds to CS1. In other embodiments, the Adapter comprises an ADBD that binds to CD22 and an ADBD that binds to CD123. In other embodiments, the Adapter comprises an ADBD that binds to PDL1 and an ADBD that binds to CD123. In some embodiments, the Adapter binds to a human CD45 AD and a second AD.

In some embodiments, the target cell is a tumor cell. In further embodiments, the tumor cell is selected from the group: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In further embodiments, the tumor cell is selected from the group: acute myeloid leukemia (AML), chronic lymphocytic leukemia (CLL), and multiple myeloma (MM). In some embodiments, the tumor cell is an AML tumor cell. In some embodiments, the tumor cell is an CLL tumor cell. In some embodiments, the tumor cell is an MM tumor cell.

In some embodiments, the target cell is a cancert cell. In further embodiments, the cancer cell is selected from the group: breast cancer, prostate cancer, ovarian cancer, pancreatic cancer, colon cancer, and lung cancer. In further embodiments, the cancer cell is breast cancer. In some embodiments, the cancer cell is ovarian cancer.

In some embodiments, the composition comprises at least two target cells. In some embodiments, at least one target cell is a tumor cell. In further embodiments, the first and second target cells are tumor cells. In certain embodiments, the first and second tumor cells are of the same tumor type. In other embodiments, the first and second tumor cells are of a different tumor type. In some embodiments, the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In some embodiments, the tumor cells are selected from: acute myeloid leukemia (AML), chronic lymphocytic leukemia (CLL), and multiple myeloma (MM).

In some embodiments, the cell expressing the CAR is an immune effector cell. In further embodiments, the immune effector cell is a T cell. In other embodiments, the immune effector cell is an NK cell. In some embodiments, the cell expressing the CAR kills the target cell. In some embodiments, binding of the Adapter to an AD blocks the activity of the antigen comprising the AD. In some embodiments, the cell expressing the CAR comprises a genetic modification that reduces or eliminates the expression of an AD described herein. In some embodiments, the cell expressing the CAR comprises a genetic modification that reduces or eliminates the expression of a human CD45 AD.

In one embodiment, the composition is within a patient, e.g., a human patient.

In some embodiments, the CAR cell binds to an AD that is present on both a target cell and an Adapter. In other embodiments, the CAR cell binds to an AD that is present on an Adapter, but is not present on a target cell. In some embodiments, the AD is a naturally occurring protein/molecule. In some embodiments, the AD is a human protein/molecule.

IX. Methods that Comprise Contacting a Target Cell

Described herein are methods of use comprising contacting a target cell with a CAR cell (e.g., as described above in Section VII and Section XI) and an Adapter (e.g., as described above in Section V and Section XI) or a composition (e.g., as described above in Section VIII and Section XI).

For example, in one embodiment, a method of delivering an immune response to a target cell comprises contacting the target cell with any of the compositions described herein (e.g., as described in Section VIII and Section XI). In another embodiment, a method of killing a target cell comprises contacting the target cell with any of the compositions described herein (e.g., as described in Section VIII and Section XI). As used herein, "contacting" can refer to contacting a target cell in vitro (e.g., in a cell culture) or contacting a target cell in vivo (e.g., in a patient).

In one embodiment, a method of delivering an immune response to a target cell comprises contacting a composition comprising a target cell with an Adapter, wherein (a) the composition comprising the target cell further comprises a cell expressing a CAR, wherein the CAR comprises (i) an antigenic determinant binding domain (ADBD) that binds to a first AD on said target cell, (ii) a transmembrane domain, and (iii) an intracellular domain; and (b) the Adapter comprises (i) said first AD and (ii) an ADBD that binds to a second AD on said target cell.

In one embodiment, a method of delivering an immune response to one or more target cells comprises contacting a composition comprising a first target cell with an Adapter, wherein (a) the composition comprising the target cell further comprises a cell expressing a chimeric antigen receptor (CAR), wherein the CAR comprises (i) an antigenic determinant binding domain (ADBD) that binds to a first AD on said first target cell, (ii) a transmembrane domain, and (iii) an intracellular domain; and (b) the Adapter comprises (i) said first AD and (ii) an ADBD that binds to a second AD on a second target cell.

In one embodiment, method of delivering an immune response to a target cell comprises contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that is an ASBD that binds to a first AD, (ii) a transmembrane domain, and (iii) an intracellular domain; and (b) the Adapter comprises (i) said first AD and (ii) an ADBD that binds to a second AD on said target cell.

In one embodiment, a method of delivering an immune response to a target cell comprises contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that binds to a first AD, (ii) a transmembrane domain, and (iii) an intracellular domain; and (b) the Adapter comprises (i) said first AD and (ii) an ADBD that is an ASBD that binds to a second AD on said target cell.

In one embodiment, a method of delivering an immune response to a target cell comprises contacting a composition comprising a target cell with a cell expressing a chimeric antigen receptor (CAR), wherein (a) a first antigenic determinant (AD) is present on the target cell; (b) the composition comprising the first target cell further comprises an Adapter comprising (i) said first AD and (ii) an antigenic determinant binding domain (ADBD) that binds to a second AD on the target cell; and (c) the CAR comprises (i) an ADBD that binds to said first AD on the target cell or the Adapter, (ii) a transmembrane domain, and (iii) an intracellular domain.

In one embodiment, a method of delivering an immune response to one or more target cells comprises contacting a composition comprising a target cell with a cell expressing a chimeric antigen receptor (CAR), wherein (a) a first AD is present on the first target cell; (b) the composition comprising the first target cell further comprises a second target cell and an Adapter comprising (i) said first AD and (ii) an antigenic determinant binding domain (ADBD) that binds to a second AD on a second target cell; and (c) the CAR comprises (i) an ADBD that binds to said first AD on the first target cell or the Adapter, (ii) a transmembrane domain, and (iii) an intracellular domain.

In one embodiment, a method of delivering an immune response to a target cell comprises contacting a composition comprising a target cell with a cell expressing a chimeric antigen receptor (CAR), wherein (a) a first antigenic determinant (AD) is present on the target cell; (b) the composition comprising the target cell further comprises an Adapter comprising (i) an antigenic determinant binding domain (ADBD) that binds to said first AD on said target cell and (ii) a second AD; and (c) the CAR comprises (i) an ADBD that is an ASBD that binds to said second AD, (ii) a transmembrane domain, and (iii) an intracellular domain.

In one embodiment, a method of delivering an immune response to a target cell comprises contacting a composition comprising a target cell with a cell expressing a chimeric antigen receptor (CAR), wherein (a) a first antigenic determinant (AD) is present on the target cell; (b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain.

In one embodiment, a method of killing a target cell comprises contacting a composition comprising a target cell with an Adapter, wherein (a) the composition comprising the target cell further comprises a cell expressing a CAR, wherein the CAR comprises (i) an antigenic determinant binding domain (ADBD) that binds to a first AD on said target cell, (ii) a transmembrane domain, and (iii) an intracellular domain; and (b) the Adapter comprises (i) said first AD and (ii) an ADBD that binds to a second AD on said target cell.

In one embodiment, a method of killing one or more target cells comprising contacting a composition comprising a first target cell with an Adapter, wherein, wherein (a) the composition comprising the target cell further comprises a cell expressing a chimeric antigen receptor (CAR), wherein the CAR comprises (i) an antigenic determinant binding domain (ADBD) that binds to a first AD on said first target cell, (ii) a transmembrane domain, and (iii) an intracellular domain; and (b) the Adapter comprises (i) said first AD and (ii) an ADBD that binds to a second AD on a second target cell.

In one embodiment, a method of killing a target cell comprises contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that is an ASBD that binds to a first AD, (ii) a transmembrane domain, and (iii) an intracellular domain; and (b) the Adapter comprises (i) said first AD and (ii) an ADBD that binds to a second AD on said target cell.

In one embodiment, a method of killing a target cell comprises contacting a composition comprising a target cell with an Adapter, wherein (a) the composition comprising the target cell further comprises a cell expressing a chimeric antigen receptor (CAR), wherein the CAR comprises (i) an antigenic determinant binding domain (ADBD) that binds to a first AD, (ii) a transmembrane domain, and (iii) an intracellular domain; and (b) the Adapter comprises (i) said first AD and (ii) an ADBD that is an ASBD (e.g., D domain) that binds to a second AD on said target cell.

In one embodiment, a method of killing a target cell comprises contacting a composition comprising a target cell with a cell expressing a CAR, wherein (a) a first AD is present on the target cell; (b) the composition comprising the target cell further comprises an Adapter comprising (i) said first AD and (ii) an ADBD that binds to a second AD on the target cell and (c) the comprises (i) an ADBD that binds to said first AD on the target cell or the Adapter, (ii) a transmembrane domain, and (iii) an intracellular domain.

In one embodiment, a method of killing one or more target cells comprises contacting a composition comprising a target cell with a cell expressing a CAR, wherein (a) a first AD is present on the first target cell, (b) the composition comprising a first target cell further comprises a second target cell and an Adapter comprising (i) said first AD and (ii) an ADBD that binds to a second AD on the second target cell; and (c) the CAR comprises (i) an ADBD that binds to said first AD on the first target cell or the Adapter, (ii) a transmembrane domain, and (iii) an intracellular domain.

In one embodiment, a method of killing a target cell comprises contacting a composition comprising a target cell with a cell expressing a CAR, wherein (a) a first AD is present on the target cell; (b) the composition comprising the target cell further comprises an Adapter comprising (i) an ADBD that binds to said first AD on said target cell and (ii) a second AD; and (c) the CAR comprises (i) an ADBD that is an ASBD that binds to said second AD, (ii) a transmembrane domain, and (iii) an intracellular domain.

In one embodiment, a method of killing a target cell comprises contacting a composition comprising a target cell with a cell expressing a CAR, wherein (a) a first AD is present on the target cell; (b) the composition comprising the target cell further comprises an Adapter comprising (i) an antigenic determinant binding domain (ADBD) that is an ASBD that binds to said first AD on said target cell and (ii) a second AD; and (c) the CAR comprises (i) an ADBD that binds to said second AD, (ii) a transmembrane domain, and (iii) an intracellular domain.

The contacting can occur in vitro, ex vivo, or in vivo. In one embodiment, the contacting occurs in a patient, e.g. a human patient, for example after administration of an Adapter to a patient who has received a cell expressing a CAR or after administration of a cell expressing a CAR to a patient who has received an Adapter.

In some embodiments, the CAR cell comprises a genetic modification that eliminates the expression of an AD recognized by a CAR described herein or by an Adapter described herein. In some embodiments, the AD is a human CD45 AD. In some embodiments, the CAR cell comprises a genetic modification that eliminates the expression of the AD recognized by the CAR or by an Adapter bound by the CAR. In some embodiments, the AD is a human CD45 AD.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3ζ primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain.

In some embodiments, the CAR binds to an antigen selected from: CD45, CD26, CD30, CD33, and CD38. In further embodiments, the CAR binds to CD26. In other embodiments, the CAR binds to CD30. In other embodiments, the CAR binds to CD33. In other embodiments, the CAR binds to CD38. In some embodiments, the CAR binds to CD45.

In some embodiments, the CAR binds to an antigen selected from: CD19, CD22, CD123, BCMA, CS1, HER2, TACI, BAFFR, and PDL1. In further embodiments, the CAR binds to BCMA. In other embodiments, the CAR binds to CS1. In other embodiments, the CAR binds to CD123. In other embodiments, the CAR binds to CD19. In other embodiments, the CAR binds to CD22. In other embodiments, the CAR binds to TACI. In other embodiments, the CAR binds to BAFFR. In other embodiments, the CAR binds to PDL1. In other embodiments, the CAR binds to HER2.

In some embodiments, the CAR comprises 2 ADBDs that bind to separate targets. In further embodiments, the CAR binds to CD19 and CD123. In other embodiments, the CAR binds to BCMA and CS1. In other embodiments, the CAR binds to CD22 and CD123. In other embodiments, the CAR binds to PDL1 and CD123. In some embodiments, the CAR binds to CD45 and second target. In certain embodiments, the CAR comprises a first ASBD that binds to CD19 and a second ASBD that binds to CD123. In other embodiments, the CAR comprises a first D domain that binds to CD19 and a second D domain that binds to CD123. In certain embodiments, the CAR comprises a first ASBD that binds to BCMA and a second ASBD that binds to CS1. In other embodiments, the CAR comprises a first D domain that binds to BCMA and a second D domain that binds to CS1. In other embodiments, the CAR comprises a D domain that binds to CS1 and a scFv that binds to BCMA. In some embodiments, the CAR comprises a first D domain that binds to a CD45 AD and a second D domain that binds to a second AD. In other embodiments, the CAR comprises a D domain that binds to CD19 and a scFv that binds to CD123. In other embodiments, the CAR comprises a first ASBD that binds to CD22 and a second ASBD that binds to CD123. In other embodiments, the CAR comprises a first D domain that binds to CD22 and a second D domain that binds to CD123. In other embodiments, the CAR comprises a D domain that binds to CD22 and a scFv that binds to CD123. In some embodiments, the CAR comprises a first ASBD that binds to PDL1 and a second ASBD that binds to CD123. In some embodiments, the CAR comprises a first D domain that binds to PDL1 and a second D domain that binds to CD123. In some embodiments, the CAR comprises a D domain that binds to PDL1 and a scFv that binds to CD123. In some embodiments, the CAR comprises an ASBD that binds to CD19 and a scFv that binds to CD123.

In some embodiments, the Adapter comprises an AD of a tumor antigen. In further embodiments, the tumor antigen is selected from the group: CD45, CD26, CD30, CD33, and CD38.

In some embodiments, the Adapter comprises an AD of a tumor antigen. In further embodiments, the tumor antigen is selected from the group: BCMA, CD123, CD19, CD22, CS1, HER2, TACI, BAFFR, and PDL1.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (e) bind to different antigens on different cells. In some embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD26. In other embodiments, the Adapter comprises an ADBD that binds to CD30. In some embodiments, the Adapter comprises an ADBD that binds to CD38. In other embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to HER2. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD19 and an ADBD that binds to CD123. In other embodiments, the Adapter comprises an ADBD that binds to BCMA and an ADBD that binds to CS1. In other embodiments, the Adapter comprises an ADBD that binds to CD22 and an ADBD that binds to CD123. In other embodiments, the Adapter comprises an ADBD that binds to PDL1 and an ADBD that binds to CD123. In some embodiments, the Adapter binds to a human CD45 AD and a second AD.

In some embodiments, the target cell is a tumor cell. In further embodiments, the tumor cell is selected from the group: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In further embodiments, the tumor cell is selected from the group: acute myeloid leukemia (AML), chronic lymphocytic leukemia (CLL), and multiple myeloma (MM). In some embodiments, the tumor cell is an AML tumor cell. In some embodiments, the tumor cell is an CLL tumor cell. In some embodiments, the tumor cell is an MM tumor cell.

In some embodiments, the composition comprises at least two target cells. In some embodiments, at least one target cell is a tumor cell. In further embodiments, the first and second target cells are tumor cells. In certain embodiments, the first and second tumor cells are of the same tumor type. In other embodiments, the first and second tumor cells are of a different tumor type. In some embodiments, the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In some embodiments, the tumor cells are selected from: acute myeloid leukemia (AML), chronic lymphocytic leukemia (CLL), and multiple myeloma (MM). In some embodiments, the tumor cells are multiple myeloma (MM). In the methods of killing a target cell provided herein, the target cell can be a cancer cell. Exemplary cancer cells the can be targeted according to the methods provided herein are discussed in Section X and Section XI.

In some embodiments, the target cell is a tumor cell. In further embodiments, the tumor cell is selected from the group: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In some embodiments, the tumor cell is selected from: acute myeloid leukemia (AML), chronic lymphocytic leukemia (CLL), and multiple myeloma (MM). In some embodiments, the tumor cell is multiple myeloma (MM).

In some embodiments, the target cell is a cancer cell. In further embodiments, the cancer cell is selected from the group: breast cancer, prostate cancer, ovarian cancer, pancreatic cancer, colon cancer, and lung cancer. In some embodiments, the cancer cell is breast cancer. In some embodiments, the cancer cell is ovarian cancer.

In some embodiments, the composition comprises at least two target cells. In some embodiments, at least one target cell is a tumor cell. In further embodiments, the first and second target cells are tumor cells. In certain embodiments, the first and second tumor cells are of the same tumor type. In other embodiments, the first and second tumor cells are of a different tumor type. In some embodiments, the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In some embodiments, the tumor cells are selected from: acute myeloid leukemia (AML), chronic lymphocytic leukemia (CLL), and multiple myeloma (MM). In some embodiments, the tumor cells are multiple myeloma (MM).

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell.

In the methods of killing a target cell provided herein, the target cell can be a bacterial cell (e.g., tuberculosis, smallpox, and anthrax), a cell of a parasite (e.g., malaria or leishmaniosis) a fungal cell, a mold, a mycoplasma, or a cell infected with a virus (e.g., HIV, hepatitis b, rabies, Nipah virus, west Nile virus, a meningitis virus, or CMV).

In some embodiments, the cell expressing the CAR is an immune effector cell. An immune effector cell is a cell that is involved in an immune response, e.g., in the promotion of an immune effector response. Examples of immune effector cells include T cells (e.g., alpha/beta T cells and gamma/delta T cells), B cells, natural killer (NK) cells, natural killer T (NKT) cells, mast cells, and myeloid-derived phagocytes. An immune effector function or immune effector response is a function or response of for example, an immune effector cell that enhances or promotes an immune attack of a target cell. In some embodiments, the immune effector function or response refers a property of a T or NK cell that promotes killing, or the inhibition of growth or proliferation, of a target cell. For example, primary stimulation and costimulation are examples of immune effector function or response of a T cell. In particular embodiments, an immune effector function or response is promoted by the action of the disclosed CAR, Adapter, and/or CAR and Adapter compositions. Such function or response results in, for example, a CAR cell that is more effective at proliferation, cytokine production, cytotoxicity or upregulation of cell surface markers such as CD25, CD69, and CD107a.

In some embodiments, the immune effector cell is a T cell. In other embodiments, the immune effector cell is an NK cell. In some embodiments, the cell expressing the CAR kills the target cell. In some embodiments, binding of the Adapter to an AD blocks the activity of the antigen comprising the AD.

Figure 3A:
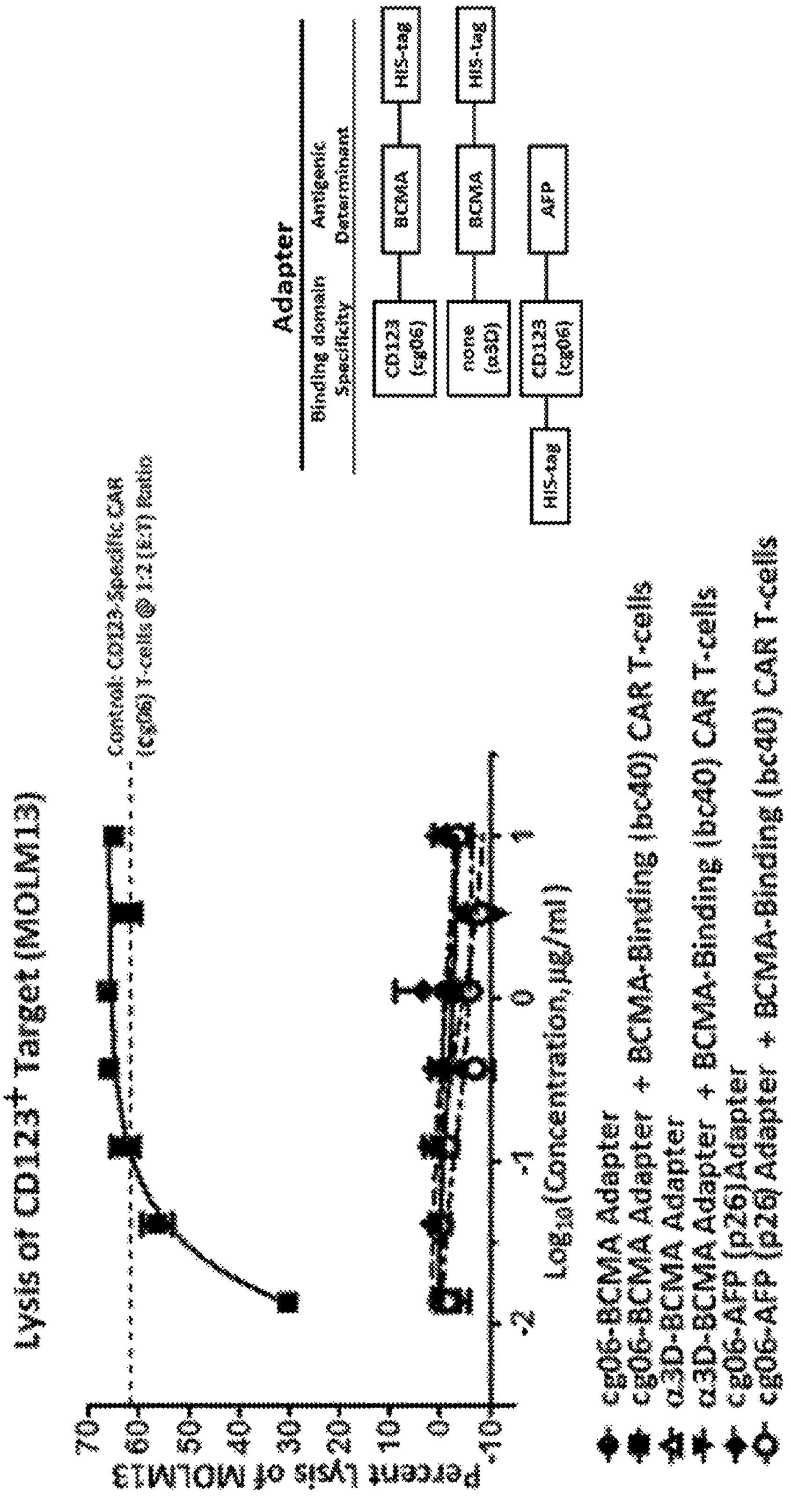
Figure 3B:
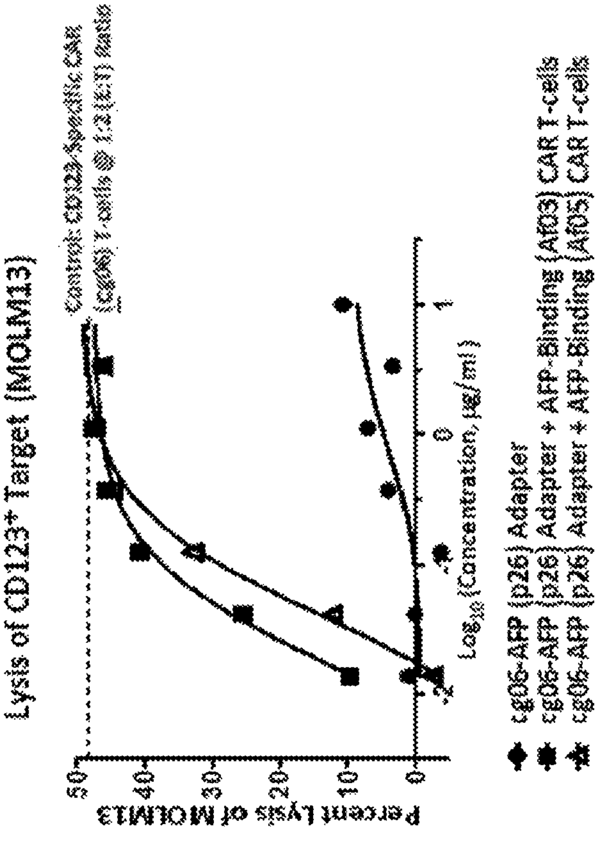
Figure 3C:
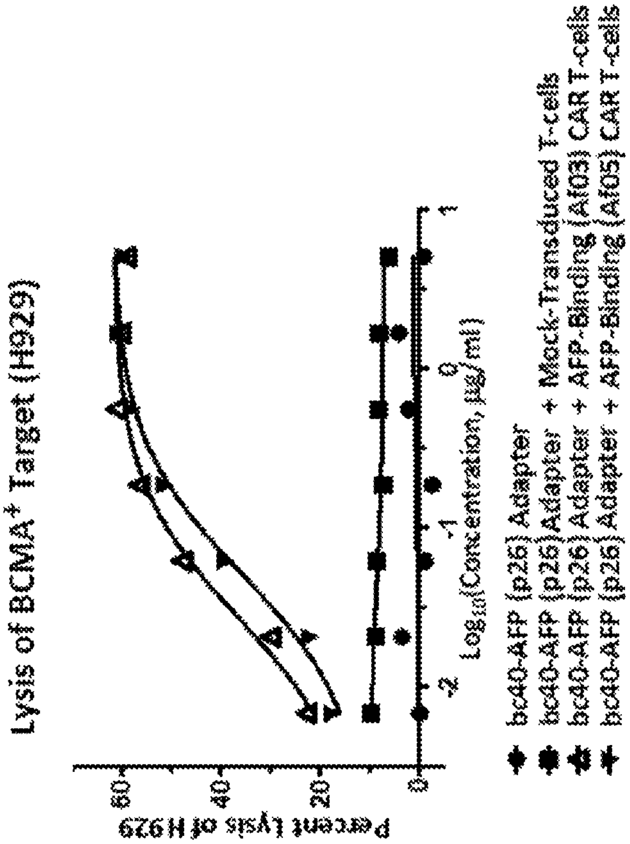
Figure 3C:
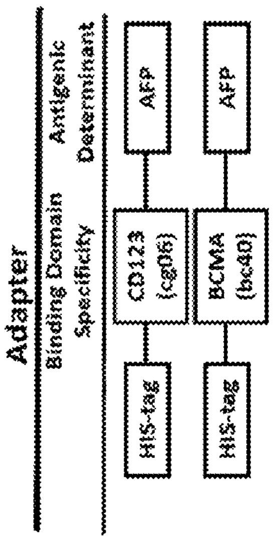

In some embodiments, the CAR cell kills the target cell upon direct binding to the target cell. In some embodiments, the CAR cell kills the target cell upon binding to the Adapter, wherein the Adapter is bound to the target cell (e.g., as depicted in FIGS. 3A-3C).

In some embodiments, binding of CAR to the target cell and/or to the Adapter results in intracellular signaling in the cell expressing the CAR.

In some embodiments, binding of the CAR to the target cell and/or to the Adapter results in degranulation. Degranulation can result in the release of, depending on the cell type, antimicrobial, cytotoxic or other molecules from secretory granules in the immune cell. Molecules like perforin (a pore forming cytotoxin) or granzymes (serine proteases that induce apoptosis in the target cell) aid T cells and NK cells in killing tumor cells (or other cell types).

In some embodiments, binding of the CAR to the target cell and/or to the Adapter results in cytokine secretion by the cell expressing the CAR. The cytokine can be, for example, interferon gamma (IFNγ).

In some embodiments, binding of the CAR to the target cell and/or to the Adapter results in proliferation of the cell expressing the CAR.

X. Therapeutic Uses

Described herein are methods of delivering an immune response to a target cell in a patient and/or killing a target cell in a patient comprising administering an Adapter (as described herein (e.g., as described in Section V and Section XI)) and/or a CAR cell described herein (e.g., as described in Section VII and Section XI) to the patient. Also described herein are methods of treating a proliferative disorder, cancer, autoimmune disease, infection, or allograft rejection comprising administering an Adapter described herein (e.g., as described in Section V and Section XI) and/or a CAR cell described herein (e.g., as described in Section VII and Section XI) to the patient. In particular embodiments, provided herein are methods of treating hematological cancer or autoimmune disease comprising administering an Adapter described herein (e.g., as described in Section V and Section XI) and/or a CAR cell described herein (e.g., as described in Section VII and Section XI) to the patient.

In one embodiment, a method of delivering an immune response to a target cell in a patient comprises administering a cell expressing a CAR to the patient. In another embodiment, a method of killing a target cell in a patient comprises administering a cell expressing a CAR to the patient. In another embodiment, a method of depleting lymphocytes in a patient comprises administering a cell expressing a CAR to the patient. In another embodiment, a method of treating a proliferative disorder, cancer, autoimmune disease, infection, or allograft rejection in a patient comprises administering a cell expressing a CAR to the patient. In certain embodiments, a method of treating hematological cancer comprises administering a cell expressing a CAR to the patient. In certain embodiments, a method of treating an autoimmune disease or disorder comprises administering a cell expressing a CAR to the patient. In one embodiment, a first AD is present on the target cell, and the CAR comprises (i) an ADBD that binds to said first AD on the target cell, (ii) a transmembrane domain, and (iii) an intracellular domain. In one embodiment, a first AD is present on the target cell; and the CAR comprises (i) an ADBD that is an ASBD that binds to said first AD, (ii) a transmembrane domain, and (iii) an intracellular domain. In the methods of killing a target cell in a patient comprising administering a cell expressing a CAR the cell expressing a CAR can be any of the cells expressing CARs described herein (e.g., as described in Section VII and Section XI). In the methods of killing a target cell in a patient comprising administering a cell expressing a CAR the cell expressing a CAR can be in a pharmaceutically acceptable composition. In some embodiments, the CAR cell comprises a genetic modification that reduces or eliminates the expression of an AD bound by the CAR.

In one embodiment, a method of delivering an immune response to a target cell in a patient comprises administering an Adapter to the patient. In another embodiment, a method of killing a target cell in a patient comprises administering an Adapter to the patient. In another embodiment, a method of depleting lymphocytes in a patient comprises administering an Adapter to the patient. In another embodiment, a method of treating a proliferative disorder, cancer, autoimmune disease, infection, or allograft rejection in a patient comprises administering an Adapter to the patient. In certain embodiments, a method of treating hematological cancer comprises administering an Adapter to the patient. In certain embodiments, a method of treating an autoimmune disease or disorder comprises administering an Adapter to the patient. In one embodiment, the patient has been treated with a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and the Adapter comprises (i) said first AD and (ii) an ADBD that binds to a second AD on said target cell. In one embodiment, the patient has been treated with a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and the Adapter comprises (i) said first AD and (ii) an ADBD that binds to a second AD on said target cell. In one embodiment, the patient has been treated with a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and the Adapter comprises (i) said first AD and (ii) an ADBD that is an ASBD that binds to a second AD on said target cell. In the methods of killing a target cell in a patient comprising administering an Adapter to a patient, the Adapter can be any of the Adapters described herein (e.g., as described in Section V and Section XI) and/or the patient can have been treated with any of the cells expressing CARS described herein (e.g., as described in Section VII and Section XI). In some embodiments of the methods of killing a target cell in a patient comprising administering an Adapter to a patient, the patient has previously been treated with an Adapter (in addition to the cell expressing a CAR). In some embodiments, the Adapter that is administered to the patient and the Adapter that was previously administered to the patient bind to different ADs (e.g., on the same or different target cells). In the methods of killing a target cell in a patient comprising administering an Adapter to a patient, the Adapter can be in a pharmaceutically acceptable composition. In some embodiments, the CAR cell comprises a genetic modification that reduces or eliminates the expression of an AD bound by the CAR or the Adapter.

In one embodiment, a method of delivering an immune response to a target cell in a patient comprises administering an Adapter to the patient. In another embodiment, a method of killing a target cell in a patient comprises administering an Adapter to the patient. In another embodiment, a method of depleting lymphocytes in a patient comprises administering an Adapter to the patient. In another embodiment, a method of treating a proliferative disorder, cancer, autoimmune disease, infection, or allograft rejection in a patient comprises administering an Adapter to the patient. In certain embodiments, a method of treating hematological cancer comprises administering an Adapter to the patient. In certain embodiments, a method of treating an autoimmune disease or disorder comprises administering an Adapter to the patient. In one embodiment, the patient comprises a cell expressing a chimeric antigen receptor (CAR), wherein the CAR comprises (i) an antigenic determinant binding domain (ADBD) that binds to a first antigenic determinant (AD) on said target cell, (ii) a transmembrane domain, and (iii) an intracellular domain; and the Adapter comprises (i) said first AD and (ii) an ADBD that binds to a second AD on said target cell. In one embodiment, the patient comprises a cell expressing a chimeric antigen receptor (CAR), wherein the CAR comprises (i) an antigenic determinant binding domain (ADBD) that is an ASBD that binds to a first antigenic determinant (AD), (ii) a transmembrane domain, and (iii) an intracellular domain; and the Adapter comprises (i) said first AD and (ii) an ADBD that binds to a second AD on said target cell. In one embodiment, the patient comprises a cell expressing a chimeric antigen receptor (CAR), wherein the CAR comprises (i) an antigenic determinant binding domain (ADBD) that binds to a first antigenic determinant (AD), (ii) a transmembrane domain, and (iii) an intracellular domain; and the Adapter comprises (i) said first AD and (ii) an ADBD that is an ASBD that binds to a second AD on said target cell. In the methods of killing a target cell in a patient comprising administering an Adapter to a patient, the Adapter can be any of the Adapters described herein (e.g., as described in Section V and Section XI) and/or the patient can comprise any of the cells expressing CARS described herein (e.g., as described in Section VII and Section XI). In some embodiments of the methods of killing a target cell in a patient comprising administering an Adapter to a patient, the patient comprises an Adapter (in addition to the cell expressing a CAR). In some embodiments, the Adapter that is administered to the patient and the Adapter comprised by the patient bind to different ADs (e.g., on the same or different target cells). In the methods of killing a target cell in a patient comprising administering an Adapter to a patient, the Adapter can be in a pharmaceutically acceptable composition. In some embodiments, the CAR cell comprises a genetic modification that reduces or eliminates the expression of an AD bound by the CAR or the Adapter.

In one embodiment, a method of redirecting an immune response to a target cell in a patient comprises administering an Adapter to the patient. In another embodiment, a method of redirecting target cell killing in a patient comprises administering an Adapter to the patient. In another embodiment, a method of redirecting lymphocyte depletion in a patient comprises administering an Adapter to the patient. In another embodiment, a method of redirecting treatment of a proliferative disorder, cancer, autoimmune disease, infection, or allograft rejection comprises administering an Adapter to the patient. In certain embodiments, a method of redirecting treatment of a hematological cancer comprises administering an Adapter to the patient. In certain embodiments, a method of redirecting treatment of an autoimmune disease or disorder comprises administering an Adapter to the patient. In one embodiment, the patient has been treated with a cell expressing a CAR, wherein the CAR comprises (i) an antigenic determinant binding domain (ADBD) that binds to a first antigenic determinant (AD) on a first target cell, (ii) a transmembrane domain, and (iii) an intracellular domain; and the Adapter comprises (i) said first AD and (ii) an ADBD that binds to a second AD on a second target cell. In the methods of redirecting target cell killing in a patient comprising administering an Adapter to a patient, the Adapter can be any of the Adapters described herein (e.g., as described in Section V and Section XI) and/or the patient can have been treated with any of the cells expressing CARS described herein (e.g., as described in Section VII and Section XI). In one embodiment, the patient comprises a cell expressing a CAR, wherein the CAR comprises (i) an antigenic determinant binding domain (ADBD) that binds to a first antigenic determinant (AD) on a first target cell, (ii) a transmembrane domain, and (iii) an intracellular domain; and the Adapter comprises (i) said first AD and (ii) an ADBD that binds to a second AD on a second target cell. In the methods of redirecting target cell killing in a patient comprising administering an Adapter to a patient, the Adapter can be any of the Adapters described herein (e.g., as described in Section V and Section XI) and/or the patient can comprise any of the cells expressing CARs described herein (e.g., as described in Section VII and Section XI). In the methods of redirecting target cell killing in a patient comprising administering an Adapter to a patient, the Adapter can be in a pharmaceutically acceptable composition. In some embodiments, the CAR cell comprises a genetic modification that reduces or eliminates the expression of an AD bound by the CAR or the Adapter.

In one embodiment, a method of delivering an immune response to a target cell in a patient comprises administering a cell expressing a CAR to the patient. In another embodiment, a method of killing a target cell in a patient comprises administering a cell expressing a CAR to the patient. In another embodiment, a method of depleting lymphocytes in a patient comprises administering a cell expressing a CAR to the patient. In another embodiment, a method of treating a proliferative disorder, cancer, autoimmune disease, infection, or allograft rejection in a patient comprises administering a cell expressing a CAR to the patient. In certain embodiments, a method of treating hematological cancer comprises administering a cell expressing a CAR to the patient. In certain embodiments, a method of treating an autoimmune disease or disorder comprises administering a cell expressing a CAR to the patient. In one embodiment, a first AD and a second AD are present on the target cell, the patient has been treated with an Adapter comprising (i) said first AD and (ii) an ADBD that binds to the second AD on said target cell; and the CAR comprises (i) an ADBD that binds to said first AD on the target cell or the Adapter, (ii) a transmembrane domain, and (iii) an intracellular domain. In one embodiment, the patient has been treated with an Adapter comprising (i) a first AD and (ii) an ADBD that binds to a second AD on the target cell; and the CAR comprises (i) an ADBD that binds to said first AD on the Adapter, (ii) a transmembrane domain, and (iii) an intracellular domain. In one embodiment, a first AD is present on the target cell; the patient has been treated with an Adapter comprising (i) an ADBD that binds to the first AD on said target cell and (ii) a second AD; and the CAR comprises (i) an ADBD that is an ASBD that binds to said second AD, (ii) a transmembrane domain, and (iii) an intracellular domain. In one embodiment, a first AD is present on the target cell; the patient has been treated with an Adapter comprising (i) an ADBD comprising an ASBD that binds to the first AD on the target cell and (ii) a second AD; and the CAR comprises (i) an ADBD that binds to said second AD, (ii) a transmembrane domain, and (iii) an intracellular domain. In the methods of killing a target cell in a patient comprising administering a cell expressing a CAR to a patient, the cell expressing a CAR can be any of the cells expressing CARs described herein (e.g., as described in Section VII and Section XI) and/or the patient can have been treated with any of Adapters described herein (e.g., as described in Section V and Section XI). In the methods of killing a target cell in a patient comprising administering a cell expressing a CAR to a patient, the cell expressing a CAR can be in a pharmaceutically acceptable composition. In some embodiments, the CAR cell comprises a genetic modification that reduces or eliminates the expression of an AD bound by the CAR or the Adapter.

In one embodiment, a method of delivering an immune response to a target cell in a patient comprises administering a cell expressing a CAR to the patient. In another embodiment, a method of killing a target cell in a patient comprises administering a cell expressing a CAR to the patient. In another embodiment, a method of depleting lymphocytes in a patient comprises administering a cell expressing a CAR to the patient. In another embodiment, a method of treating a proliferative disorder, cancer, autoimmune disease, infection, or allograft rejection in a patient comprises administering a cell expressing a CAR to the patient. In certain embodiments, a method of treating hematological cancer comprises administering a cell expressing a CAR to the patient. In certain embodiments, a method of treating an autoimmune disease or disorder comprises administering a cell expressing a CAR to the patient. In one embodiment, a first AD and a second AD are present on the target cell, the patient comprises an Adapter comprising (i) said first AD and (ii) an ADBD that binds to the second AD on said target cell; and the CAR comprises (i) an ADBD that binds to said first AD on the target cell or the Adapter, (ii) a transmembrane domain, and (iii) an intracellular domain. In one embodiment, the patient comprises an Adapter comprising (i) a first AD and (ii) an ADBD that binds to a second AD on the target cell; and the CAR comprises (i) an ADBD that binds to said first AD on the Adapter, (ii) a transmembrane domain, and (iii) an intracellular domain. In one embodiment, a first AD is present on the target cell; the patient comprises an Adapter comprising (i) an ADBD that binds to the first AD on said target cell and (ii) a second AD; and the CAR comprises (i) an ADBD that is an ASBD that binds to said second AD, (ii) a transmembrane domain, and (iii) an intracellular domain. In one embodiment, a first AD is present on the target cell; the patient comprises an Adapter comprising (i) an ADBD comprising an ASBD that binds to the first AD on the target cell and (ii) a second AD; and the CAR comprises (i) an ADBD that binds to said second AD, (ii) a transmembrane domain, and (iii) an intracellular domain. In the methods of killing a target cell in a patient comprising administering a cell expressing a CAR to a patient, the cell expressing a CAR can be any of the cells expressing CARs described herein (e.g., as described in Section VII and Section XI) and/or the patient can comprise any of Adapters described herein (e.g., as described in Section V and Section XI). In the methods of killing a target cell in a patient comprising administering a cell expressing a CAR to a patient, the cell expressing a CAR can be in a pharmaceutically acceptable composition. In some embodiments, the CAR cell comprises a genetic modification that reduces or eliminates the expression of an AD bound by the CAR or the Adapter.

In one embodiment, a method of delivering an immune response to a target cell in a patient comprises administering a cell expressing a CAR and an Adapter to the patient. In another embodiment, a method of killing a target cell in a patient comprises administering a cell expressing a CAR and an Adapter to the patient. In another embodiment, a method of depleting lymphocytes in in a patient comprises administering a cell expressing a CAR and an Adapter to the patient. In another embodiment, a method of treating a proliferative disorder, cancer, autoimmune disease, infection, or allograft rejection in a patient comprises administering a cell expressing a CAR and an Adapter to the patient. In certain embodiments, a method of treating hematological cancer comprises administering a cell expressing a CAR and an Adapter to the patient. In certain embodiments, a method of treating an autoimmune disease or disorder comprises administering a cell expressing a CAR and an Adapter to the patient. In one embodiment, a first AD and a second AD are present on the target cell, the Adapter comprises (i) said first AD and (ii) an ADBD that binds to the second AD on said target cell; and the CAR comprises (i) an ADBD that binds to said first AD on the target cell or the Adapter, (ii) a transmembrane domain, and (iii) an intracellular domain. In one embodiment, the Adapter comprises (i) a first AD and (ii) an ADBD that binds to a second AD on the target cell; and the CAR comprises (i) an ADBD that binds to said first AD on the Adapter, (ii) a transmembrane domain, and (iii) an intracellular domain. In one embodiment, a first AD is present on the target cell; the Adapter comprises (i) an ADBD that binds to the first AD on said target cell and (ii) a second AD; and the CAR comprises (i) an ADBD that is an ASBD that binds to said second AD, (ii) a transmembrane domain, and (iii) an intracellular domain. In one embodiment, a first AD is present on the target cell; the Adapter comprises (i) an ADBD comprising an ASBD that binds to the first AD on the target cell and (ii) a second AD; and the CAR comprises (i) an ADBD that binds to said second AD, (ii) a transmembrane domain, and (iii) an intracellular domain. In the methods of killing a target cell in a patient comprising administering a cell expressing a CAR and an Adapter to a patient, the cell expressing a CAR can be any of the cells expressing CARs described herein (e.g., as described in Section VII and Section XI) and the Adapter can be any of the Adapters described herein (e.g., as described in Section V and Section XI). In the methods of killing a target cell in a patient comprising administering a cell expressing a CAR and an Adapter to a patient, the cell expressing a CAR and the Adapter can be in a pharmaceutically acceptable composition. In some embodiments, the cell expressing a CAR and the Adapter are in a single pharmaceutically acceptable composition. In some embodiments, the cell expressing a CAR and the Adapter are in separate pharmaceutically acceptable compositions. In some embodiments, the CAR cell comprises a genetic modification that reduces or eliminates the expression of an AD bound by the CAR or the Adapter.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3ζ primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain.

In some embodiments, the CAR binds to an antigen selected from: CD45, CD26, CD30, CD33, and CD38. In further embodiments, the CAR binds to CD45. In other embodiments, the CAR binds to CD26. In other embodiments, the CAR binds to CD30 In other embodiments, the CAR binds to CD33. In other embodiments, the CAR binds to CD38. In some embodiments, the CAR binds to a CD45 AD.

In some embodiments, the CAR binds to an antigen selected from: CD19, CD22, CD123, BCMA, CS1, HER2, TACI, BAFFR, and PDL1. In further embodiments, the CAR binds to BCMA. In other embodiments, the CAR binds to CS1. In other embodiments, the CAR binds to CD123. In other embodiments, the CAR binds to CD19. In other embodiments, the CAR binds to CD22. In other embodiments, the CAR binds to TACI. In other embodiments, the CAR binds to BAFFR. In other embodiments, the CAR binds to PDL1. In other embodiments, the CAR binds to HER2.

In some embodiments, the CAR comprises 2 ADBDs that bind to separate targets. In further embodiments, the CAR binds to CD19 and CD123. In other embodiments, the CAR binds to BCMA and CS1. In other embodiments, the CAR binds to CD22 and CD123. In other embodiments, the CAR binds to PDL1 and CD123. In some embodiments, the CAR binds to CD45 and second target. In certain embodiments, the CAR comprises a first ASBD that binds to CD19 and a second ASBD that binds to CD123. In other embodiments, the CAR comprises a first D domain that binds to CD19 and a second D domain that binds to CD123. In other embodiments, the CAR comprises a D domain that binds to CD19 and a scFv that binds to CD123. In certain embodiments, the CAR comprises a first ASBD that binds to BCMA and a second ASBD that binds to CS1. In other embodiments, the CAR comprises a first D domain that binds to BCMA and a second D domain that binds to CS1. In other embodiments, the CAR comprises a D domain that binds to CS1 and a scFv that binds to BCMA. In other embodiments, the CAR comprises a first ASBD that binds to CD22 and a second ASBD that binds to CD123. In other embodiments, the CAR comprises a first D domain that binds to CD22 and a second D domain that binds to CD123. In some embodiments, the CAR comprises a first D domain that binds to a CD45 AD and a second D domain that binds to a second AD. In other embodiments, the CAR comprises a D domain that binds to CD22 and a scFv that binds to CD123. In some embodiments, the CAR comprises a first ASBD that binds to PDL1 and a second ASBD that binds to CD123. In some embodiments, the CAR comprises a first D domain that binds to PDL1 and a second D domain that binds to CD123. In some embodiments, the CAR comprises a D domain that binds to PDL1 and a scFv that binds to CD123. In some embodiments, the CAR comprises an ASBD that binds to CD19 and a scFv that binds to CD123.

In some embodiments, the Adapter comprises an AD of a tumor antigen. In further embodiments, the tumor antigen is selected from the group: CD45, CD26, CD30, CD33, and CD38.

In some embodiments, the Adapter comprises an AD of a tumor antigen. In further embodiments, the tumor antigen is selected from the group: BCMA, CD123, CD19, CD22, CS1, HER2, TACI, BAFFR, and PDL1.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (e) bind to different antigens on different cells. In some embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD26. In other embodiments, the Adapter comprises an ADBD that binds to CD30. In some embodiments, the Adapter comprises an ADBD that binds to CD33. In other embodiments, the Adapter comprises an ADBD that binds to CD38. In other embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD19 and an ADBD that binds to CD123. In other embodiments, the Adapter comprises an ADBD that binds to BCMA and an ADBD that binds to CS1. In other embodiments, the Adapter comprises an ADBD that binds to CD22 and an ADBD that binds to CD123. In other embodiments, the Adapter comprises an ADBD that binds to PDL1 and an ADBD that binds to CD123. In some embodiments, the Adapter comprises an ADBD that binds to a CD45 AD and an ADBD that binds to a second AD.

In some embodiments, the target cell is a tumor cell. In further embodiments, the tumor cell is selected from the group: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In further embodiments, the tumor cell is selected from the group: acute myeloid leukemia (AML), chronic lymphocytic leukemia (CLL), and multiple myeloma (MM). In some embodiments, the tumor cell is an AML tumor cell. In some embodiments, the tumor cell is a CLL tumor cell. In some embodiments, the tumor cell is an MM tumor cell.

In some embodiments, the target cell is a cancer cell. In further embodiments, the cancer cell is selected from the group: breast cancer, prostate cancer, ovarian cancer, pancreatic cancer, colon cancer, and lung cancer. In further embodiments, the cancer cell is breast cancer. In some embodiments, the cancer cell is ovarian cancer.

In some embodiments, the composition comprises at least two target cells. In some embodiments, at least one target cell is a tumor cell. In further embodiments, the first and second target cells are tumor cells. In certain embodiments, the first and second tumor cells are of the same tumor type. In other embodiments, the first and second tumor cells are of a different tumor type. In some embodiments, the tumor cells are selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia. In some embodiments, the tumor cells are selected from: acute myeloid leukemia (AML), chronic lymphocytic leukemia (CLL), and multiple myeloma (MM). In some embodiments, the tumor cells are multiple myeloma (MM).

In some embodiments, the cell expressing the CAR is an immune effector cell. In further embodiments, the immune effector cell is a T cell. In other embodiments, the immune effector cell is an NK cell. In some embodiments, the cell expressing the CAR kills the target cell. In some embodiments, binding of the Adapter to an AD blocks the activity of the antigen comprising the AD.

In embodiments, a method of killing a target cell in a patient comprises administering an Adapter and a cell expressing a CAR to the patient. The Adapter and the cell expressing the CAR can be administered in the same pharmaceutical composition or in different pharmaceutical compositions. The Adapter and the cell expressing the CAR can be administered in different pharmaceutical compositions. The Adapter and the cell expressing the CAR can be administered simultaneously or consecutively.

In one embodiment of the methods of killing a target cell in a patient or the methods of redirecting target cell killing in a patient, the patient has been diagnosed with cancer and the target cell is a cancer cell. In one embodiment, the cancer cell is a prostate cancer cell, a breast cancer cell, a colorectal cancer cell, a lung cancer cell, an osteosarcoma cell, or a glioblastoma cell. Thus, in some embodiments, the methods provided herein treat cancer.

Cancers that can be treated include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases). In some embodiments, the solid tumor is breast cancer. In some embodiments, the solid tumr is ovarian cancer.

In another embodiment, the methods described herein are useful for treating a patient having a hematological cancer. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Further examples of hematological (or hematogenous) cancers include acute myeloid leukemia (AML), chronic lymphocytic leukemia (CLL), and multiple myeloma (MM). In some embodiments, the hematological (or hematogenous) cancer is AML. In some embodiments, the hematological (or hematogenous) cancer is CLL. In some embodiments, the hematological (or hematogenous) cancer is MM.

In some embodiments, the cancer is a relapsed of refractory cancer. In some embodiments, the cancer is a relapsed cancer. In some embodiments, the cancer has relapsed following chemotherapy. In some embodiments, the cancer has relapsed following treatment with a biological agent. In some embodiments, the biological agent is a therapeutic antibody or a CAR-T cell. In some embodiments, the cancer is a refractory cancer. In some embodiments, the cancer is refractory to chemotherapy. In some embodiments, the cancer is refractory to treatment with a biological agent. In some embodiments, the biological agent is a therapeutic antibody or a CAR-T cell.

In some embodiments, the cancer is a relapsed of refractory hematological cancer. In some embodiments, the cancer is a relapsed hematological cancer. In some embodiments, the cancer is a hematological cancer that has relapsed following chemotherapy. In some embodiments, the cancer is a hematological cancer that has relapsed following treatment with a biological agent. In some embodiments, the biological agent is a therapeutic antibody or a CAR-T cell. In some embodiments, the cancer is a hematological cancer that has relapsed following autologous bone marrow transplantation. In some embodiments, the cancer is a hematological cancer that has relapsed following allogeneic bone marrow transplantation. In some embodiments, the cancer is a hematological cancer that has relapsed following hematopoietic stem cell transplantation (HSCT). In some embodiments, the HSCT is autologous HSCT. In some embodiments, the cancer is a refractory hematological cancer. In some embodiments, the cancer is a hematological cancer that is refractory to chemotherapy. In some embodiments, the cancer is a hematological cancer that is refractory to treatment with a biological agent. In some embodiments, the biological agent is a therapeutic antibody or a CAR-T cell. In some embodiments, the hematological cancer is acute myeloid leukemia (AML), chronic lymphocytic leukemia (CLL), or multiple myeloma (MM). In some embodiments, the hematological cancer is AML. In some embodiments, the hematological cancer is CLL. In some embodiments, the hematological cancer is MM. In some embodiments, the target cell cell is a B cell. In some embodiments, the target cell is a T cell. In some embodiments, the target cell is a naïve T cell. In some embodiments, the target cell is a memory T cell. In some embodiments, the target cell is a myeloma cell In one embodiment, a method of delivering an immune response to a multiple myeloma cell in a patient comprises administering an Adapter to the patient. In another embodiment, a method of killing a multiple myeloma cell in a patient comprises administering an Adapter to the patient. In another embodiment, a method of depleting multiple myeloma cells in a patient comprises administering an Adapter to the patient. In another embodiment, a method of treating multiple myeloma in a patient comprises administering an Adapter to the patient. In one embodiment, the patient has been treated with a cell expressing a chimeric antigen receptor (CAR), wherein the CAR comprises (i) an antigenic determinant binding domain (ADBD) that binds to a first antigenic determinant (AD) on said multiple myeloma cell (e.g., CS1 or BCMA), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient has been treated with a cell expressing a chimeric antigen receptor (CAR), wherein the CAR comprises (i) an antigenic determinant binding domain (ADBD) that is an ASBD that binds to a first antigenic determinant (AD) (e.g., AFP p26 or a variant thereof), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient has been treated with a cell expressing a chimeric antigen receptor (CAR), wherein the CAR comprises (i) an antigenic determinant binding domain (ADBD) that binds to a first antigenic determinant (AD) (e.g., AFP p26 or a variant thereof), (ii) a transmembrane domain, and (iii) an intracellular domain; and the Adapter comprises (i) said first AD and (ii) an ADBD that is an ASBD that binds to a second AD on said multiple myeloma cell (e.g., CS1 or BCMA). In the methods of killing a multiple myeloma cell in a patient comprising administering an Adapter to a patient, the Adapter can be any of the Adapters described herein (e.g., as described in Section V and Section XI) and/or the patient can have been treated with any of the cells expressing CARS described herein (e.g., as described in Section VII and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In some embodiments of the methods of killing a multiple myeloma cell in a patient comprising administering an Adapter to a patient, the patient has previously been treated with an Adapter (in addition to the cell expressing a CAR). In some embodiments, the Adapter that is administered to the patient and the Adapter that was previously administered to the patient bind to different ADs (e.g., on the same or different multiple myeloma cells). In some embodiments, the Adapter that is administered to the patient binds to CS1 and the Adapter that was previously administered to the patient binds to BCMA. In some embodiments, the Adapter that is administered to the patient binds to BCMA and the Adapter that was previously administered to the patient binds to CS1. In the methods of killing a multiple myeloma cell in a patient comprising administering an Adapter to a patient, the Adapter can be in a pharmaceutically acceptable composition. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, a method of delivering an immune response to a multiple myeloma cell in a patient comprises administering an Adapter to the patient. In another embodiment, a method of killing a multiple myeloma cell in a patient comprises administering an Adapter to the patient. In another embodiment, a method of depleting multiple myeloma cells in a patient comprises administering an Adapter to the patient. In another embodiment, a method of treating multiple myeloma in a patient comprises administering an Adapter to the patient. In one embodiment, the patient comprises a cell expressing a chimeric antigen receptor (CAR), wherein the CAR comprises (i) an antigenic determinant binding domain (ADBD) that binds to a first antigenic determinant (AD) on said multiple myeloma cell (e.g., CS1 or BCMA), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient comprises a cell expressing a chimeric antigen receptor (CAR), wherein the CAR comprises (i) an antigenic determinant binding domain (ADBD) that is an ASBD that binds to a first antigenic determinant (AD) (e.g., AFP p26 or a variant thereof), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient comprises a cell expressing a chimeric antigen receptor (CAR), wherein the CAR comprises (i) an antigenic determinant binding domain (ADBD) that binds to a first antigenic determinant (AD) (e.g., AFP p26 or a variant thereof), (ii) a transmembrane domain, and (iii) an intracellular domain; and the Adapter comprises (i) said first AD and (ii) an ADBD that is an ASBD that binds to a second AD on said multiple myeloma cell (e.g., CS1 or BCMA). In the methods of killing a multiple myeloma cell in a patient comprising administering an Adapter to a patient, the Adapter can be any of the Adapters described herein (e.g., as described in Section V and Section XI) and/or the patient can comprise any of the cells expressing CARS described herein (e.g., as described in Section VII and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In some embodiments of the methods of killing a multiple myeloma cell in a patient comprising administering an Adapter to a patient, the patient comprises an Adapter (in addition to the cell expressing a CAR). In some embodiments, the Adapter that is administered to the patient and the Adapter comprised by the patient bind to different ADs (e.g., on the same or different multiple myeloma cells). In some embodiments, the Adapter that is administered to the patient binds to CS1 and the Adapter comprised by the patient binds to BCMA. In some embodiments, the Adapter that is administered to the patient binds to BCMA and the Adapter comprised by the patient binds to CS1. In the methods of killing a multiple myeloma cell in a patient comprising administering an Adapter to a patient, the Adapter can be in a pharmaceutically acceptable composition. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, a method of redirecting an immune response to a multiple myeloma cell in a patient comprises administering an Adapter to the patient. In another embodiment, a method of redirecting multiple myeloma cell killing in a patient comprises administering an Adapter to the patient. In another embodiment, a method of redirecting lymphocyte depletion in a patient comprises administering an Adapter to the patient. In another embodiment, a method of redirecting treatment of multiple myeloma comprises administering an Adapter to the patient. In certain embodiments, a method of redirecting treatment of an autoimmune disease or disorder comprises administering an Adapter to the patient. In one embodiment, the patient has been treated with a cell expressing a chimeric antigen receptor (CAR), wherein the CAR comprises (i) an antigenic determinant binding domain (ADBD) that binds to a first antigenic determinant (AD) on said multiple myeloma cell (e.g., CS1 or BCMA), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient has been treated with a cell expressing a chimeric antigen receptor (CAR), wherein the CAR comprises (i) an antigenic determinant binding domain (ADBD) that is an ASBD that binds to a first antigenic determinant (AD) (e.g., AFP p26 or a variant thereof), (ii) a transmembrane domain, and (iii) an intracellular domain; and the Adapter comprises (i) said first AD and (ii) an ADBD that binds to a second AD on said multiple myeloma cell (e.g., CS1 or BCMA). In one embodiment, the patient has been treated with a cell expressing a chimeric antigen receptor (CAR), wherein the CAR comprises (i) an antigenic determinant binding domain (ADBD) that binds to a first antigenic determinant (AD) (e.g., AFP p26 or a variant thereof), (ii) a transmembrane domain, and (iii) an intracellular domain; and the Adapter comprises (i) said first AD and (ii) an ADBD that is an ASBD that binds to a second AD on said multiple myeloma cell (e.g., CS1 or BCMA). In the methods of killing a multiple myeloma cell in a patient comprising administering an Adapter to a patient, the Adapter can be any of the Adapters described herein (e.g., as described in Section V and Section XI) and/or the patient can have been treated with any of the cells expressing CARS described herein (e.g., as described in Section VII and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In some embodiments of the methods of killing a multiple myeloma cell in a patient comprising administering an Adapter to a patient, the patient has previously been treated with an Adapter (in addition to the cell expressing a CAR). In some embodiments, the Adapter that is administered to the patient and the Adapter that was previously administered to the patient bind to different ADs (e.g., on the same or different multiple myeloma cells). In some embodiments, the Adapter that is administered to the patient binds to CS1 and the Adapter that was previously administered to the patient binds to BCMA. In some embodiments, the Adapter that is administered to the patient binds to BCMA and the Adapter that was previously administered to the patient binds to CS1. In the methods of redirecting multiple myeloma cell killing in a patient comprising administering an Adapter to a patient, the Adapter can be in a pharmaceutically acceptable composition. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, a method of delivering an immune response to a multiple myeloma cell in a patient comprises administering a cell expressing a CAR to the patient. In another embodiment, a method of killing a multiple myeloma cell in a patient comprises administering a cell expressing a CAR to the patient. In another embodiment, a method of depleting multiple myeloma cells in a patient comprises administering a cell expressing a CAR to the patient. In another embodiment, a method of treating multiple myeloma in a patient comprises administering a cell expressing a CAR to the patient. In one embodiment, a first AD (e.g., BCMA) and a second AD (e.g., CS1) are present on the multiple myeloma cell, the patient has been treated with an Adapter comprising (i) said first AD and (ii) an ADBD that binds to the second AD on said multiple myeloma cell; and the CAR comprises (i) an ADBD that binds to said first AD on the multiple myeloma cell or the Adapter, (ii) a transmembrane domain, and (iii) an intracellular domain. In one embodiment, the patient has been treated with an Adapter comprising (i) a first AD (e.g., BCMA) and (ii) an ADBD that binds to a second AD on the multiple myeloma cell (e.g., CS1); and the CAR comprises (i) an ADBD that binds to said first AD on the Adapter, (ii) a transmembrane domain, and (iii) an intracellular domain. In one embodiment, a first AD is present on the multiple myeloma cell (e.g., CS1); the patient has been treated with an Adapter comprising (i) an ADBD that binds to the first AD on said multiple myeloma cell and (ii) a second AD (e.g., BCMA); and the CAR comprises (i) an ADBD that is an ASBD that binds to said second AD, (ii) a transmembrane domain, and (iii) an intracellular domain. In one embodiment, a first AD is present on the multiple myeloma cell (e.g., CS1); the patient has been treated with an Adapter comprising (i) an ADBD comprising an ASBD that binds to the first AD on the multiple myeloma cell and (ii) a second AD (e.g., BCMA); and the CAR comprises (i) an ADBD that binds to said second AD, (ii) a transmembrane domain, and (iii) an intracellular domain. In the methods of killing a multiple myeloma cell in a patient comprising administering a cell expressing a CAR to a patient, the cell expressing a CAR can be any of the cells expressing CARs described herein (e.g., as described in Section VII and Section XI) and/or the patient can have been treated with any of Adapters described herein (e.g., as described in Section V and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In the methods of killing a multiple myeloma cell in a patient comprising administering a cell expressing a CAR to a patient, the cell expressing a CAR can be in a pharmaceutically acceptable composition. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, a method of delivering an immune response to a multiple myeloma cell in a patient comprises administering a cell expressing a CAR to the patient. In another embodiment, a method of killing a multiple myeloma cell in a patient comprises administering a cell expressing a CAR to the patient. In another embodiment, a method of treating multiple myeloma in a patient comprises administering a cell expressing a CAR to the patient. In one embodiment, a first AD (e.g., BCMA) and a second AD (e.g., CS1) are present on the multiple myeloma cell, the patient comprises an Adapter comprising (i) said first AD and (ii) an ADBD that binds to the second AD on said multiple myeloma cell; and the CAR comprises (i) an ADBD that binds to said first AD on the multiple myeloma cell or the Adapter, (ii) a transmembrane domain, and (iii) an intracellular domain. In one embodiment, the patient comprises an Adapter comprising (i) a first AD (e.g., BCMA) and (ii) an ADBD that binds to a second AD (e.g., CS1) on the multiple myeloma cell; and the CAR comprises (i) an ADBD that binds to said first AD on the Adapter, (ii) a transmembrane domain, and (iii) an intracellular domain. In one embodiment, a first AD is present on the multiple myeloma cell (e.g., CS1); the patient comprises an Adapter comprising (i) an ADBD that binds to the first AD on said multiple myeloma cell and (ii) a second AD (e.g., BCMA); and the CAR comprises (i) an ADBD that is an ASBD that binds to said second AD, (ii) a transmembrane domain, and (iii) an intracellular domain. In one embodiment, a first AD is present on the multiple myeloma cell (e.g., CS1); the patient comprises an Adapter comprising (i) an ADBD comprising an ASBD that binds to the first AD on the multiple myeloma cell and (ii) a second AD (e.g., BCMA or AFP p26 or a variant thereof); and the CAR comprises (i) an ADBD that binds to said second AD, (ii) a transmembrane domain, and (iii) an intracellular domain. In the methods of killing a multiple myeloma cell in a patient comprising administering a cell expressing a CAR to a patient, the cell expressing a CAR can be any of the cells expressing CARs described herein (e.g., as described in Section VII and Section XI) and/or the patient can comprise any of Adapters described herein (e.g., as described in Section V and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In the methods of killing a multiple myeloma cell in a patient comprising administering a cell expressing a CAR to a patient, the cell expressing a CAR can be in a pharmaceutically acceptable composition. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, a method of delivering an immune response to a multiple myeloma cell in a patient comprises administering a cell expressing a CAR and an Adapter to the patient. In another embodiment, a method of killing a multiple myeloma cell in a patient comprises administering a cell expressing a CAR and an Adapter to the patient. In another embodiment, a method of depleting multiple myeloma cells in a patient comprises administering a cell expressing a CAR and an Adapter to the patient. In another embodiment, a method of treating multiple myeloma in a patient comprises administering a cell expressing a CAR and an Adapter to the patient. In one embodiment, a first AD (e.g., BCMA) and a second AD (e.g., CS1) are present on the multiple myeloma cell, the Adapter comprises (i) said first AD and (ii) an ADBD that binds to the second AD on said multiple myeloma cell; and the CAR comprises (i) an ADBD that binds to said first AD on the multiple myeloma cell or the Adapter, (ii) a transmembrane domain, and (iii) an intracellular domain. In one embodiment, the Adapter comprises (i) a first AD (e.g., BCMA) and (ii) an ADBD that binds to a second AD on the multiple myeloma cell (e.g., CS1); and the CAR comprises (i) an ADBD that binds to said first AD on the Adapter, (ii) a transmembrane domain, and (iii) an intracellular domain. In one embodiment, a first AD (e.g., CS1) is present on the multiple myeloma cell; the Adapter comprises (i) an ADBD that binds to the first AD on said multiple myeloma cell and (ii) a second AD (e.g., BCMA); and the CAR comprises (i) an ADBD that is an ASBD that binds to said second AD, (ii) a transmembrane domain, and (iii) an intracellular domain. In one embodiment, a first AD is present on the multiple myeloma cell (e.g., CS1); the Adapter comprises (i) an ADBD comprising an ASBD that binds to the first AD on the multiple myeloma cell and (ii) a second AD (e.g., BCMA or AFP p26 or a variant thereof); and the CAR comprises (i) an ADBD that binds to said second AD, (ii) a transmembrane domain, and (iii) an intracellular domain. In the methods of killing a multiple myeloma cell in a patient comprising administering a cell expressing a CAR and an Adapter to a patient, the cell expressing a CAR can be any of the cells expressing CARs described herein (e.g., as described in Section VII and Section XI) and the Adapter can be any of the Adapters described herein (e.g., as described in Section V and Section XI). In some embodiments, the Adapter comprises an ADBD (e.g., D domain) that binds to CS1, BCMA, or CS1 and BCMA. In some embodiments, the CAR comprises an ADBD (e.g., D domain) that binds to CS1, BCMA, or CS1 and BCMA. In some embodiments, the CAR comprises an ADBD (e.g., D domain) that binds to AFP p26 or a variant thereof. In the methods of killing a multiple myeloma cell in a patient comprising administering a cell expressing a CAR and an Adapter to a patient, the cell expressing a CAR and the Adapter can be in a pharmaceutically acceptable composition. In some embodiments, the cell expressing a CAR and the Adapter are in a single pharmaceutically acceptable composition. In some embodiments, the cell expressing a CAR and the Adapter are in separate pharmaceutically acceptable compositions. In some embodiments, the patient has relapsed multiple myeloma. In some embodiments, the patient has multiple myeloma that relapsed following treatment with a biologic agent, for example, antibody or CAR-T cell. In some embodiments, he patient has multiple myeloma that relapsed following treatment with antibody or CAR-T cell that targeted CS1 or BCMA.

In one embodiment, the methods described herein are useful for inhibiting tumor growth, reducing neovascularization, reducing angiogenesis, inducing differentiation, reducing tumor volume, and/or reducing the tumorigenicity of a tumor.

In one embodiment of the methods of killing a target cell in a patient or the methods of redirecting target cell killing in a patient, the patient has been diagnosed with a disease or disorder of the immune system and the target cell is a cell of the immune system. Thus in some embodiments, the methods provided herein treat a disease or disorder of the immune system.

In some embodiments, the disease or disorder of the immune system is an autoimmune disease or disorder. In some embodiments, the autoimmune disease or disorder is Type I diabetes, systemic sclerosis, multiple sclerosis, rheumatoid arthritis, juvenile idiopathic arthritis, psoriasis, inflammatory bowel disease (IBD), Crohn's disease, ulcerative colitis, or alopecia areata. In some embodiments, the autoimmune disease or disorder is Type I diabetes. In some embodiments, the autoimmune disease or disorder is systemic sclerosis. In some embodiments, the autoimmune disease or disorder is multiple sclerosis. In some embodiments, the autoimmune disease or disorder is rheumatoid arthritis. In some embodiments, the autoimmune disease or disorder is inflammatory bowel disease (IBD). In some embodiments, the autoimmune disease or disorder is Crohn's disease. In some embodiments, the autoimmune disease or disorder is ulcerative colitis.

In one embodiment of the methods of killing, a target cell in a patient or the methods of redirecting target cell killing in a patient, the target cell is a cell of the immune system. In some embodiments, the target cell is a B cell. In some embodiments, the target cell is a T cell. In some embodiments, the target cell is a naïve T cell. In some embodiments, the target cell is a memory T cell.

In one embodiment of the methods of killing, a target cell in a patient or the methods of redirecting target cell killing in a patient, the patient has been diagnosed with an autoimmune disease or disorder and the target cell is a cell of the immune system expressing a CD45 AD. In some embdoiments, the target cell is a B cell. In some embodiments, the target cel is a T cell. In some embdoments, the target cell is a mameory T cell. In some ebodiments, the target cell expresses CD45. In some embodiments, the target cell expresses CD45RO.

In one embodiment of the methods of killing a target cell in a patient or the methods of redirecting target cell killing in a patient, the patient has an infection, and the target cell is a bacterial cell (e.g., tuberculosis, smallpox, and anthrax), a cell of a parasite (e.g., malaria or leishmaniosis) a fungal cell, a mold, a mycoplasma, or a cell infected with a virus (e.g., HIV, hepatitis b, rabies, Nipah virus, west Nile virus, a meningitis virus, or CMV). Thus in some embodiments, the methods provided herein treat an infection.

In one embodiment, the methods described herein are useful for preparing or conditioning a patient for bone marrow transplantation (BMT) or hematopoietic stem cell transplantation (HSCT). Thus in some embodiments, the methods of killing a target cell in a patient or the methods of redirecting target cell killing in a patient provided herein condition a subject for BMT or HSCT. In some embodiments, the methods provided herein condition a subject for HSCT. In some embodiments, the HSCT is autologous HSCT. In some embodiments, the methods for conditioning a patient disclosed herein does not comprise high dose chemotherapy or total body irradiation (TBI). In some embodiments, the methods for conditioning disclosed herein comprise reduced intensity chemotherapy. In some embodiments, the methods for conditioning disclosed herein comprise total body irradiation. In some embodiments, the patient is more than 65 years old. In some embodiments, the patient has cancer. In some embodiments, the patient has a hematologic cancer. In some embodiments, the patient has a relapsed hematologic cancer. In some embodiments, the hematologic cancer is acute myeloid leukemia (AML), chronic lymphocytic leukemia (CLL), or multiple myeloma (MM). In some embodiments, the patient has an autoimmune disease or disorder. In some embodiments, the autoimmune disease or disorder is Type I diabetes, multiple sclerosis, rheumatoid arthritis, inflammatory bowel disease (IBD), Crohn's disease, or ulcerative.

In several embodiments, the administration of the Adapter and/or chimeric antigen receptor cells is intravenous, though other routes, such as intra-arterial, intramuscular, local, or other acceptable route can be used for a given treatment scenario.

Also provided are therapeutic compositions useful for practicing therapeutic methods described herein. In one embodiment, therapeutic compositions provided herein contain a physiologically tolerable carrier together with at least one species of Adapter as described herein, dissolved or dispersed therein as an active ingredient. In another embodiment, therapeutic compositions provided herein contain a physiologically tolerable carrier together with at least one species of a CAR cell as described herein, dissolved or dispersed therein as an active ingredient. In a preferred embodiment, therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or non-aqueous. However, solid forms suitable for solution, or suspensions, in liquid prior to use can also be prepared. The preparation can also be emulsified. Thus, an Adapter-containing composition can take the form of solutions, suspensions, tablets, capsules, sustained release formulations or powders, or other compositional forms. In some embodiments, the Adapter compositions are formulated to ensure or optimize distribution in vivo, For example, the blood-brain barrier (BBB) excludes many highly hydrophilic compounds and if so desired, the compositions are prepared so as to increase transfer across the BBB, by for example, formulation in liposomes. For methods of manufacturing liposomes, see, e.g., U.S. Pat. Nos. 4,522,811, 5,374,548, and 5,399,331. The liposomes can comprise one or more moieties that are selectively transported into specific cells or organs, thus enhance targeted drug delivery (see, e.g., Ranade, Clin. Pharmacol. 29:685 (1989)).

The Adapter (and/or CAR cell) can be mixed other active ingredients and/or excipients that are pharmaceutically acceptable and compatible with the active ingredient and in amounts suitable for use in therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and other auxiliary substances known in the art, which enhance the effectiveness of the active ingredient.

Therapeutic Adapter formulations can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and other pharmaceutically acceptable salts known in the art. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and other salts derived from inorganic bases known in the art.

Physiologically tolerable carriers are known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to, and to the exclusion of water. Exemplary of such additional liquid phases are glycerin, vegetable oils such as cottonseed oil, organic esters such as ethyl oleate, and water-oil emulsions.

In one embodiment, a therapeutic composition contains an Adapter, typically in an amount of at least 0.1 weight percent of Adapter per weight of total therapeutic composition. A weight percent is a ratio by weight of Adapter per total composition. Thus, for example, 0.1 weight percent is 0.1 grams of Adapter per 100 grams of total composition.

Adapter-containing therapeutic compositions typically contains about 10 micrograms (μg) per milliliter (ml) to about 100 milligrams (mg) per ml of Adapter as active ingredient per volume of composition, and more preferably contains about 1 mg/ml to about 10 mg/ml (i.e., about 0.1 to 1 weight percent).

The dosage ranges for the administration of the Adapter are those large enough to produce the desired effect in which the disease symptoms mediated by the target molecule are ameliorated. The dosage should not be so large as to cause adverse side effects, such as hyperviscosity syndromes, pulmonary edema, congestive heart failure, and other adverse side effects known in the art. Generally, the dosage will vary with the age, condition, sex and extent of the disease in the patient and can be determined by one of skill in the art. The dosage can be adjusted by the individual physician in the event of any complication.

The Adapter can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, Adapter can be administered intravenously, intraperitoneally, intramuscularly, subcutaneously, intracavity, transdermally, and can be delivered by peristaltic means. Adapter can also be delivered by aerosol to airways and lungs.

Therapeutic compositions containing an Adapter can be conventionally administered intravenously, as by injection of a unit dose, for example. The term "unit dose" when used in reference to a therapeutic composition provided herein refers to physically discrete units suitable as unitary dosage for the subject, each unit containing a predetermined quantity of active material calculated to produce the desired therapeutic effect in association with the required diluent; e.g., carrier, or vehicle. In a specific embodiment, therapeutic compositions containing an Adapter are administered subcutaneously.

In some embodiments, the Adapter is administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The Adapter compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dosage ranges for the administration of the Adapter are those large enough to produce the desired effect in which the disease symptoms mediated by the target molecule are ameliorated. The dosage should not be so large as to cause adverse side effects, such as, hyperviscosity syndromes, pulmonary edema, congestive heart failure, and other adverse side effects known in the art. Generally, the dosage will vary with the age, condition, sex and extent of the disease in the patient and can be determined by one of skill in the art. The dosage can be adjusted by the individual physician in the event of any complication.

The dosage schedule and amounts effective for therapeutic and prophylactic uses, i.e., the "dosing regimen," will depend upon a variety of factors, including the cause, stage and severity of the disease or disorder, the health, physical status, age of the mammal being treated, and the site and mode of the delivery of the Adapter. Therapeutic efficacy and toxicity of the complex and formation can be determined by standard pharmaceutical, pharmacological, and toxicological procedures in cell cultures or experimental animals. Data obtained from these procedures can likewise be used in formulating a range of dosages for human use. Moreover, therapeutic index (i.e., the dose therapeutically effective in 50 percent of the population divided by the dose lethal to 50 percent of the population (ED50/LD50)) can readily be determined using known procedures. The dosage is preferably within a range of concentrations that includes the ED50 with little or no toxicity, and may vary within this range depending on the dosage form employed, sensitivity of the patient, and the route of administration.

The dosage regimen also takes into consideration pharmacokinetics parameters known in the art, such as, drug absorption rate, bioavailability, metabolism and clearance (see, e.g., Hidalgo-Aragones, J. Steroid Biochem. Mol. Biol. 58:611-617 (1996); Groning et al., Pharmazie 51:337-341 (1996); Fotherby, Contraception 54:59-69 (1996); and Johnson et al., J. Pharm. Sci. 84:1144-1146 (1995)). It is well within the state of the art for the clinician to determine the dosage regimen for each subject being treated. Moreover, single or multiple administrations of Adapter compositions can be administered depending on the dosage and frequency as required and tolerated by the subject. The duration of prophylactic and therapeutic treatment will vary depending on the particular disease or condition being treated. Some diseases are amenable to acute treatment whereas others require long-term, chronic therapy. Adapter can be administered serially, or simultaneously with the additional therapeutic agent.

In some embodiments, the Adapter is administered at about 1 mg/kg to about 50 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg.

In another embodiment, an Adapter is administered in combination with more one or more additional therapeutics.

A therapeutically effective amount of an Adapter, such as an Adapter fusion protein, can be an amount such that when administered in a physiologically tolerable composition is sufficient to achieve a plasma concentration of from about 0.1 microgram (μg) per milliliter (ml) to about 100 μg/ml, preferably from about 1 μg/ml to about 5 μg/ml, and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

In one embodiment the disease or disorder is a disease or disorder of the immune system, such as inflammation or an autoimmune disease.

The cells expressing a CAR provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times.

The CAR-modified T cells can also serve as a type of vaccine for ex vivo immunization and/or in vivo therapy in a mammal. Preferably, the mammal is a human.

Cancers that can be treated with the Adapter or CAR cells include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated with the Adapter include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases). In some embodiments, the solid tumor is breast cancer. In some embodiments, the solid tumr is ovarian cancer.

In another embodiment, the Adapters and/or CAR cells described herein are useful for treating a patient having hematological cancers. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Further examples of hematological (or hematogenous) cancers include acute myeloid leukemia (AML), chronic lymphocytic leukemia (CLL), and multiple myeloma (MM). In some embodiments, the hematological (or hematogenous) cancer is AML. In some embodiments, the hematological (or hematogenous) cancer is CLL. In some embodiments, the hematological (or hematogenous) cancer is MM.

In one embodiment, the antigenic determinant binding domain portion of the Adapter and/or CAR is designed to treat a particular cancer. Cancers that can be treated include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated with the CARs include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Further examples of hematological (or hematogenous) cancers include acute myeloid leukemia (AML), chronic lymphocytic leukemia (CLL), and multiple myeloma (MM). In some embodiments, the hematological (or hematogenous) cancer is AML. In some embodiments, the hematological (or hematogenous) cancer is CLL. In some embodiments, the hematological (or hematogenous) cancer is MM.

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

In one embodiment, cancers and disorders can be treated using the Adapters or CAR cells that target CD19, CD20, CD22, and ROR1. In one specific embodiment, the CAR, Adapter and/or CAR/Adapter combination targets CD22 and is used to treat B-cell lymphoma. In another embodiment the CAR, Adapter and/or CAR/Adapter combination targets CD19 and is used to treat cancers and disorders including but are not limited to pre-B ALL (pediatric indication), adult ALL, mantle cell lymphoma, diffuse large B-cell lymphoma, and salvage post allogenic bone marrow transplantation. In another embodiment the CAR, Adapter and/or CAR/Adapter combination targets CS1 and is used to treat multiple myeloma. In another embodiment the CAR, Adapter and/or CAR/Adapter combination targets BCMA and is used to treat multiple myeloma. In another embodiment the CAR, Adapter and/or CAR/Adapter combination targets CS1 and BCMA, and is used to treat multiple myeloma.

"B-cell associated diseases" as used herein include B-cell immunodeficiencies, autoimmune diseases and/or excessive/uncontrolled cell proliferation associated with B-cells (including lymphomas and/or leukemias). Examples of such diseases, wherein the CARs, Adapters and/or CAR/Adapter combinations provided herein may be used for therapeutic approaches include but are not limited to: systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemis, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinemia and/or hyper IgM syndrome, as well as virally-mediated B-cell diseases such as EBV mediated lymphoproliferative disease, and chronic infections in which B-cells participate in the pathophysiology.

In one embodiment, the CAR, Adapter and/or CAR/Adapter combination is designed to target mesothelin to treat mesothelioma, pancreatic cancer, ovarian cancer, and other mesothelin-expressing cancers known in the art. In one embodiment, the CAR, Adapter and/or CAR/Adapter combination is designed to target CD33/IL3Ra to treat acute myelogenous leukemia and other CD33/IL3Ra-expressing cancers known in the art. In one embodiment, the CAR, Adapter and/or CAR/Adapter combination is designed to target c-Met to treat triple negative breast cancer, non-small cell lung cancer, and other c-Met expressing cancers known in the art. In one embodiment, the CAR, Adapter and/or CAR/Adapter combination is designed to target PSMA to treat prostate cancer and other PSMA-expressing cancers known in the art. In one embodiment, the CAR, Adapter and/or CAR/Adapter combination is designed to target Glycolipid F77 to treat prostate cancer and other Glycolipid F77-expressing cancers known in the art. In one embodiment, the CAR, Adapter and/or CAR/Adapter combination is designed to target EGFRvIII to treat gliobastoma and other EGFRvIII-expressing cancers known in the art. In one embodiment, the CAR, Adapter and/or CAR/Adapter combination is designed to target GD2 to treat neuroblastoma, melanoma, and other GD2 expressing cancers known in the art. In one embodiment, the CAR, Adapter and/or CAR/

Adapter combination is designed to target NY-ESO-1 to treat myeloma, sarcoma, melanoma, and other NY-ESO-1-expressing cancers known in the art. In one embodiment, CAR, Adapter and/or CAR/Adapter combination is can be designed to target MAGEA3 to treat myeloma, sarcoma, melanoma, and other MAGEA3-expressing cancers known in the art. However, the invention should not be construed to be limited to solely to the antigen targets and diseases disclosed herein. Rather, the invention should be construed to include any antigenic target that is associated with a disease where a CAR, Adapter and/or CAR/Adapter combination can be used to treat the disease.

In a preferred embodiment, the CAR is expressed in a T cell and provides a method for treating or preventing cancer, comprising the administration of host cells expressing CAR to a cancer patient in which the cancer cell expresses a tumor antigen on its surface, and wherein the Adapter specifically binds the target antigen. Exemplary target antigenic determinants that the Adapter and CAR bind include, but are not limited to, BCMA, CS1, CD19, CD123, TSLPR, and CD267. In some embodiments, the CAR is expressed in a T cell and provides a method for treating multiple myeloma, comprising the administration of host cells expressing CAR to a multiple myeloma patient in which the tumor cell expresses BCMA and/or CS1 on its surface, and wherein the Adapter specifically binds BCMA, CS1, or BCMA and CS1.

Articles of manufacture, including kits containing the Adapter, CAR cell, and/or CAR cell/Adapter compositions, are provided herein. The article of manufacture may comprise a container and a label or package insert on or associated with the container. Suitable containers include, for example, bottles, vials or syringes. The containers may be formed from a variety of materials such as glass or plastic. The container holds one or more Adapter, CAR cell, nucleic acids encoding Adapter, and/or vectors or host cells of the present disclosure. The label or package insert may include directions for administering the Adapter, CAR cell, and/or CAR cell/Adapter compositions to a patient. Such kits have uses including, but not limited to, therapeutic applications of the Adapter, CAR cell, and/or CAR/Adapter compositions.

XI. Further Compositions and Methods Using Thereof

In some embodiments, the disclosure provides:

[1.] an engineered human immune effector cell comprising
- a) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and
- b) a genetic modification that eliminates the expression of the human CD45 AD on the engineered cell, wherein the engineered cell is capable of directing an immune response to a CD45 AD expressing cell in an in vitro assay, and wherein the engineered cell does not express the CD45 AD;

[2.] the engineered cell according to [1], wherein the immune response is killing the CD45 AD expressing cell;

[3.] the engineered cell according to [1] or [2], wherein the CD45 AD is present in the human CD45R0 isoform but not in the human CD45RA, CD45RAB, or CD45RABC isoforms;

[4.] the engineered cell according to [1] or [2], wherein the CD45 AD is present in the human CD45RA isoform but not in the human CD45R0 isoform;

[5.] the engineered cell according to [1] or [2], wherein the CD45 AD is present in the human CD45R0 and CD45RABC isoforms;

[6.] the engineered cell according to any one of [1] to [5], wherein the ADBD competes with the UCHL-1, A6, or ODP4 antibody for binding to the CD45 AD in an in vitro binding assay;

[7.] the engineered cell according to any one of [1] to [5], wherein the ADBD competes with the 4KB5, MB1, KiB3, 2H4, or MT2 antibody for binding to the CD45 AD in an in vitro binding assay;

[8.] the engineered cell according to any one of [1] to [7], wherein the genetic modification is a deletion, insertion, or substitution in a gene or fragment thereof encoding the human CD45 AD;

[9.] the engineered cell according to [8], wherein the genetic modification is a deletion, insertion, or substitution that eliminates expression of human CD45;

[10.] the engineered cell according to any one of [1] to [9], wherein the genetic modification is a substitution of a gene or fragment thereof encoding the CD45 AD with a nucleotide sequence encoding a homologue, variant, or derivative of human CD45, wherein the encoded homologue, variant, or derivative does not comprise the human CD45 AD;

[11.] the engineered cell according to [10], wherein the homologue is a non-human primate CD45;

[12.] the engineered cell according to [10], wherein the variant is naturally occurring;

[13.] the engineered cell according to [10] or [12], wherein the variant or derivative is capable of signaling;

[14.] the engineered cell according to any one of [1] to [13], wherein the ADBD comprises a single-chain variable fragment (scFv);

[15.] the engineered cell according to any one of [1] to [13], wherein the ADBD comprises an alternative scaffold binding domain (ASBD);

[16.] the engineered cell according to any one of [1] to [13], wherein the ADBD comprises a D domain;

[17.] the engineered cell according to any one of [1] to [16], wherein the CAR comprises 2 or more ADBDs;

[18.] the engineered cell according to any one of [1] to [16], wherein the CAR comprises 2 ADBDs;

[19.] the engineered cell of [18], wherein the CAR comprises an ASBD and a scFv;

[20.] the engineered cell of [18], wherein the CAR comprises a D domain and a scFv;

[21.] the engineered cell of [18], wherein the CAR comprises 2 ASBDs;

[22.] the engineered cell of [18], wherein the CAR comprises 2 D domains;

[23.] the engineered cell of any one according to any one of [1] to [16], wherein the CAR comprises 2 scFvs;

[24.] the engineered cell according to any one of [1] to [16], wherein the CAR comprises 2 ASBDs;

[25.] the engineered cell according to any one of [1] to [16], wherein the CAR comprises 3, 4, or 5 ASBDs;

[26.] the engineered cell according to any one of [1] to [16], wherein the CAR comprises 2 D domains;

[27.] the engineered cell according to any one of [1] to [16], wherein the CAR comprises 3, 4, or 5 D domains;

[28.] the engineered cell according to any one of [17] to [27], wherein at least one ADBD specifically binds to an antigenic determinant of AFP, BCMA, CS1, CD123, CD19, CD20, CD22, or CD137;

[29.] the engineered cell according to any one of [17] to [27], wherein at least one ADBD specifically binds to AFP p26 or a variant thereof (e.g., a polypeptide comprising the amino acid sequence of SEQ ID NO: 16, 1117, 1118, 1119, 1120, 1121, 1122, or 1123);

[30.] the engineered cell according to any one of [17] to [27], wherein at least one ADBD comprises a sequence selected from SEQ ID NO: 841-984;

[31.] the engineered cell according to any one of [1] to [30], wherein the CAR intracellular domain is a signaling domain;

[32.] the engineered cell according to any one of [1] to [31], wherein the CAR intracellular domain comprises a primary signaling domain;

[33.] the engineered cell according to any one of [1] to [32], wherein the CAR intracellular domain comprises a CD3ζ primary signaling domain;

[34.] the engineered cell according to any one of [1] to [33], wherein the CAR intracellular domain further comprises a costimulatory signaling domain;

[35.] the engineered cell according to any one of [1] to [34], wherein the CAR intracellular domain comprises a costimulatory signaling domain selected from: CD28, 41BB, CD27, and CD134;

[36.] the engineered cell according to any one of [1] to [34], wherein the CAR intracellular domain [36.] comprises a 41BB costimulatory signaling domain;

[37.] the engineered cell according to any one of [1] to [36], wherein the immune effector cell is a T cell;

[38.] the engineered cell according to any one of [1] to [36], wherein the immune effector cell is an NK cell;

[39.] a method of killing a target cell comprising contacting the engineered cell according to any one of [1] to [38] with the target cell, wherein the target cell expresses human CD45;

[40.] the method according to [39], wherein the target cell expresses human CD45R0 or human CD45RA isoform;

[41.] a method of delivering an immune response to a target cell comprising contacting the engineered cell according to any one of [1] to [38] with the target cell, wherein the target cell expresses human CD45;

[42.] the method according to [41], wherein the target cell expresses human CD45R0 or human CD45RA isoform;

[43.] the method according to any one of [39] to [42], wherein the contacting is done in vitro;

[44] the method according to any one of [39] to [42], wherein the contacting is done in vivo; [44.]

[45.] the method according to any one of [39] to [42], wherein the contacting is done ex vivo;

[46.] a method of directing an immune response to a target cell in a subject comprising administering to the subject in need thereof a therapeutically effective amount of the engineered cell according to any one of [1] to [38];

[47.] a method of treating a proliferative disorder, cancer, autoimmune disease, infection, or allograft rejection in a subject comprising administering to the subject in need thereof a therapeutically effective amount of the engineered cell according to any one of [1 to 38;

[48.] a method of depleting lymphocytes comprising administering to a subject in need thereof an effective amount of the engineered cell according to any one of [1] to [38];

[49.] a method of depleting memory T cell comprising administering to a subject in need thereof an effective amount of the engineered cell according to any one of [1] to [38];

[50.] the method according to [49], wherein the CD45 AD is a CD45RO specific AD;

[51.] a method of treating an autoimmune disease or disorder comprising administering to a subject in need thereof a therapeutically effective amount of the engineered cell according to any one of [1] to [38];

[52.] the method according to [51], wherein the CD45 AD is a CD45RO specific AD;

[53.] the method according to [51] or [52], wherein the autoimmune disease or disorder is Type I diabetes, systemic sclerosis, multiple sclerosis, rheumatoid arthritis, juvenile idiopathic arthritis, psoriasis, Inflammatory bowel disease (IBD), Crohn's disease, ulcerative colitis, or alopecia areata;

[54.] a method of conditioning a subject for transplantation comprising administering to the subject in need thereof an effective amount of the engineered cell according to any one of [1] to [38];

[55.] the method according to [54], wherein the transplantation is bone marrow transplantation (BMT);

[56.] the method according to [54], wherein the transplantation is hematopoietic stem cell transplantation (HSCT);

[57.] the method according to any one of [54] to [56], wherein the transplantation is autologous transplantation;

[58.] the method according to any one of [54] to [56], wherein the transplantation is allogeneic transplantation;

[59.] the method according to any one of [54] to [58], wherein the subject has hematological cancer;

[60.] the method according to any one of [54] to [59], wherein the subject has relapsed hematological cancer;

[61.] a method of treating a hematological cancer comprising administering to a subject in need thereof a therapeutically effective amount of the engineered cell according to any one of [1] to [38];

[62.] the method according to any one of [59] to [61], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[63.] the method according to any one of [59] to [61], wherein the hematological cancer is AML, CLL, or multiple myeloma;

[64.] an engineered human immune effector cell comprising a) a chimeric antigen receptor (CAR) comprising (1) a first antigenic determinant binding domain (ADBD) that specifically binds to a first antigenic determinant (AD), (2) a transmembrane domain, and (3) an intracellular domain; and b) a genetic modification that eliminates the expression of at least one human CD45 AD on the engineered cell, wherein the first AD is not the at least one human CD45 AD, wherein the engineered cell used in combination with an Adapter is capable of directing an immune response to a CD45 AD expressing cell in an in vitro assay, wherein the Adapter comprises the first AD and a second ADBD that specifically binds to the at least one human CD45 AD, and wherein the engineered cell does not express the at least one human CD45 AD;

[65.] the engineered cell according to [64], wherein the immune response is killing the CD45 AD expressing cell;

[66.] the engineered cell according to [64] or [65], wherein the at least one CD45 AD is present in the human CD45R0 isoform but not in the human CD45RA, CD45RAB, or CD45RABC isoforms;

[67.] the engineered cell according to [64] or [65], wherein the at least one CD45 AD is present in the human CD45RA isoform but not in the human CD45R0 isoform;

[68.] the engineered cell according to [64] or [65], wherein the at least one CD45 AD is present in the human CD45R0 and CD45RABC isoforms;

[69.] the engineered cell according to any one of [64] to [68], wherein the second ADBD competes with the UCHL-1, A6, or ODP4 antibody for binding to the CD45 AD in an in vitro binding assay;

[70.] the engineered cell according to any one of [64] to [68], wherein the second ADBD competes with the 4KB5, MB1, KiB3, 2H4, or MT2 antibody for binding to the CD45 AD in an in vitro binding assay;

[71.] the engineered cell according to any one of [64] to [70], wherein the genetic modification is a deletion, insertion, or substitution in a gene or fragment thereof encoding the human CD45 AD;

[72.] the engineered cell according to [71], wherein the genetic modification is a deletion, insertion, or substitution that eliminates expression of human CD45;

[73.] the engineered cell according to any one of [64] to [72], wherein the genetic modification is a substitution of a gene or fragment thereof encoding the CD45 AD with a nucleotide sequence encoding a homologue, variant, or derivative of human CD45, wherein the encoded homologue, variant, or derivative does not comprise the human CD45 AD;

[74.] the engineered cell according to [73], wherein the homologue is a non-human primate CD45;

[75.] the engineered cell according to [73], wherein the variant is naturally occurring;

[76.] the engineered cell according to [73] or [75], wherein the variant or derivative is capable of signaling;

[77.] the engineered cell according to any one of [64] to [76], wherein the ADBD comprises a single-chain variable fragment (scFv);

[78.] the engineered cell according to any one of [64] to [76], wherein the ADBD comprises an alternative scaffold binding domain (ASBD);

[79.] the engineered cell according to any one of [64] to [76], wherein the ADBD comprises a D domain;

[80.] the engineered cell according to any one of [64] to [79], wherein the first ADBD specifically binds to an antigenic determinant of AFP, BCMA, CS1, CD123, CD19, CD20, CD22, or CD137;

[81] the engineered cell according to any one of [64] to [79], wherein the first ADBD specifically [81.] binds to AFP p26 or a variant thereof (e.g., a polypeptide comprising the amino acid sequence of SEQ ID NO: 16, 1117, 1118, 1119, 1120, 1121, 1122, or 1123),

[82.] the engineered cell according to any one of [64] to [79], wherein the first ADBD comprises a sequence selected from SEQ ID NO: 841-984;

[83.] the engineered cell according to any one of [64] to [82], wherein the CAR comprises 2 or more ADBDs;

[84.] the engineered cell according to any one of [64] to [82], wherein the CAR comprises 2 ADBDs;

[85.] the engineered cell of [84], wherein the CAR comprises an ASBD and a scFv;

[86.] the engineered cell of [84], wherein the CAR comprises a D domain and a scFv

[87.] the engineered cell of [84], wherein the CAR comprises 2 ASBDs;

[88.] the engineered cell of [84], wherein the CAR comprises 2 D domains;

[89.] the engineered cell of any one according to any one of [64] to [82], wherein the CAR comprises 2 scFvs;

[90.] the engineered cell of any one according to any one of [64] to [82], wherein the CAR comprises 2 ASBDs;

[91.] the engineered cell of any one according to any one of [64] to [82], wherein the CAR comprises 3, 4, or 5 ASBDs;

[92.] the engineered cell of any one according to any one of [64] to [82], wherein the CAR comprises 2 D domains;

[93.] the engineered cell of any one according to any one of [64] to [82], wherein the CAR comprises 3, 4, or 5 D domains;

[94.] the engineered cell according to any one of [64] to [93], wherein the CAR intracellular domain is a signaling domain;

[95.] the engineered cell according to any one of [64] to [94], wherein the CAR intracellular domain comprises a primary signaling domain;

[96.] the engineered cell according to any one of [64] to [95], wherein the CAR intracellular domain comprises a CD3ζ primary signaling domain;

[97.] the engineered cell according to any one of [64] to [96], wherein the CAR intracellular domain further comprises a costimulatory signaling domain;

[98.] the engineered cell according to any one of [64] to [97], wherein the CAR intracellular domain comprises a costimulatory signaling domain selected from: CD28, 41BB, CD27, and CD134;

[99.] the engineered cell according to any one of [64] to [97], wherein the CAR intracellular domain comprises a 41BB costimulatory signaling domain;

[100.] the engineered cell according to any one of [64] to [99], wherein the immune effector cell is a T cell;

[101.] the engineered cell according to any one of [64] to [99], wherein the immune effector cell is an NK cell;

[102.] a method of killing a target cell comprising contacting the engineered cell according to any one of [64] to [101] with an Adapter and the target cell, wherein the target cell expresses CD45, and wherein the Adapter comprises the first AD and a second ADBD that specifically binds to a human CD45 AD;

[103.] a method of delivering an immune response to a target cell comprising contacting the engineered cell according to any one of [64] to [101] with an Adapter and the target cell, wherein the target cell expresses CD45, and wherein the Adapter comprises the first AD and a second ADBD that specifically binds to a human CD45 AD;

[104.] the method according to [102] or [103], wherein the target cell expresses human CD45R0 or human CD45RA isoform;

[105.] a method of treating hematological cancer comprising contacting the engineered cell according to any one of [64] to [101] with an Adapter and a cancer cell, wherein the cancer cell expresses CD45, and wherein the Adapter comprises the first AD and a second ADBD that specifically binds to a human CD45 AD;

[106.] the method according to any one of [102] to [106], wherein the contacting is done in vitro;

[107.] the method according to any one of [102] to [106], wherein the contacting is done in vivo;

[108.] the method according to any one of [102] to [106], wherein the contacting is done ex vivo;

[109.] a method of directing an immune response to a target cell in a subject comprising a) administering to the subject in need thereof a therapeutically effective amount of the engineered cell according to any one of [64] to [101]; and b) administering to the subject a therapeutically effective amount of an Adapter comprising the first AD and a second ADBD that specifically binds to a human CD45 AD;

[110.] a method of directing an immune response to a target cell in a subject comprising administering to the subject in need thereof a therapeutically effective amount of the engineered cell according to any one of [64] to [101], wherein the subject has been administered an Adapter comprising the first AD and a second ADBD that specifically binds to a human CD45 AD;

[111.] a method of directing an immune response to a target cell in a subject comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[112.] a method of treating a proliferative disorder, cancer, autoimmune disease, infection, or allograft rejection in a subject comprising a) administering to the subject in need thereof a therapeutically effective amount of the engineered cell according to any one of [64] to [101]; and b) administering to the subject a therapeutically effective amount of an Adapter comprising the first AD and a second ADBD that specifically binds to a human CD45 AD;

[113.] a method of treating a proliferative disorder, cancer, autoimmune disease, infection, or allograft rejection in a subject comprising administering to the subject in need thereof a therapeutically effective amount of the engineered cell according to any one of [64] to [101], wherein the subject has been administered an Adapter comprising the first AD and a second ADBD that specifically binds to a human CD45 AD;

[114.] a method of treating a proliferative disorder, cancer, autoimmune disease, infection, or allograft rejection in a subject comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[115.] a method of depleting lymphocytes comprising a) administering to a subject in need thereof a therapeutically effective amount of the engineered cell according to any one of [64] to [101]; and b) administering to the subject a therapeutically effective amount of an Adapter comprising the first AD and a second ADBD that specifically binds to a human CD45 AD;

[116.] a method of depleting lymphocytes comprising administering to a subject in need thereof a therapeutically effective amount of the engineered cell according to any one of [64] to [101], wherein the subject has been administered an Adapter comprising the first AD and a second ADBD that specifically binds to a human CD45 AD;

[117.] a method of depleting lymphocytes comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[118.] a method of depleting memory T cell comprising a) administering to a subject in need thereof a therapeutically effective amount of the engineered cell according to any one of [64] to [101]; and b) administering to the subject a therapeutically effective amount of an Adapter comprising the first AD and a second ADBD that specifically binds to a human CD45 AD;

[119.] a method of depleting memory T cell comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[120.] a method of depleting memory T cell comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[121.] the method according to any one of [118] to [120], wherein the human CD45 AD is a CD45RO specific AD;

[122.] a method of treating an autoimmune disease or disorder comprising a) administering to a subject in need thereof a therapeutically effective amount of the engineered cell according to any one of [64] to [101]; and b) administering to the subject a therapeutically effective amount of an Adapter comprising the first AD and a second ADBD that specifically binds to a human CD45 AD;

[123.] a method of treating an autoimmune disease or disorder comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[124.] a method of treating an autoimmune disease or disorder comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[125.] the method according to any one of [122] to [124], wherein the human CD45 AD is a CD45RO specific AD;

[126.] the method according to any one of [124] to [125], wherein the autoimmune disease or disorder is Type I diabetes, systemic sclerosis, multiple sclerosis, rheumatoid arthritis, juvenile idiopathic arthritis, psoriasis, Inflammatory bowel disease (IBD), Crohn's disease, ulcerative colitis, or alopecia areata;

[127.] a method of conditioning a subject for transplantation comprising
  a) administering to a subject in need thereof a therapeutically effective amount of the engineered cell according to any one of [64] to [101]; and
  b) administering to the subject a therapeutically effective amount of an Adapter comprising the first AD and a second ADBD that specifically binds to a human CD45 AD;

[128.] a method of conditioning a subject for transplantation comprising administering to a subject in need thereof a therapeutically effective amount of the engineered cell according to any one of [64] to [101], wherein the subject has been administered an Adapter comprising the first AD and a second ADBD that specifically binds to a human CD45 AD;

[129.] a method of conditioning a subject for transplantation comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[130.] the method according to any one of [127] to [129], wherein the transplantation is bone marrow transplantation (BMT);

[131.] the method according to any one of [127] to [129], wherein the transplantation is hematopoietic stem cell transplantation (HSCT);

[132.] the method according to any one of [127] to [131], wherein the transplantation is autologous transplantation;

[133.] the method according to any one of [127] to [131], wherein the transplantation is allogeneic transplantation;

[134.] the method according to any one of [127] to [133], wherein the subject has hematological cancer;

[135.] the method according to any one of [127] to [133], wherein the subject has relapsed hematological cancer;

[136.] a method of treating a hematological cancer comprising
  a) administering to a subject in need thereof a therapeutically effective amount of the engineered cell according to any one of [64] to [101]; and
  b) administering to the subject a therapeutically effective amount of an Adapter comprising the first AD and a second ADBD that specifically binds to a human CD45 AD;

[137.] a method of treating a hematological cancer comprising administering to a subject in need thereof a therapeutically effective amount of the engineered cell according to any one of [64] to [101], wherein the subject has been administered an Adapter comprising the first AD and a second ADBD that specifically binds to a human CD45 AD;

[138.] a method of treating a hematological cancer comprising administering to a subject in need thereof a therapeutically effective amount of an Adapter comprising the first AD and a second ADBD that specifically binds to a human CD45 AD, wherein the subject has been administered the engineered cell according to any one of [64] to [101];

[139.] the method according to any one of [127] to [139], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[140.] the method according to any one of [127] to [139], wherein the hematological cancer is AML, CLL, or multiple myeloma;

[141.] the method according to any one of [64] to [140], wherein the CD45 AD is present in the human CD45R0 isoform but not in the human CD45RA, CD45RAB, or CD45RABC isoforms;

[142.] the method according to any one of [64] to [140], wherein the CD45 AD is present in the human CD45RA isoform but not in the human CD45R0 isoform;

[143.] the method according to any one of [64] to [140], wherein the CD45 AD is present in the human CD45R0 and CD45RABC isoforms;

[144.] the method according to any one of [64] to [143], wherein the second ADBD competes with the UCHL-1, A6, or ODP4 antibody for binding to the CD45 AD in an in vitro binding assay;

[145.] the method according to any one of [64] to [143], wherein the second ADBD competes with the 4KB5, MB1, KiB3, 2H4, or MT2 antibody for binding to the CD45 AD in an in vitro binding assay;

[146.] an engineered human immune effector cell comprising:
  a) a chimeric antigen receptor (CAR), wherein the CAR comprises (i) two or more antigenic determinant binding domains (ADBD) comprising a first ADBD that bind to a first antigenic determinants (AD), (ii) a transmembrane domain, and (iii) an intracellular domain; and
  b) a genetic modification that eliminates the expression of the first AD on the engineered cell, wherein the engineered cell does not express the first AD;

[147.] the engineered cell according to [146], wherein the first AD is a human CD45 AD;

[148.] the engineered cell according to [146] or [147], wherein the CD45 AD is present in the human CD45R0 isoform but not in the human CD45RA, CD45RAB, or CD45RABC isoforms;

[149.] the engineered cell according to [146] or [147], wherein the CD45 AD is present in the human CD45RA isoform but not in the human CD45R0 isoform;

[150.] the engineered cell according to [146] or [147], wherein the CD45 AD is present in the human CD45R0 and CD45RABC isoforms;

[151.] the engineered cell according to [146], wherein the first AD is a human CD26, CD30, CD33, or CD38 AD;

[152.] the engineered cell according to any one of [146] to [151], wherein the two or more ADBDs bind to ADs expressed on the same target cell;

[153.] the engineered cell according to any one of [146] to [151], wherein the two or more ADBDs bind to ADs expressed on different target cells;

[154.] the engineered cell according to any one of [146] to [153], wherein the genetic modification is a deletion, insertion, or substitution in a gene or fragment thereof encoding a polypeptide comprising the first AD;

[155.] the engineered cell according to any one of [146] to [154], wherein the genetic modification is a substitution of a gene or fragment thereof encoding a polypeptide comprising the first AD with a nucleotide sequence encoding a homologue, variant, or derivative of the polypeptide comprising the first AD, wherein the encoded homologue, variant, or derivative does not comprise the first AD;

[156.] the engineered cell according to [155], wherein the homologue is a non-human primate homologue;

[157.] the engineered cell according to [155], wherein the variant is naturally occurring;

[158.] the engineered cell according to [155] or [157], wherein the variant or derivative is capable of signaling;

[159.] the engineered cell according to any one of [146] to [158], wherein the CAR comprises 2 ADBDs that bind to different targets;

[160.] the engineered cell according to any one of [146] to [159], wherein the CAR comprises 2 ADBDs that (a) are the same, (b) bind to the same AD, (c) bind to different ADs of the same antigen, (d) bind to different ADs on the same cell, or (e) bind to different ADs on different cells;

[161.] the engineered cell according to any one of [146] to [160], wherein the first ADBD specifically binds to an antigenic determinant of AFP, BCMA, CS1, CD123, CD19, CD20, CD22, or CD137;

[162.] the engineered cell according to any one of [146] to [160], wherein the first ADBD specifically binds to AFP p26, or a variant thereof (e.g., a polypeptide comprising the amino acid sequence of SEQ ID NO: 16, 1117, 1118, 1119, 1120, 1121, 1122, or 1123);

[163.] the engineered cell according to any one of [146] to [160], wherein the first ADBD comprises a sequence selected from SEQ ID NO: 841-984;

[164.] the engineered cell according to any one of [146] to [163], wherein the CAR specifically binds to an antigen selected from: CD19, CD22, CD123, CS1, HER2, BCMA, TACI, BAFFR, and PDL1;

[165.] the engineered cell according to any one of [146] to [163], wherein the CAR specifically binds to BCMA, and optionally wherein the CAR comprises a sequence selected from SEQ ID NO: 44-338, and 339;

[166.] the engineered cell according to any one of [146] to [163], wherein the CAR specifically binds to CD123, and optionally wherein the CAR comprises a sequence selected from SEQ ID NO: 340-772 and 773;

[167.] the engineered cell according to any one of [146] to [163], wherein the CAR specifically binds to CD19, and optionally wherein the CAR comprises a sequence selected from SEQ ID NO: 1030-1058, and 1059;

[168.] the engineered cell according to any one of [146] to [163], wherein the CAR specifically binds to CD22, and optionally wherein the CAR comprises a sequence selected from SEQ ID NO: 1060-1068, and 1069;

[169.] the engineered cell according to any one of [146] to [163], wherein the CAR specifically binds to CS1, and optionally wherein the CAR comprises a sequence selected from SEQ ID NO: 780-794, and 796;

[170.] the engineered cell according to any one of [146] to [163], wherein the CAR specifically binds to PDL1, and optionally wherein the CAR comprises a sequence selected from SEQ ID NO: 1010-1016, 1074-1078, and 1079;

[171.] the engineered cell according to any one of [146] to [170], wherein the CAR comprises 2 ADBDs;

[172.] the engineered cell of [171], wherein the CAR comprises an ASBD and a scFv;

[173.] the engineered cell of [171], wherein the CAR comprises a D domain and a scFv

[174.] the engineered cell of [171], wherein the CAR comprises 2 ASBDs;

[175.] the engineered cell of [171], wherein the CAR comprises 2 D domains;

[176.] the engineered cell of any one according to any one of [146] to [170], wherein the CAR comprises 2 scFvs;

[177.] the engineered cell of any one according to any one of [146] to [170], wherein the CAR comprises 2 ASBDs;

[178.] the engineered cell of any one according to any one of [146] to [170], wherein the CAR comprises 3, 4, or 5 ASBDs;

[179.] the engineered cell of any one according to any one of [146] to [170], wherein the CAR comprises 2 D domains;

[180.] the engineered cell of any one according to any one of [146] to [170], wherein the CAR comprises 3, 4, or 5 D domains;

[181.] the engineered cell according to any one of [146] to [180], wherein the CAR intracellular domain is a signaling domain;

[182.] the engineered cell according to any one of [146] to [181], wherein the CAR intracellular domain comprises a primary signaling domain;

[183.] the engineered cell according to any one of [146] to [182], wherein the CAR intracellular domain comprises a CD3ζ primary signaling domain;

[184.] the engineered cell according to any one of [146] to [183], wherein the CAR intracellular domain further comprises a costimulatory signaling domain;

[185.] the engineered cell according to any one of [146] to [184], wherein the CAR intracellular domain comprises a costimulatory signaling domain selected from: CD28, 41BB, CD27, and CD134;

[186.] the engineered cell according to any one of [146] to [184], wherein the CAR intracellular domain comprises a 41BB costimulatory signaling domain;

[187.] the engineered cell according to any one of [146] to [186], wherein the immune effector cell is a T cell;

[188.] the engineered cell according to any one of [146] to [186], wherein the immune effector cell is an NK cell;

[189.] a method of killing a target cell comprising contacting the engineered cell according to any one of [146] to [188] with the target cell;

[190.] the method according to [189], wherein the target cell expresses human CD45;

[191.] the method according to [189], wherein the target cell expresses human CD45R0 or human CD45RA isoform;

[192.] a method of delivering an immune response to a target cell comprising contacting the engineered cell according to any one of [146] to [188] with the target cell;

[193.] the method according to [192], wherein the target cell expresses human CD45;

[194.] the method according to [192], wherein the target cell expresses human CD45R0 or human CD45RA isoform;

[195.] the method according to any one of [189] to [194], wherein the contacting is done in vitro;

[196.] the method according to any one of [189] to [194], wherein the contacting is done in vivo;

[197.] the method according to any one of [189] to [194], wherein the contacting is done ex vivo;

[198.] a method of directing an immune response to a target cell in a subject comprising administering to the subject in need thereof a therapeutically effective amount of the engineered cell according to any one of [146] to [188];

[199.] a method of treating a proliferative disorder, cancer, autoimmune disease, infection, or allograft rejection in a subject comprising administering to the subject in need thereof a therapeutically effective amount of the engineered cell according to any one of [146] to [188];

[200.] a method of depleting lymphocytes comprising administering to a subject in need thereof an effective amount of the engineered cell according to any one of [146] to [188];

[201.] a method of conditioning a subject for transplantation comprising administering to the subject in need thereof an effective amount of the engineered cell according to any one of [146] to [188];

[202.] the method according to [201], wherein the transplantation is bone marrow transplantation (BMT);

[203.] the method according to [201], wherein the transplantation is hematopoietic stem cell transplantation (HSCT);

[204.] the method according to any one of [201] to [203], wherein the transplantation is autologous transplantation;

[205.] the method according to any one of [201] to [203], wherein the transplantation is allogeneic transplantation;

[206.] the method according to any one of [201] to [205], wherein the subject has hematological cancer;

[207.] the method according to any one of [201] to [205], wherein the subject has relapsed hematological cancer;

[208.] a method of treating a hematological cancer comprising administering to a subject in need thereof a therapeutically effective amount of the engineered cell according to any one of [146] to [188];

[209.] the method according to any one of [206] to [208], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[210.] the method according to any one of [206] to [208], wherein the hematological cancer is AML, CLL, or multiple myeloma;

[211.] a method of killing a target cell comprising contacting the engineered cell according to any one of [146] to [188] with an Adapter and the target cell, wherein the Adapter comprises an AD recognized by the CAR and a second ADBD;

[212.] a method of delivering an immune response to a target cell comprising contacting the engineered cell according to any one of [146] to [188] with an Adapter and the target cell, and wherein the Adapter comprises an AD recognized by the CAR and a second ADBD that is capable of binding a second AD on the target cell;

[213.] a method of treating hematological cancer comprising contacting the engineered cell according to any one of [146] to [188] with an Adapter and a cancer cell, wherein the Adapter comprises an AD recognized by the CAR and a second ADBD that is capable of binding a second AD on the cancer cell;

[214.] the method according to any one of [211] to [213], wherein the contacting is done in vitro;

[215.] the method according to any one of [211] to [213], wherein the contacting is done in vivo;

[216.] the method according to any one of [211] to [213], wherein the contacting is done ex vivo;

[217.] a method of directing an immune response to a target cell in a subject comprising
  a) administering to the subject in need thereof a therapeutically effective amount of the engineered cell according to any one of [146] to [188]; and
  b) administering to the subject a therapeutically effective amount of an Adapter comprising an AD recognized by the CAR and a second ADBD that is capable of binding a second AD on the target cell;

[218.] a method of directing an immune response to a target cell in a subject comprising administering to the subject in need thereof a therapeutically effective amount of the engineered cell according to any one of [146] to [188], wherein the subject has been administered an Adapter comprising an AD recognized by the CAR and a second ADBD that is capable of binding a second AD on the target cell;

[219.] a method of directing an immune response to a target cell in a subject comprising administering to a subject in need thereof a therapeutically effective amount of an Adapter comprising an AD recognized by the CAR and a second ADBD that is capable of binding a second AD on the target cell, wherein the subject has been administered the engineered cell according to any one of [146] to [188];

[220.] a method of treating a proliferative disorder, cancer, autoimmune disease, infection, or allograft rejection in a subject comprising
  a) administering to the subject in need thereof a therapeutically effective amount of the engineered cell according to any one of [146] to [188]; and
  b) administering to the subject a therapeutically effective amount of an Adapter comprising an AD recognized by the CAR and a second ADBD that is capable of binding a second AD on a target cell;

[221.] a method of treating a proliferative disorder, cancer, autoimmune disease, infection, or allograft rejection in a subject comprising administering to the subject in need thereof a therapeutically effective amount of the engineered cell according to any one of [146] to [188], wherein the subject has been administered an Adapter comprising an AD recognized by the CAR and a second ADBD that is capable of binding a second AD on a target cell;

[222.] a method of treating a proliferative disorder, cancer, autoimmune disease, infection, or allograft rejection in a subject comprising administering to a subject in need thereof a therapeutically effective amount of an Adapter comprising an AD recognized by the CAR and a second ADBD that is capable of binding a second AD on a target cell, wherein the subject has been administered the engineered cell according to any one of [146] to [188];

[223.] a method of depleting lymphocytes comprising
  a) administering to a subject in need thereof a therapeutically effective amount of the engineered cell according to any one of [146] to [188]; and
  b) administering to the subject a therapeutically effective amount of an Adapter comprising an AD recognized by the CAR and a second ADBD that is capable of binding a second AD on a target cell;

[224.] a method of depleting lymphocytes comprising administering to a subject in need thereof a therapeutically effective amount of the engineered cell according to any one of [146] to [188], wherein the subject has been administered an Adapter comprising an AD recognized by the CAR and a second ADBD that is capable of binding a second AD on a target cell;

[225.] a method of depleting lymphocytes comprising administering to a subject in need thereof a therapeutically effective amount of an Adapter comprising an AD recognized by the CAR and a second ADBD that is capable of binding a second AD on a target cell, wherein the subject has been administered the engineered cell according to any one of [146] to [188];

[226.] a method of conditioning a subject for transplantation comprising
- a) administering to a subject in need thereof a therapeutically effective amount of the engineered cell according to any one of [146] to [188]; and
- b) administering to the subject a therapeutically effective amount of an Adapter comprising an AD recognized by the CAR and a second ADBD that is capable of binding a second AD on a target cell;

[227.] a method of conditioning a subject for transplantation comprising administering to a subject in need thereof a therapeutically effective amount of the engineered cell according to any one of [146] to [188], wherein the subject has been administered an Adapter comprising an AD recognized by the CAR and a second ADBD that is capable of binding a second AD on a target cell;

[228.] a method of conditioning a subject for transplantation comprising administering to a subject in need thereof a therapeutically effective amount of an Adapter comprising an AD recognized by the CAR and a second ADBD that is capable of binding a second AD on a target cell, wherein the subject has been administered the engineered cell according to any one of [146] to [188];

[229.] the method according to any one of [226] to [228], wherein the transplantation is bone marrow transplantation (BMT);

[230.] the method according to any one of [226] to [228], wherein the transplantation is hematopoietic stem cell transplantation (HSCT);

[231.] the method according to any one of [226] to [230], wherein the transplantation is autologous transplantation;

[232.] the method according to any one of [226] to [230], wherein the transplantation is allogeneic transplantation;

[233.] the method according to any one of [226] to [232], wherein the subject has hematological cancer;

[234.] the method according to any one of [226] to [232], wherein the subject has relapsed hematological cancer;

[235.] a method of treating a hematological cancer comprising
- a) administering to a subject in need thereof a therapeutically effective amount of the engineered cell according to any one of [146] to [188]; and
- b) administering to the subject a therapeutically effective amount of an Adapter comprising an AD recognized by the CAR and a second ADBD that is capable of binding a second AD on a target cell;

[236.] a method of treating a hematological cancer comprising administering to a subject in need thereof a therapeutically effective amount of the engineered cell according to any one of [146] to [188], wherein the subject has been administered an Adapter comprising an AD recognized by the CAR and a second ADBD that is capable of binding a second AD on a target cell;

[237.] a method of treating a hematological cancer comprising administering to a subject in need thereof a therapeutically effective amount of an Adapter comprising an AD recognized by the CAR and a second ADBD that is capable of binding a second AD on a target cell, wherein the subject has been administered the engineered cell according to any one of [146] to [188];

[238.] the method according to any one of [233] to [237], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[239.] the method according to any one of [233] to [237], wherein the hematological cancer is AML, CLL, or multiple myeloma;

[240.] an engineered human immune effector cell comprising:
- a) a chimeric antigen receptor (CAR), wherein the CAR comprises (i) a first antigenic determinant binding domain (ADBD) that specifically binds to a first antigenic determinant (AD), (ii) a transmembrane domain, and (iii) an intracellular domain; and
- b) a genetic modification that eliminates the expression of a second AD on the engineered cell, wherein the engineered cell used in combination with an Adapter is capable of directing an immune response to a cell expressing the second AD in an in vitro assay, wherein the Adapter comprises the first AD and a second ADBD that specifically binds to the second AD, and wherein the engineered cell does not express the second AD;

[241.] the engineered cell according to [240], wherein the immune response is killing the cell expressing the second AD;

[242.] the engineered cell according to [240] or [241], wherein the second AD is a human CD45 AD;

[243.] the engineered cell according to [242], wherein the CD45 AD is present in the human CD45R0 isoform but not in the human CD45RA, CD45RAB, or CD45RABC isoforms;

[244.] the engineered cell according to [242], wherein the CD45 AD is present in the human CD45RA isoform but not in the human CD45R0 isoform;

[245.] the engineered cell according to [242], wherein the CD45 AD is present in the human CD45R0 and CD45RABC isoforms;

[246.] the engineered cell according to [240] or [241], wherein the second AD is a human CD26, CD30, CD33, or CD38 AD;

[247.] the engineered cell according to any one of [240] to [246], wherein the first AD is not expressed on a target cell and the second AD is expressed on a target cell;

[248.] the engineered cell according to any one of [240] to [246], wherein the first AD is expressed on a target cell;

[249.] the engineered cell according to any one of [240] to [246], wherein the first AD and the second AD are expressed on the same target cell;

[250.] the engineered cell according to any one of [240] to [246], wherein the first AD and the second AD are expressed on different target cells;

[251.] the engineered cell according to any one of [240] to [250], wherein the genetic modification is a deletion, insertion, or substitution in a gene or fragment thereof encoding a polypeptide comprising the second AD;

[252.] the engineered cell according to any one of [240] to [250], wherein the genetic modification is a substitution of a gene or fragment thereof encoding a polypeptide comprising the second AD with a nucleotide sequence encoding a homologue, variant, or derivative of the polypeptide comprising the second AD, wherein the encoded homologue, variant, or derivative does not comprise the second AD;

[253.] the engineered cell of [252], wherein the homologue is a non-human primate homologue;

[254.] the engineered cell of [252], wherein the variant is naturally occurring;

[255.] the engineered cell of [252] or [254], wherein the variant or derivative is capable of signaling;

[256.] the engineered cell according to any one of [240] to [255], wherein the first ADBD comprises a single-chain variable fragment (scFv);

[257.] the engineered cell according to any one of [240] to [255], wherein the first ADBD comprises an alternative scaffold binding domain (ASBD);

[258.] the engineered cell according to any one of [240] to [255], wherein the first ADBD comprises a D domain;

[259.] the engineered cell according to any one of [240] to [258], wherein the first ADBD specifically binds to an antigenic determinant of AFP, BCMA, CS1, CD123, CD19, CD20, CD22, or CD137;

[260.] the engineered cell according to any one of [240] to [258], wherein the first ADBD specifically binds to AFP p26, or a variant thereof (e.g., a polypeptide comprising the amino acid sequence of SEQ ID NO: 16, 1117, 1118, 1119, 1120, 1121, 1122, or 1123);

[261.] the engineered cell according to any one of [240] to [258], wherein the first ADBD comprises a sequence selected from SEQ ID NO: 841-984;

[262.] the engineered cell according to any one of [240] to [261], wherein the CAR comprises 2 or more ADBDs;

[263.] the engineered cell according to any one of [240] to [261], wherein the CAR comprises 2 ADBDs;

[264.] the engineered cell of [263], wherein the CAR comprises an ASBD and a scFv;

[265.] the engineered cell of [263], wherein the CAR comprises a D domain and a scFv;

[266.] the engineered cell of [263], wherein the CAR comprises 2 ASBDs;

[267.] the engineered cell of [263], wherein the CAR comprises 2 D domains;

[268.] the engineered cell of any one according to any one of [240] to [261], wherein the CAR comprises 2 scFvs;

[269.] the engineered cell of any one according to any one of [240] to [261], wherein the CAR comprises 2 ASBDs;

[270.] the engineered cell of any one according to any one of [240] to [261], wherein the CAR comprises 3, 4, or 5 ASBDs;

[271.] the engineered cell of any one according to any one of [240] to [261], wherein the CAR comprises 2 D domains;

[272.] the engineered cell of any one according to any one of [240] to [261], wherein the CAR comprises 3, 4, or 5 D domains;

[273.] an engineered human immune effector cell comprising:

a) a chimeric antigen receptor (CAR), wherein the CAR comprises (i) two or more antigenic determinant binding domains (ADBD) comprising a first ADBD that specifically binds to a first antigenic determinants (AD), (ii) a transmembrane domain, and (iii) an intracellular domain; and b) a genetic modification that eliminates the expression of a second AD on the engineered cell, wherein the engineered cell used in combination with an Adapter is capable of directing an immune response to a cell expressing the second AD in an in vitro assay, wherein the Adapter comprises the first AD and a second ADBD that specifically binds to the second AD, and wherein the engineered cell does not express the second AD;

[274.] the engineered cell according to [273], wherein the immune response is killing the cell expressing the second AD;

[275.] the engineered cell according to [273] or [274], wherein the second AD is a human CD45 AD;

[276.] the engineered cell according to [275], wherein the CD45 AD is present in the human CD45R0 isoform but not in the human CD45RA, CD45RAB, or CD45RABC isoforms;

[277.] the engineered cell according to [275], wherein the CD45 AD is present in the human CD45RA isoform but not in the human CD45R0 isoform;

[278.] the engineered cell according to [275], wherein the CD45 AD is present in the human CD45R0 and CD45RABC isoforms;

[279.] the engineered cell according to [273] or [274], wherein the second AD is a human CD26, CD30, CD33, or CD38 AD;

[280.] the engineered cell according to any one of [273] to [279], wherein the first AD is expressed on a target cell;

[281.] the engineered cell according to any one of [273] to [279], wherein the first AD and the second AD are expressed on the same target cell;

[282.] the engineered cell according to any one of [273] to [279], wherein the first AD and the second AD are expressed on different target cells;

[283.] the engineered cell according to any one of [273] to [282], wherein the genetic modification is a deletion, insertion, or substitution in a gene or fragment thereof encoding a polypeptide comprising the second AD;

[284.] the engineered cell according to any one of [273] to [282], wherein the genetic modification is a substitution of a gene or fragment thereof encoding a polypeptide comprising the second AD with a nucleotide sequence encoding a homologue, variant, or derivative of the polypeptide comprising the second AD, wherein the encoded homologue, variant, or derivative does not comprise the second AD;

[285.] the engineered cell of [284], wherein the homologue is a non-human primate homologue;

[286.] the engineered cell of [284], wherein the variant is naturally occurring;

[287.] the engineered cell of [284] or [286], wherein the variant or derivative is capable of signaling;

[288.] the engineered cell according to any one of [273] to [287], wherein the first ADBD comprises a single-chain variable fragment (scFv);

[289.] the engineered cell according to any one of [273] to [287], wherein the first ADBD comprises an alternative scaffold binding domain (ASBD);

[290.] the engineered cell according to any one of [273] to [287], wherein the first ADBD comprises a D domain;

[291.] the engineered cell according to any one of [273] to [287], wherein the CAR comprises 2 ADBDs;

[292.] the engineered cell of [291], wherein the CAR comprises an ASBD and a scFv;

[293.] the engineered cell of [291], wherein the CAR comprises a D domain and a scFv

[294.] the engineered cell of [291], wherein the CAR comprises 2 ASBDs;

[295.] the engineered cell of [291], wherein the CAR comprises 2 D domains;

[296.] the engineered cell of any one according to any one of [273] to [287], wherein the CAR comprises 2 scFvs;

[297.] the engineered cell of any one according to any one of [273] to [287], wherein the CAR comprises 2 ASBDs;

[298.] the engineered cell of any one according to any one of [273] to [287], wherein the CAR comprises 3, 4, or 5 ASBDs;

[299.] the engineered cell of any one according to any one of [273] to [287], wherein the CAR comprises 2 D domains;

[300.] the engineered cell of any one according to any one of [273] to [287], wherein the CAR comprises 3, 4, or 5 D domains;

[301.] the engineered cell according to any one of [273] to [300], wherein the first ADBD specifically binds to an antigenic determinant of AFP, BCMA, CS1, CD123, CD19, CD20, CD22, or CD137;

[302.] the engineered cell according to any one of [273] to [300], wherein the first ADBD specifically binds to AFP p26, or a variant thereof (e.g., a polypeptide comprising the amino acid sequence of SEQ ID NO: 16, 1117, 1118, 1119, 1120, 1121, 1122, or 1123),

[303.] the engineered cell according to any one of [273] to [300], wherein the first ADBD comprises a sequence selected from SEQ ID NO: 841-984;

[304.] the engineered cell according to any one of [273] to [303], wherein the CAR comprises 2 ADBDs that bind to different targets;

[305.] the engineered cell according to any one of [273] to [303], wherein the CAR comprises 2 ADBDs that (a) are the same, (b) bind to the same AD, (c) bind to different ADs of the same antigen, (d) bind to different ADs on the same cell, or (e) bind to different ADs on different cells;

[306.] the engineered cell according to any one of [273] to [305], wherein the CAR specifically binds to an antigen selected from: CD19, CD22, CD123, BCMA, CS1, TACI, BAFFR, and PDL1;

[307.] the engineered cell according to any one of [273] to [305], wherein the CAR specifically binds to BCMA, and optionally wherein the CAR comprises a sequence selected from SEQ ID NO: SEQ ID NO: 44-338, and 339; or the engineered cell according to any one of [273] to [305], wherein the CAR specifically binds to CS1;

[308.] the engineered cell according to any one of [273] to [305], wherein the CAR specifically binds to CD123, and optionally wherein the CAR comprises a sequence selected from SEQ ID NO: 340-772 and 773;

[309.] the engineered cell according to any one of [273] to [305], wherein the CAR specifically binds to CD19, and optionally wherein the CAR comprises a sequence selected from SEQ ID NO: 1030-1058, and 1059;

[310.] the engineered cell according to any one of [273] to [305], wherein the CAR specifically binds to CD22, and optionally wherein the CAR comprises a sequence selected from SEQ ID NO: 1060-1068, and 1069;

[311.] the engineered cell according to any one of [273] to [305], wherein the CAR specifically binds to CS1, and optionally wherein the CAR comprises a sequence selected from SEQ ID NO: 780-794, and 795;

[312.] the engineered cell according to any one of [273] to [305], wherein the CAR specifically binds to PDL1, and optionally wherein the CAR comprises a sequence selected from SEQ ID NO: 1010-1016, 1074-1078, and 1079;

[313.] the engineered cell according to any one of [240] to [312], wherein the CAR intracellular domain is a signaling domain;

[314.] the engineered cell according to any one of [240] to [313], wherein the CAR intracellular domain comprises a primary signaling domain;

[315.] the engineered cell according to any one of [240] to [314], wherein the CAR intracellular domain comprises a CD3ζ primary signaling domain;

[316.] the engineered cell according to any one of [240] to [315], wherein the CAR intracellular domain further comprises a costimulatory signaling domain;

[317.] the engineered cell according to any one of [240] to [316], wherein the CAR intracellular domain comprises a costimulatory signaling domain selected from: CD28, 41BB, CD27, and CD134;

[318.] the engineered cell according to any one of [240] to [316], wherein the CAR intracellular domain comprises a 41BB costimulatory signaling domain;

[319.] the engineered cell according to any one of to [318], wherein the immune effector cell is a T cell;

[320.] the engineered cell according to any one of [240] to [318], wherein the immune effector cell is an NK cell;

[321.] a method of killing a target cell comprising contacting the engineered cell according to any one of [240] to [320] with the target cell;

[322.] the method according to [321], wherein the target cell expresses human CD45;

[323.] the method according to [321], wherein the target cell expresses human CD45R0 or human CD45RA isoform;

[324.] a method of delivering an immune response to a target cell comprising contacting the engineered cell according to any one of [240] to with the target cell;

[325.] the method according to [324], wherein the target cell expresses human CD45;

[326.] the method according to [324], wherein the target cell expresses human CD45R0 or human CD45RA isoform;

[327.] the method according to any one of [321] to [326], wherein the contacting is done in vitro;

[328.] the method according to any one of [321] to [326], wherein the contacting is done in vivo;

[329.] the method according to any one of [321] to [326], wherein the contacting is done ex vivo;

[330.] a method of directing an immune response to a target cell in a subject comprising administering to the subject in need thereof a therapeutically effective amount of the engineered cell according to any one of [240] to [320];

[331.] a method of treating a proliferative disorder, cancer, autoimmune disease, infection, or allograft rejection in a subject comprising administering to the subject in need thereof a therapeutically effective amount of the engineered cell according to any one of [240] to [320];

[332.] a method of depleting lymphocytes comprising administering to a subject in need thereof an effective amount of the engineered cell according to any one of [240] to [320];

[333.] a method of conditioning a subject for transplantation comprising administering to the subject in need thereof an effective amount of the engineered cell according to any one of [240] to [320];

[334.] the method according to [333], wherein the transplantation is bone marrow transplantation (BMT);

[335.] the method according to [333], wherein the transplantation is hematopoietic stem cell transplantation (HSCT);

[336.] the method according to any one of [333] to [335], wherein the transplantation is autologous transplantation;

[337.] the method according to any one of [333] to [335], wherein the transplantation is allogeneic transplantation;

[338.] the method according to any one of [333] to [337], wherein the subject has hematological cancer;

[339.] the method according to any one of [333] to [337], wherein the subject has relapsed hematological cancer;

[340.] a method of treating a hematological cancer comprising administering to a subject in need thereof a therapeutically effective amount of the engineered cell according to any one of [240] to [320];

[341.] the method according to any one of [338] to [340], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[342.] the method according to any one of [338] to [340], wherein the hematological cancer is AML, CLL, or multiple myeloma;

[343.] a method of killing a target cell comprising contacting the engineered cell according to any one of [240] to [320] with an Adapter and the target cell, wherein the Adapter comprises the first AD and a second ADBD that specifically binds to the second AD, and wherein the second AD is expressed on the target cell;

[344.] a method of delivering an immune response to a target cell comprising contacting the engineered cell according to any one of [240] to [320] with an Adapter and the target cell, wherein the Adapter comprises the first AD and a second ADBD that specifically binds to the second AD, and wherein the second AD is expressed on the target cell;

[345.] a method of treating hematological cancer comprising contacting the engineered cell according to any one of [240] to [320] with an Adapter and a cancer cell, wherein the Adapter comprises the first AD and a second ADBD that specifically binds to the second AD, and wherein the second AD is expressed on the cancer cell;

[346.] the method according to any one of [343] to [345], wherein the contacting is done in vitro;

[347.] the method according to any one of [343] to [345], wherein the contacting is done in vivo;

[348.] the method according to any one of [343] to [345], wherein the contacting is done ex vivo;

[349.] a method of directing an immune response to a target cell in a subject comprising a) administering to the subject in need thereof a therapeutically effective amount of the engineered cell according to any one of [240] to [320]; and b) administering to the subject a therapeutically effective amount of an Adapter comprising the first AD and a second ADBD that specifically binds to the second AD, wherein the second AD is expressed on the target cell;

[350.] a method of directing an immune response to a target cell in a subject comprising administering to the subject in need thereof a therapeutically effective amount of the engineered cell according to any one of [240] to [320], wherein the subject has been administered an Adapter comprising the first AD and a second ADBD that specifically binds to the second AD, and wherein the second AD is expressed on the target cell;

[351.] a method of directing an immune response to a target cell in a subject comprising administering to a subject in need thereof a therapeutically effective amount of an Adapter comprising the first AD and a second ADBD that specifically binds to the second AD, wherein the subject has been administered the engineered cell according to any one of [240] to [320], and wherein the second AD is expressed on the target cell;

[352.] a method of treating a proliferative disorder, cancer, autoimmune disease, infection, or allograft rejection in a subject comprising a) administering to the subject in need thereof a therapeutically effective amount of the engineered cell according to any one of [240] to [320]; and b) administering to the subject a therapeutically effective amount of an Adapter comprising the first AD and a second ADBD that specifically binds to the second AD, wherein the second AD is expressed on a target cell associated with the proliferative disorder, cancer, autoimmune disease, infection, or allograft rejection;

[353.] a method of treating a proliferative disorder, cancer, autoimmune disease, infection, or allograft rejection in a subject comprising administering to the subject in need thereof a therapeutically effective amount of the engineered cell according to any one of [240] to [320], wherein the subject has been administered an Adapter comprising the first AD and a second ADBD that specifically binds to the second AD, and wherein the second AD is expressed on a target cell associated with the proliferative disorder, cancer, autoimmune disease, infection, or allograft rejection;

[354.] a method of treating a proliferative disorder, cancer, autoimmune disease, infection, or allograft rejection in a subject comprising administering to a subject in need thereof a therapeutically effective amount of an Adapter comprising the first AD and a second ADBD that specifically binds to the second AD, wherein the subject has been administered the engineered cell according to any one of [240] to [320], and wherein the second AD is expressed on a target cell associated with the proliferative disorder, cancer, autoimmune disease, infection, or allograft rejection;

[355.] a method of depleting lymphocytes comprising a) administering to a subject in need thereof a therapeutically effective amount of the engineered cell according to any one of [240] to [320]; and b) administering to the subject a therapeutically effective amount of an Adapter comprising the first AD and a second ADBD that specifically binds to the second AD, wherein the second AD is expressed on a lymphocyte target cell;

[356.] a method of depleting lymphocytes comprising administering to a subject in need thereof a therapeutically effective amount of the engineered cell according to any one of [240] to [320], wherein the subject has been administered an Adapter comprising the first AD and a second ADBD that specifically binds to the second AD, and wherein the second AD is expressed on a lymphocyte target cell;

[357.] a method of depleting lymphocytes comprising administering to a subject in need thereof a therapeutically effective amount of an Adapter comprising the first AD and a second ADBD that specifically binds to the second AD, wherein the subject has been administered the engineered cell according to any one of [240] to [320], and wherein the second AD is expressed on a lymphocyte target cell;

[358.] a method of conditioning a subject for transplantation comprising a) administering to a subject in need thereof a therapeutically effective amount of the engineered cell according to any one of [240] to [320]; and b) administering to the subject a therapeutically effective amount of an Adapter comprising the first AD and a second ADBD that specifically binds to the second AD, wherein the second AD is expressed on a target cell associated with the transplantation;

[359.] a method of conditioning a subject for transplantation comprising administering to a subject in need thereof a therapeutically effective amount of the engineered cell according to any one of [240] to [320], wherein the subject has been administered an Adapter comprising the first AD and a second ADBD that specifically binds to the second AD, and wherein the second AD is expressed on a target cell associated with the transplantation;

[360.] a method of conditioning a subject for transplantation comprising administering to a subject in need thereof a therapeutically effective amount of an Adapter comprising the first AD and a second ADBD that specifically binds to the second AD, wherein the subject has been administered the engineered cell according to any one of [240] to [320], and wherein the second AD is expressed on a target cell associated with the transplantation;

[361.] the method according to any one of [358] to [360], wherein the transplantation is bone marrow transplantation (BMT);

[362.] the method according to any one of [358] to [360], wherein the transplantation is hematopoietic stem cell transplantation (HSCT);

[363.] the method according to any one of [358] to [362], wherein the transplantation is autologous transplantation;

[364.] the method according to any one of [358] to [362], wherein the transplantation is allogeneic transplantation;

[365.] the method according to any one of [358] to [364], wherein the subject has hematological cancer;

[366.] the method according to any one of [358] to [364], wherein the subject has relapsed hematological cancer;

[367.] a method of treating a hematological cancer comprising a) administering to a subject in need thereof a therapeutically effective amount of the engineered cell according to any one of [240] to [320]; and b) administering to the subject a therapeutically effective amount of an Adapter comprising the first AD and a second ADBD that specifically binds to the second AD, wherein the second AD is expressed on a target cell associated with the hematological cancer;

[368.] a method of treating a hematological cancer comprising administering to a subject in need thereof a therapeutically effective amount of the engineered cell according to any one of [240] to [320], wherein the subject has been administered an Adapter comprising the first AD and a second ADBD that specifically binds to the second AD, and wherein the second AD is expressed on a target cell associated with the hematological cancer;

[369.] a method of treating a hematological cancer comprising administering to a subject in need thereof a therapeutically effective amount of an Adapter comprising the first AD and a second ADBD that specifically binds to the second AD, wherein the subject has been administered the engineered cell according to any one of [240] to [320], and wherein the second AD is expressed on a target cell associated with the hematological cancer;

[370.] the method according to any one of [358] to [369], wherein the hematological cancer is selected from: acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome, hairy cell leukemia, and myelodysplasia;

[371.] the method according to any one of [358] to [369], wherein the hematological cancer is AML, CLL, or multiple myeloma;

[372.] an isolated Adapter polypeptide comprising (a) an antigenic determinant (AD) and (b) one or more antigenic determinant binding domain (ADBD), wherein at least one ADBD specifically binds to a human CD45 AD, and wherein contacting the Adaptor with a CD45 AD expressing target cell in the presence of an engineered cell according to [64] is capable of directing an immune response by the engineered cell to the target cell in an in vitro assay;

[373.] the Adapter polypeptide according to [372], wherein the immune response is killing the CD45 AD expressing cell;

[374.] the Adapter polypeptide according to [372] or [373], wherein the CD45 AD is present in the human CD45R0 isoform but not in the human CD45RA, CD45RAB, or CD45RABC isoforms;

[375.] the Adapter polypeptide according to [372] or [373], wherein the CD45 AD is present in the human CD45RA isoform but not in the human CD45R0 isoform;

[376.] the Adapter polypeptide according to [372] or [373], wherein the CD45 AD is present in the human CD45R0 and CD45RABC isoforms;

[377.] the Adapter polypeptide according to [372] or [373], which competes with the UCHL-1, A6, or ODP4 antibody for binding to the CD45 AD in an in vitro binding assay; or

[378.] the Adapter polypeptide according to [372] or [373], which competes with the 4KB5, MB1, KiB3, 2H4, or MT2 antibody for binding to the CD45 AD in an in vitro binding assay.

The term "CD45" as used herein refers to protein tyrosine phosphatase, receptor type C (PTPRC), also known as Leukocyte Common Antigen (LCA), LY5, B220, L-CA, T200, CD45R, GP180. The term "CD45" includes variants, isoforms, homologues, orthologs and paralogs. CD45 is a glycosylated type I transmembrane protein, various isoforms of which are expressed on the surface of all hematopoietic cells, except erythrocytes and plasma cells. CD45 is also expressed in lymphomas, B-cell chronic lymphocytic leukemia, hairy cell leukemia, and acute nonlymphocytic leukemia. CD45 is expressed in multiple isoforms as a result of alternative splicing of variable CD45 exons. The CD45 gene comprises 34 exons, of which exon 4 encoding peptide A, exon 5 encoding peptide B, and exon 6 encoding peptide C are alternatively spliced to generate different isoforms. The CD45R isoform, comprising peptides A, B, and C, is the longest. The CD45RO isoform, which lacks peptides A, B, and C, is the shortest. Isoforms CD45RA, CD45RB, CD45RC, CD45RAB, CD45RAC, and CD45RBC comprise the corresponding combinations of peptides A, B, and C. In some embodiments, the amino acid sequence of human CD45RABC, comprising a 25 amino acid residue N-terminal signal sequence (MTMYLWLKLLAFGFAFLDTE-VFVTG, SEQ ID NO: 1101), has Genbank Accession No. NP_002829.3 (SEQ ID NO: 1102). Peptides A, B, and C correspond to residues 34-99, 100-146, and 147-194 of SEQ ID NO: 1102, respectively. In some embodiments, the amino acid sequence of human CD45RO, comprising the 25 amino acid residue N-terminal signal sequence of SEQ ID NO: 1101, has Genbank Accession No. NP_563578.2 (SEQ ID NO: 1103).

Only the CD45RA, CD45RO, CD45RB, CD45RAB, CD45RBC and CD45RABC isoforms are traditionally identified in humans. CD45RA is expressed on naïve T cells. The CD45RO isoform is expressed on activated and memory T cells, some B cell subsets, activated monocytes/macrophages, and granulocytes. CD45RB is a 220 kD glycoprotein expressed on peripheral B cells, naïve T cells, thymocytes, weakly on macrophages, and dendritic cells. As T cells become activated and progress from naïve to memory cells, CD45RB expression is downregulated. Additionally, functionally distinct CD4+ T cell subsets, which secrete differing cytokine profiles, can be separated by CD45RB intensity.

The extracellular domain of the different CD45 isoforms comprise overlapping sets of antigenic determinants. CD45 reactive monoclonal antibodies have been categorized based on their specificity towards the different isoforms. An anti-CD45 antibody, as used herein refers to an antibody that specifically binds to CD45RO, CD45RB, CD45RAB, CD45RBC and CD45RABC isoforms. An anti-CD45RA antibody, as used herein refers to an antibody that specifically binds to CD45RA, CD45RAB, or CD45RABC isoforms, but does not bind to CD45RB or CD45RO. Anti-CD45RA antibodies include, but are not limited to, 4KB5, MB1, KiB3, MT2. An anti-CD45RB antibody, as used herein refers to an antibody that specifically binds to CD45RB, CD45RAB, CD45RBC, or CD45RABC, but does not bind to CD45RA, and CD45RO. An anti-CD45RO antibody, as used herein refers to an antibody that specifically binds to CD45RO, but does not bind to the other isoforms. CD45RO specific antibodies include, but are not limited to, UCHL1, A6, OPD4. In some embodiments, a CD45 specific antigenic determinant binding domain (ADBD) disclosed herein specifically binds to CD45RO, but does not bind to the other CD45 isoforms. In some embodiments, a CD45 specific ADBD disclosed herein specifically binds to CD45RA, CD45RAB, and CD45RABC, but does not bind to the other CD45 isoforms. In some embodiments, a CD45 specific ADBD disclosed herein specifically binds to all CD45 isoforms. Cell type specific glycosylation of CD45 contributes to the formation of human CD45 antigenic determinants. For example, differential expression of the antigenic determinant bound by the CD45RB$^{MEM55}$ antibody is regulated by cell type specific O-linked glycosylation during B cell development. Koethe et al., Journal of Leukocyte Biology, 90 (1): 5-19. Expression of the antigenic determinant bound by the UCHL1 and A6 antibodies are also dependent on the glycosylation of the CD45RO isoform. In some embodiments, a CD45 specific ADBD disclosed herein specifically binds to a glycosylation dependent antigenic determinant of human CD45. In some embodiments, a CD45 specific ADBD disclosed herein specifically binds to a glycosylation dependent antigenic determinant of human CD45RB. In some embodiments, a CD45 specific ADBD disclosed herein specifically binds to a glycosylation dependent antigenic determinant of human CD45RO.

The term "non-human primate CD45" as used herein refers to a primate ortholog of human CD45. In some embodiments, the non-human primate CD45 is a rhesus CD45. In some embodiments, the amino acid sequence of rhesus (*Macaca mulatta*) CD45RABC, comprising an N-terminal signal sequence, has Genbank Accession No. XP_014976209 (SEQ ID NO: 1104). In some embodiments, the non-human primate CD45 is a cynomolgus CD45. In some embodiments, the amino acid sequence of cynomolgus (*Macaca fascicularis*) CD45RABC, comprising an N-terminal signal sequence, has Genbank Accession No. XP_005540386 (SEQ ID NO: 1105). Due to differences in their primary amino acid sequence, human CD45 and non-human primate CD45s comprise different sets of antigenic determinants. In some embodiments, a human CD45 specific ADBD disclosed herein specifically binds to an antigenic determinant that is also present in a non-human primate CD45. In some embodiments, a human CD45 specific ADBD disclosed herein specifically binds to an antigenic determinant that is not present in a non-human primate CD45. In some embodiments, a human CD45 specific ADBD disclosed herein specifically binds to an antigenic determinant that is not present in a rhesus CD45. In some embodiments, a human CD45 specific ADBD disclosed herein specifically binds to an antigenic determinant that is not present in a cynomolgus CD45.

In some embodiments, the AD (e.g., in an Adapter and/or on a target cell) is an epitope of human CD45. In some embodiments, the AD is an epitope of the extracellular domain (ECD) of human CD45. In some embodiments, the AD is an epitope of the ECD of human CD45RA. In some embodiments, the AD is an epitope of the ECD of human CD45RB. In some embodiments, the AD is an epitope of the ECD of human CD45RAB. In some embodiments, the AD is an epitope of the ECD of human CD45RBC. In some embodiments, the AD is an epitope of the ECD of human CD45RAC. In some embodiments, the AD is an epitope of the ECD of human CD45RABC. In some embodiments, the AD is an epitope of the ECD of human CD45RO. In further embodiments, the AD comprises 5-25, 5-50, 5-75, 5-100, 5-125, or 5-150 amino acid residues, more than 150 amino acid residues, or all of the amino acid residues of SEQ ID NO: 1106. In further embodiments, the AD comprises 5-25, 5-50, 5-75, 5-100, 5-125, or 5-150 amino acid residues, more than 150 amino acid residues, or all of the amino acid residues of SEQ ID NO: 1107. In further embodiments, the AD comprises 5-25, 5-50, 5-75, 5-100, 5-125, or 5-150 amino acid residues, more than 150 amino acid residues, or all of the amino acid residues of SEQ ID NO: 1108. In further embodiments, the AD comprises 5-25, 5-50, 5-75, 5-100, 5-125, or 5-150 amino acid residues, more than 150 amino acid residues, or all of the amino acid residues of SEQ ID NO: 1109. In further embodiments, the AD comprises 5-25, 5-50, 5-75, 5-100, 5-125, or 5-150 amino acid residues, more than 150 amino acid residues, or all of the amino acid residues of SEQ ID NO: 1110. In further embodiments, the AD comprises 5-25, 5-50, 5-75, 5-100, 5-125, or 5-150 amino acid residues, more than 150 amino acid residues, or all of the amino acid residues of SEQ ID NO: 1111. In further embodiments, the AD comprises 5-25, 5-50, 5-75, 5-100, 5-125, or 5-150 amino acid residues, more than 150 amino acid residues, or all of the amino acid residues of SEQ ID NO: 1112.

In some embodiments, the AD is a glycosylation dependent epitope of human CD45.

In some embodiments, the AD is an epitope of human CD45 that is not present in a non-human primate CD45. In some embodiments, the AD is an epitope of human CD45 that is not present in a rhesus CD45. In some embodiments, the AD is an epitope of human CD45 that is not present in a cynomolgus CD45.

In some embodiments, the AD is an epitope of human CD45 that is bound by the UCHL-1, A6, or ODP4 antibody. In some embodiments, the AD is an epitope of human CD45 that is bound by the 4KB5, MB1, KiB3, 2H4, or MT2 antibody.

In some embodiments, the AD is an epitope of CD26. In further embodiments, the AD comprises 5-25, 5-50, 5-75, 5-100, 5-125, or 5-150 amino acid residues, more than 150 amino acid residues, or all of the amino acid residues of residues 29-766 of SEQ ID NO: 1113.

In some embodiments, the AD is an epitope of CD30. In further embodiments, the AD comprises 5-25, 5-50, 5-75, 5-100, 5-125, or 5-150 amino acid residues, more than 150 amino acid residues, or all of the amino acid residues of residues 19-379 of SEQ ID NO: 1114.

In some embodiments, the AD is an epitope of CD33. In further embodiments, the AD comprises 5-25, 5-50, 5-75, 5-100, 5-125, or 5-150 amino acid residues, more than 150 amino acid residues, or all of the amino acid residues of residues 18-259 of SEQ ID NO: 1115.

In some embodiments, the AD is an epitope of CD38. In further embodiments, the AD comprises 5-25, 5-50, 5-75, 5-100, 5-125, or 5-150 amino acid residues, more than 150 amino acid residues, or all of the amino acid residues of residues 43-300 of SEQ ID NO: 1116.

In some embodiments of the compositions and methods disclosed herein, the ADBD has the ability to bind to an antigenic determinant expressed on the surface of an immune effector cells. In some embodiments, the ADBD has the ability to bind to an antigenic determinant of human CD45. In some embodiments, the ADBD has the ability to bind to an antigenic determinant of human CD45R, CD45RA, CD45RB, or CD45RO. In some embodiments, the ADBD has the ability to bind to an antigenic determinant of human CD45RA. In some embodiments, the ADBD has the ability to bind to an antigenic determinant of human CD45RB. In some embodiments, the ADBD has the ability to bind to an antigenic determinant of human CD45RO. In some embodiments, the ADBD has the ability to bind to an antigenic determinant of human CD45, but does not have the ability to bind to a non-human primate homologue of CD45. In some embodiments, the ADBD has the ability to bind to an antigenic determinant of human CD45, but does not have the ability to bind to rhesus or cynomolgus CD45. In some embodiments, the ADBD has the ability to bind to an antigenic determinant of human CD45R, CD45RA, CD45RB, or CD45RO, but does not have the ability to bind to a non-human primate homologue of CD45. In some embodiments, the ADBD has the ability to bind to an antigenic determinant of human CD45R, CD45RA, CD45RB, or CD45RO, but does not have the ability to bind to rhesus or cynomolgus CD45. In some embodiments, the ADBD has the ability to bind to an antigenic determinant of human CD45RO, but does not have the ability to bind to a non-human primate homologue of CD45. In some embodiments, the ADBD has the ability to bind to an antigenic determinant of human CD45RO, but does not have the ability to bind to rhesus or cynomolgus CD45. In some embodiments, the ADBD has the ability to bind to an antigenic determinant of human CD26, CD30, CD33, or CD38. In some embodiments, the ADBD has the ability to bind to an antigenic determinant of human CD26, CD30, CD33, or CD38, but does not have the ability to bind to a non-human primate homologue of CD26, CD30, CD33, or CD38, respectively. In some embodiments, the ADBD has the ability to bind to an antigenic determinant of human CD26, CD30, CD33, or CD38, but does not have the ability to bind to rhesus or cynomolgus CD26, CD30, CD33, or CD38, respectively.

In some embodiments, the ADBD is a D domain-based polypeptide that has the ability to bind to an antigenic determinant of human CD45. In some embodiments, the ADBD is a D domain-based polypeptide that has the ability to bind to an antigenic determinant of human CD45R, CD45RA, CD45RB, or CD45RO. In some embodiments, the ADBD is a D domain-based polypeptide that has the ability to bind to an antigenic determinant of human CD45RO. In some embodiments, the ADBD is a D domain-based polypeptide that has the ability to bind to an antigenic determinant of human CD45RA. In some embodiments, the ADBD is a D domain-based polypeptide that has the ability to bind to an antigenic determinant of human CD45RB. In some embodiments, the ADBD is a D domain-based polypeptide that has the ability to bind to an antigenic determinant of human CD45, but does not have the ability to bind to a non-human primate homologue of CD45. In some embodiments, the ADBD is a D domain-based polypeptide that has the ability to bind to an antigenic determinant of human CD45, but does not have the ability to bind to rhesus or cynomolgus CD45. In some embodiments, the ADBD is a D domain-based polypeptide that has the ability to bind to an antigenic determinant of human CD45R, CD45RA, CD45RB, or CD45RO, but does not have the ability to bind to a non-human primate homologue of CD45. In some embodiments, the ADBD is a D domain-based polypeptide that has the ability to bind to an antigenic determinant of human CD45R, CD45RA, CD45RB, or CD45RO, but does not have the ability to bind to rhesus or cynomolgus CD45. In some embodiments, the ADBD is a D domain-based polypeptide that has the ability to bind to an antigenic determinant of human CD45RO, but does not have the ability to bind to a non-human primate homologue of CD45.

In some embodiments, the ADBD is a D domain-based polypeptide that has the ability to bind to an antigenic determinant of human CD45RO, but does not have the ability to bind to rhesus or cynomolgus CD45. In some embodiments, the ADBD is a D domain-based polypeptide that has the ability to bind to an antigenic determinant of human CD26, CD30, CD33, or CD38. In some embodiments, the ADBD is a D domain-based polypeptide that has the ability to bind to an antigenic determinant of human CD26, CD30, CD33, or CD38, but does not have the ability to bind to a non-human primate homologue of CD26, CD30, CD33, or CD38, respectively. In some embodiments, the ADBD is a D domain-based polypeptide that has the ability to bind to an antigenic determinant of human CD26, CD30, CD33, or CD38, but does not have the ability to bind to rhesus or cynomolgus CD26, CD30, CD33, or CD38, respectively.

In some embodiments, the ADBD (e.g., of an Adapter and/or CAR) specifically binds to an AD of human CD45. In some embodiments, the ADBD specifically binds to an AD of the extracellular domain (ECD) of human CD45. In some embodiments, the ADBD specifically binds to an AD of the ECD of human CD45RA. In some embodiments, the ADBD specifically binds to an AD of the ECD of human CD45RB. In some embodiments, the ADBD specifically binds to an AD of the ECD of human CD45RAB. In some embodiments, the ADBD specifically binds to an AD of the ECD of human CD45RBC. In some embodiments, the ADBD specifically binds to an AD of the ECD of human CD45RAC. In some embodiments, the ADBD specifically binds to an AD of the ECD of human CD45RABC. In some embodiments, the ADBD specifically binds to an AD of the ECD of human CD45RO. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1106. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1107. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1108. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1109. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1110. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1111. In some embodiments, the ADBD specifically binds to an AD of comprising 5-25, 5-50, 5-75, 5-100, 5-125, or 5-150 amino acid residues, more than 150 amino acid residues, or all of the amino acid residues of SEQ ID NO: 1112.

In some embodiments, the ADBD specifically binds to a glycosylation dependent epitope of human CD45.

In some embodiments, the ADBD specifically binds to an epitope of human CD45 that is not present in a non-human primate CD45. In some embodiments, the ADBD specifically binds to an epitope of human CD45 that is not present in a rhesus CD45. In some embodiments, the ADBD specifically binds to of human CD45 that is not present in a cynomolgus CD45.

In some embodiments, the ADBD specifically binds to the same epitope of human CD45 that is bound by the UCHL-1, A6, or ODP4 antibody. In some embodiments, the ADBD specifically binds to the same epitope of human CD45 that is bound by the 4KB5, MB1, KiB3, 2H4, or MT2 antibody.

In some embodiments, the ADBD specifically binds to an epitope of human CD45 that overlaps with the epitope bound by the UCHL-1, A6, or ODP4 antibody. In some embodiments, the ADBD specifically binds to an epitope of human CD45 that overlaps with the epitope bound by the 4KB5, MB1, KiB3, 2H4, or MT2 antibody.

In some embodiments, the ADBD competes with a reference antibody for binding to human CD45 in an in vitro binding assay, wherein the reference antibody is UCHL-1, A6, or ODP4. In some embodiments, the ADBD competes with a reference antibody for binding to human CD45 in an in vitro binding assay, wherein the reference antibody is 4KB5, MB1, KiB3, 2H4, or MT2.

In some embodiments, the ADBD specifically binds to an AD of CD26. In further embodiments, the AD comprises 5-25, 5-50, 5-75, 5-100, 5-125, or 5-150 amino acid residues, more than 150 amino acid residues, or all of the amino acid residues of residues 29-766 of SEQ ID NO: 1113.

In some embodiments, the ADBD specifically binds to an AD of CD30. In further embodiments, the AD comprises 5-25, 5-50, 5-75, 5-100, 5-125, or 5-150 amino acid residues, more than 150 amino acid residues, or all of the amino acid residues of residues 19-379 of SEQ ID NO: 1114.

In some embodiments, the ADBD specifically binds to an AD of CD33. In further embodiments, the AD comprises 5-25, 5-50, 5-75, 5-100, 5-125, or 5-150 amino acid residues, more than 150 amino acid residues, or all of the amino acid residues of residues 18-259 of SEQ ID NO: 1115.

In some embodiments, the ADBD specifically binds to an AD of CD38. In further embodiments, the AD comprises 5-25, 5-50, 5-75, 5-100, 5-125, or 5-150 amino acid residues, more than 150 amino acid residues, or all of the amino acid residues of residues 43-300 of SEQ ID NO: 1116.

In some embodiments, the ADBD specifically binds to an AD of human CD45. In some embodiments, the ADBD specifically binds to an AD of human CD26, CD30, CD33, or CD38.

In some embodiments, the ADBD comprises a fragment of an antibody that is sufficient to confer recognition and specific binding to an AD of human CD45. In some embodiments, the ADBD comprises a fragment of an antibody that is sufficient to confer recognition and specific binding to an AD of human CD26, CD30, CD33, or CD38.

In some embodiments, the ADBD is a scFv that (e.g., of an Adapter and/or CAR) specifically binds to an AD of human CD45. In some embodiments, the ADBD is a scFv that specifically binds to an AD of the extracellular domain (ECD) of human CD45. In some embodiments, the ADBD is a scFv that specifically binds to an AD of the ECD of human CD45RA. In some embodiments, the ADBD is a scFv that specifically binds to an AD of the ECD of human CD45RB. In some embodiments, the ADBD is a scFv that specifically binds to an AD of the ECD of human CD45RAB. In some embodiments, the ADBD is a scFv that specifically binds to an AD of the ECD of human CD45RBC. In some embodiments, the ADBD is a scFv that specifically binds to an AD of the ECD of human CD45RAC. In some embodiments, the ADBD is a scFv that specifically binds to an AD of the ECD of human CD45RABC. In some embodiments, the ADBD is a scFv that specifically binds to an AD of the ECD of human CD45RO. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1106. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1107. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1108. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1109. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1110. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1111. In some embodiments, the ADBD is a scFv that specifically binds to an AD of comprising 5-25, 5-50, 5-75, 5-100, 5-125, or 5-150 amino acid residues, more than 150 amino acid residues, or all of the amino acid residues of SEQ ID NO: 1112.

In some embodiments, the ADBD is a scFv that specifically binds to a glycosylation dependent epitope of human CD45.

In some embodiments, the ADBD is a scFv that specifically binds to an epitope of human CD45 that is not present in a non-human primate CD45. In some embodiments, the ADBD is a scFv that specifically binds to an epitope of human CD45 that is not present in a rhesus CD45. In some embodiments, the ADBD is a scFv that specifically binds to of human CD45 that is not present in a cynomolgus CD45.

In some embodiments, the ADBD is a scFv that specifically binds to the same epitope of human CD45 that is bound by the UCHL-1, A6, or ODP4 antibody. In some embodiments, the ADBD is a scFv that specifically binds to the same epitope of human CD45 that is bound by the 4KB5, MB1, KiB3, 2H4, or MT2 antibody.

In some embodiments, the ADBD is a scFv that specifically binds to an epitope of human CD45 that overlaps with the epitope bound by the UCHL-1, A6, or ODP4 antibody. In some embodiments, the ADBD is a scFv that specifically binds to an epitope of human CD45 that overlaps with the epitope bound by the 4KB5, MB1, KiB3, 2H4, or MT2 antibody.

In some embodiments, the ADBD is a scFv that competes with a reference antibody for binding to human CD45 in an in vitro binding assay, wherein the reference antibody is UCHL-1, A6, or ODP4. In some embodiments, the ADBD is a scFv that competes with a reference antibody for binding to human CD45 in an in vitro binding assay, wherein the reference antibody is 4KB5, MB1, KiB3, 2H4, or MT2.

In some embodiments, the ADBD is an scFv that specifically binds to an AD of human CD26, CD30, CD33, or CD38.

In some embodiments, the ADBD is a SDAB that specifically binds to an AD of human CD45. In some embodiments, the ADBD is a SDAB that specifically binds to an AD of human CD26, CD30, CD33, or CD38.

In some embodiments, the ADBD comprises a human antibody or a fragment thereof that specifically binds to an AD of human CD45. In some embodiments, the ADBD comprises a human antibody or a fragment thereof that specifically binds to an AD of human CD26, CD30, CD33, or CD38.

In some embodiments, the ADBD comprises a humanized antibody or a fragment thereof that specifically binds to an AD of human CD45. In some embodiments, the ADBD comprises a humanized antibody or a fragment thereof that specifically binds to an AD of human CD26, CD30, CD33, or CD38.

In some embodiments, the ADBD is an ASBD that specifically binds to an AD of human CD45. In some embodiments, the ADBD is an ASBD that specifically binds to an AD of human CD26, CD30, CD33, or CD38.

In some embodiments, the ASBD specifically binds to an AD of human CD45. In some embodiments, the ASBD specifically binds to an AD of human CD26, CD30, CD33, or CD38.

In some embodiments, the ASBD specifically binds to an AD of human CD45. In some embodiments, the ASBD specifically binds to an AD of human CD26, CD30, CD33, or CD38.

In some embodiments, the ADBD is a D domain that (e.g., of an Adapter and/or CAR) specifically binds to an AD of human CD45. In some embodiments, the ADBD is a D domain that specifically binds to an AD of the extracellular domain (ECD) of human CD45. In some embodiments, the ADBD is a D domain that specifically binds to an AD of the ECD of human CD45RA. In some embodiments, the ADBD is a D domain that specifically binds to an AD of the ECD of human CD45RB. In some embodiments, the ADBD is a D domain that specifically binds to an AD of the ECD of human CD45RAB. In some embodiments, the ADBD is a D domain that specifically binds to an AD of the ECD of human CD45RBC. In some embodiments, the ADBD is a D domain that specifically binds to an AD of the ECD of human CD45RAC. In some embodiments, the ADBD is a D domain that specifically binds to an AD of the ECD of human CD45RABC. In some embodiments, the ADBD is a D domain that specifically binds to an AD of the ECD of human CD45RO. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1106. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1107. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1108. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1109. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1110. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1111. In some embodiments, the ADBD is a D domain that specifically binds to an AD of comprising 5-25, 5-50, 5-75, 5-100, 5-125, or 5-150 amino acid residues, more than 150 amino acid residues, or all of the amino acid residues of SEQ ID NO: 1112.

In some embodiments, the ADBD is a D domain that specifically binds to a glycosylation dependent epitope of human CD45.

In some embodiments, the ADBD is a D domain that specifically binds to an epitope of human CD45 that is not present in a non-human primate CD45. In some embodiments, the ADBD is a D domain that specifically binds to an epitope of human CD45 that is not present in a rhesus CD45. In some embodiments, the ADBD is a D domain that specifically binds to of human CD45 that is not present in a cynomolgus CD45.

In some embodiments, the ADBD is a D domain that specifically binds to the same epitope of human CD45 that is bound by the UCHL-1, A6, or ODP4 antibody. In some embodiments, the ADBD is a D domain that specifically binds to the same epitope of human CD45 that is bound by the 4KB5, MB1, KiB3, 2H4, or MT2 antibody.

In some embodiments, the ADBD is a D domain that specifically binds to an epitope of human CD45 that overlaps with the epitope bound by the UCHL-1, A6, or ODP4 antibody. In some embodiments, the ADBD is a D domain that specifically binds to an epitope of human CD45 that overlaps with the epitope bound by the 4KB5, MB1, KiB3, 2H4, or MT2 antibody.

In some embodiments, the ADBD is a D domain that competes with a reference antibody for binding to human CD45 in an in vitro binding assay, wherein the reference antibody is UCHL-1, A6, or ODP4. In some embodiments, the ADBD is a D domain that competes with a reference antibody for binding to human CD45 in an in vitro binding assay, wherein the reference antibody is 4KB5, MB1, KiB3, 2H4, or MT2.

In some embodiments, the ASBD is a D-domain that specifically binds to an AD of human CD26, CD30, CD33, or CD38.

In some embodiments, the ASBD is a Z-domain scaffold-based binding domain that specifically binds to an AD of human CD45. In some embodiments, the ASBD is a Z-domain scaffold-based binding domain that specifically binds to an AD of human CD26, CD30, CD33, or CD38.

In some embodiments, the ASBD is a DARPin-based AD binding domain that specifically binds to an AD of human CD45. In some embodiments, the ASBD is a DARPin-based AD binding domain that specifically binds to an AD of human CD26, CD30, CD33, or CD38.

In some embodiments, the ASBD is an adnectin-based AD binding domain that specifically binds to an AD of human CD45. In some embodiments, the ASBD is an adnectin-based AD binding domain that specifically binds to an AD of human CD26, CD30, CD33, or CD38.

In some embodiments, the ASBD is a lipocalin-, affilin-, or anticalin-based AD binding domain that specifically binds to an AD of human CD45. In some embodiments, the ASBD is a lipocalin-, affilin-, or anticalin-based AD binding domain that specifically binds to an AD of human CD26, CD30, CD33, or CD38.

In some embodiments, the ASBD is an Avimer scaffold-based AD binding domain that specifically binds to an AD of human CD45. In some embodiments, the ASBD is an Avimer scaffold-based AD binding domain that specifically binds to an AD of human CD26, CD30, CD33, or CD38.

In some embodiments, the ASBD is a fynomer scaffold-based AD binding domain that specifically binds to an AD of human CD45. In some embodiments, the ASBD is a fynomer scaffold-based AD binding domain that specifically binds to an AD of human CD26, CD30, CD33, or CD38.

In some embodiments, the ASBD is a knottin scaffold-based AD binding domain that specifically binds to an AD of human CD45. In some embodiments, the ASBD is a fynomer scaffold-based AD binding domain that specifically binds to an AD of human CD26, CD30, CD33, or CD38.

In some embodiments, the ASBD is a Kunitz scaffold-based AD binding domain that specifically binds to an AD of human CD45. In some embodiments, the ASBD is a Kunitz scaffold-based AD binding domain that specifically binds to an AD of human CD26, CD30, CD33, or CD38.

In some embodiments, the ASBD is a WW domain-based AD binding domain that specifically binds to an AD of human CD45. In some embodiments, the ASBD is a WW domain-based AD binding domain that specifically binds to an AD of human CD26, CD30, CD33, or CD38.

Provided herein are multi-domain soluble Adapter proteins. The Adapter comprises an antigenic determinant (AD) (e.g., as described in Section II) and an antigenic determinant binding domain (ADBD) (e.g., as described in Section III). The Adapter can further comprise additional ADs, additional ADBDs, and/or other additional domains (e.g., as described in Section V). In some embodiments, the Adapter comprises an antigenic determinant binding domain (ADBD) that specifically binds to a human CD45 AD. In some embodiments, the Adapter comprises an antigenic determinant binding domain (ADBD) that specifically binds to an AD of human CD26, CD30, CD33, or CD38.

In some embodiments, the Adapter comprises an AD that is a human CD45 AD. In some embodiments, the Adapter comprises an AD that is an AD of human CD26, CD30, CD33, or CD38.

In some embodiments, The AD in the Adapter is an epitope of human CD45. In some embodiments, The AD in the Adapter is an epitope of the extracellular domain (ECD) of human CD45. In some embodiments, The AD in the Adapter is an epitope of the ECD of human CD45RA. In some embodiments, The AD in the Adapter is an epitope of the ECD of human CD45RB. In some embodiments, The AD in the Adapter is an epitope of the ECD of human CD45RAB. In some embodiments, The AD in the Adapter is an epitope of the ECD of human CD45RBC. In some embodiments, The AD in the Adapter is an epitope of the ECD of human CD45RAC. In some embodiments, The AD in the Adapter is an epitope of the ECD of human CD45RABC. In some embodiments, The AD in the Adapter is an epitope of the ECD of human CD45RO. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1106. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1107. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1108. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1109. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1110. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1111. In further embodiments, The AD in the Adapter comprises 5-25, 5-50, 5-75, 5-100, 5-125, or 5-150 amino acid residues, more than 150 amino acid residues, or all of the amino acid residues of SEQ ID NO: 1112.

In some embodiments, The AD in the Adapter is a glycosylation dependent epitope of human CD45.

In some embodiments, The AD in the Adapter is an epitope of human CD45 that is not present in a non-human primate CD45. In some embodiments, The AD in the Adapter is an epitope of human CD45 that is not present in a rhesus CD45. In some embodiments, The AD in the Adapter is an epitope of human CD45 that is not present in a cynomolgus CD45.

In some embodiments, The AD in the Adapter is an epitope of human CD45 that is bound by the UCHL-1, A6, or ODP4 antibody. In some embodiments, The AD in the Adapter is an epitope of human CD45 that is bound by the 4KB5, MB1, KiB3, 2H4, or MT2 antibody.

In some embodiments, The AD in the Adapter is an epitope of human CD26, CD30, CD33, or CD38.

In some embodiments, the ADBD in the Adapter specifically binds to an AD of human CD45. In some embodiments, the ADBD in the Adapter specifically binds to an AD of the extracellular domain (ECD) of human CD45. In some embodiments, the ADBD in the Adapter specifically binds to an AD of the ECD of human CD45RA. In some embodiments, the ADBD in the Adapter specifically binds to an AD of the ECD of human CD45RB. In some embodiments, the ADBD in the Adapter specifically binds to an AD of the ECD of human CD45RAB. In some embodiments, the ADBD in the Adapter specifically binds to an AD of the ECD of human CD45RBC. In some embodiments, the ADBD in the Adapter specifically binds to an AD of the ECD of human CD45RAC. In some embodiments, the ADBD in the Adapter specifically binds to an AD of the ECD of human CD45RABC. In some embodiments, the ADBD in the Adapter specifically binds to an AD of the ECD of human CD45RO. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1106. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1107. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1108. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1109. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1110. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1111. In some embodiments, the ADBD in the Adapter specifically binds to an AD of comprising 5-25, 5-50, 5-75, 5-100, 5-125, or 5-150 amino acid residues, more than 150 amino acid residues, or all of the amino acid residues of SEQ ID NO: 1112.

In some embodiments, the ADBD in the Adapter specifically binds to a glycosylation dependent epitope of human CD45.

In some embodiments, the ADBD in the Adapter specifically binds to an epitope of human CD45 that is not present in a non-human primate CD45. In some embodiments, the ADBD in the Adapter specifically binds to an epitope of human CD45 that is not present in a rhesus CD45. In some embodiments, the ADBD in the Adapter specifically binds to of human CD45 that is not present in a cynomolgus CD45.

In some embodiments, the ADBD in the Adapter specifically binds to the same epitope of human CD45 that is bound by the UCHL-1, A6, or ODP4 antibody. In some embodiments, the ADBD in the Adapter specifically binds to the same epitope of human CD45 that is bound by the 4KB5, MB1, KiB3, 2H4, or MT2 antibody.

In some embodiments, the ADBD in the Adapter specifically binds to an epitope of human CD45 that overlaps with the epitope bound by the UCHL-1, A6, or ODP4 antibody. In some embodiments, the ADBD in the Adapter specifically binds to an epitope of human CD45 that overlaps with the epitope bound by the 4KB5, MB1, KiB3, 2H4, or MT2 antibody.

In some embodiments, the ADBD in the Adapter competes with a reference antibody for binding to human CD45 in an in vitro binding assay, wherein the reference antibody is UCHL-1, A6, or ODP4. In some embodiments, the ADBD in the Adapter competes with a reference antibody for binding to human CD45 in an in vitro binding assay, wherein the reference antibody is 4KB5, MB1, KiB3, 2H4, or MT2.

In some embodiments, the ADBD in the Adapter specifically binds to an epitope of human CD26, CD30, CD33, or CD38.

In some embodiments, an ADBD in the Adapter can be an antibody, an antigen-binding fragment thereof, a ScFv, an alternative scaffold binding domain, a D domain, a T cell receptor, or an antigen-binding fragment thereof that specifically binds to a human CD45 AD. In some embodiments, an ADBD in the Adapter can be an antibody, an antigen-binding fragment thereof, a ScFv, an alternative scaffold binding domain, a D domain, a T cell receptor, or an antigen-binding fragment thereof that specifically binds to an AD of human CD26, CD30, CD33, or CD38.

In some embodiments, the Adapter is bispecific. In some embodiments, the Adapter comprises an ADBD that binds to a CD45 AD and an ADBD that binds to a second AD. In some embodiments, the Adapter comprises an ADBD that binds to a first CD45 AD and an ADBD that binds to a second CD45 AD.

As provided herein, chimeric antigen receptors (CARs) are multi-domain proteins that comprise an extracellular domain comprising an ADBD, a transmembrane domain, and an intracellular signaling domain (e.g., as described in Section VI).

In some embodiments, the ADBD in the CAR specifically binds to an AD of human CD45. In some embodiments, the ADBD in the CAR specifically binds to an AD of the extracellular domain (ECD) of human CD45. In some embodiments, the ADBD in the CAR specifically binds to an AD of the ECD of human CD45RA. In some embodiments, the ADBD in the CAR specifically binds to an AD of the ECD of human CD45RB. In some embodiments, the ADBD in the CAR specifically binds to an AD of the ECD of human CD45RAB. In some embodiments, the ADBD in the CAR specifically binds to an AD of the ECD of human CD45RBC. In some embodiments, the ADBD in the CAR specifically binds to an AD of the ECD of human CD45RAC. In some embodiments, the ADBD in the CAR specifically binds to an AD of the ECD of human CD45RABC. In some embodiments, the ADBD in the CAR specifically binds to an AD of the ECD of human CD45RO. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1106. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1107. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1108. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1109. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1110. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1111. In some embodiments, the ADBD in the CAR specifically binds to an AD of comprising 5-25, 5-50, 5-75, 5-100, 5-125, or 5-150 amino acid residues, more than 150 amino acid residues, or all of the amino acid residues of SEQ ID NO: 1112.

In some embodiments, the ADBD in the CAR specifically binds to a glycosylation dependent epitope of human CD45.

In some embodiments, the ADBD in the CAR specifically binds to an epitope of human CD45 that is not present in a non-human primate CD45. In some embodiments, the ADBD in the CAR specifically binds to an epitope of human CD45 that is not present in a rhesus CD45. In some embodiments, the ADBD in the CAR specifically binds to of human CD45 that is not present in a cynomolgus CD45.

In some embodiments, the ADBD in the CAR specifically binds to the same epitope of human CD45 that is bound by the UCHL-1, A6, or ODP4 antibody. In some embodiments, the ADBD in the CAR specifically binds to the same epitope of human CD45 that is bound by the 4KB5, MB1, KiB3, 2H4, or MT2 antibody.

In some embodiments, the ADBD in the CAR specifically binds to an epitope of human CD45 that overlaps with the epitope bound by the UCHL-1, A6, or ODP4 antibody. In some embodiments, the ADBD in the CAR specifically binds to an epitope of human CD45 that overlaps with the epitope bound by the 4KB5, MB1, KiB3, 2H4, or MT2 antibody.

In some embodiments, the ADBD in the CAR competes with a reference antibody for binding to human CD45 in an in vitro binding assay, wherein the reference antibody is UCHL-1, A6, or ODP4. In some embodiments, the ADBD in the CAR competes with a reference antibody for binding to human CD45 in an in vitro binding assay, wherein the reference antibody is 4KB5, MB1, KiB3, 2H4, or MT2.

In some embodiments, the ADBD in the CAR specifically binds to an AD of CD26. In further embodiments, the AD comprises 5-25, 5-50, 5-75, 5-100, 5-125, or 5-150 amino acid residues, more than 150 amino acid residues, or all of the amino acid residues of residues 29-766 of SEQ ID NO: 1113.

In some embodiments, the ADBD in the CAR specifically binds to an AD of CD30. In further embodiments, the AD comprises 5-25, 5-50, 5-75, 5-100, 5-125, or 5-150 amino acid residues, more than 150 amino acid residues, or all of the amino acid residues of residues 19-379 of SEQ ID NO: 1114.

In some embodiments, the ADBD in the CAR specifically binds to an AD of CD33. In further embodiments, the AD comprises 5-25, 5-50, 5-75, 5-100, 5-125, or 5-150 amino acid residues, more than 150 amino acid residues, or all of the amino acid residues of residues 18-259 of SEQ ID NO: 1115.

In some embodiments, the ADBD in the CAR specifically binds to an AD of CD38. In further embodiments, the AD comprises 5-25, 5-50, 5-75, 5-100, 5-125, or 5-150 amino acid residues, more than 150 amino acid residues, or all of the amino acid residues of residues 43-300 of SEQ ID NO: 1116.

In some embodiments, a CAR provided herein comprises an ABDB that specifically binds to an AD of human CD45. In some embodiments, a CAR provided herein comprises an ABDB that specifically binds to an AD of human CD26, CD30, CD33, or CD38. In some embodiments, a CAR provided herein comprises an ABDB that specifically binds to AFP p26, or a variant thereof (e.g., a polypeptide comprising the amino acid sequence of SEQ ID NO: 16, 1117, 1118, 1119, 1120, 1121, 1122, or 1123).

To avoid or reduce the possibility that CAR cells disclosed herein target an immune response (e.g., kill) to themselves, a CAR cell can be genetically modified to reduce or eliminate the expression of one or more AD targeted by the CAR cell directly by a CAR described herein or indirectly through an Adaptor described herein. For example, a CAR cell disclosed herein with an ADBD that specifically binds to an AD of human CD45 or a CAR cell disclosed herein suited to be used in combination with an Adapter comprising an ADBD that specifically binds to an AD of human CD45 can be engineered to reduce or eliminate the expression of the human CD45 AD recognized by the ADBD. In some embodiments, the CAR cell is a human immune effector cell.

In some embodiments, the CAR cell comprises a genetic modification that reduces or eliminates the expression of one AD bound by a CAR or Adapter disclosed herein. In some embodiments, the CAR cell comprises a genetic modification that reduces or eliminates the expression of more than one AD bound by a CAR or Adapter disclosed herein. In some embodiments, the CAR cell comprises more than one genetic modification that reduces or eliminates the expression of more than one AD bound by a CAR or Adapter disclosed herein. In some embodiments, the more than one AD is comprised by a single antigen. In some embodiments, the AD is a human CD45 AD. In some embodiments, the CAR cell is a human immune effector cell.

In some embodiments, the genetic modification reduces expression of the AD by about 50%, about 60%, about 70%, about 80%, about 90%, about 95% compared to a reference cell without the genetic modification. In some embodiments, the genetic modification eliminates expression of the AD.

In some embodiments, the genetic modification reduces expression of the polypeptide comprising the AD by about 50%, about 60%, about 70%, about 80%, about 90%, about 95% compared to a reference cell without the genetic modification. In some embodiments, the genetic modification eliminates expression of the polypeptide comprising the AD. In some embodiments, the AD is a human CD45 AD.

In some embodiments, the genetic modification is a deletion, insertion, or substitution in a gene or fragment thereof encoding the AD. In some embodiments, the genetic modification is a deletion, insertion, or substitution in a gene or fragment thereof encoding the AD that eliminates expression of the AD. In some embodiments, the AD is a human CD45 AD.

In some embodiments, the genetic modification is a substitution of a gene or fragment thereof encoding a polypeptide comprising the AD with a nucleotide sequence encoding a homologue, variant, or derivative of the polypeptide comprising the AD, wherein the encoded homologue, variant, or derivative does not comprise the AD. In some embodiments, the homologue is a non-human primate homologue. In some embodiments, the homologue is derived from rhesus macaque. In some embodiments, the homologue is derived from cynomolgus monkey. In some embodiments, the variant is a naturally occurring variant. In some embodiments, the variant is a splice variant. In some embodiments, the variant has altered glycosylation pattern. In some embodiments, the variant or derivative is capable of signaling. In some embodiments, the AD is a human CD45 AD.

The genetic modification can reduce or eliminate the expression of any AD for which it is desirable for a CAR or an Adapter to bind, e.g., any of the ADs described in Section IIa.

In some embodiments, the genetic modification reduces or eliminates the expression of a human CD45 AD. In some embodiments, the AD is an epitope of the extracellular domain (ECD) of human CD45. In some embodiments, the AD is an epitope of the ECD of human CD45RA. In some embodiments, the AD is an epitope of the ECD of human CD45RB. In some embodiments, the AD is an epitope of the ECD of human CD45RAB. In some embodiments, the AD is an epitope of the ECD of human CD45RBC. In some embodiments, the AD is an epitope of the ECD of human CD45RAC. In some embodiments, the AD is an epitope of the ECD of human CD45RABC. In some embodiments, the AD is an epitope of the ECD of human CD45RO. In further embodiments, the AD comprises 5-25, 5-50, 5-75, 5-100, 5-125, or 5-150 amino acid residues, more than 150 amino acid residues, or all of the amino acid residues of SEQ ID NO: 1106. In further embodiments, the AD comprises 5-25, 5-50, 5-75, 5-100, 5-125, or 5-150 amino acid residues, more than 150 amino acid residues, or all of the amino acid residues of SEQ ID NO: 1107. In further embodiments, the AD comprises 5-25, 5-50, 5-75, 5-100, 5-125, or 5-150 amino acid residues, more than 150 amino acid residues, or all of the amino acid residues of SEQ ID NO: 1108. In further embodiments, the AD comprises 5-25, 5-50, 5-75, 5-100, 5-125, or 5-150 amino acid residues, more than 150 amino acid residues, or all of the amino acid residues of SEQ ID NO: 1109. In further embodiments, the AD comprises 5-25, 5-50, 5-75, 5-100, 5-125, or 5-150 amino acid residues, more than 150 amino acid residues, or all of the amino acid residues of SEQ ID NO: 1110. In further embodiments, the AD comprises 5-25, 5-50, 5-75, 5-100, 5-125, or 5-150 amino acid residues, more than 150 amino acid residues, or all of the amino acid residues of SEQ ID NO: 1111. In further embodiments, the AD comprises 5-25, 5-50, 5-75, 5-100, 5-125, or 5-150 amino acid residues, more than 150 amino acid residues, or all of the amino acid residues of SEQ ID NO: 1112.

In some embodiments, the genetic modification reduces or eliminates the expression of a human CD45 AD that is a glycosylation dependent epitope of human CD45.

In some embodiments, the genetic modification reduces or eliminates the expression of a human CD45 AD. In some embodiments, the AD is an epitope of human CD45 that is not present in a non-human primate CD45. In some embodiments, the AD is an epitope of human CD45 that is not present in a rhesus CD45. In some embodiments, the AD is an epitope of human CD45 that is not present in a cynomolgus CD45.

In some embodiments, the genetic modification reduces or eliminates the expression of a human CD45 AD. In some embodiments, the AD is an epitope of human CD45 that is bound by the UCHL-1, A6, or ODP4 antibody. In some embodiments, the AD is an epitope of human CD45 that is bound by the 4KB5, MB1, KiB3, 2H4, or MT2 antibody.

In some embodiments, the genetic modification reduces or eliminates the expression of a human CD45 AD. In some embodiments, the genetic modification is a deletion, insertion, or substitution in a gene or fragment thereof encoding human CD45. In some embodiments, the genetic modification is a deletion, insertion, or substitution in a gene or fragment thereof encoding human CD45 that eliminates expression of the CD45 AD.

In some embodiments, the genetic modification reduces or eliminates the expression of a human CD45 AD. In some embodiments, the genetic modification is a substitution of a gene or fragment thereof encoding human CD45 with a nucleotide sequence encoding a homologue, variant, or derivative of human CD45, wherein the encoded homologue, variant, or derivative does not comprise the human CD45 AD. In some embodiments, the homologue is a non-human primate homologue. In some embodiments, the homologue is rhesus macaque CD45. In some embodiments, the homologue is cynomolgus CD45. In some embodiments, the variant is a naturally occurring variant of human CD45. In some embodiments, the CD45 variant is a splice variant. In some embodiments, the CD45 variant has altered glycosylation pattern. In some embodiments, the variant or derivative is capable of signaling.

In some embodiments, the genetic modification reduces or eliminates the expression of a human CD26, CD30, CD33, or CD38, AD. In some embodiments, the genetic modification reduces or eliminates the expression of human CD26, CD30, CD33, or CD38. In some embodiments, the genetic modification eliminates the expression of human CD26, CD30, CD33, or CD38. In some embodiments, the genetic modification is a substitution of a gene or fragment thereof encoding human CD26, CD30, CD33, or CD38 with a nucleotide sequence encoding a homologue, variant, or derivative of CD26, CD30, CD33, or CD38, wherein the homologue, variant, or derivative does not comprise the AD targeted by a CAR or Adapter described herein.

The production of CAR cells comprising a genetic modification, useful in practicing the provided methods, may be carried out using a variety of standard techniques for recombinant DNA methodologies, genetic manipulation, and genome editing known in the art. Genetically modified CAR cells described herein that lack expression of an AD can routinely be obtained using any suitable means known in the art, including for example, siRNA, shRNA, CRISPR, TALEN, and/or ZFN. Methods for genetic manipulation of CAR cells is described, for example, in U.S. Patent Appl. Pub. 20170204372, which is incorporated herein by reference in its entirety.

Described herein are methods of use comprising contacting a target cell with a CAR cell (e.g., as described above in Section VII) and an Adapter (e.g., as described above in Section V) or a composition (e.g., as described above in Section VIII). In some embodiments, the target cell expresses CD45. In some embodiments the CAR or Adapter comprises an ADBD that specifically binds to a CD45 AD. In some embodiments, the CAR cell comprises a genetic modification that reduces or eliminates the expression of an AD described herein. In some embodiments, the CAR cell comprises a genetic modification that reduces or eliminates the expression of a human CD45 AD.

For example, in one embodiment, a method of delivering an immune response to a target cell comprises contacting the target cell with any of the compositions described herein (e.g., as described in Section VIII). In another embodiment, a method of killing a target cell comprises contacting the target cell with any of the compositions described herein (e.g., as described in Section VIII). As used herein, "contacting" can refer to contacting a target cell in vitro (e.g., in a cell culture) or contacting a target cell in vivo (e.g., in a patient). In some embodiments, the CAR cell comprises a genetic modification that reduces or eliminates the expression of an AD described herein. In some embodiments, the CAR cell comprises a genetic modification that reduces or eliminates the expression of a human CD45 AD. In some embodiments, the target cell expresses CD45.

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell. In some embodiments, the target cell is a memory T cell expressing CD45RO.

In some embodiments, the target cell expresses CD45. In some embodiments, the target cell expresses CD45RO. In some embodiments, the target cell expresses CD45RA. In some embodiments, the target cell expresses CD45RAB. In some embodiments, the target cell expresses CD45RAC. In some embodiments, the target cell expresses CD45RBC. In some embodiments, the target cell expresses CD45RABC. In some embodiments, the CD45 is human CD45.

In some embodiments of the compositions and methods disclosed herein, the target is an antigenic determinant of human CD45. In some embodiments, the target is an antigenic determinant of human CD45R, CD45RA, CD45RB, or CD45RO. In some embodiments, the target is an antigenic determinant of human CD45 that is not present in a non-human primate homologue of CD45. In some embodiments, the target is an antigenic determinant of human CD45R, CD45RA, CD45RB, or CD45RO that is not present in a non-human primate homologue of CD45. In some embodiments, the target is an antigenic determinant of human CD45 that is not present in rhesus or cynomolgus CD45. In some embodiments, the target is an antigenic determinant of human CD26, CD30, CD33, or CD38. In some embodiments, the target is an antigenic determinant of human CD26, CD30, CD33, or CD38 that is not present in a non-human primate homologue of CD26, CD30, CD33, or CD38, respectively. In some embodiments, the target is an antigenic determinant of human CD26, CD30, CD33, or CD38 that is not present in rhesus or cynomolgus CD26, CD30, CD33, or CD38, respectively.

In some embodiments of the compositions and methods disclosed herein, the target cell can be a cell expressing CD45. In some embodiments, a target cell can be a cell expressing CD45R, CD45RA, CD45RB, or CD45RO. In some embodiments, a target cell can be a cell expressing CD26, CD30, CD33, or CD38.

Described herein are methods of delivering an immune response to a target cell in a patient and/or killing a target cell in a patient comprising administering an Adapter (as described herein (e.g., as described in Section V above)) and/or a CAR cell described herein (e.g., as described in Section VII) to the patient. Also described herein are methods of treating a proliferative disorder, cancer, autoimmune disease, infection, or allograft rejection comprising administering an Adapter described herein (e.g., as described in Section V) and/or a CAR cell described herein (e.g., as described in Section VII) to the patient. In particular embodiments, provided herein are methods of treating hematological cancer or autoimmune disease comprising administering an Adapter described herein (e.g., as described in Section V) and/or a CAR cell described herein (e.g., as described in Section VII) to the patient. In some embodiments, the target cell expresses CD45. In some embodiments the CAR or Adapter comprises an ADBD that specifically binds to a CD45 AD. In some embodiments, the CAR cell comprises a genetic modification that reduces or eliminates the expression of an AD described herein. In some embodiments, the CAR cell comprises a genetic modification that reduces or eliminates the expression of a CD45 AD.

In one embodiment of the methods of killing a target cell in a patient or the methods of redirecting target cell killing in a patient, the target cell is a cell of the immune system. In some embodiments, the target cell is a B cell. In some embodiments, the target cell is a T cell. In some embodiments, the target cell is a naïve T cell. In some embodiments, the target cell is a memory T cell. In some embodiments, the target cell is a memory T cell expressing CD45RO.

In some embodiments, the target cell expresses CD45. In some embodiments, the target cell expresses CD45RO. In some embodiments, the target cell expresses CD45RA. In some embodiments, the target cell expresses CD45RAB. In some embodiments, the target cell expresses CD45RAC. In some embodiments, the target cell expresses CD45RBC. In some embodiments, the target cell expresses CD45RABC. In some embodiments, the CD45 is human CD45.

In one embodiment of the methods of killing a target cell in a patient or the methods of redirecting target cell killing in a patient, the patient has been diagnosed with an autoimmune disease or disorder and the target cell is a cell of the immune system expressing a CD45 AD. In some embodiments, the target cell is a B cell. In some embodiments, the target cell is a T cell. In some embodiments, the target cell is a memory T cell. In some embodiments, the target cell expresses CD45. In some embodiments, the target cell expresses CD45RO.

In one embodiment, the methods described herein are useful for preparing or conditioning a patient for bone marrow transplantation (BMT) or hematopoietic stem cell transplantation (HSCT). Thus in some embodiments, the methods of killing a target cell in a patient or the methods of redirecting target cell killing in a patient provided herein condition a subject for BMT or HSCT. In some embodiments, the methods provided herein condition a subject for HSCT. In some embodiments, the HSCT is autologous HSCT. In some embodiments, the methods for conditioning a patient disclosed herein does not comprise high dose chemotherapy or total body irradiation (TBI). In some embodiments, the methods for conditioning disclosed herein comprise reduced intensity chemotherapy. In some embodiments, the methods for conditioning disclosed herein comprise total body irradiation. In some embodiments, the patient is more than 65 years old. In some embodiments, the patient has cancer. In some embodiments, the patient has a hematologic cancer. In some embodiments, the patient has a relapsed hematologic cancer. In some embodiments, the hematologic cancer is acute myeloid leukemia (AML), chronic lymphocytic leukemia (CLL), or multiple myeloma (MM). In some embodiments, the patient has an autoimmune disease or disorder. In some embodiments, the autoimmune disease or disorder is Type I diabetes, multiple sclerosis, rheumatoid arthritis, inflammatory bowel disease (IBD), Crohn's disease, or ulcerative.

In one embodiment of the methods of conditioning a patient for HSCT the patient has been diagnosed with a hematologic cancer and the target cell is a cell expressing a CD45 AD. In some embodiments, the patient is administered an engineered human immune effector cell comprising (i) a chimeric antigen receptor (CAR) comprising (1) an antigenic determinant binding domain (ADBD) that specifically binds to a human CD45 antigenic determinant (AD), (2) a transmembrane domain, and (3) an intracellular domain; and (ii) a genetic modification that eliminates the expression of the human CD45 AD on the engineered cell. In some embodiments, the patient is administered an engineered human immune effector cell comprising (i) a chimeric antigen receptor (CAR) comprising an antigenic determinant binding domain (ADBD) that specifically binds to a human CD45 antigenic determinant (AD; and (ii) a genetic modification that eliminates the expression of the human CD45 AD on the engineered cell. In some embodiments, the patient is administered an (a) engineered human immune effector cell comprising (i) a chimeric antigen receptor (CAR) comprising a first antigenic determinant binding domain (ADBD) that specifically binds to a first antigenic determinant (AD), and (ii) a genetic modification that eliminates the expression of at least one human CD45 AD on the engineered cell and (b) an Adapter comprising the first AD and a second ADBD that specifically binds to a human CD45 AD.

Articles of manufacture, including kits containing the Adapter, CAR cell, and/or CAR cell/Adapter compositions, are provided herein. The article of manufacture may comprise a container and a label or package insert on or associated with the container. Suitable containers include, for example, bottles, vials or syringes. The containers may be formed from a variety of materials such as glass or plastic. The container holds one or more Adapter, CAR cell, nucleic acids encoding Adapter, and/or vectors or host cells of the present disclosure. The label or package insert may include directions for administering the Adapter, CAR cell, and/or CAR cell/Adapter compositions to a patient. Such kits have uses including, but not limited to, therapeutic applications of the Adapter, CAR cell, and/or CAR/Adapter compositions. In some embodiments, the CAR comprises an ADBD that specifically binds to a CD45 AD. In some embodiments, the Adapter comprises an ADBD that specifically binds to a CD45 AD. In some embodiments, the CAR cell comprises a genetic modification that reduces or eliminates the expression of a CD45 AD.

Various embodiments of the invention will now be illustrated through the description of experiments in accordance therewith. The examples that follow are provided to facilitate the practice of the disclosed embodiments, and are not to be construed as limiting in any way the remainder of the disclosure. In the examples, reference is made to the appended figures.

EXAMPLES

Example 1. Exemplary D Domains and ADs

TABLE 3

Exemplary D-domains

| SEQ ID NO: | D-Domain Sequence | Target | ELISA_avg |
|---|---|---|---|
| 44 | MGSWYEFSWRLQAIHQRLNALGGSEAELAAFEKEIAAFESELQAYKGKGNP EVEELRAYAAGIRGALQAYRHN | BCMA | 9.4868 |
| 45 | MGSWHEFTWRLIAIQQRLEALGGSEAELAAFEKEIAAFESELQAYKGKGNP EVEELRAYAAGIRHHLQAYRHN | BCMA | 17.125 |
| 46 | MGSWREFAWRLVAINSRLKALGGSEAELAAFEKEIAAFESELQAYKGKGNP EVEELRHYAASIRDGLQAYRHN | BCMA | 9.66 |
| 47 | MGSWHEFAWRLQAINQRLNALGGSEAELAAFEKEIAAFESELQAYKGKGNP EVEELRHYAAHIRNGLQAYRHN | BCMA | 13.14 |
| 48 | MGSWNEFAWRLTAIEQRLMALGGSEAELAAFEKEIAAFESELQAYKGKGNP EVEELRHYAAGIRDNLQAYRHN | BCMA | 18.28 |
| 49 | MGSWTEFAWRLQAIHQRLQALGGSEAELAAFEKEIAAFESELQAYKGKGNP EVEELRVYAAKIRISLQAYRHN | BCMA | 18.71 |
| 50 | MGSWIEFAWRLQAIHQRLDALGGSEAELAAFEKEIAAFESELQAYKGKGNP EVEDLREYAANIRDSLQAYRHN | BCMA | 18.97 |
| 51 | MGSWHEFTWRLVAIQQRLQALGGSEAELAAFEKEIAAFESELQAYKGKGNP EVEELRKFAAKIRYELQAYRHN | BCMA | 19.51 |
| 52 | MGSWHEFTWRLIAIRERLFALGGSEAELAAFEKEIAAFESELQAYKGKGNP EVEELREYAASIRNMLQAYRHN | BCMA | 12.99 |

TABLE 3-continued

| Exemplary D-domains | | | |
|---|---|---|---|
| SEQ ID NO: | D-Domain Sequence | Target | ELISA_avg |
| 53 | MGSWIEFSWRLEAIRQRLQALGGSEAELAAFEKEIAAFESELQAYKGKGNP EVESLRSYAARIRQELQAYRHN | BCMA | 9.92 |
| 54 | MGSWVEFSWRLEAIRQRLQALGGSEAELAAFEKEIAAFESELQAYKGKGNP EVESLRSYAARIRQELQAYRHN | BCMA | 19.14 |
| 55 | MGSWVEFSWRLEAIRQRLTALGGSEAELAAFEKEIAAFESELQAYKGKGNP EVEDLRKYAARIRGELQAYRHN | BCMA | 21.3 |
| 56 | MGSWVEFAWRLTAIDQRLSALGGSEAELAAFEKEIAAFESELQAYKGKGNP EVENLRFYAAKIRSHLQAYRHN | BCMA | 8.43 |
| 57 | MGSWVEFAWRLEAIKQRLTALGGSEAELAAFEKEIAAFESELQAYKGKGNP EVEELRLYAAKIRRVLQAYRHN | BCMA | 8.9 |
| 58 | MGSWVEFAWRLTAIHTRLWALGGSEAELAAFEKEIAAFESELQAYKGKGNP EVESLRKYAAKIRKQLQAYRHN | BCMA | 6.08 |
| 59 | MGSWTEFAWRLEAINQRLQALGGSEAELAAFEKEIAAFESELQAYKGKGKP EVEALRAYAAKIRTRLQAYRHN | BCMA | 15.148 |
| 60 | MGSWSEFAWRLEAIHQRLSALGGSEAELAAFEKEIAAFESELQAYKGKGNP EVESLRLFAAQIRENLQAYRHN | BCMA | 18.04 |
| 61 | MGSWNEFAWRLIAINQRLWALGGSEAELAAFEKEIAAFESELQAYKGKGNP EVESLRHFAANIRNDLQAYRHN | BCMA | 11.53 |
| 62 | MGSWTEFAWRLIAIDQRLMALGGSEAELAAFEKEIAAFESELQAYKGKGNP EVEILRELAAEIRFHLQAYRHN | BCMA | 8.55 |
| 63 | MGSWSEFMNRLDAITYRLVALGGSEAELAAFEKEIAAFESELQAYKGKGNP EVELLRHYAAQIRDSLQAYRHN | BCMA | 12.9 |
| 64 | MGSWTEFMERLDAISYRLWALGGSEAELAAFEKEIAAFESELQAYKGKGNP EVEVLRDYAAIIRNSLQAYRHN | BCMA | 9.87 |
| 65 | MGSWAEFMDRLDAITYRLWALGGSEAELAAFEKEIAAFESELQAYKGKGNP EVEELRGYAAIIRSELQAYRHN | BCMA | 10.83 |
| 66 | MGSWIEFQERLDAIFYRLHALGGSEAELAAFEKEIAAFESELQAYKGKGNP EVEDLRDAAATIRRQLQAYRHN | BCMA | 18.58 |
| 67 | MGSWIEFQQRLDAIFYRLYALGGSEAELAAFEKEIAAFESELQAYKGKGNP EVENLRDMAAIIRKQLQAYRHN | BCMA | 20.02 |
| 68 | MGSWYEFQSRLDAIFYRLFALGGSEAELAAFEKEIAAFESELQAYKGKGNP EVEKLREAAASIRTQLQAYRHN | BCMA | 14.08 |
| 69 | MGSWSEFIDRLDAITYRLFALGGSEAELAAFEKEIAAFESELQAYKGKGNP EVENLRWYAGVIREQLQAYRHN | BCMA | 10.18 |
| 70 | MGSWSEFYDRLYAINQRLFALGGSEAELAAFEKEIAAFESELQAYKGKGNP EVEDLRWYAAFIRAQLQAYRHN | BCMA | 5.98 |
| 71 | MGSWYEFYDRLDAIVHRLDALGGSEAELAAFEKEIAAFESELQAYKGKGNP EVENLRWYAAMIRVRLQAYRHN | BCMA | 14.68 |
| 72 | MGSWVEFQDRLEAITDRLYALGGSEAELAAFEKEIAAFESELQAYKGKGNP EVEELRYSAAMIRVILQAYRHN | BCMA | 8.8783 |
| 73 | MGSWVEFQERLMAISDRLYALGGSEAELAAFEKEIAAFESELQAYKGKGNP EVEELRWQAAMIRYTLQAYRHN | BCMA | 6.7 |
| 74 | MGSWFEFQHRLEAISMRLHALGGSEAELAAFEKEIAAFESELQAYKGKGNP EVEELRWQAAYIRVVLQAYRHN | BCMA | 4.05 |
| 75 | MGSWVEFQSRLEAIATRLRALGGSEAELAAFEKEIAAFESELQAYKGKGNP EVEELRWQAAWIRMMLQAYRHN | BCMA | 18.008 |
| 76 | MGSWEEFQYRLGAIAARLQALGGSEAELAAFEKEIAAFESELQAYKGKGNP EVEELRWQAAMIRFMLQAYRHN | BCMA | 3.11 |
| 77 | MGSWYEFQVRLQAISWRLKALGGSEAELAAFEKEIAAFESELQAYKGKGNH EVEELRIQAALIRVMLQAYRHN | BCMA | 14.23 |

TABLE 3-continued

| Exemplary D-domains | | | |
|---|---|---|---|
| SEQ ID NO: | D-Domain Sequence | Target | ELISA_avg |
| 78 | MGSWVEFRSRLEAISNRLRALGGSEAELAAFEKEIAAFESELQAYKGKGNP EVEELRTTAALIRVYLQAYRHN | BCMA | 3.04 |
| 79 | MGSWVEFKARLEAISSRLTALGGSEAELAAFEKEIAAFESELQAYKGKGNP EVEELRYSAALIRVYLQAYRHN | BCMA | 8.7071 |
| 80 | MGSWSEFYTRLEAINNRLHALGGSEAELAAFEKEIAAFESELQAYKGKGNP EVEELRYTAALIRIYLQAYRHN | BCMA | 3.66 |
| 81 | MGSWAEFYHRLDAISSRLRALGGSEAELAAFEKEIAAFESELQAYKGKGNP EVEELRYTAALIRIYLQAYRHN | BCMA | 4.31 |
| 82 | MGSWTEFASRLVAIRQRLQALGGSEAELAAFEKEIAAFESELQAYKGKGNP EVEELRYSAAIIRVMLQAYRHN | BCMA | 7.99 |
| 83 | MGSWSEFDQRLAAIYQRLNALGGSEAELAAFEKEIAAFESELQAYKGKGNP EVEELRYSAALIRVMLQAYRHN | BCMA | 7.72 |
| 84 | MGSWVEFHNRLSAISDRLGALGGSEAELAAFEKEIAAFESELQAYKGKGNP EVEELRYSAALIRVMLQAYRHN | BCMA | 7.36 |
| 85 | MGSWNEFEDRLSAISARLSALGGSEAELAAFEKEIAAFESELQAYKGKGNP EVEELRYSAALIRVMLQAYRHN | BCMA | 4.09 |
| 86 | MGSWVEFEYRLVAIFDRLQALGGSEAELAAFEKEIAAFESELQAYKGKGNP EVEELRYQAALIRVMLQAYRHN | BCMA | 7.63 |
| 87 | MGSWVEFQGRLGAIHERLQALGGSEAELAAFEKEIAAFESELQAYKGKGNP EVEELRYSAALIRVFLQAYRHN | BCMA | 3.8343 |
| 88 | MGSWYEFSMRLSAIWERLHALGGSEAELAAFEKEIAAFESELQAYKGKGNP EVEELRYQAALIRFYLQAYRHN | BCMA | 7.12 |
| 89 | MGSWTEFSQRLGAISERLYALGGSEAELAAFEKEIAAFESELQAYKGKGNP EVEELRYSAALIRFMLQAYRHN | BCMA | 4.15 |
| 90 | MGSWTEFHDRLEAITHRLNALGGSEAELAAFEKEIAAFESELQAYKGKGNP EVEELRYSAALLRVFLQAYRHN | BCMA | 5.79 |
| 91 | MGSWTEFEHRLEAIAGRLNALGGSEAELAAFEKEIAAFESELQAYKGKGNP EVEELRYSAALIRFWLQAYRHN | BCMA | 6.34 |
| 92 | MGSWTEFANRLEAINARLHALGGSEAELAAFEKEIAAFESELQAYKGKGNP EVEELRFSAALIRVYLQAYRHN | BCMA | 6.42 |
| 93 | MGSWEEFDRRLYAIARRLEALGGSEAELAAFEKEIAAFESELQAYKGKGNP EVEELRYQAALIRVWLQAYRHN | BCMA | 8.85 |
| 94 | MGSWIEFHQRLEAIVTRLEALGGSEAELAAFEKEIAAFESELQAYKGKGNP EVEELRYQAALIRVFLQAYRHN | BCMA | 8 |
| 95 | MGSWSEFYDRLKAIADRLHALGGSEAELAAFEKEIAAFESELQAYKGKGNP EVEELRTEAAIIRVYLQAYRHN | BCMA | 8.215 |
| 96 | MGSWWEFEDRLSAIMERLHALGGSEAELAAFEKEIAAFESELQAYKGKGNP EVEELRYRAAIIRVYLQAYRHN | BCMA | 10.39 |
| 97 | MGSWVEFEERLAAIATRLHALGGSEAELAAFEKEIAAFESELQAYKGKGNP EVEELRWRAAIIRVYLQAYRHN | BCMA | 16.29 |
| 98 | MGSWSEFRGRLQAIHSRLNALGGSEAELAAFEKEIAAFESELQAYKGKGNP EVEELRYSAAIIRIYLQAYRHN | BCMA | 7.585 |
| 99 | MGSWTEFRDRLGAIYHRLDALGGSEAELAAFEKEIAAFESELQAYKGKGNP EVEELRYQAAIIRVYLQAYRHN | BCMA | 6.7 |
| 100 | MGSWVEFYHRLEAIRYRLSALGGSEAELAAFEKEIAAFESELQAYKGKGNP EVEELRYVAAVIRYRLQAYRHN | BCMA | 7.8 |
| 101 | MGSWVEFYDRLEAIRYRLSALGGSEAELAAFEKEIAAFESELQAYKGKGNP EVEELRYIAAVIRYRLQAYRHN | BCMA | 5.636 |
| 102 | MGSWVEFYDRLAAIRKRLYALGGSEAELAAFEKEIAAFESELQAYKGKGNP EVEELRFRAALIRIWLQAYRHN | BCMA | 9.76 |

TABLE 3-continued

Exemplary D-domains

| SEQ ID NO: | D-Domain Sequence | Target | ELISA_avg |
|---|---|---|---|
| 103 | MGSWEEFSERLEAISIRLRALGGSEAELAAFEKEIAAFESELQAYKGKGNP EVEELRVSAAIIRVWLQAYRHN | BCMA | 11.26 |
| 104 | MGSWSEFSDRLHAISDRLQALGGSEAELAAFEKEIAAFESELQAYKGKGNP EVEELRIQAAIIRVWLQAYRHN | BCMA | 6.3725 |
| 105 | MGSWIEFSHRLEAIVDRLGALGGSEAELAAFEKEIAAFESELQAYKGKGNP EVEELRNTAAIIRVYLQAYRHN | BCMA | 18.67 |
| 106 | MGSWEEFSDRLEAILRRLDALGGSEAELAAFEKEIAAFESELQAYKGKGNP EVEDLRFAAAIIRVQLQAYRHN | BCMA | 9.08 |
| 107 | MGSWMEFSHRLDAIHERLYALGGSEAELAAFEKEIAAFESELQAYKGKGNP EVEDLRFAAAIIRVQLQAYRHN | BCMA | 6.3 |
| 108 | MGSWSEFQQRLHAIRTRLYALGGSEAELAAFEKEIAAFESELQAYKGKGNP EVEELRFEAAIIRVMLQAYRHN | BCMA | 11.615 |
| 109 | MGSWYEFQNRLGAINRRLNALGGSEAELAAFEKEIAAFESELQAYKGKGNP EVEELRFEAAIIRVMLQAYRHN | BCMA | 4.68 |
| 110 | MGSWQEFTGRLHAIRHRLEALGGSEAELAAFEKEIAAFESELQAYKGKGNP EVEELRFEAAYIRVWLQAYRHN | BCMA | 3.315 |
| 111 | MGSWTEFDHRLGAIWERLVALGGSEAELAAFEKEIAAFESELQAYKGKGNP EVEELRFHAAIIRIFLQAYRHN | BCMA | 9.54 |
| 112 | MGSWTEFHVRLSAIWDRLVALGGSEAELAAFEKEIAAFESELQAYKGKGNP EVEELRFHAAIIRIVLQAYRHN | BCMA | 23.62 |
| 113 | MGSWNEFDNRLQAIWDRLHALGGSEAELAAFEKEIAAFESELQAYKGKGNP EVEELRFHAAMIRITLQAYRHN | BCMA | 9.87 |
| 114 | MGSWTEFHERLQAIWFRLHALGGSEAELAAFEKEIAAFESELQAYKGKGNP EVEELRFRAAIIRLYLQAYRHN | BCMA | 12.066 |
| 115 | MGSWNEFSGRLTAIKDRLAALGGSEAELAAFEKEIAAFESELQAYKGKGNP EVEELRFRAAVIRLWLQAYRHN | BCMA | 3.39 |
| 116 | MGSWVEFDERLVAIWFRLHALGGSEAELAAFEKEIAAFESELQAYKGKGNP EVEALRARAAYIRIWLQAYRHN | BCMA | 8.96 |
| 117 | MGSWSEFGQRLSAIWERLLALGGSEAELAAFEKEIAAFESELQAYKGKGNP EVEALRADAAFIRIWLQAYRHN | BCMA | 14.01 |
| 118 | MGSWYEFEDRLVAIWIRLDALGGSEAELAAFEKEIAAFESELQAYKGKGNP EVEELRYNAAFIRGALQAYRHN | BCMA | 4.93 |
| 119 | MGSWYEFGDRLSAIWERLAALGGSEAELAAFEKEIAAFESELQAYKGKGNP EVEYLRTHAAEIRTILQAYRHN | BCMA | 8.895 |
| 120 | MGSWHEFYYRLEAIEQRLHALGGSEAELAAFEKEIAAFESELQAYKGKGNP EVETLRFDAALIRIYLQAYRHN | BCMA | 3.73 |
| 121 | MGSWSEFEERLAAIGSRLFALGGSEAELAAFEKEIAAFESELQAYKGKGNP EVETLRFDAALIRIYLQAYRHN | BCMA | 4.85 |
| 122 | MGSWLEFHYRLHAIQFRLYALGGSEAELAAFEKEIAAFESELQAYKGKGNP EVETLRHIAALIRNQLQAYRHN | BCMA | 12.749 |
| 123 | MGSWQEFYNRLEAIHMRLFALGGSEAELAAFEKEIAAFESELQAYKGKGNP EVEGLRSDAAPIRDVLQAYRHN | BCMA | 6.47 |
| 124 | MGSWNEFHHRLWAIFDRLGALGGSEAELAAFEKEIAAFESELQAYKGKGNP EVEVLRKMAAGIRGGLQAYRHN | BCMA | 3.88 |
| 125 | MGSWYEFHYRLKAINDRLYALGGSEAELAAFEKEIAAFESELQAYKGKGNP EVEYLRYSAAMIRHKLQAYRHN | BCMA | 6.04 |
| 126 | MGSWTEFHQRLGAIHARLGALGGSEAELAAFEKEIAAFESELQAYKGKGNP EVEYLRFSAAFIRLKLQAYRHN | BCMA | 8.87 |
| 127 | MGSWFEFQYRLEAIFYRLLALGGSEAELAAFEKEIAAFESELQAYKGKGKP EVEELRVRAALIRHLLQAYRHN | BCMA | 17.31 |

TABLE 3-continued

| Exemplary D-domains | | | |
|---|---|---|---|
| SEQ ID NO: | D-Domain Sequence | Target | ELISA_avg |
| 128 | MGSWVEFHARLDAIYTRLGALGGSEAELAAFEKEIAAFESELQAYKGKGNP EVEYLRVLAAHIRISLQAYRHN | BCMA | 3.8 |
| 129 | MGSWVEFGTRLSAIYNRLWALGGSEAELAAFEKEIAAFESELQAYKGKGNP EVEDLRFEAAIIRIMLQAYRHN | BCMA | 15.425 |
| 130 | MGSWVEFTHRLDAIYIRLWALGGSEAELAAFEKEIAAFESELQAYKGKGNP EVEELRHEAAVIREELQAYRHN | BCMA | 13.917 |
| 131 | MGSWVEFHGRLAAIYVRLFALGGSEAELAAFEKEIAAFESELQAYKGKGNP EVESLRYHAAMIRRNLQAYRHN | BCMA | 4 |
| 132 | MGSWVEFDRRLVAIYIRLWALGGSEAELAAFEKEIAAFESELQAYKGKGNP EVEALRDDAALIRLLLQAYRHN | BCMA | 8.93 |
| 133 | MGSWVEFDRRLVAIYIRLWALGGSEAELAAFEKEIAAFESELQAYKGKGNP EVEKLRYDAATIRETLQAYRHN | BCMA | 8 |
| 134 | MGSWLEFDRRLTAIYLRLWALGGSEAELAAFEKEIAAFESELQAYKGKGNP EVEALREDAAMIRDMLQAYRHN | BCMA | 9.82 |
| 135 | MGSWIEFDRRLLAIHVRLWALGGSEAELAAFEKEIAAFESELQAYKGKGNP EVEVLRADAAKIRMELQAYRHN | BCMA | 13.72 |
| 136 | MGSWIEFDRRLIAIWIRLWALGGSEAELAAFEKEIAAFESELQAYKGKGNP EVESLRSDAADIRQKLQAYRHN | BCMA | 9.45 |
| 137 | MGSWVEFDRRLIAIWVRLWALGGSEAELAAFEKEIAAFESELQAYKGKGNP EVEFLRSDAAMIREHLQAYRHN | BCMA | 5.77 |
| 138 | MGSWYEFHTRLIAIYVRLWALGGSEAELAAFEKEIAAFESELQAYKGKGNP EVEWLRGDAAKIRGYLQAYRHN | BCMA | 4.06 |
| 139 | MGSWSEFSTRLSAIYVRLWALGGSEAELAAFEKEIAAFESELQAYKGKGNP EVEYLRNKAASIRKTLQAYRHN | BCMA | 5.35 |
| 140 | MGSWVEFRYRLGAIYHRLWALGGSEAELAAFEKEIAAFESELQAYKGKGNP EVEVLRDRAATIRRLLQAYRHN | BCMA | 10.81 |
| 141 | MGSWNEFRNRLGAIDSRLWALGGSEAELAAFEKEIAAFESELQAYKGKGNP EVETLRAHAAIIRSVLQAYRHN | BCMA | 4.6967 |
| 142 | MGSWHEFRNRLGAIDSRLWALGGSEAELAAFEKEIAAFESELQAYKGKGNP EVETLRARAAMIRSVLQAYRHN | BCMA | 3.4936 |
| 143 | MGSWTEFYQRLEAINFRLWALGGSEAELAAFEKEIAAFESELQAYKGKGNP EVEVLRDKAALIRLMLQAYRHN | BCMA | 6.955 |
| 144 | MGSWNEFYNRLHAINLRLWALGGSEAELAAFEKEIAAFESELQAYKGKGNP EVEVLREHAAIIRQALQAYRHN | BCMA | 3.004 |
| 145 | MGSWEEFYGRLSAIQDRLWALGGSEAELAAFEKEIAAFESELQAYKGKGNP EVEWLRMHAAVIRRALQAYRHN | BCMA | 3.28 |
| 146 | MGSWGEFNLRLVAIHVRLWALGGSEAELAAFEKEIAAFESELQAYKGKGNP EVEFLRSQAANIRAQLQAYRHN | BCMA | 12.81 |
| 147 | MGSWGEFSDRLEAINERLWALGGSEAELAAFEKEIAAFESELQAYKGKGNP EVEELRWQAAFIRANLQAYRHN | BCMA | 4.26 |
| 148 | MGSWMEFQGRLPAILARLRALGGSEAELAAFEKEIAAFESELQAYKGKGNP EVEHLRDKAAYIRWMLQAYRHN | BCMA | 8.32 |
| 149 | MGSWMEFEGRLPAILARLRALGGSEAELAAFEKEIAAFESELQAYKGKGNP EVEHLRDKAAYIRWMLQAYRHN | BCMA | 3.93 |
| 150 | MGSWFEFQNRLQAILFRLRALGGSEAELAAFEKEIAAFESELQAYKGKGNP EVENLRDKAAYIRLMLQAYRHN | BCMA | 5.3933 |
| 151 | MGSWVEFDMRLQAILERLRALGGSEAELAAFEKEIAAFESELQAYKGKGNP EVEHLRDSAAYIRLMLQAYRHN | BCMA | 23.525 |
| 152 | MGSWVEFNARLDAILFRLRALGGSEAELAAFEKEIAAFESELQAYKGKGNP EVEHLRDQAAYIRLMLQAYRHN | BCMA | 13.52 |

TABLE 3-continued

Exemplary D-domains

| SEQ ID NO: | D-Domain Sequence | Target | ELISA_avg |
|---|---|---|---|
| 153 | MGSWMEFNVRLRAILDRLHALGGSEAELAAFEKEIAAFESELQAYKGKGNP EVELLRDKAAYIRFMLQAYRHN | BCMA | 15.59 |
| 154 | MGSWIEFDTRLAAIVHRLRALGGSEAELAAFEKEIAAFESELQAYKGKGNP EVELLRDKAAYIRYMLQAYRHN | BCMA | 13.948 |
| 155 | MGSWIEFDYRLKAILHRLRALGGSEAELAAFEKEIAAFESELQAYKGKGNP EVEGLRDKAAYIRFLLQAYRHN | BCMA | 11.877 |
| 156 | MGSWYEFEDRLLAIKVRLRALGGSEAELAAFEKEIAAFESELQAYKGKGNP EVEYLRDQAAYIRFMLQAYRHN | BCMA | 17.613 |
| 157 | MGSWYEFQDRLSAITTRLRALGGSEAELAAFEKEIAAFESELQAYKGKGNP EVELLRDKAAYIRFMLQAYRHN | BCMA | 10.085 |
| 158 | MGSWEEFDDRLNAIVYRLRALGGSEAELAAFEKEIAAFESELQAYKGKGNP EVEMLRDQAAYIRLMLQAYRHN | BCMA | 18.64 |
| 159 | MGSWVEFEQRLHAIVVRLRALGGSEAELAAFEKEIAAFESELQAYKGGGNP EVENLRDQAAYIRFMLQAYRHN | BCMA | 17.747 |
| 160 | MGSWVEFEWRLEAIVVRLRALGGSEAELAAFEKEIAAFESELQAYKGKGNP EVEHLRDKAAYIRYMLQAYRHN | BCMA | 14.95 |
| 161 | MGSWYEFEHRLKAIVSRLGALGGSEAELAAFEKEIAAFESELQAYKGKGNP EVEHLRDKAAYIRYMLQAYRHN | BCMA | 4.55 |
| 162 | MGSWMEFKHRLAAITFRLRALGGSEAELAAFEKEIAAFESELQAYKGKGNP EVELLRDKAAYIRLLLQAYRHN | BCMA | 6.06 |
| 163 | MGSWMEFEGRLHAIKRRLRALGGSEAELAAFEKEIAAFESELQAYKGKGNP EVEVLRDQAAYIRLLLQAYRHN | BCMA | 7.335 |
| 164 | MGSWSEFVFRLDTIKSRLRALGGSEAELAAFEKEIAAFESELQAYKGKGNP EVETLRDQAAYIRLMLQAYRHN | BCMA | 19.86 |
| 165 | MGSWYEFDERLSAIKLRLRALGGSEAELAAFEKEIAAFESELQAYKGKGNP EVEVLRAQAAYIRAILQAYRHN | BCMA | 16.94 |
| 166 | MGSWMEFDERLWAIKKRLRALGGSEAELAAFEKEIAAFESELQAYKGKGNP EVEFLRHQAAYIRMLLQAYRHN | BCMA | 9.526 |
| 167 | MGSWHEFDGRLSAIKRRLWALGGSEAELAAFEKEIAAFESELQAYKGKGNP EVEHLRDQAAYIRYMLQAYRHN | BCMA | 5.4 |
| 168 | MGSWYEFDGRLQAIIARLRALGGSEAELAAFEKEIAAFESELQAYKGKGNP EVEHLRFRAAYIRWILQAYRHN | BCMA | 3.29 |
| 169 | MGSWFEFDKRLYAIIHRLRALGGSEAELAAFEKEIAAFESELQAYKGKGNP EVEKLRYKAAIIRLYLQAYRHN | BCMA | 11.82 |
| 170 | MGSWVEFDNRLYAIVDRLRALGGSEAELAAFEKEIAAFESELQAYKGKGNP EVEHLRQKAAYIRLILQAYRHN | BCMA | 11.717 |
| 171 | MGSWIEFHQRLNAIFNRLRALGGSEAELAAFEKEIAAFESELQAYKGKGNP EVEWLRHHAAYIREMLQAYRHN | BCMA | 7.3417 |
| 172 | MGSWNEFRLRLWAITERLRALGGSEAELAAFEKEIAAFESELQAYKGKGNP EVECLRAEAAWIRTMLQAYRHN | BCMA | 3.8718 |
| 173 | MGSWYEFWLRLSAISYRLQALGGSEAELAAFEKEIAAFESELQAYKGKGNP EVEWLRKEAAEIRSWLQAYRHN | BCMA | 14.465 |
| 174 | MGSWYEFQLRLWAIHWRLIALGGSEAELAAFEKEIAAFESELQAYKGKGNP EVEWLRMRAAEIRNELQAYRHN | BCMA | 20.59 |
| 175 | MGSWYEFAHRLEAIEWRLIALGGSEAELAAFEKEIAAFESELQAYKGKGNP EVEELRQYAAAIRNYLQAYRHN | BCMA | 9.48 |
| 176 | MGSWYEFDTRLGAIRNRLGALGGSEAELAAFEKEIAAFESELQAYKGKGNP EVEWLRFQAAYIRFLLQAYRHN | BCMA | 13.934 |
| 177 | MGSWYEFWVRLTAIRWRLEALGGSEAELAAFEKEIAAFESELQAYKGKGNP EVEWLREQAASIRWVLQAYRHN | BCMA | 5.72 |

TABLE 3-continued

| Exemplary D-domains | | | |
|---|---|---|---|
| SEQ ID NO: | D-Domain Sequence | Target | ELISA_avg |
| 178 | MGSWFEFDRRLKAIDRRLMALGGSEAELAAFEKEIAAFESELQAYKGKGNP EVEWLRMQAAIIRNYLQAYRHN | BCMA | 6.1625 |
| 179 | MGSWVEFWERLDAIDNRLGALGGSEAELAAFEKEIAAFESELQAYKGKGNP EVEWLRWHAAYIRGYLQAYRHN | BCMA | 11.42 |
| 180 | MGSWAEFWDRLDAIDSRLNALGGSEAELAAFEKEIAAFESELQAYKGKGNP EVEYLREWAAYIRGYLQAYRHN | BCMA | 18.22 |
| 181 | MGSWAEFDLRLRAIAKRLVALGGSEAELAAFEKEIAAFESELQAYKGKGNP EVEMLRLDAAYIRGVLQAYRHN | BCMA | 4.09 |
| 182 | MGSWSEFWDRLYAIRIRLDALGGSEAELAAFEKEIAAFESELQAYKGKGNP EVEKLRSVAARIRNWLQAYRHN | BCMA | 12.52 |
| 183 | MGSWSEFWFRLGAIRNRLDALGGSEAELAAFEKEIAAFESELQAYKGKGNP EVEKLRDVAAHIRHWLQAYRHN | BCMA | 14.93 |
| 184 | MGSWSEFNDRLDAIRWRLDALGGSEAELAAFEKEIAAFESELQAYKGKGNP EVEWLRQVAATIRYRLQAYRHN | BCMA | 13.59 |
| 185 | MGSWVEFWDRLGAIRERLQALGGSEAELAAFEKEIAAFESELQAYKGKGNP EVEKLRYTAAAIRHYLQAYRHN | BCMA | 5.22 |
| 186 | MGSWAEFWDRLGAIRERLQALGGSEAELAAFEKEIAAFESELQAYKGKGNP EVEKLRYTAAAIRHYLQAYRHN | BCMA | |
| 187 | MGSWTEFWDRLGAIRERLQALGGSEAELAAFEKEIAAFESELQAYKGKGNP EVEKLRYTAAAIRHYLQAYRHN | BCMA | |
| 188 | MGSWVEFWDRLGAIRERLQALGGSEAELAAFEKEIAAFESELQAYKGKGNP EVEKLKYTAAAIRHYLQAYRHN | BCMA | |
| 189 | MGSWVEFWDRLGAIRERLQALGGSEAELAAFEKEIAAFESELQAYKGKGNP EVEKLQYTAAAIRHYLQAYRHN | BCMA | |
| 190 | MGSWVEFWDRLGAIRERLQALGGSEAELAAFEKEIAAFESELQAYKGKGNP EVEKLRYTAAAIKHYLQAYRHN | BCMA | |
| 191 | MGSWAEFWDRLGAIRERLQALGGSEAELAAFEKEIAAFESELQAYKGKGNP EVEKLQYTAAAIKHYLQAYRHN | BCMA | |
| 192 | MGSWTEFWDRLGAIRERLQALGGSEAELAAFEKEIAAFESELQAYKGKGNP EVEKLQYTAAAIKHYLQAYRHN | BCMA | |
| 193 | MGSWVEFWDRLGAIRERLEALGGSEAELAAFEKEIAAFESELQAYKGKGNP EVEKLRYVAAVIRHRLQAYRHN | BCMA | 4.18 |
| 194 | MGSWVEFWDRLGAIRERLQALGGSEAELAAFEKEIAAFESELQAYKGKGNP EVEELRASAAAIRIALQAYRHN | BCMA | 3.07 |
| 195 | MGSWVEFWDRLGAIRDRLDALGGSEAELAAFEKEIAAFESELQAYKGKGNP EVEELRNTAAYIRTFLQAYRHN | BCMA | 16.034 |
| 196 | MGSWSEFWVRLGAIRDRLDALGGSEAELAAFEKEIAAFESELQAYKGKGNP EVEALRVTAAQIRHYLQAYRHN | BCMA | 23.5 |
| 197 | MGSWSEFWVRLGAIRERLDALGGSEAELAAFEKEIAAFESELQAYKGKGNP EVEKLRYTAATIRRFLQAYRHN | BCMA | 7.5567 |
| 198 | MGSWSEFWARLGAIRERLDALGGSEAELAAFEKEIAAFESELQAYKGKGNP EVEKLRYTAATIRRFLQAYRHN | BCMA | |
| 199 | MGSWSEFWVRLGAIRERLDALGGSEAELAAFEKEIAAFESELQAYKGKGNP EVEKLRYTAGTIRRFLQAYRHN | BCMA | |
| 200 | MGSWSEFWVRLGAIRERLDALGGSEAELAAFEKEIAAFESELQAYKGKGNP EVEKLRYTAATIKRFLQAYRHN | BCMA | |
| 201 | MGSWSEFWARLGAIRERLDALGGSEAELAAFEKEIAAFESELQAYKGKGNP EVEKLRYTAGTIKRFLQAYRHN | BCMA | |
| 202 | MGSWSEFWDRLTAIRVRLDALGGSEAELAAFEKEIAAFESELQAYKGKGNP EVEKLRYTAAHIRKFLQAYRHN | BCMA | 16.14 |

TABLE 3-continued

Exemplary D-domains

| SEQ ID NO: | D-Domain Sequence | Target | ELISA_avg |
|---|---|---|---|
| 203 | MGSWTEFWTRLNAIYERLDALGGSEAELAAFEKEIAAFESELQAYKGKGNP EVEKLRFTAASIRMYLQAYRHN | BCMA | 8.43 |
| 204 | MGSWFEFWDRLAAIRDRLEALGGSEAELAAFEKEIAAFESELQAYKGKGNP EVEDLRYVAAKIRVRLQAYRHN | BCMA | 12.78 |
| 205 | MGSWTEFWVRLNAIRDRLEALGGSEAELAAFEKEIAAFESELQAYKGKGNP EVEDLRHTAAIIRNYLQAYRHN | BCMA | 12.53 |
| 206 | MGSWVEFWHRLGAIYDRLEALGGSEAELAAFEKEIAAFESELQAYKGKGNP EVEELRRTAALIRQTLQAYRHN | BCMA | 19.904 |
| 207 | MGSWVEFWNRLGAIYDRLEALGGSEAELAAFEKEIAAFESELQAYKGKGNP EVEKLRHTAAVIRLYLQAYRHN | BCMA | 14.55 |
| 208 | MGSWSEFWERLEAIYDRLYALGGSEAELAAFEKEIAAFESELQAYKGKGNP EVEELRRTAATIRSFLQAYRHN | BCMA | 18.78 |
| 209 | MGSWEEFDNRLEAIFDRLEALGGSEAELAAFEKEIAAFESELQAYKGKGNP EVEELREFAATIRITLQAYRHN | BCMA | 3.93 |
| 210 | MGSWMEFWDRLYAIEFRLFALGGSEAELAAFEKEIAAFESELQAYKGKGNP EVEKLRRVAATIRNELQAYRHN | BCMA | 11.693 |
| 211 | MGSWTEFWERLYAIEYRLFALGGSEAELAAFEKEIAAFESELQAYKGKGNP EVEKLRSVAATIRYELQAYRHN | BCMA | 12.7 |
| 212 | MGSWNEFWERLYAIELRLFALGGSEAELAAFEKEIAAFESELQAYKGKGNP EVEKLRMTAAYIRNELQAYRHN | BCMA | 9.945 |
| 213 | MGSWYEFWKRLYAIEYRLFALGGSEAELAAFEKEIAAFESELQAYKGKGNP EVEALRKVAAKIREQLQAYRHN | BCMA | 14.785 |
| 214 | MGSWTEFWARLYAIEMRLFALGGSEAELAAFEKEIAAFESELQAYKGKGNP EVEHLRRVAALIREQLQAYRHN | BCMA | 12.46 |
| 215 | MGSWHEFWDRLYAIEFRLFALGGSEAELAAFEKEIAAFESELQAYKGKGNP EVESLRQVAAKIRWHLQAYRHN | BCMA | 7.3 |
| 216 | MGSWDEFEFRLGALRWRLIALGGSEAELAAFEKEIAAFESELQAYKGKGNP EVEYLRFGAAHIRHILQAYRHN | BCMA | 9.2 |
| 217 | MGSWTEFYHRLYAIRERLSALGGSEAELAAFEKEIAAFESELQAYKGKGNP EVEYLRFGAAHIRHLLQAYRHN | BCMA | 9.6275 |
| 218 | MGSWVEFETRLDAIRMRLGALGGSEAELAAFEKEIAAFESELQAYKGKGNP EVEYLRFGAAHIRALLQAYRHN | BCMA | 14.072 |
| 219 | MGSWGEFDVRLFAIRERLSALGGSEAELAAFEKEIAAFESELQAYKGKGNP EVEYLRGYAAQIRSFLQAYRHN | BCMA | 7.3533 |
| 220 | MGSWVEFDERLSAIRERLDALGGSEAELAAFEKEIAAFESELQAYKGKGNP EVEYLRLYAAQIRVFLQAYRHN | BCMA | 5.61 |
| 221 | MGSWSEFDGRLGAIWDRLYALGGSEAELAAFEKEIAAFESELQAYKGKGNP EVEYLRDRAAQIREFLQAYRHN | BCMA | 10.031 |
| 222 | MGSWGEFEGRLHAIRSRLSALGGSEAELAAFEKEIAAFESELQAYKGKGNP EVEVLRGYAAWIRALLQAYRHN | BCMA | 6.17 |
| 223 | MGSWGEFNGRLGAIRERLQALGGSEAELAAFEKEIAAFESELQAYKGKGNP EVEFLRAYAASIRAVLQAYRHN | BCMA | 4.9533 |
| 224 | MGSWWEFTFRLAAIEFRLEALGGSEAELAAFEKEIAAFESELQAYKGKGNP EVEDLRAIAAEIRKSLQAYRHN | BCMA | 5.75 |
| 225 | MGSWDEFQFRLAAIGFRLGALGGSEAELAAFEKEIAAFESELQAYKGKGNP EVEVLRRQAARIRHLLQAYRHN | BCMA | 6.155 |
| 226 | MGSWYEFVTRLHAIDHRLKALGGSEADLAAFEKEIAAFESELQAYKGKGNP EVEWLRFYAAGIRMNLQAYRHN | BCMA | 4.12 |
| 227 | MGSWSIEFWRLEAIKFRLIALGGSEAELAAFEKEIAAFESELQAYKGKGNP EVEFLRVEAAAIRRVLQAYRHN | BCMA | 8.43 |

TABLE 3-continued

Exemplary D-domains

| SEQ ID NO: | D-Domain Sequence | Target | ELISA_avg |
|---|---|---|---|
| 228 | MGSWGEFEHRLDPSTCVWLALGGSEAELAAFEKEIAAFESELQAYKGKGNP EVEKLRRGAAVIRHWLQAYRHN | BCMA | 4.05 |
| 229 | MGSWIEFAMRLEAIENRLTALGGSEAELAIFESMIAHFEELLQNYKGKGNP EVEALIHEAFAIHKELWAYRHN | BCMA | 10.73 |
| 230 | MGSWNEFYQRLEAIENRLQALGGSEAELAMFEVRIALFEDMLQGYKGKGNP EVEALKQEAIAILRELIAYRHN | BCMA | 6.01 |
| 231 | MGSWNEFYDRLRAIKKRLYALGGSEAELADFEEDIAQFEVDLQDYKGKGNP EVEALHREAHAITHELWAYRHN | BCMA | 12.36 |
| 232 | MGSWGEFKHRLALIKWYLEALGGSEAELAHFEDWIAVFEVQLQNYKGKGNP EVEALRKEAAAIRDELQAYRHN | BCMA | 17.09 |
| 233 | MGSWYEFKHRLAIIKWYLEALGGSEAELAKFEAWIAEFEMILQRYKGKGNP EVEALRKEAAAIRDELQAYRHN | BCMA | 5.505 |
| 234 | MGSWYEFKHRLAIIKWYLEALGGSEAELAHFEQYIADFEGTLQKYKGKGNP EVEALRKEAAAIRDELQAYRHN | BCMA | 14.833 |
| 235 | MGSWYNFKHRLAIIKWYLEALGGSEAELARFENFIANFETQLQLYKGKGNP EVEALRKEAAAIRDELQAYRHN | BCMA | 6.7615 |
| 236 | MGSWFQFKHRLAIIKWQLEALGGSEAELAWFEQWIADFEHQLQHYKGKGNP EVEALRKEAAAIRDELQAYRHN | BCMA | 10.39 |
| 237 | MGSWYNFKHRLAIIKWFLEALGGSEAELAVFEVWIADFEHQLQEYKGKGNP EVEALRKEAAAIRDELQAYRHN | BCMA | 16.38 |
| 238 | MGSWDAFKHRLALIKWYLEALGGSEAELAHFEEYIAEFESNLQSYKGKGNP EVEALRKEAAAIRDELQAYRHN | BCMA | 12.98 |
| 239 | MGSWDGFKHRLALIKWYLEALGGSEAELANFENWIAEFEQRLQYYKGKGNP EVEALRKEAAAIRDELQAYRHN | BCMA | 23.62 |
| 240 | MGSWNGFKHRLAIIKWYLEALGGSEAELASFESYIAEFESGLQEYKGKGNP EVEALRKEAAAIRDELQAYRHN | BCMA | 16.53 |
| 241 | MGSWNSFKHRLALIKWYLEALGGSEAELATFEWYIASFESELQQYKGKGNP EVEALRKEAAAIRDELQAYRHN | BCMA | 10.34 |
| 242 | MGSWSDFKYRLAVIKFYLEALGGSEAELASFESFIAHFEDDLQKYKGKGNP EVEALRKEAAAIRDELQAYRHN | BCMA | 13.04 |
| 243 | MGSWSGFKYRLAVIKFYLEALGGSEAELASFELFIAKFEIDLQNYKGKGNP EVEALRKEAAAIRDELQAYRHN | BCMA | 13.066 |
| 244 | MGSWYGFKYRLAVIKWYLEALGGSEAELASFEKYIAHFEHDLQAYKGKGNP EVEALRKEAAAIRDELQAYRHN | BCMA | 9.05 |
| 245 | MGSWYGFKYRLAVIKWYLEALGGSEAELASFEKYIAQFEHDLQAYKGKGNP EVEALRKEAAAIRDELQAYRHN | BCMA | 7.6333 |
| 246 | MGSWYGFKYRLALIKWYLEALGGSEAELASFETYIADFEDLLQAYKGKGNP EVEALRKEAAAIRDELQAYRHN | BCMA | 13.03 |
| 247 | MGSWSTFKYHLAVIKWYLEALGGSEAELASFEDYIAQFETDLQEYKGKGNP EVEALRKEAAAIRDELQAYRHN | BCMA | 11.65 |
| 248 | MGSWHEFKYRLALIKWYLEALGGSEAELATFEHHIAQFEWDLQKYKGKGNP EVEALRKEAAAIRDELQAYRHN | BCMA | 16.19 |
| 249 | MGSWNMFKYRLAHIKWYLEALGGSEAELATFEAYIADFEVDLQKYKGKGNP EVEALRKEAAAIRDELQAYRHN | BCMA | 16.33 |
| 250 | MGSWHGFKYRLAIIKWWLEALGGSEAELAFFEEWIASFERDLQIYKGKGNP EVEALRKEAAAIRDELQAYRHN | BCMA | 6.025 |
| 251 | MGSWHGFKYRLAVIKWYLEALGGSEAELAMFEGWIAQFEITLQQYKGKGNP EVEALRKEAAAIRDELQAYRHN | BCMA | 5.99 |
| 252 | MGSWQGFKYRLAVIKWMLEALGGSEAELAFFENWIAEFETKLQQYKGKGNP EVEALRKEAAAIRDELQAYRHN | BCMA | 7.75 |

TABLE 3-continued

| Exemplary D-domains | | | |
|---|---|---|---|
| SEQ ID NO: | D-Domain Sequence | Target | ELISA_avg |
| 253 | MGSWSGFKYRLAVIKWYLEALGGSEAELATFEEWIAEFETELQFYKGKGNP EVEALRKEAAAIRDELQAYRHN | BCMA | 13.975 |
| 254 | MGSWGYFKYRLAMIKWYLEALGGSEAELASFESWIAEFEGSLQAYKGKGNP EVEALRKEAAAIRDELQAYRHN | BCMA | 13.018 |
| 255 | MGSWHAFKYKLAMIKWYLEALGGSEAELAHFEEWIAEFEALLQEYKGKGNP EVEALRKEAAAIRDELQAYRHN | BCMA | 11.63 |
| 256 | MGSWQHFKYRLAIIKWYLEALGGSEAELAFFESFIAKFEHDLQKYKGKGNP EVEALRKEAAAIRDELQAYRHN | BCMA | 8.91 |
| 257 | MGSWNDFKYRLAIIKYYLEALGGSEAELAHFESYIASFEHDLQNYKGKGNP EVEALRKEAAAIRDELQAYRHN | BCMA | 15.123 |
| 258 | MGSWGAFKYRLAIIKFYLEALGGSEAELARFEEFIANFEHDLQNYKGKGNP EVEALRKEAAAIRDELQAYRHN | BCMA | 12.88 |
| 259 | MGSWYNFKYRLAIIKFYLEALGGSEAELAQFEIWIAEFEHDLQGYKGKGNP EVEALRKEAAAIRDELQAYRHN | BCMA | 19.91 |
| 260 | MGSWEQFKYRLAIIKYMLEALGGSEAELAWFESWIANFESDLQHYKGKGNP EVEALRKEAAAIRDELQAYRHN | BCMA | 11.01 |
| 261 | MGSWQQFKYRLAIIKYYLEALGGSEAELAGFETYIAKFEEVLQSYKGKGNP EVEALRKEAAAIRDELQAYRHN | BCMA | 15.12 |
| 262 | MGSWAGFKYRLAVIKYYLEALGGSEAELAHFEQWIAHFEGMLQDYKGKGNP EVEALRKEAAAIRDELQAYRHN | BCMA | 12.68 |
| 263 | MGSWTAFKYRLAIIKFYLEALGGSEAELAHFESYIAHFEDMLQHYKGKGNP EVEALRKEAAAIRDELQAYRHN | BCMA | 7.43 |
| 264 | MGSWAHFKYRLAIIKFWLEALGGSEAELANFEEYIAEFESTLQVYKGKGNP EVEALRKEAAAIRDELQAYRHN | BCMA | 13.12 |
| 265 | MGSWANFKYRLALIKWHLEALGGSEAELASFEIWIADFEESLQWYKGKGNP EVEALRKEAAAIRDELQAYRHN | BCMA | 14.288 |
| 266 | MGSWATFKYRLALIKWHLEALGGSEAELADFEEYIAGFEEGLQKYKGKGNP EVEALRKEAAAIRDELQAYRHN | BCMA | 15.07 |
| 267 | MGSWTHFKYRLALIKWWLEALGGSEAELAGFEVHIADFEAQLQMYKGKGNP EVEALRKEAAAIRDELQAYRHN | BCMA | 7.3669 |
| 268 | MGSWNTFKYHLAVIKFMLEALGGSEAELAFFEQWIAEFEVTLQSYKGKGNP EVEALRKEAAAIRDELQAYRHN | BCMA | 10.601 |
| 269 | MGSWTQFKYHLAVIKWYLEALGGSEAELAGFEQWIAEFEKTLQEYKGKGNP EVEALRKEAAAIRDELQAYRHN | BCMA | 21.118 |
| 270 | MGSWNQFKYRLAVIKFYLEALGGSEAELAHFETWIAAFEEQLQFYKGKGNP EVEALRKEAAAIRDELQAYRHN | BCMA | 12.85 |
| 271 | MGSWNEFKYHLAVIKFYLEALGGSEAELAHFETWIAEFEYELQKYKGKGNP EVEALRKEAAAIRDELQAYRHN | BCMA | 13.68 |
| 272 | MGSWVQFKYHLAVIKFYLEALGGSEAELAHFETWIAEFEVALQGYKGKGNP EVEALRKEAAAIRDELQAYRHN | BCMA | 12.696 |
| 273 | MGSWVDFKYHLAVIKFWLEALGGSEAELANFETWIANFEQELQMYKGKGNP EVEALRKEAAAIRDELQAYRHN | BCMA | 13.22 |
| 274 | MGSWVDFKYHLAVIKWYLEALGGSEAELADFENWIAHFESILQQYKGKGNP EVEALRKEAAAIRDELQAYRHN | BCMA | 10.43 |
| 275 | MGSWVEFKYHLAVIKFTLEALGGSEAELADFEEEIARFEMILQQYKGKGNP EVEALRKEAAAIRDELQAYRHN | BCMA | 6.92 |
| 276 | MGSWSHFKYHLALIKWYLEALGGSEAELAKFEFWIAEFEHNLQMYKGKGNP EVEALRKEAAAIRDELQAYRHN | BCMA | 7.93 |
| 277 | MGSWYHFKYHLALIKWYLEALGGSEAELAHFEHWIAEFEWTLQQYKGKGNP EVEALRKEAAAIRDELQAYRHN | BCMA | 8.85 |

TABLE 3-continued

Exemplary D-domains

| SEQ ID NO: | D-Domain Sequence | Target | ELISA_avg |
|---|---|---|---|
| 278 | MGSWQGFKYHLALIKFYLEALGGSEAELAHFEHWLAEFEHDLQTYKGKGNP EVEALRKEAAAIRDELQAYRHN | BCMA | 21.2 |
| 279 | MGSWLSFKHHLALIKWYLEALGGSEAELASFEAWIALFEHQLQQYKGKGNP EVEALRKEAAAIRDELQAYRHN | BCMA | 6.305 |
| 280 | MGSWSEFKYKLALIKWYLEALGGSEAELAHFEGWIANFETTLQKYKGKGNP EVEALRKEAAAIRDELQAYRHN | BCMA | 11.288 |
| 281 | MGSWIEFKYKLAIIKFYLEALGGSEAELAHFEHWIADFEFVLQQYKGKGNP EVEALRKEAAAIRDELQAYRHN | BCMA | 14.88 |
| 282 | MGSWQNFKYHLAMIKWYLEALGGSEAELANFEEFIAQFEINLQHYKGKGNP EVEALRKEAAAIRDELQAYRHN | BCMA | 9.55 |
| 283 | MGSWYNFKYHLAIIKWWLEALGGSEAELADFEHYIADFERNLQEYKGKGNP EVEALRKEAAAIRDELQAYRHN | BCMA | 8.6264 |
| 284 | MGSWYQFKYHLAIIKWYLEALGGSEAELAGFENYIATFEQELQQYKGKGNP EVEALRKEAAAIRDELQAYRHN | BCMA | 18.41 |
| 285 | MGSWSHFKYHLAIIKFYLEALGGSEAELAGFEIWIAKFEDELQMYKGKGNP EVEALRKEAAAIRDELQAYRHN | BCMA | 9.34 |
| 286 | MGSWVGFKAHLAIIKWYLEALGGSEAELAGFEIFIADFEALLQMYKGKGNP EVEALRKEAAAIRDELQAYRHN | BCMA | 9.71 |
| 287 | MGSWVNFKYKLAIIKYMLEALGGSEAELAFFEDWIAEFERTLQQYKGKGNP EVEALRKEAAAIRDELQAYRHN | BCMA | 7.3895 |
| 288 | MGSWSNFKYRLAVIKYMLEALGGSEAELAFFEDWIADFELHLQVYKGKGNP EVEALRKEAAAIRDELQAYRHN | BCMA | 9.34 |
| 289 | MGSWTNFKYKLAVIKFMLEALGGSEAELAFFEDWIAGFEIDLQNYKGKGNP EVEALRKEAAAIRDELQAYRHN | BCMA | 11.408 |
| 290 | MGSWTGFKYRLAIIKFMLEALGGSEAELAFFEQWIADFENELQYYKGKGNP EVEALRKEAAAIRDELQAYRHN | BCMA | 13.89 |
| 291 | MGSWHNFKYRLAIIKFMLEALGGSEAELAWFENWIADFEDSLQDYKGKGNP EVEALRKEAAAIRDELQAYRHN | BCMA | 13.59 |
| 292 | MGSWFAFKHRLAVIKYMLEALGGSEAELAFFEHWIAQFEHDLQQYKGKGNP EVEALRKEAAAIRDELQAYRHN | BCMA | 11.985 |
| 293 | MGSWYEFKHRLAVIKYMLEALGGSEAELAFFENWIAQFEHELQTYKGKGNP EVEALRKEAAAIRDELQAYRHN | BCMA | 3.71 |
| 294 | MGSWYKFKHKLAVIKYMLEALGGSEAELAWFEEWIAEFEVTLQDYKGKGNP EVEALRKEAAAIRDELQAYRHN | BCMA | 4.54 |
| 295 | MGSWFYFKQKLAFIKWYLEALGGSEAELANFEIYIAEFEVMLQQYKGKGNP EVEALRKEAAAIRDELQAYRHN | BCMA | 7.23 |
| 296 | MGSWFSFKHHLAVIKWNLEALGGSEAELASFEEQIAEFESVLQAYKGKGNP EVEALRKEAAAIRDELQAYRHN | BCMA | 6.45 |
| 297 | MGSWGNFKYRLAIIKFHLEALGSSEAELATFEAWIANFESMLQNYKGKGNP EVEALRKEAAAIRDELQAYRHN | BCMA | 22.7 |
| 298 | MGSWSYFKYGLAIIKIRLEALGGSEAELADFERWIAAFEHDLQYYKGKGNP EVEALRKEAAAIRDELQAYRHN | BCMA | 13.33 |
| 299 | MGSWSYFKFGLAHIKLRLEALGGSEAELADFEQWIASFEEQLQTYKGKGNP EVEALRKEAAAIRDELQAYRHN | BCMA | 18.354 |
| 300 | MGSWSYFKWGLAHIKLRLEALGGSEAELADFEFWIAEFEGLLQDYKGKGNP EVEALRKEAAAIRDELQAYRHN | BCMA | 17.64 |
| 301 | MGSWIYFKYGLAHIKTRLEALGGSEAELADFEQWIAEFEKMLQDYKGKGNP EVEALRKEAAAIRDELQAYRHN | BCMA | 21.12 |
| 302 | MGSWGYFKYGLATIKHRLEALGGSEAELADFELWIAKFEEQLQVYKGKGNP EVEALRKEAAAIRDELQAYRHN | BCMA | 14.01 |

TABLE 3-continued

| Exemplary D-domains | | | |
|---|---|---|---|
| SEQ ID NO: | D-Domain Sequence | Target | ELISA_avg |
| 303 | MGSWEYFKYGLATIKMHLEALGGSEAELADFEHWIAHFEHQLQMYKGKGNP EVEALRKEAAAIRDELQAYRHN | BCMA | 18.403 |
| 304 | MGSWSYFKYGLATIKEKLEALGGSEAELADFETWIAMFEKQLQEYKGKGNP EVEALRKEAAAIRDELQAYRHN | BCMA | 18.15 |
| 305 | MGSWHYFKNGLAIIKEKLEALGGSEAELADFEIWIAMFEMELQEYKGKGNP EVEALRKEAAAIRDELQAYRHN | BCMA | 19.85 |
| 306 | MGSWQYFKYGLAIIKIKLEALGGSEAELADFEAWIATFEKQLQHYKGKGNP EVEALRKEAAAIRDELQAYRHN | BCMA | 10.28 |
| 307 | MGSWVYFKHGLAVIKMRLEALGGSEAELADFETWIAQFEMTLQEYKGKGNP EVEALRKEAAAIRDELQAYRHN | BCMA | 21.45 |
| 308 | MGSWVYFKYGLAVIKEKLEALGGSEAELADFETWIAEFEFGLQQYKGKGNP EVEALRKEAAAIRDELQAYRHN | BCMA | 17.58 |
| 309 | MGSWYYFKYGLAVIKGKLEALGGSEAELADFETWIAKFENHLQSYKGKGNP EVEALRKEAAAIRDELQAYRHN | BCMA | 3.84 |
| 310 | MGSWTYFKYGLALIKYRLEALGGSEAELADFEEWIAQFEVSLQHYKGKGNP EVEALRKEAAAIRDELQAYRHN | BCMA | 15.21 |
| 311 | MGSWDYFKYGLALIKIKLEALGGSEAELADFEVWIAQFEMALQVYKGKGNP EVEALRKEAAAIRDELQAYRHN | BCMA | 15.76 |
| 312 | MGSWTYFKFGLAHIKDSLEALGGSEAELADFEQWIAMFEQDLQVYKGKGNP EVEALRKEAAAIRDELQAYRHN | BCMA | 17.01 |
| 313 | MGSWGYFKHGLAHIKSSLEALGGSEAELADFEVWIAAFENELQEYKGKGNP EVEALRKEAAAIRDELQAYRHN | BCMA | 18.505 |
| 314 | MGSWGYFKTGLAIIKAQLEALGGSEAELADFELWIAQFEETLQFYKGKGNP EVEALRKEAAAIRDELQAYRHN | BCMA | 12.75 |
| 315 | MGSWAYFKYGLAVIKLHLEALGGSEAELADFERYIAEFEYELQAYKGKGNP EVEALRKEAAAIRDELQAYRHN | BCMA | 13.44 |
| 316 | MGSWLDFKEGLADIKRSLEALGGSEAELADFEGVIALFEWKLQTYKGKGNP EVEALRKEAAAIRDELQAYRHN | BCMA | 3.03 |
| 317 | MGSWEVFKHELAVIKDYLEALGGSEAELAHFEWGIAWFEGFLQDYKGKGNP EVEALRKEAAAIRDELQAYRHN | BCMA | 9.33 |
| 318 | MGSWIVFKQSLAWIKEHLEALGGSEAELAEFEFYIANFEHTLQNYKGKGNP EVEALRKEAAAIRDELQAYRHN | BCMA | 10.57 |
| 319 | MGSWIYFKDSLAYIKKYLEALGGSEAELATFEYYIANFEHELQYYKGKGNP EVEALRKEAAAIRDELQAYRHN | BCMA | 3.2 |
| 320 | MGSWDHFKYNLAWIKKYLEALGGSEAELATFEWYIANFEKRLQDYKGKGNP EVEALRKEAAAIRDELQAYRHN | BCMA | 9.81 |
| 321 | MGSWFTFKQNLAWIKLHLEALGGSEAELARFEYYIADFENKLQLYKGKGNP EVEALRKEAAAIRDELQAYRHN | BCMA | 14.204 |
| 322 | MGSWREFKYGLAHIKRVLEALGGSEAELAVFEYYIAKFEQELQEYKGKGNP EVEALRKEAAAIRDELQAYRHN | BCMA | 14.7 |
| 323 | MGSWIQFKYGLAHIKRTLEALGGSEAELAVFEWYIADFEQQLQGYKGKGNP EVEALRKEAAAIRDELQAYRHN | BCMA | 8.3567 |
| 324 | MGSWVEFKHNLAWIKVTLEALGGSEAELAVFEYYIAQFEEQLQEYKGKGNP EVEALRKEAAAIRDELQAYRHN | BCMA | 15.83 |
| 325 | MGSWISFKDNLAMIKEFLEALGGSEAELAVFEWYIATFEVELQDYKGKGNP EVEALRKEAAAIRDELQAYRHN | BCMA | 7.16 |
| 326 | MGSWHIFKDNLATIKAFLEALGGSEAELAVFEWYIAKFEEELQGYKGKGNP EVEALRKEAAAIRDELQAYRHN | BCMA | 3.47 |
| 327 | MGSWTSFKHGLAGIKRVLEALGGSEAELATFEWYIAQFERHLQAYKGKGNP EVEALRKEAAAIRDELQAYRHN | BCMA | 9.765 |

TABLE 3-continued

| Exemplary D-domains | | | |
|---|---|---|---|
| SEQ ID NO: | D-Domain Sequence | Target | ELISA_avg |
| 328 | MGSWQSFKHALADIKINLEALGGSEAELAQFEYAIAVFEYRLQAYKGKGNP EVEALRKEAAAIRDELQAYRHN | BCMA | 13.719 |
| 329 | MGSWHTFKEALAQIKGELEALGGSEAELASFEYAIAVFEYRLQMYKGKGNP EVEALRKEAAAIRDELQAYRHN | BCMA | 6.76 |
| 330 | MGSWTDFKTSLADIKAELEALGGSEAELAKFEYYIAIFEYRLQEYKGKGNP EVEALRKEAAAIRDELQAYRHN | BCMA | 18.76 |
| 331 | MGSWTNFKEGLAEIKRDLEALGGSEAELARFEYVIAVFEFRLQNYKGKGNP EVEALRKEAAAIRDELQAYRHN | BCMA | 12.327 |
| 332 | MGSWHTFKDGLAEIKSELEALGGSEAELAMFEYVIAIFEYRLQNYKGKGNP EVEALRKEAAAIRDELQAYRHN | BCMA | 10.65 |
| 333 | MGSWQFFKEHLASIKFWLEALGGSEAELAFFEDAIADFEYHLQNYKGKGNP EVEALRKEAAAIRDELQAYRHN | BCMA | 10.58 |
| 334 | MGSWTYFKEHLASIKFWLEALGGSEAELAFFEDAIAEFEKDLQYYKGKGNP EVEALRKEAAAIRDELQAYRHN | BCMA | 6.5951 |
| 335 | MGSWIIFKGYLAHIKHHLEALGGSEAELADFEFYIAIFEMELQKYKGKGNP EVEALRKEAAAIRDELQAYRHN | BCMA | 5.18 |
| 336 | MGSWYLFQSHLAHIKHHLEALGGSEAELAWFEFTIAGFEQELQHYKGKGNP EVEALRKEAAAIRDELQAYRHN | BCMA | 7.69 |
| 337 | MGSWYSFKWTLARIKLELEALGGSEAELAYFENVIAHFEMELQSYKGKGNP EVEALRKEAAAIRDELQAYRHN | BCMA | 4.05 |
| 338 | MGSWTTLKWRLAHIKQHLEALGGSEAELALFEYDIAHFEELLQYYKGKGNP EVEALRKEAAAIRDELQAYRHN | BCMA | 17.82 |
| 339 | MGSWYGFKWYLATIKKHLEALGGSEAELALFETEIATFELWLQDYKGKGNP EVEALRKEAAAIRDELQAYRHN | BCMA | 10.65 |
| 340 | MGSWIEFNMRVLAIEDRLWALGGSEAELAAFEKEIAAFESELQAYKGKGNP EVESLRYEACLDPWSSAAYRHN | CD123 | 3.2 |
| 341 | MGSWIEFHERLWAIEDRLWALGGSEAELAAFEKEIAAFESELQAYKGKGNP EVESLREMAASIRHGLQAYRHN | CD123 | 3.4 |
| 342 | MGSWFEFYERLWAIDDRLWALGGSEAELAAFEKEIAAFESELQAYKGKGNP EVEWLREEAASIRSSLQAYRHN | CD123 | 6 |
| 343 | MGSWFEFWDRLEAIDDRLFALGGSEAELAAFEKEIAAFESELQAYKGKGNP EVESLRYNAAEIRKELQAYRHN | CD123 | 4.9 |
| 344 | MGSWHEFWSRLDAIDDRLFALGGSEAELAAFEKEIAAFESELQAYKGKGNP EVEYLRGAAADIRAELQAYRHN | CD123 | 3.8 |
| 345 | MGSWYEFWIRLEAIDDRLFALGGSEAELAAFEKEIAAFESELQAYKGKGNP EVDILRDFAADIRTELQAYRHN | CD123 | 10.4 |
| 346 | MGSWHEFWDRLEAIDDRLYALGGSEAELAAFEKEIAAFESELQAYKGKGNP EVEFLREEAAYIRELLQAYRHN | CD123 | 10.6 |
| 347 | MGSWEEFWDRLFAIDDRLWALGGSEAELAAFEKEIAAFESELQAYKGKGNP EVETLRNEAAEIRMALQAYRHN | CD123 | 3.1 |
| 348 | MGSWWEFDDRLFAIDTRLMALGGSEAELAAFEKEIAAFESELQAYKGKGNP EVESLREWAATIRMELQAYRHN | CD123 | 3.5 |
| 349 | MGSWTEFHDRLEAIDDRLWALGGSEAELAAFEKEIAAFESELQAYKGKGNP EVEYLREEAAQIRWELQAYRHN | CD123 | 5.8 |
| 350 | MGSWAEFEDRLWAIEDRLWALGGSEAELAAFEKEIAAFESELQAYKGKGNP EVEYLREEAAAIRFELQAYRHN | CD123 | 6.2 |
| 351 | MGSWVEFWFRLEAIDSRLWALGGSEAELAAFEKEIAAFESELQAYKGKGNP EVEWLREEAAAIREDLQAYRHN | CD123 | 3.2 |
| 352 | MGSWVEFWQRLEAIESRLWALGGSEAELAAFEKEIAAFESELQAYKGKGNP EVEFLREEAAEIRWELQAYRHN | CD123 | 7.7 |

TABLE 3-continued

Exemplary D-domains

| SEQ ID NO: | D-Domain Sequence | Target | ELISA_avg |
|---|---|---|---|
| 353 | MGSWSEFWQRLEAIEDRLWALGGSEAELAAFEKEIAAFESELQAYKGKGNP EVEWLRENAAMIRDELQAYRHN | CD123 | 4.7 |
| 354 | MGSWSEFITRLEAIDDRLWALGGSEAELAAFEKEIAAFESELQAYKGKGNP EVEILREEAAEIRQHLQAYRHN | CD123 | 3.3 |
| 355 | MGSWYEFETRLEAIYDRLWALGGSEAELAAFEKEIAAFESELQAYKGKGNP EVELLRVEAAEIREDLQAYRHN | CD123 | 3.2 |
| 356 | MGSWTEFYYRLEAIEDRLWALGGSEAELAAFEKEIAAFESELQAYKGKGNP EVEFLRVEAANIRDMLQAYRHN | CD123 | 7.5 |
| 357 | MGSWYEFVIRLEAIEDRLWALGGSEAELAAFEKEIAAFESELQAYKGKGNP EVEVLRWYAADIRHELQAYRHN | CD123 | 6.4 |
| 358 | MGSWTEFSIRLEAIYDRLVALGGSEAELAAFEKEIAAFESELQAYKGKGNP EVEVLRTYAANIRHELQAYRHN | CD123 | 11.9 |
| 359 | MGSWTEFSIRLEAIYDRLVALGGSEAELAAFEKEIAAFESELQAYKGKGNP EVEVLRTYAAFIRHELQAYRHN | CD123 | 10.2 |
| 360 | MGSWTEFVWRLEAIWDRLDALGGSEAELAAFEKEIAAFESELQAYKGKGNP EVEVLREDAAVIRHFLQAYRHN | CD123 | 3.6 |
| 361 | MGSWVEFHERLEAIEDRLMALGGSEAELAAFEKEIAAFESELQAYKGKGNP EVEYLREDAAFIRQLLQAYRHN | CD123 | 3.7 |
| 362 | MGSWVEFHDRLEAIEDRLYALGGSEAELAAFEKEIAAFESELQAYKGKGNP EVEWLREDAAYIRSILQAYRHN | CD123 | 4.6 |
| 363 | MGSWIEFYDRLEAIYDRLDALGGSEAELAAFEKEIAAFESELQAYKGKGNP EVEWLREDAAFIRSWLQAYRHN | CD123 | 7.5 |
| 364 | MGSWVEFDQRLEAIYDRLYALGGSEAELAAFEKEIAAFESELQAYKGKGNP EVEWLREDAAQIRKWLQAYRHN | CD123 | 5.1 |
| 365 | MGSWVEFHDRLEAIEDRLLALGGSEAELAAFEKEIAAFESELQAYKGKGNP EVEDLREYAAGIRWFLQAYRHN | CD123 | 3.3 |
| 366 | MGSWEEFAQRLYAIEWRLYALGGSEAELAAFEKEIAAFESELQAYKGKGNP EVEVLRYVAAQIRYHLQAYRHN | CD123 | 16.9 |
| 367 | MGSWDEFAWRLDVIFARLGALGGSEAELAAFEKEIAAFESELQAYKGKGNP EVEELRKNAAQIRDGLQAYRHN | CD123 | 4.6 |
| 368 | MGSWDEFYYRLEAIEMRLGALGGSEAELAAFEKEIAAFESELQAYKGKGNP EVEELRHYAAQIRHMLQAYRHN | CD123 | 7.2 |
| 369 | MGSWEEFYDRLEAIYNRLGALGGSEAELAAFEKEIAAFESELQAYKGKGNP EVEVLREYAADIREMLQAYRHN | CD123 | 18.6 |
| 370 | MGSWDEFGRRLYAIEWQLYALGGEEAELAAFEKEIAAFESELQAYKGKGNP EVEALRKEAAVIRENLQAYRHN | CD123 | |
| 371 | MGSWDEFGRRLYAIEWQLYALGGTEAELAAFEKEIAAFESELQAYKGKGNP EVEALRKEAAVIRENLQAYRHN | CD123 | |
| 372 | MGSWDEFGRRLYAIETQLYALGGEEAELAAFEKEIAAFESELQAYKGKGNP EVEKLREIAAVIRENLQAYRHN | CD123 | |
| 373 | MGSWDEFGRRLYAIEWQLYALGGEEAELAAFEKEIAAFESELQAYKGKGNP EVEKLREIAAVIRENLQAYRHN | CD123 | |
| 374 | MGSWDEFGRRLYAIKWQLYALGGEEAELAAFEKEIAAFESELQAYKGKGNP EVEKLREIAAVIRENLQAYRHN | CD123 | |
| 375 | MGSWDEFGRRLYAIEWQLYALGGEEAELAAFEKEIAAFESELQAYKGKGNP EVEKLRKIAAVIRENLQAYRHN | CD123 | |
| 376 | MGSWDEFGRRLYAIEWQLYALGGGEAELAAFEKEIAAFESELQAYKGKGNP EVEKLREIAAVIRENLQAYRHN | CD123 | |
| 377 | MGSWDEFGRRLYAIEWQLYALGGTEAELAAFEKEIAAFESELQAYKGKGNP EVEKLREIAAVIRENLQAYRHN | CD123 | |

TABLE 3-continued

| Exemplary D-domains | | | |
|---|---|---|---|
| SEQ ID NO: | D-Domain Sequence | Target | ELISA_avg |
| 378 | MGSWDEFGRRLYAIEWQLYALGGGEAELAAFEKEIAAFESELQAYKGKGNP EVEKLREIAAVIRSNLQAYRHN | CD123 | |
| 379 | MGSWDEFGRRLYAIEWQLYALGGTEAELAAFEKEIAAFESELQAYKGKGNP EVEKLREIAAVIRSNLQAYRHN | CD123 | |
| 380 | MGSWDEFGRRLYAIEWQLYALGGEEAELAAFEKEIAAFESELQAYKGKGNP EVEKLREIAAVIRSNLQAYRHN | CD123 | |
| 381 | MGSWDEFGRRLAAIEWQLYALGGEEAELAAFEKEIAAFESELQAYKGKGNP EVEKLREIAAVIRENLQAYRHN | CD123 | |
| 382 | MGSWDEFGRRLYAIEWQLYALGGEEAELAAFEKEIAAFESELQAYKGKGNP EVEALREIAAVIRENLQAYRHN | CD123 | |
| 383 | MGSWDEFGRRLYAIEWQLYALGGEEAELAAFEKEIAAFESELQAYKGKGNP EVEKLREEAAVIRENLQAYRHN | CD123 | |
| 384 | MGSWDEFGRRLYAIEWRLYALGGSEAELAAFEKEIAAFESELQAYKGKGSP EVEKLREIAAVIRSNLQAYRHN | CD123 | |
| 385 | MGSWDEFGRRLYAIEWRLYALGGSEAELAAFEKEIAAFESELQAYKGKGNP EVEKLREIAAVIRSNLQAYRHN | CD123 | 5.8 |
| 386 | MGSWDEFGRRLYAIEWRLYALGGEEAELAAFEKEIAAFESELQAYKGKGNP EVEKLREIAAVIRSNLQAYRHN | CD123 | |
| 387 | MGSWDEFGRRLYAIEWQLYALGGSEAELAAFEKEIAAFESELQAYKGKGNP EVEKLREIAAVIRSNLQAYRHN | CD123 | |
| 388 | MGSWDEFSRRLYAIEWRLYALGGSEAELAAFEKEIAAFESELQAYKGKGNP EVEKLREIAAVIRSNLQAYRHN | CD123 | |
| 389 | MGSWDEFGRRLYAIEWRLYALGGSEAELAAFEKEIAAFESELQAYKGKGNP EVEKLREIAAVIRENLQAYRHN | CD123 | |
| 390 | MGSWDEFGRRLAAIKTQLAALGGEEAELAAFEKEIAAFESELQAYKGKGNP EVEKLREIAAVIRENLQAYRHN | CD123 | |
| 391 | MGSWDEFGRRLAAIKTQLAALGGTEAELAAFEKEIAAFESELQAYKGKGNP EVEKLREIAAVIRENLQAYRHN | CD123 | |
| 392 | MGSWDEFGRRLAAIKTQLAALGGEEAELAAFEKEIAAFESELQAYKGKGNP EVEALRKEAAVIRENLQAYRHN | CD123 | |
| 393 | MGSWDEFGRRLAAIKTQLAALGGTEAELAAFEKEIAAFESELQAYKGKGNP EVEALRKEAAVIRENLQAYRHN | CD123 | |
| 394 | MGSWDEFEQRLIAIEERLFALGGSEAELAAFEKEIAAFESELQAYKGKGNP EVEWLREEAAVIRKYLQAYRHN | CD123 | 5.9 |
| 395 | MGSWVEFDQRLGAIWDRLVALGGSEAELAAFEKEIAAFESELQAYKGKGNP EVEHLRQGAAVIRDDLQAYRHN | CD123 | 5.3 |
| 396 | MGSWVEFDMRLSAIWERLIALGGSEAELAAFEKEIAAFESELQAYKGKGNP EVEWLREDAAEIREFLQAYRHN | CD123 | 3.3 |
| 397 | MGSWVEFDQRLDAIYERLYALGGSEAELAAFEKEIAAFESELQAYKGKGNP EVEWLRDEAAEIREHLQAYRHN | CD123 | 10.5 |
| 398 | MGSWHEFDQRLWAIEERLWALGGSEAELAAFEKEIAAFESELQAYKGKGNP EVETLRLYAALIRHDLQAYRHN | CD123 | 3.3 |
| 399 | MGSWVEFWDRLDAIEGRLWALGGSEAELAAFEKEIAAFESELQAYKGKGNP EVEDLRWLAAEIRADLQAYRHN | CD123 | 3.5 |
| 400 | MGSWVEFYSRLDAIEDRLWALGGSEAELAAFEKEIAAFESELQAYKGKGNP EVEWLRIAAASIREDLQAYRHN | CD123 | 9.4 |
| 401 | MGSWYEFYERLDAIEERLWALGGSEAELAAFEKEIAAFESELQAYKGKGNP EVEVLRDWAAWIREDLQAYRHN | CD123 | 8.4 |
| 402 | MGSWFEFDDRLWAIENRLWALGGSEAELAAFEKEIAAFESELQAYKGKGNP EVEVLRDNAAWIREILQAYRHN | CD123 | 4.2 |

TABLE 3-continued

Exemplary D-domains

| SEQ ID NO: | D-Domain Sequence | Target | ELISA_avg |
|---|---|---|---|
| 403 | MGSWYEFWDRLDALEDRLWALGGSEAELAAFEKEIAAFESELQAYKGKGNP EVEYLRDSAAFIREELQAYRHN | CD123 | 9.7 |
| 404 | MGSWMEFVDRLDAIESRLWALGGSEAELAAFEKEIAAFESELQAYKGKGNP EVEWLRIEAAFIREELQAYRHN | CD123 | 5.8 |
| 405 | MGSWDEFVDRLWAIEERLWALGGSEAELAAFEKEIAAFESELQAYKGKGNP EVEELRIQAAIIREALQAYRHN | CD123 | 6 |
| 406 | MGSWFEFNYRLGAIEDRLWALGGSEAELAAFEKEIAAFESELQAYKGKGNP EVEMLRQIAAEIREFLQAYRHN | CD123 | 6.9 |
| 407 | MGSWEEFFTRLDAINERLEALGGSEAELAAFEKEIAAFESELQAYKGKGNP EVEMLRYEAAEIRHMLQAYRHN | CD123 | 3.9 |
| 408 | MGSWYEFSNRLDAIGERLWALGGSEAELAAFEKEIAAFESELQAYKGKGNP EVEILRHQAAEIRWFLQAYRHN | CD123 | 3.9 |
| 409 | MGSWYEFWGRLDAIEERLWALGGSEAELAAFEKEIAAFESELQAYKGRGNP EVEMLREDAAEIRGQLQAYRHN | CD123 | 5.4 |
| 410 | MGSWVEFWDRLWAIDYRLFALGGSEAELAAFEKEIAAFESELQAYKGKGNP EVEALRDEAAWIREELQAYRHN | CD123 | 3.6 |
| 411 | MGSWVEFVDRLWAIDERLDALGGSEAELAAFEKEIAAFESELQAYKGKGNP EVEFLRTWAAWIREDLQAYRHN | CD123 | 3.2 |
| 412 | MGSWFEFWDRLEAIWERLDALGGSEAELAAFEKEIAAFESELQAYKGKGNP EVEELRREAAIIREDLQAYRHN | CD123 | 10.3 |
| 413 | MGSWFEFEDRLEAIYQRLDALGGSEAELAAFEKEIAAFESELQAYKGKGNP EVEWLRDEAAWIRSDLQAYRHN | CD123 | 5.5 |
| 414 | MGSWFEFHDRLWAIDERLWALGGSEAELAAFEKEIAAFESELQAYKGKGNP EVEILREEAADIRLDLQAYRHN | CD123 | 3.5 |
| 415 | MGSWYEFEDRLWAIDNRLWALGGSEAELAAFEKEIAAFESELQAYKGKGNP EVEELRVHAADIRDDLQAYRHN | CD123 | 4.9 |
| 416 | MGSWFEFQDRLWAIDNRLWALGGSEAELAAFEKEIAAFESELQAYKGKGNP EVEELRDHAAMIRWELQAYRHN | CD123 | 3.2 |
| 417 | MGSWDEFEERLFAIDERLWALGGSEAELAAFEKEIAAFESELQAYKGKGNP EVEALRYLAADIREELQAYRHN | CD123 | 5 |
| 418 | MGSWEEFWERLDAIDTRLWALGGSEAELAAFEKEIAAFESELQAYKGKGNP EVEVLRNDAADIREPLQAYRHN | CD123 | 6.8 |
| 419 | MGSWMEFWERLEAIDMRLWALGGSEAELAAFEKEIAAFESELQAYKGKGNP EVEYLRDDAAVIRDDLQAYRHN | CD123 | 4.2 |
| 420 | MGSWLEFMWRLDAIDERLWALGGSEAELAAFEKEIAAFESELQAYKGKGNP EVELLREMAAAIRDDLQAYRHN | CD123 | 5.1 |
| 421 | MGSWTEFYNRLDAIDQRLWALGGSEAELAAFEKEIAAFESELQAYKGKGNP EVEMLREYAADIRTDLQAYRHN | CD123 | 3.3 |
| 422 | MGSWWEFIWRLEAIEQRLWALGGSEAELAAFEKEIAAFESELQAYKGKGNP EVEVLRSRAADIRTDLQAYRHN | CD123 | 4 |
| 423 | MGSWSEFYDRLWAIEERLFALGGSEAELAAFEKEIAAFESELQAYKGKGNP EVEYLRYYAAEIREELQAYRHN | CD123 | 17 |
| 424 | MGSWSEFEDRLWAIDQRLFALGGSEAELAAFEKEIAAFESELQAYKGKGNP EVEWLRAYAADIRWELQAYRHN | CD123 | 4.2 |
| 425 | MGSWTEFWERLNAIDERLFALGGSEAELAAFEKEIAAFESELQAYKGKGNP EVEWLRLYAAEIRSELQAYRHN | CD123 | 4 |
| 426 | MGSWWEFEERLWAIDYRLHALGGSEAELAAFEKEIAAFESELQAYKGKGNP EVEMLRSWAAEIRALLQAYRHN | CD123 | 4.1 |
| 427 | MGSWWEFENRLWAIEERLEALGGSEAELAAFEKEIAAFESELQAYKGKGNP EVEMLRNYAAEIRWELQAYRHN | CD123 | 5.6 |

TABLE 3-continued

| Exemplary D-domains | | | |
|---|---|---|---|
| SEQ ID NO: | D-Domain Sequence | Target | ELISA_avg |
| 428 | MGSWVEFEERLWAIDERLGALGGSEAELAAFEKEIAAFESELQAYKGKGNP EVEWLRDWAADIRWWLQAYRHN | CD123 | 4.1 |
| 429 | MGSWVEFEERLEAIEERLFALGGSEAELAAFEKEIAAFESELQAYKGKGNP EVEWLRDDAANIRHWLQAYRHN | CD123 | 3.8 |
| 430 | MGSWMEFEERLWAIDSRLWALGGSEAELAAFEKEIAAFESELQAYKGKGNP EVEWLRSEAAWIRMELQAYRHN | CD123 | 3.2 |
| 431 | MGSWSEFEHRLEAIESRLFALGGSEAELAAFEKEIAAFESELQAYKGKGNP EVEDLRSEAAWIREQLQAYRHN | CD123 | 7.6 |
| 432 | MGSWFEFWERLDAIEWRLWALGGSEAELAAFEKEIAAFESELQAYKGKGNP EVEELRSTAADIRRYLQAYRHN | CD123 | 3.4 |
| 433 | MGSWFEFWGRLEAIESRLKALGGSEAELAAFEKEIAAFESELQAYKGKGNP EVEELREHAAWIRAYLQAYRHN | CD123 | 4.9 |
| 434 | MGSWQEFTMRLDAIYNRLETLGGSEAELAAFEKEIAAFESELQAYKGKGNP EVEWLRQSAANIRSELQAYRHN | CD123 | 13.7 |
| 435 | MGSWSEFNMRLDAIYERLTALGGSEAELAAFEKEIAAFESELQAYKGKGNP EVEWLRHSAARIRLELQAYRHN | CD123 | 13.7 |
| 436 | MGSWSEFNMRLDAIYERLTALGGSEAELAAFEKEIAAFESELQAYKGKGNP EVEWLRHSAALIRLELQAYRHN | CD123 | 11.4 |
| 437 | MGSWIEFNMRLDAIYERLVALGGSEAELAAFEKEIAAFESELQAYKGKGNP EVEWLRKVAANIRLELQAYRHN | CD123 | 11.4 |
| 438 | MGSWYEFHHRLDAIYERLLALGGSEAELAAFEKEIAAFESELQAYKGKGNP EVEWLRSSAANIRKELQAYRHN | CD123 | 11.9 |
| 439 | MGSWYEFAKRLDAIYERLVALGGSEAELAAFEKEIAAFESELQAYKGKGNP EVEWLRSSAANIREELQAYRHN | CD123 | 15.3 |
| 440 | MGSWTEFYVRLDAIYERLDALGGSEAELAAFEKEIAAFESELQAYKGKGNP EVEWLRMVAANIRTELQAYRHN | CD123 | 16 |
| 441 | MGSWVEFYTRLDAIYGRLDALGGSEAELAAFEKEIAAFESELQAYKGKGNP EVEWLRQVAANIRMELQAYRHN | CD123 | 14.4 |
| 442 | MGSWVEFHMRLDAIYERLDALGGSEAELAAFEKEIAAFESELQAYKGKGNP EVEWLRTAAANIRVELQAYRHN | CD123 | 9.1 |
| 443 | MGSWYEFAIRLDAIYERLHALGGSEAELAAFEKEIAAFESELQAYKGKGNP EVEYLRVWAANIRTELQAYRHN | CD123 | 25.5 |
| 444 | MGSWNEFVIRLDAIYERLLALGGSEAELAAFEKEIAAFESELQAYKGKGNP EVEYLRMAAANIRMELQAYRHN | CD123 | 16.6 |
| 445 | MGSWSEFYVRVDAIYARLSALGGSEAELAAFEKEIAAFESELQAYKGKGNP EVEKLRVWAANIRHELQAYRHN | CD123 | 14.7 |
| 446 | MGSWSEFHVRLDAIYARLDALGGSEAELAAFEKEIAAFESELQAYKGKGNP EVERLREWAANIRRELQAYRHN | CD123 | 14.4 |
| 447 | MGSWVEFHLRLDAIYGRLMALGGSEAELAAFEKEIAAFESELQAYKGKGNP EVENLRVWAANIRNELQAYRHN | CD123 | 17.5 |
| 448 | MGSWVEFEMRLDAIVGRLYALGGSEAELAAFEKEIAAFESELQAYKGKGNP EVEKLRRWAANIRSELQAYRHN | CD123 | 25.3 |
| 449 | MGSWVEFNIRLDAIYERLYALGGSEAELAAFEKEIAAFESELQAYKGKGNP EVEKLRHWAASIRRELQAYRHN | CD123 | 13.4 |
| 450 | MGSWHEFGVRLDAIYDRLMALGGSEAELAAFEKEIAAFESELQAYKGKGNP EVEFLRQAAANIRSELQAYRHN | CD123 | 15.6 |
| 451 | MGSWTEFNLRLDAIYDRLMALGGSEAELAAFEKEIAAFESELQAYKGKGNP EVEWLRASAAAIRVELQAYRHN | CD123 | 14.4 |
| 452 | MGSWTEFNLRLDAIYGRLSALGGSEAELAAFEKEIAAFESELQAYKGKGNP EVEFLRAAAANIRVELQAYRHN | CD123 | 19.3 |

TABLE 3-continued

| SEQ ID NO: | D-Domain Sequence | Target | ELISA_avg |
|---|---|---|---|
| | Exemplary D-domains | | |
| 453 | MGSWVEFNWRLDAIYDRLVALGGSEAELAAFEKEIAAFESELQAYKGKGNP EVEWLRVSAAKIRGELQAYRHN | CD123 | 9.3 |
| 454 | MGSWNEFAWRLDAIYSRLAALGGSEAELAAFEKEIAAFESELQAYKGKGNP EVEWLRVAAANIRYELQAYRHN | CD123 | 17.7 |
| 455 | MGSWTEFAWRLDAIYDRLLALGGSEAELAAFEKEIAAFESELQAYKGKGNP EVEWLRHVAANIRRELQAYRHN | CD123 | 16.1 |
| 456 | MGSWVEFSIRLDAIYTRLVALGGSEAELAAFEKEIAAFESELQAYKGKGNP EVEMLRKGAANIRKELQAYRHN | CD123 | 15.1 |
| 457 | MGSWVEFYIRLDAIYVRLMALGGSEAELAAFEKEIAAFESELQAYKGKGNP EVEKLRSYAANIRQELQAYRHN | CD123 | 16.1 |
| 458 | MGSWYEFSMRLDAIYDRLMALGGSEAELAAFEKEIAAFESELQAYKGKGNP EVEQLRGYAANIRNELQAYRHN | CD123 | 13 |
| 459 | MGSWVEFIYRLDAIYDRLEALGGSEAELAAFEKEIAAFESELQAYKGKGNP EVEVLRRYAANIRNELQAYRHN | CD123 | 17 |
| 460 | MGSWIEFEVRLDAIYNRLAALGGSEAELAAFEKEIAAFESELQAYKGKGNP EVERLRRYAANIRHELQAYRHN | CD123 | 20.8 |
| 461 | MGSWFEFYDRLDAIYMRLIALGGSEAELAAFEKEIAAFESELQAYKGKGNP EVEVLRRYAANIKAELQAYRHN | CD123 | 13.6 |
| 462 | MGSWFEFYMRLDAIYDRLTALGGSEAELAAFEKEIAAFESELQAYKGKGNP EVERLRTFAANIRKELQAYRHN | CD123 | 13.1 |
| 463 | MGSWYEFDYRLDAIYDRLAALGGSEAELAAFEKEIAAFESELQAYKGKGNP EVERLRKWAANIREELQAYRHN | CD123 | 24.9 |
| 464 | MGSWSEFYLRLDAIYDRLDALGGSEAELAAFEKEIAAFESELQAYKGKGNP EVEWLRKTAANIREELQAYRHN | CD123 | 15.7 |
| 465 | MGSWFEFYERLDAINWRLFALGGSEAELAAFEKEIAAFESELQAYKGKGNP EVEALRGEAAAIREDLQAYRHN | CD123 | 3 |
| 466 | MGSWNEFEDRLDAIWWRLFALGGSEAELAAFEKEIAAFESELQAYKGKGNP EVEALRVEAAFIRTMLQAYRHN | CD123 | 5.1 |
| 467 | MGSWFYFKDDLADINYMLEALGGSEAELAMFEDDIAGFELTLLKYKGKGNP EVEALRKEAAAIRDELQAYRHN | CD123 | 3.7 |
| 468 | MGSWHFFKDDLAWIKNELEALGGSEAELAMFEDDIAMFETMLQSYKGKGNP EVEALRKEAAAIRDELQAYRHN | CD123 | 3.2 |
| 469 | MGSWHWFKTDLADIKEELEALGGSEAELAMFEDDIAEFEEFLQMYKGKGNP EVEALRKEAAAIRDELQAYRHN | CD123 | 3.5 |
| 470 | MGSWWLFKDDLAEIKYWLEALGGSEAELAFFEDDIAEFERGLQIYKGKGNP EVEALRKEAAAIRDELQAYRHN | CD123 | 3.3 |
| 471 | MGSWYEFKDDLAEIKEWLEALGGSEAELAFFELDIADFEWLLQLYKGKGNP EVEALRKEAAAIRDELQAYRHN | CD123 | 3.8 |
| 472 | MGSWQWFKDDLAYIKETLEALGGSEAELALFEDMIADFEFELQWYKGKGNP EVEALRKEAAAIRDELQAYRHN | CD123 | 6.3 |
| 473 | MGSWILFKDDLAWIKETLEALGGSEAELAFFEDNIADFEEQLQGYKGKGNP EVEALRKEAAAIRDELQAYRHN | CD123 | 6 |
| 474 | MGSWIVFKDDLADIKRWLEALGGSEAELAMFEDEIADFEWQLQDYKGKGNP EVEALRKEAAAIRDELQAYRHN | CD123 | 3.9 |
| 475 | MGSWGHFKQDLAWIKDTLEALGGSEAELAFFEDDIAMFEMELQDYKGKGNP EVEALRKEAAAIRDELQAYRHN | CD123 | 4.9 |
| 476 | MGSWGYFKDDLAWIKGELEALGGSEAELAEFEWFIAVFEEDLQVYKGKGNP EVEALRKEAAAIRDELQAYRHN | CD123 | 4.5 |
| 477 | MGSWYWFKDDLAEIKGLLEALGGSEAELAEFEDEIAVFEQELQEYKGKGNP EVEALRKEAAAIRDELQAYRHN | CD123 | 10.4 |

TABLE 3-continued

| SEQ ID NO: | D-Domain Sequence | Target | ELISA_avg |
|---|---|---|---|
| | Exemplary D-domains | | |
| 478 | MGSWMFFKEDLADIKWALEALGGSEAELAFFEEEIALFEQHLQQYKGKGNP EVEALRKEAAAIRDELQAYRHN | CD123 | 3.2 |
| 479 | MGSWTFFKEDLAGIKWELEALGGSEAELAWFEDEIALFEEELQEYKGKGNP EVEALRKEAAAIRDELQAYRHN | CD123 | 7 |
| 480 | MGSWVFFKDDLADIKDELEALGGSEAELAFFEIAIALFEWELQEYKGKGNP EVEALRKEAAAIRDELQAYRHN | CD123 | 8.8 |
| 481 | MGSWTFFKNDLAEIKDWLEALGGSEAELADFEWDIAEFEYSLQEYKGKGNP EVEALRKEAAAIRDELQAYRHN | CD123 | 3.9 |
| 482 | MGSWTYFKDDLADIKQWLEALGGSEAELAFFEIEIAEFEEELQEYKGKGNP EVEALRKEAAAIRDELQAYRHN | CD123 | 4.6 |
| 483 | MGSWTVFKYDLADIKWWLEALGGSEAELADFEEEIAEFEEELQEYKGKGNP EVEALRKEAAAIRDELQAYRHN | CD123 | 3.9 |
| 484 | MGSWYWFKQDLAHIKSMLEALGGSEAELAWFEEDIADFESELQEYKGKGNP EVEALRKEAAAIRDELQAYRHN | CD123 | 3.3 |
| 485 | MGSWTFFKWDLADIKANLEALGGSEAELAWFEEDLAGFEAELQEYKGKGNP EVEALRKEAAAIRDELQAYRHN | CD123 | 4.8 |
| 486 | MGSWSFFKEELANIQVYLEALGGSEAELAWFEEDIADFEEDLQHYKGKGNP EVEALRKEAAAIRDELQAYRHN | CD123 | 3.8 |
| 487 | MGSWEFFKYELADIKDELEALGGSEAELAWFEEDIATFEEWLQGYKGKGNP EVEALRKEAAAIRDELQAYRHN | CD123 | 3.4 |
| 488 | MGSWQTFKDELAHIKWELEALGGSEAELAWFEWDIANFEEELQEYKGKGNP EVEALRKEAAAIRDELQAYRHN | CD123 | 5.5 |
| 489 | MGSWYWFKEELAFIKWELEALGGSEAELALFEEDIAYFEEMLQEYKGKGNP EVEALRKEAAAIRDELQAYRHN | CD123 | 9.4 |
| 490 | MGSWNSFKDELAEIKAELEALGGSEAELAFFEEDIAWFEEHLQQYKGKGNP EVEALRKEAAAIRDELQAYRHN | CD123 | 3.3 |
| 491 | MGSWDLFKWELAEIKLGLEALGGSEAELAEFEYDIAWFEEDLQDYKGKGNP EVEALRKEAAAIRDELQAYRHN | CD123 | 3.4 |
| 492 | MGSWIFFKQDLAEIKLNLEALGGSEAELAWFEDDIAWFESHLQDYKGKGNP EVEALRKEAAAIRDELQAYRHN | CD123 | 3.8 |
| 493 | MGSWHLFKWTLAEIKYELEALGGSEAELAWFEDDIATFEEELQWYKGKGNP EVEALRKEAAAIRDELQAYRHN | CD123 | 4 |
| 494 | MGSWVTFKDELADIKDFLEALGGSEAELAFFEVDIAEFEAELQFYKGKGNP EVEALRKEAAAIRDELQAYRHN | CD123 | 7.6 |
| 495 | MGSWVYFKDELADIKDFLEALGGSEAELAEFEEDIATFEYDLQWYKGKGNP EVEALRKEAAAIRDELQAYRHN | CD123 | 4.6 |
| 496 | MGSWETFKYELAEIKDYLEALGGSEAELAWFEDDIAEFEFELQYYKGKGNP EVEALRKEAAAIRDELQAYRHN | CD123 | 4.4 |
| 497 | MGSWNTFKYELAEIKHFLEALGGSEAELAMFEDDIAMFEWELQEYKGKGNP EVEALRKEAAAIRDELQAYRHN | CD123 | 5 |
| 498 | MGSWYVFKDELAEIKQFLEALGGSEAELAWFEDDIAEFETQLQHYKGKGNP EVEALRKEAAAIRDELQAYRHN | CD123 | 9.9 |
| 499 | MGSWIFFKEQLAIIKWELEALGGSEAELAWFEDDIAAFEDDLQFYKGQGNP EVEALRKEAAAIRDELQAYRHN | CD123 | 15 |
| 500 | MGSWEFFKEVLAEIKYDLEALGGSEAELAWFETDIAGFEIDLQVYKGKGNP EVEALRKEAAAIRDELQAYRHN | CD123 | 8.2 |
| 501 | MGSWVFFKEDLATIKNDLEALGGSEAELAWFEMMIADFEADLQYYKGKGNP EVEALRKEAAAIRDELQAYRHN | CD123 | 3.1 |
| 502 | MGSWEEFKEDLAEIKVWLEALGGSEAELAWFEMGIADFEDGLQFYKGKGNP EVEALRKEAAAIRDELQAYRHN | CD123 | 4.3 |

TABLE 3-continued

| SEQ ID NO: | D-Domain Sequence | Target | ELISA_avg |
|---|---|---|---|
| | Exemplary D-domains | | |
| 503 | MGSWHWFKEDLANIKDWLEALGGSEAELAWFEDNIADFEGDLQVYKGKGNP EVEALRKEAAAIRDELQAYRHN | CD123 | 3.3 |
| 504 | MGSWFWFKEDLAFIKEDLEALGGSEAELAWFEDGIAFFEWDLQDYKGKGNP EVEALRKEAAAIRDELQAYRHN | CD123 | 13.7 |
| 505 | MGSWQWFKEDLAEIKHDLEALGGSEAELAWFEDFIAQFEFDLQWYKGKGNP EVEALRKEAAAIRDELQAYRHN | CD123 | 3.8 |
| 506 | MGSWHWFKEDLAIIKQDLEALGGSEAELATFEQWIAEFEWDLQEYKGKGNP EVEALRKEAAAIRDELQAYRHN | CD123 | 5.5 |
| 507 | MGSWNWFKEDLAIIKMDLEALGGSEAELAWFEHNIAGFEFELQGYKGKGNP EVEALRKEAAAIRDELQAYRHN | CD123 | 3.1 |
| 508 | MGSWSWFKEDLAEIKMELEALGGSEAELAYFEWYIAEFEFQLQHYKGKGNP EVEALRKEAAAIRDELQAYRHN | CD123 | 4.8 |
| 509 | MGSWSWFKQDLADIKIQLEALGGSEAELAWFEWDIAEFEFELQDYKGKGNP EVEALRKEAAAIRDELQAYRHN | CD123 | 4 |
| 510 | MGSWSWFKEDLADIKFELEALGGSEAELAWFELDIADFEQALQQYKGKGNP EVEALRKEAAAIRDELQAYRHN | CD123 | 6.8 |
| 511 | MGSWSWFKEDLASIKAVLEALGGSEAELAFFESDIAEFEQELQYYKGKGNP EVEALRKEAAAIRDELQAYRHN | CD123 | 6.9 |
| 512 | MGSWWEFKEDLAEIKWFLEALGGSEAELAWFEHDIAKFEFELQYYKGKGNP EVEALRKEAAAIRDELQAYRHN | CD123 | 5.1 |
| 513 | MGSWEWFKSDLASIKWELEALGGSEAELAWFEHDIAEFEEDLQWYKGKGNP EVEALRKEAAAIRDELQAYRHN | CD123 | 5.7 |
| 514 | MGSWNEFKDDLAMIKMTLEALGGSEAELAWFEHDIAEFEDDLQWYKGKGNP EVEALRKEAAAIRDELQAYRHN | CD123 | 3.5 |
| 515 | MGSWTFFKDDLAEIKWMLEALGGSEAELAWFESDIAYFEDELQWYKGKGNP EVEALRKEAAAIRDELQAYRHN | CD123 | 3.3 |
| 516 | MGSWSDFKDDLAEIKMILEALGGSEAELAYFENDIAWFEDDLQEYKGKGNP EVEALRKEAAAIRDELQAYRHN | CD123 | 4.7 |
| 517 | MGSWSMFKDDLAEIKASLEALGGSEAELAWFEDDIAWFEDDLQHYKGKGNP EVEALRKEAAAIRDELQAYRHN | CD123 | 5.2 |
| 518 | MGSWQYFKDDLAEIKMVLEALGGSEAELAWFEADIAMFEDDLQIYKGKGNP EVEALRKEAAAIRDELQAYRHN | CD123 | 3.6 |
| 519 | MGSWSFFKDDLAEIKYFLEALGGSEAELAMFEQTIAEFEYDLQDYKGKGNP EVEALRKEAAAIRDELQAYRHN | CD123 | 10.1 |
| 520 | MGSWMEFKEELAEIKYILEALGGSEAELAWFEQSIADFEYDLQDYKGKGNP EVEALRKEAAAIRDELQAYRHN | CD123 | 5 |
| 521 | MGSWAWFKEDLAEIKVFLEALGGSEAELAEFEVSIADFEYELQDYKGKGNP EVEALRKEAAAIRDELQAYRHN | CD123 | 3.5 |
| 522 | MGSWYEFKFDLAEIKEQLEALGGSEAELALFEDDIAFFEYDLQNYKGKGNP EVEALRKEAAAIRDELQAYRHN | CD123 | 4.6 |
| 523 | MGSWYDFKYDLAEIKMDLEALGGSEAELAQFEFDIAFFEEELQDYKGKGNP EVEALRKEAAAIRDELQAYRHN | CD123 | 3.2 |
| 524 | MGSWYIFKEDLAEIKEELEALGGSEAELAYFEEEIALFEMELQWYKGKGNP EVEALRKEAAAIRDELQAYRHN | CD123 | 11.1 |
| 525 | MGSWVLFKEELAYIKFELEALGGSEAELALFENVIAIFESNLQNYKGKGNP EVEALRKEAAAIRDELQAYRHN | CD123 | 3.5 |
| 526 | MGSWQDFKEDLAWIKYELEALGGSEAELAFFEYDIAIFENNLQHYKGKGNP EVEALRKEAAAIRDELQAYRHN | CD123 | 3.2 |
| 527 | MGSWDHFKNDLAWIKKHLEALGGSEAELAEFEAVIAYFELYLQGYKGKGNP EVEALRKEAAAIRDELQAYRHN | CD123 | 3.3 |

TABLE 3-continued

| Exemplary D-domains | | | |
|---|---|---|---|
| SEQ ID NO: | D-Domain Sequence | Target | ELISA_avg |
| 528 | MGSWYDFKEDLADIKWMLEALGGSEAELAEFENVIAYFENDLQEYKGKGNP EVEALRKEAAAIRDELQAYRHN | CD123 | 8 |
| 529 | MGSWYMFKEELADIKWYLEALGGSEAELAWFEDDIAGFEWDLQAYKGKGNP EVEALRKEAAAIRDELQAYRHN | CD123 | 7 |
| 530 | MGSWYYFKDELADIKWDLEALGGSEAELAWFEMLIAQFELDLQWYKGKGNP EVEALRKEAAAIRDELQAYRHN | CD123 | 4 |
| 531 | MGSWMYFKDTLADIKWYLEALGGSEAELAFFEDWIAEFEDDLQVYKGKGNP EVEALRKEAAAIRDELQAYRHN | CD123 | 3.1 |
| 532 | MGSWYQFKHDLADIKYGLEALGGSEAELAWFEDDIADFELDLQYYKGKGNP EVEALRKEAAAIRDELQAYRHN | CD123 | 4.7 |
| 533 | MGSWYVFKDDLADIKYMLEALGGSEAELAWFEWEIANFEFDLQYYKGKGNP EVEALRKEAAAIRDELQAYRHN | CD123 | 3.8 |
| 534 | MGSWNFFKYDLADIMAYLEALGGSEAELAFFEDEIANFEHDLQKYKGKGNP EVEALRKEAAAIRDELQAYRHN | CD123 | 4.4 |
| 535 | MGSWHWFKIVLADIKDGLEALGGSEAELAYFETTIADFEMDLQHYKGKGNP EVEALRKEAAAIRDELQAYRHN | CD123 | 4.3 |
| 536 | MGSWHWFKIVLADIKDGLEALGGSEAELAYFETTIADFEMDLHHYKGKGNP EVEALRKEAAAIRDELQAYRHN | CD123 | 3.5 |
| 537 | MGSWFMFKEELADIKDWLEALGGSEAELASFESYIAWFEQDLQWYKGKGNP EVEALRKEAAAIRDELQAYRHN | CD123 | 5.7 |
| 538 | MGSWFMFKQELAWIKEDLEALGGSEAELADFEWDIAEFEWDLQYYKGKGNP EVEALRKEAAAIRDELQAYRHN | CD123 | 7.2 |
| 539 | MGSWQIFKGELAYIKQYLEALGGSEAELAFFEFDIAEFEEDLQYYKGKGNP EVEALRKEAAAIRDELQAYRHN | CD123 | 4.7 |
| 540 | MGSWDFFKEELAEIKHYLEALGGSEAELAFFEFWIADFEQDLQEYKGKGNP EVEALRKEAAAIRDELQAYRHN | CD123 | 3.7 |
| 541 | MGSWFNFKEELAVIKFQLEALGGSEAELAFFEWVIADFEDDLQEYKGKGNP EVEALRKEAAAIRDELQAYRHN | CD123 | 6.1 |
| 542 | MGSWYQFKTELAWIKDDLEALGGSEAELAWFEWVIADFEDDLQFYKGKGNP EVEALRKEAAAIRDELQAYRHN | CD123 | 6.6 |
| 543 | MGSWFEFKDYLADIKWDLEALGGSEAELAIFEHDIAYFEHNLQQYKGKGNP EVEALRKEAAAIRDELQAYRHN | CD123 | 3.8 |
| 544 | MGSWVRFKDFLADIKMDLEALGGSEAELADFEYHIAEFEHNLQEYKGKGNP EVEALRKEAAAIRDELQAYRHN | CD123 | 5.8 |
| 545 | MGSWWLFKEQLALIKYNLEALGGSEAELADFESWIAEFEHQLQEYKGKGNP EVEALRKEAAAIRDELQAYRHN | CD123 | 4.1 |
| 546 | MGSWHVFKTELADIKFYLEALGGSEAELAMFELWIAEFEHELQDYKGKGNP EVEALRKEAAAIRDELQAYRHN | CD123 | 5.4 |
| 547 | MGSWIWFKDWLADIKDLLEALGGSEAELAEFEYDIALFEDQLQAYKGKGNP EVEALRKEAAAIRDELQAYRHN | CD123 | 7.3 |
| 548 | MGSWGWFKHELAFIKADLEALGGSEAELAWFEEEIAEFEYELQFYKGKGNP EVEALRKEAAAIRDELQAYRHN | CD123 | 3.3 |
| 549 | MGSWTWFKDNLAWIKEDLEALGGSEAELAWFELEIASFETALQDYKGKGNP EVEALRKEAAAIRDELQAYRHN | CD123 | 6.9 |
| 550 | MGSWTYFKNDLAGIKEDLEALGGSEAELAQFEFEIAEFEWLLQDYKGKGNP EVEALRKEAAAIRDELQAYRHN | CD123 | 3.6 |
| 551 | MGSWTWFKWDLADIKGDLEALGGSEAELAFFEEEIAEFEWRLQDYKGKGNP EVEALRKEAAAIRDELQAYRHN | CD123 | 5.9 |
| 552 | MGSWLYFKEYLADIKSDLEALGGSEAELAWFEYEIADFEEQLQYYKGKGNP EVEALRKEAAAIRDELQAYRHN | CD123 | 3.7 |

TABLE 3-continued

Exemplary D-domains

| SEQ ID NO: | D-Domain Sequence | Target | ELISA_avg |
|---|---|---|---|
| 553 | MGSWHWFKEELAEIKEDLVALGGSEAELAWFEYDIAMFELSLQNYKGKGNP EVEALRKEAAAIRDELQAYRHN | CD123 | 3.1 |
| 554 | MGSWNDFKEELAWIKFDLEALGGSEAELAWFEEDIAMFEQQLQAYKGKGNP EVEALRKEAAAIRDELQAYRHN | CD123 | 3.8 |
| 555 | MGSWWDFKDWLAEIKHDLEALGGSEAELALFESEIADFEFGLQWYKGKGNP EVEALRKEAAAIRDELQAYRHN | CD123 | 4.2 |
| 556 | MGSWDEFKEDLAHIKTDLEALGGSEAELALFEDEIADFEMYLQHYKGKGNP EVEALRKEAAAIRDELQAYRHN | CD123 | 6.3 |
| 557 | MGSWDFFKYDLANINEWLEALGGSEAELADFEYGIADFELWLQDYKGKGNP EVEALRKEAAAIRDELQAYRHN | CD123 | 5.5 |
| 558 | MGSWYQFKDDLAHIKHLLEALGGSEAELAVFEYIIADFESFLQIYKGKGNP EVEALRKEAAAIRDELQAYRHN | CD123 | 4 |
| 559 | MGSWAEFKHDLADIKRELEALGGSEAELAWFELSIAFFEDELQHYKGKGNP EVEALRKEAAAIRDELQAYRHN | CD123 | 3.3 |
| 560 | MGSWVVFKQDLADINHQLEALGGSEAELAWFEWEIADFEWELQHYKGKGNP EVEALRKEAAAIRDELQAYRHN | CD123 | 3.6 |
| 561 | MGSWFQFKEFLAMITHNLEALGGSEAELAEFEHDIALFESELQQYKGKGNP EVEALRKEAAAIRDELQAYRHN | CD123 | 3.1 |
| 562 | MGSWHWFKEDLAMITDVLEALGGSEAELAAFESEIAVFEADLQYYKGKGNP EVEALRKEAAAIRDELQAYRHN | CD123 | 5.2 |
| 563 | MGSWSWFQWDLAGIKDHLEALGGSEAELAEFESEIAYFEDELQWYKGKGNP EVEALRKEAAAIRDELQAYRHN | CD123 | 12.9 |
| 564 | MGSWTEFKGELAEIKWILEALGGSEAELAFFEDEIAAFEWDLQKYKGKGNP EVEALRKEAAAIRDELQAYRHN | CD123 | 8.2 |
| 565 | MGSWFEFKWTLALIKQELEALGGSEAELADFEQEIAEFEWWLQTYKGKGNP EVEALRKEAAAIRDELQAYRHN | CD123 | 4.9 |
| 566 | MGSWAEFKQRLAAIKTRLEALGGSEAELAAFMDEIMAFEWELWAYKGKGNP EVEALMNEAFAIDVELYAYRHN | CD123 | 3.4 |
| 567 | MGSWAEFKQRLAAIKTRLEALGGSEAELAAFEWEIVAFFSELFAYKGKGNP EVEALRDEAIAIETELVAYRHN | CD123 | 3.6 |
| 568 | MGSWWEFDHRLTAIDTRLQALGGSEAELAEFESSIAEFEWWLQDYKGKGNP EVEALFAEAEAIYVELDAYRHN | CD123 | 4.3 |
| 569 | MGSWWEFQFRLYAIDQRLLALGGSEAELAEFEQDIADFEWMLQDYKGKGNP EVEALMLEADAIEAELKAYRHN | CD123 | 3.1 |
| 570 | MGSWYEFDHRLDAIYQRLWALGGSEAELAEFEYGIAEFEEYLQDYKGKGNP EVEALISEAWAIEWELSAYRHN | CD123 | 4.6 |
| 571 | MGSWYEFDMRLDAIWERLTALGGSEAELADFEQYIAEFERQLQDYKGKGNP EVEALFDEAWAIEDELYAYRHN | CD123 | 13.7 |
| 572 | MGSWSEFDSRLDAIAYRLFALGGSEAELAQFEWIIADFEEDLQMYKGKGNP EVEALFSEAYAIEIELNAYRHN | CD123 | 4.3 |
| 573 | MGSWYEFDDRLDAIAYRLNALGGSEAELAWFEWEIAEFELDLQWYKGKGNP EVEALVWEADAIEWELEAYRHN | CD123 | 4.6 |
| 574 | MGSWFEFDERLDAIGSRLTALGGSEAELASFEFYIADFEEWLQQYKGKGNP EVEALEWEAFAIDEELGAYRHN | CD123 | 3.8 |
| 575 | MGSWEEFDQRLDAIDVRLYALGGSEAELAEFEFDIAAFEEWLQLYKGKGNP EVEALNMEAFAITDELCAYRHN | CD123 | 3.6 |
| 576 | MGSWEEFDVRLDAIFNRLWALGGSEAELAEFEFDIAWFEMDLQEYKGKGNP EVEALFDEAEAITNELVAYRHN | CD123 | 4.7 |
| 577 | MGSWEEFDKRLDAITRRLMALGGSEAELAEFESTIAWFEWDLQEYKGKGNP EVEALDWEAYAIDYELGAYRHN | CD123 | 4.5 |

TABLE 3-continued

Exemplary D-domains

| SEQ ID NO: | D-Domain Sequence | Target | ELISA_avg |
|---|---|---|---|
| 578 | MGSWYEFDHRLEAIYDRLWALGGSEAELAFFEFDIADFEWDLQSYKGKGNP EVEALFDEAAAIGHELLAYRHN | CD123 | 4.5 |
| 579 | MGSWNEFDDRLLAIWGRLDALGGSEAELAFFEEQIAGFEDELQWYKGKGNP EVEALDQEAEAIEKELWAYRHN | CD123 | 4.1 |
| 580 | MGSWVEFDDRLDAIWERLDALGGSEAELAWFEEQIAVFEHQLQDYKGKGNP EVEALNQEAEAIDLELKAYRHN | CD123 | 5 |
| 581 | MGSWTEFDDRLFAIYWRLDALGGSEAELAWFEEVIAEFENDLQVYKGKGNP EVEALDDEAHAISIELEAYRHN | CD123 | 6.4 |
| 582 | MGSWSEFDQRLEAIWNRLDALGGSEAELADFEREIAYFENQLQWYKGKGNP EVEALNNEAFAIVDELGAYRHN | CD123 | 3.4 |
| 583 | MGSWYEFDERLWAIWERLDALGGSEAELAHFEWVIADFENDLQWYKGKGNP EVEALEFEAEAIVTELHAYRHN | CD123 | 3.6 |
| 584 | MGSWMEFDYRLEAIWMRLIALGGSEAELADFESSIADFEHHLQSYKGKGNP EVEALEWEAFAIGVELDAYRHN | CD123 | 3.1 |
| 585 | MGSWYEFESRLEAIWWRLEALGGSEAELAQFEQYIADFEQHLQWYKGKGNP EVEALDWEADAIWLELQAYRHN | CD123 | 4.4 |
| 586 | MGSWEEFYMRLVAIHMRLRALGGSEAELAVFENYIAEFEEYLQYYKGKGNP EVEALTIEADAIGTELGAYRHN | CD123 | 4.4 |
| 587 | MGSWDEFYYRLVAITHRLHALGGSEAELAWFEDDIAGFEWDLQTYKGKGNP EVEALYKEAGAIGMELTAYRHN | CD123 | 5.4 |
| 588 | MGSWEEFDTRLLAIFGRLGALGGSEAELALFEMLIAKFEDDLQNYKGKGNP EVEALSEEAFAIDHELGAYRHN | CD123 | 6.7 |
| 589 | MGSWREFDQRLWAIDWRLEALGGSEAELAMFEWMIATFEDDLQWYKGKGNP EVEALYREAFAIDWELDAYRHN | CD123 | 3.4 |
| 590 | MGSWEEFHERLDAIDERLEALGGSEAELAFFEDDIASFEDWLQWYKGKGNP EVEALSREADAINFELEAYRHN | CD123 | 4.3 |
| 591 | MGSWNEFYERLEAIDRRLFALGGSEAELALFEWMIADFEDDLQMYKGKGNP EVEALINEAGAIGFELEAYRHN | CD123 | 5.2 |
| 592 | MGSWTEFTQRLEAIVDRLFALGGSEAELAEFENSIADFEWDLQWYKGKGNP EVEALNREAVAIDNELWAYRHN | CD123 | 3.9 |
| 593 | MGSWVEFIMRLDAIYERLDALGGSEAELAEFEWHIADFEDHLQWYKGKGNP EVEALFEEADAIWEELWAYRHN | CD123 | 6.4 |
| 594 | MGSWNEFLLRLDAIEHRLFALGGSEAELAEFEWEIADFEDDLQWYKGKGNP EVEALVEEAEAIDVELVAYRHN | CD123 | 3.2 |
| 595 | MGSWYEFNMRLGAIDDRLQALGGSEAELAWFEDMIAIFEDDLQIYKGKGNP EVEALEQEAAAIHQELWAYRHN | CD123 | 3.8 |
| 596 | MGSWEEFHWRLGAIDARLEALGGSEAELAWFEDGIADFEAILQDYKGKGNP EVEALDSEAVAIHHELWAYRHN | CD123 | 3.3 |
| 597 | MGSWYEFYERLWAIDDRLWALGGSEAELAEFEDSIATFEPSLQMYKGKGNP EVEALVAEAWAIFDELAAYRHN | CD123 | 3.6 |
| 598 | MGSWFEFDQRLDAITFRLWALGGSEAELAEFEDVIALFEYHLQDYKGKGNP EVEALEVEAWAIFHELGAYRHN | CD123 | 3.2 |
| 599 | MGSWSEFWFRLDAIEDRLWALGGSEAELAEFEDNIALFEYSLQHYKGKGNP EVEALVKEANAIDDELGAYRHN | CD123 | 4.5 |
| 600 | MGSWYEFWDRLTAIEHRLWALGGSEAELAYFEDSIAHFEGSLQVYKGKGNP EVEALYKEAEAIEWELEAYRHN | CD123 | 4.4 |
| 601 | MGSWYEFDDRLWAIFDRLFALGGSEAELAFFEDSIAEFEEELQHYKGKGNP EVEALYLEAWAIENELGAYRHN | CD123 | 4.7 |
| 602 | MGSWNEFVERLSAIDHRLWALGGSEAELADFEQQIAEFEIHLQEYKGKGNP EVEALDFEADAIFDELLAYRHN | CD123 | 3.2 |

TABLE 3-continued

Exemplary D-domains

| SEQ ID NO: | D-Domain Sequence | Target | ELISA_avg |
|---|---|---|---|
| 603 | MGSWSEFVDRLDAIFDRLWALGGSEAELAWFEDTIAHFEWNLQEYKGKGNP EVEALNGEADAITDELHAYRHN | CD123 | 5.3 |
| 604 | MGSWAEFDSRLDAIAQRLFALGGSEAELAHFEDFIAQFEYSLQEYKGKGNP EVEALSNEADAIFNELKAYRHN | CD123 | 3.6 |
| 605 | MGSWAEFDSRLIAIFDRLWALGGSEAELAWFEDDIAQFEQHLQAYKGKGNP EVEALRQEADAITFELKAYRHN | CD123 | 3.6 |
| 606 | MGSWTEFEERLEAIWDRLYALGGSEAELAAFEWDIAYFEDGLQEYKGKGNP EVEALFMEAEAIIRELKAYRHN | CD123 | 5.9 |
| 607 | MGSWYEFEDRLAAIWDRLNALGGSEAELAIFEWDIAWFEEGLQEYKGKGNP EVEALKHEASAIQTELFAYRHN | CD123 | 6.4 |
| 608 | MGSWLEFESRLWAIWDRLDALGGSEAELAHFEQDIADFEMSLQEYKGKGNP EVEALIREAEAIETELYAYRHN | CD123 | 3.4 |
| 609 | MGSWMEFEDRLIAIWARLDALGGSEAELAWFEADIADFEESLQEYKGKGNP EVEALIFEAIAINKELMAYRHN | CD123 | 3.7 |
| 610 | MGSWFEFTIRLEAIQDRLDALGGSEAELAWFEWDIAEFEEGLQFYKGKGNP EVEALHTEADAIMNELVAYRHN | CD123 | 3.5 |
| 611 | MGSWYEFVSRLDAIEYRLWALGGSEAELAWFEWDIADFEQGLQFYKGKGNP EVEALAQEANAIGSELTAYRHN | CD123 | 3.2 |
| 612 | MGSWEEFDYRLYAIQDRLYALGGSEAELAFFEWEIADFEHMLQMYKGKGNP EVEALFQEADAIDAELHAYRHN | CD123 | 4.4 |
| 613 | MGSWIEFFHRLDAIQDRLDALGGSEAELAYFEWAIADFEHMLQLYKGKGNP EVEALQFEAFAIEGELYAYRHN | CD123 | 3.5 |
| 614 | MGSWYEFSSRLNAIDDRLWALGGSEAELAYFETDIADFESLLQWYKGKGNP EVEALLNEADAIDYELYAYRHN | CD123 | 3.8 |
| 615 | MGSWFEFEYRLDAIIDRLFALGGSEAELAEFESMIANFEYSLQEYKGKGNP EVEALYFEADAIVDELTAYRHN | CD123 | 4 |
| 616 | MGSWLEFEYRLDAIYDRLFALGGSEAELAAFEQDIADFEKYLQYYKGKGNP EVEALWEEADAIMWELFAYRHN | CD123 | 3.1 |
| 617 | MGSWHEFEERLMAIEDRLWALGGSEAELAEFEQWIALFEYDLQEYKGKGNP EVEALGMEAFAINNELSAYRHN | CD123 | 5.8 |
| 618 | MGSWYEFEERLDAIEDRLIALGGSEAELAIFEDIIAFFEQDLQYYKGKGNP EVEALEMEAEAISIELDAYRHN | CD123 | 4.1 |
| 619 | MGSWHEFEKRLYAIEDRLIALGGSEAELAWFEDSIAWFEWDLQMYKGKGNP EVEALNEEADAIYQELDAYRHN | CD123 | 3.6 |
| 620 | MGSWIEFEDRLDAITDRLWALGGSEAELAEFEHQIAFFEEDLQWYKGKGNP EVEALHMEAEAIMEELGAYRHN | CD123 | 9.5 |
| 621 | MGSWMEFEDRLMAIVDRLWALGGSEAELADFEWNIAMFEEELQWYKGKGNP EVEALGDEAEAIEWELYAYRHN | CD123 | 6.8 |
| 622 | MGSWEEFEDRLFAIDSRLWALGGSEAELAEFENIIASFEEVLQEYKGKGNP EVEALSVEAFAIDRELGAYRHN | CD123 | 3.7 |
| 623 | MGSWEEFLFRLEAIQDRLWALGGSEAELAWFEYEIASFEDVLQSYKGKGNP EVEALSTEAKAIDYELFAYRHN | CD123 | 8.2 |
| 624 | MGSWVEFDNRLFAIDERLWALGGSEAELAWFEEEIASFEDNLQKYKGKGNP EVEALQLEAFAIMEELDAYRHN | CD123 | 3.3 |
| 625 | MGSWFEFDDRLEAIFDRLWALGGSEAELAMFEFAIAEFEDALQEYKGKGNP EVEALYEEAVAIDEELYAYRHN | CD123 | 4.1 |
| 626 | MGSWFEFDARLMAINDRLWALGGSEAELAAFEYHIALFEDQLQMYKGKGNP EVEALTLEAVAINEELWAYRHN | CD123 | 4 |
| 627 | MGSWVEFDSRLAAIDYRLEALGGSEAELAWFEYTIANFEHTLQMYKGKGNP EVEALVYEAHAIATELQAYRHN | CD123 | 3.4 |

TABLE 3-continued

Exemplary D-domains

| SEQ ID NO: | D-Domain Sequence | Target | ELISA_avg |
|---|---|---|---|
| 628 | MGSWTEFDERLDAIDWRLEALGGSEAELAWFEGDIALFEQYLQVYKGKGNP EVEALMEEADAIKAELDAYRHN | CD123 | 4.5 |
| 629 | MGSWIEFDERLDAIDFRLWALGGSEAELAWFEGWIAEFESDLQLYKGKGNP EVEALNEEANAIFHELSAYRHN | CD123 | 7 |
| 630 | MGSWWEFDSRLDAIDFRLWALGGSEAELAWFEVEIADFEDWLQLYKGKGNP EVEALWHEADAIVTELYAYRHN | CD123 | 3.2 |
| 631 | MGSWYEFDERLDAIFDRLWALGGSEAELAYFEQVIATFEKTLQRYKGKGNP EVEALDTEAKAISWELDAYRHN | CD123 | 3 |
| 632 | MGSWYEFQERLDAIDSRLWALGGSEAELAWFEYTIAEFEKELQMYKGKGNP EVEALGTEAVAISEELMAYRHN | CD123 | 5.5 |
| 633 | MGSWEEFEDRLWAIDGRLYALGGSEAELAWFEQWIATFEEDLQDYKGKGNP EVEALEYEASAIFEELEAYRHN | CD123 | 9.4 |
| 634 | MGSWFEFGDRLEAIDERLYALGGSEAELAQFEWWIAEFEHHLQDYKGKGNP EVEALEYEADAIWGELHAYRHN | CD123 | 4.5 |
| 635 | MGSWFEFNDRLDAISERLSALGGSEAELAYFEWQIAVFEKTLQNYKGKGNP EVEALTLEANAIFEELEAYRHN | CD123 | 3.9 |
| 636 | MGSWVEFMDRLEAIEERLSALGGSEAELAFFEWEIAEFEEHLQVYKGKGNP EVEALEWEALAITEELAAYRHN | CD123 | 4 |
| 637 | MGSWIEFMDRLWAIDQRLWALGGSEAELAWFEEEIAWFEEELQVYKGKGNP EVEALEWEATAISEELWAYRHN | CD123 | 6.5 |
| 638 | MGSWEEFNWRLRAIDERLFALGGSEAELAWFEYDIAEFEEQLQVYKGKGNP EVEALRVEAAAIAEELYAYRHN | CD123 | 5.4 |
| 639 | MGSWWEFEIRLDAIDERLWALGGSEAELAWFEQSIAFFENDLQVYKGKGNP EVEALRWEANAIIEELFAYRHN | CD123 | 3.2 |
| 640 | MGSWYEFEWRLDAIDRRLWALGGSEAELADFEEEIADFEWMLQNYKGKGNP EVEALVDEASAIQTELWAYRHN | CD123 | 10 |
| 641 | MGSWYEFVYRLRAIDERLDALGGSEAELAMFEFEIAFFEDQLQRYKGKGNP EVEALVDEAQAIDFELFAYRHN | CD123 | 4.5 |
| 642 | MGSWWEFEDRLYAIDDRLWALGGSEAELAQFEREIAQFEIWLQEYKGKGNP EVEALDDEATAINSELFAYRHN | CD123 | 5.5 |
| 643 | MGSWDEFEFRLEAIDSRLWALGGSEAELAVFEYEIAQFEFMLQEYKGKGNP EVEALGMEAWAIENELFAYRHN | CD123 | 3.6 |
| 644 | MGSWEEFEWRLDAIDERLWALGGSEAELATFEYEIAIFENELQQYKGKGNP EVEALDSEAYAIERELGAYRHN | CD123 | 4.3 |
| 645 | MGSWYEFFDRLDAIDERLWALGGSEAELAWFEAEIAEFEMELQGYKGKGNP EVEALDVEAHAIEMELFAYRHN | CD123 | 3.7 |
| 646 | MGSWYEFMGRLEAIDERLQALGGSEAELAWFEHEIAEFEWSLQWYKGKGNP EVEALRFEAGAIPWELWAYRHN | CD123 | 3.5 |
| 647 | MGSWVEFSNRLDAIWERLQALGGSEAELAYFEWEIAEFEWELQSYKGKGNP EVEALNAEADAIEWELEAYRHN | CD123 | 5.1 |
| 648 | MGSWEEFHMRLIAIDERLWALGGSEAELAGFEESIAYFESQLQDYKGKGNP EVEALDYEAHAIWRELYAYRHN | CD123 | 3.9 |
| 649 | MGSWWEFKYRLDAICFRLAALGGSEAELASFEDEIAYFEEDLQGYKGKGNP EVEALDYEALAIWDELAAYRHN | CD123 | 3.1 |
| 650 | MGSWDEFAMRLEAIQARLFALGGSEAELAIFEDEIAFFETMLQDYKGKGNP EVEALEYEAAAIEAELGAYRHN | CD123 | 3.7 |
| 651 | MGSWWEFNARLDAIEDRLMALGGSEAELAYFEDIIASFENILQQYKGKGNP EVEALWYEAYAIEKELNAYRHN | CD123 | 3.4 |
| 652 | MGSWIEFWNRLEAIEERLYALGGSEAELAYFEDEIAEFEIYLQQYKGKGNP EVEALKHEAEAINKELMAYRHN | CD123 | 5.2 |

TABLE 3-continued

Exemplary D-domains

| SEQ ID NO: | D-Domain Sequence | Target | ELISA_avg |
|---|---|---|---|
| 653 | MGSWNEFVIRLFAIDDRLYALGGSEAELAWFEDEIATFEYELQRYKGKGNP EVEALEYEAEAIVSELFAYRHN | CD123 | 3.5 |
| 654 | MGSWYEFLARLYAIDERLWALGGSEAELATFEHWIADFEEQLQSYKGKGNP EVEALTDEAVAIGEELSAYRHN | CD123 | 4.5 |
| 655 | MGSWLEFETRLHAIDERLWALGGSEAELAEFEEHIAWFEEDLQFYKGKGNP EVEALDFEADAIGWELWAYRHN | CD123 | 4.6 |
| 656 | MGSWFEFETRLEAIDLRLWALGGSEAELATFEDVIAFFEDWLQFYKGKGNP EVEALKMEAWAIGEELHAYRHN | CD123 | 6.6 |
| 657 | MGSWHEFWQRLEAIEGRLWALGGSEAELADFESLIADFEEQLQEYKGKGNP EVEALMAEAEAIDNELRAYRHN | CD123 | 7 |
| 658 | MGSWYEFEQRLEAIEWRLGALGGSEAELATFEEDIADFEEWLQEYKGKGNP EVEALQYEAYAIAEELHAYRHN | CD123 | 4.4 |
| 659 | MGSWYEFENRLFAIEERLWALGGSEAELAWFEYEIANFEWGLQSYKGKGNP EVEALDNEAEAIDIELAAYRHN | CD123 | 3.3 |
| 660 | MGSWYEFEQRLGAIEERLWALGGSEAELAAFEDIIAYFEYQLQSYKGKGNP EVEALDEEAWAIDDELWAYRHN | CD123 | 10.6 |
| 661 | MGSWWEFEQRLDAIETRLWALGGSEAELAYFEHIIADFEDELQIYKGKGNP EVEALGWEAFAIDGELTAYRHN | CD123 | 4.7 |
| 662 | MGSWFEFPYRLEAIEERLYALGGSEAELAQFEQFIAWFEMDLQDYKGKGNP EVEALWFEANAIVEELDAYRHN | CD123 | 3.1 |
| 663 | MGSWVEFYDRLEAIEIRLWALGGSEAELADFESFIAHFEDDLQAYKGKGNP EVEALMDEANAIVFELDAYRHN | CD123 | 4 |
| 664 | MGSWVEFWDRLDAIEERLWALGGSEAELAEFEFMIAMFEQHLQEYKGKGNP EVEALIPEAGAIDKELTAYRHN | CD123 | 10 |
| 665 | MGSWDEFDARLWAIEERLWALGGSEAELAEFEFMIAAFEDVLQEYKGKGNP EVEALMGEANAIVMELDAYRHN | CD123 | 4.3 |
| 666 | MGSWYEFWRRLDAIEERLWALGGSEAELAMFETDIAGFEWMLQLYKGKGNP EVEALEHEAWAINSELDAYRHN | CD123 | 3.6 |
| 667 | MGSWHEFIWRLDAIEERLWALGGSEAELAWFETEIATFEAQLQDYKGKGNP EVEALEWEAIAIAWELDAYRHN | CD123 | 3.3 |
| 668 | MGSWYEFYWRLEAIEERLWALGGSEAELAEFEKAIATFEDQLQTYKGKGNP EVEALETEALAIHAELEAYRHN | CD123 | 3.7 |
| 669 | MGSWFEFQWRLEAIEDRLWALGGSEAELAEFETIIAGFEEQLQVYKGKGNP EVEALEEEAMAIQTELHAYRHN | CD123 | 3.4 |
| 670 | MGSWWEFEDRLWAIEQRLDALGGSEAELAVFENSIAKFEDMLQVYKGKGNP EVEALHEEADAIIWELYAYRHN | CD123 | 4.4 |
| 671 | MGSWWEFEDRLWAIDRRLMALGGSEAELAVFEQMIAHFEQILQVYKGKGNP EVEALHFEAHAIGMELAAYRHN | CD123 | 4.6 |
| 672 | MGSWWEFLDRLEAIEYRLQALGGSEAELAVFEWEIAMFEDHLQGYKGKGNP EVEALHSEAHAIISELSAYRHN | CD123 | 3.1 |
| 673 | MGSWAEFEDRLAAIERRLEALGGSEAELADFESSIAWFEPDLQYYKGKGNP EVEALMYEAEAIFSELYAYRHN | CD123 | 4.2 |
| 674 | MGSWWEFYDRLTAIEARLWALGGSEAELADFEEGIADFEYDLQDYKGKGNP EVEALFWEAWAIQSELTAYRHN | CD123 | 3.2 |
| 675 | MGSWYEFEDRLAAIEARLWALGGSEAELADFEEEIAYFEHGLQWYKGKGNP EVEALESEAMAIIDELHAYRHN | CD123 | 3.8 |
| 676 | MGSWWEFSWRLEAIETRLDALGGSEAELAFFEMDIAWFEQDLQLYKGKGNP EVEALEEEAYAIYEELEAYRHN | CD123 | 3.3 |
| 677 | MGSWEEFFFRLEAIDDRLYALGGSEAELALFEEVIAYFEQDLQWYKGKGNP EVEALYVEAYAIQEELYAYRHN | CD123 | 3.2 |

TABLE 3-continued

Exemplary D-domains

| SEQ ID NO: | D-Domain Sequence | Target | ELISA_avg |
|---|---|---|---|
| 678 | MGSWFEFEERLNAISWRLHALGGSEAELAYFEEDIAWFEDDLQFYKGKGNP EVEALENEAYAIWEELDAYRHN | CD123 | 13 |
| 679 | MGSWFEFEERLEAIIYRLWALGGSEAELAMFEESIAWFESDLQQYKGKGNP EVEALEYEAMAISKELKAYRHN | CD123 | 3.7 |
| 680 | MGSWAEFDDRLEAIEYRLHALGGSEAELAWFEEGIAGFEHALQSYKGKGNP EVEALETEAGAINEELWAYRHN | CD123 | 5.8 |
| 681 | MGSWDEFEERLQAIEYRLWALGGSEAELAWFEEVIAQFEYDLQKYKGKGNP EVEALSTEAQAIQDELWAYRHN | CD123 | 3.8 |
| 682 | MGSWWEFTDRLDAIFDRLWALGGSEAELAAFEESIAIFEQDLQYYKGKGNP EVEALEYEANAIQYELEAYRHN | CD123 | 7.5 |
| 683 | MGSWWEFTDRLEAIEDRLWALGGSEAELAHFEDSIAQFEQELQWYKGKGNP EVEALADEADAIESELHAYRHN | CD123 | 16.6 |
| 684 | MGSWVEFFWRLDAIEDRLWALGGSEAELANFEFEIADFEAWLQKYKGKGNP EVEALHSEADAIQLELRAYRHN | CD123 | 4 |
| 685 | MGSWVEFYNRLDAIENRLWALGGSEAELAFFEELIAQFEFALQDYKGKGNP EVEALEDEADAIWEELMAYRHN | CD123 | 6.9 |
| 686 | MGSWEEFYYRLHAIDNRLWALGGSEAELAYFEWHIADFELELQDYKGKGNP EVEALSEEATAIFEELWAYRHN | CD123 | 3 |
| 687 | MGSWREFHDRLFAIDGRLWALGGSEAELANFEWDIADFEFELQDYKGKGNP EVEALSWEADAIMQELGAYRHN | CD123 | 5.6 |
| 688 | MGSWEEFDERLWAISDRLWALGGSEAELAYFEGEIAYFEQNLQTYKGKGNP EVEALQTEALAIDTELWAYRHN | CD123 | 6.5 |
| 689 | MGSWEEFEQRLWAIDDRLWALGGSEAELAFFEYEIAEFEMDLQWYKGKGNP EVEALFYEAHAINEELWAYRHN | CD123 | 5.7 |
| 690 | MGSWDEFHQRLAAIGDRLWALGGSEAELAYFEWEIATFEWDLQVYKGKGNP EVEALYFEATAIDEELMAYRHN | CD123 | 3.7 |
| 691 | MGSWVEFEYRLDAISDRLWALGGSEAELAFFENEIASFESDLQFYKGKGNP EVEALMFEAEAIDDELHAYRHN | CD123 | 6.5 |
| 692 | MGSWDEFDTRLDAIFSRLYALGGSEAELAMFEGEIAEFEGSLQHYKGKGNP EVEALDFEAHAIDEELWAYRHN | CD123 | 4 |
| 693 | MGSWHEFDDRLDAIMSRLDALGGSEAELATFEAEIATFEFVLQLYKGKGNP EVEALLAEAYAIDWELEAYRHN | CD123 | 7.7 |
| 694 | MGSWYEFFDRLDAIYDRLYALGGSEAELASFEAQIAEFEVELQSYKGKGNP EVEALEWEAWAIDEELYAYRHN | CD123 | 4.7 |
| 695 | MGSWFEFLYRLDAIEDRLWALGGSEAELAEFEQEIAKFESELQSYKGKGNP EVEALEWEAHAIDMELEAYRHN | CD123 | 6.6 |
| 696 | MGSWLEFEDRLVAIDHRLFALGGSEAELAEFEEEIALFESYLQDYKGKGNP EVEALNWEADAIHAELYAYRHN | CD123 | 3.9 |
| 697 | MGSWYEFESRLDAIVDRLWALGGSEAELAEFEYEIAKFEWELQDYKGKGNP EVEALNWEAGAIEFELYAYRHN | CD123 | 5.1 |
| 698 | MGSWYEFEDRLDAILYRLLALGGSEAELAWFERDIAFFESELQWYKGKGNP EVEALEWEAMAIDDELFAYRHN | CD123 | 4.3 |
| 699 | MGSWGEFMDRLEAIDYRLWALGGSEAELAWFESDIAEFEQELQMYKGKGNP EVEALWDEAMAIRDELFAYRHN | CD123 | 4.6 |
| 700 | MGSWEEFDDRLDAIEHRLWALGGSEAELADFEGSIAAFESWLQVYKGKGNP EVEALEAEAEAIADELWAYRHN | CD123 | 4 |
| 701 | MGSWYEFADRLDAIMDRLVALGGSEAELAYFEWEIAAFEEFLQMYKGKGNP EVEALDEEAEAIKDELMAYRHN | CD123 | 3.3 |
| 702 | MGSWNEFWERLDAIEWRLFALGGSEAELAFFELDIAWFEEELQWYKGKGNP EVEALIFEAHAITLELDAYRHN | CD123 | 3 |

TABLE 3-continued

| SEQ ID NO: | D-Domain Sequence | Target | ELISA_avg |
|---|---|---|---|
| | Exemplary D-domains | | |
| 703 | MGSWYEFDARLDAIEERLYALGGSEAELAAFEFEIAGFEEALQWYKGKGNP EVEALLKEAEAITDELYAYRHN | CD123 | 8.9 |
| 704 | MGSWDEFSERLDAIWGRLEALGGSEAELATFEFHIAEFEHELQYYKGKGNP EVEALQGEAAAIINELYAYRHN | CD123 | 3.2 |
| 705 | MGSWDEFWDRLDAIEDRLFALGGSEAELADFERVIAWFENDLQEYKGKGNP EVEALDNEADAIRIELHAYRHN | CD123 | 3.9 |
| 706 | MGSWDEFDDRLEAIVDRLFALGGSEAELAMFEFEIAQFEHQLQYYKGKGNP EVEALRDEADAIWIELDAYRHN | CD123 | 5.6 |
| 707 | MGSWEEFTIRLGAIYWRLFALGGSEAELANFEWFIAEFEYELQPYKGKGNP EVEALVIEANAIDGELQAYRHN | CD123 | 3.3 |
| 708 | MGSWFEFEWRLDAIENRLNALGGSEAELAWFEYHIAAFEDSLQHYKGKGNP EVEALEWEAHAIQSELQAYRHN | CD123 | 3.3 |
| 709 | MGSWYEFDDRLEAIWDRLGALGGSEAELAAFEKEIAAFESELQAYKGKGNP EVEWLRETAADIRAELQAYRHN | CD123 | 3.3 |
| 710 | MGSWGEFWARLEAIWIRLDALGGSEAELAAFEKEIAAFESELQAYKGKGNP EVEWLREEAADIRRSLQAYRHN | CD123 | 15 |
| 711 | MGSWIEFEVRLDAIWDRLFALGGSEAELAAFEKEIAAFESELQAYKGKGNP EVEYLRDEAADIRQSLQAYRHN | CD123 | 4.2 |
| 712 | MGSWTEFDRRLDAIWDRLFALGGSEAELAAFEKEIAAFESELQAYKGKGNP EVEWLREEAADIRDYLQAYRHN | CD123 | 9.2 |
| 713 | MGSWTEFDMRLDAIWDRLFALGGSEAELAAFEKEIAAFESELQAYKGKGNP EVEELREEAATIRGVLQAYRHN | CD123 | 3.1 |
| 714 | MGSWEEFHDRLMAIETRLWALGGSEAELAAFEKEIAAFESELQAYKGKGNP EVEWLRYEAADIRDYLQAYRHN | CD123 | 4.3 |
| 715 | MGSWVEFRDRLDAIETRLWALGGSEAELAAFEKEIAAFESELQAYKGKGNP EVEWLRYEAAEIRMVLQAYRHN | CD123 | 4.2 |
| 716 | MGSWMEFIDRLDAIEHRLWALGGSEAELAAFEKEIAAFESELQAYKGKGNP EVEFLREEAAEIRMYLQAYRHN | CD123 | 4.3 |
| 717 | MGSWTEFVWRLDAIEWRLEALGGSEAELAAFEKEIAAFESELQAYKGKGNP EVEFLREEAAEIRDWLQAYRHN | CD123 | 4.2 |
| 718 | MGSWVEFYDRLYAIEVRLLALGGSEAELAAFEKEIAAFESELQAYKGKGNP EVEFLRQEAAEIRDWLQAYRHN | CD123 | 5.8 |
| 719 | MGSWYEFYDRLDAIEWRLWALGGSEAELAAFEKEIAAFESELQAYKGKGNP EVEWLRDEAAQIRDFLQAYRHN | CD123 | 6.2 |
| 720 | MGSWVEFYDRLDAIEHRLDALGGSEAELAAFEKEIAAFESELQAYKGKGNP EVEWLRDEAAFIRDMLQAYRHN | CD123 | 3.4 |
| 721 | MGSWFEFVDRLTAIQVRLWALGGSEAELAAFEKEIAAFESELQAYKGKGNP EVEYLREEAALIRYSLQAYRHN | CD123 | 5.1 |
| 722 | MGSWFEFLDRLDAIEERLWALGGSEAELAAFEKEIAAFESELQAYKGKGNP EVEWLREEAAVIRDSLQAYRHN | CD123 | 12.2 |
| 723 | MGSWYEFMVRLDAIEERLFALGGSEAELAAFEKEIAAFESELQAYKGKGNP EVEFLREEAASIRYHLQAYRHN | CD123 | 4.1 |
| 724 | MGSWYEFEDRLDAIQWRLWALGGSEAELAAFEKEIAAFESELQAYKGKGNP EVEFLRESAANIRQHLQAYRHN | CD123 | 6.3 |
| 725 | MGSWSEFEYRLFAIENRLDALGGSEAELAAFEKEIAAFESELQAYKGKGNP EVEFLREEAAMIRQLLQAYRHN | CD123 | 3.2 |
| 726 | MGSWVEFEYRLDAITERLLALGGSEAELAAFEKEIAAFESELQAYKGKGNP EVEILREEAAFIRQWLQAYRHN | CD123 | 3.9 |
| 727 | MGSWWEFLDRLDAIEMRLFALGGSEAELAAFEKEIAAFESELQAYKGKGNP EVEYLREEAALIRNMLQAYRHN | CD123 | 9 |

TABLE 3-continued

| Exemplary D-domains | | | |
|---|---|---|---|
| SEQ ID NO: | D-Domain Sequence | Target | ELISA_avg |
| 728 | MGSWWEFEDRLDAIEYRLFALGGSEAELAAFEKEIAAFESELQAYKGKGNP EVEFLREEAAFIRIFLQAYRHN | CD123 | 4.9 |
| 729 | MGSWWEFESRLDAIFMRLTALGGSEAELAAFEKEIAAFESELQAYKGKGNP EVEDLREDAAFIREFLQAYRHN | CD123 | 3.7 |
| 730 | MGSWVEFWHRLDAIKARLNALGGSEAELAAFEKEIAAFESELQAYKGKGNP EVEDLRWYAADFRLILQAYRHN | CD123 | 3.5 |
| 731 | MGSWYEFYNRLSAIYARLQALGGSEAELAAFEKEIAAFESELQAYKGKGNP EVEDLRWYAADIRYMLQAYRHN | CD123 | 10.6 |
| 732 | MGSWYEFYDRLSAIYARLQALGGSEAELAAFEKEIAAFESELQAYKGKGNP EVEDLRWYAADIRYMLQAYRHN | CD123 | 5.3 |
| 733 | MGSWNEFYDRLSAIYFRLQALGGSEAELAAFEKEIAAFESELQAYKGKGNP EVEHLRWYAADIRMILQAYRHN | CD123 | 10.6 |
| 734 | MGSWNEFYDRLSAIYFRLQALGGFEAELAAFEKEIAAFESELQAYKGKGNP EVEHLRWYAADIRMILQAYRHN | CD123 | 9 |
| 735 | MGSWEEFYDRLGAIFARLHALGGSEAELAAFEKEIAAFESELQAYKGKGNP EVEDLRWYAADIRMILQAYRHN | CD123 | 3.9 |
| 736 | MGSWVEFYDRLHAIYFRLLALGGSEAELAAFEKEIAAFESELQAYKGKGNP EVEDLRWYAADIRLVLQAYRHN | CD123 | 4.8 |
| 737 | MGSWKEFDNRLYAIEDRLRALGGSEAELAAFEKEIAAFESELQAYKGKGNP EVEHLRWYAADIRMILQAYRHN | CD123 | 3.9 |
| 738 | MGSWVEFWDRLWAIEDRLWALGGSEAELAAFEKEIAAFESELQAYKGKGNP EVEHLRHYAADIRVWLQAYRHN | CD123 | 4.5 |
| 739 | MGSWYEFADRLWAIEDRLWALGGSEAELAAFEKEIAAFESELQAYKGKGNP EVEFLRYYAADIRWVLQAYRHN | CD123 | 4 |
| 740 | MGSWYEFEERLYAIEDRLYALGGSEAELAAFEKEIAAFESELQAYKGKGNP EVEFLRQEAADIRLMLQAYRHN | CD123 | 11.5 |
| 741 | MGSWTEFEWRLYAIEDRLMALGGSEAELAAFEKEIAAFESELQAYKGKGNP EVEFLRDEAADIRQYLQAYRHN | CD123 | 4.2 |
| 742 | MGSWIEFESRLWAIEDRLLALGGSEAELAAFEKEIAAFESELQAYKGKGNP EVEFLRLEAADIREDLQAYRHN | CD123 | 8.7 |
| 743 | MGSWFEFEDRLDAIWDRLWALGGSEAELAAFEKEIAAFESELQAYKGKGNP EVEFLRMDAAMIRYILQAYRHN | CD123 | 5.1 |
| 744 | MGSWEEFEDRLWAIEDRLWALGGSEAELAAFEKEIAAFESELQAYKGKGNP EVEILRYDAAYIREILQAYRHN | CD123 | 4.1 |
| 745 | MGSWIEFEDRLYAIEDRLWALGGSEAELAAFEKEIAAFESELQAYKGKGNP EVEFLRYEAAEIRYWLQAYRHN | CD123 | 4 |
| 746 | MGSWYEFWDRLEAIEDRLWALGGSEAELAAFEKEIAAFESELQAYKGKGNP EVEFLRYSAAEIRYQLQAYRHN | CD123 | 4.2 |
| 747 | MGSWVEFESRLAAIEHRLWALGGSEAELAAFEKEIAAFESELQAYKGKGNP EVEELREYAAEIRDWLQAYRHN | CD123 | 3.7 |
| 748 | MGSWWEFEHRLFAIEDRLWALGGSEAELAAFEKEIAAFESELQAYKGKGNP EVEFLRDYAAEIRDYLQAYRHN | CD123 | 7.6 |
| 749 | MGSWYEFDSRLMAIEDRLWALGGSEAELAAFEKEIAAFESELQAYKGKGNP EVEYLRQEAAEIRMILQAYRHN | CD123 | 3.2 |
| 750 | MGSWYEFEWRLMAIEDRLWALGGSEAELAAFEKEIAAFESELQAYKGKGNP EVEYLRHEAAEIRDVLQAYRHN | CD123 | 3.4 |
| 751 | MGSWYEFYNRLDAIEDRLWALGGSEAELAAFEKEIAAFESELQAYKGKGNP EVEYLRQEAADIRGQLQAYRHN | CD123 | 11.3 |
| 752 | MGSWWEFHDRLEAIEDRLWALGGSEAELAAFEKEIAAFESELQAYKGKGNP EVEYLRIEAADIRRQLQAYRHN | CD123 | 6.4 |

TABLE 3-continued

Exemplary D-domains

| SEQ ID NO: | D-Domain Sequence | Target | ELISA_avg |
|---|---|---|---|
| 753 | MGSWYEFWDRLEAIEERLWALGGSEAELAAFEKEIAAFESELQAYKGKGNP EVEYLRLEAADIRRILQAYRHN | CD123 | 4.6 |
| 754 | MGSWYEFEERLWAIEERLYALGGSEAELAAFEKEIAAFESELQAYKGKGNP EVEYLRYEAAWIRDFLQAYRHN | CD123 | 5.4 |
| 755 | MGSWYEFENRLEAIEERLWALGGSEAELAAFEKEIAAFESELQAYKGKGNP EVEMLREEAAFIRDWLQAYRHN | CD123 | 6.1 |
| 756 | MGSWYEFEYRLEAIEDRLWALGGSEAELAAFEKEIAAFESELQAYKGKGNP EVEYLREEAAWIRVWLQAYRHN | CD123 | 6.2 |
| 757 | MGSWYEFENRLGAIGDRLWALGGSEAELAAFEKEIAAFESELQAYKGKGNP EVEWLRDEAAYIRAVLQAYRHN | CD123 | 4.8 |
| 758 | MGSWYEFEHRLDAIYDRLWALGGSEAELAAFEKEIAAFESELQAYKGKGNP EVEWLREEAAWIRLWLQAYRHN | CD123 | 6.3 |
| 759 | MGSWYEFEWRLDAIYDRLGALGGSEAELAAFEKEIAAFESELQAYKGKGNP EVEWLREDAAEIRALLQAYRHN | CD123 | 6 |
| 760 | MGSWVEFENRLEAIENRLWALGGSEAELAAFEKEIAAFESELQAYKGKGNP EVEWLREDAAQIRMMLQAYRHN | CD123 | 6.2 |
| 761 | MGSWYEFEERLEAIEDRLWALGGSEAELAAFEKEIAAFESELQAYKGKGNP EVEWLREQAAFIRTMLQAYRHN | CD123 | 6 |
| 762 | MGSWFEFEWRLEAIFDRLYALGGSEAELAAFEKEIAAFESELQAYKGKGNP EVEVLRAEAAEIRLRLQAYRHN | CD123 | 6.9 |
| 763 | MGSWWEFEDRLMAIYDRLYALGGSEAELAAFEKEIAAFESELQAYKGKGNP EVEYLRAEAALIRETLQAYRHN | CD123 | 15.3 |
| 764 | MGSWFEFEDRLYAIEDRLYALGGSEAELAAFEKEIAAFESELQAYKGKGNP EVEYLRWGAATIRDELQAYRHN | CD123 | 4.7 |
| 765 | MGSWIEFWDRLEAIEDRLWALGGSEAELAAFEKEIAAFESELQAYKGKGNP EVEELRDEAAWIRDSLQAYRHN | CD123 | 4.5 |
| 766 | MGSWFEFWDRLDAIEDRLYALGGSEAELAAFEKEIAAFESELQAYKGKGNP EVEELRDEAAWIRGTLQAYRHN | CD123 | 4.9 |
| 767 | MGSWEEFTDRLWAIEDRLYALGGSEAELAAFEKEIAAFESELQAYKGKGNP EVEWLRDEAAFIRKSLQAYRHN | CD123 | 8.9 |
| 768 | MGSWVEFVDRLEAIEDRLFALGGSEAELAAFEKEIAAFESELQAYKGKGNP EVEFLRDQAAYIRFMLQAYRHN | CD123 | 4.9 |
| 769 | MGSWFEFVDRLEAIEMRLFALGGSEAELAAFEKEIAAFESELQAYKGKGNP EVELLRWRAAMIRYDLQAYRHN | CD123 | 7.1 |
| 770 | MGSWWEFEMRLEAIEDRLFALGGSEAELAAFEKEIAAFESELQAYKGKGNP EVESLRWEAAFIRDILQAYRHN | CD123 | 4 |
| 771 | MGSWFEFEIRLEAIEDRLFALGGSEAELAAFEKEIAAFESELQAYKGKGNP EVEFLRDEAAEIRQVLQAYRHN | CD123 | 3 |
| 772 | MGSWYEFYQRLEAIEDRLFALGGSEAELAAFEKEIAAFESELQAYKGKGNP EVEWLRDEAAEIRVVLQAYRHN | CD123 | 3 |
| 773 | MGSWIEFEDRLEAIEDRLFALGGSEAELAAFEKEIAAFESELQAYKGKGNP EVEWLRQEAAEIRLMLQAYRHN | CD123 | 21.8 |
| 841 | MGSWVEFYERLDAIDRRLWALGGSEAELAAFEKEIAAFESELQAYKGKGNP EVEELRVHAASIRAWLQAYRHN | P26 | |
| 842 | MGSWFEFYDRLNAIDARLWALGGSEAELAAFEKEIAAFESELQAYKGKGNP EVESLRAHAAAIREWLQAYRHN | P26 | |
| 843 | MGSWSEFYDRLNAIDARLWALGGSEAELAAFEKEIAAFESELQAYKGKGNP EVESLRVHAAAIREWLQAYRHN | P26 | |
| 844 | MGSWSEFYDRLNAIDARLWALGGSEAELAAFEKEIAAFESELQAYKGKGNP EVESLRAHAAAIREWLQAYRHN | P26 | |

TABLE 3-continued

Exemplary D-domains

| SEQ ID NO: | D-Domain Sequence | Target | ELISA_avg |
|---|---|---|---|
| 845 | MGSWSEFYDRLNAIDARLWALGGSEAELAAFEKEIAAFESELQAYKGKGNP EVESLKAHAAAIREWLQAYRHN | P26 | |
| 846 | MGSWSEFYDRLNAIDARLWALGGSEAELAAFEKEIAAFESELQAYKGKGNP EVESLQAHAAAIREWLQAYRHN | P26 | |
| 847 | MGSWSEFYDRLNAIDARLWALGGSEAELAAFEKEIAAFESELQAYKGKGNP EVESLRAHAAGIREWLQAYRHN | P26 | |
| 848 | MGSWFEFYDRLNAIDARLWALGGSEAELAAFEKEIAAFESELQAYKGKGNP EVESLREHAAHIREWLQAYRHN | P26 | |
| 849 | MGSWFEFYDRLNAIDARLWALGGSEAELAAFEKEIAAFESELQAYKGKGNP EVESLREHAAAIREWLQAYRHN | P26 | |
| 850 | MGSWSEFYDRLNAIDARLWALGGSEAELAAFEKEIAAFESELQAYKGKGNP EVESLREHAAAIREWLQAYRHN | P26 | |
| 851 | MGSWHEFYDRLDAIYFRLWALGGSEAELAAFEKEIAAFESELQAYKGKGNP EVELLRLLAAEIRKELQAYRHN | P26 | 9.6 |
| 852 | MGSWHEFITRLEAIDQRLWALGGSEAELAAFEKEIAAFESELQAYKGKGNP EVEYLRFWAAEIRFILQAYRHN | P26 | 16.91 |
| 853 | MGSWMEFFDRLVAIDERLWALGGSEAELAAFEKEIAAFESELQAYKGKGNP EVEYLRMWAAEIRFLLQAYRHN | P26 | 18.62 |
| 854 | MGSWVEFSGRLIAIDNRLWALGGSEAELAAFEKEIAAFESELQAYKGKGNP EVEYLRMWAAEIRYILQAYRHN | P26 | 5.28 |
| 855 | MGSWVEFHHRLFAIDERLWALGGSEAELAAFEKEIAAFESELQAYKGKGNP EVEYLRMVAAEIRYILQAYRHN | P26 | 21.39 |
| 856 | MGSWHEFMERLIAIDGRLWALGGSEAELAAFEKEIAAFESELQAYKGKGNP EVEYLRFVAAFIRDVLQAYRHN | P26 | 17.85 |
| 857 | MGSWKEFIQRLDAIHYRLWALGGSEAELAAFEKEIAAFESELQAYKGKGNP EVEYLRFVAAFIRFELQAYRHN | P26 | 18.41 |
| 858 | MGSWSEFIFRLDAIHSRLQALGGSEAELAAFEKEIAAFESELQAYKGKGNP EVEYLRFIAAEIRLKLQAYRHN | P26 | 28.3 |
| 859 | MGSWFEFYDRLNAIDARLWALGGSEAELAAFEKEIAAFESELQAYKGKGNP EVENLRVHAAAIREWLQAYRHN | P26 | 5.92 |
| 860 | MGSWLEFYDRLNAIDARLWALGGSEAELAAFEKEIAAFESELQAYKGKGNP EVENLRVHAAAIREWLQAYRHN | P26 | |
| 861 | MGSWFEFYHRLNAIDARLWALGGSEAELAAFEKEIAAFESELQAYKGKGNP EVENLRVHAAAIREWLQAYRHN | P26 | |
| 862 | MGSWFEFYDRLNAIDSRLWALGGSEAELAAFEKEIAAFESELQAYKGKGNP EVENLRVHAAAIREWLQAYRHN | P26 | |
| 863 | MGSWFEFYDRLNAIDARLWALGGSEAELAAFEKEIAAFESELQAYKGKGNP EVESLRVHAAAIREWLQAYRHN | P26 | |
| 864 | MGSWFEFYDRLNAIDARLWALGGSEAELAAFEKEIAAFESELQAYKGKGNP EVENLRDHAAAIREWLQAYRHN | P26 | |
| 865 | MGSWFEFYDRLNAIDARLWALGGSEAELAAFEKEIAAFESELQAYKGKGNP EVENLREHAAAIREWLQAYRHN | P26 | |
| 866 | MGSWFEFYDRLNAIDARLWALGGSEAELAAFEKEIAAFESELQAYKGKGNP EVENLRVHAAHIREWLQAYRHN | P26 | |
| 867 | MGSWLEFYHRLNAIDSRLWALGGSEAELAAFEKEIAAFESELQAYKGKGNP EVENLRVHAAAIREWLQAYRHN | P26 | |
| 868 | MGSWLEFYHRLNAIDSRLWALGGSEAELAAFEKEIAAFESELQAYKGKGNP EVESLRDHAAHIREWLQAYRHN | P26 | 19.23 |
| 869 | MGSWFEFYHRLNAIDSRLWALGGSEAELAAFEKEIAAFESELQAYKGKGNP EVESLRDHAAHIREWLQAYRHN | P26 | |

TABLE 3-continued

| Exemplary D-domains | | | |
|---|---|---|---|
| SEQ ID NO: | D-Domain Sequence | Target | ELISA_avg |
| 870 | MGSWLEFYDRLNAIDSRLWALGGSEAELAAFEKEIAAFESELQAYKGKGNP EVESLRDHAAHIREWLQAYRHN | P26 | |
| 871 | MGSWLEFYHRLNAIDARLWALGGSEAELAAFEKEIAAFESELQAYKGKGNP EVESLRDHAAHIREWLQAYRHN | P26 | |
| 872 | MGSWLEFYHRLNAIDSRLWALGGSEAELAAFEKEIAAFESELQAYKGKGNP EVENLRDHAAHIREWLQAYRHN | P26 | |
| 873 | MGSWLEFYHRLNAIDSRLWALGGSEAELAAFEKEIAAFESELQAYKGKGNP EVESLRVHAAHIREWLQAYRHN | P26 | |
| 874 | MGSWLEFYHRLNAIDSRLWALGGSEAELAAFEKEIAAFESELQAYKGKGNP EVESLRDHAAAIREWLQAYRHN | P26 | |
| 875 | MGSWFEFYDRLNAIDARLWALGGSEAELAAFEKEIAAFESELQAYKGKGNP EVESLRDHAAHIREWLQAYRHN | P26 | |
| 876 | MGSWFEFYERLNAIDSRLWALGGSEAELAAFEKEIAAFESELQAYKGKGNP EVEKLRAHAASIRTWLQAYRHN | P26 | 27.1 |
| 877 | MGSWIEFYWRLEAIDQRLWALGGSEAELAAFEKEIAAFESELQAYKGKGNP EVEDLRVHAAAIRWWLQAYRHN | P26 | 9.4 |
| 878 | MGSWSEFVKRLDAIDQRLWALGGSEAELAAFEKEIAAFESELQAYKGKGNP EVESLRVHAAAIRAWLQAYRHN | P26 | 27 |
| 879 | MGSWEEFYYRLEAIDARLFALGGSEAELAAFEKEIAAFESELQAYKGKGNP EVEELRVHAAHIRDWLQAYRHN | P26 | 30.3 |
| 880 | MGSWVEFHYRLQAIDARLWALGGSEAELAAFEKEIAAFESELQAYKGKGNP EVEELRVHAAHIRKWLQAYRHN | P26 | 14.8 |
| 881 | MGSWVEFVGRLNAIDARLWALGGSEAELAAFEKEIAAFESELQAYKGKGNP EVEELRHHAAEIRNWLQAYRHN | P26 | 26 |
| 882 | MGSWNEFMDRLNAIDNRLWALGGSEAELAAFEKEIAAFESELQAYKGKGNP EVENLRKQAASIRLWLQAYRHN | P26 | 10 |
| 883 | MGSWNEFFQRLNAIDERLWALGGSEAELAAFEKEIAAFESELQAYKGKGNP EVEDLRQHAANIRWWLQAYRHN | P26 | 28.7 |
| 884 | MGSWYEFVVRLFAIDERLWALGGSEAELAAFEKEIAAFESELQAYKGKGNP EVESLREHAAHIRSWLQAYRHN | P26 | 18.25 |
| 885 | MGSWYEFYLRLDAIDHRLWALGGSEAELAAFEKEIAAFESELQAYKGKGNP EVEMLREHAAHIRKWLQAYRHN | P26 | 16 |
| 886 | MGSWYEFRARLLAIDERLWALGGSEAELAAFEKEIAAFESELQAYKGKGNP EVEHLREHAAHIRNFLQAYRHN | P26 | 20.9 |
| 887 | MGSWTEFWHRLEAIDSRLWALGGSEAELAAFEKEIAAFESELQAYKGKGNP EVESLREHAAHIRVWLQAYRHN | P26 | 13.19 |
| 888 | MGSWTEFQNRLNAIDHRLWALGGSEAELAAFEKEIAAFESELQAYKGKGNP EVESLREHAAKIRVWLQAYRHN | P26 | 30.5 |
| 889 | MGSWSEFFKRLEAIDRRLWALGGSEAELAAFEKEIAAFESELQAYKGKGNP EVEELREHAAHIRVWLQAYRHN | P26 | 30.2 |
| 890 | MGSWYEFQQRLEAIDTRLWALGGSEAELAAFEKEIAAFESELQAYKGKGNP EVEELREHAAHIRHWLQAYRHN | P26 | 27.3 |
| 891 | MGSWTEFEKRLHAIDYRLWALGGSEAELAAFEKEIAAFESELQAYKGKGNP EVEDLREHAAAIRHWLQAYRHN | P26 | 17.1 |
| 892 | MGSWTEFHQRLDAIDERLWALGGSEAELAAFEKEIAAFESELQAYKGKGNP EVEFLREHAAKIRMWLQAYRHN | P26 | 24.4 |
| 893 | MGSWLEFSQRLTAIDSRLWALGGSEAELAAFEKEIAAFESELQAYKGKGNP EVENLREHAAKIRNWLQAYRHN | P26 | 30.4 |
| 894 | MGSWTEFVNRLYAIDSRLWALGGSEAELAAFEKEIAAFESELQAYKGKGNP EVEGLRTHAAKIRHWLQAYRHN | P26 | 16.7 |

TABLE 3-continued

Exemplary D-domains

| SEQ ID NO: | D-Domain Sequence | Target | ELISA_avg |
|---|---|---|---|
| 895 | MGSWMEFVDRLSAIDRRLWALGGSEAELAAFEKEIAAFESELQAYKGKGNP EVEVLREHAANIRQWLQAYRHN | P26 | 32.1 |
| 896 | MGSWVEFVSRLYAIDFRLWALGGSEAELAAFEKEIAAFESELQAYKGKGNP EVEALREHAAQIRDWLQAYRHN | P26 | 29 |
| 897 | MGSWSEFHTRLDAIDTRLWALGGSEAELAAFEKEIAAFESELQAYKGKGNP EVEDLRRHAAAIRFWLQAYRHN | P26 | 23.5 |
| 898 | MGSWLEFHSRLDAIDTRLWALGGSEAELAAFEKEIAAFESELQAYKGKGNP EVEKLREHAAAIRHYLQAYRHN | P26 | 30.8 |
| 899 | MGSWTEFYQRLDAIDTRLWALGGSEAELAAFEKEIAAFESELQAYKGKGNP EVEGLRQQAAQIRAWLQAYRHN | P26 | 29.7 |
| 900 | MGSWAEFSDRLNAIDQRLWALGGSEAELAAFEKEIAAFESELQAYKGKGNP EVEILREHAAEIRKFLQAYRHN | P26 | 25.3 |
| 901 | MGSWMEFNHRLQAIDGRLWALGGSEAELAAFEKEIAAFESELQAYKGKGNP EVEMLREHAAAIRAFLQAYRHN | P26 | 33.4 |
| 902 | MGSWYEFYKRLEAIDNRLYALGGSEAELAAFEKEIAAFESELQAYKGKGNP EVEYLREHAAAIRHWLQAYRHN | P26 | 30.8 |
| 903 | MGSWYEFYYRLEAIDNRLIALGGSEAELAAFEKEIAAFESELQAYKGKGNP EVEVLREHAAKIREWLQAYRHN | P26 | 29.6 |
| 904 | MGSWYEFVSRLEAIDDRLYALGGSEAELAAFEKEIAAFESELQAYKGKGNP EVEMLRQHAAAIRHWLQAYRHN | P26 | 33.1 |
| 905 | MGSWYEFSHRLEAIEDRLFALGGSEAELAAFEKEIAAFESELQAYKGKGNP EVEPLREHAAYIRHWLQAYRHN | P26 | 26 |
| 906 | MGSWFEFFERLAAIEDRLWALGGSEAELAAFEKEIAAFESELQAYKGKGNP EVESLRVHAAAIRAFLQAYRHN | P26 | 20.3 |
| 907 | MGSWIEFKYRLDAIEWRLEALGGSEAELAAFEKEIAAFESELQAYKGKGNP EVESLRIHAAAIRTWLQAYRHN | P26 | 18.3 |
| 908 | MGSWYEFMYRLDAIEYRLFALGGSEAELAAFEKEIAAFESELQAYKGKGNP EVESLRIHAAMIREWLQAYRHN | P26 | 19.4 |
| 909 | MGSWVEFVTRLEAIEDRLFALGGSEAELAAFEKEIAAFESELQAYKGKGNP EVEHLRAHAAHIRHWLQAYRHN | P26 | 11.7 |
| 910 | MGSWYEFVIRLDAIEDRLFALGGSEAELAAFEKEIAAFESELQAYKGKGNP EVEHLRVHAAHIRVWLQAYRHN | P26 | 30.1 |
| 911 | MGSWVEFVERLDAIEFRLFALGGSEAELAAFEKEIAAFESELQAYKGKGNP EVEKLRNHAAHIRSWLQAYRHN | P26 | 23.8 |
| 912 | MGSWSEFVHRLDAIEVRLFALGGSEAELAAFEKEIAAFESELQAYKGKGNP EVEELRYHAAKIRSWLQAYRHN | P26 | 16.9 |
| 913 | MGSWSEFYYRLAAIESRLFALGGSEAELAAFEKEIAAFESELQAYKGKGNP EVERLREHAAHIRRWLQAYRHN | P26 | 30.8 |
| 914 | MGSWYEFYLRLSAIEDRLFALGGSEAELAAFEKEIAAFESELQAYKGKGNP EVESLRVQAAHIRTWLQAYRHN | P26 | 27.4 |
| 915 | MGSWYEFYDRLDAIEDRLFALGGSEAELAAFEKEIAAFESELQAYKGKGNP EVESLRDQAAYIRTWLQAYRHN | P26 | 31.9 |
| 916 | MGSWHEFWVRLEAIESRLFALGGSEAELAAFEKEIAAFESELQAYKGKGNP EVESLRVQAAHIRSWLQAYRHN | P26 | 26.9 |
| 917 | MGSWVEFYHRLEAIEQRLMALGGSEAELAAFEKEIAAFESELQAYKGKGNP EVESLREQAAAIRSWLQAYRHN | P26 | 28.5 |
| 918 | MGSWVEFYERLNAIEYRLEALGGSEAELAAFEKEIAAFESELQAYKGKGNP EVESLREHAAYIRQWLQAYRHN | P26 | 28.7 |
| 919 | MGSWVEFYHRLDAIFDRLDALGGSEAELAAFEKEIAAFESELQAYKGKGNP EVEELRANAAGIRSWLQAYRHN | P26 | 20 |

TABLE 3-continued

| Exemplary D-domains | | | |
|---|---|---|---|
| SEQ ID NO: | D-Domain Sequence | Target | ELISA_avg |
| 920 | MGSWSEFTDRLFAIEDRLLALGGSEAELAAFEKEIAAFESELQAYKGKGNP EVEDLRMHAASIRLWLQAYRHN | P26 | 25.4 |
| 921 | MGSWHEFYDRLYAIWDRLDALGGSEAELAAFEKEIAAFESELQAYKGKGNP EVEGLRNAAAVIRIFLQAYRHN | P26 | 22.91 |
| 922 | MGSWFEFSNRLYAIWHRLTALGGSEAELAAFEKEIAAFESELQAYKGKGNP EVESLRTQAAFIRILLQAYRHN | P26 | 15.25 |
| 923 | MGSWFEFSDRLYAIWERLDALGGSEAELAAFEKEIAAFESELQAYKGKGNP EVESLRFQAAFIRYQLQAYRHN | P26 | 18.99 |
| 924 | MGSWFEFEDRLFAIWTRLEALGGSEAELAAFEKEIAAFESELQAYKGKGNP EVESLRQSAASIRWLLQAYRHN | P26 | 10.89 |
| 925 | MGSWHEFSERLFAIWTRLEALGGSEAELAAFEKEIAAFESELQAYKGKGNP EVEALRQSAAFIRVMLQAYRHN | P26 | 8.21 |
| 926 | MGSWGEFTVRLYAIDRRLDALGGSEAELAAFEKEIAAFESELQAYKGKGNP EVEELRRFAAIIRAFLQAYRHN | P26 | 8.54 |
| 927 | MGSWYEFDHRLMAISFRLVALGGSEAELAAFEKEIAAFESELQAYKGKGNP EVETLRRRAANIRHLLQAYRHN | P26 | 20.1 |
| 928 | MGSWSIFKYHLADIKLLLEALGGSEAELAYFEFLIADFEFTLQDYKGKGNP EVEALRKEAAAIRDELQAYRHN | P26 | 20.21 |
| 929 | MGSWHHFKYFLADIKSILEALGGSEAELAIFEVQIAYFEDLLQSYKGKGNP EVEALRKEAAAIRDELQAYRHN | P26 | 8 |
| 930 | MGSWLYFKYNLAVIKHWLEALGGSEAELAIFEMSIADFEYELQWYKGKGNP EVEALRKEAAAIRDELQAYRHN | P26 | 13.3 |
| 931 | MGSWFYFKYELAWIKHWLEALGGSEAELASFETHIAFFEHQLQYYKGKGNP EVEALRKEAAAIRDELQAYRHN | P26 | 13.7 |
| 932 | MGSWADFKWTLAYIKHRLEALGGSEAELAFFEMEIAYFEQSLQNYKGKGNP EVEALRKEAAAIRDELQAYRHN | P26 | 31.5 |
| 933 | MGSWAYFKGQLAYIKSGLEALGGSEAELAYFELRIAYFEHWLQNYKGKGNP EVEALRKEAAAIRDELQAYRHN | P26 | 11.4 |
| 934 | MGSWENFKDTLAWIKEYLEALGGSEAELAGFEHRIAIFEHYLQYYKGKGNP EVEALRKEAAAIRDELQAYRHN | P26 | 19.2 |
| 935 | MGSWVLFKDYLADIKHYLEALGGSEAELANFEHLIANFEGDLQTYKGKGNP EVEALRKEAAAIRDELQAYRHN | P26 | 13.8 |
| 936 | MGSWSLFKHRLANIKVYLEALGGSEAELADFETFIAYFEKDLQEYKGKGNP EVEALRKEAAAIRDELQAYRHN | P26 | 19.6 |
| 937 | MGSWEHFKVELAGIKAYLEALGGSEAELALFEWAIADFESILQDYKGKGNP EVEALRKEAAAIRDELQAYRHN | P26 | 18.1 |
| 938 | MGSWIYFKDELAGIKKYLEALGGSEAELAMFEVAIADFEAILQKYKGKGNP EVEALRKEAAAIRDELQAYRHN | P26 | 15.9 |
| 939 | MGSWVLFKQELAWIKWLLEALGGSEAELAAFEEQIARFEHDLQKYKGKGNP EVEALRKEAAAIRDELQAYRHN | P26 | 29.5 |
| 940 | MGSWVLFKQELAWIKWYLEALGGSEAELAAFEWEIAAFEQRLQIYKGKGNP EVEALRKEAAAIRDELQAYRHN | P26 | 22.5 |
| 941 | MGSWFLFKSELAWIKWRLEALGGSEAELAYFEYQIAEFEFWLQSYKGKGNP EVEALRKEAAAIRDELQAYRHN | P26 | 25.8 |
| 942 | MGSWLLFKSELAWIKWYLEALGGSEAELAEFEWNIAEFEKNLQKYKGKGNP EVEALRKEAAAIRDELQAYRHN | P26 | 25.7 |
| 943 | MGSWLLFKSDLAWIKWRLEALGGSEAELAEFEESIAMFEHWLQEYKGKGNP EVEALRKEAAAIRDELQAYRHN | P26 | 33.3 |
| 944 | MGSWLYFKSDLAWIKWRLEALGGSEAELADFEEAIAEFEQALQIYKGKGNP EVEALRKEAAAIRDELQAYRHN | P26 | 21.2 |

TABLE 3-continued

| SEQ ID NO: | D-Domain Sequence | Target | ELISA_avg |
|---|---|---|---|
| | Exemplary D-domains | | |
| 945 | MGSWKLFKYELAWIKWRLEALGGSEAELADFEASIAQFEKYLQTYKGKGNP EVEALRKEAAAIRDELQAYRHN | P26 | 23.4 |
| 946 | MGSWYLFKNELAWIKWRLEALGGSEAELADFEMVIAMFEDHLQEYKGKGNP EVEALRKEAAAIRDELQAYRHN | P26 | 31.1 |
| 947 | MGSWVYFKAHLAFIKWELEALGGSEAELANFESTIAEFEKYLQVYKGKGNP EVEALRKEAAAIRDELQAYRHN | P26 | 20.8 |
| 948 | MGSWMYFKSHLAWIKWELEALGGSEAELAFFEDNIAQFEYWLQLYKGKGNP EVEALRKEAAAIRDELQAYRHN | P26 | 19.8 |
| 949 | MGSWTLFKWDLAFIKWQLEALGGSEAELAWFEYEIAAFEDSLQNYKGKGNP EVEALRKEAAAIRDELQAYRHN | P26 | 12.1 |
| 950 | MGSWILFKEDLAFIKWQLEALGGSEAELAWFETTIANFESDLQKYKGKGNP EVEALRKEAAAIRDELQAYRHN | P26 | 23.3 |
| 951 | MGSWYFFKSRLAYIKVYLEALGGSEAELAGFEWEIAHFEEWLQRYKGKGNP EVEALRKEAAAIRDELQAYRHN | P26 | 30.1 |
| 952 | MGSWYIFKSELAWIKWYLEALGGSEAELANFEVEIATFETWLQGYKGKGNP EVEALRKEAAAIRDELQAYRHN | P26 | 29.6 |
| 953 | MGSWYIFKQELASIKLSLEALGGSEAELAHFEAEIAWFEWWLQWYKGKGNP EVEALRKEAAAIRDELQAYRHN | P26 | 19.4 |
| 954 | MGSWVRFKTELAYIKESLEALGGSEAELAMFESEIAIFEHSLQTYKGKGNP EVEALRKEAAAIRDELQAYRHN | P26 | 20.5 |
| 955 | MGSWYLFKTELAAIKYRLEALGGSEAELASFEYEIAWFEHILQFYKGKGNP EVEALRKEAAAIRDELQAYRHN | P26 | 20.1 |
| 956 | MGSWYWFKYELAEIKWHLEALGGSEAELAHFEHSIAVFESQLQQYKGKGNP EVEALRKEAAAIRDELQAYRHN | P26 | 21.5 |
| 957 | MGSWWVFKKTLAEIKWTLEALGGSEAELAYFEAEIAFFEFILQQYKGKGNP EVEALRKEAAAIRDELQAYRHN | P26 | 18.6 |
| 958 | MGSWVYFKDHLAEIKSQLEALGGSEAELALFEYDIAWFEFILQYYKGKGNP EVEALRKEAAAIRDELQAYRHN | P26 | 22.1 |
| 959 | MGSWVYFKHRLAEIKDQLEALGGSEAELAEFETDIAWFEWMLQYYKGKGNP EVEALRKEAAAIRDELQAYRHN | P26 | 11.1 |
| 960 | MGSWIIFKTDLARIKNYLEALGGSEAELATFERDIAWFEFMLQIYKGKGNP EVEALRKEAAAIRDELQAYRHN | P26 | 16.7 |
| 961 | MGSWMHFKQDLAEIKGYLEALGGSEAELAIFEMDIAWFEYMLQYYKGKGNP EVEALRKEAAAIRDELQAYRHN | P26 | 18.9 |
| 962 | MGSWQIFKQDLAAIKDYLEALGGSEAELAIFEFDIAWFEHMLQWYKGKGNP EVEALRKEAAAIRDELQAYRHN | P26 | 17.4 |
| 963 | MGSWLAFKEDLAHIKSILEALGGSEAELAEFEHDIAWFEYMLQYYKGKGNP EVEALRKEAAAIRDELQAYRHN | P26 | 18.6 |
| 964 | MGSWFVFKEDLAGIKFILEALGGSEAELAMFETDIAWFEYMLQYYKGKGNP EVEALRKEAAAIRDELQAYRHN | P26 | 14.2 |
| 965 | MGSWTHFKEDLAHIKDRLEALGGSEAELAAFELDIAWFEFMLQYYKGKGNP EVEALRKEAAAIRDELQAYRHN | P26 | 30.4 |
| 966 | MGSWYYFKERLAAIKDRLEALGGSEAELAIFEADIAWFEFMLQYYKGKGNP EVEALRKEAAAIRDELQAYRHN | P26 | 31.5 |
| 967 | MGSWYTFKGSLAEIKNRLEALGGSEAELAMFESDIAWFEFMLQFYKGKGNP EVEALRKEAAAIRDELQAYRHN | P26 | 32.3 |
| 968 | MGSWFTFKDDLAQIKNRLEALGGSEAELANFEMSIAWFEFMLQYYKGKGNP EVEALRKEAAAIRDELQAYRHN | P26 | 30.8 |
| 969 | MGSWVLFKQDLAMIKQRLEALGGSEAELAMFEYDIAWFEHMLQYYKGKGNP EVEALRKEAAAIRDELQAYRHN | P26 | 29.7 |

TABLE 3-continued

Exemplary D-domains

| SEQ ID NO: | D-Domain Sequence | Target | ELISA_avg |
|---|---|---|---|
| 970 | MGSWVEFKRDLANIKQRLEALGGSEAELAQFEMQIAWFEHTLQYYKGKGNP EVEALRKEAAAIRDELQAYRHN | P26 | 30.4 |
| 971 | MGSWSYFKEDLANIKSSLEALGGSEAELAWFESSIAWFEHTLQYYKGKGNP EVEALRKEAAAIRDELQAYRHN | P26 | 11.6 |
| 972 | MGSWSIFKQDLADIKDSLEALGGSEAELAMFEMDIAWFEHTLQYYKGKGNP EVEALRKEAAAIRDELQAYRHN | P26 | 16.6 |
| 973 | MGSWEIFKDDLASIKKVLEALGGSEAELALFESDIAWFELMLQYYKGKGNP EVEALRKEAAAIRDELQAYRHN | P26 | 27.9 |
| 974 | MGSWSIFKDDLAVIKERLEALGGSEAELAHFEQDIAWFEHLLQYYKGKGNP EVEALRKEAAAIRDELQAYRHN | P26 | 25.6 |
| 975 | MGSWSVFKDDLAQIKDRLEALGGSEAELAQFELDIAWFEYVLQFYKGKGNP EVEALRKEAAAIRDELQAYRHN | P26 | 30.3 |
| 976 | MGSWAVFKDSLAHIKDVLEALGGSEAELALFEMDIAWFEYVLQDYKGKGNP EVEALRKEAAAIRDELQAYRHN | P26 | 24.1 |
| 977 | MGSWIAFKDHLAIIKQRLEALGGSEAELARFEFEIAWFEWMLQYYKGKGNP EVEALRKEAAAIRDELQAYRHN | P26 | 29.9 |
| 978 | MGSWIHFKNDLAVIKDELEALGGSEAELARFEIMIAWFEDALQWYKGKGNP EVEALRKEAAAIRDELQAYRHN | P26 | 17.9 |
| 979 | MGSWMVFKQDLAEIKANLEALGGSEAELADFEFAIAWFEYELQWYKGKGNP EVEALRKEAAAIRDELQAYRHN | P26 | 17.8 |
| 980 | MGSWKNFKLELALIKSKLEALGGSEAELAQFEADIAFFEWSLQWYKGKGNP EVEALRKEAAAIRDELQAYRHN | P26 | 20.6 |
| 981 | MGSWHSFKQDLAYIKYLLEALGGSEAELAQFEELIAFFEYYLQTYKGKGNP EVEALRKEAAAIRDELQAYRHN | P26 | 25.6 |
| 982 | MGSWVVFKSSLAQIKILLEALGGSEAELAIFEVKIAHFEQELQEYKGKGNP EVEALRKEAAAIRDELQAYRHN | P26 | 8.6 |
| 983 | MGSWDQFKNSLASIKRVLEALGGSEAELAIFEVKIAHFEHFLQQYKGKGNP EVEALRKEAAAIRDELQAYRHN | P26 | 15.6 |
| 984 | MGSWNNFKSSLASIKQVLEALGGSEAELAVFELQIAHFERELQYYKGKGNP EVEALRKEAAAIRDELQAYRHN | P26 | 24.1 |
| 985 | MGSWVEFGHRLWAIDQRLYALGGSEAELAAFEKEIAAFESELQAYKGKGNP EVEKLRQRAAFIRFRLQAYRHN | CD137 | |
| 986 | MGSWVEFANRLWAIDQRLFALGGSEAELAAFEKEIAAFESELQAYKGKGNP EVEHLRDQAAFIRHKLQAYRHN | CD137 | |
| 987 | MGSWYEFRHRLWAIDQRLYALGGSEAELAAFEKEIAAFESELQAYKGKGNP EVEGLREAAAFIRAKLQAYRHN | CD137 | |
| 988 | MGSWYEFSMRLWAIDQRLYALGGSEAELAAFEKEIAAFESELQAYKGKGNP EVEALRAKAAYIRWKLQAYRHN | CD137 | |
| 989 | MGSWYEFGHRLWAIDQRLYALGGSEAELAAFEKEIAAFESELQAYKGKGNP EVEYLRETAAHIRTRLQAYRHN | CD137 | |
| 990 | MGSWYEFHYRLHAIDQRLYALGGSEAELAAFEKEIAAFESELQAYKGKGNP EVEELRIKAAFIRDRLQAYRHN | CD137 | |
| 991 | MGSWAEFKQRLAAIKTRLEALGGSEAELAAFLGEIWAFEMELAAYKGKGNP EVEALGREAAAIRMELQAYRHN | CD137 | |
| 992 | MGSWYEFDLRLHAIYDRLVALGGSEAELAAFEKEIAAFESELQAYKGKGNP EVEILRDNAAYIRQMLQAYRHN | CD47 | |
| 993 | MGSWTEFTYRLSAIEWRLWALGGSEAELAWFEQKIAFFEDFLQYYKGKGNP EVEALKHEAGAILNELMAYRHN | CD47 | |
| 994 | MGSWAEFDHRLHAIRERLHALGGSEAELAAFEKEIAAFESELQAYKGKGNP EVEILRGNAAYIKALLQAYRHN | CD47 | |

TABLE 3-continued

Exemplary D-domains

| SEQ ID NO: | D-Domain Sequence | Target | ELISA_avg |
|---|---|---|---|
| 995 | MGSWTEFVGRLAAIEFRLWALGGSEAELAWFEAHIAFFEDYLQWYKGKGNPEVEALREEAGAIMEELKAYRHN | CD47 | |
| 996 | MGSWTEFYSRLEAIWVRLQALGGSEAELAMFEDRIAHFEWFLQQYKGKGNPEVEALHEEAIAIRKELAAYRHN | CD47 | |
| 997 | MGSWHEFHDRLQAIHERLYALGGSEAELAAFEKEIAAFESELQAYKGKGNPEVESLRIAAAHIRQVLQAYRHN | CTLA4 | |
| 998 | MGSWNYFKDHLAWIKNSLEALGGSEAELAHFETAIASFERQLQEYKGKGNPEVEALRKEAAAIRDELQAYRHN | DR5 | |
| 999 | MGSWLYFKEHLAHIKAWLEALGGSEAELAHFELAIADFEYHLQEYKGKGNPEVEALRKEAAAIRDELQAYRHN | DR5 | |
| 1000 | MGSWVYFKEHLAWIKTELEALGGSEAELAHFEHSIADFEMSLQFYKGKGNPEVEALRKEAAAIRDELQAYRHN | DR5 | |
| 1001 | MGSWFYFKQHLAWIKSYLEALGGSEAELAHFERAIAAFEQHLQMYKGKGNPEVEALRKEAAAIRDELQAYRHN | DR5 | |
| 1002 | MGSWHYFKDHLAEIKGLLEALGGSEAELAHFEMAIADFEHNLQYYKGKGNPEVEALRKEAAAIRDELQAYRHN | DR5 | |
| 1003 | MGSWHYFKGHLAEIKNHLEALGGSEAELAHFERAIAAFERSLQWYKGKGNPEVEALRKEAAAIRDELQAYRHN | DR5 | |
| 1004 | MGSWIYFKEHLAYIKKELEALGGSEAELAHFESAIAVFESTLQYYKGKGNPEVEALRKEAAAIRDELQAYRHN | DR5 | |
| 1005 | MGSWTYFKEHLAEIKYMLEALGGSEAELAHFEVAIADFEKMLQYYKGKGNPEVEALRKEAAAIRDELQAYRHN | DR5 | |
| 1006 | MGSWWLFKDHLAEIKTALEALGGSEAELAHFEMAIAAFEKQLQYYKGKGNPEVEALRKEAAAIRDELQAYRHN | DR5 | |
| 1007 | MGSWSEFYNRLDAIESRLLALGGSEAELALFEIQIARFEKVLQAYKGKGNPEVEALRGEARAIFAELYAYRHN | KIR | |
| 1008 | MGSWYEFYNRLYAIEIRLYALGGSEAELAAFEKEIAAFESELQAYKGKGNPEVERLRVRAAKIRVILQAYRHN | KIR | |
| 1009 | MGSWLWFKIFLAEIKYFLEALGGSEAELAAFDFEIHAFHVELFAYKGKGNPEVEVLREVAAEIRWDLQAYRHN | KIR | |
| 1010 | MGSWTEFQSRLDAIHSRLRALGGSEAELAAFEKEIAAFESELQAYKGKGNPEVELLRDDAAFIRHFLQAYRHN | PDL1 | |
| 1011 | MGSWQEFDDRLNAIKARLQALGGSEAELAAFEKEIAAFESELQAYKGKGNPEVEDLRDDAAFIRRFLQAYRHN | PDL1 | |
| 1012 | MGSWYEFQNRLHAIHERLNALGGSEAELAAFEKEIAAFESELQAYKGKGNPEVELLRDDAAFIRHFLQAYRHN | PDL1 | |
| 1013 | MGSWFEFQDRLTAINERLSALGGSEAELAAFEKEIAAFESELQAYKGKGNPEVETLRSDAAFIRRFLQAYRHN | PDL1 | |
| 1014 | MGSWYEFESRLDAIHERLHALGGSEAELAAFEKEIAAFESELQAYKGKGNPEVENLRGDAAFIRHFLQAYRHN | PDL1 | |
| 1015 | MGSWYEFNHRLDAISKRLNALGGSEAELAAFEKEIAAFESELQAYKGKGNPEVEELRGDAAFIRHFLQAYRHN | PDL1 | |
| 1016 | MGSWFEFENRLHAIVHRLGALGGSEAELAAFEKEIAAFESELQAYKGKGNPEVETLRADAAFIRHYLQAYRHN | PDL1 | |
| 1017 | MGSWVVFKVDLATIKYILEALGGSEAELAEFEGEIAGFEYSLQFYKGKGNPEVEALRKEAAAIRDELQAYRHN | TIM3 | |
| 1018 | MGSWTIFKEWLAFIKTDLEALGGSEAELAFFEGWIASFEMELQKYKGKGNPEVEALRKEAAAIRDELQAYRHN | PD1 | |
| 1019 | MGSWVMFKWLLADIKSHLEALGGSEAELAFFEGFIAAFETHLQVYKGKGNPEVEALRKEAAAIRDELQAYRHN | PD1 | |

TABLE 3-continued

| Exemplary D-domains | | | |
|---|---|---|---|
| SEQ ID NO: | D-Domain Sequence | Target | ELISA_avg |
| 1020 | MGSWYAFKDYLADIKGWLEALGGSEAELAFFEIFIARFELELQAYKGKGNP EVEALRKEAAAIRDELQAYRHN | PD1 | |
| 1021 | MGSWAEFKQRLAAIKTRLEALGGSEAELAAFEKEIAAFESELQAYKGKGNP EVEALRKEAAAIRDELQAYRHN | None known | |
| 1030 | MGSWEEFELRLNAIEERLYALGGSEAELAYFEYVIADFEGNLQRYKGKGNP EVEALYFEADAIFEELVAYRHN | CD19 | |
| 1031 | MGSWFEFNHRLWAIFERLMALGGSEAELAAFEKEIAAFESELQAYKGKGNP EVEYLRAMAAVIRYHLQAYRHN | CD19 | |
| 1032 | MGSWEEFDGRLFAIEQRLQALGGSEAELAAFEKEIAAFESELQAYKGKGNP EVEVLRWFAAGIRDFLQAYRHN | CD19 | |
| 1033 | MGSWAEFYHRLYAIETRLSALGGSEAELAAFEKEIAAFESELQAYKGKGNP EVEYLRHWAAWIRTYLQAYRHN | CD19 | |
| 1034 | MGSWVEFSDRLYAIEERLWALGGSEAELAAFEKEIAAFESELQAYKGKGNP EVEELRELAAIIRHSLQAYRHN | CD19 | |
| 1035 | MGSWWEFEGRLYAIEERLTALGGSEAELAAFEKEIAAFESELQAYKGKGNP EVEYLREWAAWIRQMLQAYRHN | CD19 | |
| 1036 | MGSWWEFEHRLYAIEERLVALGGSEAELAAFEKEIAAFESELQAYKGKGNP EVEYLRNWAAYIRMALQAYRHN | CD19 | |
| 1037 | MGSWWEFEARLYAIEFRLSALGGSEAELAAFEKEIAAFESELQAYKGKGNP EVEYLRSWAAYIRTSLQAYRHN | CD19 | |
| 1038 | MGSWWEFEARLWAIESRLKALGGSEAELAAFEKEIAAFESELQAYKGKGNP EVEYLRHWAAYIRVILQAYRHN | CD19 | |
| 1039 | MGSWWEFEARLYAIEFRLSALGGSEAELAAFEKEIAAFESELQAYKGKGNP EVEYLRSWAAYIRTSLQAYRHN | CD19 | |
| 1040 | MGSWEEFYHRLDAIELRLYALGGSEAELAAFEKEIAAFESELQAYKGKGNP EVEYLRWYAAEIREILQAYRHN | CD19 | |
| 1041 | MGSWYEFYERLDAIDTRLWALGGSEAELAAFEKEIAAFESELQAYKGKGNP EVEFLREYAAEIRHFLQAYRHN | CD19 | |
| 1042 | MGSWNEFFDRLDAILYRLDALGGSEAELAAFEKEIAAFESELQAYKGKGNP EVEYLRFVAADIRSWLQAYRHN | CD19 | |
| 1043 | MGSWIEFDDRLLAIMDRLWALGGSEAELAAFEKEIAAFESELQAYKGKGNP EVEDLRDVAADIRHYLQAYRHN | CD19 | |
| 1044 | MGSWYEFWERLDAITFRLYALGGSEAELAAFEKEIAAFESELQAYKGKGNP EVEDLRTWAADIRAILQAYRHN | CD19 | |
| 1045 | MGSWEEFYIRLDAIMERLWALGGSEAELAAFEKEIAAFESELQAYKGKGNP EVEDLRYAAADIRHFLQAYRHN | CD19 | |
| 1046 | MGSWIEFEERLYAIETRLLALGGSEAELAAFEKEIAAFESELQAYKGKGNP EVEFLRVVAADIREWLQAYRHN | CD19 | |
| 1047 | MGSWIEFEHRLSAINDRLYALGGSEAELAAFEKEIAAFESELQAYKGKGNP EVEDLREWAADIRSLLQAYRHN | CD19 | |
| 1048 | MGSWFEFEMRLDAIMARLWALGGSEAELAAFEKEIAAFESELQAYKGKGNP EVEDLRYAAADIRDYLQAYRHN | CD19 | |
| 1049 | MGSWYEFVYRLDAIYDRLWALGGSEAELAAFEKEIAAFESELQAYKGKGNP EVEDLRYAAADIRDFLQAYRHN | CD19 | |
| 1050 | MGSWVEFEDRLDAILERLWALGGSEAELAAFEKEIAAFESELQAYKGKGNP EVEDLRELAADIRDFLQAYRHN | CD19 | |
| 1051 | MGSWFEFEERLIAIEERLFALGGSEAELAAFEKEIAAFESELQAYKGKGNP EVEYLRWIAADIRDVLQAYRHN | CD19 | |
| 1052 | MGSWIEFADRLDAILDRLDALGGSEAELAAFEKEIAAFESELQAYKGKGNP EVEWLREIAADIRAYLQAYRHN | CD19 | |

TABLE 3-continued

Exemplary D-domains

| SEQ ID NO: | D-Domain Sequence | Target | ELISA_avg |
|---|---|---|---|
| 1053 | MGSWLEFEYRLDAILDRLFALGGSEAELAAFEKEIAAFESELQAYKGKGNP EVEDLREVAADIRMLLQAYRHN | CD19 | |
| 1054 | MGSWYEFHDRLDAITNRLYALGGSEAELAAFEKEIAAFESELQAYKGKGNP EVEDLRDWAADIRVWLQAYRHN | CD19 | |
| 1055 | MGSWQEFEQRLDAINWRLWALGGSEAELAAFEKEIAAFESELQAYKGKGNP EVEELREWAADIRIFLQAYRHN | CD19 | |
| 1056 | MGSWYEFYSRLDAIDSRLYALGGSEAELAAFEKEIAAFESELQAYKGKGNP EVEFLRDYAAEIRRYLQAYRHN | CD19 | |
| 1057 | MGSWEEFHDRLEAISDRLWALGGSEAELAAFEKEIAAFESELQAYKGKGNP EVEDLRDWAADIRFYLQAYRHN | CD19 | |
| 1058 | MGSWWEFDERLYAIEDRLFALGGSEAELAAFEKEIAAFESELQAYKGKGNP EVEWLRIVAADIREILQAYRHN | CD19 | |
| 1059 | MGSWEEFEYRLMAIEVRLWALGGSEAELAAFEKEIAAFESELQAYKGKGNP EVEVLREIAADIRQILQAYRHN | CD19 | |
| 1060 | MGSWVVFKQRLAYIKDLLEALGGSEAELAYFEMSIAFFEEDLQVYKGKGNP EVEALRKEAAAIRDELQAYRHN | CD22 | |
| 1061 | MGSWYEFKNDLAWIKVHLEALGGSEAELAYFEFRIAHFENALQYYKGKGNP EVEALRKEAAAIRDELQAYRHN | CD22 | |
| 1062 | MGSWVEFYNRLWAIDHRLHALGGSEAELAAFEKEIAAFESELQAYKGKGNP EVEVLRYHAASIRVTLQAYRHN | CD22 | |
| 1063 | MGSWSEFYDRLHAIHHRLYALGGSEAELAAFEKEIAAFESELQAYKGKGNP EVEALRDTAAFIRTRLQAYRHN | CD22 | |
| 1064 | MGSWKEFHFRLHAIEHRLIALGGSEAELAAFEKEIAAFESELQAYKGKGNP EVEFLRAKAANIRTHLQAYRHN | CD22 | |
| 1065 | MGSWFEFHGRLHAIYGRLSALGGSEAELAAFEKEIAAFESELQAYKGKGNP EVEHLRAHAAHIRDHLQAYRHN | CD22 | |
| 1066 | MGSWYEFADRLHAIHQRLYALGGSEAELAAFEKEIAAFESELQAYKGKGNP EVEALRMTAAFIRSRLQAYRHN | CD22 | |
| 1067 | MGSWNEFYNRLHAIHQRLYALGGSEAELAAFEKEIAAFESELQAYKGKGNP EVESLRQTAAYIRDRLQAYRHN | CD22 | |
| 1068 | MGSWNEFADRLHAIHQRLYALGGSEAELAAFEKEIAAFESELQAYKGKGNP EVESLRMTAAFIRSRLQAYRHN | CD22 | |
| 1069 | MGSWTEFSYRLGAIQSRLHALGGSEAELAAFEKEIAAFESELQAYKGKGNP EVEHLRYNAAKIRHFLQAYRHN | CD22 | |
| 1070 | MGSWQEFTTRLEAIYHRLRALGGSEAELANFEGFIAEFEGNLQMYKGKGNP EVEALVHEAYAIMEELHAYRHN | DR5 | |
| 1071 | MGSWVEFFDRLKAIHDRLEALGGSEAELAHFEKLIAHFEHRLQNYKGKGNP EVEALEKEADAILYELAAYRHN | DR5 | |
| 1072 | MGSWYYFKHHLAWIKMELEALGGSEAELAHFESSIASFERDLQQYKGKGNP EVEALRKEAAAIRDELQAYRHN | DR5 | |
| 1073 | MGSWVEFHIRLHAIQYRLYALGGSEAELAAFEKEIAAFESELQAYKGKGNP EVEELRHWAAFIRLQLQAYRHN | DR5 | |
| 1074 | MGSWNEFHDRLNAIHARLHALGGSEAELAAFEKEIAAFESELQAYKGKGNP EVENLRDDAAFIRRFLQAYRHN | PDL1 | |
| 1075 | MGSWYEFTVRLEAIHERLKALGGSEAELAAFEKEIAAFESELQAYKGKGNP EVEILRDDAAFIRRFLQAYRHN | PDL1 | |
| 1076 | MGSWKEFDDRLNAIKARLQALGGSEAELAAFEKEIAAFESELQAYKGKGNP EVEDLRDDAAFIRRFLQAYRHN | PDL1 | |
| 1077 | MGSWYEFDDRLNAIHDRLQALGGSEAELAAFEKEIAAFESELQAYKGKGNP EVEDLRDDAAFIRRFLQAYRHN | PDL1 | |

TABLE 3-continued

Exemplary D-domains

| SEQ ID NO: | D-Domain Sequence | Target | ELISA_avg |
|---|---|---|---|
| 1078 | MGSWNEFKNRLDAIHKRLNALGGSEAELAAFEKEIAAFESELQAYKGKGNP EVENLRDDAAFIRHFLQAYRHN | PDL1 | |
| 1079 | MGSWTEFEQRLEAIHNRLQALGGSEAELAAFEKEIAAFESELQAYKGKGNP EVEELRNDAAFIRHFLQAYRHN | PDL1 | |
| 780 | MGSWVEFEARLSAIYERLEALGGSEAELAAFEKEIAAFESELQAYKGKGNP EVEKLRRHAAGIRSNLQAYRHN | CS1 | |
| 781 | MGSWVEFFVRLDAIWERLEALGGSEAELAAFEKEIAAFESELQAYKGKGNP EVETLRFHAAGIRQKLQAYRHN | CS1 | |
| 782 | MGSWTEFNLRLDAIYERLEALGGSEAELAAFEKEIAAFESELQAYKGKGNP EVEALRWHAAGIRQQLQAYRHN | CS1 | |
| 783 | MGSWMEFYDRLDAIWVRLEALGGSEAELAAFEKEIAAFESELQAYKGKGNP EVEVLRFHAAGIREQLQAYRHN | CS1 | |
| 784 | MGSWHEFNGRLWAIYARLDALGGSEAELAAFEKEIAAFESELQAYKGKGNP EVETLRRHAAGIRGILQAYRHN | CS1 | |
| 785 | MGSWYEFVQRLHAINDRLSALGGSEAELAAFEKEIAAFESELQAYKGKGNP EVEVLRRHAAGIRYTLQAYRHN | CS1 | |
| 786 | MGSWAEFYQRLNAIWNRLEALGGSEAELAAFEKEIAAFESELQAYKGKGNP EVEVLRRHAAGIRGQLQAYRHN | CS1 | |
| 787 | MGSWVEFNERLHAIYLRLDALGGSEAELAAFEKEIAAFESELQAYKGKGNP EVETLRRHAAGIRWQLQAYRHN | CS1 | |
| 788 | MGSWNEFKLELAFIKDWLEALGGSEAELANFEEAIAEFEAGLQGYKGKGNP EVEALRKEAAAIRDELQAYRHN | CS1 | |
| 789 | MGSWMEFEARLEAIWDRLEALGGSEAELAAFEKEIAAFESELQAYKGKGNP EVESLRFHAAGIRQHLQAYRHN | CS1 | |
| 790 | MGSWVEFEDRLNAIWWRLEALGGSEAELAAFEKEIAAFESELQAYKGKGNP EVEKLRRHAAGIRTQLQAYRHN | CS1 | |
| 791 | MGSWHHFKMHLAGIKLQLEALGGSEAELAEFEEWIADFEGALQDYKGKGNP EVEALRKEAAAIRDELQAYRHN | CS1 | |
| 792 | MGSWAEFFARLDAIWERLEALGGSEAELAAFEKEIAAFESELQAYKGKGNP EVETLRFHAAGIRQKLQAYRHN | CS1 | |
| 793 | MGSWAEFFARLDAIWDRLEALGGSEAELAAFEKEIAAFESELQAYKGKGNP EVETLRFHAAGIRQKLQAYRHN | CS1 | |
| 794 | MGSWAEFFARLDAIWERLEALGGSEAELAAFEKEIAAFESELQAYKGKGNP EVETLKFHAAGIRQKLQAYRHN | CS1 | |
| 795 | MGSWAEFFARLDAIWDRLEALGGSEAELAAFEKEIAAFESELQAYKGKGNP EVETLKFHAAGIRQKLQAYRHN | CS1 | |
| 800 | MGSWHEFRWRLFAIWQRLHALGGSEAELAAFEKEIAAFESELQAYKGKGNP EVEWLRLDAALIRVMLQAYRHN | HER2 | 10.02 |
| 801 | MGSWAEFRWRLHAIWLKLGELGGSEAELAAFEKEIAAFESELQAYKGKGNP EVEWLREDAEQIKYILQAYRHN | HER2 | |
| 802 | MGSWAEFRWALHAIWLKLGELGGSEAELAAFEKEIAAFESELQAYKGKGNP EVEWLREDAEQIKYILQAYRHN | HER2 | |
| 803 | MGSWAEFRWRLHAIWLKLGALGGSEAELAAFEKEIAAFESELQAYKGKGNP EVEWLRQDAAQIKYILQAYRHN | HER2 | |
| 804 | MGSWAEFRWRLHAIWLQLGALGGSEAELAAFEKEIAAFESELQAYKGKGNP EVEWLRQDAAQIKYILQAYRHN | HER2 | |
| 805 | MGSWAEFRWRLHAIWLRLGALGGTEAELAAFEKEIAAFESELQAYKGKGNP EVEWLRQDAAQIKYILQAYRHN | HER2 | |
| 806 | MGSWAEFRWRLHAIWLRLGALGGSEAELAAFEKEIAAFESELQAYKGKGNP EVEWLRQDAAQIKYILQAYRHN | HER2 | |

TABLE 3-continued

| SEQ ID NO: | D-Domain Sequence | Target | ELISA_avg |
|---|---|---|---|
| | Exemplary D-domains | | |
| 807 | MGSWAEFRWKLEAIWLRLGALGGSEAELAAFEKEIAAFESELQAYKGKGNP EVEWLRQDAAQIKYILQAYRHN | HER2 | |
| 808 | MGSWAEFRWKLGAIWLRLGALGGSEAELAAFEKEIAAFESELQAYKGKGNP EVEWLRQDAAQIKYILQAYRHN | HER2 | |
| 809 | MGSWYEFRWRLHAIWLRLGALGGSEAELAAFEKEIAAFESELQAYKGKGNP EVEWLRQDAAQIRYILQAYRHN | HER2 | 7.18 |
| 810 | MGSWHEFLRRLLAIEMRLYALGGSEAELAAFEKEIAAFESELQAYKGKGNP EVEHLRVRAASIRQMLQAYRHN | HER2 | 8.15 |
| 811 | MGSWWGFKVNLAWIKWKLEALGGSEAELAYFELWIANFEHSLQEYKGKGNP EVEALRKEAAAIRDELQAYRHN | HER2 | 8.69 |
| 812 | MGSWVNFKTHLARIKVHLEALGGSEAELALFEHDIANFEQVLQQYKGKGNP EVEALRKEAAAIRDELQAYRHN | HER2 | 7.91 |
| 813 | MGSWLVFKDELAGIKNYLEALGGSEAELATFEQDIAWFEQWLQNYKGKGNP EVEALRKEAAAIRDELQAYRHN | HER2 | 3.28 |
| 814 | MGSWKTFKIELAGIKLELEALGGSEAELAGFENAIAQFESSLQYYKGKGNP EVEALRKEAAAIRDELQAYRHN | HER2 | 4.95 |
| 815 | MGSWWEFKVRLSAIQYRLYALGGSEAELAAFEKEIAAFESELQAYKGKGNP EVEALREQAALIRTILQAYRHN | HER2 | 5.17 |
| 816 | MGSWWEFHIRLHAINYRLAALGGSEAELAAFEKEIAAFESELQAYKGKGNP EVEALRELAAKIRGDLQAYRHN | HER2 | 11.90 |
| 817 | MGSWWEFQVRLRAIQYRLNALGGSEAELAAFEKEIAAFESELQAYKGKGNP EVEYLRGLAAQIRFDLQAYRHN | HER2 | 14.39 |
| 818 | MGSWWEFKIRLYAIEYRLNALGGSEAELAAFEKEIAAFESELQAYKGKGNP EVEALRAKAAQIRYNLQAYRHN | HER2 | 4.49 |
| 819 | MGSWFEFNIRLHAIEYRLKALGGSEAELAAFEKEIAAFESELQAYKGKGNP EVEELRNYAASIRKLLQAYRHN | HER2 | 7.86 |
| 820 | MGSWFEFEIRLRAIEYRLSALGGSEAELAAFEKEIAAFESELQAYKGKGNP EVEKLRELAAEIRYALQAYRHN | HER2 | 7.75 |
| 821 | MGSWFEFKIRLYAIQYRLSALGGSEAELAAFEKEIAAFESELQAYKGKGNP EVEELRNLAAEIRHSLQAYRHN | HER2 | 13.08 |
| 822 | MGSWWEFKVRLRAIEYRLSALGGSEAELAAFEKEIAAFESELQAYKGKGNP EVEELRVLAASIRIHLQAYRHN | HER2 | 10.09 |
| 823 | MGSWSEFWFRLHAILYRLQALGGSEAELAAFEKEIAAFESELQAYKGKGNP EVETLRDAAAEIRVALQAYRHN | HER2 | 14.79 |
| 824 | MGSWIEFWVRLNAILYRLYALGGSEAELAAFEKEIAAFESELQAYKGKGNP EVEALRDSAAEIRRWLQAYRHN | HER2 | 3.91 |
| 825 | MGSWVEFWIRLNAIKYRLLALGGSEAELAAFEKEIAAFESELQAYKGKGNP EVEKLRQDAADIRELLQAYRHN | HER2 | 10.62 |
| 826 | MGSWTEFWWRLSAIVYRLNALGGSEAELAAFEKEIAAFESELQAYKGKGNP EVEELRDMAADIRSLLQAYRHN | HER2 | 5.76 |
| 827 | MGSWWEFYLRLRAISYRLQALGGSEAELAAFEKEIAAFESELQAYKGKGNP EVEGLRQDAAEIRKLLQAYRHN | HER2 | 5.10 |
| 828 | MGSWWEFHVRLRAIEYRLEALGGSEAELAAFEKEIAAFESELQAYKGKGNP EVEQLRLIAANIRHLLQAYRHN | HER2 | 5.48 |
| 829 | MGSWWEFHVRLKAIEYRLLALGGSEAELAAFEKEIAAFESELQAYKGKGNP EVEDLRYIAANIRQLLQAYRHN | HER2 | 4.56 |
| 830 | MGSWWEFKVRLKAIEYRLLALGGSEAELAAFEKEIAAFESELQAYKGKGNP EVEDLRYIAANIRQLLQAYRHN | HER2 | |
| 831 | MGSWWEFQVRLAAIEYRLKALGGSEAELAAFEKEIAAFESELQAYKGKGNP EVENLRQLAAHIRSVLQAYRHN | HER2 | 6.33 |

TABLE 3-continued

| Exemplary D-domains | | | |
|---|---|---|---|
| SEQ ID NO: | D-Domain Sequence | Target | ELISA_avg |
| 832 | MGSWWEFQVRLSAIEYRLTALGGSEAELAAFEKEIAAFESELQAYKGKGNP EVEELRQKAARIRSLLQAYRHN | HER2 | 9.61 |
| 833 | MGSWWEFNIRLHAIDYRLKALGGSEAELAAFEKEIAAFESELQAYKGKGNP EVELLREKAAQIRAQLQAYRHN | HER2 | 9.75 |
| 834 | MGSWWEFRVRLEAIDYRLKALGGSEAELAAFEKEIAAFESELQAYKGKGNP EVEYLRMKAATIRAILQAYRHN | HER2 | 6.82 |
| 835 | MGSWYEFDIRLEAIKYRLSALGGSEAELAAFEKEIAAFESELQAYKGKGNP EVEYLRKKAAVIRSMLQAYRHN | HER2 | 5.35 |
| 836 | MGSWWEFRIRLEAIWYRLHALGGSEAELAAFEKEIAAFESELQAYKGKGNP EVEDLRIFAANIRSKLQAYRHN | HER2 | 8.04 |
| 837 | MGSWWEFNVRLQAIKYRLSALGGSEAELAAFEKEIAAFESELQAYKGKGNP EVEDLRKTAAHIRWQLQAYRHN | HER2 | 5.23 |
| 838 | MGSWWEFNVRLSAIRYRLLALGGSEAELAAFEKEIAAFESELQAYKGKGNP EVEDLRASAAQIRAMLQAYRHN | HER2 | 6.73 |
| 839 | MGSWWEFNMRLSAIKYRLYALGGSEAELAAFEKEIAAFESELQAYKGKGNP EVEILRRLAADIRERLQAYRHN | HER2 | 3.08 |
| 840 | MGSWWEFHIRLRAIKYRLYALGGSEAELAAFEKEIAAFESELQAYKGKGNP EVEDLRILAAEIRAQLQAYRHN | HER2 | 14.79 |

TABLE 4

| Exemplary Antigenic Determinant Sequences | | |
|---|---|---|
| SEQ ID | Antigen | Sequence |
| 2 | CD19 | MPPPRLLFFLLFLTPMEVRPEEPLVVKVEEGDNAVLQCLKGTSDGPTQQLTWSRESPLKPFL KLSLGLPGLGIHMRPLAIWLFIFNVSQQMGGFYLCQPGPPSEKAWQPGWTVNVEGSGELFRW NVSDLGGLGCGLKNRSSEGPSSPSGKLMSPKLYVWAKDRPEIWEGEPPCLPPRDSLNQSLSQ DLTMAPGSTLWLSCGVPPDSVSRGPLSWTHVHPKGPKSLLSLELKDDRPARDMWVMETGLLL PRATAQDAGKYYCHRGNLTMSFHLEITARPVLWHWLLRTGGWK |
| 3 | CD19-Signal | PEEPLVVKVEEGDNAVLQCLKGTSDGPTQQLTWSRESPLKPFLKLSLGLPGLGIHMRPLAIW LFIFNVSQQMGGFYLCQPGPPSEKAWQPGWTVNVEGSGELFRWNVSDLGGLGCGLKNRSSEG PSSPSGKLMSPKLYVWAKDRPEIWEGEPPCLPPRDSLNQSLSQDLTMAPGSTLWLSCGVPPD SVSRGPLSWTHVHPKGPKSLLSLELKDDRPARDMWVMETGLLLPRATAQDAGKYYCHRGNLT MSFHLEITARPVLWHWLLRTGGWK |
| 4 | BCMA | MLQMAGQCSQNEYFDSLLHACIPCQLRCSSNTPPLTCQRYCNASVTNSVKGTNAILWTCLGL SLIISLAVFVLMFLLRKINSEPLKDEFKNTGSGLLGMANIDLEKSRTGDEIILPRGLEYTVE ECTCEDCIKSKPKVDSDHCFPLPAMEEGATILVTTKTNDYCKSLPAALSATEIEKSISAR |
| 5 | BCMA_ECD | MLQMAGQCSQNEYFDSLLHACIPCQLRCSSNTPPLTCQRYCNASVTNSVKGTNA |
| 6 | CD20 | AGIYAPI |
| 7 | CD20 | FLKMESLNFIRAHTP |
| 8 | CD20 | EPANPSEK |
| 9 | CD20 | KISHFLKMESLNFIRAHTPYINIYNCEPANPSEKNSPSTQYCYSIQS |
| 10 | CD20 | PICVTV |
| 11 | CD123-Signal | TKEDPNPPITNLRMKAKAQQLTWDLNRNVTDIECVKDADYSMPAVNNSYCQFGAISLCEVTN YTVRVANPPFSTWILFPENSGKPWAGAENLTCWIHDVDFLSCSWAVGPGAPADVQYDLYLNV ANRRQQYECLHYKTDAQGTRIGCRFDDISRLSSGSQSSHILVRGRSAAFGIPCTDKFVVFSQ IEILTPPNMTAKCNKTHSFMHWKMRSHFNRKFRYELQIQKRMQPVITEQVRDRTSFQLLNPG TYTVQIRARERVYEFLSAWSTPQRFECDQEEGANTRAWR |
| 12 | CD37 | DKTSFVSFVGLAFVPLQIWSK |

TABLE 4-continued

Exemplary Antigenic Determinant Sequences

| SEQ ID | Antigen | Sequence |
|---|---|---|
| 13 | CD37 | RAQLERSLRDVVEKTIQKYGTNPEETAAEESWDYVQFQLRCCGWHYPQDWFQVLILRGNGSE AHRVPCSCYNLSATNDSTILDKVILPQLSRLGHLARSRHSADICAVPAESHIYREGCAQGLQ KWLHNN |
| 14 | AFP | MKWVESIFLIFLLNFTESRTLHRNEYGIASILDSYQCTAEISLADLATIFFAQFVQEATYKE VSKMVKDALTAIEKPTGDEQSSGCLENQLPAFLEELCHEKEILEKYGHSDCCSQSEEGRHNC FLAHKKPTPASIPLFQVPEPVTSCEAYEEDRETFMNKFIYEIARRHPFLYAPTILLWAARYD KIIPSCCKAENAVECFQTKAATVTKELRESSLLNQHACAVMKNFGTRTFQAITVTKLSQKFT KVNFTEIQKLVLDVAHVHEHCCRGDVLDCLQDGEKIMSYICSQQDTLSNKITECCKLTTLER GQCIIHAENDEKPEGLSPNLNRFLGDRDFNQFSSGEKNIFLASFVHEYSRRHPQLAVSVILR VAKGYQELLEKCFQTENPLECQDKGEEELQKYIQESQALAKRSCGLFQKLGEYYLQNAFLVA YTKKAPQLTSSELMAITRKMAATAATCCQLSEDKLLACGEGAADIIIGHLCIRHEMTPVNPG VGQCCTSSYANRRPCFSSLVVDETYVPPAFSDDKFIFHKDLCQAQGVALQTMKQEFLINLVK QKPQITEEQLEAVIADFSGLLEKCCQGQEQEVCFAEEGQKLISKTRAALGV |
| 15 | AFP-Signal | RTLHRNEYGIASILDSYQCTAEISLADLATIFFAQFVQEATYKEVSKMVKDALTAIEKPTGD EQSSGCLENQLPAFLEELCHEKEILEKYGHSDCCSQSEEGRHNCFLAHKKPTPASIPLFQVP EPVTSCEAYEEDRETFMNKFIYEIARRHPFLYAPTILLWAARYDKIIPSCCKAENAVECFQT KAATVTKELRESSLLNQHACAVMKNFGTRTFQAITVTKLSQKFTKVNFTEIQKLVLDVAHVH EHCCRGDVLDCLQDGEKIMSYICSQQDTLSNKITECCKLTTLERGQCIIHAENDEKPEGLSP NLNRFLGDRDFNQFSSGEKNIFLASFVHEYSRRHPQLAVSVILRVAKGYQELLEKCFQTENP LECQDKGEEELQKYIQESQALAKRSCGLFQKLGEYYLQNAFLVAYTKKAPQLTSSELMAITR KMAATAATCCQLSEDKLLACGEGAADIIIGHLCIRHEMTPVNPGVGQCCTSSYANRRPCFSS LVVDETYVPPAFSDDKFIFHKDLCQAQGVALQTMKQEFLINLVKQKPQITEEQLEAVIADFS GLLEKCCQGQEQEVCFAEEGQKLISKTRAALGV |
| 16 | P26 | LEKCFQTENPLECQDKGEEELQKYIQESQALAKRSCGLFQKLGEYYLQNAFLVAYTKKAPQL TSSELMAITRKMAATAATCCQLSEDKLLACGEGAADIIIGHLCIRHEMTPVNPGVGQCCTSS YANRRPCFSSLVVDETYVPPAFSDDKFIFHKDLCQAQGVALQTMKQEFLINLVKQKPQITEE QLEAVIADFSGLLEKCCQGQEQEVCFAEEGQKLISKTRAALGV |
| 1117 | P26Q217P | LEKCFQTENPLECQDKGEEELQKYIQESQALAKRSCGLFQKLGEYYLQNAFLVAYTKKAPQL TSSELMAITRKMAATAATCCQLSEDKLLACGEGAADIIIGHLCIRHEMTPVNPGVGQCCTSS YANRRPCFSSLVVDETYVPPAFSDDKFIFHKDLCQAQGVALQTMKQEFLINLVKQKPQITEE QLEAVIADFSGLLEKCCQGQEQEVCFAEEGPKLISKTRAALGV |
| 1118 | P26(Q26-V229) | QESQALAKRSCGLFQKLGEYYLQNAFLVAYTKKAPQLTSSELMAITRKMAATAATCCQLSED KLLACGEGAADIIIGHLCIRHEMTPVNPGVGQCCTSSYANRRPCFSSLVVDETYVPPAFSDD KFIFHKDLCQAQGVALQTMKQEFLINLVKQKPQITEEQLEAVIADFSGLLEKCCQGQEQEVC FAEEGQKLISKTRAALGV |
| 1119 | P26(Q26-V229) Q217P | QESQALAKRSCGLFQKLGEYYLQNAFLVAYTKKAPQLTSSELMAITRKMAATAATCCQLSED KLLACGEGAADIIIGHLCIRHEMTPVNPGVGQCCTSSYANRRPCFSSLVVDETYVPPAFSDD KFIFHKDLCQAQGVALQTMKQEFLINLVKQKPQITEEQLEAVIADFSGLLEKCCQGQEQEVC FAEEGPKLISKTRAALGV |
| 1120 | p26(K23-V229) | KYIQESQALAKRSCGLFQKLGEYYLQNAFLVAYTKKAPQLTSSELMAITRKMAATAATCCQL SEDKLLACGEGAADIIIGHLCIRHEMTPVNPGVGQCCTSSYANRRPCFSSLVVDETYVPPAF SDDKFIFHKDLCQAQGVALQTMKQEFLINLVKQKPQITEEQLEAVIADFSGLLEKCCQGQEQ EVCFAEEGQKLISKTRAALGV |
| 1121 | p26(K23-V229) Q217P | KYIQESQALAKRSCGLFQKLGEYYLQNAFLVAYTKKAPQLTSSELMAITRKMAATAATCCQL SEDKLLACGEGAADIIIGHLCIRHEMTPVNPGVGQCCTSSYANRRPCFSSLVVDETYVPPAF SDDKFIFHKDLCQAQGVALQTMKQEFLINLVKQKPQITEEQLEAVIADFSGLLEKCCQGQEQ EVCFAEEGPKLISKTRAALGV |
| 1122 | p26(G17-V229) | GEEELQKYIQESQALAKRSCGLFQKLGEYYLQNAFLVAYTKKAPQLTSSELMAITRKMAATA ATCCQLSEDKLLACGEGAADIIIGHLCIRHEMTPVNPGVGQCCTSSYANRRPCFSSLVVDET YVPPAFSDDKFIFHKDLCQAQGVALQTMKQEFLINLVKQKPQITEEQLEAVIADFSGLLEKC CQGQEQEVCFAEEGQKLISKTRAALGV |
| 1123 | p26(G17-V229) Q217P | GEEELQKYIQESQALAKRSCGLFQKLGEYYLQNAFLVAYTKKAPQLTSSELMAITRKMAATA ATCCQLSEDKLLACGEGAADIIIGHLCIRHEMTPVNPGVGQCCTSSYANRRPCFSSLVVDET YVPPAFSDDKFIFHKDLCQAQGVALQTMKQEFLINLVKQKPQITEEQLEAVIADFSGLLEKC CQGQEQEVCFAEEGPKLISKTRAALGV |
| 41 | CD22 mature ECD | DSSKWVFEHPETLYAWEGACVWIPCTYRALDGDLESFILFHNPEYNKNTSKFDGTRLYESTKDGKVPSE QKRVQFLGDKNKNCTLSIHPVHLNDSGQLGLRMESKTEKWMERIHLNVSERPFPPHIQLPPEIQESQEV TLTCLLNFSCYGYPIQLQWLLEGVPMRQAAVTSTSLTIKSVFTRSELKFSPQWSHHGKIVTCQLQDADG KFLSNDTVQLNVKHTPKLEIKVTPSDAIVREGDSVTMTCEVSSSNPEYTTVSWLKDGTSLKKQNTFTLN LREVTKDQSGKYCCQVSNDVGPGRSEEVFLQVQYAPEPSTVQILHSPAVEGSQVEFLCMSLANPLPTNY TWYHNGKEMQGRTEEKVHIPKILPWHAGTYSCVAENILGTGQRGPGAELDVQYPPKKVTTVIQNPMPIR EGDTVTLSCNYNSSNPSVTRYEWKPHGAWEEPSLGVLKIQNVGWDNTTIACAACNSWCSWASPVALNVQ YAPRDVRVRKIKPLSEIHSGNSVSLQCDFSSSHPKEVQFFWEKNGRLLGKESQLNFDSISPEDAGSYSC WVNNSIGQTASKAWTLEVLYAPRRLRVSMSPGDQVMEGKSATLTCESDANPPVSHYTWFDWNNQSLPYH SQKLRLEPVKVQHSGAYWCQGTNSVGKGRSPLSTLTVYYSPETIGRR |

TABLE 4-continued

Exemplary Antigenic Determinant Sequences

| SEQ ID | Antigen | Sequence |
|---|---|---|
| 1081 | CD137 mature ECD | LQDPCSNCPAGTFCDNNRNQICSPCPPNSFSSAGGQRTCDICRQCKGVFRTRKECSSTSNAECDCTPGF<br>HCLGAGCSMCEQDCKQGQELTKKGCKDCCFGTFNDQKRGICRPWTNCSLDGKSVLVNGTKERDVVCGPS<br>PADLSPGASSVTPPAPAREPGHSPQ |
| 1102 | Human CD45RABC | MTMYLWLKLLAFGFAFLDTEVFVTGQSPTPSPTGLTTAKMPSVPLSSDPLPTHTTAFSPASTFERENDF<br>SETTTSLSPDNTSTQVSPDSLDNASAFNTTGVSSVQTPHLPTHADSQTPSAGTDTQTFSGSAANAKLNP<br>TPGSNAISDVPGERSTASTFPTDPVSPLTTTLSLAHHSSAALPARTSNTTITANTSDAYLNASETTTLS<br>PSGSAVISTTTIATTPSKPTCDEKYANITVDYLYNKETKLFTAKLNVNENVECGNNTCTNNEVHNLTEC<br>KNASVSISHNSCTAPDKTLILDVPPGVEKFQLHDCTQVEKADTTICLKWKNIETFTCDTQNITYRFQCG<br>NMIFDNKEIKLENLEPEHEYKCDSEILYNNHKFTNASKIIKTDFGSPGEPQIIFCRSEAAHQGVITWNP<br>PQRSFHNFTLCYIKETEKDCLNLDKNLIKYDLQNLKPYTKYVLSLHAYIIAKVQRNGSAAMCHFTTKSA<br>PPSQVWNMTVSMTSDNSMHVKCRPPRDRNGPHERYHLEVEAGNTLVRNESHKNCDFRVKDLQYSTDYTF<br>KAYFHNGDYPGEPFILHHSTSYNSKALIAFLAFLIIVTSIALLVVLYKIYDLHKKRSCNLDEQQELVER<br>DDEKQLMNVEPIHADILLETYKRKIADEGRLFLAEFQSIPRVFSKFPIKEARKPFNQNKNRYVDILPYD<br>YNRVELSEINGDAGSNYINASYIDGFKEPRKYIAAQGPRDETVDDFWRMIWEQKATVIVMVTRCEEGNR<br>NKCAEYWPSMEEGTRAFGDVVVKINQHKRCPDYIIQKLNIVNKKEKATGREVTHIQFTSWPDHGVPEDP<br>HLLLKLRRRVNAFSNFFSGPIVVHCSAGVGRTGTYIGIDAMLEGLEAENKVDVYGYVVKLRRQRCLMVQ<br>VEAQYILIHQALVEYNQFGETEVNLSELHPYLHNMKKRDPPSEPSPLEAEFQRLPSYRSWRTQHIGNQE<br>ENKSKNRNSNVIPYDYNRVPLKHELEMSKESEHDSDESSDDDSDSEEPSKYINASFIMSYWKPEVMIAA<br>QGPLKETIGDFWQMIFQRKVKVIVMLTELKHGDQEICAQYWGEGKQTYGDIEVDLKDTDKSSTYTLRVF<br>ELRHSKRKDSRTVYQYQYTNWSVEQLPAEPKELISMIQVVKQKLPQKNSSEGNKHHKSTPLLIHCRDGS<br>QQTGIFCALLNLLESAETEEVVDIFQVVKALRKARPGMVSTFEQYQFLYDVIASTYPAQNGQVKKNNHQ<br>EDKIEFDNEVDKVKQDANCVNPLGAPEKLPEAKEQAEGSEPTSGTEGPEHSVNGPASPALNQGS |
| 1103 | Human CD45RO | MTMYLWLKLLAFGFAFLDTEVFVTGQSPTPSPTDAYLNASETTTLSPSGSAVISTTTIATTPSKPTCDE<br>KYANITVDYLYNKETKLFTAKLNVNENVECGNNTCTNNEVHNLTECKNASVSISHNSCTAPDKTLILDV<br>PPGVEKFQLHDCTQVEKADTTICLKWKNIETFTCDTQNITYRFQCGNMIFDNKEIKLENLEPEHEYKCD<br>SEILYNNHKFTNASKIIKTDFGSPGEPQIIFCRSEAAHQGVITWNPPQRSFHNFTLCYIKETEKDCLNL<br>DKNLIKYDLQNLKPYTKYVLSLHAYIIAKVQRNGSAAMCHFTTKSAPPSQVWNMTVSMTSDNSMHVKCR<br>PPRDRNGPHERYHLEVEAGNTLVRNESHKNCDFRVKDLQYSTDYTFKAYFHNGDYPGEPFILHHSTSYN<br>SKALIAFLAFLIIVTSIALLVVLYKIYDLHKKRSCNLDEQQELVERDDEKQLMNVEPIHADILLETYKR<br>KIADEGRLFLAEFQSIPRVFSKFPIKEARKPFNQNKNRYVDILPYDYNRVELSEINGDAGSNYINASYI<br>DGFKEPRKYIAAQGPRDETVDDFWRMIWEQKATVIVMVTRCEEGNRNKCAEYWPSMEEGTRAFGDVVVK<br>INQHKRCPDYIIQKLNIVNKKEKATGREVTHIQFTSWPDHGVPEDPHLLLKLRRRVNAFSNFFSGPIVV<br>HCSAGVGRTGTYIGIDAMLEGLEAENKVDVYGYVVKLRRQRCLMVQVEAQYILIHQALVEYNQFGETEV<br>NLSELHPYLHNMKKRDPPSEPSPLEAEFQRLPSYRSWRTQHIGNQEENKSKNRNSNVIPYDYNRVPLKH<br>ELEMSKESEHDSDESSDDDSDSEEPSKYINASFIMSYWKPEVMIAAQGPLKETIGDFWQMIFQRKVKVI<br>VMLTELKHGDQEICAQYWGEGKQTYGDIEVDLKDTDKSSTYTLRVFELRHSKRKDSRTVYQYQYTNWSV<br>EQLPAEPKELISMIQVVKQKLPQKNSSEGNKHHKSTPLLIHCRDGSQQTGIFCALLNLLESAETEEVVD<br>IFQVVKALRKARPGMVSTFEQYQFLYDVIASTYPAQNGQVKKNNHQEDKIEFDNEVDKVKQDANCVNPL<br>GAPEKLPEAKEQAEGSEPTSGTEGPEHSVNGPASPALNQGS |
| 1104 | Rhesus CD45RABC | MTMCLWLKLLAFVFAFLDTEVFVTGQGSTLSPTGRRTTKMPSVPLSSDPLPTHTTAFSPASISERENDF<br>SETTPSLSSDNTSTHVSPDSLDNASAFNTTGVSSALTPHLPTHADSQTPSTGTDTQTPSGSAANTTLSP<br>TPRSNDISDVPGERSTASTFPTDPISPLATTLIPARNSSAALPARTSNTTITANTSVSYLNASETTTPS<br>PSGSTVISTPTIATTTSKPTCAEKYATIPVDYLYNNKTKLFTAKLNVNENVECTNNNHTHNICTNNEVL<br>NLPECKEMNVFVSHNSCTDRHKELKLDVPPEVEKFQLDDCTPDVEANTTICLKWKIIETFACDKSKITY<br>RFQCGNKTYNKEGIYLENLEPEYEYKCDSEILYNNHKYINITKLIKTDFGIPGQPQNVVCRHEDAHQGV<br>ITWNPPQRSFHNFTLCYVSKTAKKCLSLDKHLTTYHLQNLKPYTNYSLSLHAYIIAKVQRNGTAATCNF<br>TTESAPPSQVQNMIVSTSDNSMRVKCEGPRDVNGPTGLYHLEVEAGNTLVRNLSQSKCDFSVNNLQYST<br>YYNLKAYYHNGKYSGEPVILRESTSYNSKALIAFLAFLIIVTSIALLVVLYKIYDLHKKRSCNLDEQQE<br>LVERDDEKQLMNVEPIHADILLETYKRKIADEGRLFLAEFQSIPRVFSKFPIKEARKPFNQNKNRYVDI<br>LPYDYNRVELSEINGDAGSNYINASYIDGFKEPRKYIAAQGPRDETVDDFWRMIWEQKATVIVMVTRCE<br>EGNRNKCAEYWPSMEEGTRAFGDVVVKINQHKRCPDYIIQKLNIVNKKEKATGREVTHIQFTSWPDHGV<br>PEDPHLLLKLRRRVNAFSNFFSGPIVVHCSAGVGRTGTYIGIDAMLEGLEAENKVDVYGYVVKLRRQRC<br>LMVQVEAQYILIHQALVEYNQFGETEVNLSELHPYLHNMKKRDPPSEPSPLEAEFQRLPSYRSWRTQHI<br>GNQEENKNKNRNSNVIPYDYNRVPLKHELEMSKESDHDSDESSDDDSDSEEPSKYINASFIMSYWKPEV<br>MIAAQGPLKETIGDFWQMIFQRKVKVIVMLTELKHGDQEICAQYWGEGKQTYGDIEVDMKDTNKSSTYT<br>LRVFELRHSKRKDSRTVYQYQYTNWSVEQLPAEPKELVSLIQVLKEKLPQKNSSEGNKHHKSTPLLIHC<br>RDGSQQTGIFCALLNLLESAETEEVVDIFQVVKALRKARPGMVSTFEQYQFLYDIIASTYPAQNGQVKK<br>NNHQEDKIEFDNEVDKVKQDANCVNPLGATEKLPEAKEQATGSEPTSGTEGPEHSVNGPASPALNQGS |
| 1105 | cynomolgus CD45RABC | MTMCLWLKLLAFVFAFLDTEVFVTGQGSTLSPTGRRTTKMPSVPLSSDPLPTHTTAFSPASISERENDF<br>SETTPSLSSDNTSTQVSPDSLDNASAFNTTGVSSALTPHLPTHADSQTPSTGTDTQTPSGSAANTTLSP<br>TPRSNDISDVPGERSTASTFPTDPISPLATTLIPARNSSAALPARTSNTTITANTSVSYLNASETTTPS<br>PSGSTVISTPTIATTTSKPTCAEKYATIPVDYLYNNKTKLFTAKLNVNENVECTNNNHTHNICTNNEVL<br>NLPECKEMNVFVSHNSCTDRHKELKLDVPPEVEKFQLDDCTPDVEANTTICLKWKIIETFACDKSKITY<br>RFQCGNKTYNKEGIYLENLEPEYEYKCDSEILYNNHKYINITKLIKTDFGIPGQPQNVVCRHEDAHQGV<br>ITWNPPQRSFHNFTLCYVNKPAKKCLILDKHLTTYHLQNLKPYTNYSLSLHAYIIAKVQRNGTAATCNF<br>TTESAPPSQVQNMIVSTSDNSMHVKCEVPRDVNGPTGLYHLEVEAGNTLVRNLSQSKCDFSVNNLQYST<br>YYNLKAYYHNGKYSGEPVILRESTSYNSKALIAFLAFLIIVTSIALLVVLYKIYDLHKKRSCNLDEQQE<br>LVERDDEKQLMNVEPIHADILLETYKRKIADEGRLFLAEFQSIPRVFSKFPIKEARKPFNQNKNRYVDI<br>LPYDYNRVELSEINGDAGSNYINASYIDGFKEPRKYIAAQGPRDETVDDFWRMIWEQKATVIVMVTRCE<br>EGNRNKCAEYWPSMEEGTRAFGDIVVKINQHKRCPDYIIQKLNIVNKKEKATGREVTHIQFTSWPDHGV<br>PEDPHLLLKLRRRVNAFSNFFSGPIVVHCSAGVGRTGTYIGIDAMLEGLEAENKVDVYGYVVKLRRQRC |

TABLE 4-continued

Exemplary Antigenic Determinant Sequences

| SEQ ID | Antigen | Sequence |
|---|---|---|
| | | LMVQVEAQYILIHQALVEYNQFGETEVNLSELHPYLHNMKKRDPPSEPSPLEAEFQRLPSYRSWRTQHI GNQEENKNKNRNSNVIPYDYNRVPLKHELEMSKESDHDSDESSDDDSDSEEPSKYINASFIMSYWKPEV MIAAQGPLKETIGDFWQMIFQRKVKVIVMLTELKHGDQEICAQYWGEGKQTYGDIEVDMKDTNKSSTYT LRVFELRHSKRKDSRTVYQYQYTNWSVEQLPAEPKELVSLIQVLKEKLPQKNFSEGNKHHKSTPLLIHC RDGSQQTGIFCALLNLLESAETEEVVDIFQVVKALRKARPGMVSTFEQYQFLYDIIASTYPAQNGQVKK NNHQEDKIEFDNEVDKVKQDANCVNPLGATEKLPEAKEQATGSEPTSGTEGPEHSVNGPASPALNQGS |
| 1106 | Human CD45RABC ECD | QSPTPSPTGLTTAKMPSVPLSSDPLPTHTTAFSPASTFERENDFSETTTSLSPDNTSTQVSPDSLDNAS AFNTTGVSSVQTPHLPTHADSQTPSAGTDTQTFSGSAANAKLNPTPGSNAISDVPGERSTASTFPTDPV SPLTTTLSLAHHSSAALPARTSNTTITANTSDAYLNASETTTLSPSGSAVISTTTIATTPSKPTCDEKY ANITVDYLYNKETKLFTAKLNVNENVECGNNTCTNNEVHNLTECKNASVSISHNSCTAPDKTLILDVPP GVEKFQLHDCTQVEKADTTICLKWKNIETFTCDTQNITYRFQCGNMIFDNKEIKLENLEPEHEYKCDSE ILYNNHKFTNASKIIKTDFGSPGEPQIIFCRSEAAHQGVITWNPPQRSFHNFTLCYIKETEKDCLNLDK NLIKYDLQNLKPYTKYVLSLHAYIIAKVQRNGSAAMCHFTTKSAPPSQVWNMTVSMTSDNSMHVKCRPP RDRNGPHERYHLEVEAGNTLVRNESHKNCDFRVKDLQYSTDYTFKAYFHNGDYPGEPFILHHSTSYNSK |
| 1107 | Human CD45RO ECD | QSPTPSPTDAYLNASETTTLSPSGSAVISTTTIATTPSKPTCDEKYANITVDYLYNKETKLFTAKLNVN ENVECGNNTCTNNEVHNLTECKNASVSISHNSCTAPDKTLILDVPPGVEKFQLHDCTQVEKADTTICLK WKNIETFTCDTQNITYRFQCGNMIFDNKEIKLENLEPEHEYKCDSEILYNNHKFTNASKIIKTDFGSPG EPQIIFCRSEAAHQGVITWNPPQRSFHNFTLCYIKETEKDCLNLDKNLIKYDLQNLKPYTKYVLSLHAY IIAKVQRNGSAAMCHFTTKSAPPSQVWNMTVSMTSDNSMHVKCRPPRDRNGPHERYHLEVEAGNTLVRN ESHKNCDFRVKDLQYSTDYTFKAYFHNGDYPGEPFILHHSTSYNSK |
| 1108 | Human CD45RA ECD | QSPTPSPTGLTTAKMPSVPLSSDPLPTHTTAFSPASTFERENDFSETTTSLSPDNTSTQVSPDSLDNAS AFNTTDAYLNASETTTLSPSGSAVISTTTIATTPSKPTCDEKYANITVDYLYNKETKLFTAKLNVNENV ECGNNTCTNNEVHNLTECKNASVSISHNSCTAPDKTLILDVPPGVEKFQLHDCTQVEKADTTICLKWKN IETFTCDTQNITYRFQCGNMIFDNKEIKLENLEPEHEYKCDSEILYNNHKFTNASKIIKTDFGSPGEPQ IIFCRSEAAHQGVITWNPPQRSFHNFTLCYIKETEKDCLNLDKNLIKYDLQNLKPYTKYVLSLHAYIIA KVQRNGSAAMCHFTTKSAPPSQVWNMTVSMTSDNSMHVKCRPPRDRNGPHERYHLEVEAGNTLVRNESH KNCDFRVKDLQYSTDYTFKAYFHNGDYPGEPFILHHSTSYNSK |
| 1109 | Human CD45RB | QSPTPSPTGVSSVQTPHLPTHADSQTPSAGTDTQTFSGSAANAKLNPTPGSNAISDAYLNASETTTLSP SGSAVISTTTIATTPSKPTCDEKYANITVDYLYNKETKLFTAKLNVNENVECGNNTCTNNEVHNLTECK NASVSISHNSCTAPDKTLILDVPPGVEKFQLHDCTQVEKADTTICLKWKNIETFTCDTQNITYRFQCGN MIFDNKEIKLENLEPEHEYKCDSEILYNNHKFTNASKIIKTDFGSPGEPQIIFCRSEAAHQGVITWNPP QRSFHNFTLCYIKETEKDCLNLDKNLIKYDLQNLKPYTKYVLSLHAYIIAKVQRNGSAAMCHFTTKSAP PSQVWNMTVSMTSDNSMHVKCRPPRDRNGPHERYHLEVEAGNTLVRNESHKNCDFRVKDLQYSTDYTFK AYFHNGDYPGEPFILHHSTSYNSK |
| 1110 | Human CD45RAB ECD | QSPTPSPTGLTTAKMPSVPLSSDPLPTHTTAFSPASTFERENDFSETTTSLSPDNTSTQVSPDSLDNAS AFNTTGVSSVQTPHLPTHADSQTPSAGTDTQTFSGSAANAKLNPTPGSNAISDAYLNASETTTLSPSGS AVISTTTIATTPSKPTCDEKYANITVDYLYNKETKLFTAKLNVNENVECGNNTCTNNEVHNLTECKNAS VSISHNSCTAPDKTLILDVPPGVEKFQLHDCTQVEKADTTICLKWKNIETFTCDTQNITYRFQCGNMIF DNKEIKLENLEPEHEYKCDSEILYNNHKFTNASKIIKTDFGSPGEPQIIFCRSEAAHQGVITWNPPQRS FHNFTLCYIKETEKDCLNLDKNLIKYDLQNLKPYTKYVLSLHAYIIAKVQRNGSAAMCHFTTKSAPPSQ VWNMTVSMTSDNSMHVKCRPPRDRNGPHERYHLEVEAGNTLVRNESHKNCDFRVKDLQYSTDYTFKAYF HNGDYPGEPFILHHSTSYNSK |
| 1111 | Human CD45RAC ECD | QSPTPSPTGLTTAKMPSVPLSSDPLPTHTTAFSPASTFERENDFSETTTSLSPDNTSTQVSPDSLDNAS AFNTTDVPGERSTASTFPTDPVSPLTTTLSLAHHSSAALPARTSNTTITANTSDAYLNASETTTLSPSG SAVISTTTIATTPSKPTCDEKYANITVDYLYNKETKLFTAKLNVNENVECGNNTCTNNEVHNLTECKNA SVSISHNSCTAPDKTLILDVPPGVEKFQLHDCTQVEKADTTICLKWKNIETFTCDTQNITYRFQCGNMI FDNKEIKLENLEPEHEYKCDSEILYNNHKFTNASKIIKTDFGSPGEPQIIFCRSEAAHQGVITWNPPQR SFHNFTLCYIKETEKDCLNLDKNLIKYDLQNLKPYTKYVLSLHAYIIAKVQRNGSAAMCHFTTKSAPPS QVWNMTVSMTSDNSMHVKCRPPRDRNGPHERYHLEVEAGNTLVRNESHKNCDFRVKDLQYSTDYTFKAY FHNGDYPGEPFILHHSTSYNSK |
| 1112 | Human CD45RBC ECD | QSPTPSPTGVSSVQTPHLPTHADSQTPSAGTDTQTFSGSAANAKLNPTPGSNAISDVPGERSTASTFPT DPVSPLTTTLSLAHHSSAALPARTSNTTITANTSDAYLNASETTTLSPSGSAVISTTTIATTPSKPTCD EKYANITVDYLYNKETKLFTAKLNVNENVECGNNTCTNNEVHNLTECKNASVSISHNSCTAPDKTLILD VPPGVEKFQLHDCTQVEKADTTICLKWKNIETFTCDTQNITYRFQCGNMIFDNKEIKLENLEPEHEYKC DSEILYNNHKFTNASKIIKTDFGSPGEPQIIFCRSEAAHQGVITWNPPQRSFHNFTLCYIKETEKDCLN LDKNLIKYDLQNLKPYTKYVLSLHAYIIAKVQRNGSAAMCHFTTKSAPPSQVWNMTVSMTSDNSMHVKC RPPRDRNGPHERYHLEVEAGNTLVRNESHKNCDFRVKDLQYSTDYTFKAYFHNGDYPGEPFILHRSTSY NSK |
| 1113 | Human CD26 | MKTPWKVLLGLLGAAALVTIITVPVVLLNKGTDDATADSRKTYTLTDYLKNTYRLKLYSLRWISDHEYL YKQENNILVFNAEYGNSSVFLENSTFDEFGHSINDYSISPDGQFILLEYNYVKQWRHSYTASYDIYDLN KRQLITEERIPNNTQWVTWSPVGHKLAYVWNNDIYVKIEPNLPSYRITWTGKEDIIYNGITDWVYEEEV FSAYSALWWSPNGTFLAYAQFNDTEVPLIEYSFYSDESLQYPKTVRVPYPKAGAVNPTVKFFVVNTDSL SSVTNATSIQITAPASMLIGDHYLCDVTWATQERISLQWLRRIQNYSVMDICDYDESSGRWNCLVARQH IEMSTTGWVGRFRPSEPHFTLDGNSFYKIISNEEGYRHICYFQIDKKDCTFITKGTWEVIGIEALTSDY LYYISNEYKGMPGGRNLYKIQLSDYTKVTCLSCELNPERCQYYSVSFSKEAKYYQLRCSGPGLPLYTLH SSVNDKGLRVLEDNSALDKMLQNVQMPSKKLDFIILNETKFWYQMILPPHFDKSKKYPLLLDVYAGPCS QKADTVFRLNWATYLASTENIIVASFDGRGSGYQGDKIMHAINRRLGTFEVEDQIEAARQFSKMGFVDN |

TABLE 4-continued

| Exemplary Antigenic Determinant Sequences | | |
|---|---|---|
| SEQ ID | Antigen | Sequence |
| | | KRIAIWGWSYGGYVTSMVLGSGSGVFKCGIAVAPVSRWEYYDSVYTERYMGLPTPEDNLDHYRNSTVMS RAENFKQVEYLLIHGTADDNVHFQQSAQISKALVDVGVDFQAMWYTDEDHGIASSTAHQHIYTHMSHFI KQCFSLP |
| 1114 | Human CD30 | MRVLLAALGLLFLGALRAFPQDRPFEDTCHGNPSHYYDKAVRRCCYRCPMGLFPTQQCPQRPTDCRKQC EPDYYLDEADRCTACVTCSRDDLVEKTPCAWNSSRVCECRPGMFCSTSAVNSCARCFFHSVCPAGMIVK FPGTAQKNTVCEPASPGVSPACASPENCKEPSSGTIPQAKPTPVSPATSSASTMPVRGGTRLAQEAASK LTRAPDSPSSVGRPSSDPGLSPTQPCPEGSGDCRKQCEPDYYLDEAGRCTACVSCSRDDLVEKTPCAWN SSRTCECRPGMICATSATNSCARCVPYPICAAETVTKPQDMAEKDTTFEAPPLGTQPDCNPTPENGEAP ASTSPTQSLLVDSQASKTLPIPTSAPVALSSTGKPVLDAGPVLFWVILVLVVVVGSSAFLLCHRRACRK RIRQKLHLCYPVQTSQPKLELVDSRPRRSSTQLRSGASVTEPVAEERGLMSQPLMETCHSVGAAYLESL PLQDASPAGGPSSPRDLPEPRVSTEHTNNKIEKIYIMKADTVIVGTVKAELPEGRGLAGPAEPELEEEL EADHTPHYPEQETEPPLGSCSDVMLSVEEEGKEDPLPTAASGK |
| 1115 | Human CD33 | MPLLLLLPLLWAGALAMDPNFWLQVQESVTVQEGLCVLVPCTFFHPIPYYDKNSPVHGYWFREGAIISR DSPVATNKLDQEVQEETQGRFRLLGDPSRNNCSLSIVDARRRDNGSYFFRMERGSTKYSYKSPQLSVHV TDLTHRPKILIPGTLEPGHSKNLTCSVSWACEQGTPPIFSWLSAAPTSLGPRTTHSSVLIITPRPQDHG TNLTCQVKFAGAGVTTERTIQLNVTYVPQNPTTGIFPGDGSGKQETRAGVVHGAIGGAGVTALLALCLC LIFFIVKTHRRKAARTAVGRNDTHPTTGSASPKHQKKSKLHGPTETSSCSGAAPTVEMDEELHYASLNF HGMNPSKDTSTEYSEVRTQ |
| 1116 | Human CD38 | MANCEFSPVSGDKPCCRLSRRAQLCLGVSILVLILVVVLAVVVPRWRQQWSGPGTTKRFPETVLARCVK YTEIHPEMRHVDCQSVWDAFKGAFISKHPCNITEEDYQPLMKLGTQTVPCNKILLWSRIKDLAHQFTQV QRDMFTLEDTLLGYLADDLTWCGEFNTSKINYQSCPDWRKDCSNNPVSVFWKTVSRRFAEAACDVVHVM LNGSRSKIFDKNSTFGSVEVHNLQPEKVQTLEAWVIHGGREDSRDLCQDPTIKELESIISKRNIQFSCK NIYRPDKFLQCVKNPEDSSCTSEI |
| 1138 | CS1 mature ECD | SGPVKELVGSVGGAVTFPLKSKVKQVDSIVWTFNTTPLVTIQPEGGTIIVTQNRNRERVDFPDGGYSLK LSKLKKNDSGIYYVGIYSSSLQQPSTQEYVLHVYEHLSKPKVTMGLQSNKNGTCVTNLTCCMEHGEEDV IYTWKALGQAANESHNGSILPISWRWGESDMTFICVARNPVSRNFSSPILARKLCEGAADDPDSSM |
| 1139 | CS1 | MAGSPTCLTLIYILWQLTGSAASGPVKELVGSVGGAVTFPLKSKVKQVDSIVWTFNTTPLVTIQPEGGT IIVTQNRNRERVDFPDGGYSLKLSKLKKNDSGIYYVGIYSSSLQQPSTQEYVLHVYEHLSKPKVTMGLQ SNKNGTCVTNLTCCMEHGEEDVIYTWKALGQAANESHNGSILPISWRWGESDMTFICVARNPVSRNFSS PILARKLCEGAADDPDSSMVLLCLLLVPLLLSLFVLGLFLWFLKRERQEEYIEEKKRVDICRETPNICP HSGENTEYDTIPHTNRTILKEDPANTVYSTVEIPKKMENPHSLLTMPDTPRLFAYENVI |
| 42 | HER2 mature ECD | TQVCTGTDMKLRLPASPETHLDMLRHLYQGCQVVQGNLELTYLPTNASLSFLQDIQEVQGYVLIAHNQV RQVPLQRLRIVRGTQLFEDNYALAVLDNGDPLNNTTPVTGASPGGLRELQLRSLTEILKGGVLIQRNPQ LCYQDTILWKDIFHKNNQLALTLIDTNRSRACHPCSPMCKGSRCWGESSEDCQSLTRTVCAGGCARCKG PLPTDCCHEQCAAGCTGPKHSDCLACLHFNHSGICELHCPALVTYNTDTFESMPNPEGRYTFGASCVTA CPYNYLSTDVGSCTLVCPLHNQEVTAEDGTQRCEKCSKPCARVCYGLGMEHLREVRAVTSANIQEFAGC KKIFGSLAFLPESFDGDPASNTAPLQPEQLQVFETLEEITGYLYISAWPDSLPDLSVFQNLQVIRGRIL HNGAYSLTLQGLGISWLGLRSLRELGSGLALIHHNTHLCFVHTVPWDQLFRNPHQALLHTANRPEDECV GEGLACHQLCARGHCWGPGPTQCVNCSQFLRGQECVEECRVLQGLPREYVNARHCLPCHPECQPQNGSV TCFGPEADQCVACARYKEPPFCVARCPSGVKPELSYMPIWKFPDEEGACQPCPINCTHSCVELDEKGCP AEQRASPLT |

TABLE: 5

| Exemplary Adapters | |
|---|---|
| SEQ ID NO: | Adapter Sequence |
| 1082 | DEMGSWDEFGRRLYAIEWRLYALGGSEAELAAFEKEIAAFESELQAYKGKGNPEVEKLREIAAVIRSNLQ AYRHNGGGGSGGGGGGGGSGMLQMAGQCSQNEYFDSLLHACIPCQLRCSSNTPPLTCQRYCNASVTNSV KGTNAGGGGSGGGGSGGGGSHHHHHHHHHH |
| 1083 | DEGGGGSMGSWAEFKQRLAAIKTRLQALGGSEAELAAFEKEIAAFESELQAYKGKGNPEVEALRKEAAAI RDELQAYRHNGGGGSGGGGSGGGGSGMLQMAGQCSQNEYFDSLLHACIPCQLRCSSNTPPLICQRYCNAS VTNSVKGTNAGGGGSGGGGSGGGGSHHHHHHHHHH |
| 1084 | DEHHHHHHHHHHKLENLYFQGGGGGSMGSWDEFGRRLYAIEWRLYALGGSEAELAAFEKEIAAFESELQA YKGKGNPEVEKLREIAAVIRSNLQAYRHNGGGGSGGGGSGGGGSLEKCFQTENPLECQDKGEEELQKYIQ ESQALAKRSCGLFQKLGEYYLQNAFLVAYTKKAPQLTSSELMAITRKMAATAATCCQLSEDKLLACGEGA ADIIIGHLCIRHEMTPVNPGVGQCCTSSYANRRPCFSSLVVDETYVPPAFSDDKFIFHKDLCQAQGVALQ TMKQEFLINLVKQKPQITEEQLEAVIADFSGLLEKCCQGQEQEVCFAEEGQKLISKTRAALGV |
| 1085 | DEHHHHHHHHHHKLENLYFQGGGGGSMGSWSEFWVRLGAIRERLDALGGSEAELAAFEKEIAAFESELQA YKGKGNPEVEKLRYTAATIRRFLQAYRHNGGGGSGGGGSGGGGSLEKCFQTENPLECQDKGEEELQKYIQ ESQALAKRSCGLFQKLGEYYLQNAFLVAYTKKAPQLTSSELMAITRKMAATAATCCQLSEDKLLACGEGA ADIIIGHLCIRHEMTPVNPGVGQCCTSSYANRRPCFSSLVVDETYVPPAFSDDKFIFHKDLCQAQGVALQ TMKQEFLINLVKQKPQITEEQLEAVIADFSGLLEKCCQGQEQEVCFAEEGQKLISKTRAALGV |

TABLE: 5 -continued

| Exemplary Adapters | |
|---|---|
| SEQ ID NO: | Adapter Sequence |
| 1086 | DEHHHHHHHHHHKLENLYFQGGGGGSMGSWAEFKQRLAAIKTRLEALGGSEAELAAFEKEIAAFESELQAYKGKGNPEVEALRKEAAAIRDELQAYRHNGGGGSGGGGSGGGGSLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGV |
| 1087 | DEGGGGSMGSWDEFGRRLYAIEWQLYALGGTEAELAAFEKEIAAFESELQAYKGKGNPEVEKLREIAAVIRENLQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSMGSWDEFGRRLYAIEWQLYALGGTEAELAAFEKEIAAFESELQAYKGKGNPEVEKLREIAAVIRENLQAYRHNGGGGSGGGGSGGGGSHHHHHHHHHH |
| 1088 | DEGGGGSMGSWSEFWVRLGAIRERLDALGGSEAELAAFEKEIAAFESELQAYKGKGNPEVEKLRYTAATIRRFLQAYRHNGGGGGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSMGSWSEFWVRLGAIRERLDALGGSEAELAAFEKEIAAFESELQAYKGKGNPEVEKLRYTAATIRRFLQAYRHNGGGGSGGGGSGGGGSHHHHHHHHHH |
| 1124 | DEGGGGSMGSWSEFWARLGAIRERLDALGGSEAELAAFEKEIAAFESELQAYKGKGNPEVEKLRYTAGTIKRFLQAYRHNGGGGDGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSHHHHHHHHHH |
| 1125 | DEMGSWSEFWARLGAIRERLDALGGSEAELAAFEKEIAAFESELQAYKGKGNPEVEKLRYTAGTIKRFLQAYRHNGGGGDGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSHHHHHHHHHH |
| 1126 | DEMGSWSEFWARLGAIRERLDALGGSEAELAAFEKEIAAFESELQAYKGKGNPEVEKLRYTAGTIKRFLQAYRHNGGGGDGGGGSGGGGSGQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSHHHHHHHHHH |
| 1127 | DEMGSWSEFWARLGAIRERLDALGGSEAELAAFEKEIAAFESELQAYKGKGNPEVEKLRYTAGTIKRFLQAYRHNGGGGDGGGGSGGGGSGKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGGGGGSHHHHHHHHHH |
| 1128 | DEMGSWSEFWARLGAIRERLDALGGSEAELAAFEKEIAAFESELQAYKGKGNPEVEKLRYTAGTIKRFLQAYRHNGGGGDGGGGSGGGGSGGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGGGGGSGGGGSHHHHHHHHHH |
| 1129 | DEGGGGSMGSWSEFWARLGAIRERLDALGGSEAELAAFEKEIAAFESELQAYKGKGNPEVEKLRYTAGTIKRFLQAYRHNGGGGDGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSMGSWSEFWARLGAIRERLDALGGSEAELAAFEKEIAAFESELQAYKGKGNPEVEKLRYTAGTIKRFLQAYRHNGGGGDGGGGSGGGGSHHHHHHHHHH |
| 1130 | DEMGSWSEFWARLGAIRERLDALGGSEAELAAFEKEIAAFESELQAYKGKGNPEVEKLRYTAGTIKRFLQAYRHNGGGGDGGGGSGGGGSGQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGPKLISKTRAALGVGGGGSGGGGSGGGGSMGSWSEFWARLGAIRERLDALGGSEAELAAFEKEIAAFESELQAYKGKGNPEVEKLRYTAGTIKRFLQAYRHNGGGGSGGGGSGGGGSHHHHHHHHHH |
| 1131 | DEMGSWSEFWARLGAIRERLDALGGSEAELAAFEKEIAAFESELQAYKGKGNPEVEKLRYTAGTIKRFLQAYRHNGGGGDGGGGSGGGGSGQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGPKLISKTRAALGVGGGGSGGGGSGGGGSHHHHHHHHHH |
| 1132 | DEMGSWSEFWARLGAIRERLDALGGSEAELAAFEKEIAAFESELQAYKGKGNPEVEKLRYTAGTIKRFLQAYRHNGGGGDGGGGSGGGGSGQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPP |

TABLE: 5 -continued

Exemplary Adapters

| SEQ ID NO: | Adapter Sequence |
|---|---|
| | AFSDDKFIFHKDLCQAQGVALQTMKQEFLINLVKQKPQITEEQLEAVIADFSGLLEKCCQGQEQEVCFAE<br>EGQKLISKTRAALGVGGGGSGGGGSGGGGSMGSWSEFWARLGAIRERLDALGGSEAELAAFEKEIAAFES<br>ELQAYKGKGNPEVEKLRYTAGTIKRFLQAYRHNGGGGSGGGGSGGGGSHHHHHHHHH |
| 1141 | QVQLVESGGGLVQPGGSLKLSCAASGFDESRYWMSWVRQAPGKGLEWIGEINPTSSTINFTPSLKDKVFI<br>SRDNAKNTLYLQMSKVRSEDTALYYCARGNYYRYGDAMDYWGQGTSVTVSGGGGSGGGGSAGGGSDIVLT<br>QSPASLAVSLGQRATISCRASKSVSTSGYSYLHWYQQKPGQPPKLLIYLASNLESGVPARFSGSGSGTDE<br>TLNIHPVEEEDAATYYCQHSRELPFTFGSGTKLEIKGGGGSGGGGSGGGGSGLEKCFQTENPLECQDKGE<br>EELQKYIQESQALAKRSCGLFQKLGEYYLQNAFLVAYTKKAPQLTSSELMAITRKMAATAATCCQLSEDK<br>LLACGEGAADIIIGHLCIRHEMTPVNPGVGQCCTSSYANRRPCFSSLVVDETYVPPAFSDDKFIFHKDLC<br>QAQGVALQTMKQEFLINLVKQKPQITEEQLEAVIADFSGLLEKCCQGQEQEVCFAEEGQKLISKTRAALG<br>V |
| 1142 | DIVLTQSPASLAVSLGQRATISCRASKSVSTSGYSYLHWYQQKPGQPPKLLIYLASNLESGVPARFSGSG<br>SGTDFTLNIHPVEEEDAATYYCQHSRELPFTFGSGTKLEIKGGGGSGGGGSAGGGSQVQLVESGGGLVQP<br>GGSLKLSCAASGFDFSRYWMSWVRQAPGKGLEWIGEINPTSSTINFTPSLKDKVFISRDNAKNTLYLQMS<br>KVRSEDTALYYCARGNYYRYGDAMDYWGQGTSVTVSGGGGSGGGGSGGGGSGLEKCFQTENPLECQDKGE<br>EELQKYIQESQALAKRSCGLFQKLGEYYLQNAFLVAYTKKAPQLTSSELMAITRKMAATAATCCQLSEDK<br>LLACGEGAADIIIGHLCIRHEMTPVNPGVGQCCTSSYANRRPCFSSLVVDETYVPPAFSDDKFIFHKDLC<br>QAQGVALQTMKQEFLINLVKQKPQITEEQLEAVIADFSGLLEKCCQGQEQEVCFAEEGQKLISKTRAALG<br>V |
| 1143 | LEKCFQTENPLECQDKGEEELQKYIQESQALAKRSCGLFQKLGEYYLQNAFLVAYTKKAPQLTSSELMAI<br>TRKMAATAATCCQLSEDKLLACGEGAADIIIGHLCIRHEMTPVNPGVGQCCTSSYANRRPCFSSLVVDET<br>YVPPAFSDDKFIFHKDLCQAQGVALQTMKQEFLINLVKQKPQITEEQLEAVIADFSGLLEKCCQGQEQEV<br>CFAEEGQKLISKTRAALGVGGGGSGGGGSGGGGSGQVQLVESGGGLVQPGGSLKLSCAASGFDFSRYWMS<br>WVRQAPGKGLEWIGEINPTSSTINFTPSLKDKVFISRDNAKNTLYLQMSKVRSEDTALYYCARGNYYRYG<br>DAMDYWGQGTSVTVSGGGGSGGGGSAGGGSDIVLTQSPASLAVSLGQRATISCRASKSVSTSGYSYLHWY<br>QQKPGQPPKLLIYLASNLESGVPARFSGSGSGTDFTLNIHPVEEEDAATYYCQHSRELPFTFGSGTKLEI<br>K |
| 1144 | LEKCFQTENPLECQDKGEEELQKYIQESQALAKRSCGLFQKLGEYYLQNAFLVAYTKKAPQLTSSELMAI<br>TRKMAATAATCCQLSEDKLLACGEGAADIIIGHLCIRHEMTPVNPGVGQCCTSSYANRRPCFSSLVVDET<br>YVPPAFSDDKFIFHKDLCQAQGVALQTMKQEFLINLVKQKPQITEEQLEAVIADESGLLEKCCQGQEQEV<br>CFAEEGQKLISKTRAALGVGGGGSGGGGSGGGGSGDIVLTQSPASLAVSLGQRATISCRASKSVSTSGYS<br>YLHWYQQKPGQPPKLLIYLASNLESGVPARFSGSGSGTDFTLNIHPVEEEDAATYYCQHSRELPFTFGSG<br>TKLEIKGGGGSGGGGSAGGGSQVQLVESGGGLVQPGGSLKLSCAASGFDFSRYWMSWVRQAPGKGLEWIG<br>EINPTSSTINFTPSLKDKVFISRDNAKNTLYLQMSKVRSEDTALYYCARGNYYRYGDAMDYWGQGTSVTV<br>S |
| 1145 | DIVLTQSPASLAVSLGQRATISCRASKSVSTSGYSYLHWYQQKPGQPPKLLIYLASNLESGVPARESGSG<br>SGTDFTLNIHPVEEEDAATYYCQHSRELPFTFGSGTKLEIKGGGGSGGGGSAGGGSQVQLVESGGGLVQP<br>GGSLKLSCAASGFDFSRYWMSWVRQAPGKGLEWIGEINPTSSTINFTPSLKDKVFISRDNAKNTLYLQMS<br>KVRSEDTALYYCARGNYYRYGDAMDYWGQGTSVTVSGGGGSGGGGSGGGGSGLEKCFQTENPLECQDKGE<br>EELQKYIQESQALAKRSCGLFQKLGEYYLQNAFLVAYTKKAPQLTSSELMAITRKMAATAATCCQLSEDK<br>LLACGEGAADIIIGHLCIRHEMTPVNPGVGQCCTSSYANRRPCFSSLVVDETYVPPAFSDDKFIFHKDLC<br>QAQGVALQTMKQEFLINLVKQKPQITEEQLEAVIADFSGLLEKCCQGQEQEVCFAEEGQKLISKTRAALG<br>VGGGGSGGGGSGGGGSGDIVLTQSPASLAVSLGQRATISCRASKSVSTSGYSYLHWYQQKPGQPPKLLIY<br>LASNLESGVPARFSGSGSGTDFTLNIHPVEEEDAATYYCQHSRELPFTFGSGTKLEIKGGGGSGGGGSAG<br>GGSQVQLVESGGGLVQPGGSLKLSCAASGFDFSRYWMSWVRQAPGKGLEWIGEINPTSSTINFTPSLKDK<br>VFISRDNAKNTLYLQMSKVRSEDTALYYCARGNYYRYGDAMDYWGQGTSVTVS |
| 1146 | QVQLVESGGGLVQPGGSLKLSCAASGEDFSRYWMSWVRQAPGKGLEWIGEINPTSSTINFTPSLKDKVFI<br>SRDNAKNTLYLQMSKVRSEDTALYYCARGNYYRYGDAMDYWGQGTSVTVSGGGGSGGGGSAGGGSDIVLT<br>QSPASLAVSLGQRATISCRASKSVSTSGYSYLHWYQQKPGQPPKLLIYLASNLESGVPARFSGSGSGTDF<br>TLNIHPVEEEDAATYYCQHSRELPFTFGSGTKLEIKGGGGSGGGGSGGGGSGLEKCFQTENPLECQDKGE<br>EELQKYIQESQALAKRSCGLFQKLGEYYLQNAFLVAYTKKAPQLTSSELMAITRKMAATAATCCQLSEDK<br>LLACGEGAADIIIGHLCIRHEMTPVNPGVGQCCTSSYANRRPCFSSLVVDETYVPPAFSDDKFIFHKDLC<br>QAQGVALQTMKQEFLINLVKQKPQITEEQLEAVIADFSGLLEKCCQGQEQEVCFAEEGQKLISKTRAALG<br>VGGGGSGGGGSGGGGSGQVQLVESGGGLVQPGGSLKLSCAASGFDFSRYWMSWVRQAPGKGLEWIGEINP<br>TSSTINFTPSLKDKVFISRDNAKNTLYLQMSKVRSEDTALYYCARGNYYRYGDAMDYWGQGTSVTVSGGG<br>GSGGGGSAGGGSDIVLTQSPASLAVSLGQRATISCRASKSVSTSGYSYLHWYQQKPGQPPKLLIYLASNL<br>ESGVPARFSGSGSGTDFTLNIHPVEEEDAATYYCQHSRELPFTFGSGTKLEIK |
| 1147 | DIVLTQSPASLAVSLGQRATISCRASKSVSTSGYSYLHWYQQKPGQPPKLLIYLASNLESGVPARFSGSG<br>SGTDFTLNIHPVEEEDAATYYCQHSRELPFTFGSGTKLEIKGGGGSGGGGSAGGGSQVQLVESGGGLVQP<br>GGSLKLSCAASGFDFSRYWMSWVRQAPGKGLEWIGEINPTSSTINFTPSLKDKVFISRDNAKNTLYLQMS<br>KVRSEDTALYYCARGNYYRYGDAMDYWGQGTSVTVSGGGGSGGGGSGGGGSGLEKCFQTENPLECQDKGE<br>EELQKYIQESQALAKRSCGLFQKLGEYYLQNAFLVAYTKKAPQLTSSELMAITRKMAATAATCCQLSEDK<br>LLACGEGAADIIIGHLCIRHEMTPVNPGVGQCCTSSYANRRPCFSSLVVDETYVPPAFSDDKFIFHKDLC<br>QAQGVALQTMKQEFLINLVKQKPQITEEQLEAVIADFSGLLEKCCQGQEQEVCFAEEGQKLISKTRAALG<br>VGGGGSGGGGSGGGGSGQVQLVESGGGLVQPGGSLKLSCAASGFDFSRYWMSWVRQAPGKGLEWIGEINP<br>TSSTINFTPSLKDKVFISRDNAKNTLYLQMSKVRSEDTALYYCARGNYYRYGDAMDYWGQGTSVTVSGGG<br>GSGGGGSAGGGSDIVLTQSPASLAVSLGQRATISCRASKSVSTSGYSYLHWYQQKPGQPPKLLIYLASNL<br>ESGVPARFSGSGSGTDFTLNIHPVEEEDAATYYCQHSRELPFTFGSGTKLEIK |

TABLE: 5 -continued

| Exemplary Adapters | |
|---|---|
| SEQ ID NO: | Adapter Sequence |
| 1148 | QVQLVESGGGLVQPGGSLKLSCAASGFDESRYWMSWVRQAPGKGLEWIGEINPTSSTINFTPSLKDKVFISRDNAKNTLYLQMSKVRSEDTALYYCARGNYYRYGDAMDYWGQGTSVTVSGGGGSGGGGSAGGGSDIVLTQSPASLAVSLGQRATISCRASKSVSTSGYSYLHWYQQKPGQPPKLLIYLASNLESGVPARFSGSGSGTDFTLNIHPVEEEDAATYYCQHSRELPFTFGSGTKLEIKGGGGSGGGGGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGDIVLTQSPASLAVSLGQRATISCRASKSVSTSGYSYLHWYQQKPGQPPKLLIYLASNLESGVPARFSGSGSGTDFTLNIHPVEEEDAATYYCQHSRELPFTFGSGTKLEIKGGGGSGGGGSAGGGSQVQLVESGGGLVQPGGSLKLSCAASGFDFSRYWMSWVRQAPGKGLEWIGEINPTSSTINFTPSLKDKVFISRDNAKNTLYLQMSKVRSEDTALYYCARGNYYRYGDAMDYWGQGTSVTVS |
| 1150 | MGSWAEFKQRLAAIKTRLEALGGSEAELAAFEKEIAAFESELQAYKGKGNPEVEALRKEAAAIRDELQAYRHNGGGGGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWVEFNERLHAIYLRLDALGGSEAELAAFEKEIAAFESELQAYKGKGNPEVETLRRHAAGIRWQLQAYRHNGGGGSGGGGSGGGSHHHHHHHHHH |
| 1151 | MGSWAEFKQRLAAIKTRLEALGGSEAELAAFEKEIAAFESELQAYKGKGNPEVEALRKEAAAIRDELQAYRHNGGGGSGGGGGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGGGGGSGMGSWVEFEARLSAIYERLEALGGSEAELAAFEKEIAAFESELQAYKGKGNPEVEKLRRHAAGIRSNLQAYRHNGGGGSGGGGSGGGSHHHHHHHHHH |
| 1152 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWVEFFVRLDAIWERLEALGGSEAELAAFEKEIAAFESELQAYKGKGNPEVETLRFHAAGIRQKLQAYRHNGGGGSGGGGSGGGSHHHHHHHHHH |
| 1153 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWNEFKLELAFIKDWLEALGGSEAELANFEEAIAEFEAGLQGYKGKGNPEVEALRKEAAAIRDELQAYRHNGGGGSGGGGSGGGSHHHHHHHHHH |
| 1154 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWMEFEARLEAIWDRLEALGGSEAELAAFEKEIAAFESELQAYKGKGNPEVESLRFHAAGIRQHLQAYRHNGGGGSGGGGSGGGSHHHHHHHHHH |
| 1155 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWHHFKMHLAGIKLQLEALGGSEAELAEFEEWIADFEGALQDYKGKGNPEVEALRKEAAAIRDELQAYRHNGGGGSGGGGSGGGSHHHHHHHHHH |
| 1156 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWAEFKQRLAAIKTRLEALGGSEAELAAFEKEIAAFESELQAYKGKGNPEVEALRKEAAAIRDELQAYRHNGGGGSGGGGSGGGSHHHHHHHHHH |
| 1157 | MGSWAEFKQRLAAIKTRLEALGGSEAELAAFEKEIAAFESELQAYKGKGNPEVEALRKEAAAIRDELQAYRHNGGGGSGGGGSGGGGSGLEKCFQTENPLECQDKGEEELQKYIQESQALAKRSCGLFQKLGEYYLQNAFLVAYTKKAPQLTSSELMAITRKMAATAATCCQLSEDKLLACGEGAADIIIGHLCIRHEMTPVNPGVGQCCTSSYANRRPCFSSLVVDETYVPPAFSDDKFIFHKDLCQAQGVALQTMKQEFLINLVKQKPQITEEQLEAVIADFSGLLEKCCQGQEQEVCFAEEGQKLISKTRAALGVGGGGSGGGGSGGGGSGMGSWAEFRWRLHAIWLQLGALGGSEAELAAFEKEIAAFESELQAYKGKGNPEVEWLRQDAAQIKYILQAYRHNGGGGSGGGGSGGGSHHHHHHHHHH |

TABLE: 5 -continued

| Exemplary Adapters | |
|---|---|
| SEQ ID NO: | Adapter Sequence |
| 1158 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWKTFKIELAGIKL<br>ELEALGGSEAELAGFENAIAQFESSLQYYKGKGNPEVEALRKEAAAIRDELQAYRHNGGGGSGGGGSGGG<br>GSHHHHHHHHHH |
| 1159 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWHEFLRRLLAIEM<br>RLYALGGSEAELAAFEKEIAAFESELQAYKGKGNPEVEHLRVRAASIRQMLQAYRHNGGGGSGGGGSGGG<br>GSHHHHHHHHHH |
| 1160 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWWEFRVRLEAIDY<br>RLKALGGSEAELAAFEKEIAAFESELQAYKGKGNPEVEYLRMKAATIRAILQAYRHNGGGGSGGGGSGGG<br>GSHHHHHHHHHH |
| 1161 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWYEFRWRLHAIWL<br>RLGALGGSEAELAAFEKEIAAFESELQAYKGKGNPEVEWLRQDAAQIRYILQAYRHNGGGGSGGGGSGGG<br>GSHHHHHHHHHH |
| 1162 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWWEFNIRLHAIDY<br>RLKALGGSEAELAAFEKEIAAFESELQAYKGKGNPEVELLREKAAQIRAQLQAYRHNGGGGSGGGGSGGG<br>GSHHHHHHHHHH |
| 1163 | MGSWAEFKQRLAAIKTRLEALGGSEAELAAFEKEIAAFESELQAYKGKGNPEVEALRKEAAAIRDELQAY<br>RHNGGGGSGGGGSGGGGSGLEKCFQTENPLECQDKGEEELQKYIQESQALAKRSCGLFQKLGEYYLQNAF<br>LVAYTKKAPQLTSSELMAITRKMAATAATCCQLSEDKLLACGEGAADIIIGHLCIRHEMTPVNPGVGQCC<br>TSSYANRRPCFSSLVVDETYVPPAFSDDKFIFHKDLCQAQGVALQTMKQEFLINLVKQKPQITEEQLEAV<br>IADFSGLLEKCCQGQEQEVCFAEEGQKLISKTRAALGVGGGGSGGGGSGGGGSGMGSWWEFNMRLSAIKY<br>RLYALGGSEAELAAFEKEIAAFESELQAYKGKGNPEVEILRRLAADIRERLQAYRHNGGGGSGGGGSGGG<br>GSHHHHHHHHHH |

TABLE 6

| Exemplary ADBD CAR Sequences | | |
|---|---|---|
| SEQ ID NO: | CAR Design | CAR Sequence |
| 1089 | CTsp-Flag-GSlinker-α3D(Q19E)-GSlinker-CD8H-TM-41BB-CD3ζ | MAFLWLLSCWALLGTTFGDYKDDDDKGGGGSGGGGSMGSWAEFKQRLAAIKTRLEALGGSE<br>AELAAFEKEIAAFESELQAYKGKGNPEVEALRKEAAAIRDELQAYRHNGQAGSGTTTPAPR<br>PPTPAPTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAYKQGQN<br>QLYNELNLGRREEYDVLDKRRGRDPEMGGKPRRKNPQEGLYNELQKDKMAEAYSEIGMKGE<br>RRRGKGHDGLYQGLSTATKDTYDALHMQALPPR |
| 1090 | CTsp-Flag-GSlinker-cg06-GSlinker-CD8H-TM-41BB-CD3ζ | MAFLWLLSCWALLGTTFGDYKDDDDKGGGGSGGGGSMGSWDEFGRRLYAIEWRLYALGGSE<br>AELAAFEKEIAAFESELQAYKGKGNPEVEKLREIAAVIRSNLQAYRHNGGGGSGGGGSGTT<br>TPAPRPPTPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSRSADAPAY<br>KQGQNQLYNELNLGRREEYDVLDKRRGRDPEMGGKPRRKNPQEGLYNELQKDKMAEAYSEI<br>GMKGERRRGKGHDGLYQGLSTATKDTYDALHMQALPPR |
| 1091 | CTsp-Flag-GSlinker-bc40-GSlinker-CD8H-TM-41BB-CD3ζ | MAFLWLLSCWALLGTTFGDYKDDDDKGGGGSGGGGSMGSWSEFWVRLGAIRERLDALGGSE<br>AELAAFEKEIAAFESELQAYKGKGNPEVEKLRYTAATIRRFLQAYRHNGGGGSGGGGSGTT<br>TPAPRPPTPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSRSADAPAY |

TABLE 6-continued

Exemplary ADBD CAR Sequences

| SEQ ID NO: | CAR Design | CAR Sequence |
|---|---|---|
| | | KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| 1092 | CTsp-Flag-GSlinker-af03-GSlinker-CD8H-TM-41BB-CD3ζ | MAFLWLLSCWALLGTTFGDYKDDDDKGGGGSGGGGSMGSWFEFYDRLNAIDARLWALGGSE AELAAFEKEIAAFESELQAYKGKGNPEVENLRVHAAAIREWLQAYRHNGGGGSGGGGSGTT TPAPRPPTPAPTIASMGSWAEFKQRLAAIKTRLEALGGSEAELAAFEKEIAAFESELQAYK GKGNPEVEALRKEAAAIRDELQAYRHNQPLSLRPEACRPAAGGAVHTRGLDFACDIYIWAP LAGTCGVLLLSLVITLYCKRGRKKLLYIFKQPFMRPVQTTQEEDGCSCRFPEEEEGGCELR VKFSRSADAPAYKQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR |
| 1093 | CTsp-Flag-GSlinker-af05-GSlinker-CD8H-TM-41BB-CD3ζ | MAFLWLLSCWALLGTTFGDYKDDDDKGGGGSGGGGSMGSWLEFYHRLNAIDSRLWALGGSE AELAAFEKEIAAFESELQAYKGKGNPEVESLRDHAAHIREWLQAYRHNGGGGSGGGGSGTT TPAPRPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| 1133 | CTsp-Flag-GSlinker-af59-GSlinker-CD8H-TM-41BB-CD3ζ | MAFLWLLSCWALLGTTFGDYKDDDDKGGGGSGGGGSMGSWFEFYDRLNAIDARLWALGGSE AELAAFEKEIAAFESELQAYKGKGNPEVESLRVHAAAIREWLQAYRHNGGGGSGGGGSGTT TPAPRPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| 1134 | CTsp-Flag-GSlinker-af83-GSlinker-CD8H-TM-41BB-CD3ζ | MAFLWLLSCWALLGTTFGDYKDDDDKGGGGSGGGGSMGSWSEFYDRLNAIDARLWALGGSE AELAAFEKEIAAFESELQAYKGKGNPEVESLRVHAAAIREWLQAYRHNGGGGSGGGGSGTT TPAPRPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| 1135 | CTsp-Flag-GSlinker-af99-GSlinker-CD8H-TM-41BB-CD3ζ | MAFLWLLSCWALLGTTFGDYKDDDDKGGGGSGGGGSMGSWFEFYDRLNAIDARLWALGGSE AELAAFEKEIAAFESELQAYKGKGNPEVESLREHAAAIREWLQAYRHNGGGGSGGGGSGTT TPAPRPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| 1136 | CTsp-Flag-GSlinker-af101-GSlinker-CD8H-TM-41BB-CD3ζ | MAFLWLLSCWALLGTTFGDYKDDDDKGGGGSGGGGSMGSWSEFYDRLNAIDARLWALGGSE AELAAFEKEIAAFESELQAYKGKGNPEVESLREHAAAIREWLQAYRHNGGGGSGGGGSGTT TPAPRPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |

Example 2. D-Domain CAR T Cells Kill Tumor Cells Expressing the D Domain Target The cytolytic activity of ADBD CAR expressing T cells was assessed on a panel of tumors using effector cell to target cell ratios ranging from 1:4 to 1:64. The cytolytic activity of a CD123-binding CAR (cg06, SEQ ID NO: 1090); a BCMA binding CAR (bc40, SEQ ID NO: 1091) were compared to a CAR with no known target-specificity (α3D-Q19E, SEQ ID NO: 1089).

10,000 T cells expressing the indicated CARs were incubated with increasing numbers of a $CD123^{+}/BCMA^{-}$ tumor target (MOLM13) (FIG. 1A); a $CD123^{-}/BCMA^{+}$ tumor target (H929) (FIG. 1B); a $CD123^{-}$ tumor target (RAJI) (FIG. 1C); or a $CD123^{+}/BCMA^{-}$ tumor target (MOLM13) (FIG. 1D). After 16 hours, cells were washed and luciferase activity was assessed.

Figure 2A:
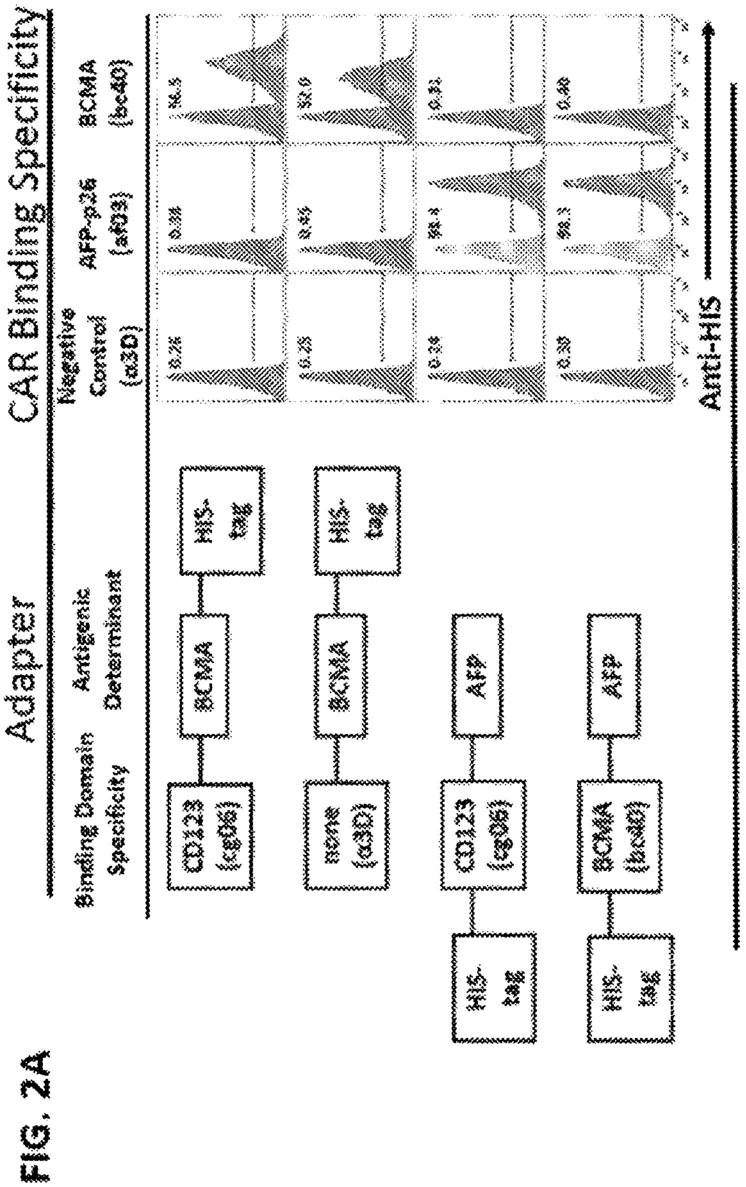
Figure 2B:
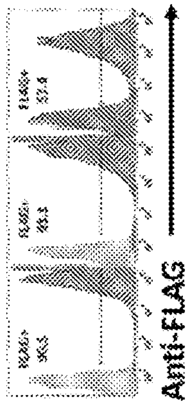

Example 3. Adapter Binding Associates with Adapter and CAR Binding Specificity Jurkat NFAT-Luciferase reporter cells were transduced with a negative control CAR (α3D-Q19E, SEQ ID NO: 1089), an p26-binding CAR (af03, SEQ ID NO: 1092), or a BCMA-binding CAR (bc40, SEQ ID NO: 1091). In FIG. 2A, CAR transduced Jurkat cells were incubated with 0.5 μg of Adapter protein (SEQ ID NO: 1082-1085) at 4° C. for 20 minutes, washed, and then stained with anti-HIS PE (clone J095G46, 4° C. for 20 minutes). CAR expression based on FLAG staining (clone L5) versus mock transduced Jurkat cells was also evaluated (FIG. 2B).

Example 4. Adapter Binding of Matching CAR: Adapter and Target: Adapter Specificity Drives Lysis of Target Cells 40,000 $CD123^{+}BCMA^{-}$ MOLM13-GFP/Luciferase cells were incubated with various Adapters (SEQ ID NO: 1082-1084) in the presence or absence of 20,000 T cells (E:T ratio of 1:2, donor D14-053017, Day 7) transduced with BCMA-binding CAR (bc40, SEQ ID NO: 1091) for 16 hours. After 16 hours, cells were washed and luciferase activity was assessed. Percent lysis was assessed based on wells of MOLM13-GFP/Luciferase cultured in the absence of T cells or Adapter protein (see, FIG. 3A). A control of CD123-specific CAR T cells (cg06, SEQ ID NO: 1090) cultured at the same ratio was used as a positive control for lysis.

In FIG. 3B, 40,000 CD123⁺BCMA⁻ MOLM13-GFP/Luciferase cells were incubated with Adapter (cg06-p26, SEQ ID NO: 1084) in the presence or absence of 20,000 T cells (E:T ratio of 1:2, donor D16-061317, Day 7) transduced with p26-binding CARs (Af03, SEQ ID NO: 1092) or Af05, SEQ ID NO: 1093) for 16 hours. After 16 hours, cells were washed and luciferase activity was assessed. Percent lysis was assessed based on wells of MOLM13-GFP/Luciferase cultured in the absence of T cells or Adapter protein. A control of CD123-binding CAR T cells (cg06, SEQ ID NO: 1090) cultured at the same ratio was used as a positive control for lysis In FIG. 3C, 40,000 BCMA⁺ NCI H929-GFP/Luciferase cells were incubated with Adapter (bc40-p26, SEQ ID NO: 1085 in the presence or absence of 10,000 T cells (E:T ratio of 1:4, donor D15-062017, Day 8) mock transduced, or transduced with p26-binding CARs (Af03, SEQ ID NO: 1092 or Af05, SEQ ID NO: 1093) for 16 hours. After 16 hours, cells were washed and luciferase activity was assessed. Percent lysis was assessed based on wells of NCI-H929-GFP/Luciferase cultured in the absence of T cells or Adapter protein.

Figure 4B:
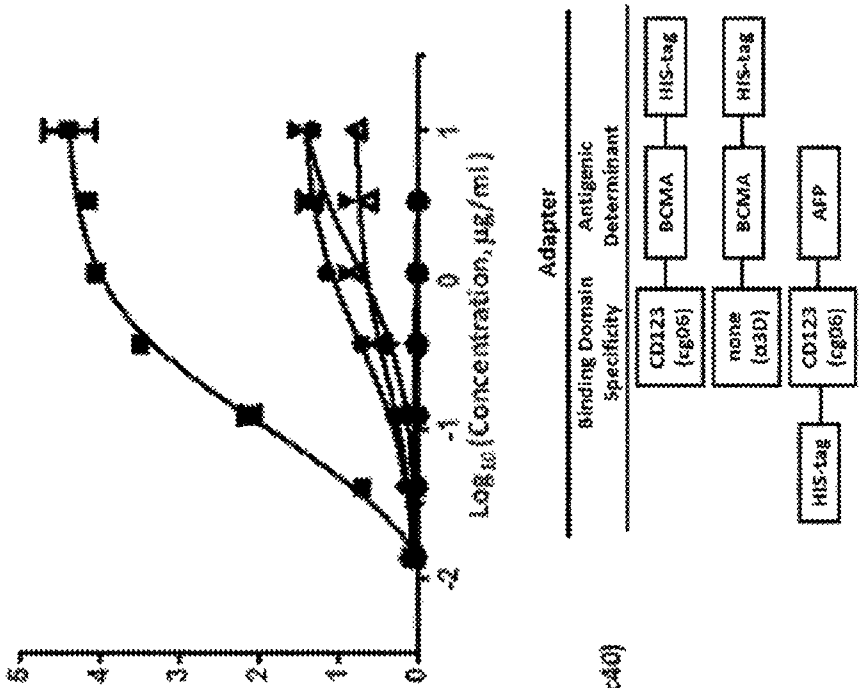
Figure 4A:
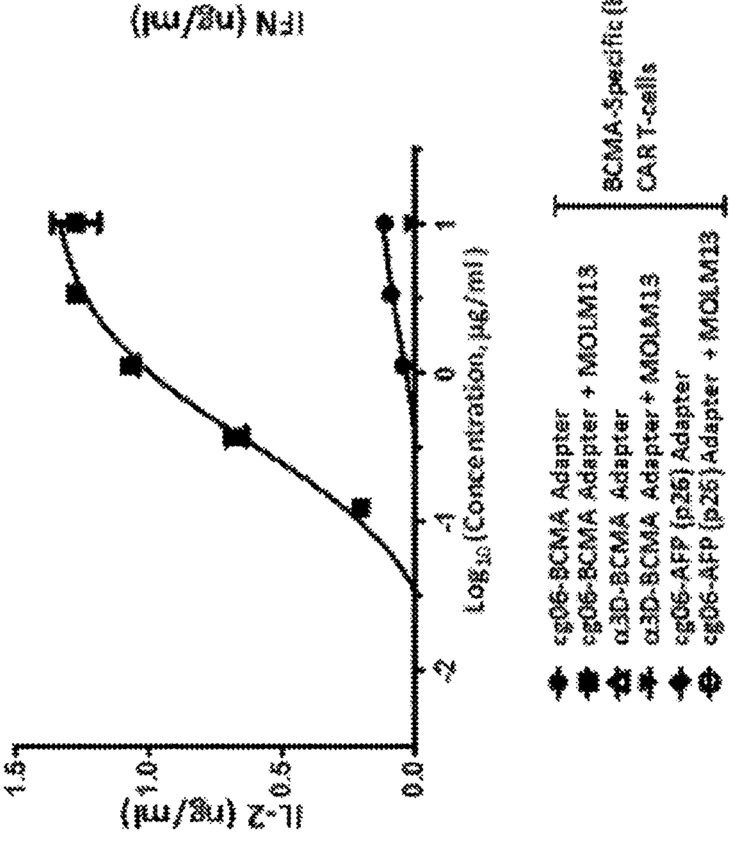
Figures 4C, 4D:
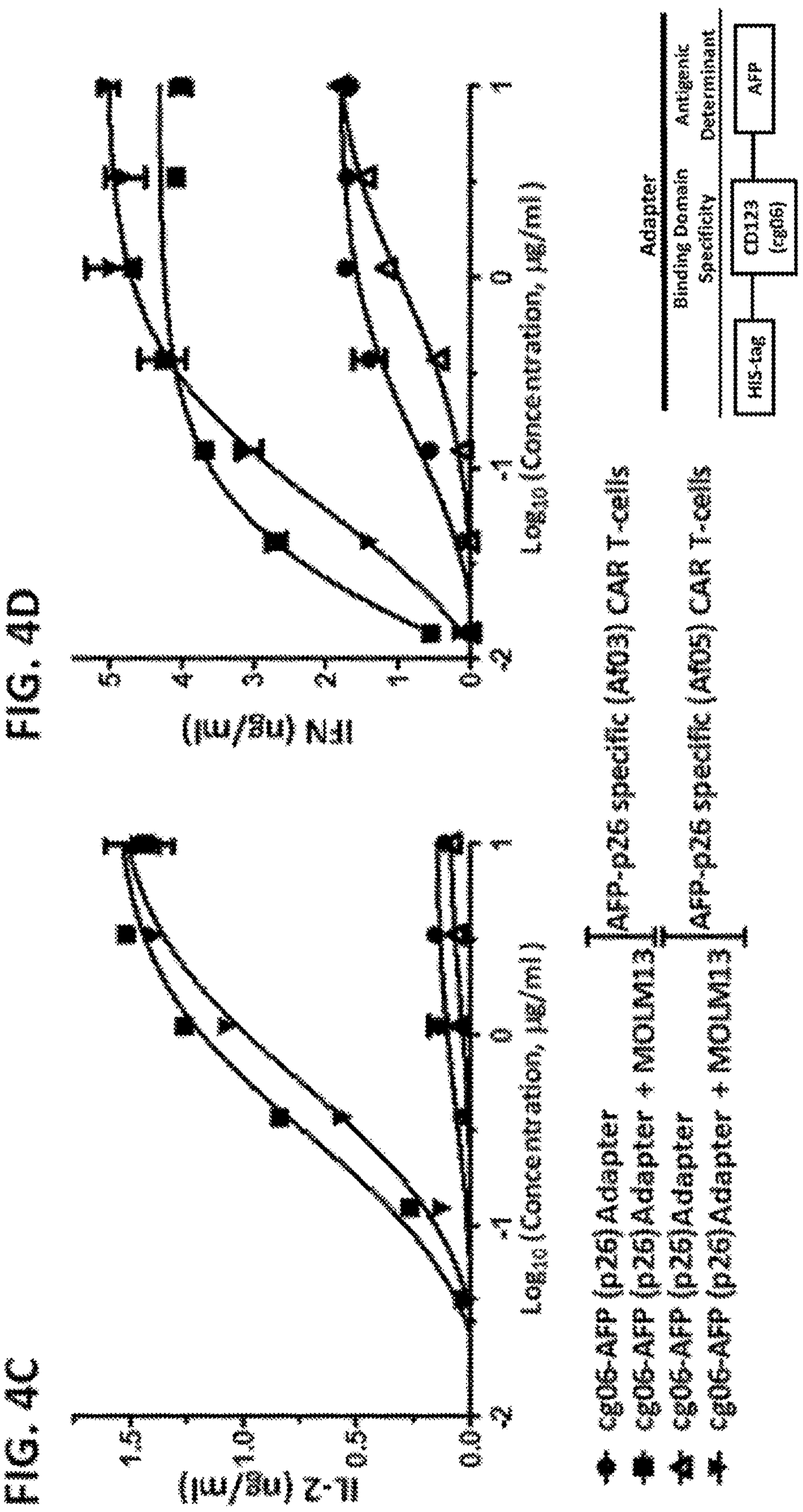

Example 5. Adapter Binding of Matching CAR: Adapter and Target: Adapter Specificity Drives Cytokine Production by CAR T-Cells Donor D14-053017 T cells transduced with BCMA-binding CAR (bc40, SEQ ID NO: 1091) were cultured overnight with various Adapters (cg06-BCMA, SEQ ID NO: 1082; α3D-BCMA, SEQ ID NO: 1083; or cg06-p26, SEQ ID NO: 1084) in the presence or absence of CD123⁺BCMA⁻ MOLM13 cells (25,000 T cells and target cells). Cultured supernatants were collected and assessed for the production of IL-2 (FIG. 4A) and IFN-γ (FIG. 4B). In FIGS. 4C and 4D, donor D15-062017 T cells transduced with p26-binding CARs (Af03, SEQ ID NO: 1092 or Af05, SEQ ID NO: 1093) were cultured overnight with CD123 binding Adapter (cg06p26, SEQ ID NO: 1084) Adapter in the presence or absence of CD123⁺BCMA⁻ MOLM13 cells (25,000 T cells and target cells). Cultured supernatants were collected and assessed for the production of IL-2 (FIG. 4C) and IFN-γ (FIG. 4D).

Figure 5:
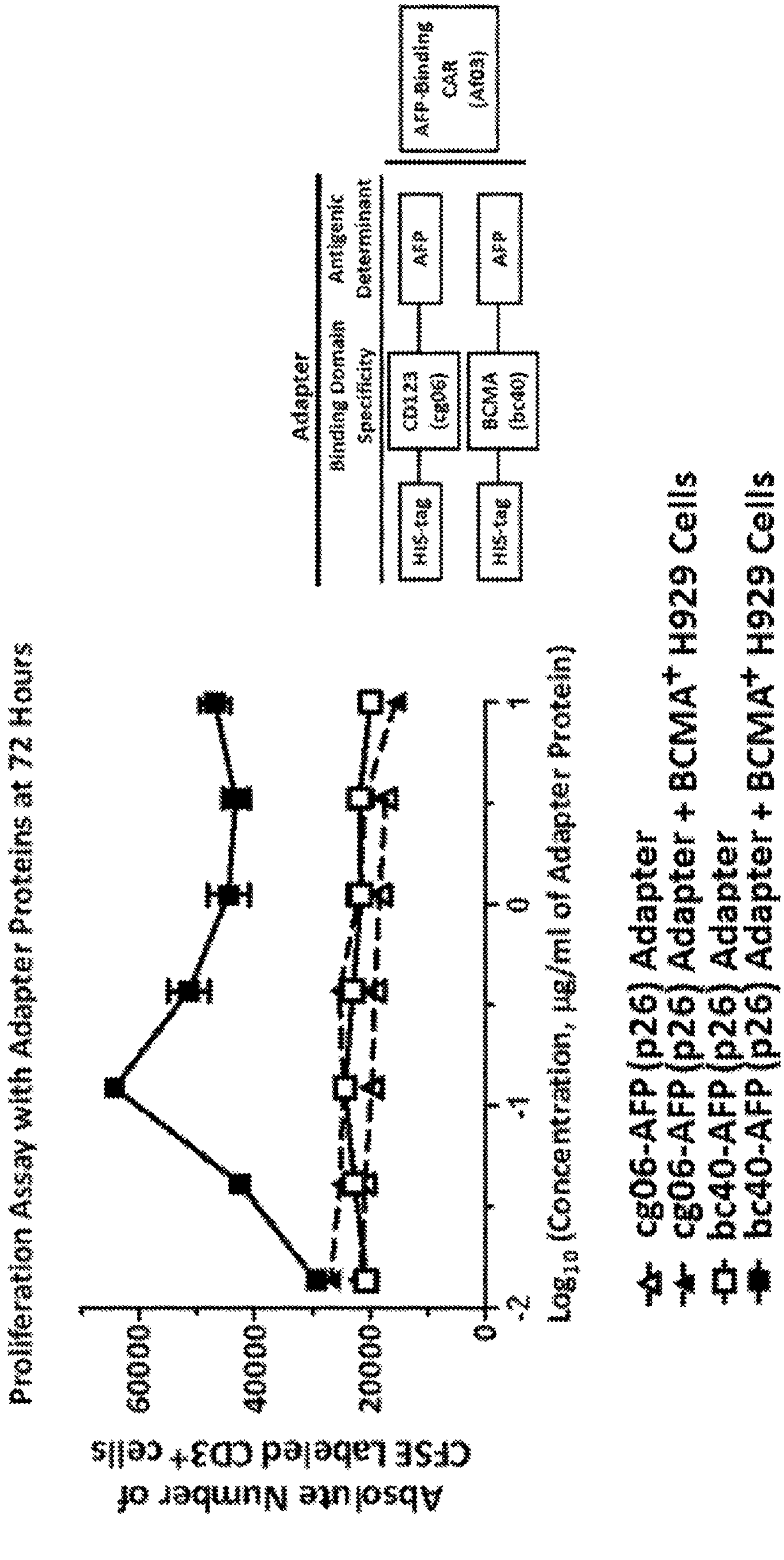

Example 6. CAR T Cells Proliferate Following Exposure to an Adapter that is Bound by the CAR and Bound to a Tumor Expressing the AD Recognized by the Adapter In FIG. 5, Donor D16-062717 cells transduced with AFP-binding CAR (Af03, SEQ ID NO: 1092) were CFSE labeled (10 minutes at 0.5 μM), then cultured (25,000) in the presence of CD123-binding Adapter (cg06-p26, SEQ ID NO: 1084) or BCMA-binding Adapter (bc40-p26, SEQ ID NO: 1085) in the presence or absence of mitomycin-C treated CD123⁻BCMA⁺ NCI-H929 cells (25,000) for 72 hours. At 72 hours, cells were stained for CD3, then analyzed for absolute numbers of CD3+ cells via flow cytometry.

Example 7. Adapter Binding of Matching CAR: Adapter and Target: Adapter Specificity Signaling by CAR T Cells 50,000 reporter cells previously transduced with a BCMA-binding CAR (bc40, SEQ ID NO: 1091) were cultured for 5 hours in the presence of various Adapters (cg06-BCMA, SEQ ID NO: 1082; α3D-BCMA, SEQ ID NO: 1083; or cg06-p26, SEQ ID NO: 1084) in the presence or absence of 50,000 CD123⁺BCMA⁻ MOLM14 cells, then assessed for luciferase activity (FIG. 6A).

Figure 6A:
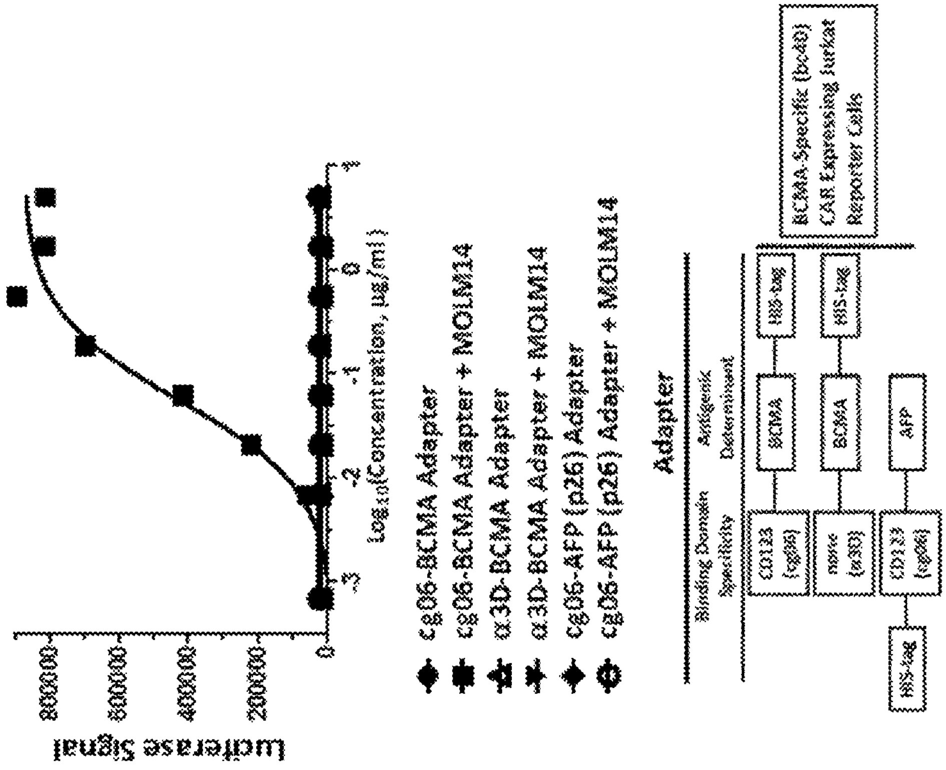
Figure 6B:
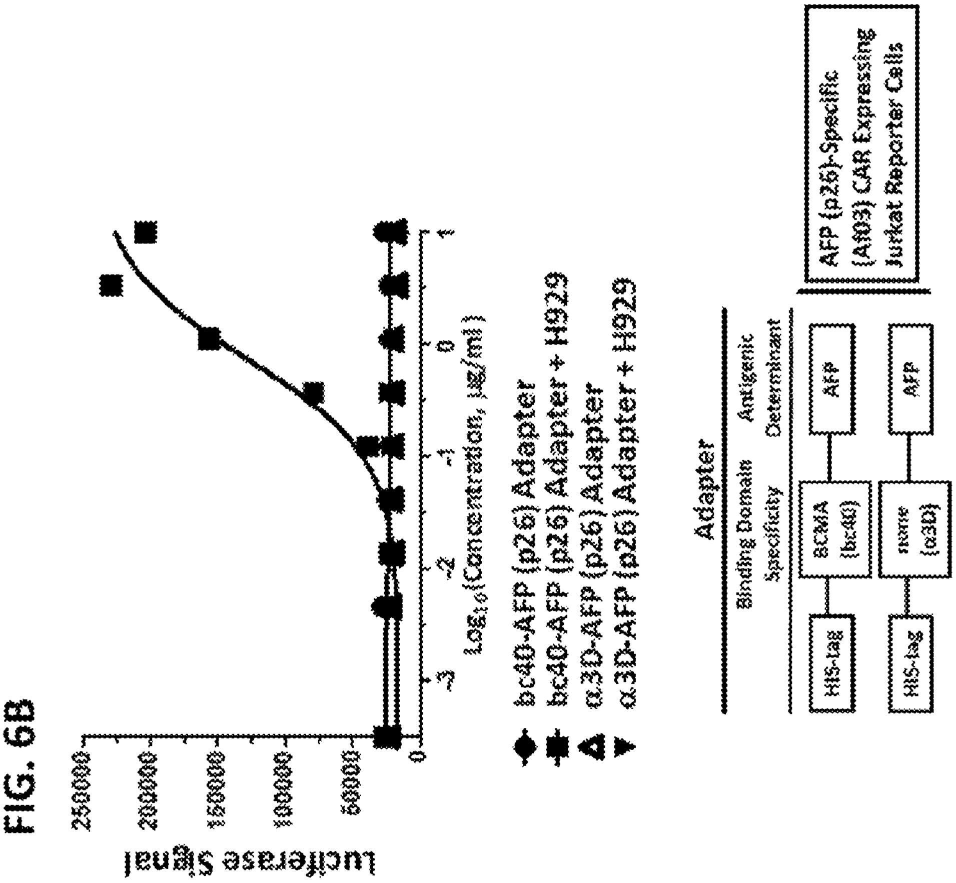

50,000 reporter cells previously transduced with an p26-binding CAR (af03, SEQ ID NO: 1092) were cultured for 5 hours in the presence of Adapters (α3DQ19E-BCMA, SEQ ID: 1086; bc40-p26, SEQ ID NO: 1085) in the presence or absence of 50,000 BCMA⁺ NCI-H929 cells, then assessed for luciferase activity (FIG. 6B).

FIGS. 6A and 6B show that Adapter binding of matching CAR: Adapter and Target: Adapter drives signaling by CAR-expressing Jurkat NFAT-Luciferase reporter cells.

Example 8. Adapters Containing D Domains or ScFvs Drive CAR Cell: Adapter Mediated Lysis of Target Cells A CD123-binding Adapter with a BCMA AD (SEQ ID NO: 1082) was evaluated for its ability to function with a control CAR (α3DQ19E, SEQ ID NO: 1089), a BCMA-binding CAR (bc40, SEQ ID NO: 1091) or a BCMA-specific scFv CAR (c11D5-3) obtained from WO 2010/104949 A2.

Figures 7A, 7B:
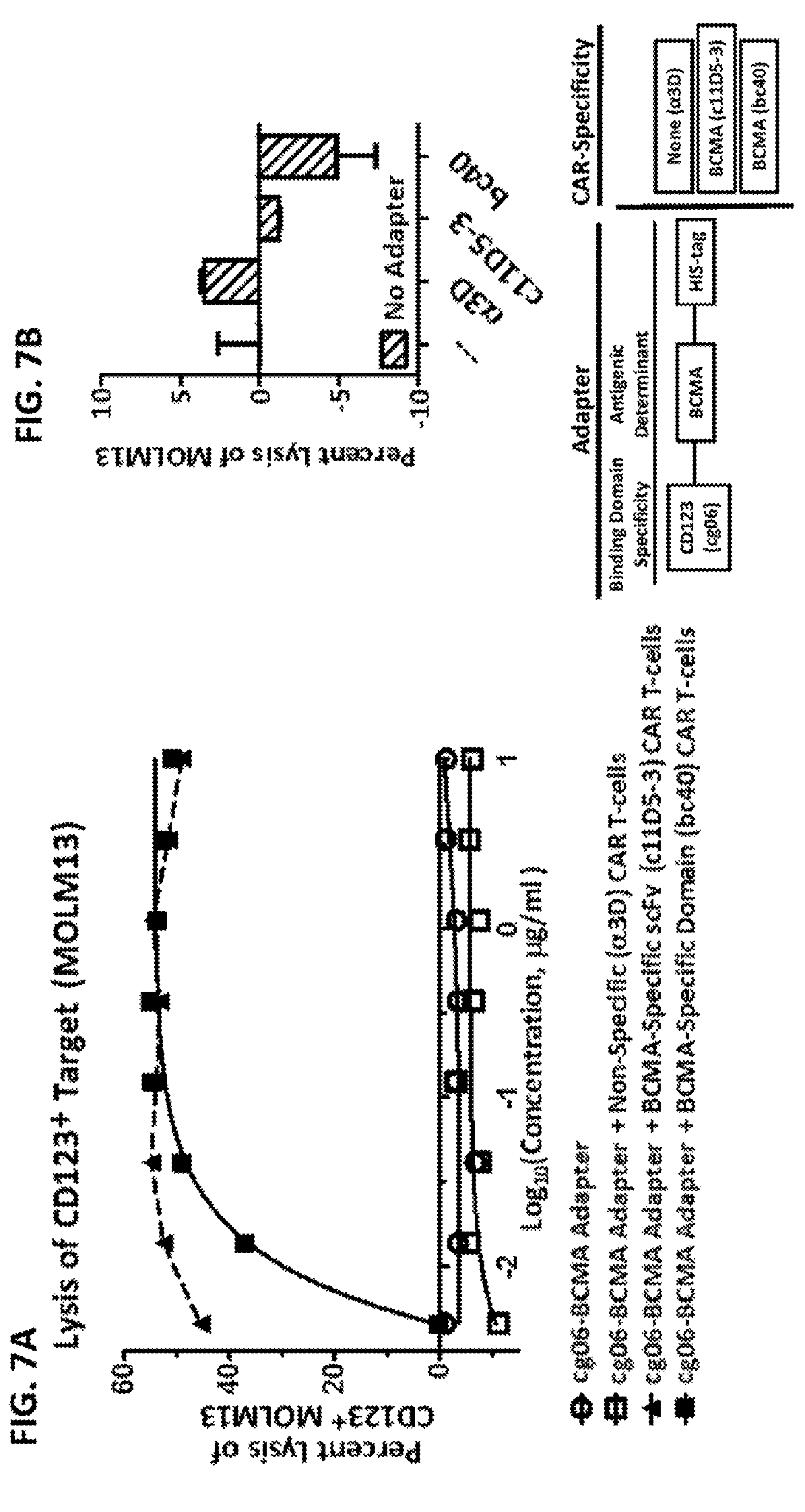

40,000 CD123⁺BCMA⁻ MOLM13-GFP/Luciferase cells were incubated with the Cg06-BCMA Adapter (SEQ ID NO: 1082) in the presence or absence of 20,000 T cells (E:T ratio of 1:2, donor D14-062717, Day 9) transduced with a control CAR (SEQ ID NO: 1089), the BCMA-binding CAR (SEQ ID NO: 1091), or the BCMA-binding scFv CAR (c11D5-3) for 16 hours. After 16 hours, cells were washed and luciferase activity was assessed. Percent lysis was assessed based on wells of MOLM13-GFP/Luciferase cultured in the absence of T cells or Adapter protein. Solid lines indicate calculated 3-parameter non-linear curves, while the dashed line for c11D5-3 is present for illustrative purposes only (FIG. 7A). CD123⁺BCMA⁻ MOLM13-GFP/Luciferase cells were cultured in the same experiment as in FIG. 7A with transduced T cells in the absence of Adapter protein (FIG. 7B).

FIGS. 7A and 7B show that the CD123-specific Adapter with a BCMA antigenic determinant can function with either a BCMA-specific D domain CAR (bc40) or a BCMA-specific scFv CAR (c11D5-3).

Figure 8A:
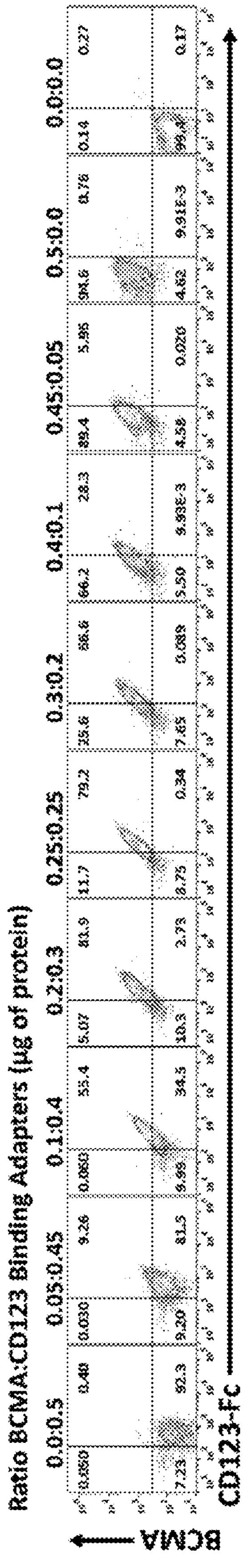

Example 9. Use of Multiple Adapters Target a CAR Cell to Multiple Antigen Targets $10^5$ Jurkat NFAT-Luciferase transduced with a p26-binding CAR (af03, SEQ ID NO: 1092) were incubated with a total of 0.5 μg of Adapters (SEQ ID NO: 1084, SEQ ID NO: 1085) at the indicated ratiosat4° C. for 20 minutes, washed, and then incubated with CD123-Fc and biotinylated BCMA (0.5 μg of each/(4° C. for 20 minutes), washed, then binding detected with Anti-Fc A488 and Streptavidin-PE. FIG. 8A presents a flow cytometric analysis of CD123-binding and BCMA-binding to their respective target proteins, FIG. 8B provides a comparison of mean fluorescence intensity (MFI) of A488 MFI (CD123-binding, left axis) and PE MFI (BCMA-binding, right axis) flow cytometric data presented in FIG. 8A.

Figure 8B:
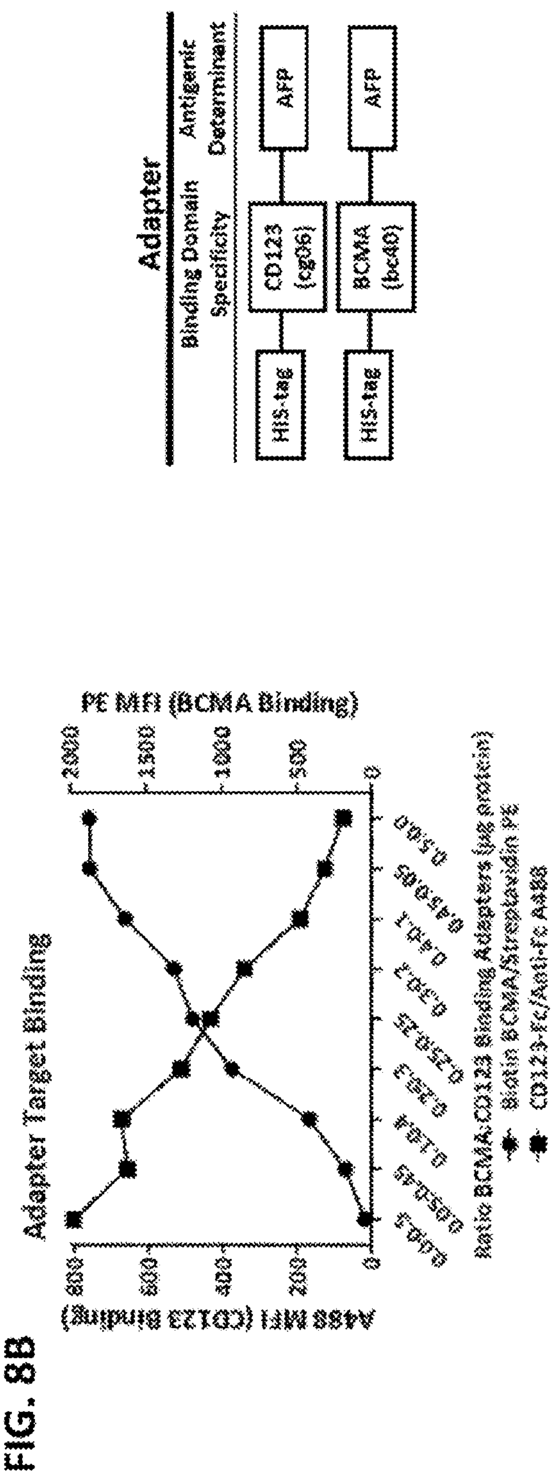

FIGS. 8A and 8B show that AFP-specific CARs can simultaneously have CD123 and BCMA-binding capacity via incubation with multiple Adapter proteins.

Example 10. Use of Dual Binding Domain Adapters to Enhance CAR Signaling 50,000 reporter cells previously transduced with an p26-binding CAR (af03, SEQ ID NO: 1092) were cultured for 5 hours in the presence of the CD123-binding Adaptor (cg06-p26, SEQ ID NO: 1084) or the bivalent Adaptor (cg06-p26-cg06, SEQ ID NO: 1087) in the presence of 50,000 CD123$^+$ MOLM13 or CD123-deficient MOLM13 cells, then assessed for luciferase activity. CD123 deficient cells were generated using CRISPR/Cas9 genetic engineering technology (FIG. 9A). 50,000 reporter cells previously transduced with an p26-binding CAR (af03, SEQ ID NO: 1092) were cultured for 5 hours in the presence of the BCMA-binding Adaptor (bc40-p26, SEQ ID NO: 1085) or the bivalent Adapter ((bc40-p26-bc40, SEQ ID NO: 1088) in the presence or absence of 50,000 BCMA$^+$ U266 cells, then assessed for luciferase activity (FIG. 9B).

Figure 9A:
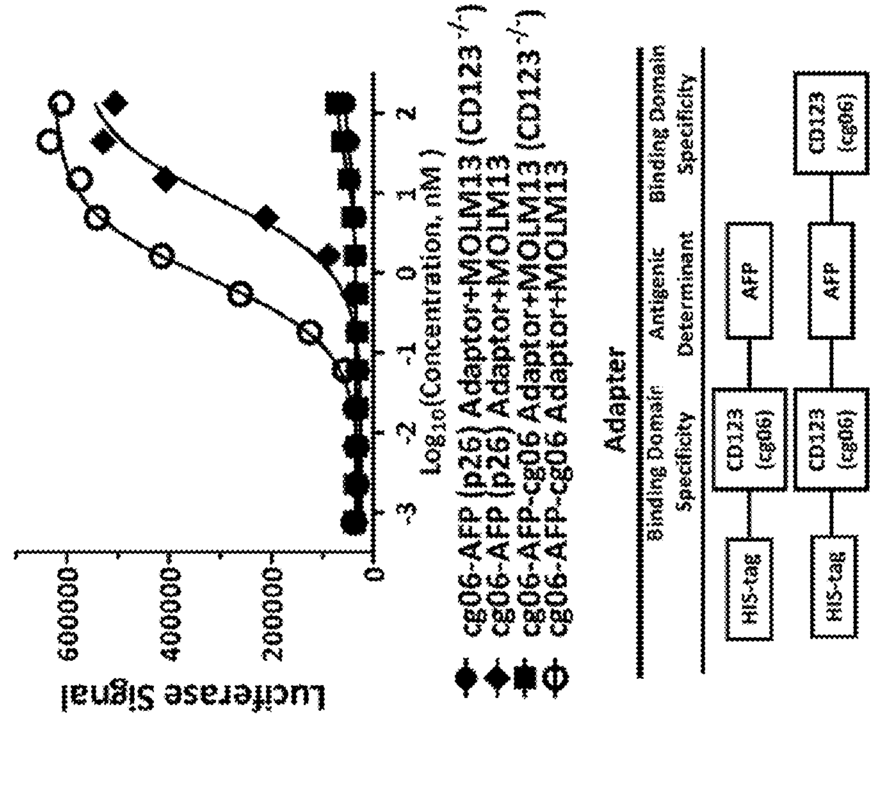
Figure 9B:
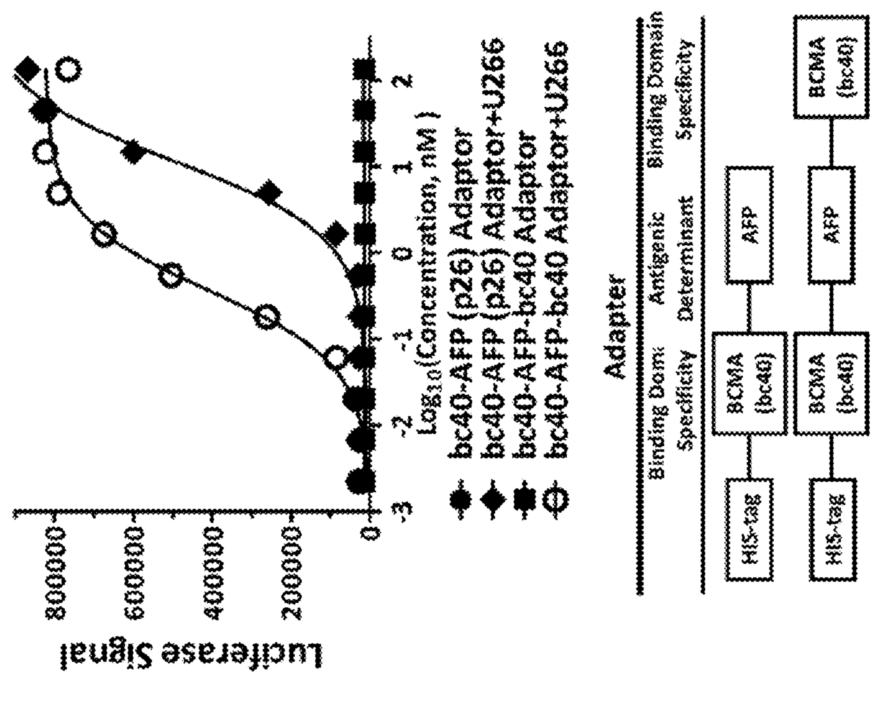

FIGS. 9A and 9B show that dual-binding domain adaptor proteins drive enhanced signaling by CAR-expressing Jurkat cells over single-binding domain adaptor proteins.

Example 11. CD45 Specific D-Domain CAR T Cells Kill CD45 Expressing Target Cells T-cells will be transduced with a CAR comprising a CD45 specific D domain. CD45-CAR T-cells expressing a CAR comprising a human CD45 specific D domain will be generated using CRISPR/Cas9 genetic engineering technology. CD45 specific gRNA and crRNA and Cas9 will be obtained from commercial sources. The self-lysing activity of the CD45-CAR T cells will be assessed using assays for cell proliferation, viability and/or cytotoxicity, for example 7-AAD staining and chromium release assay. Self-lysing of CD45-CAR T-cells will be compared to CD45+ control CAR T-cells expressing the same CAR comprising the CD45 specific D domain.

The cytolytic activity of CD45-T cells expressing a CAR comprising a human CD45 specific D domain will be assessed on a panel of CD45+ target cells using effector cell to target cell ratios ranging from 1:4 to 1:64. The cytolytic activity of the CD45-CAR T cells will be compared to a CAR with no known target-specificity.

Example 12. CD45 Specific Adapter Directed Lysis of Target Cells

CD45− CAR T-cells will be generated using CRISPR/Cas9 genetic engineering technology. CD45 specific gRNA and crRNA and Cas9 will be obtained from commercial sources. The self-lysing activity of the CD45− CAR T cells will be assessed using assays for cell proliferation, viability and/or cytotoxicity, for example 7-AAD staining and chromium release assay. Self-lysing of CD45− CAR T-cells will be compared to CD45+ control CAR T-cells.

The cytolytic activity of CD45-T cells expressing a CAR comprising a human CD45 specific D domain will be assessed on a panel of CD45+ target cells using effector cell to target cell ratios ranging from 1:4 to 1:64. The cytolytic activity of the CD45− CAR T cells will be compared to a CAR with no known target-specificity.

CD45+ target cells will be incubated with various Adapters comprising a CD45 specific D domain and p26 in the presence or absence of CD45-T cells transduced with a p26-binding CAR for 16 hours. After 16 hours, cells will be washed and luciferase activity will be assessed. Percent lysis will be assessed based on wells of target cells cultured in the absence of T cells or Adapter protein. A control of CD45-specific CAR T cells cultured at the same ratio will be used as a positive control for lysis.

Example 13. Adapter Comprising Truncated p26 have Improved Bioactivity in Cytotoxicity Assay Analysis of p26 structure revealed an N-terminal stretch of residues that were predicted to increase the potential for aggregation and/or proteolysis. This N-terminal sequence also contains a predicted disulfide bond pair, which could potentially destabilize the protein if the cysteines are unpaired, or reinforce a suboptimal protein conformation if the disulfide bond is formed. To eliminate these potential developmental liabilities, N-terminal truncated variants of p26 were prepared. In p26 (G17-V229) (SEQ ID NO: 1122) the first 16 residues of p26 were removed to eliminate the disulfide pair of cysteines (C4-C13). In p26 (K23-V229) (SEQ ID NO: 1120) the first 22 residues of p26 were removed to additionally eliminate the beginning of a predicted albumin 3 domain. In p26 (Q26-V229) (SEQ ID NO: 1118) the first 25 residues were removed to eliminate two hydrophobic residues (YI) beyond the K23 truncation and thus make the N-terminus flush with the predicted globular region of p26. The binding of full length and truncated p26 to FcRn was assessed using ELISA. Adapters comprising full-length p26 or the truncated p26 (Q26-V229) variant bind to FcRn in a pH dependent manner, with higher binding affinity observed at pH 6.0 than at pH 7.4.

The bioactivity of Adapters comprising full length p26 or the truncated p26 (G17-V229), p26 (K23-V229) or p26 (Q26-V229) variants were tested in various Luciferase-based Cytotoxicity Assays. Surprisingly, Adapters comprising truncated p26 had higher bioactivity than Adapters comprising full-length p26.

40,000 BCMA$^+$ NALM6/Luciferase cells were incubated with Adapters BCMA (bc98)-p26 JPE (SEQ ID NO: 1124), BCMA (bc98)-p26 (SEQ ID NO: 1125), BCMA (bc98)-p26 (Q26-V229) (SEQ ID NO: 1126), BCMA (bc98)-p26 (K23-V229) (SEQ ID NO: 1127), or BCMA (bc98)-p26 (G17-V229) (SEQ ID NO: 1128), in the presence of 10,000 T cells (E:T ratio of 1:4) transduced with a p26-binding CAR (Af59, SEQ ID NO: 1133) for 16 hours. After 16 hours, cells were washed and luciferase activity was assessed. Percent lysis was assessed based on wells of NALM6/Luciferase cultured in the absence of T cells or Adapter protein. Adapters comprising the truncated p26 variants had higher bioactivity than the Adapters comprising the full-length p26. The EC50 values measured for the Adaptors were as follows:

| Adapter | EC50 |
|---|---|
| BCMA(bc98)-p26 JPE | 1.135 |
| BCMA(bc98)-p26 | 1.962 |
| BCMA(bc98)-p26(Q26-V229) | 0.1294 |
| BCMA(bc98)-p26(K23-V229) | 0.2232 |
| BCMA(bc98)-p26(G17-V229) | 0.367 |

40,000 BCMA$^+$ NCI H929/Luciferase cells were incubated with Adapters BCMA (bc98)-p26 JPE (SEQ ID NO: 1124), BCMA (bc98)-p26 (SEQ ID NO: 1125), BCMA (bc98)-p26 (Q26-V229) (SEQ ID NO: 1126), BCMA (bc98)-p26 (K23-V229) (SEQ ID NO: 1127), or BCMA (bc98)-p26 (G17-V229) (SEQ ID NO: 1128), in the presence of 10,000 T cells (E:T ratio of 1:4) transduced with a p26-binding CAR (Af59, SEQ ID NO: 1133) for 16 hours.

After 16 hours, cells were washed and luciferase activity was assessed. Percent lysis was assessed based on wells of NCI-H929/Luciferase cultured in the absence of T cells or Adapter protein. Adapters comprising the truncated p26 variants had higher bioactivity than the Adapters comprising the full-length p26. The EC50 values measured for the Adaptors were as follows:

| Adapter | EC50 |
|---|---|
| BCMA(bc98)-p26 JPE | 0.367 |
| BCMA(bc98)-p26 | 0.3869 |
| BCMA(bc98)-p26(Q26-V229) | 0.04357 |
| BCMA(bc98)-p26(K23-V229) | 0.06069 |
| BCMA(bc98)-p26(G17-V229) | 0.1318 |

The presence of the Q127P substitution in the truncated p26 did not alter the Adapter's bioactivity. 40,000 BCMA$^+$ NCI H929/Luciferase cells were incubated with Adapters BCMA (bc98)-p26 (SEQ ID NO: 1124), BCMA (bc98)-p26 (Q26-V229) (SEQ ID NO: 1126), or BCMA (bc98)-p26 (Q26-V229) Q217P (SEQ ID NO: 1131), in the presence of 10,000 T cells (E:T ratio of 1:4) transduced with a p26-binding CAR (Af59, SEQ ID NO: 1133) for 16 hours. After 16 hours, cells were washed and luciferase activity was assessed. Percent lysis was assessed based on wells of NCI-H929/Luciferase cultured in the absence of T cells or Adapter protein. Adapters comprising the truncated p26 variants had higher bioactivity than the Adapters comprising the full-length p26. Adapters comprising the truncated p26 variants with or without the Q217P substitution had substantially the same bioactivity. The EC50 values measured were as follows:

| Adapter | EC50 |
|---|---|
| BCMA(bc98)-p26 | 0.5243 |
| BCMA(bc98)-p26(Q26-V229) | 0.1142 |
| BCMA(bc98)-p26(Q26-V229)Q217P | 0.143 |

Bivalent Adapters comprising a truncated p26 variant also performed better than a corresponding Adapter comprising full-length p26. 40,000 BCMA$^+$ NCI H929/Luciferase cells were incubated with Adapters BCMA (bc98)-p26-BCMA (bc98) (SEQ ID NO: 1129), BCMA (bc98)-p26 (Q26-V229)-BCMA (bc98) (SEQ ID NO: 1132), or BCMA (bc98)-p26 (Q26-V229) Q217P-BCMA (bc98) (SEQ ID NO: 1130), in the presence of 10,000 T cells (E:T ratio of 1:4) transduced with a p26-binding CAR (Af59, SEQ ID NO: 1133) for 16 hours. After 16 hours, cells were washed and luciferase activity was assessed. Percent lysis was assessed based on wells of NCI-H929/Luciferase cultured in the absence of T cells or Adapter protein. Adapters comprising the truncated p26 variants had higher bioactivity than the Adapters comprising the full-length p26. Adapters comprising the truncated p26 variants with or without the Q217P substitution had substantially the same bioactivity. The EC50 values measured for the Adaptors were as follows:

| Adapter | EC50 |
|---|---|
| BCMA(bc98)-p26-BCMA(bc98) | 0.008227 |
| BCMA(bc98)-p26(Q26-V229)-BCMA(bc98) | 0.00256 |
| BCMA(bc98)-p26(Q26-V229)Q217P-BCMA(bc98) | 0.001812 |

Figure 10:
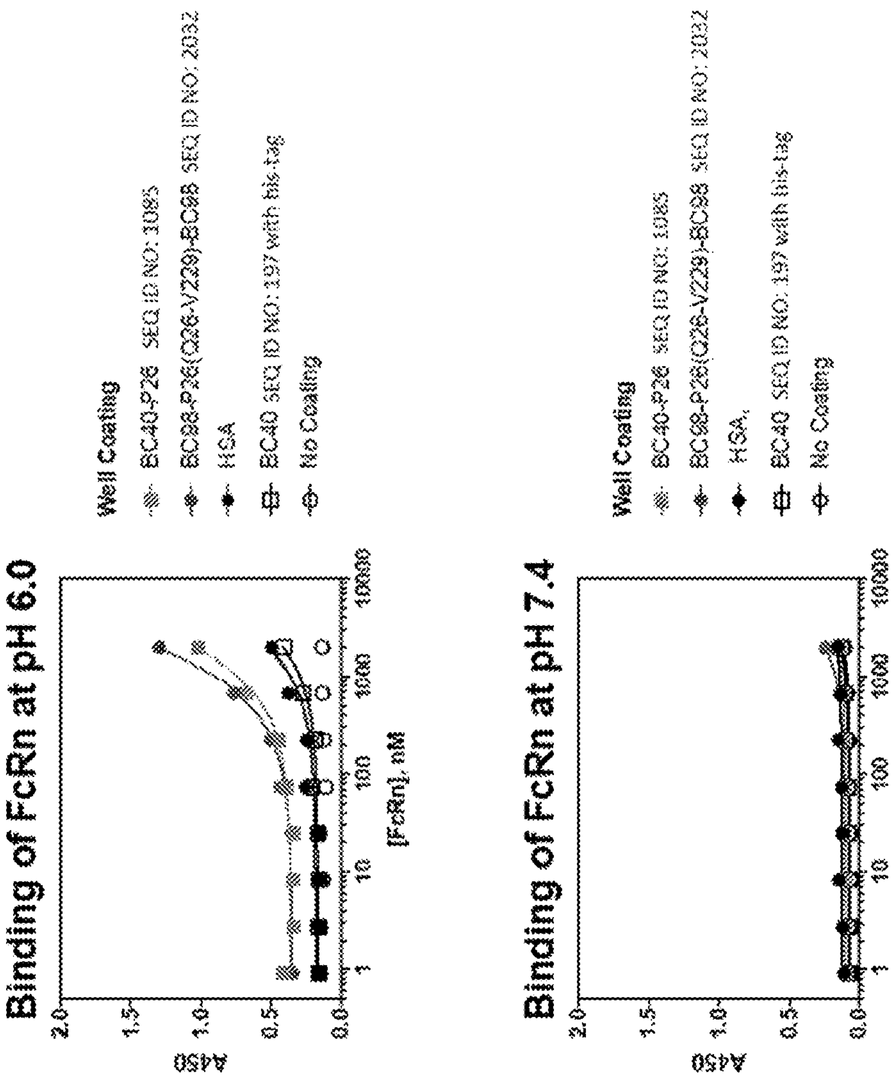

Example 14. Binding of Truncated and Full Length p26 to Human FcRn is pH Dependent The binding of full length and truncated p26 to FcRn was assessed using an ELISA format in which wells of 96-well plate were coated with adapter (bc40-p26 (SEQ ID NO:1085), bc98-p26 (Q26-V229)-bc98 (SEQ ID NO:1132), HSA, bc40 (SEQ ID NO: 197 with HIS-tag) or uncoated) overnight at 4° C. Wells were then blocked with PBS+1% fish gelatin for 1 hour at 22° C. Parallel wells were then washed with PBS+0.1% Tween at pH 6.0 or 7.4. Biotinylated human FcRn in PBS+1% fish gelatin (either pH 6.0 or 7.4) was serially diluted and added to wells and incubated for 1 hour at 22° C. After washing with PBS+0.1% Tween at pH 6.0 or 7.4, streptavidin-HRP (in PBS+1% fish gelatin at pH 6.0 or 7.4) was added. After a final wash, signal was developed using TMB reagent and quantified by reading absorbance at A450. As shown in FIG. 10, adapters comprising full-length p26 or the truncated p26 (Q26-V229) variant bind to FcRn in a pH dependent manner, with higher binding affinity observed at pH 6.0 than at pH 7.4.

Example 15. Adapters Comprising CS1 (SLAMF7, CRACC, CD319) Specific ADBD Modulate Intracellular Signaling and Killing of CS1 Positive Tumors CS1 binding domains (ADBD) were isolated by panning ADBD phage libraries on the extracellular domain of human CS1 protein. Representative CS1 binding ADBD were fused to p26 in a bispecific format with non-binding α3DQ19E (SEQ ID NO: 1021) to generate adapter proteins for functional testing in combination with af59-CAR (SEQ ID NO: 1133) expressing JNL10 cells or human T cells expressing af59-CAR.

| CS1 (SLAMF7, CRACC, CD319) Adapter Constructs | Adapter SEQ ID NO: | CS1 ADBD SEQ ID NO: | CS1 ADBD clone ID |
|---|---|---|---|
| α3D Q19E-p26-cc08.HIS | 1150 | 787 | cc08 |
| α3D Q19E-p26-cc01.HIS | 1151 | 780 | cc01 |
| α3D Q19E-p26-cc02.HIS | 1152 | 781 | cc02 |
| α3D Q19E-p26-cc09.HIS | 1153 | 788 | cc09 |
| α3D Q19E-p26-cc10.HIS | 1154 | 789 | cc10 |
| α3D Q19E-p26-cc12.HIS | 1155 | 791 | cc12 |

Figure 11A:
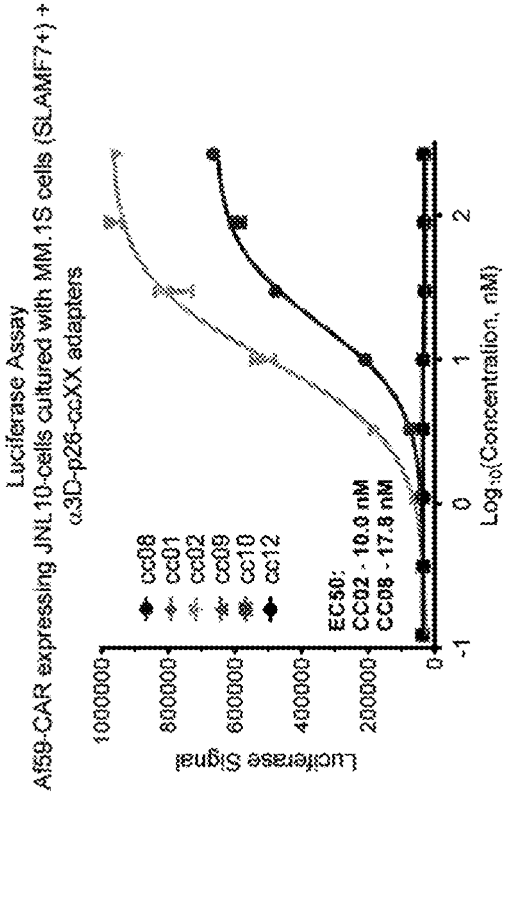

Among the adapters tested in, the cc02 and cc08 ADBD displayed the most potent NFAT signaling when cultured in the presence of af59-CAR expressing JNL10 cells and the CS1 positive tumor cell line, MM.1S (FIG. 11A).

Figure 11B:
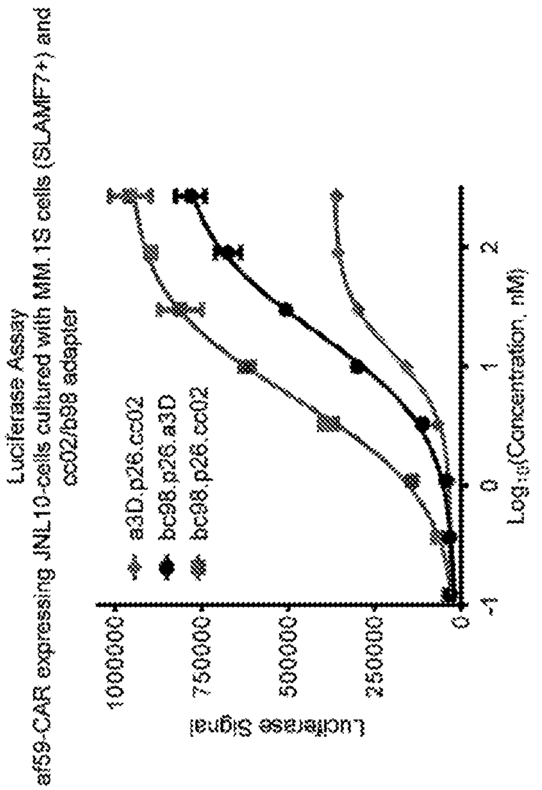

The cc02 CS1 ADBD (SEQ ID NO: 781) was fused to p26 and either the non-binding α3DQ19E DD (SEQ ID NO: 1021) or the BCMA-binding bc98 DD (SEQ ID NO: 201). The ability of the resulting adapters to induce signaling in af59-CAR expressing JNL10 cells in the presence of the BCMA positive and CS1 positive cell line, MM.1S was assessed. As shown in FIG. 11B, the bispecific bc98-p26-cc02 adapter capable of binding both CS1 and BCMA was more potent in its ability to signal than were the monospecific BCMA-binding bc98-p26-α3DQ19E adapter and the monospecific CS1-binding α3DQ19E-p26-cc02 adapter.

Figure 11C:
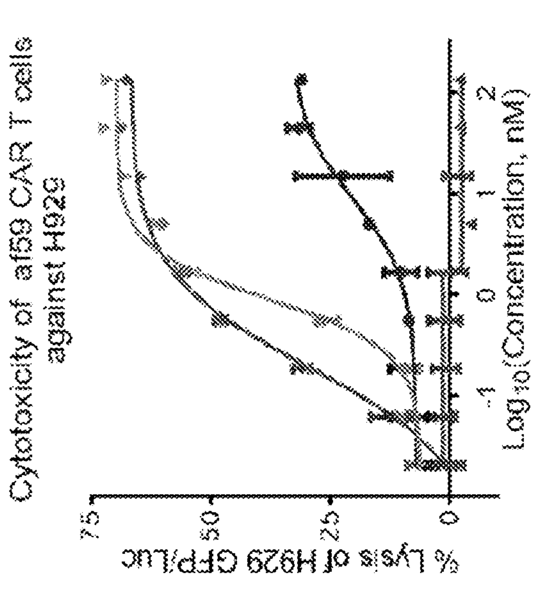
Figure 11D:
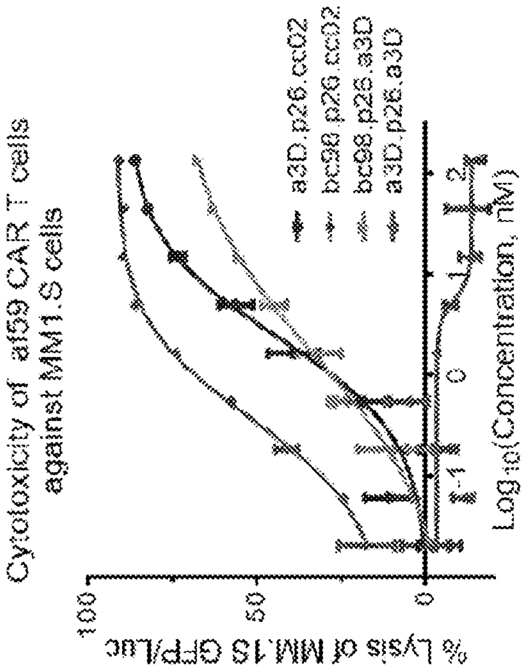

The af59-CAR (SEQ ID NO: 1133) was transduced into normal human T cells and the ability of those cells to kill H929 (BCMA++, CS1+) and MM.1S (BCMA++, CS1++) tumors using the indicated adapters was assessed. The data shown in FIGS. 11C and D indicate the bispecific bc98-p26-cc02 is an effective adapter in killing HT929 (high expression of both BCMA and CS1) and MM.1S (high BCMA, low CS1).

Example 16. Adapters Comprising HER2 Binding ADBD Induce Signaling in Af59-CAR Expressing JNL10-Cells Cultured with HER2-Positive SKBR3 Tumor Cells α3D (Q19E)-p26-Eb (08), or Affibody/Darpin-Based Adaptors HER2 (ERBB2, CD340) binding domains (ADBD) were isolated by panning ADBD phage libraries on the extracellular domain of human HER2 protein. Representative HER2 binding ADBD were fused to p26 in a bispecific format with non-binding α3DQ19E (SEQ ID NO: 1021) to generate adapter proteins for functional testing in combination with af59-CAR (SEQ ID NO: 1133) expressing JNL10 cells or human T cells expressing af59-CAR.

| HER2 (erbB2) Adapter Constructs | Adapter Construct SEQ ID NO: | HER2 ADBD SEQ ID NO: | ADBD clone ID |
|---|---|---|---|
| α3D(Q19E).3xGS.p26.3xGS.α3D(Q19E).HIS | 1156 | N/A | N/A |
| α3D(Q19E).3xGS.p26.3xGS.eb03.HIS | 1157 | 804 | eb03 |
| α3D(Q19E).3xGS.p26.3xGS.eb04.HIS | 1158 | 814 | eb04 |
| α3D(Q19E).3xGS.p26.3xGS.eb05.HIS | 1159 | 810 | eb05 |
| α3D(Q19E).3xGS.p26.3xGS.eb06.HIS | 1160 | 834 | eb06 |
| α3D(Q19E).3xGS.p26.3xGS.eb08.HIS | 1161 | 809 | eb08 |
| α3D(Q19E).3xGS.p26.3xGS.eb09.HIS | 1162 | 833 | eb09 |
| α3D(Q19E).3xGS.p26.3xGS.eb10.HIS | 1163 | 839 | eb10 |

Figure 12A:
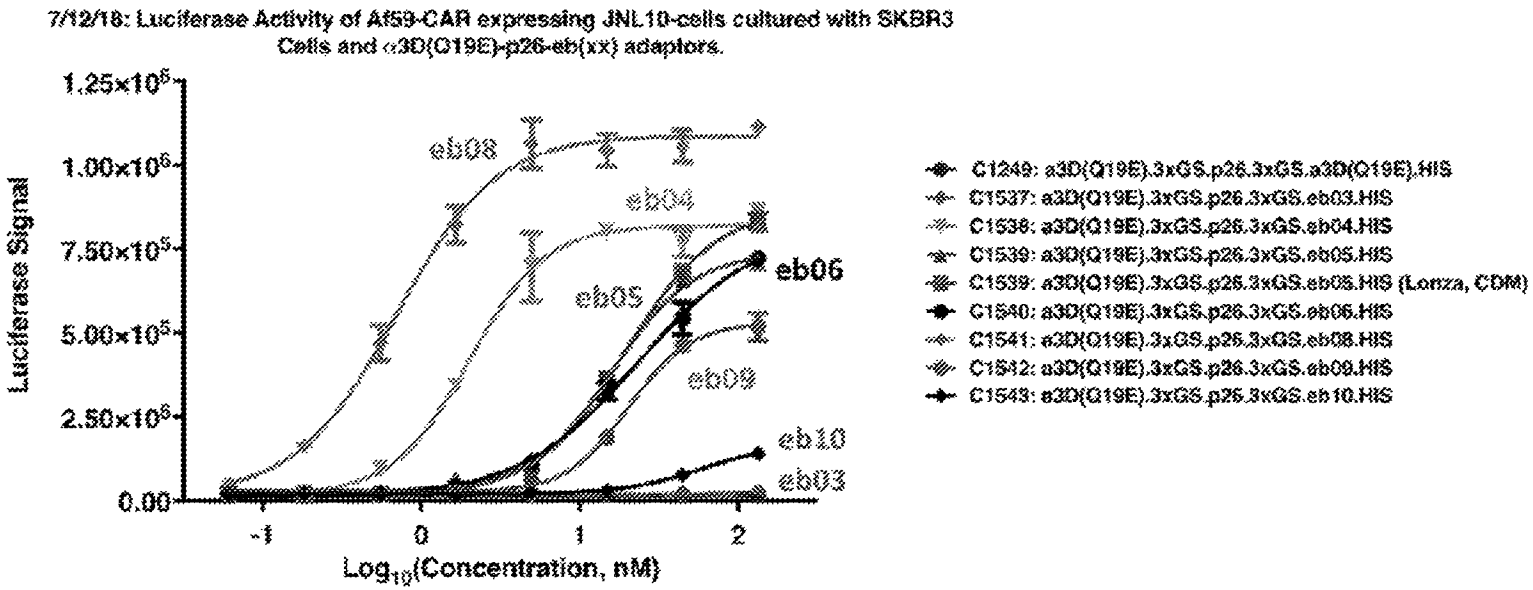
FIGS. 12A-12C show that adapters comprising HER2 binding ADBD induce signaling in Af59-CAR expressing JNL10-cells cultured with HER2-positive SKBR3 tumor.

The adapters demonstrated a range of activities in their ability to induce JNL10 NFAT signaling when cultured in the presence of af59-CAR expressing JNL10 cells and HER2 positive SKBR3 tumor cells. As shown in FIG. 12A, the adapter comprising eb08 was the most potent stimulator in this assay.

Figure 12B:
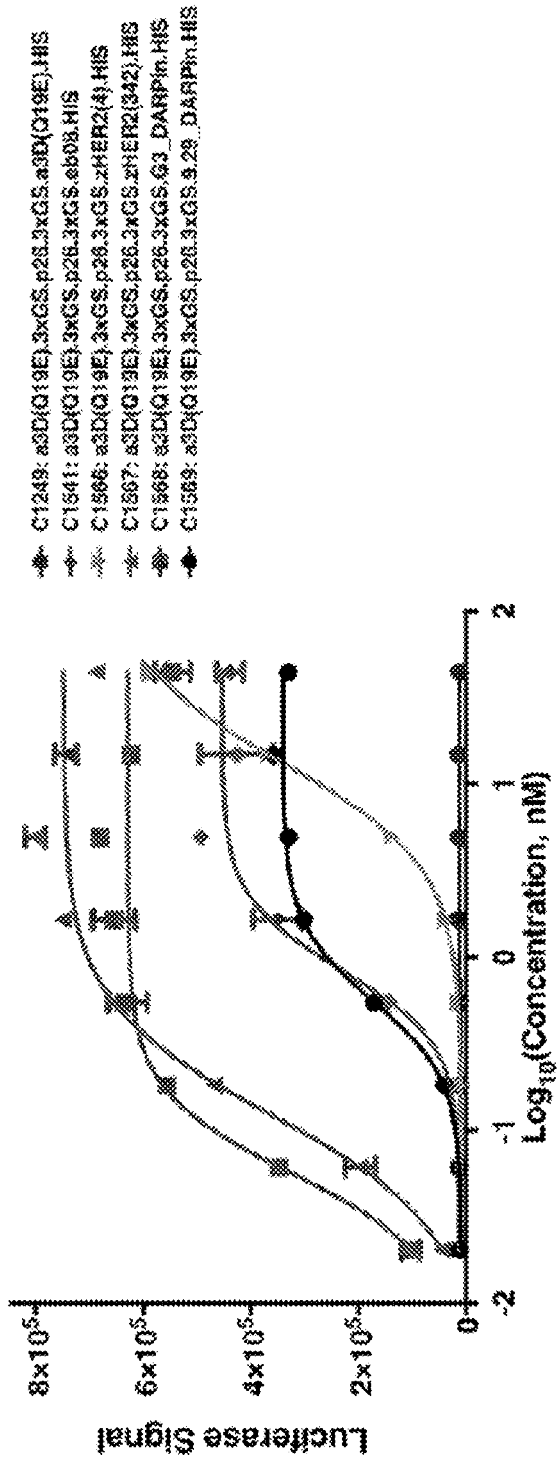

The adapter comprising eb08 was then compared to other adapters containing a HER2 binding domains derived from affibodies (zHER2 (4) and zHER2 (342)) or DARPins (9.29 and G3). As shown in FIG. 12B, the NFAT signaling in JNL10 cells mediated by the adapter comprising eb08 is greater than that of mediated by the adapter comprising zHERs: 4, comparable to that of mediated by the adapter comprising 9.29, and less than that of G3 and zHER2:342.

Figure 12C:
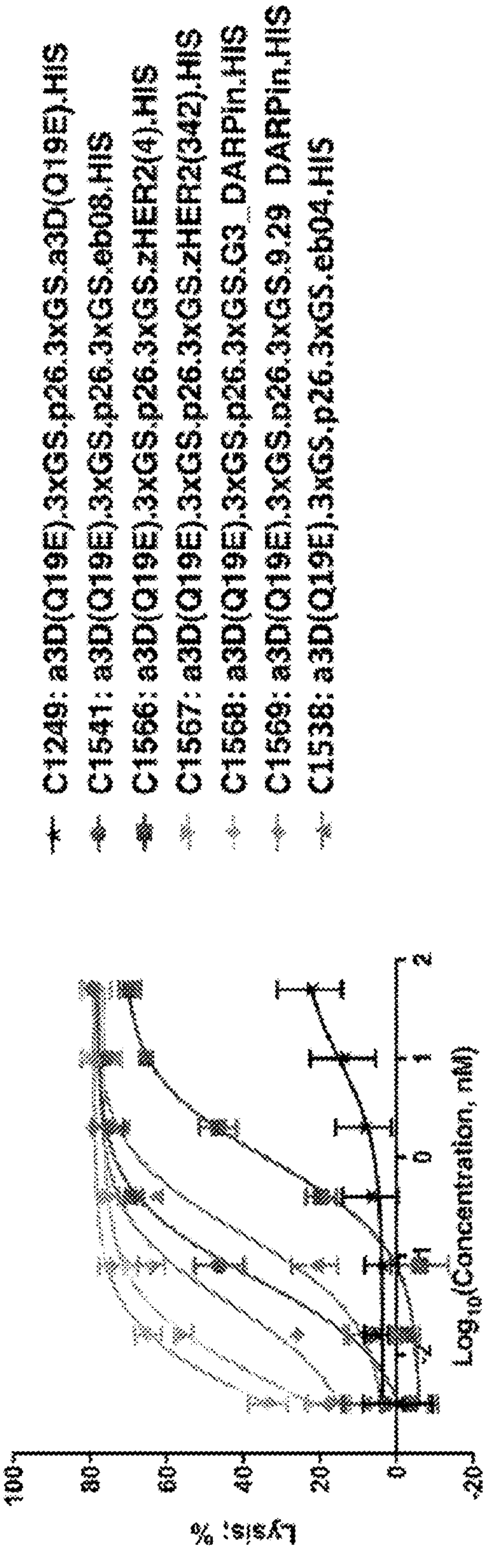
Figure 13A:
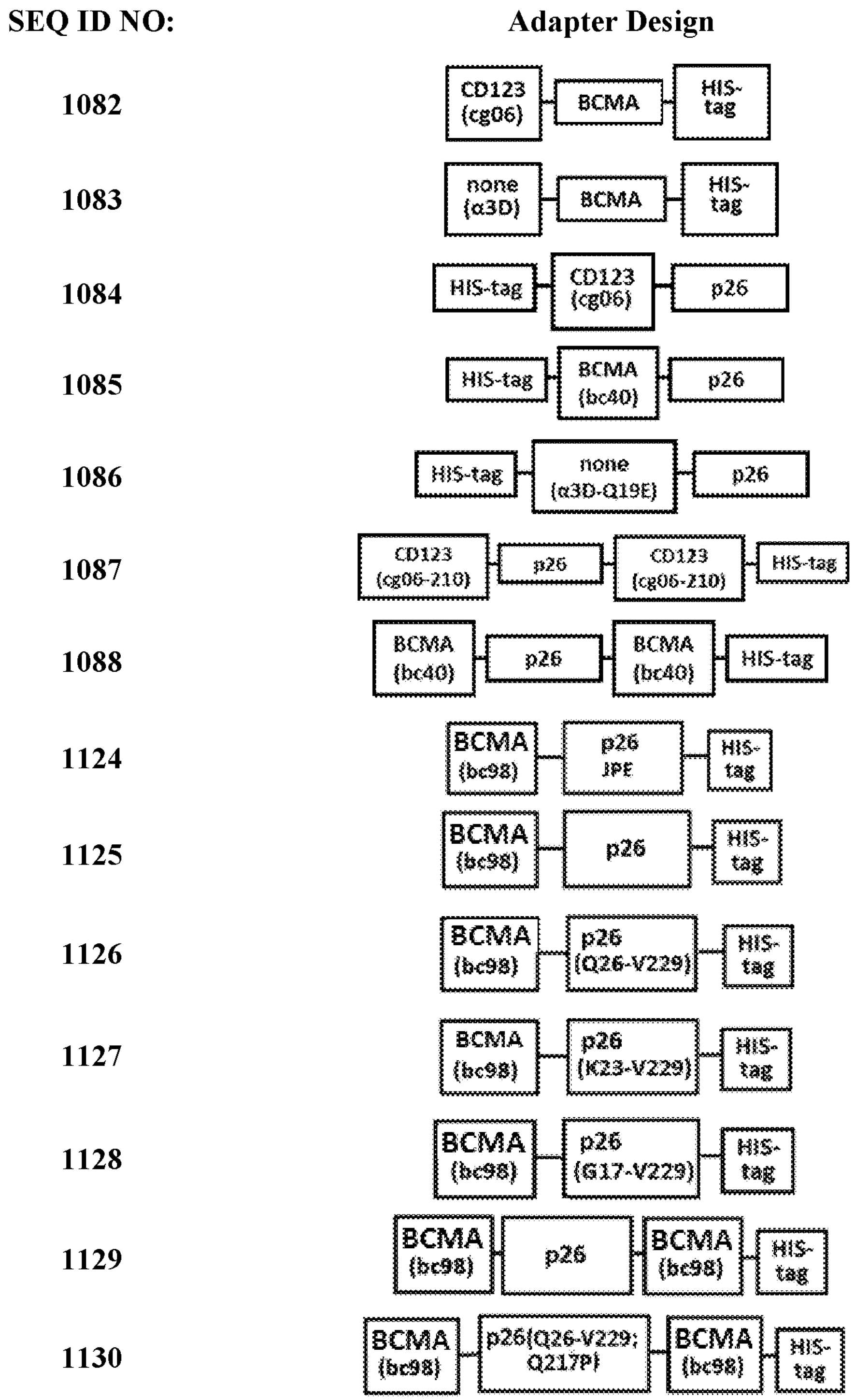
Figure 13B:
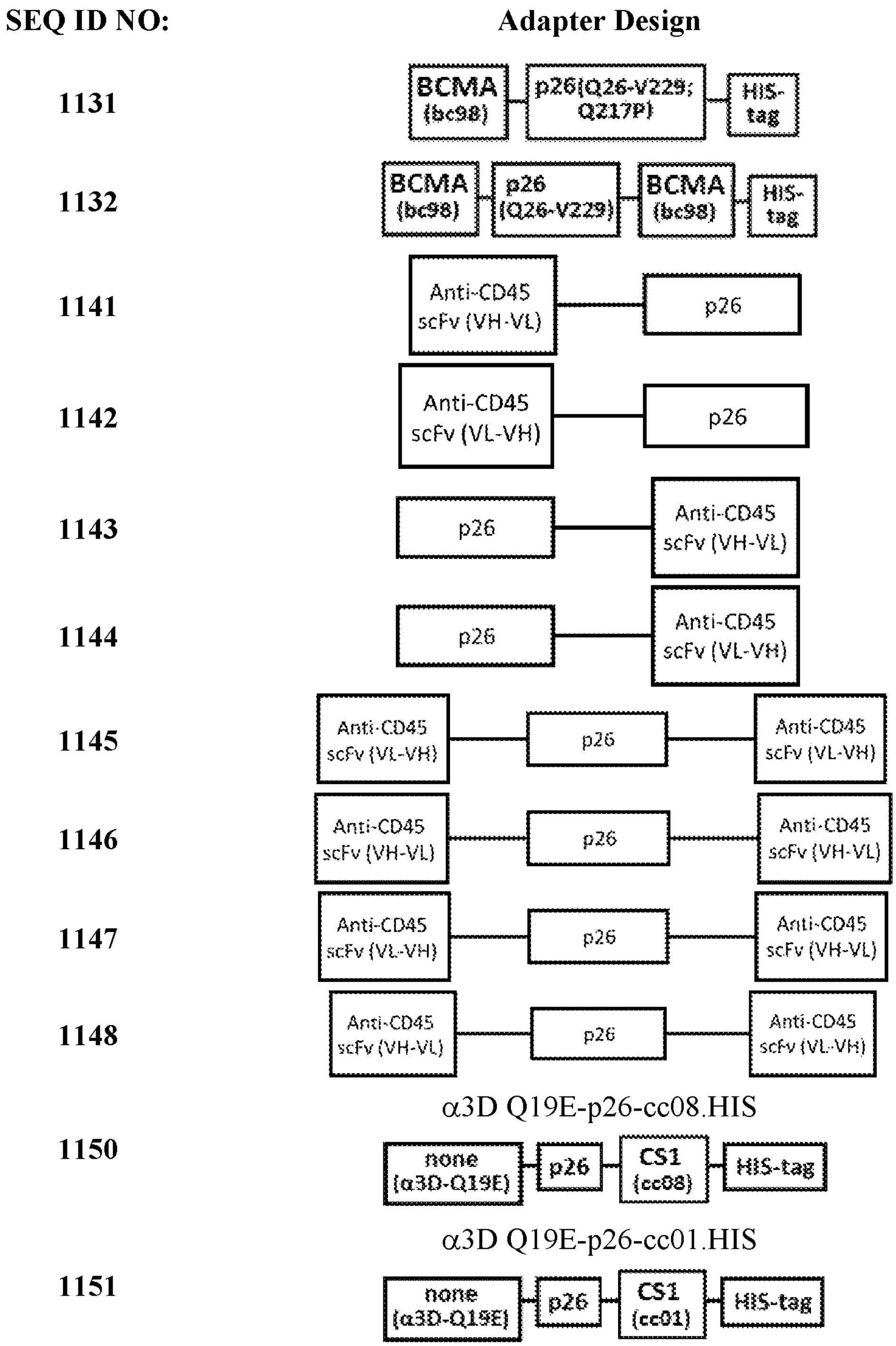
Figure 13C:
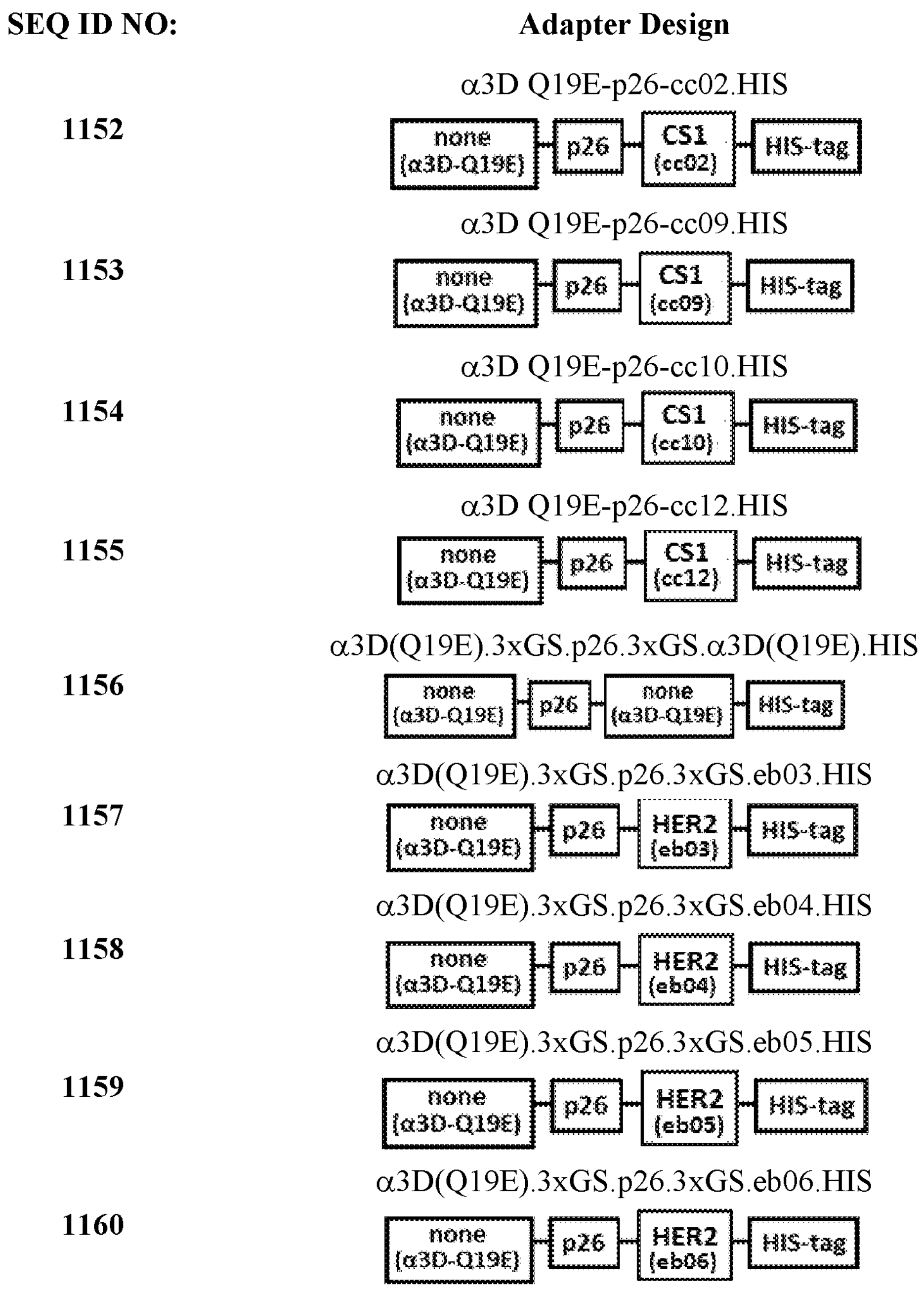
Figure 13D:
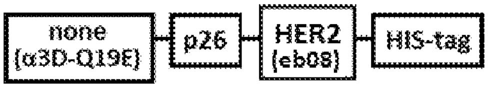
Figure 13D:
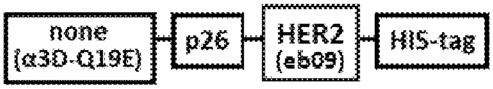
Figure 13D:
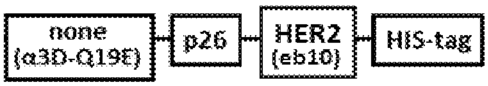

The ability of adapters comprising the HER2-binding eb08 and eb04 domain to induce tumor (SKBR3) kill was compared with adapters containing other HER2 binding domains derived from affibodies (zHER2 (4) and zHER2 (342)) or DARPins (9.29 and G3). Each adapter was incubated with normal human T cells transduced with af59-CAR that binds p26 found in each adapter. SKBR3 lysis was quantitated in a 16-hour luciferase-based assay at an effector to target ratio of 1:5. The results of the assay shown in FIG. 12C demonstrate that adapters comprising eb08 or eb04 modulate tumor lysis in a dose-dependent manner.

Throughout this application, various publications are referenced by author name and date, or by Patent No. or Patent Publication No. The disclosure of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

What is claimed is:

1. A method of treating a cancer in a subject, the method comprising:

a) administering to the subject an effective amount of an immune cell comprising a chimeric antigen receptor (CAR), wherein the CAR comprises a first D domain that specifically binds to an AFP p26 polypeptide; and b) administering via continuous infusion a fusion protein comprising (i) the AFP p26 polypeptide comprising the amino acid sequence of any one of SEQ ID NOs: 16, 1117, 1118, 1119, 1120, 1121, 1122, or 1123 and (ii) a second D domain that binds to a cancer antigen, wherein the first D domain and the second D domain each comprise an antiparallel three helical bundle.

2. The method of claim 1, wherein the first D domain comprises the amino acid sequence of any one of SEQ ID NOs: 841-984.

3. The method of claim 1, wherein the first D domain comprises the amino acid sequence of SEQ ID NO: 850.

4. The method of claim 1, wherein the AFP p26 polypeptide comprises the amino acid sequence of SEQ ID NO: 1118.

5. The method of claim 1, wherein the second D domain comprises any one of SEQ ID NOs: 44-773, 780-795, 800-840, or 985-1079.

6. The method of claim 1, wherein the second D domain specifically binds to CD123.

7. The method of claim 1, wherein the second D domain specifically binds to BCMA.

8. The method of claim 7, wherein the second D domain comprises SEQ ID NO: 201.

9. The method of claim 1, wherein the CAR further comprises a transmembrane domain.

10. The method of claim 9, wherein the transmembrane domain comprises a CD8, 41BB or CD28 transmembrane domain.

11. The method of claim 10, wherein the transmembrane domain comprises a CD8 transmembrane domain.

12. The method of claim 1, wherein the CAR further comprises an intracellular domain.

13. The method of claim 12, wherein the intracellular domain comprises an intracellular signaling domain.

14. The method of claim 13, wherein the intracellular signaling domain comprises a domain of a human T cell receptor alpha, beta, or zeta chain; a human 41BB domain; a human CD28 domain; or any combination thereof.

15. The method of claim 14, wherein the intracellular signaling domain comprises a human 41BB domain.

16. The method of claim 13, wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, and a ligand that specifically binds with CD83.

17. The method of claim 12, wherein the intracellular domain comprises a domain of a human T cell receptor zeta.

18. The method of claim 1, wherein the immune cell is a T cell or a natural killer (NK) cell.

19. The method of claim 1, wherein the subject is suffering from lymphoma or leukemia.

20. The method of claim 1, wherein the subject is suffering from multiple myeloma.

21. The method of claim 1, wherein the fusion protein is administered in a continuous manner to achieve a plasma concentration of about 0.1 μg/mL to about 100 μg/mL.

22. The method of claim 21, wherein the fusion protein is administered in a continuous manner to achieve a plasma concentration of about 1 μg/mL to about 5 μg/mL.

23. The method of claim 1, wherein the fusion protein has a plasma half-life of at least 1 hour.

24. The method of claim 23, wherein the fusion protein has a plasma half-life of 1 hour to 10 hours.

25. The method of claim 1, wherein the fusion protein is administered for one day.

26. The method of claim 1, wherein the fusion protein is administered for several days.

* * * * *

SEQUENCE LISTING

```
Sequence total quantity: 1163
SEQ ID NO: 1           moltype = AA  length = 73
FEATURE                Location/Qualifiers
REGION                 1..73
                       note = artificial construct
source                 1..73
                       mol_type = protein
                       organism = synthetic construct
SEQUENCE: 1
MGSWAEFKQR LAAIKTRLQA LGGSEAELAA FEKEIAAFES ELQAYKGKGN PEVEALRKEA  60
AAIRDELQAY RHN                                                     73

SEQ ID NO: 2           moltype = AA  length = 291
FEATURE                Location/Qualifiers
source                 1..291
                       mol_type = protein
                       organism = Homo sapiens
SEQUENCE: 2
MPPPRLLFFL LFLTPMEVRP EEPLVVKVEE GDNAVLQCLK GTSDGPTQQL TWSRESPLKP  60
FLKLSLGLPG LGIHMRPLAI WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCLPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW K          291

SEQ ID NO: 3           moltype = AA  length = 272
FEATURE                Location/Qualifiers
source                 1..272
                       mol_type = protein
                       organism = Homo sapiens
SEQUENCE: 3
PEEPLVVKVE EGDNAVLQCL KGTSDGPTQQ LTWSRESPLK PFLKLSLGLP GLGIHMRPLA  60
IWLFIFNVSQ QMGGFYLCQP GPPSEKAWQP GWTVNVEGSG ELFRWNVSDL GGLGCGLKNR  120
SSEGPSSPSG KLMSPKLYVW AKDRPEIWEG EPPCLPPRDS LNQSLSQDLT MAPGSTLWLS  180
CGVPPDSVSR GPLSWTHVHP KGPKSLLSLE LKDDRPARDM WVMETGLLLP RATAQDAGKY  240
```

```
YCHRGNLTMS FHLEITARPV LWHWLLRTGG WK                          272

SEQ ID NO: 4             moltype = AA  length = 184
FEATURE                  Location/Qualifiers
source                   1..184
                         mol_type = protein
                         organism = Homo sapiens
SEQUENCE: 4
MLQMAGQCSQ NEYFDSLLHA CIPCQLRCSS NTPPLTCQRY CNASVTNSVK GTNAILWTCL  60
GLSLIISLAV FVLMFLLRKI NSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                         184

SEQ ID NO: 5             moltype = AA  length = 54
FEATURE                  Location/Qualifiers
source                   1..54
                         mol_type = protein
                         organism = Homo sapiens
SEQUENCE: 5
MLQMAGQCSQ NEYFDSLLHA CIPCQLRCSS NTPPLTCQRY CNASVTNSVK GTNA        54

SEQ ID NO: 6             moltype = AA  length = 7
FEATURE                  Location/Qualifiers
source                   1..7
                         mol_type = protein
                         organism = Homo sapiens
SEQUENCE: 6
AGIYAPI                                                      7

SEQ ID NO: 7             moltype = AA  length = 15
FEATURE                  Location/Qualifiers
source                   1..15
                         mol_type = protein
                         organism = Homo sapiens
SEQUENCE: 7
FLKMESLNFI RAHTP                                             15

SEQ ID NO: 8             moltype = AA  length = 8
FEATURE                  Location/Qualifiers
source                   1..8
                         mol_type = protein
                         organism = Homo sapiens
SEQUENCE: 8
EPANPSEK                                                     8

SEQ ID NO: 9             moltype = AA  length = 47
FEATURE                  Location/Qualifiers
source                   1..47
                         mol_type = protein
                         organism = Homo sapiens
SEQUENCE: 9
KISHFLKMES LNFIRAHTPY INIYNCEPAN PSEKNSPSTQ YCYSIQS          47

SEQ ID NO: 10            moltype = AA  length = 6
FEATURE                  Location/Qualifiers
source                   1..6
                         mol_type = protein
                         organism = Homo sapiens
SEQUENCE: 10
PICVTV                                                       6

SEQ ID NO: 11            moltype = AA  length = 287
FEATURE                  Location/Qualifiers
source                   1..287
                         mol_type = protein
                         organism = Homo sapiens
SEQUENCE: 11
TKEDPNPPIT NLRMKAKAQQ LTWDLNRNVT DIECVKDADY SMPAVNNSYC QFGAISLCEV  60
TNYTVRVANP PFSTWILFPE NSGKPWAGAE NLTCWIHDVD FLSCSWAVGP GAPADVQYDL  120
YLNVANRRQQ YECLHYKTDA QGTRIGCRFD DISRLSSGSQ SSHILVRGRS AAFGIPCTDK  180
FVVFSQIEIL TPPNMTAKCN KTHSFMHWKM RSHFNRKFRY ELQIQKRMQP VITEQVRDRT  240
SFQLLNPGTY TVQIRARERV YEFLSAWSTP QRFECDQEEG ANTRAWR             287

SEQ ID NO: 12            moltype = AA  length = 21
FEATURE                  Location/Qualifiers
source                   1..21
                         mol_type = protein
                         organism = Homo sapiens
SEQUENCE: 12
```

```
DKTSFVSFVG LAFVPLQIWS K                                         21

SEQ ID NO: 13           moltype = AA  length = 130
FEATURE                 Location/Qualifiers
source                  1..130
                        mol_type = protein
                        organism = Homo sapiens
SEQUENCE: 13
RAQLERSLRD VVEKTIQKYG TNPEETAAEE SWDYVQFQLR CCGWHYPQDW FQVLILRGNG  60
SEAHRVPCSC YNLSATNDST ILDKVILPQL SRLGHLARSR HSADICAVPA ESHIYREGCA  120
QGLQKWLHNN                                                       130

SEQ ID NO: 14           moltype = AA  length = 609
FEATURE                 Location/Qualifiers
source                  1..609
                        mol_type = protein
                        organism = Homo sapiens
SEQUENCE: 14
MKWVESIFLI FLLNFTESRT LHRNEYGIAS ILDSYQCTAE ISLADLATIF FAQFVQEATY  60
KEVSKMVKDA LTAIEKPTGD EQSSGCLENQ LPAFLEELCH EKEILEKYGH SDCCSQSEEG  120
RHNCFLAHKK PTPASIPLFQ VPEPVTSCEA YEEDRETFMN KFIYEIARRH PFLYAPTILL  180
WAARYDKIIP SCCKAENAVE CFQTKAATVT KELRESSLLN QHACAVMKNF GTRTFQAITV  240
TKLSQKFTKV NFTEIQKLVL DVAHVHEHCC RGDVLDCLQD GEKIMSYICS QQDTLSNKIT  300
ECCKLTTLER GQCIIHAEND EKPEGLSPNL NRFLGDRDFN QFSSGEKNIF LASFVHEYSR  360
RHPQLAVSVI LRVAKGYQEL LEKCFQTENP LECQDKGEEE LQKYIQESQA LAKRSCGLFQ  420
KLGEYYLQNA FLVAYTKKAP QLTSSELMAI TRKMAATAAT CCQLSEDKLL ACGEGAADII  480
IGHLCIRHEM TPVNPGVGQC CTSSYANRRP CFSSLVVDET YVPPAFSDDK FIFHKDLCQA  540
QGVALQTMKQ EFLINLVKQK PQITEEQLEA VIADFSGLLE KCCQGQEQEV CFAEEGQKLI  600
SKTRAALGV                                                        609

SEQ ID NO: 15           moltype = AA  length = 591
FEATURE                 Location/Qualifiers
source                  1..591
                        mol_type = protein
                        organism = Homo sapiens
SEQUENCE: 15
RTLHRNEYGI ASILDSYQCT AEISLADLAT IFFAQFVQEA TYKEVSKMVK DALTAIEKPT  60
GDEQSSGCLE NQLPAFLEEL CHEKEILEKY GHSDCCSQSE EGRHNCFLAH KKPTPASIPL  120
FQVPEPVTSC EAYEEDRETF MNKFIYEIAR RHPFLYAPTI LLWAARYDKI IPSCCKAENA  180
VECFQTKAAT VTKELRESSL LNQHACAVMK NFGTRTFQAI TVTKLSQKFT KVNFTEIQKL  240
VLDVAHVHEH CCRGDVLDCL QDGEKIMSYI CSQQDTLSNK ITECCKLTTL ERGQCIIHAE  300
NDEKPEGLSP NLNRFLGDRD FNQFSSGEKN IFLASFVHEY SRRHPQLAVS VILRVAKGYQ  360
ELLEKCFQTE NPLECQDKGE EELQKYIQES QALAKRSCGL FQKLGEYYLQ NAFLVAYTKK  420
APQLTSSELM AITRKMAATA ATCCQLSEDK LLACGEGAAD IIIGHLCIRH EMTPVNPGVG  480
QCCTSSYANR RPCFSSLVVD ETYVPPAFSD DKFIFHKDLC QAQGVALQTM KQEFLINLVK  540
QKPQITEEQL EAVIADFSGL LEKCCQGQEQ EVCFAEEGQK LISKTRAALG V          591

SEQ ID NO: 16           moltype = AA  length = 229
FEATURE                 Location/Qualifiers
REGION                  1..229
                        note = artificial construct
source                  1..229
                        mol_type = protein
                        organism = synthetic construct
SEQUENCE: 16
LEKCFQTENP LECQDKGEEE LQKYIQESQA LAKRSCGLFQ KLGEYYLQNA FLVAYTKKAP  60
QLTSSELMAI TRKMAATAAT CCQLSEDKLL ACGEGAADII IGHLCIRHEM TPVNPGVGQC  120
CTSSYANRRP CFSSLVVDET YVPPAFSDDK FIFHKDLCQA QGVALQTMKQ EFLINLVKQK  180
PQITEEQLEA VIADFSGLLE KCCQGQEQEV CFAEEGQKLI SKTRAALGV            229

SEQ ID NO: 17           moltype = AA  length = 73
FEATURE                 Location/Qualifiers
REGION                  1..73
                        note = artificial construct
VARIANT                 5..6
                        note = MISC_FEATURE - Xaa can be any natural and
                         non-natural amino acid
VARIANT                 9..10
                        note = MISC_FEATURE - Xaa can be any natural and
                         non-natural amino acid
VARIANT                 13
                        note = MISC_FEATURE - Xaa can be any natural and
                         non-natural amino acid
VARIANT                 16..17
                        note = MISC_FEATURE - Xaa can be any natural and
                         non-natural amino acid
VARIANT                 30
                        note = MISC_FEATURE - Xaa can be any natural and
                         non-natural amino acid
```

```
VARIANT                 33..34
                        note = MISC_FEATURE - Xaa can be any natural and
                         non-natural amino acid
VARIANT                 37
                        note = MISC_FEATURE - Xaa can be any natural and
                         non-natural amino acid
VARIANT                 40..41
                        note = MISC_FEATURE - Xaa can be any natural and
                         non-natural amino acid
VARIANT                 44
                        note = MISC_FEATURE - Xaa can be any natural and
                         non-natural amino acid
source                  1..73
                        mol_type = protein
                        organism = synthetic construct
SEQUENCE: 17
MGSWXXFKXX LAXIKXXLEA LGGSEAELAX FEXXIAXFEX XLQXYKGKGN PEVEALRKEA  60
AAIRDELQAY RHN                                                     73

SEQ ID NO: 18           moltype = AA  length = 73
FEATURE                 Location/Qualifiers
REGION                  1..73
                        note = artificial construct
VARIANT                 32..33
                        note = MISC_FEATURE - Xaa can be any natural and
                         non-natural amino acid
VARIANT                 36
                        note = MISC_FEATURE - Xaa can be any natural and
                         non-natural amino acid
VARIANT                 39..40
                        note = MISC_FEATURE - Xaa can be any natural and
                         non-natural amino acid
VARIANT                 43
                        note = MISC_FEATURE - Xaa can be any natural and
                         non-natural amino acid
VARIANT                 57..58
                        note = MISC_FEATURE - Xaa can be any natural and
                         non-natural amino acid
VARIANT                 61
                        note = MISC_FEATURE - Xaa can be any natural and
                         non-natural amino acid
VARIANT                 64..65
                        note = MISC_FEATURE - Xaa can be any natural and
                         non-natural amino acid
VARIANT                 68
                        note = MISC_FEATURE - Xaa can be any natural and
                         non-natural amino acid
source                  1..73
                        mol_type = protein
                        organism = synthetic construct
SEQUENCE: 18
MGSWAEFKQR LAAIKTRLEA LGGSEAELAA FXXEIXAFXX ELXAYKGKGN PEVEALXXEA  60
XAIXXELXAY RHN                                                     73

SEQ ID NO: 19           moltype = AA  length = 73
FEATURE                 Location/Qualifiers
REGION                  1..73
                        note = artificial construct
VARIANT                 5
                        note = MISC_FEATURE - Xaa can be any natural and
                         non-natural amino acid
VARIANT                 8..9
                        note = MISC_FEATURE - Xaa can be any natural and
                         non-natural amino acid
VARIANT                 12
                        note = MISC_FEATURE - Xaa can be any natural and
                         non-natural amino acid
VARIANT                 15..16
                        note = MISC_FEATURE - Xaa can be any natural and
                         non-natural amino acid
VARIANT                 19
                        note = MISC_FEATURE - Xaa can be any natural and
                         non-natural amino acid
VARIANT                 55
                        note = MISC_FEATURE - Xaa can be any natural and
                         non-natural amino acid
VARIANT                 58..59
                        note = MISC_FEATURE - Xaa can be any natural and
                         non-natural amino acid
```

```
VARIANT                62
                       note = MISC_FEATURE - Xaa can be any natural and
                        non-natural amino acid
VARIANT                65..66
                       note = MISC_FEATURE - Xaa can be any natural and
                        non-natural amino acid
source                 1..73
                       mol_type = protein
                       organism = synthetic construct
SEQUENCE: 19
MGSWXEFXXR LXAIXXRLXA LGGSEAELAA FEKEIAAFES ELQAYKGKGN PEVEXLRXXA  60
AXIRXXLQAY RHN                                                     73

SEQ ID NO: 20          moltype = AA  length = 73
FEATURE                Location/Qualifiers
REGION                 1..73
                       note = artificial construct
VARIANT                5..6
                       note = MISC_FEATURE - Xaa can be any natural and
                        non-natural amino acid
VARIANT                9..10
                       note = MISC_FEATURE - Xaa can be any natural and
                        non-natural amino acid
VARIANT                13
                       note = MISC_FEATURE - Xaa can be any natural and
                        non-natural amino acid
VARIANT                16..17
                       note = MISC_FEATURE - Xaa can be any natural and
                        non-natural amino acid
VARIANT                32..33
                       note = MISC_FEATURE - Xaa can be any natural and
                        non-natural amino acid
VARIANT                36
                       note = MISC_FEATURE - Xaa can be any natural and
                        non-natural amino acid
VARIANT                39..40
                       note = MISC_FEATURE - Xaa can be any natural and
                        non-natural amino acid
VARIANT                43
                       note = MISC_FEATURE - Xaa can be any natural and
                        non-natural amino acid
VARIANT                50
                       note = MISC_FEATURE - Xaa can be any natural and
                        non-natural amino acid
VARIANT                55
                       note = misc_feature - Xaa can be any naturally occurring
                        amino acid
VARIANT                58..59
                       note = MISC_FEATURE - Xaa can be any natural and
                        non-natural amino acid
VARIANT                62
                       note = MISC_FEATURE - Xaa can be any natural and
                        non-natural amino acid
VARIANT                65..66
                       note = MISC_FEATURE - Xaa can be any natural and
                        non-natural amino acid
source                 1..73
                       mol_type = protein
                       organism = synthetic construct
SEQUENCE: 20
MGSWXXFKXX LAXIKXXLEA LGGSEAELAA FXXEIXAFXX ELXAYKGKGN PEVEXLRXXA  60
AXIRXXLQAY RHN                                                     73

SEQ ID NO: 21          moltype = AA  length = 73
FEATURE                Location/Qualifiers
REGION                 1..73
                       note = artificial construct
VARIANT                5
                       note = MISC_FEATURE - Xaa can be any natural and
                        non-natural amino acid
VARIANT                8..9
                       note = MISC_FEATURE - Xaa can be any natural and
                        non-natural amino acid
VARIANT                12
                       note = MISC_FEATURE - Xaa can be any natural and
                        non-natural amino acid
VARIANT                15..16
                       note = MISC_FEATURE - Xaa can be any natural and
                        non-natural amino acid
```

```
VARIANT                 19
                        note = MISC_FEATURE - Xaa can be any natural and
                         non-natural amino acid
VARIANT                 30
                        note = MISC_FEATURE - Xaa can be any natural and
                         non-natural amino acid
VARIANT                 33..34
                        note = MISC_FEATURE - Xaa can be any natural and
                         non-natural amino acid
VARIANT                 37
                        note = MISC_FEATURE - Xaa can be any natural and
                         non-natural amino acid
VARIANT                 40..41
                        note = MISC_FEATURE - Xaa can be any natural and
                         non-natural amino acid
VARIANT                 44
                        note = MISC_FEATURE - Xaa can be any natural and
                         non-natural amino acid
VARIANT                 57..58
                        note = MISC_FEATURE - Xaa can be any natural and
                         non-natural amino acid
VARIANT                 61
                        note = MISC_FEATURE - Xaa can be any natural and
                         non-natural amino acid
VARIANT                 64..65
                        note = MISC_FEATURE - Xaa can be any natural and
                         non-natural amino acid
VARIANT                 68
                        note = MISC_FEATURE - Xaa can be any natural and
                         non-natural amino acid
source                  1..73
                        mol_type = protein
                        organism = synthetic construct
SEQUENCE: 21
MGSWXEFXXR LXAIXXRLXA LGGSEAELAX FEXXIAXFEX XLQXYKGKGN PEVEALXXEA  60
XAIXXELXAY RHN                                                     73

SEQ ID NO: 22           moltype = AA  length = 126
FEATURE                 Location/Qualifiers
REGION                  1..126
                        note = artificial construct
VARIANT                 5..6
                        note = MISC_FEATURE - Xaa can be any natural and
                         non-natural amino acid
VARIANT                 9..10
                        note = MISC_FEATURE - Xaa can be any natural and
                         non-natural amino acid
VARIANT                 13
                        note = MISC_FEATURE - Xaa can be any natural and
                         non-natural amino acid
VARIANT                 16..17
                        note = MISC_FEATURE - Xaa can be any natural and
                         non-natural amino acid
VARIANT                 22..51
                        note = Xaa is 2-30 natural and/or non-natural amino acid
                         residues and up to 28 positions may be absent
VARIANT                 57
                        note = MISC_FEATURE - Xaa can be any natural and
                         non-natural amino acid
VARIANT                 60..61
                        note = MISC_FEATURE - Xaa can be any natural and
                         non-natural amino acid
VARIANT                 64
                        note = MISC_FEATURE - Xaa can be any natural and
                         non-natural amino acid
VARIANT                 67
                        note = MISC_FEATURE - Xaa can be any natural and
                         non-natural amino acid
VARIANT                 68
                        note = misc_feature - Xaa can be any naturally occurring
                         amino acid
VARIANT                 71
                        note = MISC_FEATURE - Xaa can be any natural and
                         non-natural amino acid
VARIANT                 73..102
                        note = Xaa is 2-30 natural and/or non-natural amino acid
                         residues and up to 28 positions may be absent
source                  1..126
                        mol_type = protein
```

```
                        organism = synthetic construct
SEQUENCE: 22
MGSWXXFKXX LAXIKXXLEA LXXXXXXXXX XXXXXXXXXX XXXXXXXXXX XEAELAXFEX  60
XIAXFEXXLQ XYXXXXXXXX XXXXXXXXXX XXXXXXXXXX XXNPEVEALR KEAAAIRDEL  120
QAYRHN                                                             126

SEQ ID NO: 23           moltype = AA  length = 126
FEATURE                 Location/Qualifiers
REGION                  1..126
                        note = artificial construct
VARIANT                 22..51
                        note = Xaa is 2-30 natural and/or non-natural amino acid
                         residues and up to 28 positions may be absent
VARIANT                 59..60
                        note = MISC_FEATURE - Xaa can be any natural and
                         non-natural amino acid
VARIANT                 63
                        note = MISC_FEATURE - Xaa can be any natural and
                         non-natural amino acid
VARIANT                 66..67
                        note = MISC_FEATURE - Xaa can be any natural and
                         non-natural amino acid
VARIANT                 70
                        note = MISC_FEATURE - Xaa can be any natural and
                         non-natural amino acid
VARIANT                 73..102
                        note = Xaa is 2-30 natural and/or non-natural amino acid
                         residues and up to 28 positions may be absent
VARIANT                 110..111
                        note = MISC_FEATURE - Xaa can be any natural and
                         non-natural amino acid
VARIANT                 114
                        note = MISC_FEATURE - Xaa can be any natural and
                         non-natural amino acid
VARIANT                 117..118
                        note = MISC_FEATURE - Xaa can be any natural and
                         non-natural amino acid
VARIANT                 121
                        note = MISC_FEATURE - Xaa can be any natural and
                         non-natural amino acid
source                  1..126
                        mol_type = protein
                        organism = synthetic construct
SEQUENCE: 23
MGSWAEFKQR LAAIKTRLEA LXXXXXXXXX XXXXXXXXXX XXXXXXXXXX XEAELAAFXX  60
EIXAFXXELX AYXXXXXXXX XXXXXXXXXX XXXXXXXXXX XXNPEVEALX XEAXAIXXEL  120
XAYRHN                                                             126

SEQ ID NO: 24           moltype = AA  length = 126
FEATURE                 Location/Qualifiers
REGION                  1..126
                        note = artificial construct
VARIANT                 5
                        note = MISC_FEATURE - Xaa can be any natural and
                         non-natural amino acid
VARIANT                 8..9
                        note = MISC_FEATURE - Xaa can be any natural and
                         non-natural amino acid
VARIANT                 12
                        note = MISC_FEATURE - Xaa can be any natural and
                         non-natural amino acid
VARIANT                 15..16
                        note = MISC_FEATURE - Xaa can be any natural and
                         non-natural amino acid
VARIANT                 19
                        note = MISC_FEATURE - Xaa can be any natural and
                         non-natural amino acid
VARIANT                 22..51
                        note = Xaa is 2-30 natural and/or non-natural amino acid
                         residues and up to 28 positions may be absent
VARIANT                 73..102
                        note = Xaa is 2-30 natural and/or non-natural amino acid
                         residues and up to 28 positions may be absent
VARIANT                 108
                        note = MISC_FEATURE - Xaa can be any natural and
                         non-natural amino acid
VARIANT                 111..112
                        note = MISC_FEATURE - Xaa can be any natural and
                         non-natural amino acid
```

```
VARIANT                 115
                        note = MISC_FEATURE - Xaa can be any natural and
                         non-natural amino acid
VARIANT                 118..119
                        note = MISC_FEATURE - Xaa can be any natural and
                         non-natural amino acid
source                  1..126
                        mol_type = protein
                        organism = synthetic construct
SEQUENCE: 24
MGSWXEFXXR LXAIXXRLXA LXXXXXXXXX XXXXXXXXXX XXXXXXXXXX XEAELAAFEK  60
EIAAFESELQ AYXXXXXXXX XXXXXXXXXX XXXXXXXXXX XXNPEVEXLR XXAAXIRXXL  120
QAYRHN                                                             126

SEQ ID NO: 25           moltype = AA  length = 126
FEATURE                 Location/Qualifiers
REGION                  1..126
                        note = artificial construct
VARIANT                 5..6
                        note = MISC_FEATURE - Xaa can be any natural and
                         non-natural amino acid
VARIANT                 9..10
                        note = MISC_FEATURE - Xaa can be any natural and
                         non-natural amino acid
VARIANT                 13
                        note = MISC_FEATURE - Xaa can be any natural and
                         non-natural amino acid
VARIANT                 16..17
                        note = MISC_FEATURE - Xaa can be any natural and
                         non-natural amino acid
VARIANT                 22..51
                        note = Xaa is 2-30 natural and/or non-natural amino acid
                         residues and up to 28 positions may be absent
VARIANT                 59..60
                        note = MISC_FEATURE - Xaa can be any natural and
                         non-natural amino acid
VARIANT                 63
                        note = MISC_FEATURE - Xaa can be any natural and
                         non-natural amino acid
VARIANT                 66..67
                        note = MISC_FEATURE - Xaa can be any natural and
                         non-natural amino acid
VARIANT                 70
                        note = MISC_FEATURE - Xaa can be any natural and
                         non-natural amino acid
VARIANT                 73..102
                        note = Xaa is 2-30 natural and/or non-natural amino acid
                         residues and up to 28 positions may be absent
VARIANT                 108
                        note = MISC_FEATURE - Xaa can be any natural and
                         non-natural amino acid
VARIANT                 111..112
                        note = MISC_FEATURE - Xaa can be any natural and
                         non-natural amino acid
VARIANT                 115
                        note = MISC_FEATURE - Xaa can be any natural and
                         non-natural amino acid
VARIANT                 118..119
                        note = MISC_FEATURE - Xaa can be any natural and
                         non-natural amino acid
source                  1..126
                        mol_type = protein
                        organism = synthetic construct
SEQUENCE: 25
MGSWXXFKXX LAXIKXXLEA LXXXXXXXXX XXXXXXXXXX XXXXXXXXXX XEAELAAFXX  60
EIXAFXXELX AYXXXXXXXX XXXXXXXXXX XXXXXXXXXX XXNPEVEXLR XXAAXIRXXL  120
QAYRHN                                                             126

SEQ ID NO: 26           moltype = AA  length = 126
FEATURE                 Location/Qualifiers
REGION                  1..126
                        note = artificial construct
VARIANT                 5
                        note = MISC_FEATURE - Xaa can be any natural and
                         non-natural amino acid
VARIANT                 8..9
                        note = MISC_FEATURE - Xaa can be any natural and
                         non-natural amino acid
VARIANT                 12
```

```
                          note = MISC_FEATURE - Xaa can be any natural and
                           non-natural amino acid
VARIANT                   15..16
                          note = MISC_FEATURE - Xaa can be any natural and
                           non-natural amino acid
VARIANT                   19
                          note = MISC_FEATURE - Xaa can be any natural and
                           non-natural amino acid
VARIANT                   22..51
                          note = Xaa is 2-30 natural and/or non-natural amino acid
                           residues and up to 28 positions may be absent
VARIANT                   57
                          note = MISC_FEATURE - Xaa can be any natural and
                           non-natural amino acid
VARIANT                   60..61
                          note = MISC_FEATURE - Xaa can be any natural and
                           non-natural amino acid
VARIANT                   64
                          note = MISC_FEATURE - Xaa can be any natural and
                           non-natural amino acid
VARIANT                   67..68
                          note = MISC_FEATURE - Xaa can be any natural and
                           non-natural amino acid
VARIANT                   71
                          note = MISC_FEATURE - Xaa can be any natural and
                           non-natural amino acid
VARIANT                   73..102
                          note = Xaa is 2-30 natural and/or non-natural amino acid
                           residues and up to 28 positions may be absent
VARIANT                   110..111
                          note = MISC_FEATURE - Xaa can be any natural and
                           non-natural amino acid
VARIANT                   114
                          note = MISC_FEATURE - Xaa can be any natural and
                           non-natural amino acid
VARIANT                   117..118
                          note = MISC_FEATURE - Xaa can be any natural and
                           non-natural amino acid
VARIANT                   121
                          note = MISC_FEATURE - Xaa can be any natural and
                           non-natural amino acid
source                    1..126
                          mol_type = protein
                          organism = synthetic construct
SEQUENCE: 26
MGSWXEFXXR LXAIXXRLXA LXXXXXXXXX XXXXXXXXXX XXXXXXXXXX XEAELAXFEX  60
XIAXFEXXLQ XYXXXXXXXX XXXXXXXXXX XXXXXXXXXX XXNPEVEALX XEAXAIXXEL  120
XAYRHN                                                             126

SEQ ID NO: 27             moltype = AA  length = 73
FEATURE                   Location/Qualifiers
REGION                    1..73
                          note = artificial construct
VARIANT                   5
                          note = MISC_FEATURE - Xaa can be any natural and
                           non-natural amino acid
VARIANT                   8..9
                          note = MISC_FEATURE - Xaa can be any natural and
                           non-natural amino acid
VARIANT                   12..13
                          note = MISC_FEATURE - Xaa can be any natural and
                           non-natural amino acid
VARIANT                   15..16
                          note = MISC_FEATURE - Xaa can be any natural and
                           non-natural amino acid
VARIANT                   19
                          note = MISC_FEATURE - Xaa can be any natural and
                           non-natural amino acid
VARIANT                   36
                          note = MISC_FEATURE - Xaa can be any natural and
                           non-natural amino acid
VARIANT                   39..40
                          note = MISC_FEATURE - Xaa can be any natural and
                           non-natural amino acid
VARIANT                   43
                          note = MISC_FEATURE - Xaa can be any natural and
                           non-natural amino acid
VARIANT                   58
                          note = MISC_FEATURE - Xaa can be any natural and
```

```
                          non-natural amino acid
VARIANT                  61..62
                         note = MISC_FEATURE - Xaa can be any natural and
                          non-natural amino acid
VARIANT                  65
                         note = MISC_FEATURE - Xaa can be any natural and
                          non-natural amino acid
VARIANT                  68..69
                         note = MISC_FEATURE - Xaa can be any natural and
                          non-natural amino acid
VARIANT                  72..73
                         note = MISC_FEATURE - Xaa can be any natural and
                          non-natural amino acid
source                   1..73
                         mol_type = protein
                         organism = synthetic construct
SEQUENCE: 27
MGSWXEFXXR LXXIXXRLXA LGGSEAELAA FEKEIXAFXX ELXAYKGKGN PEVEALRXEA  60
XXIRXELXXY RXX                                                     73

SEQ ID NO: 28            moltype = AA  length = 58
FEATURE                  Location/Qualifiers
REGION                   1..58
                         note = artificial construct
VARIANT                  9..11
                         note = MISC_FEATURE - Xaa can be any natural and
                          non-natural amino acid
VARIANT                  13..14
                         note = MISC_FEATURE - Xaa can be any natural and
                          non-natural amino acid
VARIANT                  17..18
                         note = MISC_FEATURE - Xaa can be any natural and
                          non-natural amino acid
VARIANT                  24..25
                         note = MISC_FEATURE - Xaa can be any natural and
                          non-natural amino acid
VARIANT                  27..28
                         note = MISC_FEATURE - Xaa can be any natural and
                          non-natural amino acid
VARIANT                  32
                         note = MISC_FEATURE - Xaa can be any natural and
                          non-natural amino acid
VARIANT                  35
                         note = MISC_FEATURE - Xaa can be any natural and
                          non-natural amino acid
source                   1..58
                         mol_type = protein
                         organism = synthetic construct
SEQUENCE: 28
VDNKFNKEXX XAXXEIXXLP NLNXXQXXAF IXSLXDDPSQ SANLLAEAKK LNDAQAPK    58

SEQ ID NO: 29            moltype = AA  length = 33
FEATURE                  Location/Qualifiers
REGION                   1..33
                         note = artificial construct
VARIANT                  4..6
                         note = MISC_FEATURE - Xaa can be any natural and
                          non-natural amino acid
VARIANT                  8..9
                         note = MISC_FEATURE - Xaa can be any natural and
                          non-natural amino acid
VARIANT                  12..13
                         note = MISC_FEATURE - Xaa can be any natural and
                          non-natural amino acid
VARIANT                  19..20
                         note = MISC_FEATURE - Xaa can be any natural and
                          non-natural amino acid
VARIANT                  22..23
                         note = MISC_FEATURE - Xaa can be any natural and
                          non-natural amino acid
VARIANT                  27
                         note = MISC_FEATURE - Xaa can be any natural and
                          non-natural amino acid
VARIANT                  30
                         note = MISC_FEATURE - Xaa can be any natural and
                          non-natural amino acid
source                   1..33
                         mol_type = protein
                         organism = synthetic construct
```

```
SEQUENCE: 29
NKEXXXAXXE IXXLPNLNXX QXXAFIXSLX DDP                              33

SEQ ID NO: 30           moltype = AA  length = 33
FEATURE                 Location/Qualifiers
REGION                  1..33
                        note = artificial construct
VARIANT                 2..3
                        note = MISC_FEATURE - Xaa is any amino acid but Cys, Arg,
                         or Pro
VARIANT                 5
                        note = MISC_FEATURE - Xaa is any amino acid but Cys, Arg,
                         or Pro
VARIANT                 13..14
                        note = MISC_FEATURE - Xaa is any amino acid but Cys, Arg,
                         or Pro
VARIANT                 26
                        note = MISC_FEATURE - Xaa is His, Asn, or Tyr
VARIANT                 33
                        note = MISC_FEATURE - Xaa is any amino acid but Cys, Arg,
                         or Pro
source                  1..33
                        mol_type = protein
                        organism = synthetic construct
SEQUENCE: 30
DXXGXTPLHL AAXXGHLEIV EVLLKXGADV NAX                              33

SEQ ID NO: 31           moltype = AA  length = 166
FEATURE                 Location/Qualifiers
REGION                  1..166
                        note = artificial construct
VARIANT                 44..45
                        note = MISC_FEATURE - Xaa is any amino acid but Cys, Arg,
                         or Pro
VARIANT                 47
                        note = MISC_FEATURE - Xaa is any amino acid but Cys, Arg,
                         or Pro
VARIANT                 55..56
                        note = MISC_FEATURE - Xaa is any amino acid but Cys, Arg,
                         or Pro
VARIANT                 68
                        note = MISC_FEATURE - Xaa is His, Asn, or Tyr
VARIANT                 75
                        note = MISC_FEATURE - Xaa is any amino acid but Cys, Arg,
                         or Pro
VARIANT                 77..78
                        note = MISC_FEATURE - Xaa is any amino acid but Cys, Arg,
                         or Pro
VARIANT                 80
                        note = MISC_FEATURE - Xaa is any amino acid but Cys, Arg,
                         or Pro
VARIANT                 88..89
                        note = MISC_FEATURE - Xaa is any amino acid but Cys, Arg,
                         or Pro
VARIANT                 101
                        note = MISC_FEATURE - Xaa is His, Asn, or Tyr
VARIANT                 108
                        note = MISC_FEATURE - Xaa is any amino acid but Cys, Arg,
                         or Pro
VARIANT                 109..141
                        note = positions 109 to 141 may be absent
VARIANT                 110..111
                        note = MISC_FEATURE - Xaa is any amino acid but Cys, Arg,
                         or Pro
VARIANT                 113
                        note = MISC_FEATURE - Xaa is any amino acid but Cys, Arg,
                         or Pro
VARIANT                 121..122
                        note = MISC_FEATURE - Xaa is any amino acid but Cys, Arg,
                         or Pro
VARIANT                 134
                        note = MISC_FEATURE - Xaa is His, Asn, or Tyr
VARIANT                 141
                        note = MISC_FEATURE - Xaa is any amino acid but Cys, Arg,
                         or Pro
source                  1..166
                        mol_type = protein
                        organism = synthetic construct
SEQUENCE: 31
```

```
MRGSHHHHHH GSDLGKKLLE AARAGQDDEV RILMANGADV NADXXGXTPL HLAAXXGHLE  60
IVEVLLKXGA DVNAXDXXGX TPLHLAAXXG HLEIVEVLLK XGADVNAXDX XGXTPLHLAA  120
XXGHLEIVEV LLKXGADVNA XQDKFGKTAF DISIDNGNED LAEILQ                 166

SEQ ID NO: 32          moltype = AA  length = 25
FEATURE                Location/Qualifiers
REGION                 1..25
                       note = artificial construct
source                 1..25
                       mol_type = protein
                       organism = synthetic construct
SEQUENCE: 32
QDKFGKTAFD ISIDNGNEDL AEILQ                                        25

SEQ ID NO: 33          moltype = AA  length = 28
FEATURE                Location/Qualifiers
REGION                 1..28
                       note = artificial construct
VARIANT                3
                       note = MISC_FEATURE - Xaa is any amino acid
VARIANT                5
                       note = MISC_FEATURE - Xaa is any amino acid
VARIANT                8
                       note = MISC_FEATURE - Xaa is any amino acid
VARIANT                12..13
                       note = MISC_FEATURE - Xaa is any amino acid
VARIANT                15
                       note = MISC_FEATURE - Xaa is any amino acid
VARIANT                19
                       note = MISC_FEATURE - Xaa is any amino acid
VARIANT                25
                       note = MISC_FEATURE - Xaa is any amino acid
source                 1..28
                       mol_type = protein
                       organism = synthetic construct
SEQUENCE: 33
EFXCXNGXCI PXXWXCDGXD DCGDXSDE                                     28

SEQ ID NO: 34          moltype = AA  length = 74
FEATURE                Location/Qualifiers
REGION                 1..74
                       note = artificial construct
VARIANT                12..22
                       note = MISC_FEATURE - Xaa is any amino acid
VARIANT                13..21
                       note = MISC_FEATURE - Xaa may be absent
VARIANT                41..48
                       note = MISC_FEATURE - Xaa is any amino acid
VARIANT                42..46
                       note = MISC_FEATURE - Xaa may be absent
VARIANT                61
                       note = MISC_FEATURE - Xaa is any amino acid
source                 1..74
                       mol_type = protein
                       organism = synthetic construct
SEQUENCE: 34
GVTLFVALYD YXXXXXXXXX XXLSFHKGEK FQILSTHEYE XXXXXXXXWE ARSLTTGETG  60
XIPSNYVAPV DSIQ                                                    74

SEQ ID NO: 35          moltype = AA  length = 68
FEATURE                Location/Qualifiers
REGION                 1..68
                       note = artificial construct
VARIANT                12..22
                       note = MISC_FEATURE - Xaa is any amino acid
VARIANT                16..21
                       note = MISC_FEATURE - Xaa is optionally absent
source                 1..68
                       mol_type = protein
                       organism = synthetic construct
SEQUENCE: 35
GVTLFVALYD YXXXXXXXXX XXLSFHKGEK FQILSTHEYE DWWEARSLTT GETGYIPSNY  60
VAPVDSIQ                                                           68

SEQ ID NO: 36          moltype = AA  length = 60
FEATURE                Location/Qualifiers
REGION                 1..60
                       note = artificial construct
VARIANT                11
```

```
                     note = MISC_FEATURE - Xaa is one of: Ala, Asp, Glu, Phe,
                      Gly, His, Ile, Lys, Leu, Met, Asn, Pro, Gln, Arg, Ser,
                      Thr, Val, Trp, Tyr
VARIANT              13
                     note = MISC_FEATURE - Xaa is one of: Ala, Asp, Glu, Phe,
                      Gly, His, Ile, Lys, Leu, Met, Asn, Pro, Gln, Arg, Ser,
                      Thr, Val, Trp, Tyr
VARIANT              15
                     note = MISC_FEATURE - Xaa is one of: Ala, Asp, Glu, Phe,
                      Gly, His, Ile, Lys, Leu, Met, Asn, Gln, Arg, Ser, Thr,
                      Val, Trp, Tyr
VARIANT              16
                     note = MISC_FEATURE - Xaa is one of: Ala, Gly, Glu, Asp,
                      His, Thr
VARIANT              17
                     note = MISC_FEATURE - Xaa is one of: Ala, Asp, Glu, Phe,
                      Gly, His, Ile, Lys, Leu, Met, Asn, Gln, Arg, Ser, Thr,
                      Val, Trp, Tyr
VARIANT              18
                     note = MISC_FEATURE - Xaa is one of: Ala, Asp, Glu, Phe,
                      Gly, His, Ile, Lys, Leu, Met, Asn, Gln, Arg, Ser, Thr,
                      Val, Trp, Tyr
VARIANT              19
                     note = MISC_FEATURE - Xaa is one of: Ala, Asp, Glu, Phe,
                      Gly, His, Ile, Lys, Leu, Met, Asn, Pro, Gln, Arg, Ser,
                      Thr, Val, Trp, Tyr
VARIANT              34
                     note = MISC_FEATURE - Xaa is one of: Ala, Cys, Asp, Glu,
                      Phe, Gly, His, Ile, Lys, Leu, Met, Asn, Pro, Gln, Arg,
                      Ser, Thr, Val, Trp, Tyr
VARIANT              39
                     note = MISC_FEATURE - Xaa is one of: Ala, Cys, Asp, Glu,
                      Phe, Gly, His, Ile, Lys, Leu, Met, Asn, Pro, Gln, Arg,
                      Ser, Thr, Val, Trp, Tyr
VARIANT              40
                     note = MISC_FEATURE - Xaa is one of: Gly, and Ala
source               1..60
                     mol_type = protein
                     organism = synthetic construct
SEQUENCE: 36
MHSFCAFKAD XGXCXXXXXR FFFNIFTRQC EEFXYGGCXX NQNRFESLEE CKKMCTRDGA  60

SEQ ID NO: 37        moltype = AA  length = 32
FEATURE              Location/Qualifiers
REGION               1..32
                     note = artificial construct
VARIANT              7
                     note = MISC_FEATURE - Xaa is any amino acid
VARIANT              9
                     note = MISC_FEATURE - Xaa is any amino acid
VARIANT              12..14
                     note = MISC_FEATURE - Xaa is any amino acid
VARIANT              14
                     note = MISC_FEATURE - Xaa is optionally absent
VARIANT              18
                     note = MISC_FEATURE - Xaa is any amino acid
VARIANT              20
                     note = MISC_FEATURE - Xaa is any amino acid
VARIANT              22
                     note = MISC_FEATURE - Xaa is any amino acid
VARIANT              25
                     note = MISC_FEATURE - Xaa is any amino acid
VARIANT              27
                     note = MISC_FEATURE - Xaa is any amino acid
source               1..32
                     mol_type = protein
                     organism = synthetic construct
SEQUENCE: 37
KLPPGWXKXW SXXXGRVXYX NXITXAXQWE RP                                 32

SEQ ID NO: 38        moltype = AA  length = 31
FEATURE              Location/Qualifiers
REGION               1..31
                     note = artificial construct
VARIANT              7
                     note = MISC_FEATURE - Xaa is any amino acid
VARIANT              9
                     note = MISC_FEATURE - Xaa is any amino acid
VARIANT              12..13
```

```
                        note = MISC_FEATURE - Xaa is any amino acid
VARIANT                 14
                        note = MISC_FEATURE - Xaa is Gly that is optionally absent
VARIANT                 17
                        note = MISC_FEATURE - Xaa is any amino acid
VARIANT                 19
                        note = MISC_FEATURE - Xaa is any amino acid
VARIANT                 21
                        note = MISC_FEATURE - Xaa is any amino acid
VARIANT                 24
                        note = MISC_FEATURE - Xaa is any amino acid
VARIANT                 26
                        note = MISC_FEATURE - Xaa is any amino acid
source                  1..31
                        mol_type = protein
                        organism = synthetic construct
SEQUENCE: 38
KLPPGWXKXW SXXXRVXYXN XITXAXQWER P                                  31

SEQ ID NO: 39           moltype = AA  length = 10
FEATURE                 Location/Qualifiers
REGION                  1..10
                        note = artificial construct
source                  1..10
                        mol_type = protein
                        organism = synthetic construct
SEQUENCE: 39
GGGGTGGGGS                                                          10

SEQ ID NO: 40           moltype = AA  length = 10
FEATURE                 Location/Qualifiers
REGION                  1..10
                        note = artificial construct
source                  1..10
                        mol_type = protein
                        organism = synthetic construct
SEQUENCE: 40
GGGGDGGGGS                                                          10

SEQ ID NO: 41           moltype = AA  length = 668
FEATURE                 Location/Qualifiers
source                  1..668
                        mol_type = protein
                        organism = Homo sapiens
SEQUENCE: 41
DSSKWVFEHP ETLYAWEGAC VWIPCTYRAL DGDLESFILF HNPEYNKNTS KFDGTRLYES  60
TKDGKVPSEQ KRVQFLGDKN KNCTLSIHPV HLNDSGQLGL RMESKTEKWM ERIHLNVSER  120
PFPPHIQLPP EIQESQEVTL TCLLNFSCYG YPIQLQWLLE GVPMRQAAVT STSLTIKSVF  180
TRSELKFSPQ WSHHGKIVTC QLQDADGKFL SNDTVQLNVK HTPKLEIKVT PSDAIVREGD  240
SVTMTCEVSS SNPEYTTVSW LKDGTSLKKQ NTFTLNLREV TKDQSGKYCC QVSNDVGPGR  300
SEEVFLQVQY APEPSTVQIL HSPAVEGSQV EFLCMSLANP LPTNYTWYHN GKEMQGRTEE  360
KVHIPKILPW HAGTYSCVAE NILGTGQRGP GAELDVQYPP KKVTTVIQNP MPIREGDTVT  420
LSCNYNSSNP SVTRYEWKPH GAWEEPSLGV LKIQNVGWDN TTIACAACNS WCSWASPVAL  480
NVQYAPRDVR VRKIKPLSEI HSGNSVSLQC DFSSSHPKEV QFFWEKNGRL LGKESQLNFD  540
SISPEDAGSY SCWVNNSIGQ TASKAWTLEV LYAPRRLRVS MSPGDQVMEG KSATLTCESD  600
ANPPVSHYTW FDWNNQSLPY HSQKLRLEPV KVQHSGAYWC QGTNSVGKGR SPLSTLTVYY  660
SPETIGRR                                                            668

SEQ ID NO: 42           moltype = AA  length = 630
FEATURE                 Location/Qualifiers
source                  1..630
                        mol_type = protein
                        organism = Homo sapiens
SEQUENCE: 42
TQVCTGTDMK LRLPASPETH LDMLRHLYQG CQVVQGNLEL TYLPTNASLS FLQDIQEVQG  60
YVLIAHNQVR QVPLQRLRIV RGTQLFEDNY ALAVLDNGDP LNNTTPVTGA SPGGLRELQL  120
RSLTEILKGG VLIQRNPQLC YQDTILWKDI FHKNNQLALT LIDTNRSRAC HPCSPMCKGS  180
RCWGESSEDC QSLTRTVCAG GCARCKGPLP TDCCHEQCAA GCTGPKHSDC LACLHFNHSG  240
ICELHCPALV TYNTDTFESM PNPEGRYTFG ASCVTACPYN YLSTDVGSCT LVCPLHNQEV  300
TAEDGTQRCE KCSKPCARVC YGLGMEHLRE VRAVTSANIQ EFAGCKKIFG SLAFLPESFD  360
GDPASNTAPL QPEQLQVFET LEEITGYLYI SAWPDSLPDL SVFQNLQVIR GRILHNGAYS  420
LTLQGLGISW LGLRSLRELG SGLALIHHNT HLCFVHTVPW DQLFRNPHQA LLHTANRPED  480
ECVGEGLACH QLCARGHCWG PGPTQCVNCS QFLRGQECVE ECRVLQGLPR EYVNARHCLP  540
CHPECQPQNG SVTCFGPEAD QCVACAHYKD PPFCVARCPS GVKPDLSYMP IWKFPDEEGA  600
CQPCPINCTH SCVDLDDKGC PAEQRASPLT                                    630

SEQ ID NO: 43           moltype = AA  length = 5
FEATURE                 Location/Qualifiers
REGION                  1..5
```

```
                         note = artificial construct
source                   1..5
                         mol_type = protein
                         organism = synthetic construct
SEQUENCE: 43
GGGGS                                                                    5

SEQ ID NO: 44            moltype = AA  length = 73
FEATURE                  Location/Qualifiers
REGION                   1..73
                         note = artificial construct
source                   1..73
                         mol_type = protein
                         organism = synthetic construct
SEQUENCE: 44
MGSWYEFSWR LQAIHQRLNA LGGSEAELAA FEKEIAAFES ELQAYKGKGN PEVEELRAYA  60
AGIRGALQAY RHN                                                     73

SEQ ID NO: 45            moltype = AA  length = 73
FEATURE                  Location/Qualifiers
REGION                   1..73
                         note = artificial construct
source                   1..73
                         mol_type = protein
                         organism = synthetic construct
SEQUENCE: 45
MGSWHEFTWR LIAIQQRLEA LGGSEAELAA FEKEIAAFES ELQAYKGKGN PEVEELRAYA  60
AGIRHHLQAY RHN                                                     73

SEQ ID NO: 46            moltype = AA  length = 73
FEATURE                  Location/Qualifiers
REGION                   1..73
                         note = artificial construct
source                   1..73
                         mol_type = protein
                         organism = synthetic construct
SEQUENCE: 46
MGSWREFAWR LVAINSRLKA LGGSEAELAA FEKEIAAFES ELQAYKGKGN PEVEELRHYA  60
ASIRDGLQAY RHN                                                     73

SEQ ID NO: 47            moltype = AA  length = 73
FEATURE                  Location/Qualifiers
REGION                   1..73
                         note = artificial construct
source                   1..73
                         mol_type = protein
                         organism = synthetic construct
SEQUENCE: 47
MGSWHEFAWR LQAINQRLNA LGGSEAELAA FEKEIAAFES ELQAYKGKGN PEVEELRHYA  60
AHIRNGLQAY RHN                                                     73

SEQ ID NO: 48            moltype = AA  length = 73
FEATURE                  Location/Qualifiers
REGION                   1..73
                         note = artificial construct
source                   1..73
                         mol_type = protein
                         organism = synthetic construct
SEQUENCE: 48
MGSWNEFAWR LTAIEQRLMA LGGSEAELAA FEKEIAAFES ELQAYKGKGN PEVEELRHYA  60
AGIRDNLQAY RHN                                                     73

SEQ ID NO: 49            moltype = AA  length = 73
FEATURE                  Location/Qualifiers
REGION                   1..73
                         note = artificial construct
source                   1..73
                         mol_type = protein
                         organism = synthetic construct
SEQUENCE: 49
MGSWTEFAWR LQAIHQRLQA LGGSEAELAA FEKEIAAFES ELQAYKGKGN PEVEELRVYA  60
AKIRISLQAY RHN                                                     73

SEQ ID NO: 50            moltype = AA  length = 73
FEATURE                  Location/Qualifiers
REGION                   1..73
                         note = artificial construct
source                   1..73
                         mol_type = protein
```

```
                        organism = synthetic construct
SEQUENCE: 50
MGSWIEFAWR LQAIHQRLDA LGGSEAELAA FEKEIAAFES ELQAYKGKGN PEVEDLREYA  60
ANIRDSLQAY RHN                                                      73

SEQ ID NO: 51           moltype = AA  length = 73
FEATURE                 Location/Qualifiers
REGION                  1..73
                        note = artificial construct
source                  1..73
                        mol_type = protein
                        organism = synthetic construct
SEQUENCE: 51
MGSWHEFTWR LVAIQQRLQA LGGSEAELAA FEKEIAAFES ELQAYKGKGN PEVEELRKFA  60
AKIRYELQAY RHN                                                      73

SEQ ID NO: 52           moltype = AA  length = 73
FEATURE                 Location/Qualifiers
REGION                  1..73
                        note = artificial construct
source                  1..73
                        mol_type = protein
                        organism = synthetic construct
SEQUENCE: 52
MGSWHEFTWR LIAIRERLFA LGGSEAELAA FEKEIAAFES ELQAYKGKGN PEVEELREYA  60
ASIRNMLQAY RHN                                                      73

SEQ ID NO: 53           moltype = AA  length = 73
FEATURE                 Location/Qualifiers
REGION                  1..73
                        note = artificial construct
source                  1..73
                        mol_type = protein
                        organism = synthetic construct
SEQUENCE: 53
MGSWIEFSWR LEAIRQRLQA LGGSEAELAA FEKEIAAFES ELQAYKGKGN PEVESLRSYA  60
ARIRQELQAY RHN                                                      73

SEQ ID NO: 54           moltype = AA  length = 73
FEATURE                 Location/Qualifiers
REGION                  1..73
                        note = artificial construct
source                  1..73
                        mol_type = protein
                        organism = synthetic construct
SEQUENCE: 54
MGSWVEFSWR LEAIRQRLQA LGGSEAELAA FEKEIAAFES ELQAYKGKGN PEVESLRSYA  60
ARIRQELQAY RHN                                                      73

SEQ ID NO: 55           moltype = AA  length = 73
FEATURE                 Location/Qualifiers
REGION                  1..73
                        note = artificial construct
source                  1..73
                        mol_type = protein
                        organism = synthetic construct
SEQUENCE: 55
MGSWVEFSWR LEAIRQRLTA LGGSEAELAA FEKEIAAFES ELQAYKGKGN PEVEDLRKYA  60
ARIRGELQAY RHN                                                      73

SEQ ID NO: 56           moltype = AA  length = 73
FEATURE                 Location/Qualifiers
REGION                  1..73
                        note = artificial construct
source                  1..73
                        mol_type = protein
                        organism = synthetic construct
SEQUENCE: 56
MGSWVEFAWR LTAIDQRLSA LGGSEAELAA FEKEIAAFES ELQAYKGKGN PEVENLRFYA  60
AKIRSHLQAY RHN                                                      73

SEQ ID NO: 57           moltype = AA  length = 73
FEATURE                 Location/Qualifiers
REGION                  1..73
                        note = artificial construct
source                  1..73
                        mol_type = protein
                        organism = synthetic construct
SEQUENCE: 57
```

```
MGSWVEFAWR LEAIKQRLTA LGGSEAELAA FEKEIAAFES ELQAYKGKGN PEVEELRLYA  60
AKIRRVLQAY RHN                                                    73

SEQ ID NO: 58          moltype = AA  length = 73
FEATURE                Location/Qualifiers
REGION                 1..73
                       note = artificial construct
source                 1..73
                       mol_type = protein
                       organism = synthetic construct
SEQUENCE: 58
MGSWVEFAWR LTAIHTRLWA LGGSEAELAA FEKEIAAFES ELQAYKGKGN PEVESLRKYA  60
AKIRKQLQAY RHN                                                    73

SEQ ID NO: 59          moltype = AA  length = 73
FEATURE                Location/Qualifiers
REGION                 1..73
                       note = artificial construct
source                 1..73
                       mol_type = protein
                       organism = synthetic construct
SEQUENCE: 59
MGSWTEFAWR LEAINQRLQA LGGSEAELAA FEKEIAAFES ELQAYKGKGK PEVEALRAYA  60
AKIRTRLQAY RHN                                                    73

SEQ ID NO: 60          moltype = AA  length = 73
FEATURE                Location/Qualifiers
REGION                 1..73
                       note = artificial construct
source                 1..73
                       mol_type = protein
                       organism = synthetic construct
SEQUENCE: 60
MGSWSEFAWR LEAIHQRLSA LGGSEAELAA FEKEIAAFES ELQAYKGKGN PEVESLRLFA  60
AQIRENLQAY RHN                                                    73

SEQ ID NO: 61          moltype = AA  length = 73
FEATURE                Location/Qualifiers
REGION                 1..73
                       note = artificial construct
source                 1..73
                       mol_type = protein
                       organism = synthetic construct
SEQUENCE: 61
MGSWNEFAWR LIAINQRLWA LGGSEAELAA FEKEIAAFES ELQAYKGKGN PEVESLRHFA  60
ANIRNDLQAY RHN                                                    73

SEQ ID NO: 62          moltype = AA  length = 73
FEATURE                Location/Qualifiers
REGION                 1..73
                       note = artificial construct
source                 1..73
                       mol_type = protein
                       organism = synthetic construct
SEQUENCE: 62
MGSWTEFAWR LIAIDQRLMA LGGSEAELAA FEKEIAAFES ELQAYKGKGN PEVEILRELA  60
AEIRFHLQAY RHN                                                    73

SEQ ID NO: 63          moltype = AA  length = 73
FEATURE                Location/Qualifiers
REGION                 1..73
                       note = artificial construct
source                 1..73
                       mol_type = protein
                       organism = synthetic construct
SEQUENCE: 63
MGSWSEFMNR LDAITYRLVA LGGSEAELAA FEKEIAAFES ELQAYKGKGN PEVELLRHYA  60
AQIRDSLQAY RHN                                                    73

SEQ ID NO: 64          moltype = AA  length = 73
FEATURE                Location/Qualifiers
REGION                 1..73
                       note = artificial construct
source                 1..73
                       mol_type = protein
                       organism = synthetic construct
SEQUENCE: 64
MGSWTEFMER LDAISYRLWA LGGSEAELAA FEKEIAAFES ELQAYKGKGN PEVEVLRDYA  60
AIIRNSLQAY RHN                                                    73
```

```
SEQ ID NO: 65          moltype = AA  length = 73
FEATURE                Location/Qualifiers
REGION                 1..73
                       note = artificial construct
source                 1..73
                       mol_type = protein
                       organism = synthetic construct
SEQUENCE: 65
MGSWAEFMDR LDAITYRLWA LGGSEAELAA FEKEIAAFES ELQAYKGKGN PEVEELRGYA  60
AIIRSELQAY RHN                                                     73

SEQ ID NO: 66          moltype = AA  length = 73
FEATURE                Location/Qualifiers
REGION                 1..73
                       note = artificial construct
source                 1..73
                       mol_type = protein
                       organism = synthetic construct
SEQUENCE: 66
MGSWIEFQER LDAIFYRLHA LGGSEAELAA FEKEIAAFES ELQAYKGKGN PEVEDLRDAA  60
ATIRRQLQAY RHN                                                     73

SEQ ID NO: 67          moltype = AA  length = 73
FEATURE                Location/Qualifiers
REGION                 1..73
                       note = artificial construct
source                 1..73
                       mol_type = protein
                       organism = synthetic construct
SEQUENCE: 67
MGSWIEFQQR LDAIFYRLYA LGGSEAELAA FEKEIAAFES ELQAYKGKGN PEVENLRDMA  60
AIIRKQLQAY RHN                                                     73

SEQ ID NO: 68          moltype = AA  length = 73
FEATURE                Location/Qualifiers
REGION                 1..73
                       note = artificial construct
source                 1..73
                       mol_type = protein
                       organism = synthetic construct
SEQUENCE: 68
MGSWYEFQSR LDAIFYRLFA LGGSEAELAA FEKEIAAFES ELQAYKGKGN PEVEKLREAA  60
ASIRTQLQAY RHN                                                     73

SEQ ID NO: 69          moltype = AA  length = 73
FEATURE                Location/Qualifiers
REGION                 1..73
                       note = artificial construct
source                 1..73
                       mol_type = protein
                       organism = synthetic construct
SEQUENCE: 69
MGSWSEFIDR LDAITYRLFA LGGSEAELAA FEKEIAAFES ELQAYKGKGN PEVENLRWYA  60
GVIREQLQAY RHN                                                     73

SEQ ID NO: 70          moltype = AA  length = 73
FEATURE                Location/Qualifiers
REGION                 1..73
                       note = artificial construct
source                 1..73
                       mol_type = protein
                       organism = synthetic construct
SEQUENCE: 70
MGSWSEFYDR LYAINQRLFA LGGSEAELAA FEKEIAAFES ELQAYKGKGN PEVEDLRWYA  60
AFIRAQLQAY RHN                                                     73

SEQ ID NO: 71          moltype = AA  length = 73
FEATURE                Location/Qualifiers
REGION                 1..73
                       note = artificial construct
source                 1..73
                       mol_type = protein
                       organism = synthetic construct
SEQUENCE: 71
MGSWYEFYDR LDAIVHRLDA LGGSEAELAA FEKEIAAFES ELQAYKGKGN PEVENLRWYA  60
AMIRVRLQAY RHN                                                     73

SEQ ID NO: 72          moltype = AA  length = 73
```

```
FEATURE                 Location/Qualifiers
REGION                  1..73
                        note = artificial construct
source                  1..73
                        mol_type = protein
                        organism = synthetic construct
SEQUENCE: 72
MGSWVEFQDR LEAITDRLYA LGGSEAELAA FEKEIAAFES ELQAYKGKGN PEVEELRYSA  60
AMIRVILQAY RHN                                                     73

SEQ ID NO: 73           moltype = AA  length = 73
FEATURE                 Location/Qualifiers
REGION                  1..73
                        note = artificial construct
source                  1..73
                        mol_type = protein
                        organism = synthetic construct
SEQUENCE: 73
MGSWVEFQER LMAISDRLYA LGGSEAELAA FEKEIAAFES ELQAYKGKGN PEVEELRWQA  60
AMIRYTLQAY RHN                                                     73

SEQ ID NO: 74           moltype = AA  length = 73
FEATURE                 Location/Qualifiers
REGION                  1..73
                        note = artificial construct
source                  1..73
                        mol_type = protein
                        organism = synthetic construct
SEQUENCE: 74
MGSWFEFQHR LEAISMRLHA LGGSEAELAA FEKEIAAFES ELQAYKGKGN PEVEELRWQA  60
AYIRVVLQAY RHN                                                     73

SEQ ID NO: 75           moltype = AA  length = 73
FEATURE                 Location/Qualifiers
REGION                  1..73
                        note = artificial construct
source                  1..73
                        mol_type = protein
                        organism = synthetic construct
SEQUENCE: 75
MGSWVEFQSR LEAIATRLRA LGGSEAELAA FEKEIAAFES ELQAYKGKGN PEVEELRWQA  60
AWIRMMLQAY RHN                                                     73

SEQ ID NO: 76           moltype = AA  length = 73
FEATURE                 Location/Qualifiers
REGION                  1..73
                        note = artificial construct
source                  1..73
                        mol_type = protein
                        organism = synthetic construct
SEQUENCE: 76
MGSWEEFQYR LGAIAARLQA LGGSEAELAA FEKEIAAFES ELQAYKGKGN PEVEELRWQA  60
AMIRFMLQAY RHN                                                     73

SEQ ID NO: 77           moltype = AA  length = 73
FEATURE                 Location/Qualifiers
REGION                  1..73
                        note = artificial construct
source                  1..73
                        mol_type = protein
                        organism = synthetic construct
SEQUENCE: 77
MGSWYEFQVR LQAISWRLKA LGGSEAELAA FEKEIAAFES ELQAYKGKGN HEVEELRIQA  60
ALIRVMLQAY RHN                                                     73

SEQ ID NO: 78           moltype = AA  length = 73
FEATURE                 Location/Qualifiers
REGION                  1..73
                        note = artificial construct
source                  1..73
                        mol_type = protein
                        organism = synthetic construct
SEQUENCE: 78
MGSWVEFRSR LEAISNRLRA LGGSEAELAA FEKEIAAFES ELQAYKGKGN PEVEELRTTA  60
ALIRVYLQAY RHN                                                     73

SEQ ID NO: 79           moltype = AA  length = 73
FEATURE                 Location/Qualifiers
REGION                  1..73
```

```
                        note = artificial construct
source                  1..73
                        mol_type = protein
                        organism = synthetic construct
SEQUENCE: 79
MGSWVEFKAR LEAISSRLTA LGGSEAELAA FEKEIAAFES ELQAYKGKGN PEVEELRYSA  60
ALIRVYLQAY RHN                                                     73

SEQ ID NO: 80           moltype = AA  length = 73
FEATURE                 Location/Qualifiers
REGION                  1..73
                        note = artificial construct
source                  1..73
                        mol_type = protein
                        organism = synthetic construct
SEQUENCE: 80
MGSWSEFYTR LEAINNRLHA LGGSEAELAA FEKEIAAFES ELQAYKGKGN PEVEELRYTA  60
ALIRIYLQAY RHN                                                     73

SEQ ID NO: 81           moltype = AA  length = 73
FEATURE                 Location/Qualifiers
REGION                  1..73
                        note = artificial construct
source                  1..73
                        mol_type = protein
                        organism = synthetic construct
SEQUENCE: 81
MGSWAEFYHR LDAISSRLRA LGGSEAELAA FEKEIAAFES ELQAYKGKGN PEVEELRYTA  60
ALIRIYLQAY RHN                                                     73

SEQ ID NO: 82           moltype = AA  length = 73
FEATURE                 Location/Qualifiers
REGION                  1..73
                        note = artificial construct
source                  1..73
                        mol_type = protein
                        organism = synthetic construct
SEQUENCE: 82
MGSWTEFASR LVAIRQRLQA LGGSEAELAA FEKEIAAFES ELQAYKGKGN PEVEELRYSA  60
AIIRVMLQAY RHN                                                     73

SEQ ID NO: 83           moltype = AA  length = 73
FEATURE                 Location/Qualifiers
REGION                  1..73
                        note = artificial construct
source                  1..73
                        mol_type = protein
                        organism = synthetic construct
SEQUENCE: 83
MGSWSEFDQR LAAIYQRLNA LGGSEAELAA FEKEIAAFES ELQAYKGKGN PEVEELRYSA  60
ALIRVMLQAY RHN                                                     73

SEQ ID NO: 84           moltype = AA  length = 73
FEATURE                 Location/Qualifiers
REGION                  1..73
                        note = artificial construct
source                  1..73
                        mol_type = protein
                        organism = synthetic construct
SEQUENCE: 84
MGSWVEFHNR LSAISDRLGA LGGSEAELAA FEKEIAAFES ELQAYKGKGN PEVEELRYSA  60
ALIRVMLQAY RHN                                                     73

SEQ ID NO: 85           moltype = AA  length = 73
FEATURE                 Location/Qualifiers
REGION                  1..73
                        note = artificial construct
source                  1..73
                        mol_type = protein
                        organism = synthetic construct
SEQUENCE: 85
MGSWNEFEDR LSAISARLSA LGGSEAELAA FEKEIAAFES ELQAYKGKGN PEVEELRYSA  60
ALIRVMLQAY RHN                                                     73

SEQ ID NO: 86           moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 86
MGSWVEFEYR LVAIFDRLQA LGGSEAELAA FEKEIAAFES ELQAYKGKGN PEVEELRYQA  60
ALIRVMLQAY RHN                                                     73

SEQ ID NO: 87           moltype = AA  length = 73
FEATURE                 Location/Qualifiers
REGION                  1..73
                        note = artificial construct
source                  1..73
                        mol_type = protein
                        organism = synthetic construct
SEQUENCE: 87
MGSWVEFQGR LGAIHERLQA LGGSEAELAA FEKEIAAFES ELQAYKGKGN PEVEELRYSA  60
ALIRVFLQAY RHN                                                     73

SEQ ID NO: 88           moltype = AA  length = 73
FEATURE                 Location/Qualifiers
REGION                  1..73
                        note = artificial construct
source                  1..73
                        mol_type = protein
                        organism = synthetic construct
SEQUENCE: 88
MGSWYEFSMR LSAIWERLHA LGGSEAELAA FEKEIAAFES ELQAYKGKGN PEVEELRYQA  60
ALIRFYLQAY RHN                                                     73

SEQ ID NO: 89           moltype = AA  length = 73
FEATURE                 Location/Qualifiers
REGION                  1..73
                        note = artificial construct
source                  1..73
                        mol_type = protein
                        organism = synthetic construct
SEQUENCE: 89
MGSWTEFSQR LGAISERLYA LGGSEAELAA FEKEIAAFES ELQAYKGKGN PEVEELRYSA  60
ALIRFMLQAY RHN                                                     73

SEQ ID NO: 90           moltype = AA  length = 73
FEATURE                 Location/Qualifiers
REGION                  1..73
                        note = artificial construct
source                  1..73
                        mol_type = protein
                        organism = synthetic construct
SEQUENCE: 90
MGSWTEFHDR LEAITHRLNA LGGSEAELAA FEKEIAAFES ELQAYKGKGN PEVEELRYSA  60
ALLRVFLQAY RHN                                                     73

SEQ ID NO: 91           moltype = AA  length = 73
FEATURE                 Location/Qualifiers
REGION                  1..73
                        note = artificial construct
source                  1..73
                        mol_type = protein
                        organism = synthetic construct
SEQUENCE: 91
MGSWTEFEHR LEAIAGRLNA LGGSEAELAA FEKEIAAFES ELQAYKGKGN PEVEELRYSA  60
ALIRFWLQAY RHN                                                     73

SEQ ID NO: 92           moltype = AA  length = 73
FEATURE                 Location/Qualifiers
REGION                  1..73
                        note = artificial construct
source                  1..73
                        mol_type = protein
                        organism = synthetic construct
SEQUENCE: 92
MGSWTEFANR LEAINARLHA LGGSEAELAA FEKEIAAFES ELQAYKGKGN PEVEELRFSA  60
ALIRVYLQAY RHN                                                     73

SEQ ID NO: 93           moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 93
MGSWEEFDRR LYAIARRLEA LGGSEAELAA FEKEIAAFES ELQAYKGKGN PEVEELRYQA  60
ALIRVWLQAY RHN                                                     73

SEQ ID NO: 94          moltype = AA  length = 73
FEATURE                Location/Qualifiers
REGION                 1..73
                       note = artificial construct
source                 1..73
                       mol_type = protein
                       organism = synthetic construct
SEQUENCE: 94
MGSWIEFHQR LEAIVTRLEA LGGSEAELAA FEKEIAAFES ELQAYKGKGN PEVEELRYQA  60
ALIRVFLQAY RHN                                                     73

SEQ ID NO: 95          moltype = AA  length = 73
FEATURE                Location/Qualifiers
REGION                 1..73
                       note = artificial construct
source                 1..73
                       mol_type = protein
                       organism = synthetic construct
SEQUENCE: 95
MGSWSEFYDR LKAIADRLHA LGGSEAELAA FEKEIAAFES ELQAYKGKGN PEVEELRTEA  60
AIIRVYLQAY RHN                                                     73

SEQ ID NO: 96          moltype = AA  length = 73
FEATURE                Location/Qualifiers
REGION                 1..73
                       note = artificial construct
source                 1..73
                       mol_type = protein
                       organism = synthetic construct
SEQUENCE: 96
MGSWWEFEDR LSAIMERLHA LGGSEAELAA FEKEIAAFES ELQAYKGKGN PEVEELRYRA  60
AIIRVYLQAY RHN                                                     73

SEQ ID NO: 97          moltype = AA  length = 73
FEATURE                Location/Qualifiers
REGION                 1..73
                       note = artificial construct
source                 1..73
                       mol_type = protein
                       organism = synthetic construct
SEQUENCE: 97
MGSWVEFEER LAAIATRLHA LGGSEAELAA FEKEIAAFES ELQAYKGKGN PEVEELRWRA  60
AIIRVYLQAY RHN                                                     73

SEQ ID NO: 98          moltype = AA  length = 73
FEATURE                Location/Qualifiers
REGION                 1..73
                       note = artificial construct
source                 1..73
                       mol_type = protein
                       organism = synthetic construct
SEQUENCE: 98
MGSWSEFRGR LQAIHSRLNA LGGSEAELAA FEKEIAAFES ELQAYKGKGN PEVEELRYSA  60
AIIRIYLQAY RHN                                                     73

SEQ ID NO: 99          moltype = AA  length = 73
FEATURE                Location/Qualifiers
REGION                 1..73
                       note = artificial construct
source                 1..73
                       mol_type = protein
                       organism = synthetic construct
SEQUENCE: 99
MGSWTEFRDR LGAIYHRLDA LGGSEAELAA FEKEIAAFES ELQAYKGKGN PEVEELRYQA  60
AIIRVYLQAY RHN                                                     73

SEQ ID NO: 100         moltype = AA  length = 73
FEATURE                Location/Qualifiers
REGION                 1..73
                       note = artificial construct
source                 1..73
                       mol_type = protein
                       organism = synthetic construct
SEQUENCE: 100
MGSWVEFYHR LEAIRYRLSA LGGSEAELAA FEKEIAAFES ELQAYKGKGN PEVEELRYVA  60
```

```
AVIRYRLQAY RHN                                                    73

SEQ ID NO: 101         moltype = AA  length = 73
FEATURE                Location/Qualifiers
REGION                 1..73
                       note = artificial construct
source                 1..73
                       mol_type = protein
                       organism = synthetic construct
SEQUENCE: 101
MGSWVEFYDR LEAIRYRLSA LGGSEAELAA FEKEIAAFES ELQAYKGKGN PEVEELRYIA  60
AVIRYRLQAY RHN                                                    73

SEQ ID NO: 102         moltype = AA  length = 73
FEATURE                Location/Qualifiers
REGION                 1..73
                       note = artificial construct
source                 1..73
                       mol_type = protein
                       organism = synthetic construct
SEQUENCE: 102
MGSWVEFYDR LAAIRKRLYA LGGSEAELAA FEKEIAAFES ELQAYKGKGN PEVEELRFRA  60
ALIRIWLQAY RHN                                                    73

SEQ ID NO: 103         moltype = AA  length = 73
FEATURE                Location/Qualifiers
REGION                 1..73
                       note = artificial construct
source                 1..73
                       mol_type = protein
                       organism = synthetic construct
SEQUENCE: 103
MGSWEEFSER LEAISIRLRA LGGSEAELAA FEKEIAAFES ELQAYKGKGN PEVEELRVSA  60
AIIRVWLQAY RHN                                                    73

SEQ ID NO: 104         moltype = AA  length = 73
FEATURE                Location/Qualifiers
REGION                 1..73
                       note = artificial construct
source                 1..73
                       mol_type = protein
                       organism = synthetic construct
SEQUENCE: 104
MGSWSEFSDR LHAISDRLQA LGGSEAELAA FEKEIAAFES ELQAYKGKGN PEVEELRIQA  60
AIIRVWLQAY RHN                                                    73

SEQ ID NO: 105         moltype = AA  length = 73
FEATURE                Location/Qualifiers
REGION                 1..73
                       note = artificial construct
source                 1..73
                       mol_type = protein
                       organism = synthetic construct
SEQUENCE: 105
MGSWIEFSHR LEAIVDRLGA LGGSEAELAA FEKEIAAFES ELQAYKGKGN PEVEELRNTA  60
AIIRVYLQAY RHN                                                    73

SEQ ID NO: 106         moltype = AA  length = 73
FEATURE                Location/Qualifiers
REGION                 1..73
                       note = artificial construct
source                 1..73
                       mol_type = protein
                       organism = synthetic construct
SEQUENCE: 106
MGSWEEFSDR LEAILRRLDA LGGSEAELAA FEKEIAAFES ELQAYKGKGN PEVEDLRFAA  60
AIIRVQLQAY RHN                                                    73

SEQ ID NO: 107         moltype = AA  length = 73
FEATURE                Location/Qualifiers
REGION                 1..73
                       note = artificial construct
source                 1..73
                       mol_type = protein
                       organism = synthetic construct
SEQUENCE: 107
MGSWMEFSHR LDAIHERLYA LGGSEAELAA FEKEIAAFES ELQAYKGKGN PEVEDLRFAA  60
AIIRVQLQAY RHN                                                    73
```

```
SEQ ID NO: 108         moltype = AA  length = 73
FEATURE                Location/Qualifiers
REGION                 1..73
                       note = artificial construct
source                 1..73
                       mol_type = protein
                       organism = synthetic construct
SEQUENCE: 108
MGSWSEFQQR LHAIRTRLYA LGGSEAELAA FEKEIAAFES ELQAYKGKGN PEVEELRFEA  60
AIIRVMLQAY RHN                                                     73

SEQ ID NO: 109         moltype = AA  length = 73
FEATURE                Location/Qualifiers
REGION                 1..73
                       note = artificial construct
source                 1..73
                       mol_type = protein
                       organism = synthetic construct
SEQUENCE: 109
MGSWYEFQNR LGAINRRLNA LGGSEAELAA FEKEIAAFES ELQAYKGKGN PEVEELRFEA  60
AIIRVMLQAY RHN                                                     73

SEQ ID NO: 110         moltype = AA  length = 73
FEATURE                Location/Qualifiers
REGION                 1..73
                       note = artificial construct
source                 1..73
                       mol_type = protein
                       organism = synthetic construct
SEQUENCE: 110
MGSWQEFTGR LHAIRHRLEA LGGSEAELAA FEKEIAAFES ELQAYKGKGN PEVEELRFEA  60
AYIRVWLQAY RHN                                                     73

SEQ ID NO: 111         moltype = AA  length = 73
FEATURE                Location/Qualifiers
REGION                 1..73
                       note = artificial construct
source                 1..73
                       mol_type = protein
                       organism = synthetic construct
SEQUENCE: 111
MGSWTEFDHR LGAIWERLVA LGGSEAELAA FEKEIAAFES ELQAYKGKGN PEVEELRFHA  60
AIIRIFLQAY RHN                                                     73

SEQ ID NO: 112         moltype = AA  length = 73
FEATURE                Location/Qualifiers
REGION                 1..73
                       note = artificial construct
source                 1..73
                       mol_type = protein
                       organism = synthetic construct
SEQUENCE: 112
MGSWTEFHVR LSAIWDRLVA LGGSEAELAA FEKEIAAFES ELQAYKGKGN PEVEELRFHA  60
AIIRIVLQAY RHN                                                     73

SEQ ID NO: 113         moltype = AA  length = 73
FEATURE                Location/Qualifiers
REGION                 1..73
                       note = artificial construct
source                 1..73
                       mol_type = protein
                       organism = synthetic construct
SEQUENCE: 113
MGSWNEFDNR LQAIWDRLHA LGGSEAELAA FEKEIAAFES ELQAYKGKGN PEVEELRFHA  60
AMIRITLQAY RHN                                                     73

SEQ ID NO: 114         moltype = AA  length = 73
FEATURE                Location/Qualifiers
REGION                 1..73
                       note = artificial construct
source                 1..73
                       mol_type = protein
                       organism = synthetic construct
SEQUENCE: 114
MGSWTEFHER LQAIWFRLHA LGGSEAELAA FEKEIAAFES ELQAYKGKGN PEVEELRFRA  60
AIIRLYLQAY RHN                                                     73

SEQ ID NO: 115         moltype = AA  length = 73
FEATURE                Location/Qualifiers
```

```
REGION                 1..73
                       note = artificial construct
source                 1..73
                       mol_type = protein
                       organism = synthetic construct
SEQUENCE: 115
MGSWNEFSGR LTAIKDRLAA LGGSEAELAA FEKEIAAFES ELQAYKGKGN PEVEELRFRA  60
AVIRLWLQAY RHN                                                     73

SEQ ID NO: 116         moltype = AA  length = 73
FEATURE                Location/Qualifiers
REGION                 1..73
                       note = artificial construct
source                 1..73
                       mol_type = protein
                       organism = synthetic construct
SEQUENCE: 116
MGSWVEFDER LVAIWFRLHA LGGSEAELAA FEKEIAAFES ELQAYKGKGN PEVEALRARA  60
AYIRIWLQAY RHN                                                     73

SEQ ID NO: 117         moltype = AA  length = 73
FEATURE                Location/Qualifiers
REGION                 1..73
                       note = artificial construct
source                 1..73
                       mol_type = protein
                       organism = synthetic construct
SEQUENCE: 117
MGSWSEFGQR LSAIWERLLA LGGSEAELAA FEKEIAAFES ELQAYKGKGN PEVEALRADA  60
AFIRIWLQAY RHN                                                     73

SEQ ID NO: 118         moltype = AA  length = 73
FEATURE                Location/Qualifiers
REGION                 1..73
                       note = artificial construct
source                 1..73
                       mol_type = protein
                       organism = synthetic construct
SEQUENCE: 118
MGSWYEFEDR LVAIWIRLDA LGGSEAELAA FEKEIAAFES ELQAYKGKGN PEVEELRYNA  60
AFIRGALQAY RHN                                                     73

SEQ ID NO: 119         moltype = AA  length = 73
FEATURE                Location/Qualifiers
REGION                 1..73
                       note = artificial construct
source                 1..73
                       mol_type = protein
                       organism = synthetic construct
SEQUENCE: 119
MGSWYEFGDR LSAIWERLAA LGGSEAELAA FEKEIAAFES ELQAYKGKGN PEVEYLRTHA  60
AEIRTILQAY RHN                                                     73

SEQ ID NO: 120         moltype = AA  length = 73
FEATURE                Location/Qualifiers
REGION                 1..73
                       note = artificial construct
source                 1..73
                       mol_type = protein
                       organism = synthetic construct
SEQUENCE: 120
MGSWHEFYYR LEAIEQRLHA LGGSEAELAA FEKEIAAFES ELQAYKGKGN PEVETLRFDA  60
ALIRIYLQAY RHN                                                     73

SEQ ID NO: 121         moltype = AA  length = 73
FEATURE                Location/Qualifiers
REGION                 1..73
                       note = artificial construct
source                 1..73
                       mol_type = protein
                       organism = synthetic construct
SEQUENCE: 121
MGSWSEFEER LAAIGSRLFA LGGSEAELAA FEKEIAAFES ELQAYKGKGN PEVETLRFDA  60
ALIRIYLQAY RHN                                                     73

SEQ ID NO: 122         moltype = AA  length = 73
FEATURE                Location/Qualifiers
REGION                 1..73
                       note = artificial construct
```

```
source                 1..73
                       mol_type = protein
                       organism = synthetic construct
SEQUENCE: 122
MGSWLEFHYR LHAIQFRLYA LGGSEAELAA FEKEIAAFES ELQAYKGKGN PEVETLRHIA  60
ALIRNQLQAY RHN                                                     73

SEQ ID NO: 123         moltype = AA  length = 73
FEATURE                Location/Qualifiers
REGION                 1..73
                       note = artificial construct
source                 1..73
                       mol_type = protein
                       organism = synthetic construct
SEQUENCE: 123
MGSWQEFYNR LEAIHMRLFA LGGSEAELAA FEKEIAAFES ELQAYKGKGN PEVEGLRSDA  60
APIRDVLQAY RHN                                                     73

SEQ ID NO: 124         moltype = AA  length = 73
FEATURE                Location/Qualifiers
REGION                 1..73
                       note = artificial construct
source                 1..73
                       mol_type = protein
                       organism = synthetic construct
SEQUENCE: 124
MGSWNEFHHR LWAIFDRLGA LGGSEAELAA FEKEIAAFES ELQAYKGKGN PEVEVLRKMA  60
AGIRGGLQAY RHN                                                     73

SEQ ID NO: 125         moltype = AA  length = 73
FEATURE                Location/Qualifiers
REGION                 1..73
                       note = artificial construct
source                 1..73
                       mol_type = protein
                       organism = synthetic construct
SEQUENCE: 125
MGSWYEFHYR LKAINDRLYA LGGSEAELAA FEKEIAAFES ELQAYKGKGN PEVEYLRYSA  60
AMIRHKLQAY RHN                                                     73

SEQ ID NO: 126         moltype = AA  length = 73
FEATURE                Location/Qualifiers
REGION                 1..73
                       note = artificial construct
source                 1..73
                       mol_type = protein
                       organism = synthetic construct
SEQUENCE: 126
MGSWTEFHQR LGAIHARLGA LGGSEAELAA FEKEIAAFES ELQAYKGKGN PEVEYLRFSA  60
AFIRLKLQAY RHN                                                     73

SEQ ID NO: 127         moltype = AA  length = 73
FEATURE                Location/Qualifiers
REGION                 1..73
                       note = artificial construct
source                 1..73
                       mol_type = protein
                       organism = synthetic construct
SEQUENCE: 127
MGSWFEFQYR LEAIFYRLLA LGGSEAELAA FEKEIAAFES ELQAYKGKGK PEVEELRVRA  60
ALIRHLLQAY RHN                                                     73

SEQ ID NO: 128         moltype = AA  length = 73
FEATURE                Location/Qualifiers
REGION                 1..73
                       note = artificial construct
source                 1..73
                       mol_type = protein
                       organism = synthetic construct
SEQUENCE: 128
MGSWVEFHAR LDAIYTRLGA LGGSEAELAA FEKEIAAFES ELQAYKGKGN PEVEYLRVLA  60
AHIRISLQAY RHN                                                     73

SEQ ID NO: 129         moltype = AA  length = 73
FEATURE                Location/Qualifiers
REGION                 1..73
                       note = artificial construct
source                 1..73
                       mol_type = protein
```

```
                        organism = synthetic construct
SEQUENCE: 129
MGSWVEFGTR LSAIYNRLWA LGGSEAELAA FEKEIAAFES ELQAYKGKGN PEVEDLRFEA  60
AIIRIMLQAY RHN                                                     73

SEQ ID NO: 130          moltype = AA  length = 73
FEATURE                 Location/Qualifiers
REGION                  1..73
                        note = artificial construct
source                  1..73
                        mol_type = protein
                        organism = synthetic construct
SEQUENCE: 130
MGSWVEFTHR LDAIYIRLWA LGGSEAELAA FEKEIAAFES ELQAYKGKGN PEVEELRHEA  60
AVIREELQAY RHN                                                     73

SEQ ID NO: 131          moltype = AA  length = 73
FEATURE                 Location/Qualifiers
REGION                  1..73
                        note = artificial construct
source                  1..73
                        mol_type = protein
                        organism = synthetic construct
SEQUENCE: 131
MGSWVEFHGR LAAIYVRLFA LGGSEAELAA FEKEIAAFES ELQAYKGKGN PEVESLRYHA  60
AMIRRNLQAY RHN                                                     73

SEQ ID NO: 132          moltype = AA  length = 73
FEATURE                 Location/Qualifiers
REGION                  1..73
                        note = artificial construct
source                  1..73
                        mol_type = protein
                        organism = synthetic construct
SEQUENCE: 132
MGSWVEFDRR LVAIYIRLWA LGGSEAELAA FEKEIAAFES ELQAYKGKGN PEVEALRDDA  60
ALIRLLLQAY RHN                                                     73

SEQ ID NO: 133          moltype = AA  length = 73
FEATURE                 Location/Qualifiers
REGION                  1..73
                        note = artificial construct
source                  1..73
                        mol_type = protein
                        organism = synthetic construct
SEQUENCE: 133
MGSWVEFDRR LVAIYIRLWA LGGSEAELAA FEKEIAAFES ELQAYKGKGN PEVEKLRYDA  60
ATIRETLQAY RHN                                                     73

SEQ ID NO: 134          moltype = AA  length = 73
FEATURE                 Location/Qualifiers
REGION                  1..73
                        note = artificial construct
source                  1..73
                        mol_type = protein
                        organism = synthetic construct
SEQUENCE: 134
MGSWLEFDRR LTAIYLRLWA LGGSEAELAA FEKEIAAFES ELQAYKGKGN PEVEALREDA  60
AMIRDMLQAY RHN                                                     73

SEQ ID NO: 135          moltype = AA  length = 73
FEATURE                 Location/Qualifiers
REGION                  1..73
                        note = artificial construct
source                  1..73
                        mol_type = protein
                        organism = synthetic construct
SEQUENCE: 135
MGSWIEFDRR LLAIHVRLWA LGGSEAELAA FEKEIAAFES ELQAYKGKGN PEVEVLRADA  60
AKIRMELQAY RHN                                                     73

SEQ ID NO: 136          moltype = AA  length = 73
FEATURE                 Location/Qualifiers
REGION                  1..73
                        note = artificial construct
source                  1..73
                        mol_type = protein
                        organism = synthetic construct
SEQUENCE: 136
```

```
MGSWIEFDRR LIAIWIRLWA LGGSEAELAA FEKEIAAFES ELQAYKGKGN PEVESLRSDA  60
ADIRQKLQAY RHN                                                     73

SEQ ID NO: 137         moltype = AA  length = 73
FEATURE                Location/Qualifiers
REGION                 1..73
                       note = artificial construct
source                 1..73
                       mol_type = protein
                       organism = synthetic construct
SEQUENCE: 137
MGSWVEFDRR LIAIWVRLWA LGGSEAELAA FEKEIAAFES ELQAYKGKGN PEVEFLRSDA  60
AMIREHLQAY RHN                                                     73

SEQ ID NO: 138         moltype = AA  length = 73
FEATURE                Location/Qualifiers
REGION                 1..73
                       note = artificial construct
source                 1..73
                       mol_type = protein
                       organism = synthetic construct
SEQUENCE: 138
MGSWYEFHTR LIAIYVRLWA LGGSEAELAA FEKEIAAFES ELQAYKGKGN PEVEWLRGDA  60
AKIRGYLQAY RHN                                                     73

SEQ ID NO: 139         moltype = AA  length = 73
FEATURE                Location/Qualifiers
REGION                 1..73
                       note = artificial construct
source                 1..73
                       mol_type = protein
                       organism = synthetic construct
SEQUENCE: 139
MGSWSEFSTR LSAIYVRLWA LGGSEAELAA FEKEIAAFES ELQAYKGKGN PEVEYLRNKA  60
ASIRKTLQAY RHN                                                     73

SEQ ID NO: 140         moltype = AA  length = 73
FEATURE                Location/Qualifiers
REGION                 1..73
                       note = artificial construct
source                 1..73
                       mol_type = protein
                       organism = synthetic construct
SEQUENCE: 140
MGSWVEFRYR LGAIYHRLWA LGGSEAELAA FEKEIAAFES ELQAYKGKGN PEVEVLRDRA  60
ATIRRLLQAY RHN                                                     73

SEQ ID NO: 141         moltype = AA  length = 73
FEATURE                Location/Qualifiers
REGION                 1..73
                       note = artificial construct
source                 1..73
                       mol_type = protein
                       organism = synthetic construct
SEQUENCE: 141
MGSWNEFRNR LGAIDSRLWA LGGSEAELAA FEKEIAAFES ELQAYKGKGN PEVETLRAHA  60
AIIRSVLQAY RHN                                                     73

SEQ ID NO: 142         moltype = AA  length = 73
FEATURE                Location/Qualifiers
REGION                 1..73
                       note = artificial construct
source                 1..73
                       mol_type = protein
                       organism = synthetic construct
SEQUENCE: 142
MGSWHEFRNR LGAIDSRLWA LGGSEAELAA FEKEIAAFES ELQAYKGKGN PEVETLRARA  60
AMIRSVLQAY RHN                                                     73

SEQ ID NO: 143         moltype = AA  length = 73
FEATURE                Location/Qualifiers
REGION                 1..73
                       note = artificial construct
source                 1..73
                       mol_type = protein
                       organism = synthetic construct
SEQUENCE: 143
MGSWTEFYQR LEAINFRLWA LGGSEAELAA FEKEIAAFES ELQAYKGKGN PEVEVLRDKA  60
ALIRLMLQAY RHN                                                     73
```

```
SEQ ID NO: 144          moltype = AA  length = 73
FEATURE                 Location/Qualifiers
REGION                  1..73
                        note = artificial construct
source                  1..73
                        mol_type = protein
                        organism = synthetic construct
SEQUENCE: 144
MGSWNEFYNR LHAINLRLWA LGGSEAELAA FEKEIAAFES ELQAYKGKGN PEVEVLREHA  60
AIIRQALQAY RHN                                                     73

SEQ ID NO: 145          moltype = AA  length = 73
FEATURE                 Location/Qualifiers
REGION                  1..73
                        note = artificial construct
source                  1..73
                        mol_type = protein
                        organism = synthetic construct
SEQUENCE: 145
MGSWEEFYGR LSAIQDRLWA LGGSEAELAA FEKEIAAFES ELQAYKGKGN PEVEWLRMHA  60
AVIRRALQAY RHN                                                     73

SEQ ID NO: 146          moltype = AA  length = 73
FEATURE                 Location/Qualifiers
REGION                  1..73
                        note = artificial construct
source                  1..73
                        mol_type = protein
                        organism = synthetic construct
SEQUENCE: 146
MGSWGEFNLR LVAIHVRLWA LGGSEAELAA FEKEIAAFES ELQAYKGKGN PEVEFLRSQA  60
ANIRAQLQAY RHN                                                     73

SEQ ID NO: 147          moltype = AA  length = 73
FEATURE                 Location/Qualifiers
REGION                  1..73
                        note = artificial construct
source                  1..73
                        mol_type = protein
                        organism = synthetic construct
SEQUENCE: 147
MGSWGEFSDR LEAINERLWA LGGSEAELAA FEKEIAAFES ELQAYKGKGN PEVEELRWQA  60
AFIRANLQAY RHN                                                     73

SEQ ID NO: 148          moltype = AA  length = 73
FEATURE                 Location/Qualifiers
REGION                  1..73
                        note = artificial construct
source                  1..73
                        mol_type = protein
                        organism = synthetic construct
SEQUENCE: 148
MGSWMEFQGR LPAILARLRA LGGSEAELAA FEKEIAAFES ELQAYKGKGN PEVEHLRDKA  60
AYIRWMLQAY RHN                                                     73

SEQ ID NO: 149          moltype = AA  length = 73
FEATURE                 Location/Qualifiers
REGION                  1..73
                        note = artificial construct
source                  1..73
                        mol_type = protein
                        organism = synthetic construct
SEQUENCE: 149
MGSWMEFEGR LPAILARLRA LGGSEAELAA FEKEIAAFES ELQAYKGKGN PEVEHLRDKA  60
AYIRWMLQAY RHN                                                     73

SEQ ID NO: 150          moltype = AA  length = 73
FEATURE                 Location/Qualifiers
REGION                  1..73
                        note = artificial construct
source                  1..73
                        mol_type = protein
                        organism = synthetic construct
SEQUENCE: 150
MGSWFEFQNR LQAILFRLRA LGGSEAELAA FEKEIAAFES ELQAYKGKGN PEVENLRDKA  60
AYIRLMLQAY RHN                                                     73

SEQ ID NO: 151          moltype = AA  length = 73
```

```
FEATURE                 Location/Qualifiers
REGION                  1..73
                        note = artificial construct
source                  1..73
                        mol_type = protein
                        organism = synthetic construct
SEQUENCE: 151
MGSWVEFDMR LQAILERLRA LGGSEAELAA FEKEIAAFES ELQAYKGKGN PEVEHLRDSA  60
AYIRLMLQAY RHN                                                     73

SEQ ID NO: 152          moltype = AA  length = 73
FEATURE                 Location/Qualifiers
REGION                  1..73
                        note = artificial construct
source                  1..73
                        mol_type = protein
                        organism = synthetic construct
SEQUENCE: 152
MGSWVEFNAR LDAILFRLRA LGGSEAELAA FEKEIAAFES ELQAYKGKGN PEVEHLRDQA  60
AYIRLMLQAY RHN                                                     73

SEQ ID NO: 153          moltype = AA  length = 73
FEATURE                 Location/Qualifiers
REGION                  1..73
                        note = artificial construct
source                  1..73
                        mol_type = protein
                        organism = synthetic construct
SEQUENCE: 153
MGSWMEFNVR LRAILDRLHA LGGSEAELAA FEKEIAAFES ELQAYKGKGN PEVELLRDKA  60
AYIRFMLQAY RHN                                                     73

SEQ ID NO: 154          moltype = AA  length = 73
FEATURE                 Location/Qualifiers
REGION                  1..73
                        note = artificial construct
source                  1..73
                        mol_type = protein
                        organism = synthetic construct
SEQUENCE: 154
MGSWIEFDTR LAAIVHRLRA LGGSEAELAA FEKEIAAFES ELQAYKGKGN PEVELLRDKA  60
AYIRYMLQAY RHN                                                     73

SEQ ID NO: 155          moltype = AA  length = 73
FEATURE                 Location/Qualifiers
REGION                  1..73
                        note = artificial construct
source                  1..73
                        mol_type = protein
                        organism = synthetic construct
SEQUENCE: 155
MGSWIEFDYR LKAILHRLRA LGGSEAELAA FEKEIAAFES ELQAYKGKGN PEVEGLRDKA  60
AYIRFLLQAY RHN                                                     73

SEQ ID NO: 156          moltype = AA  length = 73
FEATURE                 Location/Qualifiers
REGION                  1..73
                        note = artificial construct
source                  1..73
                        mol_type = protein
                        organism = synthetic construct
SEQUENCE: 156
MGSWYEFEDR LLAIKVRLRA LGGSEAELAA FEKEIAAFES ELQAYKGKGN PEVEYLRDQA  60
AYIRFMLQAY RHN                                                     73

SEQ ID NO: 157          moltype = AA  length = 73
FEATURE                 Location/Qualifiers
REGION                  1..73
                        note = artificial construct
source                  1..73
                        mol_type = protein
                        organism = synthetic construct
SEQUENCE: 157
MGSWYEFQDR LSAITTRLRA LGGSEAELAA FEKEIAAFES ELQAYKGKGN PEVELLRDKA  60
AYIRFMLQAY RHN                                                     73

SEQ ID NO: 158          moltype = AA  length = 73
FEATURE                 Location/Qualifiers
REGION                  1..73
```

```
                         note = artificial construct
source                   1..73
                         mol_type = protein
                         organism = synthetic construct
SEQUENCE: 158
MGSWEEFDDR LNAIVYRLRA LGGSEAELAA FEKEIAAFES ELQAYKGKGN PEVEMLRDQA  60
AYIRLMLQAY RHN                                                    73

SEQ ID NO: 159           moltype = AA  length = 73
FEATURE                  Location/Qualifiers
REGION                   1..73
                         note = artificial construct
source                   1..73
                         mol_type = protein
                         organism = synthetic construct
SEQUENCE: 159
MGSWVEFEQR LHAIVVRLRA LGGSEAELAA FEKEIAAFES ELQAYKGGGN PEVENLRDQA  60
AYIRFMLQAY RHN                                                    73

SEQ ID NO: 160           moltype = AA  length = 73
FEATURE                  Location/Qualifiers
REGION                   1..73
                         note = artificial construct
source                   1..73
                         mol_type = protein
                         organism = synthetic construct
SEQUENCE: 160
MGSWVEFEWR LEAIVVRLRA LGGSEAELAA FEKEIAAFES ELQAYKGKGN PEVEHLRDKA  60
AYIRYMLQAY RHN                                                    73

SEQ ID NO: 161           moltype = AA  length = 73
FEATURE                  Location/Qualifiers
REGION                   1..73
                         note = artificial construct
source                   1..73
                         mol_type = protein
                         organism = synthetic construct
SEQUENCE: 161
MGSWYEFEHR LKAIVSRLGA LGGSEAELAA FEKEIAAFES ELQAYKGKGN PEVEHLRDKA  60
AYIRYMLQAY RHN                                                    73

SEQ ID NO: 162           moltype = AA  length = 73
FEATURE                  Location/Qualifiers
REGION                   1..73
                         note = artificial construct
source                   1..73
                         mol_type = protein
                         organism = synthetic construct
SEQUENCE: 162
MGSWMEFKHR LAAITFRLRA LGGSEAELAA FEKEIAAFES ELQAYKGKGN PEVELLRDKA  60
AYIRLLLQAY RHN                                                    73

SEQ ID NO: 163           moltype = AA  length = 73
FEATURE                  Location/Qualifiers
REGION                   1..73
                         note = artificial construct
source                   1..73
                         mol_type = protein
                         organism = synthetic construct
SEQUENCE: 163
MGSWMEFEGR LHAIKRRLRA LGGSEAELAA FEKEIAAFES ELQAYKGKGN PEVEVLRDQA  60
AYIRLLLQAY RHN                                                    73

SEQ ID NO: 164           moltype = AA  length = 73
FEATURE                  Location/Qualifiers
REGION                   1..73
                         note = artificial construct
source                   1..73
                         mol_type = protein
                         organism = synthetic construct
SEQUENCE: 164
MGSWSEFVFR LDTIKSRLRA LGGSEAELAA FEKEIAAFES ELQAYKGKGN PEVETLRDQA  60
AYIRLMLQAY RHN                                                    73

SEQ ID NO: 165           moltype = AA  length = 73
FEATURE                  Location/Qualifiers
REGION                   1..73
                         note = artificial construct
source                   1..73
```

```
                         mol_type = protein
                         organism = synthetic construct
SEQUENCE: 165
MGSWYEFDER LSAIKLRLRA LGGSEAELAA FEKEIAAFES ELQAYKGKGN PEVEVLRAQA  60
AYIRAILQAY RHN                                                     73

SEQ ID NO: 166           moltype = AA  length = 73
FEATURE                  Location/Qualifiers
REGION                   1..73
                         note = artificial construct
source                   1..73
                         mol_type = protein
                         organism = synthetic construct
SEQUENCE: 166
MGSWMEFDER LWAIKKRLRA LGGSEAELAA FEKEIAAFES ELQAYKGKGN PEVEFLRHQA  60
AYIRMLLQAY RHN                                                     73

SEQ ID NO: 167           moltype = AA  length = 73
FEATURE                  Location/Qualifiers
REGION                   1..73
                         note = artificial construct
source                   1..73
                         mol_type = protein
                         organism = synthetic construct
SEQUENCE: 167
MGSWHEFDGR LSAIKRRLWA LGGSEAELAA FEKEIAAFES ELQAYKGKGN PEVEHLRDQA  60
AYIRYMLQAY RHN                                                     73

SEQ ID NO: 168           moltype = AA  length = 73
FEATURE                  Location/Qualifiers
REGION                   1..73
                         note = artificial construct
source                   1..73
                         mol_type = protein
                         organism = synthetic construct
SEQUENCE: 168
MGSWYEFDGR LQAIIARLRA LGGSEAELAA FEKEIAAFES ELQAYKGKGN PEVEHLRFRA  60
AYIRWILQAY RHN                                                     73

SEQ ID NO: 169           moltype = AA  length = 73
FEATURE                  Location/Qualifiers
REGION                   1..73
                         note = artificial construct
source                   1..73
                         mol_type = protein
                         organism = synthetic construct
SEQUENCE: 169
MGSWFEFDKR LYAIIHRLRA LGGSEAELAA FEKEIAAFES ELQAYKGKGN PEVEKLRYKA  60
AIIRLYLQAY RHN                                                     73

SEQ ID NO: 170           moltype = AA  length = 73
FEATURE                  Location/Qualifiers
REGION                   1..73
                         note = artificial construct
source                   1..73
                         mol_type = protein
                         organism = synthetic construct
SEQUENCE: 170
MGSWVEFDNR LYAIVDRLRA LGGSEAELAA FEKEIAAFES ELQAYKGKGN PEVEHLRQKA  60
AYIRLILQAY RHN                                                     73

SEQ ID NO: 171           moltype = AA  length = 73
FEATURE                  Location/Qualifiers
REGION                   1..73
                         note = artificial construct
source                   1..73
                         mol_type = protein
                         organism = synthetic construct
SEQUENCE: 171
MGSWIEFHQR LNAIFNRLRA LGGSEAELAA FEKEIAAFES ELQAYKGKGN PEVEWLRHHA  60
AYIREMLQAY RHN                                                     73

SEQ ID NO: 172           moltype = AA  length = 73
FEATURE                  Location/Qualifiers
REGION                   1..73
                         note = artificial construct
source                   1..73
                         mol_type = protein
                         organism = synthetic construct
```

```
SEQUENCE: 172
MGSWNEFRLR LWAITERLRA LGGSEAELAA FEKEIAAFES ELQAYKGKGN PEVECLRAEA  60
AWIRTMLQAY RHN                                                    73

SEQ ID NO: 173         moltype = AA  length = 73
FEATURE                Location/Qualifiers
REGION                 1..73
                       note = artificial construct
source                 1..73
                       mol_type = protein
                       organism = synthetic construct
SEQUENCE: 173
MGSWYEFWLR LSAISYRLQA LGGSEAELAA FEKEIAAFES ELQAYKGKGN PEVEWLRKEA  60
AEIRSWLQAY RHN                                                    73

SEQ ID NO: 174         moltype = AA  length = 73
FEATURE                Location/Qualifiers
REGION                 1..73
                       note = artificial construct
source                 1..73
                       mol_type = protein
                       organism = synthetic construct
SEQUENCE: 174
MGSWYEFQLR LWAIHWRLIA LGGSEAELAA FEKEIAAFES ELQAYKGKGN PEVEWLRMRA  60
AEIRNELQAY RHN                                                    73

SEQ ID NO: 175         moltype = AA  length = 73
FEATURE                Location/Qualifiers
REGION                 1..73
                       note = artificial construct
source                 1..73
                       mol_type = protein
                       organism = synthetic construct
SEQUENCE: 175
MGSWYEFAHR LEAIEWRLIA LGGSEAELAA FEKEIAAFES ELQAYKGKGN PEVEELRQYA  60
AAIRNYLQAY RHN                                                    73

SEQ ID NO: 176         moltype = AA  length = 73
FEATURE                Location/Qualifiers
REGION                 1..73
                       note = artificial construct
source                 1..73
                       mol_type = protein
                       organism = synthetic construct
SEQUENCE: 176
MGSWYEFDTR LGAIRNRLGA LGGSEAELAA FEKEIAAFES ELQAYKGKGN PEVEWLRFQA  60
AYIRFLLQAY RHN                                                    73

SEQ ID NO: 177         moltype = AA  length = 73
FEATURE                Location/Qualifiers
REGION                 1..73
                       note = artificial construct
source                 1..73
                       mol_type = protein
                       organism = synthetic construct
SEQUENCE: 177
MGSWYEFWVR LTAIRWRLEA LGGSEAELAA FEKEIAAFES ELQAYKGKGN PEVEWLREQA  60
ASIRWVLQAY RHN                                                    73

SEQ ID NO: 178         moltype = AA  length = 73
FEATURE                Location/Qualifiers
REGION                 1..73
                       note = artificial construct
source                 1..73
                       mol_type = protein
                       organism = synthetic construct
SEQUENCE: 178
MGSWFEFDRR LKAIDRRLMA LGGSEAELAA FEKEIAAFES ELQAYKGKGN PEVEWLRMQA  60
AIIRNYLQAY RHN                                                    73

SEQ ID NO: 179         moltype = AA  length = 73
FEATURE                Location/Qualifiers
REGION                 1..73
                       note = artificial construct
source                 1..73
                       mol_type = protein
                       organism = synthetic construct
SEQUENCE: 179
MGSWVEFWER LDAIDNRLGA LGGSEAELAA FEKEIAAFES ELQAYKGKGN PEVEWLRWHA  60
```

```
AYIRGYLQAY RHN                                                    73

SEQ ID NO: 180          moltype = AA  length = 73
FEATURE                 Location/Qualifiers
REGION                  1..73
                        note = artificial construct
source                  1..73
                        mol_type = protein
                        organism = synthetic construct
SEQUENCE: 180
MGSWAEFWDR LDAIDSRLNA LGGSEAELAA FEKEIAAFES ELQAYKGKGN PEVEYLREWA  60
AYIRGYLQAY RHN                                                    73

SEQ ID NO: 181          moltype = AA  length = 73
FEATURE                 Location/Qualifiers
REGION                  1..73
                        note = artificial construct
source                  1..73
                        mol_type = protein
                        organism = synthetic construct
SEQUENCE: 181
MGSWAEFDLR LRAIAKRLVA LGGSEAELAA FEKEIAAFES ELQAYKGKGN PEVEMLRLDA  60
AYIRGVLQAY RHN                                                    73

SEQ ID NO: 182          moltype = AA  length = 73
FEATURE                 Location/Qualifiers
REGION                  1..73
                        note = artificial construct
source                  1..73
                        mol_type = protein
                        organism = synthetic construct
SEQUENCE: 182
MGSWSEFWDR LYAIRIRLDA LGGSEAELAA FEKEIAAFES ELQAYKGKGN PEVEKLRSVA  60
ARIRNWLQAY RHN                                                    73

SEQ ID NO: 183          moltype = AA  length = 73
FEATURE                 Location/Qualifiers
REGION                  1..73
                        note = artificial construct
source                  1..73
                        mol_type = protein
                        organism = synthetic construct
SEQUENCE: 183
MGSWSEFWFR LGAIRNRLDA LGGSEAELAA FEKEIAAFES ELQAYKGKGN PEVEKLRDVA  60
AHIRHWLQAY RHN                                                    73

SEQ ID NO: 184          moltype = AA  length = 73
FEATURE                 Location/Qualifiers
REGION                  1..73
                        note = artificial construct
source                  1..73
                        mol_type = protein
                        organism = synthetic construct
SEQUENCE: 184
MGSWSEFNDR LDAIRWRLDA LGGSEAELAA FEKEIAAFES ELQAYKGKGN PEVEWLRQVA  60
ATIRYRLQAY RHN                                                    73

SEQ ID NO: 185          moltype = AA  length = 73
FEATURE                 Location/Qualifiers
REGION                  1..73
                        note = artificial construct
source                  1..73
                        mol_type = protein
                        organism = synthetic construct
SEQUENCE: 185
MGSWVEFWDR LGAIRERLQA LGGSEAELAA FEKEIAAFES ELQAYKGKGN PEVEKLRYTA  60
AAIRHYLQAY RHN                                                    73

SEQ ID NO: 186          moltype = AA  length = 73
FEATURE                 Location/Qualifiers
REGION                  1..73
                        note = artificial construct
source                  1..73
                        mol_type = protein
                        organism = synthetic construct
SEQUENCE: 186
MGSWAEFWDR LGAIRERLQA LGGSEAELAA FEKEIAAFES ELQAYKGKGN PEVEKLRYTA  60
AAIRHYLQAY RHN                                                    73
```

```
SEQ ID NO: 187         moltype = AA  length = 73
FEATURE                Location/Qualifiers
REGION                 1..73
                       note = artificial construct
source                 1..73
                       mol_type = protein
                       organism = synthetic construct
SEQUENCE: 187
MGSWTEFWDR LGAIRERLQA LGGSEAELAA FEKEIAAFES ELQAYKGKGN PEVEKLRYTA  60
AAIRHYLQAY RHN                                                     73

SEQ ID NO: 188         moltype = AA  length = 73
FEATURE                Location/Qualifiers
REGION                 1..73
                       note = artificial construct
source                 1..73
                       mol_type = protein
                       organism = synthetic construct
SEQUENCE: 188
MGSWVEFWDR LGAIRERLQA LGGSEAELAA FEKEIAAFES ELQAYKGKGN PEVEKLKYTA  60
AAIRHYLQAY RHN                                                     73

SEQ ID NO: 189         moltype = AA  length = 73
FEATURE                Location/Qualifiers
REGION                 1..73
                       note = artificial construct
source                 1..73
                       mol_type = protein
                       organism = synthetic construct
SEQUENCE: 189
MGSWVEFWDR LGAIRERLQA LGGSEAELAA FEKEIAAFES ELQAYKGKGN PEVEKLQYTA  60
AAIRHYLQAY RHN                                                     73

SEQ ID NO: 190         moltype = AA  length = 73
FEATURE                Location/Qualifiers
REGION                 1..73
                       note = artificial construct
source                 1..73
                       mol_type = protein
                       organism = synthetic construct
SEQUENCE: 190
MGSWVEFWDR LGAIRERLQA LGGSEAELAA FEKEIAAFES ELQAYKGKGN PEVEKLRYTA  60
AAIKHYLQAY RHN                                                     73

SEQ ID NO: 191         moltype = AA  length = 73
FEATURE                Location/Qualifiers
REGION                 1..73
                       note = artificial construct
source                 1..73
                       mol_type = protein
                       organism = synthetic construct
SEQUENCE: 191
MGSWAEFWDR LGAIRERLQA LGGSEAELAA FEKEIAAFES ELQAYKGKGN PEVEKLQYTA  60
AAIKHYLQAY RHN                                                     73

SEQ ID NO: 192         moltype = AA  length = 73
FEATURE                Location/Qualifiers
REGION                 1..73
                       note = artificial construct
source                 1..73
                       mol_type = protein
                       organism = synthetic construct
SEQUENCE: 192
MGSWTEFWDR LGAIRERLQA LGGSEAELAA FEKEIAAFES ELQAYKGKGN PEVEKLQYTA  60
AAIKHYLQAY RHN                                                     73

SEQ ID NO: 193         moltype = AA  length = 73
FEATURE                Location/Qualifiers
REGION                 1..73
                       note = artificial construct
source                 1..73
                       mol_type = protein
                       organism = synthetic construct
SEQUENCE: 193
MGSWVEFWDR LGAIRERLEA LGGSEAELAA FEKEIAAFES ELQAYKGKGN PEVEKLRYVA  60
AVIRHRLQAY RHN                                                     73

SEQ ID NO: 194         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 194
MGSWVEFWDR LGAIRERLQA LGGSEAELAA FEKEIAAFES ELQAYKGKGN PEVEELRASA  60
AAIRIALQAY RHN                                                    73

SEQ ID NO: 195          moltype = AA  length = 73
FEATURE                 Location/Qualifiers
REGION                  1..73
                        note = artificial construct
source                  1..73
                        mol_type = protein
                        organism = synthetic construct
SEQUENCE: 195
MGSWVEFWDR LGAIRDRLDA LGGSEAELAA FEKEIAAFES ELQAYKGKGN PEVEELRNTA  60
AYIRTFLQAY RHN                                                    73

SEQ ID NO: 196          moltype = AA  length = 73
FEATURE                 Location/Qualifiers
REGION                  1..73
                        note = artificial construct
source                  1..73
                        mol_type = protein
                        organism = synthetic construct
SEQUENCE: 196
MGSWSEFWVR LGAIRDRLDA LGGSEAELAA FEKEIAAFES ELQAYKGKGN PEVEALRVTA  60
AQIRHYLQAY RHN                                                    73

SEQ ID NO: 197          moltype = AA  length = 73
FEATURE                 Location/Qualifiers
REGION                  1..73
                        note = artificial construct
source                  1..73
                        mol_type = protein
                        organism = synthetic construct
SEQUENCE: 197
MGSWSEFWVR LGAIRERLDA LGGSEAELAA FEKEIAAFES ELQAYKGKGN PEVEKLRYTA  60
ATIRRFLQAY RHN                                                    73

SEQ ID NO: 198          moltype = AA  length = 73
FEATURE                 Location/Qualifiers
REGION                  1..73
                        note = artificial construct
source                  1..73
                        mol_type = protein
                        organism = synthetic construct
SEQUENCE: 198
MGSWSEFWAR LGAIRERLDA LGGSEAELAA FEKEIAAFES ELQAYKGKGN PEVEKLRYTA  60
ATIRRFLQAY RHN                                                    73

SEQ ID NO: 199          moltype = AA  length = 73
FEATURE                 Location/Qualifiers
REGION                  1..73
                        note = artificial construct
source                  1..73
                        mol_type = protein
                        organism = synthetic construct
SEQUENCE: 199
MGSWSEFWVR LGAIRERLDA LGGSEAELAA FEKEIAAFES ELQAYKGKGN PEVEKLRYTA  60
GTIRRFLQAY RHN                                                    73

SEQ ID NO: 200          moltype = AA  length = 73
FEATURE                 Location/Qualifiers
REGION                  1..73
                        note = artificial construct
source                  1..73
                        mol_type = protein
                        organism = synthetic construct
SEQUENCE: 200
MGSWSEFWVR LGAIRERLDA LGGSEAELAA FEKEIAAFES ELQAYKGKGN PEVEKLRYTA  60
ATIKRFLQAY RHN                                                    73

SEQ ID NO: 201          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 201
MGSWSEFWAR LGAIRERLDA LGGSEAELAA FEKEIAAFES ELQAYKGKGN PEVEKLRYTA  60
GTIKRFLQAY RHN                                                     73

SEQ ID NO: 202          moltype = AA  length = 73
FEATURE                 Location/Qualifiers
REGION                  1..73
                        note = artificial construct
source                  1..73
                        mol_type = protein
                        organism = synthetic construct
SEQUENCE: 202
MGSWSEFWDR LTAIRVRLDA LGGSEAELAA FEKEIAAFES ELQAYKGKGN PEVEKLRYTA  60
AHIRKFLQAY RHN                                                     73

SEQ ID NO: 203          moltype = AA  length = 73
FEATURE                 Location/Qualifiers
REGION                  1..73
                        note = artificial construct
source                  1..73
                        mol_type = protein
                        organism = synthetic construct
SEQUENCE: 203
MGSWTEFWTR LNAIYERLDA LGGSEAELAA FEKEIAAFES ELQAYKGKGN PEVEKLRFTA  60
ASIRMYLQAY RHN                                                     73

SEQ ID NO: 204          moltype = AA  length = 73
FEATURE                 Location/Qualifiers
REGION                  1..73
                        note = artificial construct
source                  1..73
                        mol_type = protein
                        organism = synthetic construct
SEQUENCE: 204
MGSWFEFWDR LAAIRDRLEA LGGSEAELAA FEKEIAAFES ELQAYKGKGN PEVEDLRYVA  60
AKIRVRLQAY RHN                                                     73

SEQ ID NO: 205          moltype = AA  length = 73
FEATURE                 Location/Qualifiers
REGION                  1..73
                        note = artificial construct
source                  1..73
                        mol_type = protein
                        organism = synthetic construct
SEQUENCE: 205
MGSWTEFWVR LNAIRDRLEA LGGSEAELAA FEKEIAAFES ELQAYKGKGN PEVEDLRHTA  60
AIIRNYLQAY RHN                                                     73

SEQ ID NO: 206          moltype = AA  length = 73
FEATURE                 Location/Qualifiers
REGION                  1..73
                        note = artificial construct
source                  1..73
                        mol_type = protein
                        organism = synthetic construct
SEQUENCE: 206
MGSWVEFWHR LGAIYDRLEA LGGSEAELAA FEKEIAAFES ELQAYKGKGN PEVEELRRTA  60
ALIRQTLQAY RHN                                                     73

SEQ ID NO: 207          moltype = AA  length = 73
FEATURE                 Location/Qualifiers
REGION                  1..73
                        note = artificial construct
source                  1..73
                        mol_type = protein
                        organism = synthetic construct
SEQUENCE: 207
MGSWVEFWNR LGAIYDRLEA LGGSEAELAA FEKEIAAFES ELQAYKGKGN PEVEKLRHTA  60
AVIRLYLQAY RHN                                                     73

SEQ ID NO: 208          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 208
MGSWSEFWER LEAIYDRLYA LGGSEAELAA FEKEIAAFES ELQAYKGKGN PEVEELRRTA  60
ATIRSFLQAY RHN                                                     73

SEQ ID NO: 209           moltype = AA  length = 73
FEATURE                  Location/Qualifiers
REGION                   1..73
                         note = artificial construct
source                   1..73
                         mol_type = protein
                         organism = synthetic construct
SEQUENCE: 209
MGSWEEFDNR LEAIFDRLEA LGGSEAELAA FEKEIAAFES ELQAYKGKGN PEVEELREFA  60
ATIRITLQAY RHN                                                     73

SEQ ID NO: 210           moltype = AA  length = 73
FEATURE                  Location/Qualifiers
REGION                   1..73
                         note = artificial construct
source                   1..73
                         mol_type = protein
                         organism = synthetic construct
SEQUENCE: 210
MGSWMEFWDR LYAIEFRLFA LGGSEAELAA FEKEIAAFES ELQAYKGKGN PEVEKLRRVA  60
ATIRNELQAY RHN                                                     73

SEQ ID NO: 211           moltype = AA  length = 73
FEATURE                  Location/Qualifiers
REGION                   1..73
                         note = artificial construct
source                   1..73
                         mol_type = protein
                         organism = synthetic construct
SEQUENCE: 211
MGSWTEFWER LYAIEYRLFA LGGSEAELAA FEKEIAAFES ELQAYKGKGN PEVEKLRSVA  60
ATIRYELQAY RHN                                                     73

SEQ ID NO: 212           moltype = AA  length = 73
FEATURE                  Location/Qualifiers
REGION                   1..73
                         note = artificial construct
source                   1..73
                         mol_type = protein
                         organism = synthetic construct
SEQUENCE: 212
MGSWNEFWER LYAIELRLFA LGGSEAELAA FEKEIAAFES ELQAYKGKGN PEVEKLRMTA  60
AYIRNELQAY RHN                                                     73

SEQ ID NO: 213           moltype = AA  length = 73
FEATURE                  Location/Qualifiers
REGION                   1..73
                         note = artificial construct
source                   1..73
                         mol_type = protein
                         organism = synthetic construct
SEQUENCE: 213
MGSWYEFWKR LYAIEYRLFA LGGSEAELAA FEKEIAAFES ELQAYKGKGN PEVEALRKVA  60
AKIREQLQAY RHN                                                     73

SEQ ID NO: 214           moltype = AA  length = 73
FEATURE                  Location/Qualifiers
REGION                   1..73
                         note = artificial construct
source                   1..73
                         mol_type = protein
                         organism = synthetic construct
SEQUENCE: 214
MGSWTEFWAR LYAIEMRLFA LGGSEAELAA FEKEIAAFES ELQAYKGKGN PEVEHLRRVA  60
ALIREQLQAY RHN                                                     73

SEQ ID NO: 215           moltype = AA  length = 73
FEATURE                  Location/Qualifiers
REGION                   1..73
                         note = artificial construct
source                   1..73
                         mol_type = protein
                         organism = synthetic construct
SEQUENCE: 215
```

```
MGSWHEFWDR LYAIEFRLFA LGGSEAELAA FEKEIAAFES ELQAYKGKGN PEVESLRQVA  60
AKIRWHLQAY RHN                                                    73

SEQ ID NO: 216         moltype = AA  length = 73
FEATURE                Location/Qualifiers
REGION                 1..73
                       note = artificial construct
source                 1..73
                       mol_type = protein
                       organism = synthetic construct
SEQUENCE: 216
MGSWDEFEFR LGALRWRLIA LGGSEAELAA FEKEIAAFES ELQAYKGKGN PEVEYLRFGA  60
AHIRHILQAY RHN                                                    73

SEQ ID NO: 217         moltype = AA  length = 73
FEATURE                Location/Qualifiers
REGION                 1..73
                       note = artificial construct
source                 1..73
                       mol_type = protein
                       organism = synthetic construct
SEQUENCE: 217
MGSWTEFYHR LYAIRERLSA LGGSEAELAA FEKEIAAFES ELQAYKGKGN PEVEYLRFGA  60
AHIRHLLQAY RHN                                                    73

SEQ ID NO: 218         moltype = AA  length = 73
FEATURE                Location/Qualifiers
REGION                 1..73
                       note = artificial construct
source                 1..73
                       mol_type = protein
                       organism = synthetic construct
SEQUENCE: 218
MGSWVEFETR LDAIRMRLGA LGGSEAELAA FEKEIAAFES ELQAYKGKGN PEVEYLRFGA  60
AHIRALLQAY RHN                                                    73

SEQ ID NO: 219         moltype = AA  length = 73
FEATURE                Location/Qualifiers
REGION                 1..73
                       note = artificial construct
source                 1..73
                       mol_type = protein
                       organism = synthetic construct
SEQUENCE: 219
MGSWGEFDVR LFAIRERLSA LGGSEAELAA FEKEIAAFES ELQAYKGKGN PEVEYLRGYA  60
AQIRSFLQAY RHN                                                    73

SEQ ID NO: 220         moltype = AA  length = 73
FEATURE                Location/Qualifiers
REGION                 1..73
                       note = artificial construct
source                 1..73
                       mol_type = protein
                       organism = synthetic construct
SEQUENCE: 220
MGSWVEFDER LSAIRERLDA LGGSEAELAA FEKEIAAFES ELQAYKGKGN PEVEYLRLYA  60
AQIRVFLQAY RHN                                                    73

SEQ ID NO: 221         moltype = AA  length = 73
FEATURE                Location/Qualifiers
REGION                 1..73
                       note = artificial construct
source                 1..73
                       mol_type = protein
                       organism = synthetic construct
SEQUENCE: 221
MGSWSEFDGR LGAIWDRLYA LGGSEAELAA FEKEIAAFES ELQAYKGKGN PEVEYLRDRA  60
AQIREFLQAY RHN                                                    73

SEQ ID NO: 222         moltype = AA  length = 73
FEATURE                Location/Qualifiers
REGION                 1..73
                       note = artificial construct
source                 1..73
                       mol_type = protein
                       organism = synthetic construct
SEQUENCE: 222
MGSWGEFEGR LHAIRSRLSA LGGSEAELAA FEKEIAAFES ELQAYKGKGN PEVEVLRGYA  60
AWIRALLQAY RHN                                                    73
```

```
SEQ ID NO: 223          moltype = AA  length = 73
FEATURE                 Location/Qualifiers
REGION                  1..73
                        note = artificial construct
source                  1..73
                        mol_type = protein
                        organism = synthetic construct
SEQUENCE: 223
MGSWGEFNGR LGAIRERLQA LGGSEAELAA FEKEIAAFES ELQAYKGKGN PEVEFLRAYA  60
ASIRAVLQAY RHN                                                     73

SEQ ID NO: 224          moltype = AA  length = 73
FEATURE                 Location/Qualifiers
REGION                  1..73
                        note = artificial construct
source                  1..73
                        mol_type = protein
                        organism = synthetic construct
SEQUENCE: 224
MGSWWEFTFR LAAIEFRLEA LGGSEAELAA FEKEIAAFES ELQAYKGKGN PEVEDLRAIA  60
AEIRKSLQAY RHN                                                     73

SEQ ID NO: 225          moltype = AA  length = 73
FEATURE                 Location/Qualifiers
REGION                  1..73
                        note = artificial construct
source                  1..73
                        mol_type = protein
                        organism = synthetic construct
SEQUENCE: 225
MGSWDEFQFR LAAIGFRLGA LGGSEAELAA FEKEIAAFES ELQAYKGKGN PEVEVLRRQA  60
ARIRHLLQAY RHN                                                     73

SEQ ID NO: 226          moltype = AA  length = 73
FEATURE                 Location/Qualifiers
REGION                  1..73
                        note = artificial construct
source                  1..73
                        mol_type = protein
                        organism = synthetic construct
SEQUENCE: 226
MGSWYEFVTR LHAIDHRLKA LGGSEADLAA FEKEIAAFES ELQAYKGKGN PEVEWLRFYA  60
AGIRMNLQAY RHN                                                     73

SEQ ID NO: 227          moltype = AA  length = 73
FEATURE                 Location/Qualifiers
REGION                  1..73
                        note = artificial construct
source                  1..73
                        mol_type = protein
                        organism = synthetic construct
SEQUENCE: 227
MGSWSIEFWR LEAIKFRLIA LGGSEAELAA FEKEIAAFES ELQAYKGKGN PEVEFLRVEA  60
AAIRRVLQAY RHN                                                     73

SEQ ID NO: 228          moltype = AA  length = 73
FEATURE                 Location/Qualifiers
REGION                  1..73
                        note = artificial construct
source                  1..73
                        mol_type = protein
                        organism = synthetic construct
SEQUENCE: 228
MGSWGEFEHR LDPSTCVWLA LGGSEAELAA FEKEIAAFES ELQAYKGKGN PEVEKLRRGA  60
AVIRHWLQAY RHN                                                     73

SEQ ID NO: 229          moltype = AA  length = 73
FEATURE                 Location/Qualifiers
REGION                  1..73
                        note = artificial construct
source                  1..73
                        mol_type = protein
                        organism = synthetic construct
SEQUENCE: 229
MGSWIEFAMR LEAIENRLTA LGGSEAELAI FESMIAHFEE LLQNYKGKGN PEVEALIHEA  60
FAIHKELWAY RHN                                                     73

SEQ ID NO: 230          moltype = AA  length = 73
```

```
FEATURE                Location/Qualifiers
REGION                 1..73
                       note = artificial construct
source                 1..73
                       mol_type = protein
                       organism = synthetic construct
SEQUENCE: 230
MGSWNEFYQR LEAIENRLQA LGGSEAELAM FEVRIALFED MLQGYKGKGN PEVEALKQEA  60
IAILRELIAY RHN                                                     73

SEQ ID NO: 231         moltype = AA  length = 73
FEATURE                Location/Qualifiers
REGION                 1..73
                       note = artificial construct
source                 1..73
                       mol_type = protein
                       organism = synthetic construct
SEQUENCE: 231
MGSWNEFYDR LRAIKKRLYA LGGSEAELAD FEEDIAQFEV DLQDYKGKGN PEVEALHREA  60
HAITHELWAY RHN                                                     73

SEQ ID NO: 232         moltype = AA  length = 73
FEATURE                Location/Qualifiers
REGION                 1..73
                       note = artificial construct
source                 1..73
                       mol_type = protein
                       organism = synthetic construct
SEQUENCE: 232
MGSWGEFKHR LALIKWYLEA LGGSEAELAH FEDWIAVFEV QLQNYKGKGN PEVEALRKEA  60
AAIRDELQAY RHN                                                     73

SEQ ID NO: 233         moltype = AA  length = 73
FEATURE                Location/Qualifiers
REGION                 1..73
                       note = artificial construct
source                 1..73
                       mol_type = protein
                       organism = synthetic construct
SEQUENCE: 233
MGSWYEFKHR LAIIKWYLEA LGGSEAELAK FEAWIAEFEM ILQRYKGKGN PEVEALRKEA  60
AAIRDELQAY RHN                                                     73

SEQ ID NO: 234         moltype = AA  length = 73
FEATURE                Location/Qualifiers
REGION                 1..73
                       note = artificial construct
source                 1..73
                       mol_type = protein
                       organism = synthetic construct
SEQUENCE: 234
MGSWYEFKHR LAIIKWYLEA LGGSEAELAH FEQYIADFEG TLQKYKGKGN PEVEALRKEA  60
AAIRDELQAY RHN                                                     73

SEQ ID NO: 235         moltype = AA  length = 73
FEATURE                Location/Qualifiers
REGION                 1..73
                       note = artificial construct
source                 1..73
                       mol_type = protein
                       organism = synthetic construct
SEQUENCE: 235
MGSWYNFKHR LAIIKWYLEA LGGSEAELAR FENFIANFET QLQLYKGKGN PEVEALRKEA  60
AAIRDELQAY RHN                                                     73

SEQ ID NO: 236         moltype = AA  length = 73
FEATURE                Location/Qualifiers
REGION                 1..73
                       note = artificial construct
source                 1..73
                       mol_type = protein
                       organism = synthetic construct
SEQUENCE: 236
MGSWFQFKHR LAIIKWQLEA LGGSEAELAW FEQWIADFEH QLQHYKGKGN PEVEALRKEA  60
AAIRDELQAY RHN                                                     73

SEQ ID NO: 237         moltype = AA  length = 73
FEATURE                Location/Qualifiers
REGION                 1..73
```

```
                        note = artificial construct
source                  1..73
                        mol_type = protein
                        organism = synthetic construct
SEQUENCE: 237
MGSWYNFKHR LAIIKWFLEA LGGSEAELAV FEVWIADFEH QLQEYKGKGN PEVEALRKEA  60
AAIRDELQAY RHN                                                     73

SEQ ID NO: 238          moltype = AA  length = 73
FEATURE                 Location/Qualifiers
REGION                  1..73
                        note = artificial construct
source                  1..73
                        mol_type = protein
                        organism = synthetic construct
SEQUENCE: 238
MGSWDAFKHR LALIKWYLEA LGGSEAELAH FEEYIAEFES NLQSYKGKGN PEVEALRKEA  60
AAIRDELQAY RHN                                                     73

SEQ ID NO: 239          moltype = AA  length = 73
FEATURE                 Location/Qualifiers
REGION                  1..73
                        note = artificial construct
source                  1..73
                        mol_type = protein
                        organism = synthetic construct
SEQUENCE: 239
MGSWDGFKHR LALIKWYLEA LGGSEAELAN FENWIAEFEQ RLQYYKGKGN PEVEALRKEA  60
AAIRDELQAY RHN                                                     73

SEQ ID NO: 240          moltype = AA  length = 73
FEATURE                 Location/Qualifiers
REGION                  1..73
                        note = artificial construct
source                  1..73
                        mol_type = protein
                        organism = synthetic construct
SEQUENCE: 240
MGSWNGFKHR LAIIKWYLEA LGGSEAELAS FESYIAEFES GLQEYKGKGN PEVEALRKEA  60
AAIRDELQAY RHN                                                     73

SEQ ID NO: 241          moltype = AA  length = 73
FEATURE                 Location/Qualifiers
REGION                  1..73
                        note = artificial construct
source                  1..73
                        mol_type = protein
                        organism = synthetic construct
SEQUENCE: 241
MGSWNSFKHR LALIKWYLEA LGGSEAELAT FEWYIASFES ELQQYKGKGN PEVEALRKEA  60
AAIRDELQAY RHN                                                     73

SEQ ID NO: 242          moltype = AA  length = 73
FEATURE                 Location/Qualifiers
REGION                  1..73
                        note = artificial construct
source                  1..73
                        mol_type = protein
                        organism = synthetic construct
SEQUENCE: 242
MGSWSDFKYR LAVIKFYLEA LGGSEAELAS FESFIAHFED DLQKYKGKGN PEVEALRKEA  60
AAIRDELQAY RHN                                                     73

SEQ ID NO: 243          moltype = AA  length = 73
FEATURE                 Location/Qualifiers
REGION                  1..73
                        note = artificial construct
source                  1..73
                        mol_type = protein
                        organism = synthetic construct
SEQUENCE: 243
MGSWSGFKYR LAVIKFYLEA LGGSEAELAS FELFIAKFEI DLQNYKGKGN PEVEALRKEA  60
AAIRDELQAY RHN                                                     73

SEQ ID NO: 244          moltype = AA  length = 73
FEATURE                 Location/Qualifiers
REGION                  1..73
                        note = artificial construct
source                  1..73
```

```
                         mol_type = protein
                         organism = synthetic construct
SEQUENCE: 244
MGSWYGFKYR LAVIKWYLEA LGGSEAELAS FEKYIAHFEH DLQAYKGKGN PEVEALRKEA  60
AAIRDELQAY RHN                                                     73

SEQ ID NO: 245           moltype = AA  length = 73
FEATURE                  Location/Qualifiers
REGION                   1..73
                         note = artificial construct
source                   1..73
                         mol_type = protein
                         organism = synthetic construct
SEQUENCE: 245
MGSWYGFKYR LAVIKWYLEA LGGSEAELAS FEKYIAQFEH DLQAYKGKGN PEVEALRKEA  60
AAIRDELQAY RHN                                                     73

SEQ ID NO: 246           moltype = AA  length = 73
FEATURE                  Location/Qualifiers
REGION                   1..73
                         note = artificial construct
source                   1..73
                         mol_type = protein
                         organism = synthetic construct
SEQUENCE: 246
MGSWYGFKYR LALIKWYLEA LGGSEAELAS FETYIADFED LLQAYKGKGN PEVEALRKEA  60
AAIRDELQAY RHN                                                     73

SEQ ID NO: 247           moltype = AA  length = 73
FEATURE                  Location/Qualifiers
REGION                   1..73
                         note = artificial construct
source                   1..73
                         mol_type = protein
                         organism = synthetic construct
SEQUENCE: 247
MGSWSTFKYH LAVIKWYLEA LGGSEAELAS FEDYIAQFET DLQEYKGKGN PEVEALRKEA  60
AAIRDELQAY RHN                                                     73

SEQ ID NO: 248           moltype = AA  length = 73
FEATURE                  Location/Qualifiers
REGION                   1..73
                         note = artificial construct
source                   1..73
                         mol_type = protein
                         organism = synthetic construct
SEQUENCE: 248
MGSWHEFKYR LALIKWYLEA LGGSEAELAT FEHHIAQFEW DLQKYKGKGN PEVEALRKEA  60
AAIRDELQAY RHN                                                     73

SEQ ID NO: 249           moltype = AA  length = 73
FEATURE                  Location/Qualifiers
REGION                   1..73
                         note = artificial construct
source                   1..73
                         mol_type = protein
                         organism = synthetic construct
SEQUENCE: 249
MGSWNMFKYR LAHIKWYLEA LGGSEAELAT FEAYIADFEV DLQKYKGKGN PEVEALRKEA  60
AAIRDELQAY RHN                                                     73

SEQ ID NO: 250           moltype = AA  length = 73
FEATURE                  Location/Qualifiers
REGION                   1..73
                         note = artificial construct
source                   1..73
                         mol_type = protein
                         organism = synthetic construct
SEQUENCE: 250
MGSWHGFKYR LAIIKWWLEA LGGSEAELAF FEEWIASFER DLQIYKGKGN PEVEALRKEA  60
AAIRDELQAY RHN                                                     73

SEQ ID NO: 251           moltype = AA  length = 73
FEATURE                  Location/Qualifiers
REGION                   1..73
                         note = artificial construct
source                   1..73
                         mol_type = protein
                         organism = synthetic construct
```

```
SEQUENCE: 251
MGSWHGFKYR LAVIKWYLEA LGGSEAELAM FEGWIAQFEI TLQQYKGKGN PEVEALRKEA  60
AAIRDELQAY RHN                                                    73

SEQ ID NO: 252         moltype = AA  length = 73
FEATURE                Location/Qualifiers
REGION                 1..73
                       note = artificial construct
source                 1..73
                       mol_type = protein
                       organism = synthetic construct
SEQUENCE: 252
MGSWQGFKYR LAVIKWMLEA LGGSEAELAF FENWIAEFET KLQQYKGKGN PEVEALRKEA  60
AAIRDELQAY RHN                                                    73

SEQ ID NO: 253         moltype = AA  length = 73
FEATURE                Location/Qualifiers
REGION                 1..73
                       note = artificial construct
source                 1..73
                       mol_type = protein
                       organism = synthetic construct
SEQUENCE: 253
MGSWSGFKYR LAVIKWYLEA LGGSEAELAT FEEWIAEFET ELQFYKGKGN PEVEALRKEA  60
AAIRDELQAY RHN                                                    73

SEQ ID NO: 254         moltype = AA  length = 73
FEATURE                Location/Qualifiers
REGION                 1..73
                       note = artificial construct
source                 1..73
                       mol_type = protein
                       organism = synthetic construct
SEQUENCE: 254
MGSWGYFKYR LAMIKWYLEA LGGSEAELAS FESWIAEFEG SLQAYKGKGN PEVEALRKEA  60
AAIRDELQAY RHN                                                    73

SEQ ID NO: 255         moltype = AA  length = 73
FEATURE                Location/Qualifiers
REGION                 1..73
                       note = artificial construct
source                 1..73
                       mol_type = protein
                       organism = synthetic construct
SEQUENCE: 255
MGSWHAFKYK LAMIKWYLEA LGGSEAELAH FEEWIAEFEA LLQEYKGKGN PEVEALRKEA  60
AAIRDELQAY RHN                                                    73

SEQ ID NO: 256         moltype = AA  length = 73
FEATURE                Location/Qualifiers
REGION                 1..73
                       note = artificial construct
source                 1..73
                       mol_type = protein
                       organism = synthetic construct
SEQUENCE: 256
MGSWQHFKYR LAIIKWYLEA LGGSEAELAF FESFIAKFEH DLQKYKGKGN PEVEALRKEA  60
AAIRDELQAY RHN                                                    73

SEQ ID NO: 257         moltype = AA  length = 73
FEATURE                Location/Qualifiers
REGION                 1..73
                       note = artificial construct
source                 1..73
                       mol_type = protein
                       organism = synthetic construct
SEQUENCE: 257
MGSWNDFKYR LAIIKYYLEA LGGSEAELAH FESYIASFEH DLQNYKGKGN PEVEALRKEA  60
AAIRDELQAY RHN                                                    73

SEQ ID NO: 258         moltype = AA  length = 73
FEATURE                Location/Qualifiers
REGION                 1..73
                       note = artificial construct
source                 1..73
                       mol_type = protein
                       organism = synthetic construct
SEQUENCE: 258
MGSWGAFKYR LAIIKFYLEA LGGSEAELAR FEEFIANFEH DLQNYKGKGN PEVEALRKEA  60
```

```
AAIRDELQAY RHN                                                    73

SEQ ID NO: 259          moltype = AA  length = 73
FEATURE                 Location/Qualifiers
REGION                  1..73
                        note = artificial construct
source                  1..73
                        mol_type = protein
                        organism = synthetic construct
SEQUENCE: 259
MGSWYNFKYR LAIIKFYLEA LGGSEAELAQ FEIWIAEFEH DLQGYKGKGN PEVEALRKEA  60
AAIRDELQAY RHN                                                    73

SEQ ID NO: 260          moltype = AA  length = 73
FEATURE                 Location/Qualifiers
REGION                  1..73
                        note = artificial construct
source                  1..73
                        mol_type = protein
                        organism = synthetic construct
SEQUENCE: 260
MGSWEQFKYR LAIIKYMLEA LGGSEAELAW FESWIANFES DLQHYKGKGN PEVEALRKEA  60
AAIRDELQAY RHN                                                    73

SEQ ID NO: 261          moltype = AA  length = 73
FEATURE                 Location/Qualifiers
REGION                  1..73
                        note = artificial construct
source                  1..73
                        mol_type = protein
                        organism = synthetic construct
SEQUENCE: 261
MGSWQQFKYR LAIIKYYLEA LGGSEAELAG FETYIAKFEE VLQSYKGKGN PEVEALRKEA  60
AAIRDELQAY RHN                                                    73

SEQ ID NO: 262          moltype = AA  length = 73
FEATURE                 Location/Qualifiers
REGION                  1..73
                        note = artificial construct
source                  1..73
                        mol_type = protein
                        organism = synthetic construct
SEQUENCE: 262
MGSWAGFKYR LAVIKYYLEA LGGSEAELAH FEQWIAHFEG MLQDYKGKGN PEVEALRKEA  60
AAIRDELQAY RHN                                                    73

SEQ ID NO: 263          moltype = AA  length = 73
FEATURE                 Location/Qualifiers
REGION                  1..73
                        note = artificial construct
source                  1..73
                        mol_type = protein
                        organism = synthetic construct
SEQUENCE: 263
MGSWTAFKYR LAIIKFYLEA LGGSEAELAH FESYIAHFED MLQHYKGKGN PEVEALRKEA  60
AAIRDELQAY RHN                                                    73

SEQ ID NO: 264          moltype = AA  length = 73
FEATURE                 Location/Qualifiers
REGION                  1..73
                        note = artificial construct
source                  1..73
                        mol_type = protein
                        organism = synthetic construct
SEQUENCE: 264
MGSWAHFKYR LAIIKFWLEA LGGSEAELAN FEEYIAEFES TLQVYKGKGN PEVEALRKEA  60
AAIRDELQAY RHN                                                    73

SEQ ID NO: 265          moltype = AA  length = 73
FEATURE                 Location/Qualifiers
REGION                  1..73
                        note = artificial construct
source                  1..73
                        mol_type = protein
                        organism = synthetic construct
SEQUENCE: 265
MGSWANFKYR LALIKWHLEA LGGSEAELAS FEIWIADFEE SLQWYKGKGN PEVEALRKEA  60
AAIRDELQAY RHN                                                    73
```

```
SEQ ID NO: 266         moltype = AA  length = 73
FEATURE                Location/Qualifiers
REGION                 1..73
                       note = artificial construct
source                 1..73
                       mol_type = protein
                       organism = synthetic construct
SEQUENCE: 266
MGSWATFKYR LALIKWHLEA LGGSEAELAD FEEYIAGFEE GLQKYKGKGN PEVEALRKEA  60
AAIRDELQAY RHN                                                    73

SEQ ID NO: 267         moltype = AA  length = 73
FEATURE                Location/Qualifiers
REGION                 1..73
                       note = artificial construct
source                 1..73
                       mol_type = protein
                       organism = synthetic construct
SEQUENCE: 267
MGSWTHFKYR LALIKWWLEA LGGSEAELAG FEVHIADFEA QLQMYKGKGN PEVEALRKEA  60
AAIRDELQAY RHN                                                    73

SEQ ID NO: 268         moltype = AA  length = 73
FEATURE                Location/Qualifiers
REGION                 1..73
                       note = artificial construct
source                 1..73
                       mol_type = protein
                       organism = synthetic construct
SEQUENCE: 268
MGSWNTFKYH LAVIKFMLEA LGGSEAELAF FEQWIAEFEV TLQSYKGKGN PEVEALRKEA  60
AAIRDELQAY RHN                                                    73

SEQ ID NO: 269         moltype = AA  length = 73
FEATURE                Location/Qualifiers
REGION                 1..73
                       note = artificial construct
source                 1..73
                       mol_type = protein
                       organism = synthetic construct
SEQUENCE: 269
MGSWTQFKYH LAVIKWYLEA LGGSEAELAG FEQWIAEFEK TLQEYKGKGN PEVEALRKEA  60
AAIRDELQAY RHN                                                    73

SEQ ID NO: 270         moltype = AA  length = 73
FEATURE                Location/Qualifiers
REGION                 1..73
                       note = artificial construct
source                 1..73
                       mol_type = protein
                       organism = synthetic construct
SEQUENCE: 270
MGSWNQFKYR LAVIKFYLEA LGGSEAELAH FETWIAAFEE QLQFYKGKGN PEVEALRKEA  60
AAIRDELQAY RHN                                                    73

SEQ ID NO: 271         moltype = AA  length = 73
FEATURE                Location/Qualifiers
REGION                 1..73
                       note = artificial construct
source                 1..73
                       mol_type = protein
                       organism = synthetic construct
SEQUENCE: 271
MGSWNEFKYH LAVIKFYLEA LGGSEAELAH FETWIAEFEY ELQKYKGKGN PEVEALRKEA  60
AAIRDELQAY RHN                                                    73

SEQ ID NO: 272         moltype = AA  length = 73
FEATURE                Location/Qualifiers
REGION                 1..73
                       note = artificial construct
source                 1..73
                       mol_type = protein
                       organism = synthetic construct
SEQUENCE: 272
MGSWVQFKYH LAVIKFYLEA LGGSEAELAH FETWIAEFEV ALQGYKGKGN PEVEALRKEA  60
AAIRDELQAY RHN                                                    73

SEQ ID NO: 273         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 273
MGSWVDFKYH LAVIKFWLEA LGGSEAELAN FETWIANFEQ ELQMYKGKGN PEVEALRKEA  60
AAIRDELQAY RHN                                                     73

SEQ ID NO: 274          moltype = AA  length = 73
FEATURE                 Location/Qualifiers
REGION                  1..73
                        note = artificial construct
source                  1..73
                        mol_type = protein
                        organism = synthetic construct
SEQUENCE: 274
MGSWVDFKYH LAVIKWYLEA LGGSEAELAD FENWIAHFES ILQQYKGKGN PEVEALRKEA  60
AAIRDELQAY RHN                                                     73

SEQ ID NO: 275          moltype = AA  length = 73
FEATURE                 Location/Qualifiers
REGION                  1..73
                        note = artificial construct
source                  1..73
                        mol_type = protein
                        organism = synthetic construct
SEQUENCE: 275
MGSWVEFKYH LAVIKFTLEA LGGSEAELAD FEEEIARFEM ILQQYKGKGN PEVEALRKEA  60
AAIRDELQAY RHN                                                     73

SEQ ID NO: 276          moltype = AA  length = 73
FEATURE                 Location/Qualifiers
REGION                  1..73
                        note = artificial construct
source                  1..73
                        mol_type = protein
                        organism = synthetic construct
SEQUENCE: 276
MGSWSHFKYH LALIKWYLEA LGGSEAELAK FEFWIAEFEH NLQMYKGKGN PEVEALRKEA  60
AAIRDELQAY RHN                                                     73

SEQ ID NO: 277          moltype = AA  length = 73
FEATURE                 Location/Qualifiers
REGION                  1..73
                        note = artificial construct
source                  1..73
                        mol_type = protein
                        organism = synthetic construct
SEQUENCE: 277
MGSWYHFKYH LALIKWYLEA LGGSEAELAH FEHWIAEFEW TLQQYKGKGN PEVEALRKEA  60
AAIRDELQAY RHN                                                     73

SEQ ID NO: 278          moltype = AA  length = 73
FEATURE                 Location/Qualifiers
REGION                  1..73
                        note = artificial construct
source                  1..73
                        mol_type = protein
                        organism = synthetic construct
SEQUENCE: 278
MGSWQGFKYH LALIKFYLEA LGGSEAELAH FEHWLAEFEH DLQTYKGKGN PEVEALRKEA  60
AAIRDELQAY RHN                                                     73

SEQ ID NO: 279          moltype = AA  length = 73
FEATURE                 Location/Qualifiers
REGION                  1..73
                        note = artificial construct
source                  1..73
                        mol_type = protein
                        organism = synthetic construct
SEQUENCE: 279
MGSWLSFKHH LALIKWYLEA LGGSEAELAS FEAWIALFEH QLQQYKGKGN PEVEALRKEA  60
AAIRDELQAY RHN                                                     73

SEQ ID NO: 280          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 280
MGSWSEFKYK LALIKWYLEA LGGSEAELAH FEGWIANFET TLQKYKGKGN PEVEALRKEA  60
AAIRDELQAY RHN                                                    73

SEQ ID NO: 281          moltype = AA  length = 73
FEATURE                 Location/Qualifiers
REGION                  1..73
                        note = artificial construct
source                  1..73
                        mol_type = protein
                        organism = synthetic construct
SEQUENCE: 281
MGSWIEFKYK LAIIKFYLEA LGGSEAELAH FEHWIADFEF VLQQYKGKGN PEVEALRKEA  60
AAIRDELQAY RHN                                                    73

SEQ ID NO: 282          moltype = AA  length = 73
FEATURE                 Location/Qualifiers
REGION                  1..73
                        note = artificial construct
source                  1..73
                        mol_type = protein
                        organism = synthetic construct
SEQUENCE: 282
MGSWQNFKYH LAMIKWYLEA LGGSEAELAN FEEFIAQFEI NLQHYKGKGN PEVEALRKEA  60
AAIRDELQAY RHN                                                    73

SEQ ID NO: 283          moltype = AA  length = 73
FEATURE                 Location/Qualifiers
REGION                  1..73
                        note = artificial construct
source                  1..73
                        mol_type = protein
                        organism = synthetic construct
SEQUENCE: 283
MGSWYNFKYH LAIIKWWLEA LGGSEAELAD FEHYIADFER NLQEYKGKGN PEVEALRKEA  60
AAIRDELQAY RHN                                                    73

SEQ ID NO: 284          moltype = AA  length = 73
FEATURE                 Location/Qualifiers
REGION                  1..73
                        note = artificial construct
source                  1..73
                        mol_type = protein
                        organism = synthetic construct
SEQUENCE: 284
MGSWYQFKYH LAIIKWYLEA LGGSEAELAG FENYIATFEQ ELQQYKGKGN PEVEALRKEA  60
AAIRDELQAY RHN                                                    73

SEQ ID NO: 285          moltype = AA  length = 73
FEATURE                 Location/Qualifiers
REGION                  1..73
                        note = artificial construct
source                  1..73
                        mol_type = protein
                        organism = synthetic construct
SEQUENCE: 285
MGSWSHFKYH LAIIKFYLEA LGGSEAELAG FEIWIAKFED ELQMYKGKGN PEVEALRKEA  60
AAIRDELQAY RHN                                                    73

SEQ ID NO: 286          moltype = AA  length = 73
FEATURE                 Location/Qualifiers
REGION                  1..73
                        note = artificial construct
source                  1..73
                        mol_type = protein
                        organism = synthetic construct
SEQUENCE: 286
MGSWVGFKAH LAIIKWYLEA LGGSEAELAG FEIFIADFEA LLQMYKGKGN PEVEALRKEA  60
AAIRDELQAY RHN                                                    73

SEQ ID NO: 287          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 287
MGSWVNFKYK LAIIKYMLEA LGGSEAELAF FEDWIAEFER TLQQYKGKGN PEVEALRKEA  60
AAIRDELQAY RHN                                                     73

SEQ ID NO: 288           moltype = AA  length = 73
FEATURE                  Location/Qualifiers
REGION                   1..73
                         note = artificial construct
source                   1..73
                         mol_type = protein
                         organism = synthetic construct
SEQUENCE: 288
MGSWSNFKYR LAVIKYMLEA LGGSEAELAF FEDWIADFEL HLQVYKGKGN PEVEALRKEA  60
AAIRDELQAY RHN                                                     73

SEQ ID NO: 289           moltype = AA  length = 73
FEATURE                  Location/Qualifiers
REGION                   1..73
                         note = artificial construct
source                   1..73
                         mol_type = protein
                         organism = synthetic construct
SEQUENCE: 289
MGSWTNFKYK LAVIKFMLEA LGGSEAELAF FEDWIAGFEI DLQNYKGKGN PEVEALRKEA  60
AAIRDELQAY RHN                                                     73

SEQ ID NO: 290           moltype = AA  length = 73
FEATURE                  Location/Qualifiers
REGION                   1..73
                         note = artificial construct
source                   1..73
                         mol_type = protein
                         organism = synthetic construct
SEQUENCE: 290
MGSWTGFKYR LAIIKFMLEA LGGSEAELAF FEQWIADFEN ELQYYKGKGN PEVEALRKEA  60
AAIRDELQAY RHN                                                     73

SEQ ID NO: 291           moltype = AA  length = 73
FEATURE                  Location/Qualifiers
REGION                   1..73
                         note = artificial construct
source                   1..73
                         mol_type = protein
                         organism = synthetic construct
SEQUENCE: 291
MGSWHNFKYR LAIIKFMLEA LGGSEAELAW FENWIADFED SLQDYKGKGN PEVEALRKEA  60
AAIRDELQAY RHN                                                     73

SEQ ID NO: 292           moltype = AA  length = 73
FEATURE                  Location/Qualifiers
REGION                   1..73
                         note = artificial construct
source                   1..73
                         mol_type = protein
                         organism = synthetic construct
SEQUENCE: 292
MGSWFAFKHR LAVIKYMLEA LGGSEAELAF FEHWIAQFEH DLQQYKGKGN PEVEALRKEA  60
AAIRDELQAY RHN                                                     73

SEQ ID NO: 293           moltype = AA  length = 73
FEATURE                  Location/Qualifiers
REGION                   1..73
                         note = artificial construct
source                   1..73
                         mol_type = protein
                         organism = synthetic construct
SEQUENCE: 293
MGSWYEFKHR LAVIKYMLEA LGGSEAELAF FENWIAQFEH ELQTYKGKGN PEVEALRKEA  60
AAIRDELQAY RHN                                                     73

SEQ ID NO: 294           moltype = AA  length = 73
FEATURE                  Location/Qualifiers
REGION                   1..73
                         note = artificial construct
source                   1..73
                         mol_type = protein
                         organism = synthetic construct
SEQUENCE: 294
```

```
MGSWYKFKHK LAVIKYMLEA LGGSEAELAW FEEWIAEFEV TLQDYKGKGN PEVEALRKEA  60
AAIRDELQAY RHN                                                    73

SEQ ID NO: 295         moltype = AA  length = 73
FEATURE                Location/Qualifiers
REGION                 1..73
                       note = artificial construct
source                 1..73
                       mol_type = protein
                       organism = synthetic construct
SEQUENCE: 295
MGSWFYFKQK LAFIKWYLEA LGGSEAELAN FEIYIAEFEV MLQQYKGKGN PEVEALRKEA  60
AAIRDELQAY RHN                                                    73

SEQ ID NO: 296         moltype = AA  length = 73
FEATURE                Location/Qualifiers
REGION                 1..73
                       note = artificial construct
source                 1..73
                       mol_type = protein
                       organism = synthetic construct
SEQUENCE: 296
MGSWFSFKHH LAVIKWNLEA LGGSEAELAS FEEQIAEFES VLQAYKGKGN PEVEALRKEA  60
AAIRDELQAY RHN                                                    73

SEQ ID NO: 297         moltype = AA  length = 73
FEATURE                Location/Qualifiers
REGION                 1..73
                       note = artificial construct
source                 1..73
                       mol_type = protein
                       organism = synthetic construct
SEQUENCE: 297
MGSWGNFKYR LAIIKFHLEA LGSSEAELAT FEAWIANFES MLQNYKGKGN PEVEALRKEA  60
AAIRDELQAY RHN                                                    73

SEQ ID NO: 298         moltype = AA  length = 73
FEATURE                Location/Qualifiers
REGION                 1..73
                       note = artificial construct
source                 1..73
                       mol_type = protein
                       organism = synthetic construct
SEQUENCE: 298
MGSWSYFKYG LAIIKIRLEA LGGSEAELAD FERWIAAFEH DLQYYKGKGN PEVEALRKEA  60
AAIRDELQAY RHN                                                    73

SEQ ID NO: 299         moltype = AA  length = 73
FEATURE                Location/Qualifiers
REGION                 1..73
                       note = artificial construct
source                 1..73
                       mol_type = protein
                       organism = synthetic construct
SEQUENCE: 299
MGSWSYFKFG LAHIKLRLEA LGGSEAELAD FEQWIASFEE QLQTYKGKGN PEVEALRKEA  60
AAIRDELQAY RHN                                                    73

SEQ ID NO: 300         moltype = AA  length = 73
FEATURE                Location/Qualifiers
REGION                 1..73
                       note = artificial construct
source                 1..73
                       mol_type = protein
                       organism = synthetic construct
SEQUENCE: 300
MGSWSYFKWG LAHIKLRLEA LGGSEAELAD FEFWIAEFEG LLQDYKGKGN PEVEALRKEA  60
AAIRDELQAY RHN                                                    73

SEQ ID NO: 301         moltype = AA  length = 73
FEATURE                Location/Qualifiers
REGION                 1..73
                       note = artificial construct
source                 1..73
                       mol_type = protein
                       organism = synthetic construct
SEQUENCE: 301
MGSWIYFKYG LAHIKTRLEA LGGSEAELAD FEQWIAEFEK MLQDYKGKGN PEVEALRKEA  60
AAIRDELQAY RHN                                                    73
```

```
SEQ ID NO: 302          moltype = AA  length = 73
FEATURE                 Location/Qualifiers
REGION                  1..73
                        note = artificial construct
source                  1..73
                        mol_type = protein
                        organism = synthetic construct
SEQUENCE: 302
MGSWGYFKYG LATIKHRLEA LGGSEAELAD FELWIAKFEE QLQVYKGKGN PEVEALRKEA  60
AAIRDELQAY RHN                                                    73

SEQ ID NO: 303          moltype = AA  length = 73
FEATURE                 Location/Qualifiers
REGION                  1..73
                        note = artificial construct
source                  1..73
                        mol_type = protein
                        organism = synthetic construct
SEQUENCE: 303
MGSWEYFKYG LATIKMHLEA LGGSEAELAD FEHWIAHFEH QLQMYKGKGN PEVEALRKEA  60
AAIRDELQAY RHN                                                    73

SEQ ID NO: 304          moltype = AA  length = 73
FEATURE                 Location/Qualifiers
REGION                  1..73
                        note = artificial construct
source                  1..73
                        mol_type = protein
                        organism = synthetic construct
SEQUENCE: 304
MGSWSYFKYG LATIKEKLEA LGGSEAELAD FETWIAMFEK QLQEYKGKGN PEVEALRKEA  60
AAIRDELQAY RHN                                                    73

SEQ ID NO: 305          moltype = AA  length = 73
FEATURE                 Location/Qualifiers
REGION                  1..73
                        note = artificial construct
source                  1..73
                        mol_type = protein
                        organism = synthetic construct
SEQUENCE: 305
MGSWHYFKNG LAIIKEKLEA LGGSEAELAD FEIWIAMFEM ELQEYKGKGN PEVEALRKEA  60
AAIRDELQAY RHN                                                    73

SEQ ID NO: 306          moltype = AA  length = 73
FEATURE                 Location/Qualifiers
REGION                  1..73
                        note = artificial construct
source                  1..73
                        mol_type = protein
                        organism = synthetic construct
SEQUENCE: 306
MGSWQYFKYG LAIIKIKLEA LGGSEAELAD FEAWIATFEK QLQHYKGKGN PEVEALRKEA  60
AAIRDELQAY RHN                                                    73

SEQ ID NO: 307          moltype = AA  length = 73
FEATURE                 Location/Qualifiers
REGION                  1..73
                        note = artificial construct
source                  1..73
                        mol_type = protein
                        organism = synthetic construct
SEQUENCE: 307
MGSWVYFKHG LAVIKMRLEA LGGSEAELAD FETWIAQFEM TLQEYKGKGN PEVEALRKEA  60
AAIRDELQAY RHN                                                    73

SEQ ID NO: 308          moltype = AA  length = 73
FEATURE                 Location/Qualifiers
REGION                  1..73
                        note = artificial construct
source                  1..73
                        mol_type = protein
                        organism = synthetic construct
SEQUENCE: 308
MGSWVYFKYG LAVIKEKLEA LGGSEAELAD FETWIAEFEF GLQQYKGKGN PEVEALRKEA  60
AAIRDELQAY RHN                                                    73

SEQ ID NO: 309          moltype = AA  length = 73
```

```
FEATURE                Location/Qualifiers
REGION                 1..73
                       note = artificial construct
source                 1..73
                       mol_type = protein
                       organism = synthetic construct
SEQUENCE: 309
MGSWYYFKYG LAVIKGKLEA LGGSEAELAD FETWIAKFEN HLQSYKGKGN PEVEALRKEA  60
AAIRDELQAY RHN                                                     73

SEQ ID NO: 310         moltype = AA  length = 73
FEATURE                Location/Qualifiers
REGION                 1..73
                       note = artificial construct
source                 1..73
                       mol_type = protein
                       organism = synthetic construct
SEQUENCE: 310
MGSWTYFKYG LALIKYRLEA LGGSEAELAD FEEWIAQFEV SLQHYKGKGN PEVEALRKEA  60
AAIRDELQAY RHN                                                     73

SEQ ID NO: 311         moltype = AA  length = 73
FEATURE                Location/Qualifiers
REGION                 1..73
                       note = artificial construct
source                 1..73
                       mol_type = protein
                       organism = synthetic construct
SEQUENCE: 311
MGSWDYFKYG LALIKIKLEA LGGSEAELAD FEVWIAQFEM ALQVYKGKGN PEVEALRKEA  60
AAIRDELQAY RHN                                                     73

SEQ ID NO: 312         moltype = AA  length = 73
FEATURE                Location/Qualifiers
REGION                 1..73
                       note = artificial construct
source                 1..73
                       mol_type = protein
                       organism = synthetic construct
SEQUENCE: 312
MGSWTYFKFG LAHIKDSLEA LGGSEAELAD FEQWIAMFEQ DLQVYKGKGN PEVEALRKEA  60
AAIRDELQAY RHN                                                     73

SEQ ID NO: 313         moltype = AA  length = 73
FEATURE                Location/Qualifiers
REGION                 1..73
                       note = artificial construct
source                 1..73
                       mol_type = protein
                       organism = synthetic construct
SEQUENCE: 313
MGSWGYFKHG LAHIKSSLEA LGGSEAELAD FEVWIAAFEN ELQEYKGKGN PEVEALRKEA  60
AAIRDELQAY RHN                                                     73

SEQ ID NO: 314         moltype = AA  length = 73
FEATURE                Location/Qualifiers
REGION                 1..73
                       note = artificial construct
source                 1..73
                       mol_type = protein
                       organism = synthetic construct
SEQUENCE: 314
MGSWGYFKTG LAIIKAQLEA LGGSEAELAD FELWIAQFEE TLQFYKGKGN PEVEALRKEA  60
AAIRDELQAY RHN                                                     73

SEQ ID NO: 315         moltype = AA  length = 73
FEATURE                Location/Qualifiers
REGION                 1..73
                       note = artificial construct
source                 1..73
                       mol_type = protein
                       organism = synthetic construct
SEQUENCE: 315
MGSWAYFKYG LAVIKLHLEA LGGSEAELAD FERYIAEFEY ELQAYKGKGN PEVEALRKEA  60
AAIRDELQAY RHN                                                     73

SEQ ID NO: 316         moltype = AA  length = 73
FEATURE                Location/Qualifiers
REGION                 1..73
```

```
                        note = artificial construct
source                  1..73
                        mol_type = protein
                        organism = synthetic construct
SEQUENCE: 316
MGSWLDFKEG LADIKRSLEA LGGSEAELAD FEGVIALFEW KLQTYKGKGN PEVEALRKEA  60
AAIRDELQAY RHN                                                    73

SEQ ID NO: 317          moltype = AA  length = 73
FEATURE                 Location/Qualifiers
REGION                  1..73
                        note = artificial construct
source                  1..73
                        mol_type = protein
                        organism = synthetic construct
SEQUENCE: 317
MGSWEVFKHE LAVIKDYLEA LGGSEAELAH FEWGIAWFEG FLQDYKGKGN PEVEALRKEA  60
AAIRDELQAY RHN                                                    73

SEQ ID NO: 318          moltype = AA  length = 73
FEATURE                 Location/Qualifiers
REGION                  1..73
                        note = artificial construct
source                  1..73
                        mol_type = protein
                        organism = synthetic construct
SEQUENCE: 318
MGSWIVFKQS LAWIKEHLEA LGGSEAELAE FEFYIANFEH TLQNYKGKGN PEVEALRKEA  60
AAIRDELQAY RHN                                                    73

SEQ ID NO: 319          moltype = AA  length = 73
FEATURE                 Location/Qualifiers
REGION                  1..73
                        note = artificial construct
source                  1..73
                        mol_type = protein
                        organism = synthetic construct
SEQUENCE: 319
MGSWIYFKDS LAYIKKYLEA LGGSEAELAT FEYYIANFEH ELQYYKGKGN PEVEALRKEA  60
AAIRDELQAY RHN                                                    73

SEQ ID NO: 320          moltype = AA  length = 73
FEATURE                 Location/Qualifiers
REGION                  1..73
                        note = artificial construct
source                  1..73
                        mol_type = protein
                        organism = synthetic construct
SEQUENCE: 320
MGSWDHFKYN LAWIKKYLEA LGGSEAELAT FEWYIANFEK RLQDYKGKGN PEVEALRKEA  60
AAIRDELQAY RHN                                                    73

SEQ ID NO: 321          moltype = AA  length = 73
FEATURE                 Location/Qualifiers
REGION                  1..73
                        note = artificial construct
source                  1..73
                        mol_type = protein
                        organism = synthetic construct
SEQUENCE: 321
MGSWFTFKQN LAWIKLHLEA LGGSEAELAR FEYYIADFEN KLQLYKGKGN PEVEALRKEA  60
AAIRDELQAY RHN                                                    73

SEQ ID NO: 322          moltype = AA  length = 73
FEATURE                 Location/Qualifiers
REGION                  1..73
                        note = artificial construct
source                  1..73
                        mol_type = protein
                        organism = synthetic construct
SEQUENCE: 322
MGSWREFKYG LAHIKRVLEA LGGSEAELAV FEYYIAKFEQ ELQEYKGKGN PEVEALRKEA  60
AAIRDELQAY RHN                                                    73

SEQ ID NO: 323          moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 323
MGSWIQFKYG LAHIKRTLEA LGGSEAELAV FEWYIADFEQ QLQGYKGKGN PEVEALRKEA  60
AAIRDELQAY RHN                                                    73

SEQ ID NO: 324          moltype = AA  length = 73
FEATURE                 Location/Qualifiers
REGION                  1..73
                        note = artificial construct
source                  1..73
                        mol_type = protein
                        organism = synthetic construct
SEQUENCE: 324
MGSWVEFKHN LAWIKVTLEA LGGSEAELAV FEYYIAQFEE QLQEYKGKGN PEVEALRKEA  60
AAIRDELQAY RHN                                                    73

SEQ ID NO: 325          moltype = AA  length = 73
FEATURE                 Location/Qualifiers
REGION                  1..73
                        note = artificial construct
source                  1..73
                        mol_type = protein
                        organism = synthetic construct
SEQUENCE: 325
MGSWISFKDN LAMIKEFLEA LGGSEAELAV FEWYIATFEV ELQDYKGKGN PEVEALRKEA  60
AAIRDELQAY RHN                                                    73

SEQ ID NO: 326          moltype = AA  length = 73
FEATURE                 Location/Qualifiers
REGION                  1..73
                        note = artificial construct
source                  1..73
                        mol_type = protein
                        organism = synthetic construct
SEQUENCE: 326
MGSWHIFKDN LATIKAFLEA LGGSEAELAV FEWYIAKFEE ELQGYKGKGN PEVEALRKEA  60
AAIRDELQAY RHN                                                    73

SEQ ID NO: 327          moltype = AA  length = 73
FEATURE                 Location/Qualifiers
REGION                  1..73
                        note = artificial construct
source                  1..73
                        mol_type = protein
                        organism = synthetic construct
SEQUENCE: 327
MGSWTSFKHG LAGIKRVLEA LGGSEAELAT FEWYIAQFER HLQAYKGKGN PEVEALRKEA  60
AAIRDELQAY RHN                                                    73

SEQ ID NO: 328          moltype = AA  length = 73
FEATURE                 Location/Qualifiers
REGION                  1..73
                        note = artificial construct
source                  1..73
                        mol_type = protein
                        organism = synthetic construct
SEQUENCE: 328
MGSWQSFKHA LADIKINLEA LGGSEAELAQ FEYAIAVFEY RLQAYKGKGN PEVEALRKEA  60
AAIRDELQAY RHN                                                    73

SEQ ID NO: 329          moltype = AA  length = 73
FEATURE                 Location/Qualifiers
REGION                  1..73
                        note = artificial construct
source                  1..73
                        mol_type = protein
                        organism = synthetic construct
SEQUENCE: 329
MGSWHTFKEA LAQIKGELEA LGGSEAELAS FEYAIAVFEY RLQMYKGKGN PEVEALRKEA  60
AAIRDELQAY RHN                                                    73

SEQ ID NO: 330          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 330
MGSWTDFKTS LADIKAELEA LGGSEAELAK FEYYIAIFEY RLQEYKGKGN PEVEALRKEA  60
AAIRDELQAY RHN                                                    73

SEQ ID NO: 331         moltype = AA  length = 73
FEATURE                Location/Qualifiers
REGION                 1..73
                       note = artificial construct
source                 1..73
                       mol_type = protein
                       organism = synthetic construct
SEQUENCE: 331
MGSWTNFKEG LAEIKRDLEA LGGSEAELAR FEYVIAVFEF RLQNYKGKGN PEVEALRKEA  60
AAIRDELQAY RHN                                                    73

SEQ ID NO: 332         moltype = AA  length = 73
FEATURE                Location/Qualifiers
REGION                 1..73
                       note = artificial construct
source                 1..73
                       mol_type = protein
                       organism = synthetic construct
SEQUENCE: 332
MGSWHTFKDG LAEIKSELEA LGGSEAELAM FEYVIAIFEY RLQNYKGKGN PEVEALRKEA  60
AAIRDELQAY RHN                                                    73

SEQ ID NO: 333         moltype = AA  length = 73
FEATURE                Location/Qualifiers
REGION                 1..73
                       note = artificial construct
source                 1..73
                       mol_type = protein
                       organism = synthetic construct
SEQUENCE: 333
MGSWQFFKEH LASIKFWLEA LGGSEAELAF FEDAIADFEY HLQNYKGKGN PEVEALRKEA  60
AAIRDELQAY RHN                                                    73

SEQ ID NO: 334         moltype = AA  length = 73
FEATURE                Location/Qualifiers
REGION                 1..73
                       note = artificial construct
source                 1..73
                       mol_type = protein
                       organism = synthetic construct
SEQUENCE: 334
MGSWTYFKEH LASIKFWLEA LGGSEAELAF FEDAIAEFEK DLQYYKGKGN PEVEALRKEA  60
AAIRDELQAY RHN                                                    73

SEQ ID NO: 335         moltype = AA  length = 73
FEATURE                Location/Qualifiers
REGION                 1..73
                       note = artificial construct
source                 1..73
                       mol_type = protein
                       organism = synthetic construct
SEQUENCE: 335
MGSWIIFKGY LAHIKHHLEA LGGSEAELAD FEFYIAIFEM ELQKYKGKGN PEVEALRKEA  60
AAIRDELQAY RHN                                                    73

SEQ ID NO: 336         moltype = AA  length = 73
FEATURE                Location/Qualifiers
REGION                 1..73
                       note = artificial construct
source                 1..73
                       mol_type = protein
                       organism = synthetic construct
SEQUENCE: 336
MGSWYLFQSH LAHIKHHLEA LGGSEAELAW FEFTIAGFEQ ELQHYKGKGN PEVEALRKEA  60
AAIRDELQAY RHN                                                    73

SEQ ID NO: 337         moltype = AA  length = 73
FEATURE                Location/Qualifiers
REGION                 1..73
                       note = artificial construct
source                 1..73
                       mol_type = protein
                       organism = synthetic construct
SEQUENCE: 337
MGSWYSFKWT LARIKLELEA LGGSEAELAY FENVIAHFEM ELQSYKGKGN PEVEALRKEA  60
```

```
AAIRDELQAY RHN                                                    73

SEQ ID NO: 338          moltype = AA  length = 73
FEATURE                 Location/Qualifiers
REGION                  1..73
                        note = artificial construct
source                  1..73
                        mol_type = protein
                        organism = synthetic construct
SEQUENCE: 338
MGSWTTLKWR LAHIKQHLEA LGGSEAELAL FEYDIAHFEE LLQYYKGKGN PEVEALRKEA  60
AAIRDELQAY RHN                                                    73

SEQ ID NO: 339          moltype = AA  length = 73
FEATURE                 Location/Qualifiers
REGION                  1..73
                        note = artificial construct
source                  1..73
                        mol_type = protein
                        organism = synthetic construct
SEQUENCE: 339
MGSWYGFKWY LATIKKHLEA LGGSEAELAL FETEIATFEL WLQDYKGKGN PEVEALRKEA  60
AAIRDELQAY RHN                                                    73

SEQ ID NO: 340          moltype = AA  length = 73
FEATURE                 Location/Qualifiers
REGION                  1..73
                        note = artificial construct
source                  1..73
                        mol_type = protein
                        organism = synthetic construct
SEQUENCE: 340
MGSWIEFNMR VLAIEDRLWA LGGSEAELAA FEKEIAAFES ELQAYKGKGN PEVESLRYEA  60
CLDPWSSAAY RHN                                                    73

SEQ ID NO: 341          moltype = AA  length = 73
FEATURE                 Location/Qualifiers
REGION                  1..73
                        note = artificial construct
source                  1..73
                        mol_type = protein
                        organism = synthetic construct
SEQUENCE: 341
MGSWIEFHER LWAIEDRLWA LGGSEAELAA FEKEIAAFES ELQAYKGKGN PEVESLREMA  60
ASIRHGLQAY RHN                                                    73

SEQ ID NO: 342          moltype = AA  length = 73
FEATURE                 Location/Qualifiers
REGION                  1..73
                        note = artificial construct
source                  1..73
                        mol_type = protein
                        organism = synthetic construct
SEQUENCE: 342
MGSWFEFYER LWAIDDRLWA LGGSEAELAA FEKEIAAFES ELQAYKGKGN PEVEWLREEA  60
ASIRSSLQAY RHN                                                    73

SEQ ID NO: 343          moltype = AA  length = 73
FEATURE                 Location/Qualifiers
REGION                  1..73
                        note = artificial construct
source                  1..73
                        mol_type = protein
                        organism = synthetic construct
SEQUENCE: 343
MGSWFEFWDR LEAIDDRLFA LGGSEAELAA FEKEIAAFES ELQAYKGKGN PEVESLRYNA  60
AEIRKELQAY RHN                                                    73

SEQ ID NO: 344          moltype = AA  length = 73
FEATURE                 Location/Qualifiers
REGION                  1..73
                        note = artificial construct
source                  1..73
                        mol_type = protein
                        organism = synthetic construct
SEQUENCE: 344
MGSWHEFWSR LDAIDDRLFA LGGSEAELAA FEKEIAAFES ELQAYKGKGN PEVEYLRGAA  60
ADIRAELQAY RHN                                                    73
```

```
SEQ ID NO: 345          moltype = AA  length = 73
FEATURE                 Location/Qualifiers
REGION                  1..73
                        note = artificial construct
source                  1..73
                        mol_type = protein
                        organism = synthetic construct
SEQUENCE: 345
MGSWYEFWIR LEAIDDRLFA LGGSEAELAA FEKEIAAFES ELQAYKGKGN PEVDILRDFA  60
ADIRTELQAY RHN                                                     73

SEQ ID NO: 346          moltype = AA  length = 73
FEATURE                 Location/Qualifiers
REGION                  1..73
                        note = artificial construct
source                  1..73
                        mol_type = protein
                        organism = synthetic construct
SEQUENCE: 346
MGSWHEFWDR LEAIDDRLYA LGGSEAELAA FEKEIAAFES ELQAYKGKGN PEVEFLREEA  60
AYIRELLQAY RHN                                                     73

SEQ ID NO: 347          moltype = AA  length = 73
FEATURE                 Location/Qualifiers
REGION                  1..73
                        note = artificial construct
source                  1..73
                        mol_type = protein
                        organism = synthetic construct
SEQUENCE: 347
MGSWEEFWDR LFAIDDRLWA LGGSEAELAA FEKEIAAFES ELQAYKGKGN PEVETLRNEA  60
AEIRMALQAY RHN                                                     73

SEQ ID NO: 348          moltype = AA  length = 73
FEATURE                 Location/Qualifiers
REGION                  1..73
                        note = artificial construct
source                  1..73
                        mol_type = protein
                        organism = synthetic construct
SEQUENCE: 348
MGSWWEFDDR LFAIDTRLMA LGGSEAELAA FEKEIAAFES ELQAYKGKGN PEVESLREWA  60
ATIRMELQAY RHN                                                     73

SEQ ID NO: 349          moltype = AA  length = 73
FEATURE                 Location/Qualifiers
REGION                  1..73
                        note = artificial construct
source                  1..73
                        mol_type = protein
                        organism = synthetic construct
SEQUENCE: 349
MGSWTEFHDR LEAIDDRLWA LGGSEAELAA FEKEIAAFES ELQAYKGKGN PEVEYLREEA  60
AQIRWELQAY RHN                                                     73

SEQ ID NO: 350          moltype = AA  length = 73
FEATURE                 Location/Qualifiers
REGION                  1..73
                        note = artificial construct
source                  1..73
                        mol_type = protein
                        organism = synthetic construct
SEQUENCE: 350
MGSWAEFEDR LWAIEDRLWA LGGSEAELAA FEKEIAAFES ELQAYKGKGN PEVEYLREEA  60
AAIRFELQAY RHN                                                     73

SEQ ID NO: 351          moltype = AA  length = 73
FEATURE                 Location/Qualifiers
REGION                  1..73
                        note = artificial construct
source                  1..73
                        mol_type = protein
                        organism = synthetic construct
SEQUENCE: 351
MGSWVEFWFR LEAIDSRLWA LGGSEAELAA FEKEIAAFES ELQAYKGKGN PEVEWLREEA  60
AAIREDLQAY RHN                                                     73

SEQ ID NO: 352          moltype = AA  length = 73
FEATURE                 Location/Qualifiers
```

```
REGION                  1..73
                        note = artificial construct
source                  1..73
                        mol_type = protein
                        organism = synthetic construct
SEQUENCE: 352
MGSWVEFWQR LEAIESRLWA LGGSEAELAA FEKEIAAFES ELQAYKGKGN PEVEFLREEA  60
AEIRWELQAY RHN                                                     73

SEQ ID NO: 353          moltype = AA  length = 73
FEATURE                 Location/Qualifiers
REGION                  1..73
                        note = artificial construct
source                  1..73
                        mol_type = protein
                        organism = synthetic construct
SEQUENCE: 353
MGSWSEFWQR LEAIEDRLWA LGGSEAELAA FEKEIAAFES ELQAYKGKGN PEVEWLRENA  60
AMIRDELQAY RHN                                                     73

SEQ ID NO: 354          moltype = AA  length = 73
FEATURE                 Location/Qualifiers
REGION                  1..73
                        note = artificial construct
source                  1..73
                        mol_type = protein
                        organism = synthetic construct
SEQUENCE: 354
MGSWSEFITR LEAIDDRLWA LGGSEAELAA FEKEIAAFES ELQAYKGKGN PEVEILREEA  60
AEIRQHLQAY RHN                                                     73

SEQ ID NO: 355          moltype = AA  length = 73
FEATURE                 Location/Qualifiers
REGION                  1..73
                        note = artificial construct
source                  1..73
                        mol_type = protein
                        organism = synthetic construct
SEQUENCE: 355
MGSWYEFETR LEAIYDRLWA LGGSEAELAA FEKEIAAFES ELQAYKGKGN PEVELLRVEA  60
AEIREDLQAY RHN                                                     73

SEQ ID NO: 356          moltype = AA  length = 73
FEATURE                 Location/Qualifiers
REGION                  1..73
                        note = artificial construct
source                  1..73
                        mol_type = protein
                        organism = synthetic construct
SEQUENCE: 356
MGSWTEFYYR LEAIEDRLWA LGGSEAELAA FEKEIAAFES ELQAYKGKGN PEVEFLRVEA  60
ANIRDMLQAY RHN                                                     73

SEQ ID NO: 357          moltype = AA  length = 73
FEATURE                 Location/Qualifiers
REGION                  1..73
                        note = artificial construct
source                  1..73
                        mol_type = protein
                        organism = synthetic construct
SEQUENCE: 357
MGSWYEFVIR LEAIEDRLWA LGGSEAELAA FEKEIAAFES ELQAYKGKGN PEVEVLRWYA  60
ADIRHELQAY RHN                                                     73

SEQ ID NO: 358          moltype = AA  length = 73
FEATURE                 Location/Qualifiers
REGION                  1..73
                        note = artificial construct
source                  1..73
                        mol_type = protein
                        organism = synthetic construct
SEQUENCE: 358
MGSWTEFSIR LEAIYDRLVA LGGSEAELAA FEKEIAAFES ELQAYKGKGN PEVEVLRTYA  60
ANIRHELQAY RHN                                                     73

SEQ ID NO: 359          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 359
MGSWTEFSIR LEAIYDRLVA LGGSEAELAA FEKEIAAFES ELQAYKGKGN PEVEVLRTYA  60
AFIRHELQAY RHN                                                     73

SEQ ID NO: 360          moltype = AA  length = 73
FEATURE                 Location/Qualifiers
REGION                  1..73
                        note = artificial construct
source                  1..73
                        mol_type = protein
                        organism = synthetic construct
SEQUENCE: 360
MGSWTEFVWR LEAIWDRLDA LGGSEAELAA FEKEIAAFES ELQAYKGKGN PEVEVLREDA  60
AVIRHFLQAY RHN                                                     73

SEQ ID NO: 361          moltype = AA  length = 73
FEATURE                 Location/Qualifiers
REGION                  1..73
                        note = artificial construct
source                  1..73
                        mol_type = protein
                        organism = synthetic construct
SEQUENCE: 361
MGSWVEFHER LEAIEDRLMA LGGSEAELAA FEKEIAAFES ELQAYKGKGN PEVEYLREDA  60
AFIRQLLQAY RHN                                                     73

SEQ ID NO: 362          moltype = AA  length = 73
FEATURE                 Location/Qualifiers
REGION                  1..73
                        note = artificial construct
source                  1..73
                        mol_type = protein
                        organism = synthetic construct
SEQUENCE: 362
MGSWVEFHDR LEAIEDRLYA LGGSEAELAA FEKEIAAFES ELQAYKGKGN PEVEWLREDA  60
AYIRSILQAY RHN                                                     73

SEQ ID NO: 363          moltype = AA  length = 73
FEATURE                 Location/Qualifiers
REGION                  1..73
                        note = artificial construct
source                  1..73
                        mol_type = protein
                        organism = synthetic construct
SEQUENCE: 363
MGSWIEFYDR LEAIYDRLDA LGGSEAELAA FEKEIAAFES ELQAYKGKGN PEVEWLREDA  60
AFIRSWLQAY RHN                                                     73

SEQ ID NO: 364          moltype = AA  length = 73
FEATURE                 Location/Qualifiers
REGION                  1..73
                        note = artificial construct
source                  1..73
                        mol_type = protein
                        organism = synthetic construct
SEQUENCE: 364
MGSWVEFDQR LEAIYDRLYA LGGSEAELAA FEKEIAAFES ELQAYKGKGN PEVEWLREDA  60
AQIRKWLQAY RHN                                                     73

SEQ ID NO: 365          moltype = AA  length = 73
FEATURE                 Location/Qualifiers
REGION                  1..73
                        note = artificial construct
source                  1..73
                        mol_type = protein
                        organism = synthetic construct
SEQUENCE: 365
MGSWVEFHDR LEAIEDRLLA LGGSEAELAA FEKEIAAFES ELQAYKGKGN PEVEDLREYA  60
AGIRWFLQAY RHN                                                     73

SEQ ID NO: 366          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 366
MGSWEEFAQR LYAIEWRLYA LGGSEAELAA FEKEIAAFES ELQAYKGKGN PEVEVLRYVA  60
AQIRYHLQAY RHN                                                     73

SEQ ID NO: 367           moltype = AA  length = 73
FEATURE                  Location/Qualifiers
REGION                   1..73
                         note = artificial construct
source                   1..73
                         mol_type = protein
                         organism = synthetic construct
SEQUENCE: 367
MGSWDEFAWR LDVIFARLGA LGGSEAELAA FEKEIAAFES ELQAYKGKGN PEVEELRKNA  60
AQIRDGLQAY RHN                                                     73

SEQ ID NO: 368           moltype = AA  length = 73
FEATURE                  Location/Qualifiers
REGION                   1..73
                         note = artificial construct
source                   1..73
                         mol_type = protein
                         organism = synthetic construct
SEQUENCE: 368
MGSWDEFYYR LEAIEMRLGA LGGSEAELAA FEKEIAAFES ELQAYKGKGN PEVEELRHYA  60
AQIRHMLQAY RHN                                                     73

SEQ ID NO: 369           moltype = AA  length = 73
FEATURE                  Location/Qualifiers
REGION                   1..73
                         note = artificial construct
source                   1..73
                         mol_type = protein
                         organism = synthetic construct
SEQUENCE: 369
MGSWEEFYDR LEAIYNRLGA LGGSEAELAA FEKEIAAFES ELQAYKGKGN PEVEVLREYA  60
ADIREMLQAY RHN                                                     73

SEQ ID NO: 370           moltype = AA  length = 73
FEATURE                  Location/Qualifiers
REGION                   1..73
                         note = artificial construct
source                   1..73
                         mol_type = protein
                         organism = synthetic construct
SEQUENCE: 370
MGSWDEFGRR LYAIEWQLYA LGGEEAELAA FEKEIAAFES ELQAYKGKGN PEVEALRKEA  60
AVIRENLQAY RHN                                                     73

SEQ ID NO: 371           moltype = AA  length = 73
FEATURE                  Location/Qualifiers
REGION                   1..73
                         note = artificial construct
source                   1..73
                         mol_type = protein
                         organism = synthetic construct
SEQUENCE: 371
MGSWDEFGRR LYAIEWQLYA LGGTEAELAA FEKEIAAFES ELQAYKGKGN PEVEALRKEA  60
AVIRENLQAY RHN                                                     73

SEQ ID NO: 372           moltype = AA  length = 73
FEATURE                  Location/Qualifiers
REGION                   1..73
                         note = artificial construct
source                   1..73
                         mol_type = protein
                         organism = synthetic construct
SEQUENCE: 372
MGSWDEFGRR LYAIETQLYA LGGEEAELAA FEKEIAAFES ELQAYKGKGN PEVEKLREIA  60
AVIRENLQAY RHN                                                     73

SEQ ID NO: 373           moltype = AA  length = 73
FEATURE                  Location/Qualifiers
REGION                   1..73
                         note = artificial construct
source                   1..73
                         mol_type = protein
                         organism = synthetic construct
SEQUENCE: 373
```

```
MGSWDEFGRR LYAIEWQLYA LGGEEAELAA FEKEIAAFES ELQAYKGKGN PEVEKLREIA  60
AVIRENLQAY RHN                                                     73

SEQ ID NO: 374         moltype = AA  length = 73
FEATURE                Location/Qualifiers
REGION                 1..73
                       note = artificial construct
source                 1..73
                       mol_type = protein
                       organism = synthetic construct
SEQUENCE: 374
MGSWDEFGRR LYAIKWQLYA LGGEEAELAA FEKEIAAFES ELQAYKGKGN PEVEKLREIA  60
AVIRENLQAY RHN                                                     73

SEQ ID NO: 375         moltype = AA  length = 73
FEATURE                Location/Qualifiers
REGION                 1..73
                       note = artificial construct
source                 1..73
                       mol_type = protein
                       organism = synthetic construct
SEQUENCE: 375
MGSWDEFGRR LYAIEWQLYA LGGEEAELAA FEKEIAAFES ELQAYKGKGN PEVEKLRKIA  60
AVIRENLQAY RHN                                                     73

SEQ ID NO: 376         moltype = AA  length = 73
FEATURE                Location/Qualifiers
REGION                 1..73
                       note = artificial construct
source                 1..73
                       mol_type = protein
                       organism = synthetic construct
SEQUENCE: 376
MGSWDEFGRR LYAIEWQLYA LGGGEAELAA FEKEIAAFES ELQAYKGKGN PEVEKLREIA  60
AVIRENLQAY RHN                                                     73

SEQ ID NO: 377         moltype = AA  length = 73
FEATURE                Location/Qualifiers
REGION                 1..73
                       note = artificial construct
source                 1..73
                       mol_type = protein
                       organism = synthetic construct
SEQUENCE: 377
MGSWDEFGRR LYAIEWQLYA LGGTEAELAA FEKEIAAFES ELQAYKGKGN PEVEKLREIA  60
AVIRENLQAY RHN                                                     73

SEQ ID NO: 378         moltype = AA  length = 73
FEATURE                Location/Qualifiers
REGION                 1..73
                       note = artificial construct
source                 1..73
                       mol_type = protein
                       organism = synthetic construct
SEQUENCE: 378
MGSWDEFGRR LYAIEWQLYA LGGGEAELAA FEKEIAAFES ELQAYKGKGN PEVEKLREIA  60
AVIRSNLQAY RHN                                                     73

SEQ ID NO: 379         moltype = AA  length = 73
FEATURE                Location/Qualifiers
REGION                 1..73
                       note = artificial construct
source                 1..73
                       mol_type = protein
                       organism = synthetic construct
SEQUENCE: 379
MGSWDEFGRR LYAIEWQLYA LGGTEAELAA FEKEIAAFES ELQAYKGKGN PEVEKLREIA  60
AVIRSNLQAY RHN                                                     73

SEQ ID NO: 380         moltype = AA  length = 73
FEATURE                Location/Qualifiers
REGION                 1..73
                       note = artificial construct
source                 1..73
                       mol_type = protein
                       organism = synthetic construct
SEQUENCE: 380
MGSWDEFGRR LYAIEWQLYA LGGEEAELAA FEKEIAAFES ELQAYKGKGN PEVEKLREIA  60
AVIRSNLQAY RHN                                                     73
```

```
SEQ ID NO: 381         moltype = AA  length = 73
FEATURE                Location/Qualifiers
REGION                 1..73
                       note = artificial construct
source                 1..73
                       mol_type = protein
                       organism = synthetic construct
SEQUENCE: 381
MGSWDEFGRR LAAIEWQLYA LGGEEAELAA FEKEIAAFES ELQAYKGKGN PEVEKLREIA  60
AVIRENLQAY RHN                                                     73

SEQ ID NO: 382         moltype = AA  length = 73
FEATURE                Location/Qualifiers
REGION                 1..73
                       note = artificial construct
source                 1..73
                       mol_type = protein
                       organism = synthetic construct
SEQUENCE: 382
MGSWDEFGRR LYAIEWQLYA LGGEEAELAA FEKEIAAFES ELQAYKGKGN PEVEALREIA  60
AVIRENLQAY RHN                                                     73

SEQ ID NO: 383         moltype = AA  length = 73
FEATURE                Location/Qualifiers
REGION                 1..73
                       note = artificial construct
source                 1..73
                       mol_type = protein
                       organism = synthetic construct
SEQUENCE: 383
MGSWDEFGRR LYAIEWQLYA LGGEEAELAA FEKEIAAFES ELQAYKGKGN PEVEKLREEA  60
AVIRENLQAY RHN                                                     73

SEQ ID NO: 384         moltype = AA  length = 73
FEATURE                Location/Qualifiers
REGION                 1..73
                       note = artificial construct
source                 1..73
                       mol_type = protein
                       organism = synthetic construct
SEQUENCE: 384
MGSWDEFGRR LYAIEWRLYA LGGSEAELAA FEKEIAAFES ELQAYKGKGS PEVEKLREIA  60
AVIRSNLQAY RHN                                                     73

SEQ ID NO: 385         moltype = AA  length = 73
FEATURE                Location/Qualifiers
REGION                 1..73
                       note = artificial construct
source                 1..73
                       mol_type = protein
                       organism = synthetic construct
SEQUENCE: 385
MGSWDEFGRR LYAIEWRLYA LGGSEAELAA FEKEIAAFES ELQAYKGKGN PEVEKLREIA  60
AVIRSNLQAY RHN                                                     73

SEQ ID NO: 386         moltype = AA  length = 73
FEATURE                Location/Qualifiers
REGION                 1..73
                       note = artificial construct
source                 1..73
                       mol_type = protein
                       organism = synthetic construct
SEQUENCE: 386
MGSWDEFGRR LYAIEWRLYA LGGEEAELAA FEKEIAAFES ELQAYKGKGN PEVEKLREIA  60
AVIRSNLQAY RHN                                                     73

SEQ ID NO: 387         moltype = AA  length = 73
FEATURE                Location/Qualifiers
REGION                 1..73
                       note = artificial construct
source                 1..73
                       mol_type = protein
                       organism = synthetic construct
SEQUENCE: 387
MGSWDEFGRR LYAIEWQLYA LGGSEAELAA FEKEIAAFES ELQAYKGKGN PEVEKLREIA  60
AVIRSNLQAY RHN                                                     73

SEQ ID NO: 388         moltype = AA  length = 73
```

```
FEATURE                 Location/Qualifiers
REGION                  1..73
                        note = artificial construct
source                  1..73
                        mol_type = protein
                        organism = synthetic construct
SEQUENCE: 388
MGSWDEFSRR LYAIEWRLYA LGGSEAELAA FEKEIAAFES ELQAYKGKGN PEVEKLREIA  60
AVIRSNLQAY RHN                                                     73

SEQ ID NO: 389          moltype = AA  length = 73
FEATURE                 Location/Qualifiers
REGION                  1..73
                        note = artificial construct
source                  1..73
                        mol_type = protein
                        organism = synthetic construct
SEQUENCE: 389
MGSWDEFGRR LYAIEWRLYA LGGSEAELAA FEKEIAAFES ELQAYKGKGN PEVEKLREIA  60
AVIRENLQAY RHN                                                     73

SEQ ID NO: 390          moltype = AA  length = 73
FEATURE                 Location/Qualifiers
REGION                  1..73
                        note = artificial construct
source                  1..73
                        mol_type = protein
                        organism = synthetic construct
SEQUENCE: 390
MGSWDEFGRR LAAIKTQLAA LGGEEAELAA FEKEIAAFES ELQAYKGKGN PEVEKLREIA  60
AVIRENLQAY RHN                                                     73

SEQ ID NO: 391          moltype = AA  length = 73
FEATURE                 Location/Qualifiers
REGION                  1..73
                        note = artificial construct
source                  1..73
                        mol_type = protein
                        organism = synthetic construct
SEQUENCE: 391
MGSWDEFGRR LAAIKTQLAA LGGTEAELAA FEKEIAAFES ELQAYKGKGN PEVEKLREIA  60
AVIRENLQAY RHN                                                     73

SEQ ID NO: 392          moltype = AA  length = 73
FEATURE                 Location/Qualifiers
REGION                  1..73
                        note = artificial construct
source                  1..73
                        mol_type = protein
                        organism = synthetic construct
SEQUENCE: 392
MGSWDEFGRR LAAIKTQLAA LGGEEAELAA FEKEIAAFES ELQAYKGKGN PEVEALRKEA  60
AVIRENLQAY RHN                                                     73

SEQ ID NO: 393          moltype = AA  length = 73
FEATURE                 Location/Qualifiers
REGION                  1..73
                        note = artificial construct
source                  1..73
                        mol_type = protein
                        organism = synthetic construct
SEQUENCE: 393
MGSWDEFGRR LAAIKTQLAA LGGTEAELAA FEKEIAAFES ELQAYKGKGN PEVEALRKEA  60
AVIRENLQAY RHN                                                     73

SEQ ID NO: 394          moltype = AA  length = 73
FEATURE                 Location/Qualifiers
REGION                  1..73
                        note = artificial construct
source                  1..73
                        mol_type = protein
                        organism = synthetic construct
SEQUENCE: 394
MGSWDEFEQR LIAIEERLFA LGGSEAELAA FEKEIAAFES ELQAYKGKGN PEVEWLREEA  60
AVIRKYLQAY RHN                                                     73

SEQ ID NO: 395          moltype = AA  length = 73
FEATURE                 Location/Qualifiers
REGION                  1..73
```

```
                          note = artificial construct
source                    1..73
                          mol_type = protein
                          organism = synthetic construct
SEQUENCE: 395
MGSWVEFDQR LGAIWDRLVA LGGSEAELAA FEKEIAAFES ELQAYKGKGN PEVEHLRQGA  60
AVIRDDLQAY RHN                                                    73

SEQ ID NO: 396            moltype = AA  length = 73
FEATURE                   Location/Qualifiers
REGION                    1..73
                          note = artificial construct
source                    1..73
                          mol_type = protein
                          organism = synthetic construct
SEQUENCE: 396
MGSWVEFDMR LSAIWERLIA LGGSEAELAA FEKEIAAFES ELQAYKGKGN PEVEWLREDA  60
AEIREFLQAY RHN                                                    73

SEQ ID NO: 397            moltype = AA  length = 73
FEATURE                   Location/Qualifiers
REGION                    1..73
                          note = artificial construct
source                    1..73
                          mol_type = protein
                          organism = synthetic construct
SEQUENCE: 397
MGSWVEFDQR LDAIYERLYA LGGSEAELAA FEKEIAAFES ELQAYKGKGN PEVEWLRDEA  60
AEIREHLQAY RHN                                                    73

SEQ ID NO: 398            moltype = AA  length = 73
FEATURE                   Location/Qualifiers
REGION                    1..73
                          note = artificial construct
source                    1..73
                          mol_type = protein
                          organism = synthetic construct
SEQUENCE: 398
MGSWHEFDQR LWAIEERLWA LGGSEAELAA FEKEIAAFES ELQAYKGKGN PEVETLRLYA  60
ALIRHDLQAY RHN                                                    73

SEQ ID NO: 399            moltype = AA  length = 73
FEATURE                   Location/Qualifiers
REGION                    1..73
                          note = artificial construct
source                    1..73
                          mol_type = protein
                          organism = synthetic construct
SEQUENCE: 399
MGSWVEFWDR LDAIEGRLWA LGGSEAELAA FEKEIAAFES ELQAYKGKGN PEVEDLRWLA  60
AEIRADLQAY RHN                                                    73

SEQ ID NO: 400            moltype = AA  length = 73
FEATURE                   Location/Qualifiers
REGION                    1..73
                          note = artificial construct
source                    1..73
                          mol_type = protein
                          organism = synthetic construct
SEQUENCE: 400
MGSWVEFYSR LDAIEDRLWA LGGSEAELAA FEKEIAAFES ELQAYKGKGN PEVEWLRIAA  60
ASIREDLQAY RHN                                                    73

SEQ ID NO: 401            moltype = AA  length = 73
FEATURE                   Location/Qualifiers
REGION                    1..73
                          note = artificial construct
source                    1..73
                          mol_type = protein
                          organism = synthetic construct
SEQUENCE: 401
MGSWYEFYER LDAIEERLWA LGGSEAELAA FEKEIAAFES ELQAYKGKGN PEVEVLRDWA  60
AWIREDLQAY RHN                                                    73

SEQ ID NO: 402            moltype = AA  length = 73
FEATURE                   Location/Qualifiers
REGION                    1..73
                          note = artificial construct
source                    1..73
```

```
                        mol_type = protein
                        organism = synthetic construct
SEQUENCE: 402
MGSWFEFDDR LWAIENRLWA LGGSEAELAA FEKEIAAFES ELQAYKGKGN PEVEVLRDNA  60
AWIREILQAY RHN                                                     73

SEQ ID NO: 403          moltype = AA  length = 73
FEATURE                 Location/Qualifiers
REGION                  1..73
                        note = artificial construct
source                  1..73
                        mol_type = protein
                        organism = synthetic construct
SEQUENCE: 403
MGSWYEFWDR LDALEDRLWA LGGSEAELAA FEKEIAAFES ELQAYKGKGN PEVEYLRDSA  60
AFIREELQAY RHN                                                     73

SEQ ID NO: 404          moltype = AA  length = 73
FEATURE                 Location/Qualifiers
REGION                  1..73
                        note = artificial construct
source                  1..73
                        mol_type = protein
                        organism = synthetic construct
SEQUENCE: 404
MGSWMEFVDR LDAIESRLWA LGGSEAELAA FEKEIAAFES ELQAYKGKGN PEVEWLRIEA  60
AFIREELQAY RHN                                                     73

SEQ ID NO: 405          moltype = AA  length = 73
FEATURE                 Location/Qualifiers
REGION                  1..73
                        note = artificial construct
source                  1..73
                        mol_type = protein
                        organism = synthetic construct
SEQUENCE: 405
MGSWDEFVDR LWAIEERLWA LGGSEAELAA FEKEIAAFES ELQAYKGKGN PEVEELRIQA  60
AIIREALQAY RHN                                                     73

SEQ ID NO: 406          moltype = AA  length = 73
FEATURE                 Location/Qualifiers
REGION                  1..73
                        note = artificial construct
source                  1..73
                        mol_type = protein
                        organism = synthetic construct
SEQUENCE: 406
MGSWFEFNYR LGAIEDRLWA LGGSEAELAA FEKEIAAFES ELQAYKGKGN PEVEMLRQIA  60
AEIREFLQAY RHN                                                     73

SEQ ID NO: 407          moltype = AA  length = 73
FEATURE                 Location/Qualifiers
REGION                  1..73
                        note = artificial construct
source                  1..73
                        mol_type = protein
                        organism = synthetic construct
SEQUENCE: 407
MGSWEEFFTR LDAINERLEA LGGSEAELAA FEKEIAAFES ELQAYKGKGN PEVEMLRYEA  60
AEIRHMLQAY RHN                                                     73

SEQ ID NO: 408          moltype = AA  length = 73
FEATURE                 Location/Qualifiers
REGION                  1..73
                        note = artificial construct
source                  1..73
                        mol_type = protein
                        organism = synthetic construct
SEQUENCE: 408
MGSWYEFSNR LDAIGERLWA LGGSEAELAA FEKEIAAFES ELQAYKGKGN PEVEILRHQA  60
AEIRWFLQAY RHN                                                     73

SEQ ID NO: 409          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 409
MGSWYEFWGR LDAIEERLWA LGGSEAELAA FEKEIAAFES ELQAYKGRGN PEVEMLREDA  60
AEIRGQLQAY RHN                                                    73

SEQ ID NO: 410         moltype = AA  length = 73
FEATURE                Location/Qualifiers
REGION                 1..73
                       note = artificial construct
source                 1..73
                       mol_type = protein
                       organism = synthetic construct
SEQUENCE: 410
MGSWVEFWDR LWAIDYRLFA LGGSEAELAA FEKEIAAFES ELQAYKGKGN PEVEALRDEA  60
AWIREELQAY RHN                                                    73

SEQ ID NO: 411         moltype = AA  length = 73
FEATURE                Location/Qualifiers
REGION                 1..73
                       note = artificial construct
source                 1..73
                       mol_type = protein
                       organism = synthetic construct
SEQUENCE: 411
MGSWVEFVDR LWAIDERLDA LGGSEAELAA FEKEIAAFES ELQAYKGKGN PEVEFLRTWA  60
AWIREDLQAY RHN                                                    73

SEQ ID NO: 412         moltype = AA  length = 73
FEATURE                Location/Qualifiers
REGION                 1..73
                       note = artificial construct
source                 1..73
                       mol_type = protein
                       organism = synthetic construct
SEQUENCE: 412
MGSWFEFWDR LEAIWERLDA LGGSEAELAA FEKEIAAFES ELQAYKGKGN PEVEELRREA  60
AIIREDLQAY RHN                                                    73

SEQ ID NO: 413         moltype = AA  length = 73
FEATURE                Location/Qualifiers
REGION                 1..73
                       note = artificial construct
source                 1..73
                       mol_type = protein
                       organism = synthetic construct
SEQUENCE: 413
MGSWFEFEDR LEAIYQRLDA LGGSEAELAA FEKEIAAFES ELQAYKGKGN PEVEWLRDEA  60
AWIRSDLQAY RHN                                                    73

SEQ ID NO: 414         moltype = AA  length = 73
FEATURE                Location/Qualifiers
REGION                 1..73
                       note = artificial construct
source                 1..73
                       mol_type = protein
                       organism = synthetic construct
SEQUENCE: 414
MGSWFEFHDR LWAIDERLWA LGGSEAELAA FEKEIAAFES ELQAYKGKGN PEVEILREEA  60
ADIRLDLQAY RHN                                                    73

SEQ ID NO: 415         moltype = AA  length = 73
FEATURE                Location/Qualifiers
REGION                 1..73
                       note = artificial construct
source                 1..73
                       mol_type = protein
                       organism = synthetic construct
SEQUENCE: 415
MGSWYEFEDR LWAIDNRLWA LGGSEAELAA FEKEIAAFES ELQAYKGKGN PEVEELRVHA  60
ADIRDDLQAY RHN                                                    73

SEQ ID NO: 416         moltype = AA  length = 73
FEATURE                Location/Qualifiers
REGION                 1..73
                       note = artificial construct
source                 1..73
                       mol_type = protein
                       organism = synthetic construct
SEQUENCE: 416
MGSWFEFQDR LWAIDNRLWA LGGSEAELAA FEKEIAAFES ELQAYKGKGN PEVEELRDHA  60
```

```
AMIRWELQAY RHN                                                   73

SEQ ID NO: 417         moltype = AA  length = 73
FEATURE                Location/Qualifiers
REGION                 1..73
                       note = artificial construct
source                 1..73
                       mol_type = protein
                       organism = synthetic construct
SEQUENCE: 417
MGSWDEFEER LFAIDERLWA LGGSEAELAA FEKEIAAFES ELQAYKGKGN PEVEALRYLA  60
ADIREELQAY RHN                                                   73

SEQ ID NO: 418         moltype = AA  length = 73
FEATURE                Location/Qualifiers
REGION                 1..73
                       note = artificial construct
source                 1..73
                       mol_type = protein
                       organism = synthetic construct
SEQUENCE: 418
MGSWEEFWER LDAIDTRLWA LGGSEAELAA FEKEIAAFES ELQAYKGKGN PEVEVLRNDA  60
ADIREPLQAY RHN                                                   73

SEQ ID NO: 419         moltype = AA  length = 73
FEATURE                Location/Qualifiers
REGION                 1..73
                       note = artificial construct
source                 1..73
                       mol_type = protein
                       organism = synthetic construct
SEQUENCE: 419
MGSWMEFWER LEAIDMRLWA LGGSEAELAA FEKEIAAFES ELQAYKGKGN PEVEYLRDDA  60
AVIRDDLQAY RHN                                                   73

SEQ ID NO: 420         moltype = AA  length = 73
FEATURE                Location/Qualifiers
REGION                 1..73
                       note = artificial construct
source                 1..73
                       mol_type = protein
                       organism = synthetic construct
SEQUENCE: 420
MGSWLEFMWR LDAIDERLWA LGGSEAELAA FEKEIAAFES ELQAYKGKGN PEVELLREMA  60
AAIRDDLQAY RHN                                                   73

SEQ ID NO: 421         moltype = AA  length = 73
FEATURE                Location/Qualifiers
REGION                 1..73
                       note = artificial construct
source                 1..73
                       mol_type = protein
                       organism = synthetic construct
SEQUENCE: 421
MGSWTEFYNR LDAIDQRLWA LGGSEAELAA FEKEIAAFES ELQAYKGKGN PEVEMLREYA  60
ADIRTDLQAY RHN                                                   73

SEQ ID NO: 422         moltype = AA  length = 73
FEATURE                Location/Qualifiers
REGION                 1..73
                       note = artificial construct
source                 1..73
                       mol_type = protein
                       organism = synthetic construct
SEQUENCE: 422
MGSWWEFIWR LEAIEQRLWA LGGSEAELAA FEKEIAAFES ELQAYKGKGN PEVEVLRSRA  60
ADIRTDLQAY RHN                                                   73

SEQ ID NO: 423         moltype = AA  length = 73
FEATURE                Location/Qualifiers
REGION                 1..73
                       note = artificial construct
source                 1..73
                       mol_type = protein
                       organism = synthetic construct
SEQUENCE: 423
MGSWSEFYDR LWAIEERLFA LGGSEAELAA FEKEIAAFES ELQAYKGKGN PEVEYLRYYA  60
AEIREELQAY RHN                                                   73
```

```
SEQ ID NO: 424         moltype = AA  length = 73
FEATURE                Location/Qualifiers
REGION                 1..73
                       note = artificial construct
source                 1..73
                       mol_type = protein
                       organism = synthetic construct
SEQUENCE: 424
MGSWSEFEDR LWAIDQRLFA LGGSEAELAA FEKEIAAFES ELQAYKGKGN PEVEWLRAYA  60
ADIRWELQAY RHN                                                     73

SEQ ID NO: 425         moltype = AA  length = 73
FEATURE                Location/Qualifiers
REGION                 1..73
                       note = artificial construct
source                 1..73
                       mol_type = protein
                       organism = synthetic construct
SEQUENCE: 425
MGSWTEFWER LNAIDERLFA LGGSEAELAA FEKEIAAFES ELQAYKGKGN PEVEWLRLYA  60
AEIRSELQAY RHN                                                     73

SEQ ID NO: 426         moltype = AA  length = 73
FEATURE                Location/Qualifiers
REGION                 1..73
                       note = artificial construct
source                 1..73
                       mol_type = protein
                       organism = synthetic construct
SEQUENCE: 426
MGSWWEFEER LWAIDYRLHA LGGSEAELAA FEKEIAAFES ELQAYKGKGN PEVEMLRSWA  60
AEIRALLQAY RHN                                                     73

SEQ ID NO: 427         moltype = AA  length = 73
FEATURE                Location/Qualifiers
REGION                 1..73
                       note = artificial construct
source                 1..73
                       mol_type = protein
                       organism = synthetic construct
SEQUENCE: 427
MGSWWEFENR LWAIEERLEA LGGSEAELAA FEKEIAAFES ELQAYKGKGN PEVEMLRNYA  60
AEIRWELQAY RHN                                                     73

SEQ ID NO: 428         moltype = AA  length = 73
FEATURE                Location/Qualifiers
REGION                 1..73
                       note = artificial construct
source                 1..73
                       mol_type = protein
                       organism = synthetic construct
SEQUENCE: 428
MGSWVEFEER LWAIDERLGA LGGSEAELAA FEKEIAAFES ELQAYKGKGN PEVEWLRDWA  60
ADIRWWLQAY RHN                                                     73

SEQ ID NO: 429         moltype = AA  length = 73
FEATURE                Location/Qualifiers
REGION                 1..73
                       note = artificial construct
source                 1..73
                       mol_type = protein
                       organism = synthetic construct
SEQUENCE: 429
MGSWVEFEER LEAIEERLFA LGGSEAELAA FEKEIAAFES ELQAYKGKGN PEVEWLRDDA  60
ANIRHWLQAY RHN                                                     73

SEQ ID NO: 430         moltype = AA  length = 73
FEATURE                Location/Qualifiers
REGION                 1..73
                       note = artificial construct
source                 1..73
                       mol_type = protein
                       organism = synthetic construct
SEQUENCE: 430
MGSWMEFEER LWAIDSRLWA LGGSEAELAA FEKEIAAFES ELQAYKGKGN PEVEWLRSEA  60
AWIRMELQAY RHN                                                     73

SEQ ID NO: 431         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 431
MGSWSEFEHR LEAIESRLFA LGGSEAELAA FEKEIAAFES ELQAYKGKGN PEVEDLRSEA  60
AWIREQLQAY RHN                                                    73

SEQ ID NO: 432          moltype = AA  length = 73
FEATURE                 Location/Qualifiers
REGION                  1..73
                        note = artificial construct
source                  1..73
                        mol_type = protein
                        organism = synthetic construct
SEQUENCE: 432
MGSWFEFWER LDAIEWRLWA LGGSEAELAA FEKEIAAFES ELQAYKGKGN PEVEELRSTA  60
ADIRRYLQAY RHN                                                    73

SEQ ID NO: 433          moltype = AA  length = 73
FEATURE                 Location/Qualifiers
REGION                  1..73
                        note = artificial construct
source                  1..73
                        mol_type = protein
                        organism = synthetic construct
SEQUENCE: 433
MGSWFEFWGR LEAIESRLKA LGGSEAELAA FEKEIAAFES ELQAYKGKGN PEVEELREHA  60
AWIRAYLQAY RHN                                                    73

SEQ ID NO: 434          moltype = AA  length = 73
FEATURE                 Location/Qualifiers
REGION                  1..73
                        note = artificial construct
source                  1..73
                        mol_type = protein
                        organism = synthetic construct
SEQUENCE: 434
MGSWQEFTMR LDAIYNRLET LGGSEAELAA FEKEIAAFES ELQAYKGKGN PEVEWLRQSA  60
ANIRSELQAY RHN                                                    73

SEQ ID NO: 435          moltype = AA  length = 73
FEATURE                 Location/Qualifiers
REGION                  1..73
                        note = artificial construct
source                  1..73
                        mol_type = protein
                        organism = synthetic construct
SEQUENCE: 435
MGSWSEFNMR LDAIYERLTA LGGSEAELAA FEKEIAAFES ELQAYKGKGN PEVEWLRHSA  60
ARIRLELQAY RHN                                                    73

SEQ ID NO: 436          moltype = AA  length = 73
FEATURE                 Location/Qualifiers
REGION                  1..73
                        note = artificial construct
source                  1..73
                        mol_type = protein
                        organism = synthetic construct
SEQUENCE: 436
MGSWSEFNMR LDAIYERLTA LGGSEAELAA FEKEIAAFES ELQAYKGKGN PEVEWLRHSA  60
ALIRLELQAY RHN                                                    73

SEQ ID NO: 437          moltype = AA  length = 73
FEATURE                 Location/Qualifiers
REGION                  1..73
                        note = artificial construct
source                  1..73
                        mol_type = protein
                        organism = synthetic construct
SEQUENCE: 437
MGSWIEFNMR LDAIYERLVA LGGSEAELAA FEKEIAAFES ELQAYKGKGN PEVEWLRKVA  60
ANIRLELQAY RHN                                                    73

SEQ ID NO: 438          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 438
MGSWYEFHHR LDAIYERLLA LGGSEAELAA FEKEIAAFES ELQAYKGKGN PEVEWLRSSA  60
ANIRKELQAY RHN                                                     73

SEQ ID NO: 439          moltype = AA  length = 73
FEATURE                 Location/Qualifiers
REGION                  1..73
                        note = artificial construct
source                  1..73
                        mol_type = protein
                        organism = synthetic construct
SEQUENCE: 439
MGSWYEFAKR LDAIYERLVA LGGSEAELAA FEKEIAAFES ELQAYKGKGN PEVEWLRSSA  60
ANIREELQAY RHN                                                     73

SEQ ID NO: 440          moltype = AA  length = 73
FEATURE                 Location/Qualifiers
REGION                  1..73
                        note = artificial construct
source                  1..73
                        mol_type = protein
                        organism = synthetic construct
SEQUENCE: 440
MGSWTEFYVR LDAIYERLDA LGGSEAELAA FEKEIAAFES ELQAYKGKGN PEVEWLRMVA  60
ANIRTELQAY RHN                                                     73

SEQ ID NO: 441          moltype = AA  length = 73
FEATURE                 Location/Qualifiers
REGION                  1..73
                        note = artificial construct
source                  1..73
                        mol_type = protein
                        organism = synthetic construct
SEQUENCE: 441
MGSWVEFYTR LDAIYGRLDA LGGSEAELAA FEKEIAAFES ELQAYKGKGN PEVEWLRQVA  60
ANIRMELQAY RHN                                                     73

SEQ ID NO: 442          moltype = AA  length = 73
FEATURE                 Location/Qualifiers
REGION                  1..73
                        note = artificial construct
source                  1..73
                        mol_type = protein
                        organism = synthetic construct
SEQUENCE: 442
MGSWVEFHMR LDAIYERLDA LGGSEAELAA FEKEIAAFES ELQAYKGKGN PEVEWLRTAA  60
ANIRVELQAY RHN                                                     73

SEQ ID NO: 443          moltype = AA  length = 73
FEATURE                 Location/Qualifiers
REGION                  1..73
                        note = artificial construct
source                  1..73
                        mol_type = protein
                        organism = synthetic construct
SEQUENCE: 443
MGSWYEFAIR LDAIYERLHA LGGSEAELAA FEKEIAAFES ELQAYKGKGN PEVEYLRVWA  60
ANIRTELQAY RHN                                                     73

SEQ ID NO: 444          moltype = AA  length = 73
FEATURE                 Location/Qualifiers
REGION                  1..73
                        note = artificial construct
source                  1..73
                        mol_type = protein
                        organism = synthetic construct
SEQUENCE: 444
MGSWNEFVIR LDAIYERLLA LGGSEAELAA FEKEIAAFES ELQAYKGKGN PEVEYLRMAA  60
ANIRMELQAY RHN                                                     73

SEQ ID NO: 445          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 445
MGSWSEFYVR VDAIYARLSA LGGSEAELAA FEKEIAAFES ELQAYKGKGN PEVEKLRVWA  60
ANIRHELQAY RHN                                                     73

SEQ ID NO: 446           moltype = AA  length = 73
FEATURE                  Location/Qualifiers
REGION                   1..73
                         note = artificial construct
source                   1..73
                         mol_type = protein
                         organism = synthetic construct
SEQUENCE: 446
MGSWSEFHVR LDAIYARLDA LGGSEAELAA FEKEIAAFES ELQAYKGKGN PEVERLREWA  60
ANIRRELQAY RHN                                                     73

SEQ ID NO: 447           moltype = AA  length = 73
FEATURE                  Location/Qualifiers
REGION                   1..73
                         note = artificial construct
source                   1..73
                         mol_type = protein
                         organism = synthetic construct
SEQUENCE: 447
MGSWVEFHLR LDAIYGRLMA LGGSEAELAA FEKEIAAFES ELQAYKGKGN PEVENLRVWA  60
ANIRNELQAY RHN                                                     73

SEQ ID NO: 448           moltype = AA  length = 73
FEATURE                  Location/Qualifiers
REGION                   1..73
                         note = artificial construct
source                   1..73
                         mol_type = protein
                         organism = synthetic construct
SEQUENCE: 448
MGSWVEFEMR LDAIVGRLYA LGGSEAELAA FEKEIAAFES ELQAYKGKGN PEVEKLRRWA  60
ANIRSELQAY RHN                                                     73

SEQ ID NO: 449           moltype = AA  length = 73
FEATURE                  Location/Qualifiers
REGION                   1..73
                         note = artificial construct
source                   1..73
                         mol_type = protein
                         organism = synthetic construct
SEQUENCE: 449
MGSWVEFNIR LDAIYERLYA LGGSEAELAA FEKEIAAFES ELQAYKGKGN PEVEKLRHWA  60
ASIRRELQAY RHN                                                     73

SEQ ID NO: 450           moltype = AA  length = 73
FEATURE                  Location/Qualifiers
REGION                   1..73
                         note = artificial construct
source                   1..73
                         mol_type = protein
                         organism = synthetic construct
SEQUENCE: 450
MGSWHEFGVR LDAIYDRLMA LGGSEAELAA FEKEIAAFES ELQAYKGKGN PEVEFLRQAA  60
ANIRSELQAY RHN                                                     73

SEQ ID NO: 451           moltype = AA  length = 73
FEATURE                  Location/Qualifiers
REGION                   1..73
                         note = artificial construct
source                   1..73
                         mol_type = protein
                         organism = synthetic construct
SEQUENCE: 451
MGSWTEFNLR LDAIYDRLMA LGGSEAELAA FEKEIAAFES ELQAYKGKGN PEVEWLRASA  60
AAIRVELQAY RHN                                                     73

SEQ ID NO: 452           moltype = AA  length = 73
FEATURE                  Location/Qualifiers
REGION                   1..73
                         note = artificial construct
source                   1..73
                         mol_type = protein
                         organism = synthetic construct
SEQUENCE: 452
```

```
MGSWTEFNLR LDAIYGRLSA LGGSEAELAA FEKEIAAFES ELQAYKGKGN PEVEFLRAAA  60
ANIRVELQAY RHN                                                    73

SEQ ID NO: 453         moltype = AA  length = 73
FEATURE                Location/Qualifiers
REGION                 1..73
                       note = artificial construct
source                 1..73
                       mol_type = protein
                       organism = synthetic construct
SEQUENCE: 453
MGSWVEFNWR LDAIYDRLVA LGGSEAELAA FEKEIAAFES ELQAYKGKGN PEVEWLRVSA  60
AKIRGELQAY RHN                                                    73

SEQ ID NO: 454         moltype = AA  length = 73
FEATURE                Location/Qualifiers
REGION                 1..73
                       note = artificial construct
source                 1..73
                       mol_type = protein
                       organism = synthetic construct
SEQUENCE: 454
MGSWNEFAWR LDAIYSRLAA LGGSEAELAA FEKEIAAFES ELQAYKGKGN PEVEWLRVAA  60
ANIRYELQAY RHN                                                    73

SEQ ID NO: 455         moltype = AA  length = 73
FEATURE                Location/Qualifiers
REGION                 1..73
                       note = artificial construct
source                 1..73
                       mol_type = protein
                       organism = synthetic construct
SEQUENCE: 455
MGSWTEFAWR LDAIYDRLLA LGGSEAELAA FEKEIAAFES ELQAYKGKGN PEVEWLRHVA  60
ANIRRELQAY RHN                                                    73

SEQ ID NO: 456         moltype = AA  length = 73
FEATURE                Location/Qualifiers
REGION                 1..73
                       note = artificial construct
source                 1..73
                       mol_type = protein
                       organism = synthetic construct
SEQUENCE: 456
MGSWVEFSIR LDAIYTRLVA LGGSEAELAA FEKEIAAFES ELQAYKGKGN PEVEMLRKGA  60
ANIRKELQAY RHN                                                    73

SEQ ID NO: 457         moltype = AA  length = 73
FEATURE                Location/Qualifiers
REGION                 1..73
                       note = artificial construct
source                 1..73
                       mol_type = protein
                       organism = synthetic construct
SEQUENCE: 457
MGSWVEFYIR LDAIYVRLMA LGGSEAELAA FEKEIAAFES ELQAYKGKGN PEVEKLRSYA  60
ANIRQELQAY RHN                                                    73

SEQ ID NO: 458         moltype = AA  length = 73
FEATURE                Location/Qualifiers
REGION                 1..73
                       note = artificial construct
source                 1..73
                       mol_type = protein
                       organism = synthetic construct
SEQUENCE: 458
MGSWYEFSMR LDAIYDRLMA LGGSEAELAA FEKEIAAFES ELQAYKGKGN PEVEQLRGYA  60
ANIRNELQAY RHN                                                    73

SEQ ID NO: 459         moltype = AA  length = 73
FEATURE                Location/Qualifiers
REGION                 1..73
                       note = artificial construct
source                 1..73
                       mol_type = protein
                       organism = synthetic construct
SEQUENCE: 459
MGSWVEFIYR LDAIYDRLEA LGGSEAELAA FEKEIAAFES ELQAYKGKGN PEVEVLRRYA  60
ANIRNELQAY RHN                                                    73
```

```
SEQ ID NO: 460         moltype = AA  length = 73
FEATURE                Location/Qualifiers
REGION                 1..73
                       note = artificial construct
source                 1..73
                       mol_type = protein
                       organism = synthetic construct
SEQUENCE: 460
MGSWIEFEVR LDAIYNRLAA LGGSEAELAA FEKEIAAFES ELQAYKGKGN PEVERLRRYA  60
ANIRHELQAY RHN                                                     73

SEQ ID NO: 461         moltype = AA  length = 73
FEATURE                Location/Qualifiers
REGION                 1..73
                       note = artificial construct
source                 1..73
                       mol_type = protein
                       organism = synthetic construct
SEQUENCE: 461
MGSWFEFYDR LDAIYMRLIA LGGSEAELAA FEKEIAAFES ELQAYKGKGN PEVEVLRRYA  60
ANIRAELQAY RHN                                                     73

SEQ ID NO: 462         moltype = AA  length = 73
FEATURE                Location/Qualifiers
REGION                 1..73
                       note = artificial construct
source                 1..73
                       mol_type = protein
                       organism = synthetic construct
SEQUENCE: 462
MGSWFEFYMR LDAIYDRLTA LGGSEAELAA FEKEIAAFES ELQAYKGKGN PEVERLRTFA  60
ANIRKELQAY RHN                                                     73

SEQ ID NO: 463         moltype = AA  length = 73
FEATURE                Location/Qualifiers
REGION                 1..73
                       note = artificial construct
source                 1..73
                       mol_type = protein
                       organism = synthetic construct
SEQUENCE: 463
MGSWYEFDYR LDAIYDRLAA LGGSEAELAA FEKEIAAFES ELQAYKGKGN PEVERLRKWA  60
ANIREELQAY RHN                                                     73

SEQ ID NO: 464         moltype = AA  length = 73
FEATURE                Location/Qualifiers
REGION                 1..73
                       note = artificial construct
source                 1..73
                       mol_type = protein
                       organism = synthetic construct
SEQUENCE: 464
MGSWSEFYLR LDAIYDRLDA LGGSEAELAA FEKEIAAFES ELQAYKGKGN PEVEWLRKTA  60
ANIREELQAY RHN                                                     73

SEQ ID NO: 465         moltype = AA  length = 73
FEATURE                Location/Qualifiers
REGION                 1..73
                       note = artificial construct
source                 1..73
                       mol_type = protein
                       organism = synthetic construct
SEQUENCE: 465
MGSWFEFYER LDAINWRLFA LGGSEAELAA FEKEIAAFES ELQAYKGKGN PEVEALRGEA  60
AAIREDLQAY RHN                                                     73

SEQ ID NO: 466         moltype = AA  length = 73
FEATURE                Location/Qualifiers
REGION                 1..73
                       note = artificial construct
source                 1..73
                       mol_type = protein
                       organism = synthetic construct
SEQUENCE: 466
MGSWNEFEDR LDAIWWRLFA LGGSEAELAA FEKEIAAFES ELQAYKGKGN PEVEALRVEA  60
AFIRTMLQAY RHN                                                     73

SEQ ID NO: 467         moltype = AA  length = 73
```

```
FEATURE                Location/Qualifiers
REGION                 1..73
                       note = artificial construct
source                 1..73
                       mol_type = protein
                       organism = synthetic construct
SEQUENCE: 467
MGSWFYFKDD LADINYMLEA LGGSEAELAM FEDDIAGFEL TLLKYKGKGN PEVEALRKEA  60
AAIRDELQAY RHN                                                    73

SEQ ID NO: 468         moltype = AA  length = 73
FEATURE                Location/Qualifiers
REGION                 1..73
                       note = artificial construct
source                 1..73
                       mol_type = protein
                       organism = synthetic construct
SEQUENCE: 468
MGSWHFFKDD LAWIKNELEA LGGSEAELAM FEDDIAMFET MLQSYKGKGN PEVEALRKEA  60
AAIRDELQAY RHN                                                    73

SEQ ID NO: 469         moltype = AA  length = 73
FEATURE                Location/Qualifiers
REGION                 1..73
                       note = artificial construct
source                 1..73
                       mol_type = protein
                       organism = synthetic construct
SEQUENCE: 469
MGSWHWFKTD LADIKEELEA LGGSEAELAM FEDDIAEFEE FLQMYKGKGN PEVEALRKEA  60
AAIRDELQAY RHN                                                    73

SEQ ID NO: 470         moltype = AA  length = 73
FEATURE                Location/Qualifiers
REGION                 1..73
                       note = artificial construct
source                 1..73
                       mol_type = protein
                       organism = synthetic construct
SEQUENCE: 470
MGSWWLFKDD LAEIKYWLEA LGGSEAELAF FEDDIAEFER GLQIYKGKGN PEVEALRKEA  60
AAIRDELQAY RHN                                                    73

SEQ ID NO: 471         moltype = AA  length = 73
FEATURE                Location/Qualifiers
REGION                 1..73
                       note = artificial construct
source                 1..73
                       mol_type = protein
                       organism = synthetic construct
SEQUENCE: 471
MGSWYEFKDD LAEIKEWLEA LGGSEAELAF FELDIADFEW LLQLYKGKGN PEVEALRKEA  60
AAIRDELQAY RHN                                                    73

SEQ ID NO: 472         moltype = AA  length = 73
FEATURE                Location/Qualifiers
REGION                 1..73
                       note = artificial construct
source                 1..73
                       mol_type = protein
                       organism = synthetic construct
SEQUENCE: 472
MGSWQWFKDD LAYIKETLEA LGGSEAELAL FEDMIADFEF ELQWYKGKGN PEVEALRKEA  60
AAIRDELQAY RHN                                                    73

SEQ ID NO: 473         moltype = AA  length = 73
FEATURE                Location/Qualifiers
REGION                 1..73
                       note = artificial construct
source                 1..73
                       mol_type = protein
                       organism = synthetic construct
SEQUENCE: 473
MGSWILFKDD LAWIKETLEA LGGSEAELAF FEDNIADFEE QLQGYKGKGN PEVEALRKEA  60
AAIRDELQAY RHN                                                    73

SEQ ID NO: 474         moltype = AA  length = 73
FEATURE                Location/Qualifiers
REGION                 1..73
```

```
                        note = artificial construct
source                  1..73
                        mol_type = protein
                        organism = synthetic construct
SEQUENCE: 474
MGSWIVFKDD LADIKRWLEA LGGSEAELAM FEDEIADFEW QLQDYKGKGN PEVEALRKEA  60
AAIRDELQAY RHN                                                    73

SEQ ID NO: 475          moltype = AA  length = 73
FEATURE                 Location/Qualifiers
REGION                  1..73
                        note = artificial construct
source                  1..73
                        mol_type = protein
                        organism = synthetic construct
SEQUENCE: 475
MGSWGHFKQD LAWIKDTLEA LGGSEAELAF FEDDIAMFEM ELQDYKGKGN PEVEALRKEA  60
AAIRDELQAY RHN                                                    73

SEQ ID NO: 476          moltype = AA  length = 73
FEATURE                 Location/Qualifiers
REGION                  1..73
                        note = artificial construct
source                  1..73
                        mol_type = protein
                        organism = synthetic construct
SEQUENCE: 476
MGSWGYFKDD LAWIKGELEA LGGSEAELAE FEWFIAVFEE DLQVYKGKGN PEVEALRKEA  60
AAIRDELQAY RHN                                                    73

SEQ ID NO: 477          moltype = AA  length = 73
FEATURE                 Location/Qualifiers
REGION                  1..73
                        note = artificial construct
source                  1..73
                        mol_type = protein
                        organism = synthetic construct
SEQUENCE: 477
MGSWYWFKDD LAEIKGLLEA LGGSEAELAE FEDEIAVFEQ ELQEYKGKGN PEVEALRKEA  60
AAIRDELQAY RHN                                                    73

SEQ ID NO: 478          moltype = AA  length = 73
FEATURE                 Location/Qualifiers
REGION                  1..73
                        note = artificial construct
source                  1..73
                        mol_type = protein
                        organism = synthetic construct
SEQUENCE: 478
MGSWMFFKED LADIKWALEA LGGSEAELAF FEEEIALFEQ HLQQYKGKGN PEVEALRKEA  60
AAIRDELQAY RHN                                                    73

SEQ ID NO: 479          moltype = AA  length = 73
FEATURE                 Location/Qualifiers
REGION                  1..73
                        note = artificial construct
source                  1..73
                        mol_type = protein
                        organism = synthetic construct
SEQUENCE: 479
MGSWTFFKED LAGIKWELEA LGGSEAELAW FEDEIALFEE ELQEYKGKGN PEVEALRKEA  60
AAIRDELQAY RHN                                                    73

SEQ ID NO: 480          moltype = AA  length = 73
FEATURE                 Location/Qualifiers
REGION                  1..73
                        note = artificial construct
source                  1..73
                        mol_type = protein
                        organism = synthetic construct
SEQUENCE: 480
MGSWVFFKDD LADIKDELEA LGGSEAELAF FEIAIALFEW ELQEYKGKGN PEVEALRKEA  60
AAIRDELQAY RHN                                                    73

SEQ ID NO: 481          moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 481
MGSWTFFKND LAEIKDWLEA LGGSEAELAD FEWDIAEFEY SLQEYKGKGN PEVEALRKEA  60
AAIRDELQAY RHN                                                    73

SEQ ID NO: 482          moltype = AA  length = 73
FEATURE                 Location/Qualifiers
REGION                  1..73
                        note = artificial construct
source                  1..73
                        mol_type = protein
                        organism = synthetic construct
SEQUENCE: 482
MGSWTYFKDD LADIKQWLEA LGGSEAELAF FEIEIAEFEE ELQEYKGKGN PEVEALRKEA  60
AAIRDELQAY RHN                                                    73

SEQ ID NO: 483          moltype = AA  length = 73
FEATURE                 Location/Qualifiers
REGION                  1..73
                        note = artificial construct
source                  1..73
                        mol_type = protein
                        organism = synthetic construct
SEQUENCE: 483
MGSWTVFKYD LADIKWWLEA LGGSEAELAD FEEEIAEFEE ELQEYKGKGN PEVEALRKEA  60
AAIRDELQAY RHN                                                    73

SEQ ID NO: 484          moltype = AA  length = 73
FEATURE                 Location/Qualifiers
REGION                  1..73
                        note = artificial construct
source                  1..73
                        mol_type = protein
                        organism = synthetic construct
SEQUENCE: 484
MGSWYWFKQD LAHIKSMLEA LGGSEAELAW FEEDIADFES ELQEYKGKGN PEVEALRKEA  60
AAIRDELQAY RHN                                                    73

SEQ ID NO: 485          moltype = AA  length = 73
FEATURE                 Location/Qualifiers
REGION                  1..73
                        note = artificial construct
source                  1..73
                        mol_type = protein
                        organism = synthetic construct
SEQUENCE: 485
MGSWTFFKWD LADIKANLEA LGGSEAELAW FEEDLAGFEA ELQEYKGKGN PEVEALRKEA  60
AAIRDELQAY RHN                                                    73

SEQ ID NO: 486          moltype = AA  length = 73
FEATURE                 Location/Qualifiers
REGION                  1..73
                        note = artificial construct
source                  1..73
                        mol_type = protein
                        organism = synthetic construct
SEQUENCE: 486
MGSWSFFKEE LANIQVYLEA LGGSEAELAW FEEDIADFEE DLQHYKGKGN PEVEALRKEA  60
AAIRDELQAY RHN                                                    73

SEQ ID NO: 487          moltype = AA  length = 73
FEATURE                 Location/Qualifiers
REGION                  1..73
                        note = artificial construct
source                  1..73
                        mol_type = protein
                        organism = synthetic construct
SEQUENCE: 487
MGSWEFFKYE LADIKDELEA LGGSEAELAW FEEDIATFEE WLQGYKGKGN PEVEALRKEA  60
AAIRDELQAY RHN                                                    73

SEQ ID NO: 488          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 488
MGSWQTFKDE LAHIKWELEA LGGSEAELAW FEWDIANFEE ELQEYKGKGN PEVEALRKEA  60
AAIRDELQAY RHN                                                     73

SEQ ID NO: 489         moltype = AA  length = 73
FEATURE                Location/Qualifiers
REGION                 1..73
                       note = artificial construct
source                 1..73
                       mol_type = protein
                       organism = synthetic construct
SEQUENCE: 489
MGSWYWFKEE LAFIKWELEA LGGSEAELAL FEEDIAYFEE MLQEYKGKGN PEVEALRKEA  60
AAIRDELQAY RHN                                                     73

SEQ ID NO: 490         moltype = AA  length = 73
FEATURE                Location/Qualifiers
REGION                 1..73
                       note = artificial construct
source                 1..73
                       mol_type = protein
                       organism = synthetic construct
SEQUENCE: 490
MGSWNSFKDE LAEIKAELEA LGGSEAELAF FEEDIAWFEE HLQQYKGKGN PEVEALRKEA  60
AAIRDELQAY RHN                                                     73

SEQ ID NO: 491         moltype = AA  length = 73
FEATURE                Location/Qualifiers
REGION                 1..73
                       note = artificial construct
source                 1..73
                       mol_type = protein
                       organism = synthetic construct
SEQUENCE: 491
MGSWDLFKWE LAEIKLGLEA LGGSEAELAE FEYDIAWFEE DLQDYKGKGN PEVEALRKEA  60
AAIRDELQAY RHN                                                     73

SEQ ID NO: 492         moltype = AA  length = 73
FEATURE                Location/Qualifiers
REGION                 1..73
                       note = artificial construct
source                 1..73
                       mol_type = protein
                       organism = synthetic construct
SEQUENCE: 492
MGSWIFFKQD LAEIKLNLEA LGGSEAELAW FEDDIAWFES HLQDYKGKGN PEVEALRKEA  60
AAIRDELQAY RHN                                                     73

SEQ ID NO: 493         moltype = AA  length = 73
FEATURE                Location/Qualifiers
REGION                 1..73
                       note = artificial construct
source                 1..73
                       mol_type = protein
                       organism = synthetic construct
SEQUENCE: 493
MGSWHLFKWT LAEIKYELEA LGGSEAELAW FEDDIATFEE ELQWYKGKGN PEVEALRKEA  60
AAIRDELQAY RHN                                                     73

SEQ ID NO: 494         moltype = AA  length = 73
FEATURE                Location/Qualifiers
REGION                 1..73
                       note = artificial construct
source                 1..73
                       mol_type = protein
                       organism = synthetic construct
SEQUENCE: 494
MGSWVTFKDE LADIKDFLEA LGGSEAELAF FEVDIAEFEA ELQFYKGKGN PEVEALRKEA  60
AAIRDELQAY RHN                                                     73

SEQ ID NO: 495         moltype = AA  length = 73
FEATURE                Location/Qualifiers
REGION                 1..73
                       note = artificial construct
source                 1..73
                       mol_type = protein
                       organism = synthetic construct
SEQUENCE: 495
MGSWVYFKDE LADIKDFLEA LGGSEAELAE FEEDIATFEY DLQWYKGKGN PEVEALRKEA  60
```

```
AAIRDELQAY RHN                                                    73

SEQ ID NO: 496          moltype = AA  length = 73
FEATURE                 Location/Qualifiers
REGION                  1..73
                        note = artificial construct
source                  1..73
                        mol_type = protein
                        organism = synthetic construct
SEQUENCE: 496
MGSWETFKYE LAEIKDYLEA LGGSEAELAW FEDDIAEFEF ELQYYKGKGN PEVEALRKEA  60
AAIRDELQAY RHN                                                    73

SEQ ID NO: 497          moltype = AA  length = 73
FEATURE                 Location/Qualifiers
REGION                  1..73
                        note = artificial construct
source                  1..73
                        mol_type = protein
                        organism = synthetic construct
SEQUENCE: 497
MGSWNTFKYE LAEIKHFLEA LGGSEAELAM FEDDIAMFEW ELQEYKGKGN PEVEALRKEA  60
AAIRDELQAY RHN                                                    73

SEQ ID NO: 498          moltype = AA  length = 73
FEATURE                 Location/Qualifiers
REGION                  1..73
                        note = artificial construct
source                  1..73
                        mol_type = protein
                        organism = synthetic construct
SEQUENCE: 498
MGSWYVFKDE LAEIKQFLEA LGGSEAELAW FEDDIAEFET QLQHYKGKGN PEVEALRKEA  60
AAIRDELQAY RHN                                                    73

SEQ ID NO: 499          moltype = AA  length = 73
FEATURE                 Location/Qualifiers
REGION                  1..73
                        note = artificial construct
source                  1..73
                        mol_type = protein
                        organism = synthetic construct
SEQUENCE: 499
MGSWIFFKEQ LAIIKWELEA LGGSEAELAW FEDDIAAFED DLQFYKGQGN PEVEALRKEA  60
AAIRDELQAY RHN                                                    73

SEQ ID NO: 500          moltype = AA  length = 73
FEATURE                 Location/Qualifiers
REGION                  1..73
                        note = artificial construct
source                  1..73
                        mol_type = protein
                        organism = synthetic construct
SEQUENCE: 500
MGSWEFFKEV LAEIKYDLEA LGGSEAELAW FETDIAGFEI DLQVYKGKGN PEVEALRKEA  60
AAIRDELQAY RHN                                                    73

SEQ ID NO: 501          moltype = AA  length = 73
FEATURE                 Location/Qualifiers
REGION                  1..73
                        note = artificial construct
source                  1..73
                        mol_type = protein
                        organism = synthetic construct
SEQUENCE: 501
MGSWVFFKED LATIKNDLEA LGGSEAELAW FEMMIADFEA DLQYYKGKGN PEVEALRKEA  60
AAIRDELQAY RHN                                                    73

SEQ ID NO: 502          moltype = AA  length = 73
FEATURE                 Location/Qualifiers
REGION                  1..73
                        note = artificial construct
source                  1..73
                        mol_type = protein
                        organism = synthetic construct
SEQUENCE: 502
MGSWEEFKED LAEIKVWLEA LGGSEAELAW FEMGIADFED GLQFYKGKGN PEVEALRKEA  60
AAIRDELQAY RHN                                                    73
```

```
SEQ ID NO: 503         moltype = AA  length = 73
FEATURE                Location/Qualifiers
REGION                 1..73
                       note = artificial construct
source                 1..73
                       mol_type = protein
                       organism = synthetic construct
SEQUENCE: 503
MGSWHWFKED LANIKDWLEA LGGSEAELAW FEDNIADFEG DLQVYKGKGN PEVEALRKEA  60
AAIRDELQAY RHN                                                      73

SEQ ID NO: 504         moltype = AA  length = 73
FEATURE                Location/Qualifiers
REGION                 1..73
                       note = artificial construct
source                 1..73
                       mol_type = protein
                       organism = synthetic construct
SEQUENCE: 504
MGSWFWFKED LAFIKEDLEA LGGSEAELAW FEDGIAFFEW DLQDYKGKGN PEVEALRKEA  60
AAIRDELQAY RHN                                                      73

SEQ ID NO: 505         moltype = AA  length = 73
FEATURE                Location/Qualifiers
REGION                 1..73
                       note = artificial construct
source                 1..73
                       mol_type = protein
                       organism = synthetic construct
SEQUENCE: 505
MGSWQWFKED LAEIKHDLEA LGGSEAELAW FEDFIAQFEF DLQWYKGKGN PEVEALRKEA  60
AAIRDELQAY RHN                                                      73

SEQ ID NO: 506         moltype = AA  length = 73
FEATURE                Location/Qualifiers
REGION                 1..73
                       note = artificial construct
source                 1..73
                       mol_type = protein
                       organism = synthetic construct
SEQUENCE: 506
MGSWHWFKED LAIIKQDLEA LGGSEAELAT FEQWIAEFEW DLQEYKGKGN PEVEALRKEA  60
AAIRDELQAY RHN                                                      73

SEQ ID NO: 507         moltype = AA  length = 73
FEATURE                Location/Qualifiers
REGION                 1..73
                       note = artificial construct
source                 1..73
                       mol_type = protein
                       organism = synthetic construct
SEQUENCE: 507
MGSWNWFKED LAIIKMDLEA LGGSEAELAW FEHNIAGFEF ELQGYKGKGN PEVEALRKEA  60
AAIRDELQAY RHN                                                      73

SEQ ID NO: 508         moltype = AA  length = 73
FEATURE                Location/Qualifiers
REGION                 1..73
                       note = artificial construct
source                 1..73
                       mol_type = protein
                       organism = synthetic construct
SEQUENCE: 508
MGSWSWFKED LAEIKMELEA LGGSEAELAY FEWYIAEFEF QLQHYKGKGN PEVEALRKEA  60
AAIRDELQAY RHN                                                      73

SEQ ID NO: 509         moltype = AA  length = 73
FEATURE                Location/Qualifiers
REGION                 1..73
                       note = artificial construct
source                 1..73
                       mol_type = protein
                       organism = synthetic construct
SEQUENCE: 509
MGSWSWFKQD LADIKIQLEA LGGSEAELAW FEWDIAEFEF ELQDYKGKGN PEVEALRKEA  60
AAIRDELQAY RHN                                                      73

SEQ ID NO: 510         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 510
MGSWSWFKED LADIKFELEA LGGSEAELAW FELDIADFEQ ALQQYKGKGN PEVEALRKEA  60
AAIRDELQAY RHN                                                    73

SEQ ID NO: 511          moltype = AA  length = 73
FEATURE                 Location/Qualifiers
REGION                  1..73
                        note = artificial construct
source                  1..73
                        mol_type = protein
                        organism = synthetic construct
SEQUENCE: 511
MGSWSWFKED LASIKAVLEA LGGSEAELAF FESDIAEFEQ ELQYYKGKGN PEVEALRKEA  60
AAIRDELQAY RHN                                                    73

SEQ ID NO: 512          moltype = AA  length = 73
FEATURE                 Location/Qualifiers
REGION                  1..73
                        note = artificial construct
source                  1..73
                        mol_type = protein
                        organism = synthetic construct
SEQUENCE: 512
MGSWWEFKED LAEIKWFLEA LGGSEAELAW FEHDIAKFEF ELQYYKGKGN PEVEALRKEA  60
AAIRDELQAY RHN                                                    73

SEQ ID NO: 513          moltype = AA  length = 73
FEATURE                 Location/Qualifiers
REGION                  1..73
                        note = artificial construct
source                  1..73
                        mol_type = protein
                        organism = synthetic construct
SEQUENCE: 513
MGSWEWFKSD LASIKWELEA LGGSEAELAW FEHDIAEFEE DLQWYKGKGN PEVEALRKEA  60
AAIRDELQAY RHN                                                    73

SEQ ID NO: 514          moltype = AA  length = 73
FEATURE                 Location/Qualifiers
REGION                  1..73
                        note = artificial construct
source                  1..73
                        mol_type = protein
                        organism = synthetic construct
SEQUENCE: 514
MGSWNEFKDD LAMIKMTLEA LGGSEAELAW FEHDIAEFED DLQWYKGKGN PEVEALRKEA  60
AAIRDELQAY RHN                                                    73

SEQ ID NO: 515          moltype = AA  length = 73
FEATURE                 Location/Qualifiers
REGION                  1..73
                        note = artificial construct
source                  1..73
                        mol_type = protein
                        organism = synthetic construct
SEQUENCE: 515
MGSWTFFKDD LAEIKWMLEA LGGSEAELAW FESDIAYFED ELQWYKGKGN PEVEALRKEA  60
AAIRDELQAY RHN                                                    73

SEQ ID NO: 516          moltype = AA  length = 73
FEATURE                 Location/Qualifiers
REGION                  1..73
                        note = artificial construct
source                  1..73
                        mol_type = protein
                        organism = synthetic construct
SEQUENCE: 516
MGSWSDFKDD LAEIKMILEA LGGSEAELAY FENDIAWFED DLQEYKGKGN PEVEALRKEA  60
AAIRDELQAY RHN                                                    73

SEQ ID NO: 517          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 517
MGSWSMFKDD LAEIKASLEA LGGSEAELAW FEDDIAWFED DLQHYKGKGN PEVEALRKEA  60
AAIRDELQAY RHN                                                    73

SEQ ID NO: 518          moltype = AA  length = 73
FEATURE                 Location/Qualifiers
REGION                  1..73
                        note = artificial construct
source                  1..73
                        mol_type = protein
                        organism = synthetic construct
SEQUENCE: 518
MGSWQYFKDD LAEIKMVLEA LGGSEAELAW FEADIAMFED DLQIYKGKGN PEVEALRKEA  60
AAIRDELQAY RHN                                                    73

SEQ ID NO: 519          moltype = AA  length = 73
FEATURE                 Location/Qualifiers
REGION                  1..73
                        note = artificial construct
source                  1..73
                        mol_type = protein
                        organism = synthetic construct
SEQUENCE: 519
MGSWSFFKDD LAEIKYFLEA LGGSEAELAM FEQTIAEFEY DLQDYKGKGN PEVEALRKEA  60
AAIRDELQAY RHN                                                    73

SEQ ID NO: 520          moltype = AA  length = 73
FEATURE                 Location/Qualifiers
REGION                  1..73
                        note = artificial construct
source                  1..73
                        mol_type = protein
                        organism = synthetic construct
SEQUENCE: 520
MGSWMEFKEE LAEIKYILEA LGGSEAELAW FEQSIADFEY DLQDYKGKGN PEVEALRKEA  60
AAIRDELQAY RHN                                                    73

SEQ ID NO: 521          moltype = AA  length = 73
FEATURE                 Location/Qualifiers
REGION                  1..73
                        note = artificial construct
source                  1..73
                        mol_type = protein
                        organism = synthetic construct
SEQUENCE: 521
MGSWAWFKED LAEIKVFLEA LGGSEAELAE FEVSIADFEY ELQDYKGKGN PEVEALRKEA  60
AAIRDELQAY RHN                                                    73

SEQ ID NO: 522          moltype = AA  length = 73
FEATURE                 Location/Qualifiers
REGION                  1..73
                        note = artificial construct
source                  1..73
                        mol_type = protein
                        organism = synthetic construct
SEQUENCE: 522
MGSWYEFKFD LAEIKEQLEA LGGSEAELAL FEDDIAFFEY DLQNYKGKGN PEVEALRKEA  60
AAIRDELQAY RHN                                                    73

SEQ ID NO: 523          moltype = AA  length = 73
FEATURE                 Location/Qualifiers
REGION                  1..73
                        note = artificial construct
source                  1..73
                        mol_type = protein
                        organism = synthetic construct
SEQUENCE: 523
MGSWYDFKYD LAEIKMDLEA LGGSEAELAQ FEFDIAFFEE ELQDYKGKGN PEVEALRKEA  60
AAIRDELQAY RHN                                                    73

SEQ ID NO: 524          moltype = AA  length = 73
FEATURE                 Location/Qualifiers
REGION                  1..73
                        note = artificial construct
source                  1..73
                        mol_type = protein
```

```
                          organism = synthetic construct
SEQUENCE: 524
MGSWYIFKED LAEIKEELEA LGGSEAELAY FEEEIALFEM ELQWYKGKGN PEVEALRKEA  60
AAIRDELQAY RHN                                                    73

SEQ ID NO: 525          moltype = AA  length = 73
FEATURE                 Location/Qualifiers
REGION                  1..73
                        note = artificial construct
source                  1..73
                        mol_type = protein
                        organism = synthetic construct
SEQUENCE: 525
MGSWVLFKEE LAYIKFELEA LGGSEAELAL FENVIAIFES NLQNYKGKGN PEVEALRKEA  60
AAIRDELQAY RHN                                                    73

SEQ ID NO: 526          moltype = AA  length = 73
FEATURE                 Location/Qualifiers
REGION                  1..73
                        note = artificial construct
source                  1..73
                        mol_type = protein
                        organism = synthetic construct
SEQUENCE: 526
MGSWQDFKED LAWIKYELEA LGGSEAELAF FEYDIAIFEN NLQHYKGKGN PEVEALRKEA  60
AAIRDELQAY RHN                                                    73

SEQ ID NO: 527          moltype = AA  length = 73
FEATURE                 Location/Qualifiers
REGION                  1..73
                        note = artificial construct
source                  1..73
                        mol_type = protein
                        organism = synthetic construct
SEQUENCE: 527
MGSWDHFKND LAWIKKHLEA LGGSEAELAE FEAVIAYFEL YLQGYKGKGN PEVEALRKEA  60
AAIRDELQAY RHN                                                    73

SEQ ID NO: 528          moltype = AA  length = 73
FEATURE                 Location/Qualifiers
REGION                  1..73
                        note = artificial construct
source                  1..73
                        mol_type = protein
                        organism = synthetic construct
SEQUENCE: 528
MGSWYDFKED LADIKWMLEA LGGSEAELAE FENVIAYFEN DLQEYKGKGN PEVEALRKEA  60
AAIRDELQAY RHN                                                    73

SEQ ID NO: 529          moltype = AA  length = 73
FEATURE                 Location/Qualifiers
REGION                  1..73
                        note = artificial construct
source                  1..73
                        mol_type = protein
                        organism = synthetic construct
SEQUENCE: 529
MGSWYMFKEE LADIKWYLEA LGGSEAELAW FEDDIAGFEW DLQAYKGKGN PEVEALRKEA  60
AAIRDELQAY RHN                                                    73

SEQ ID NO: 530          moltype = AA  length = 73
FEATURE                 Location/Qualifiers
REGION                  1..73
                        note = artificial construct
source                  1..73
                        mol_type = protein
                        organism = synthetic construct
SEQUENCE: 530
MGSWYYFKDE LADIKWDLEA LGGSEAELAW FEMLIAQFEL DLQWYKGKGN PEVEALRKEA  60
AAIRDELQAY RHN                                                    73

SEQ ID NO: 531          moltype = AA  length = 73
FEATURE                 Location/Qualifiers
REGION                  1..73
                        note = artificial construct
source                  1..73
                        mol_type = protein
                        organism = synthetic construct
SEQUENCE: 531
```

```
MGSWMYFKDT LADIKWYLEA LGGSEAELAF FEDWIAEFED DLQVYKGKGN PEVEALRKEA  60
AAIRDELQAY RHN                                                     73

SEQ ID NO: 532         moltype = AA  length = 73
FEATURE                Location/Qualifiers
REGION                 1..73
                       note = artificial construct
source                 1..73
                       mol_type = protein
                       organism = synthetic construct
SEQUENCE: 532
MGSWYQFKHD LADIKYGLEA LGGSEAELAW FEDDIADFEL DLQYYKGKGN PEVEALRKEA  60
AAIRDELQAY RHN                                                     73

SEQ ID NO: 533         moltype = AA  length = 73
FEATURE                Location/Qualifiers
REGION                 1..73
                       note = artificial construct
source                 1..73
                       mol_type = protein
                       organism = synthetic construct
SEQUENCE: 533
MGSWYVFKDD LADIKYMLEA LGGSEAELAW FEWEIANFEF DLQYYKGKGN PEVEALRKEA  60
AAIRDELQAY RHN                                                     73

SEQ ID NO: 534         moltype = AA  length = 73
FEATURE                Location/Qualifiers
REGION                 1..73
                       note = artificial construct
source                 1..73
                       mol_type = protein
                       organism = synthetic construct
SEQUENCE: 534
MGSWNFFKYD LADIMAYLEA LGGSEAELAF FEDEIANFEH DLQKYKGKGN PEVEALRKEA  60
AAIRDELQAY RHN                                                     73

SEQ ID NO: 535         moltype = AA  length = 73
FEATURE                Location/Qualifiers
REGION                 1..73
                       note = artificial construct
source                 1..73
                       mol_type = protein
                       organism = synthetic construct
SEQUENCE: 535
MGSWHWFKIV LADIKDGLEA LGGSEAELAY FETTIADFEM DLQHYKGKGN PEVEALRKEA  60
AAIRDELQAY RHN                                                     73

SEQ ID NO: 536         moltype = AA  length = 73
FEATURE                Location/Qualifiers
REGION                 1..73
                       note = artificial construct
source                 1..73
                       mol_type = protein
                       organism = synthetic construct
SEQUENCE: 536
MGSWHWFKIV LADIKDGLEA LGGSEAELAY FETTIADFEM DLHHYKGKGN PEVEALRKEA  60
AAIRDELQAY RHN                                                     73

SEQ ID NO: 537         moltype = AA  length = 73
FEATURE                Location/Qualifiers
REGION                 1..73
                       note = artificial construct
source                 1..73
                       mol_type = protein
                       organism = synthetic construct
SEQUENCE: 537
MGSWFMFKEE LADIKDWLEA LGGSEAELAS FESYIAWFEQ DLQWYKGKGN PEVEALRKEA  60
AAIRDELQAY RHN                                                     73

SEQ ID NO: 538         moltype = AA  length = 73
FEATURE                Location/Qualifiers
REGION                 1..73
                       note = artificial construct
source                 1..73
                       mol_type = protein
                       organism = synthetic construct
SEQUENCE: 538
MGSWFMFKQE LAWIKEDLEA LGGSEAELAD FEWDIAEFEW DLQYYKGKGN PEVEALRKEA  60
AAIRDELQAY RHN                                                     73
```

```
SEQ ID NO: 539         moltype = AA  length = 73
FEATURE                Location/Qualifiers
REGION                 1..73
                       note = artificial construct
source                 1..73
                       mol_type = protein
                       organism = synthetic construct
SEQUENCE: 539
MGSWQIFKGE LAYIKQYLEA LGGSEAELAF FEFDIAEFEE DLQYYKGKGN PEVEALRKEA  60
AAIRDELQAY RHN                                                    73

SEQ ID NO: 540         moltype = AA  length = 73
FEATURE                Location/Qualifiers
REGION                 1..73
                       note = artificial construct
source                 1..73
                       mol_type = protein
                       organism = synthetic construct
SEQUENCE: 540
MGSWDFFKEE LAEIKHYLEA LGGSEAELAF FEFWIADFEQ DLQEYKGKGN PEVEALRKEA  60
AAIRDELQAY RHN                                                    73

SEQ ID NO: 541         moltype = AA  length = 73
FEATURE                Location/Qualifiers
REGION                 1..73
                       note = artificial construct
source                 1..73
                       mol_type = protein
                       organism = synthetic construct
SEQUENCE: 541
MGSWFNFKEE LAVIKFQLEA LGGSEAELAF FEWVIADFED DLQEYKGKGN PEVEALRKEA  60
AAIRDELQAY RHN                                                    73

SEQ ID NO: 542         moltype = AA  length = 73
FEATURE                Location/Qualifiers
REGION                 1..73
                       note = artificial construct
source                 1..73
                       mol_type = protein
                       organism = synthetic construct
SEQUENCE: 542
MGSWYQFKTE LAWIKDDLEA LGGSEAELAW FEWVIADFED DLQFYKGKGN PEVEALRKEA  60
AAIRDELQAY RHN                                                    73

SEQ ID NO: 543         moltype = AA  length = 73
FEATURE                Location/Qualifiers
REGION                 1..73
                       note = artificial construct
source                 1..73
                       mol_type = protein
                       organism = synthetic construct
SEQUENCE: 543
MGSWFEFKDY LADIKWDLEA LGGSEAELAI FEHDIAYFEH NLQQYKGKGN PEVEALRKEA  60
AAIRDELQAY RHN                                                    73

SEQ ID NO: 544         moltype = AA  length = 73
FEATURE                Location/Qualifiers
REGION                 1..73
                       note = artificial construct
source                 1..73
                       mol_type = protein
                       organism = synthetic construct
SEQUENCE: 544
MGSWVRFKDF LADIKMDLEA LGGSEAELAD FEYHIAEFEH NLQEYKGKGN PEVEALRKEA  60
AAIRDELQAY RHN                                                    73

SEQ ID NO: 545         moltype = AA  length = 73
FEATURE                Location/Qualifiers
REGION                 1..73
                       note = artificial construct
source                 1..73
                       mol_type = protein
                       organism = synthetic construct
SEQUENCE: 545
MGSWWLFKEQ LALIKYNLEA LGGSEAELAD FESWIAEFEH QLQEYKGKGN PEVEALRKEA  60
AAIRDELQAY RHN                                                    73

SEQ ID NO: 546         moltype = AA  length = 73
```

```
FEATURE                 Location/Qualifiers
REGION                  1..73
                        note = artificial construct
source                  1..73
                        mol_type = protein
                        organism = synthetic construct
SEQUENCE: 546
MGSWHVFKTE LADIKFYLEA LGGSEAELAM FELWIAEFEH ELQDYKGKGN PEVEALRKEA  60
AAIRDELQAY RHN                                                     73

SEQ ID NO: 547          moltype = AA  length = 73
FEATURE                 Location/Qualifiers
REGION                  1..73
                        note = artificial construct
source                  1..73
                        mol_type = protein
                        organism = synthetic construct
SEQUENCE: 547
MGSWIWFKDW LADIKDLLEA LGGSEAELAE FEYDIALFED QLQAYKGKGN PEVEALRKEA  60
AAIRDELQAY RHN                                                     73

SEQ ID NO: 548          moltype = AA  length = 73
FEATURE                 Location/Qualifiers
REGION                  1..73
                        note = artificial construct
source                  1..73
                        mol_type = protein
                        organism = synthetic construct
SEQUENCE: 548
MGSWGWFKHE LAFIKADLEA LGGSEAELAW FEEEIAEFEY ELQFYKGKGN PEVEALRKEA  60
AAIRDELQAY RHN                                                     73

SEQ ID NO: 549          moltype = AA  length = 73
FEATURE                 Location/Qualifiers
REGION                  1..73
                        note = artificial construct
source                  1..73
                        mol_type = protein
                        organism = synthetic construct
SEQUENCE: 549
MGSWTWFKDN LAWIKEDLEA LGGSEAELAW FELEIASFET ALQDYKGKGN PEVEALRKEA  60
AAIRDELQAY RHN                                                     73

SEQ ID NO: 550          moltype = AA  length = 73
FEATURE                 Location/Qualifiers
REGION                  1..73
                        note = artificial construct
source                  1..73
                        mol_type = protein
                        organism = synthetic construct
SEQUENCE: 550
MGSWTYFKND LAGIKEDLEA LGGSEAELAQ FEFEIAEFEW LLQDYKGKGN PEVEALRKEA  60
AAIRDELQAY RHN                                                     73

SEQ ID NO: 551          moltype = AA  length = 73
FEATURE                 Location/Qualifiers
REGION                  1..73
                        note = artificial construct
source                  1..73
                        mol_type = protein
                        organism = synthetic construct
SEQUENCE: 551
MGSWTWFKWD LADIKGDLEA LGGSEAELAF FEEEIAEFEW RLQDYKGKGN PEVEALRKEA  60
AAIRDELQAY RHN                                                     73

SEQ ID NO: 552          moltype = AA  length = 73
FEATURE                 Location/Qualifiers
REGION                  1..73
                        note = artificial construct
source                  1..73
                        mol_type = protein
                        organism = synthetic construct
SEQUENCE: 552
MGSWLYFKEY LADIKSDLEA LGGSEAELAW FEYEIADFEE QLQYYKGKGN PEVEALRKEA  60
AAIRDELQAY RHN                                                     73

SEQ ID NO: 553          moltype = AA  length = 73
FEATURE                 Location/Qualifiers
REGION                  1..73
```

```
                        note = artificial construct
source                  1..73
                        mol_type = protein
                        organism = synthetic construct
SEQUENCE: 553
MGSWHWFKEE LAEIKEDLVA LGGSEAELAW FEYDIAMFEL SLQNYKGKGN PEVEALRKEA  60
AAIRDELQAY RHN                                                     73

SEQ ID NO: 554          moltype = AA  length = 73
FEATURE                 Location/Qualifiers
REGION                  1..73
                        note = artificial construct
source                  1..73
                        mol_type = protein
                        organism = synthetic construct
SEQUENCE: 554
MGSWNDFKEE LAWIKFDLEA LGGSEAELAW FEEDIAMFEQ QLQAYKGKGN PEVEALRKEA  60
AAIRDELQAY RHN                                                     73

SEQ ID NO: 555          moltype = AA  length = 73
FEATURE                 Location/Qualifiers
REGION                  1..73
                        note = artificial construct
source                  1..73
                        mol_type = protein
                        organism = synthetic construct
SEQUENCE: 555
MGSWWDFKDW LAEIKHDLEA LGGSEAELAL FESEIADFEF GLQWYKGKGN PEVEALRKEA  60
AAIRDELQAY RHN                                                     73

SEQ ID NO: 556          moltype = AA  length = 73
FEATURE                 Location/Qualifiers
REGION                  1..73
                        note = artificial construct
source                  1..73
                        mol_type = protein
                        organism = synthetic construct
SEQUENCE: 556
MGSWDEFKED LAHIKTDLEA LGGSEAELAL FEDEIADFEM YLQHYKGKGN PEVEALRKEA  60
AAIRDELQAY RHN                                                     73

SEQ ID NO: 557          moltype = AA  length = 73
FEATURE                 Location/Qualifiers
REGION                  1..73
                        note = artificial construct
source                  1..73
                        mol_type = protein
                        organism = synthetic construct
SEQUENCE: 557
MGSWDFFKYD LANINEWLEA LGGSEAELAD FEYGIADFEL WLQDYKGKGN PEVEALRKEA  60
AAIRDELQAY RHN                                                     73

SEQ ID NO: 558          moltype = AA  length = 73
FEATURE                 Location/Qualifiers
REGION                  1..73
                        note = artificial construct
source                  1..73
                        mol_type = protein
                        organism = synthetic construct
SEQUENCE: 558
MGSWYQFKDD LAHIKHLLEA LGGSEAELAV FEYIIADFES FLQIYKGKGN PEVEALRKEA  60
AAIRDELQAY RHN                                                     73

SEQ ID NO: 559          moltype = AA  length = 73
FEATURE                 Location/Qualifiers
REGION                  1..73
                        note = artificial construct
source                  1..73
                        mol_type = protein
                        organism = synthetic construct
SEQUENCE: 559
MGSWAEFKHD LADIKRELEA LGGSEAELAW FELSIAFFED ELQHYKGKGN PEVEALRKEA  60
AAIRDELQAY RHN                                                     73

SEQ ID NO: 560          moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 560
MGSWVVFKQD LADINHQLEA LGGSEAELAW FEWEIADFEW ELQHYKGKGN PEVEALRKEA  60
AAIRDELQAY RHN                                                     73

SEQ ID NO: 561          moltype = AA  length = 73
FEATURE                 Location/Qualifiers
REGION                  1..73
                        note = artificial construct
source                  1..73
                        mol_type = protein
                        organism = synthetic construct
SEQUENCE: 561
MGSWFQFKEF LAMITHNLEA LGGSEAELAE FEHDIALFES ELQQYKGKGN PEVEALRKEA  60
AAIRDELQAY RHN                                                     73

SEQ ID NO: 562          moltype = AA  length = 73
FEATURE                 Location/Qualifiers
REGION                  1..73
                        note = artificial construct
source                  1..73
                        mol_type = protein
                        organism = synthetic construct
SEQUENCE: 562
MGSWHWFKED LAMITDVLEA LGGSEAELAA FESEIAVFEA DLQYYKGKGN PEVEALRKEA  60
AAIRDELQAY RHN                                                     73

SEQ ID NO: 563          moltype = AA  length = 73
FEATURE                 Location/Qualifiers
REGION                  1..73
                        note = artificial construct
source                  1..73
                        mol_type = protein
                        organism = synthetic construct
SEQUENCE: 563
MGSWSWFQWD LAGIKDHLEA LGGSEAELAE FESEIAYFED ELQWYKGKGN PEVEALRKEA  60
AAIRDELQAY RHN                                                     73

SEQ ID NO: 564          moltype = AA  length = 73
FEATURE                 Location/Qualifiers
REGION                  1..73
                        note = artificial construct
source                  1..73
                        mol_type = protein
                        organism = synthetic construct
SEQUENCE: 564
MGSWTEFKGE LAEIKWILEA LGGSEAELAF FEDEIAAFEW DLQKYKGKGN PEVEALRKEA  60
AAIRDELQAY RHN                                                     73

SEQ ID NO: 565          moltype = AA  length = 73
FEATURE                 Location/Qualifiers
REGION                  1..73
                        note = artificial construct
source                  1..73
                        mol_type = protein
                        organism = synthetic construct
SEQUENCE: 565
MGSWFEFKWT LALIKQELEA LGGSEAELAD FEQEIAEFEW WLQTYKGKGN PEVEALRKEA  60
AAIRDELQAY RHN                                                     73

SEQ ID NO: 566          moltype = AA  length = 73
FEATURE                 Location/Qualifiers
REGION                  1..73
                        note = artificial construct
source                  1..73
                        mol_type = protein
                        organism = synthetic construct
SEQUENCE: 566
MGSWAEFKQR LAAIKTRLEA LGGSEAELAA FMDEIMAFEW ELWAYKGKGN PEVEALMNEA  60
FAIDVELYAY RHN                                                     73

SEQ ID NO: 567          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 567
MGSWAEFKQR LAAIKTRLEA LGGSEAELAA FEWEIVAFFS ELFAYKGKGN PEVEALRDEA  60
IAIETELVAY RHN                                                     73

SEQ ID NO: 568         moltype = AA  length = 73
FEATURE                Location/Qualifiers
REGION                 1..73
                       note = artificial construct
source                 1..73
                       mol_type = protein
                       organism = synthetic construct
SEQUENCE: 568
MGSWWEFDHR LTAIDTRLQA LGGSEAELAE FESSIAEFEW WLQDYKGKGN PEVEALFAEA  60
EAIYVELDAY RHN                                                     73

SEQ ID NO: 569         moltype = AA  length = 73
FEATURE                Location/Qualifiers
REGION                 1..73
                       note = artificial construct
source                 1..73
                       mol_type = protein
                       organism = synthetic construct
SEQUENCE: 569
MGSWWEFQFR LYAIDQRLLA LGGSEAELAE FEQDIADFEW MLQDYKGKGN PEVEALMLEA  60
DAIEAELKAY RHN                                                     73

SEQ ID NO: 570         moltype = AA  length = 73
FEATURE                Location/Qualifiers
REGION                 1..73
                       note = artificial construct
source                 1..73
                       mol_type = protein
                       organism = synthetic construct
SEQUENCE: 570
MGSWYEFDHR LDAIYQRLWA LGGSEAELAE FEYGIAEFEE YLQDYKGKGN PEVEALISEA  60
WAIEWELSAY RHN                                                     73

SEQ ID NO: 571         moltype = AA  length = 73
FEATURE                Location/Qualifiers
REGION                 1..73
                       note = artificial construct
source                 1..73
                       mol_type = protein
                       organism = synthetic construct
SEQUENCE: 571
MGSWYEFDMR LDAIWERLTA LGGSEAELAD FEQYIAEFER QLQDYKGKGN PEVEALFDEA  60
WAIEDELYAY RHN                                                     73

SEQ ID NO: 572         moltype = AA  length = 73
FEATURE                Location/Qualifiers
REGION                 1..73
                       note = artificial construct
source                 1..73
                       mol_type = protein
                       organism = synthetic construct
SEQUENCE: 572
MGSWSEFDSR LDAIAYRLFA LGGSEAELAQ FEWIIADFEE DLQMYKGKGN PEVEALFSEA  60
YAIEIELNAY RHN                                                     73

SEQ ID NO: 573         moltype = AA  length = 73
FEATURE                Location/Qualifiers
REGION                 1..73
                       note = artificial construct
source                 1..73
                       mol_type = protein
                       organism = synthetic construct
SEQUENCE: 573
MGSWYEFDDR LDAIAYRLNA LGGSEAELAW FEWEIAEFEL DLQWYKGKGN PEVEALVWEA  60
DAIEWELEAY RHN                                                     73

SEQ ID NO: 574         moltype = AA  length = 73
FEATURE                Location/Qualifiers
REGION                 1..73
                       note = artificial construct
source                 1..73
                       mol_type = protein
                       organism = synthetic construct
SEQUENCE: 574
MGSWFEFDER LDAIGSRLTA LGGSEAELAS FEFYIADFEE WLQQYKGKGN PEVEALEWEA  60
```

```
FAIDEELGAY RHN                                                      73

SEQ ID NO: 575          moltype = AA  length = 73
FEATURE                 Location/Qualifiers
REGION                  1..73
                        note = artificial construct
source                  1..73
                        mol_type = protein
                        organism = synthetic construct
SEQUENCE: 575
MGSWEEFDQR LDAIDVRLYA LGGSEAELAE FEFDIAAFEE WLQLYKGKGN PEVEALNMEA  60
FAITDELCAY RHN                                                      73

SEQ ID NO: 576          moltype = AA  length = 73
FEATURE                 Location/Qualifiers
REGION                  1..73
                        note = artificial construct
source                  1..73
                        mol_type = protein
                        organism = synthetic construct
SEQUENCE: 576
MGSWEEFDVR LDAIFNRLWA LGGSEAELAE FEFDIAWFEM DLQEYKGKGN PEVEALFDEA  60
EAITNELVAY RHN                                                      73

SEQ ID NO: 577          moltype = AA  length = 73
FEATURE                 Location/Qualifiers
REGION                  1..73
                        note = artificial construct
source                  1..73
                        mol_type = protein
                        organism = synthetic construct
SEQUENCE: 577
MGSWEEFDKR LDAITRRLMA LGGSEAELAE FESTIAWFEW DLQEYKGKGN PEVEALDWEA  60
YAIDYELGAY RHN                                                      73

SEQ ID NO: 578          moltype = AA  length = 73
FEATURE                 Location/Qualifiers
REGION                  1..73
                        note = artificial construct
source                  1..73
                        mol_type = protein
                        organism = synthetic construct
SEQUENCE: 578
MGSWYEFDHR LEAIYDRLWA LGGSEAELAF FEFDIADFEW DLQSYKGKGN PEVEALFDEA  60
AAIGHELLAY RHN                                                      73

SEQ ID NO: 579          moltype = AA  length = 73
FEATURE                 Location/Qualifiers
REGION                  1..73
                        note = artificial construct
source                  1..73
                        mol_type = protein
                        organism = synthetic construct
SEQUENCE: 579
MGSWNEFDDR LLAIWGRLDA LGGSEAELAF FEEQIAGFED ELQWYKGKGN PEVEALDQEA  60
EAIEKELWAY RHN                                                      73

SEQ ID NO: 580          moltype = AA  length = 73
FEATURE                 Location/Qualifiers
REGION                  1..73
                        note = artificial construct
source                  1..73
                        mol_type = protein
                        organism = synthetic construct
SEQUENCE: 580
MGSWVEFDDR LDAIWERLDA LGGSEAELAW FEEQIAVFEH QLQDYKGKGN PEVEALNQEA  60
EAIDLELKAY RHN                                                      73

SEQ ID NO: 581          moltype = AA  length = 73
FEATURE                 Location/Qualifiers
REGION                  1..73
                        note = artificial construct
source                  1..73
                        mol_type = protein
                        organism = synthetic construct
SEQUENCE: 581
MGSWTEFDDR LFAIYWRLDA LGGSEAELAW FEEVIAEFEN DLQVYKGKGN PEVEALDDEA  60
HAISIELEAY RHN                                                      73
```

```
SEQ ID NO: 582         moltype = AA  length = 73
FEATURE                Location/Qualifiers
REGION                 1..73
                       note = artificial construct
source                 1..73
                       mol_type = protein
                       organism = synthetic construct
SEQUENCE: 582
MGSWSEFDQR LEAIWNRLDA LGGSEAELAD FEREIAYFEN QLQWYKGKGN PEVEALNNEA  60
FAIVDELGAY RHN                                                     73

SEQ ID NO: 583         moltype = AA  length = 73
FEATURE                Location/Qualifiers
REGION                 1..73
                       note = artificial construct
source                 1..73
                       mol_type = protein
                       organism = synthetic construct
SEQUENCE: 583
MGSWYEFDER LWAIWERLDA LGGSEAELAH FEWVIADFEN DLQWYKGKGN PEVEALEFEA  60
EAIVTELHAY RHN                                                     73

SEQ ID NO: 584         moltype = AA  length = 73
FEATURE                Location/Qualifiers
REGION                 1..73
                       note = artificial construct
source                 1..73
                       mol_type = protein
                       organism = synthetic construct
SEQUENCE: 584
MGSWMEFDYR LEAIWMRLIA LGGSEAELAD FESSIADFEH HLQSYKGKGN PEVEALEWEA  60
FAIGVELDAY RHN                                                     73

SEQ ID NO: 585         moltype = AA  length = 73
FEATURE                Location/Qualifiers
REGION                 1..73
                       note = artificial construct
source                 1..73
                       mol_type = protein
                       organism = synthetic construct
SEQUENCE: 585
MGSWYEFESR LEAIWWRLEA LGGSEAELAQ FEQYIADFEQ HLQWYKGKGN PEVEALDWEA  60
DAIWLELQAY RHN                                                     73

SEQ ID NO: 586         moltype = AA  length = 73
FEATURE                Location/Qualifiers
REGION                 1..73
                       note = artificial construct
source                 1..73
                       mol_type = protein
                       organism = synthetic construct
SEQUENCE: 586
MGSWEEFYMR LVAIHMRLRA LGGSEAELAV FENYIAEFEE YLQYYKGKGN PEVEALTIEA  60
DAIGTELGAY RHN                                                     73

SEQ ID NO: 587         moltype = AA  length = 73
FEATURE                Location/Qualifiers
REGION                 1..73
                       note = artificial construct
source                 1..73
                       mol_type = protein
                       organism = synthetic construct
SEQUENCE: 587
MGSWDEFYYR LVAITHRLHA LGGSEAELAW FEDDIAGFEW DLQTYKGKGN PEVEALYKEA  60
GAIGMELTAY RHN                                                     73

SEQ ID NO: 588         moltype = AA  length = 73
FEATURE                Location/Qualifiers
REGION                 1..73
                       note = artificial construct
source                 1..73
                       mol_type = protein
                       organism = synthetic construct
SEQUENCE: 588
MGSWEEFDTR LLAIFGRLGA LGGSEAELAL FEMLIAKFED DLQNYKGKGN PEVEALSEEA  60
FAIDHELGAY RHN                                                     73

SEQ ID NO: 589         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 589
MGSWREFDQR LWAIDWRLEA LGGSEAELAM FEWMIATFED DLQWYKGKGN PEVEALYREA  60
FAIDWELDAY RHN                                                     73

SEQ ID NO: 590          moltype = AA  length = 73
FEATURE                 Location/Qualifiers
REGION                  1..73
                        note = artificial construct
source                  1..73
                        mol_type = protein
                        organism = synthetic construct
SEQUENCE: 590
MGSWEEFHER LDAIDERLEA LGGSEAELAF FEDDIASFED WLQWYKGKGN PEVEALSREA  60
DAINFELEAY RHN                                                     73

SEQ ID NO: 591          moltype = AA  length = 73
FEATURE                 Location/Qualifiers
REGION                  1..73
                        note = artificial construct
source                  1..73
                        mol_type = protein
                        organism = synthetic construct
SEQUENCE: 591
MGSWNEFYER LEAIDRRLFA LGGSEAELAL FEWMIADFED DLQMYKGKGN PEVEALINEA  60
GAIGFELEAY RHN                                                     73

SEQ ID NO: 592          moltype = AA  length = 73
FEATURE                 Location/Qualifiers
REGION                  1..73
                        note = artificial construct
source                  1..73
                        mol_type = protein
                        organism = synthetic construct
SEQUENCE: 592
MGSWTEFTQR LEAIVDRLFA LGGSEAELAE FENSIADFEW DLQWYKGKGN PEVEALNREA  60
VAIDNELWAY RHN                                                     73

SEQ ID NO: 593          moltype = AA  length = 73
FEATURE                 Location/Qualifiers
REGION                  1..73
                        note = artificial construct
source                  1..73
                        mol_type = protein
                        organism = synthetic construct
SEQUENCE: 593
MGSWVEFIMR LDAIYERLDA LGGSEAELAE FEWHIADFED HLQWYKGKGN PEVEALFEEA  60
DAIWEELWAY RHN                                                     73

SEQ ID NO: 594          moltype = AA  length = 73
FEATURE                 Location/Qualifiers
REGION                  1..73
                        note = artificial construct
source                  1..73
                        mol_type = protein
                        organism = synthetic construct
SEQUENCE: 594
MGSWNEFLLR LDAIEHRLFA LGGSEAELAE FEWEIADFED DLQWYKGKGN PEVEALVEEA  60
EAIDVELVAY RHN                                                     73

SEQ ID NO: 595          moltype = AA  length = 73
FEATURE                 Location/Qualifiers
REGION                  1..73
                        note = artificial construct
source                  1..73
                        mol_type = protein
                        organism = synthetic construct
SEQUENCE: 595
MGSWYEFNMR LGAIDDRLQA LGGSEAELAW FEDMIAIFED DLQIYKGKGN PEVEALEQEA  60
AAIHQELWAY RHN                                                     73

SEQ ID NO: 596          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 596
MGSWEEFHWR LGAIDARLEA LGGSEAELAW FEDGIADFEA ILQDYKGKGN PEVEALDSEA  60
VAIHHELWAY RHN                                                     73

SEQ ID NO: 597          moltype = AA  length = 73
FEATURE                 Location/Qualifiers
REGION                  1..73
                        note = artificial construct
source                  1..73
                        mol_type = protein
                        organism = synthetic construct
SEQUENCE: 597
MGSWYEFYER LWAIDDRLWA LGGSEAELAE FEDSIATFEP SLQMYKGKGN PEVEALVAEA  60
WAIFDELAAY RHN                                                     73

SEQ ID NO: 598          moltype = AA  length = 73
FEATURE                 Location/Qualifiers
REGION                  1..73
                        note = artificial construct
source                  1..73
                        mol_type = protein
                        organism = synthetic construct
SEQUENCE: 598
MGSWFEFDQR LDAITFRLWA LGGSEAELAE FEDVIALFEY HLQDYKGKGN PEVEALEVEA  60
WAIFHELGAY RHN                                                     73

SEQ ID NO: 599          moltype = AA  length = 73
FEATURE                 Location/Qualifiers
REGION                  1..73
                        note = artificial construct
source                  1..73
                        mol_type = protein
                        organism = synthetic construct
SEQUENCE: 599
MGSWSEFWFR LDAIEDRLWA LGGSEAELAE FEDNIALFEY SLQHYKGKGN PEVEALVKEA  60
NAIDDELGAY RHN                                                     73

SEQ ID NO: 600          moltype = AA  length = 73
FEATURE                 Location/Qualifiers
REGION                  1..73
                        note = artificial construct
source                  1..73
                        mol_type = protein
                        organism = synthetic construct
SEQUENCE: 600
MGSWYEFWDR LTAIEHRLWA LGGSEAELAY FEDSIAHFEG SLQVYKGKGN PEVEALYKEA  60
EAIEWELEAY RHN                                                     73

SEQ ID NO: 601          moltype = AA  length = 73
FEATURE                 Location/Qualifiers
REGION                  1..73
                        note = artificial construct
source                  1..73
                        mol_type = protein
                        organism = synthetic construct
SEQUENCE: 601
MGSWYEFDDR LWAIFDRLFA LGGSEAELAF FEDSIAEFEE ELQHYKGKGN PEVEALYLEA  60
WAIENELGAY RHN                                                     73

SEQ ID NO: 602          moltype = AA  length = 73
FEATURE                 Location/Qualifiers
REGION                  1..73
                        note = artificial construct
source                  1..73
                        mol_type = protein
                        organism = synthetic construct
SEQUENCE: 602
MGSWNEFVER LSAIDHRLWA LGGSEAELAD FEQQIAEFEI HLQEYKGKGN PEVEALDFEA  60
DAIFDELLAY RHN                                                     73

SEQ ID NO: 603          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 603
MGSWSEFVDR LDAIFDRLWA LGGSEAELAW FEDTIAHFEW NLQEYKGKGN PEVEALNGEA  60
DAITDELHAY RHN                                                     73

SEQ ID NO: 604           moltype = AA  length = 73
FEATURE                  Location/Qualifiers
REGION                   1..73
                         note = artificial construct
source                   1..73
                         mol_type = protein
                         organism = synthetic construct
SEQUENCE: 604
MGSWAEFDSR LDAIAQRLFA LGGSEAELAH FEDFIAQFEY SLQEYKGKGN PEVEALSNEA  60
DAIFNELKAY RHN                                                     73

SEQ ID NO: 605           moltype = AA  length = 73
FEATURE                  Location/Qualifiers
REGION                   1..73
                         note = artificial construct
source                   1..73
                         mol_type = protein
                         organism = synthetic construct
SEQUENCE: 605
MGSWAEFDSR LIAIFDRLWA LGGSEAELAW FEDDIAQFEQ HLQAYKGKGN PEVEALRQEA  60
DAITFELKAY RHN                                                     73

SEQ ID NO: 606           moltype = AA  length = 73
FEATURE                  Location/Qualifiers
REGION                   1..73
                         note = artificial construct
source                   1..73
                         mol_type = protein
                         organism = synthetic construct
SEQUENCE: 606
MGSWTEFEER LEAIWDRLYA LGGSEAELAA FEWDIAYFED GLQEYKGKGN PEVEALFMEA  60
EAIIRELKAY RHN                                                     73

SEQ ID NO: 607           moltype = AA  length = 73
FEATURE                  Location/Qualifiers
REGION                   1..73
                         note = artificial construct
source                   1..73
                         mol_type = protein
                         organism = synthetic construct
SEQUENCE: 607
MGSWYEFEDR LAAIWDRLNA LGGSEAELAI FEWDIAWFEE GLQEYKGKGN PEVEALKHEA  60
SAIQTELFAY RHN                                                     73

SEQ ID NO: 608           moltype = AA  length = 73
FEATURE                  Location/Qualifiers
REGION                   1..73
                         note = artificial construct
source                   1..73
                         mol_type = protein
                         organism = synthetic construct
SEQUENCE: 608
MGSWLEFESR LWAIWDRLDA LGGSEAELAH FEQDIADFEM SLQEYKGKGN PEVEALIREA  60
EAIETELYAY RHN                                                     73

SEQ ID NO: 609           moltype = AA  length = 73
FEATURE                  Location/Qualifiers
REGION                   1..73
                         note = artificial construct
source                   1..73
                         mol_type = protein
                         organism = synthetic construct
SEQUENCE: 609
MGSWMEFEDR LIAIWARLDA LGGSEAELAW FEADIADFEE SLQEYKGKGN PEVEALIFEA  60
IAINKELMAY RHN                                                     73

SEQ ID NO: 610           moltype = AA  length = 73
FEATURE                  Location/Qualifiers
REGION                   1..73
                         note = artificial construct
source                   1..73
                         mol_type = protein
                         organism = synthetic construct
SEQUENCE: 610
```

```
MGSWFEFTIR LEAIQDRLDA LGGSEAELAW FEWDIAEFEE GLQFYKGKGN PEVEALHTEA  60
DAIMNELVAY RHN                                                     73

SEQ ID NO: 611         moltype = AA  length = 73
FEATURE                Location/Qualifiers
REGION                 1..73
                       note = artificial construct
source                 1..73
                       mol_type = protein
                       organism = synthetic construct
SEQUENCE: 611
MGSWYEFVSR LDAIEYRLWA LGGSEAELAW FEWDIADFEQ GLQFYKGKGN PEVEALAQEA  60
NAIGSELTAY RHN                                                     73

SEQ ID NO: 612         moltype = AA  length = 73
FEATURE                Location/Qualifiers
REGION                 1..73
                       note = artificial construct
source                 1..73
                       mol_type = protein
                       organism = synthetic construct
SEQUENCE: 612
MGSWEEFDYR LYAIQDRLYA LGGSEAELAF FEWEIADFEH MLQMYKGKGN PEVEALFQEA  60
DAIDAELHAY RHN                                                     73

SEQ ID NO: 613         moltype = AA  length = 73
FEATURE                Location/Qualifiers
REGION                 1..73
                       note = artificial construct
source                 1..73
                       mol_type = protein
                       organism = synthetic construct
SEQUENCE: 613
MGSWIEFFHR LDAIQDRLDA LGGSEAELAY FEWAIADFEH MLQLYKGKGN PEVEALQFEA  60
FAIEGELYAY RHN                                                     73

SEQ ID NO: 614         moltype = AA  length = 73
FEATURE                Location/Qualifiers
REGION                 1..73
                       note = artificial construct
source                 1..73
                       mol_type = protein
                       organism = synthetic construct
SEQUENCE: 614
MGSWYEFSSR LNAIDDRLWA LGGSEAELAY FETDIADFES LLQWYKGKGN PEVEALLNEA  60
DAIDYELYAY RHN                                                     73

SEQ ID NO: 615         moltype = AA  length = 73
FEATURE                Location/Qualifiers
REGION                 1..73
                       note = artificial construct
source                 1..73
                       mol_type = protein
                       organism = synthetic construct
SEQUENCE: 615
MGSWFEFEYR LDAIIDRLFA LGGSEAELAE FESMIANFEY SLQEYKGKGN PEVEALYFEA  60
DAIVDELTAY RHN                                                     73

SEQ ID NO: 616         moltype = AA  length = 73
FEATURE                Location/Qualifiers
REGION                 1..73
                       note = artificial construct
source                 1..73
                       mol_type = protein
                       organism = synthetic construct
SEQUENCE: 616
MGSWLEFEYR LDAIYDRLFA LGGSEAELAA FEQDIADFEK YLQYYKGKGN PEVEALWEEA  60
DAIMWELFAY RHN                                                     73

SEQ ID NO: 617         moltype = AA  length = 73
FEATURE                Location/Qualifiers
REGION                 1..73
                       note = artificial construct
source                 1..73
                       mol_type = protein
                       organism = synthetic construct
SEQUENCE: 617
MGSWHEFEER LMAIEDRLWA LGGSEAELAE FEQWIALFEY DLQEYKGKGN PEVEALGMEA  60
FAINNELSAY RHN                                                     73
```

```
SEQ ID NO: 618         moltype = AA  length = 73
FEATURE                Location/Qualifiers
REGION                 1..73
                       note = artificial construct
source                 1..73
                       mol_type = protein
                       organism = synthetic construct
SEQUENCE: 618
MGSWYEFEER LDAIEDRLIA LGGSEAELAI FEDIIAFFEQ DLQYYKGKGN PEVEALEMEA  60
EAISIELDAY RHN                                                    73

SEQ ID NO: 619         moltype = AA  length = 73
FEATURE                Location/Qualifiers
REGION                 1..73
                       note = artificial construct
source                 1..73
                       mol_type = protein
                       organism = synthetic construct
SEQUENCE: 619
MGSWHEFEKR LYAIEDRLIA LGGSEAELAW FEDSIAWFEW DLQMYKGKGN PEVEALNEEA  60
DAIYQELDAY RHN                                                    73

SEQ ID NO: 620         moltype = AA  length = 73
FEATURE                Location/Qualifiers
REGION                 1..73
                       note = artificial construct
source                 1..73
                       mol_type = protein
                       organism = synthetic construct
SEQUENCE: 620
MGSWIEFEDR LDAITDRLWA LGGSEAELAE FEHQIAFFEE DLQWYKGKGN PEVEALHMEA  60
EAIMEELGAY RHN                                                    73

SEQ ID NO: 621         moltype = AA  length = 73
FEATURE                Location/Qualifiers
REGION                 1..73
                       note = artificial construct
source                 1..73
                       mol_type = protein
                       organism = synthetic construct
SEQUENCE: 621
MGSWMEFEDR LMAIVDRLWA LGGSEAELAD FEWNIAMFEE ELQWYKGKGN PEVEALGDEA  60
EAIEWELYAY RHN                                                    73

SEQ ID NO: 622         moltype = AA  length = 73
FEATURE                Location/Qualifiers
REGION                 1..73
                       note = artificial construct
source                 1..73
                       mol_type = protein
                       organism = synthetic construct
SEQUENCE: 622
MGSWEEFEDR LFAIDSRLWA LGGSEAELAE FENIIASFEE VLQEYKGKGN PEVEALSVEA  60
FAIDRELGAY RHN                                                    73

SEQ ID NO: 623         moltype = AA  length = 73
FEATURE                Location/Qualifiers
REGION                 1..73
                       note = artificial construct
source                 1..73
                       mol_type = protein
                       organism = synthetic construct
SEQUENCE: 623
MGSWEEFLFR LEAIQDRLWA LGGSEAELAW FEYEIASFED VLQSYKGKGN PEVEALSTEA  60
KAIDYELFAY RHN                                                    73

SEQ ID NO: 624         moltype = AA  length = 73
FEATURE                Location/Qualifiers
REGION                 1..73
                       note = artificial construct
source                 1..73
                       mol_type = protein
                       organism = synthetic construct
SEQUENCE: 624
MGSWVEFDNR LFAIDERLWA LGGSEAELAW FEEEIASFED NLQKYKGKGN PEVEALQLEA  60
FAIMEELDAY RHN                                                    73

SEQ ID NO: 625         moltype = AA  length = 73
```

```
FEATURE                Location/Qualifiers
REGION                 1..73
                       note = artificial construct
source                 1..73
                       mol_type = protein
                       organism = synthetic construct
SEQUENCE: 625
MGSWFEFDDR LEAIFDRLWA LGGSEAELAM FEFAIAEFED ALQEYKGKGN PEVEALYEEA  60
VAIDEELYAY RHN                                                    73

SEQ ID NO: 626         moltype = AA  length = 73
FEATURE                Location/Qualifiers
REGION                 1..73
                       note = artificial construct
source                 1..73
                       mol_type = protein
                       organism = synthetic construct
SEQUENCE: 626
MGSWFEFDAR LMAINDRLWA LGGSEAELAA FEYHIALFED QLQMYKGKGN PEVEALTLEA  60
VAINEELWAY RHN                                                    73

SEQ ID NO: 627         moltype = AA  length = 73
FEATURE                Location/Qualifiers
REGION                 1..73
                       note = artificial construct
source                 1..73
                       mol_type = protein
                       organism = synthetic construct
SEQUENCE: 627
MGSWVEFDSR LAAIDYRLEA LGGSEAELAW FEYTIANFEH TLQMYKGKGN PEVEALVYEA  60
HAIATELQAY RHN                                                    73

SEQ ID NO: 628         moltype = AA  length = 73
FEATURE                Location/Qualifiers
REGION                 1..73
                       note = artificial construct
source                 1..73
                       mol_type = protein
                       organism = synthetic construct
SEQUENCE: 628
MGSWTEFDER LDAIDWRLEA LGGSEAELAW FEGDIALFEQ YLQVYKGKGN PEVEALMEEA  60
DAIKAELDAY RHN                                                    73

SEQ ID NO: 629         moltype = AA  length = 73
FEATURE                Location/Qualifiers
REGION                 1..73
                       note = artificial construct
source                 1..73
                       mol_type = protein
                       organism = synthetic construct
SEQUENCE: 629
MGSWIEFDER LDAIDFRLWA LGGSEAELAW FEGWIAEFES DLQLYKGKGN PEVEALNEEA  60
NAIFHELSAY RHN                                                    73

SEQ ID NO: 630         moltype = AA  length = 73
FEATURE                Location/Qualifiers
REGION                 1..73
                       note = artificial construct
source                 1..73
                       mol_type = protein
                       organism = synthetic construct
SEQUENCE: 630
MGSWWEFDSR LDAIDFRLWA LGGSEAELAW FEVEIADFED WLQLYKGKGN PEVEALWHEA  60
DAIVTELYAY RHN                                                    73

SEQ ID NO: 631         moltype = AA  length = 73
FEATURE                Location/Qualifiers
REGION                 1..73
                       note = artificial construct
source                 1..73
                       mol_type = protein
                       organism = synthetic construct
SEQUENCE: 631
MGSWYEFDER LDAIFDRLWA LGGSEAELAY FEQVIATFEK TLQRYKGKGN PEVEALDTEA  60
KAISWELDAY RHN                                                    73

SEQ ID NO: 632         moltype = AA  length = 73
FEATURE                Location/Qualifiers
REGION                 1..73
```

```
                        note = artificial construct
source                  1..73
                        mol_type = protein
                        organism = synthetic construct
SEQUENCE: 632
MGSWYEFQER LDAIDSRLWA LGGSEAELAW FEYTIAEFEK ELQMYKGKGN PEVEALGTEA  60
VAISEELMAY RHN                                                     73

SEQ ID NO: 633          moltype = AA  length = 73
FEATURE                 Location/Qualifiers
REGION                  1..73
                        note = artificial construct
source                  1..73
                        mol_type = protein
                        organism = synthetic construct
SEQUENCE: 633
MGSWEEFEDR LWAIDGRLYA LGGSEAELAW FEQWIATFEE DLQDYKGKGN PEVEALEYEA  60
SAIFEELEAY RHN                                                     73

SEQ ID NO: 634          moltype = AA  length = 73
FEATURE                 Location/Qualifiers
REGION                  1..73
                        note = artificial construct
source                  1..73
                        mol_type = protein
                        organism = synthetic construct
SEQUENCE: 634
MGSWFEFGDR LEAIDERLYA LGGSEAELAQ FEWWIAEFEH HLQDYKGKGN PEVEALEYEA  60
DAIWGELHAY RHN                                                     73

SEQ ID NO: 635          moltype = AA  length = 73
FEATURE                 Location/Qualifiers
REGION                  1..73
                        note = artificial construct
source                  1..73
                        mol_type = protein
                        organism = synthetic construct
SEQUENCE: 635
MGSWFEFNDR LDAISERLSA LGGSEAELAY FEWQIAVFEK TLQNYKGKGN PEVEALTLEA  60
NAIFEELEAY RHN                                                     73

SEQ ID NO: 636          moltype = AA  length = 73
FEATURE                 Location/Qualifiers
REGION                  1..73
                        note = artificial construct
source                  1..73
                        mol_type = protein
                        organism = synthetic construct
SEQUENCE: 636
MGSWVEFMDR LEAIEERLSA LGGSEAELAF FEWEIAEFEE HLQVYKGKGN PEVEALEWEA  60
LAITEELAAY RHN                                                     73

SEQ ID NO: 637          moltype = AA  length = 73
FEATURE                 Location/Qualifiers
REGION                  1..73
                        note = artificial construct
source                  1..73
                        mol_type = protein
                        organism = synthetic construct
SEQUENCE: 637
MGSWIEFMDR LWAIDQRLWA LGGSEAELAW FEEEIAWFEE ELQVYKGKGN PEVEALEWEA  60
TAISEELWAY RHN                                                     73

SEQ ID NO: 638          moltype = AA  length = 73
FEATURE                 Location/Qualifiers
REGION                  1..73
                        note = artificial construct
source                  1..73
                        mol_type = protein
                        organism = synthetic construct
SEQUENCE: 638
MGSWEEFNWR LRAIDERLFA LGGSEAELAW FEYDIAEFEE QLQVYKGKGN PEVEALRVEA  60
AAIAEELYAY RHN                                                     73

SEQ ID NO: 639          moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 639
MGSWWEFEIR LDAIDERLWA LGGSEAELAW FEQSIAFFEN DLQVYKGKGN PEVEALRWEA  60
NAIIEELFAY RHN                                                     73

SEQ ID NO: 640          moltype = AA  length = 73
FEATURE                 Location/Qualifiers
REGION                  1..73
                        note = artificial construct
source                  1..73
                        mol_type = protein
                        organism = synthetic construct
SEQUENCE: 640
MGSWYEFEWR LDAIDRRLWA LGGSEAELAD FEEEIADFEW MLQNYKGKGN PEVEALVDEA  60
SAIQTELWAY RHN                                                     73

SEQ ID NO: 641          moltype = AA  length = 73
FEATURE                 Location/Qualifiers
REGION                  1..73
                        note = artificial construct
source                  1..73
                        mol_type = protein
                        organism = synthetic construct
SEQUENCE: 641
MGSWYEFVYR LRAIDERLDA LGGSEAELAM FEFEIAFFED QLQRYKGKGN PEVEALVDEA  60
QAIDFELFAY RHN                                                     73

SEQ ID NO: 642          moltype = AA  length = 73
FEATURE                 Location/Qualifiers
REGION                  1..73
                        note = artificial construct
source                  1..73
                        mol_type = protein
                        organism = synthetic construct
SEQUENCE: 642
MGSWWEFEDR LYAIDDRLWA LGGSEAELAQ FEREIAQFEI WLQEYKGKGN PEVEALDDEA  60
TAINSELFAY RHN                                                     73

SEQ ID NO: 643          moltype = AA  length = 73
FEATURE                 Location/Qualifiers
REGION                  1..73
                        note = artificial construct
source                  1..73
                        mol_type = protein
                        organism = synthetic construct
SEQUENCE: 643
MGSWDEFEFR LEAIDSRLWA LGGSEAELAV FEYEIAQFEF MLQEYKGKGN PEVEALGMEA  60
WAIENELFAY RHN                                                     73

SEQ ID NO: 644          moltype = AA  length = 73
FEATURE                 Location/Qualifiers
REGION                  1..73
                        note = artificial construct
source                  1..73
                        mol_type = protein
                        organism = synthetic construct
SEQUENCE: 644
MGSWEEFEWR LDAIDERLWA LGGSEAELAT FEYEIAIFEN ELQQYKGKGN PEVEALDSEA  60
YAIERELGAY RHN                                                     73

SEQ ID NO: 645          moltype = AA  length = 73
FEATURE                 Location/Qualifiers
REGION                  1..73
                        note = artificial construct
source                  1..73
                        mol_type = protein
                        organism = synthetic construct
SEQUENCE: 645
MGSWYEFFDR LDAIDERLWA LGGSEAELAW FEAEIAEFEM ELQGYKGKGN PEVEALDVEA  60
HAIEMELFAY RHN                                                     73

SEQ ID NO: 646          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 646
MGSWYEFMGR LEAIDERLQA LGGSEAELAW FEHEIAEFEW SLQWYKGKGN PEVEALRFEA  60
GAIPWELWAY RHN                                                    73

SEQ ID NO: 647          moltype = AA  length = 73
FEATURE                 Location/Qualifiers
REGION                  1..73
                        note = artificial construct
source                  1..73
                        mol_type = protein
                        organism = synthetic construct
SEQUENCE: 647
MGSWVEFSNR LDAIWERLQA LGGSEAELAY FEWEIAEFEW ELQSYKGKGN PEVEALNAEA  60
DAIEWELEAY RHN                                                    73

SEQ ID NO: 648          moltype = AA  length = 73
FEATURE                 Location/Qualifiers
REGION                  1..73
                        note = artificial construct
source                  1..73
                        mol_type = protein
                        organism = synthetic construct
SEQUENCE: 648
MGSWEEFHMR LIAIDERLWA LGGSEAELAG FEESIAYFES QLQDYKGKGN PEVEALDYEA  60
HAIWRELYAY RHN                                                    73

SEQ ID NO: 649          moltype = AA  length = 73
FEATURE                 Location/Qualifiers
REGION                  1..73
                        note = artificial construct
source                  1..73
                        mol_type = protein
                        organism = synthetic construct
SEQUENCE: 649
MGSWWEFKYR LDAICFRLAA LGGSEAELAS FEDEIAYFEE DLQGYKGKGN PEVEALDYEA  60
LAIWDELAAY RHN                                                    73

SEQ ID NO: 650          moltype = AA  length = 73
FEATURE                 Location/Qualifiers
REGION                  1..73
                        note = artificial construct
source                  1..73
                        mol_type = protein
                        organism = synthetic construct
SEQUENCE: 650
MGSWDEFAMR LEAIQARLFA LGGSEAELAI FEDEIAFFET MLQDYKGKGN PEVEALEYEA  60
AAIEAELGAY RHN                                                    73

SEQ ID NO: 651          moltype = AA  length = 73
FEATURE                 Location/Qualifiers
REGION                  1..73
                        note = artificial construct
source                  1..73
                        mol_type = protein
                        organism = synthetic construct
SEQUENCE: 651
MGSWWEFNAR LDAIEDRLMA LGGSEAELAY FEDIIASFEN ILQQYKGKGN PEVEALWYEA  60
YAIEKELNAY RHN                                                    73

SEQ ID NO: 652          moltype = AA  length = 73
FEATURE                 Location/Qualifiers
REGION                  1..73
                        note = artificial construct
source                  1..73
                        mol_type = protein
                        organism = synthetic construct
SEQUENCE: 652
MGSWIEFWNR LEAIEERLYA LGGSEAELAY FEDEIAEFEI YLQQYKGKGN PEVEALKHEA  60
EAINKELMAY RHN                                                    73

SEQ ID NO: 653          moltype = AA  length = 73
FEATURE                 Location/Qualifiers
REGION                  1..73
                        note = artificial construct
source                  1..73
                        mol_type = protein
                        organism = synthetic construct
SEQUENCE: 653
MGSWNEFVIR LFAIDDRLYA LGGSEAELAW FEDEIATFEY ELQRYKGKGN PEVEALEYEA  60
```

```
EAIVSELFAY RHN                                                    73

SEQ ID NO: 654          moltype = AA  length = 73
FEATURE                 Location/Qualifiers
REGION                  1..73
                        note = artificial construct
source                  1..73
                        mol_type = protein
                        organism = synthetic construct
SEQUENCE: 654
MGSWYEFLAR LYAIDERLWA LGGSEAELAT FEHWIADFEE QLQSYKGKGN PEVEALTDEA  60
VAIGEELSAY RHN                                                    73

SEQ ID NO: 655          moltype = AA  length = 73
FEATURE                 Location/Qualifiers
REGION                  1..73
                        note = artificial construct
source                  1..73
                        mol_type = protein
                        organism = synthetic construct
SEQUENCE: 655
MGSWLEFETR LHAIDERLWA LGGSEAELAE FEEHIAWFEE DLQFYKGKGN PEVEALDFEA  60
DAIGWELWAY RHN                                                    73

SEQ ID NO: 656          moltype = AA  length = 73
FEATURE                 Location/Qualifiers
REGION                  1..73
                        note = artificial construct
source                  1..73
                        mol_type = protein
                        organism = synthetic construct
SEQUENCE: 656
MGSWFEFETR LEAIDLRLWA LGGSEAELAT FEDVIAFFED WLQFYKGKGN PEVEALKMEA  60
WAIGEELHAY RHN                                                    73

SEQ ID NO: 657          moltype = AA  length = 73
FEATURE                 Location/Qualifiers
REGION                  1..73
                        note = artificial construct
source                  1..73
                        mol_type = protein
                        organism = synthetic construct
SEQUENCE: 657
MGSWHEFWQR LEAIEGRLWA LGGSEAELAD FESLIADFEE QLQEYKGKGN PEVEALMAEA  60
EAIDNELRAY RHN                                                    73

SEQ ID NO: 658          moltype = AA  length = 73
FEATURE                 Location/Qualifiers
REGION                  1..73
                        note = artificial construct
source                  1..73
                        mol_type = protein
                        organism = synthetic construct
SEQUENCE: 658
MGSWYEFEQR LEAIEWRLGA LGGSEAELAT FEEDIADFEE WLQEYKGKGN PEVEALQYEA  60
YAIAEELHAY RHN                                                    73

SEQ ID NO: 659          moltype = AA  length = 73
FEATURE                 Location/Qualifiers
REGION                  1..73
                        note = artificial construct
source                  1..73
                        mol_type = protein
                        organism = synthetic construct
SEQUENCE: 659
MGSWYEFENR LFAIEERLWA LGGSEAELAW FEYEIANFEW GLQSYKGKGN PEVEALDNEA  60
EAIDIELAAY RHN                                                    73

SEQ ID NO: 660          moltype = AA  length = 73
FEATURE                 Location/Qualifiers
REGION                  1..73
                        note = artificial construct
source                  1..73
                        mol_type = protein
                        organism = synthetic construct
SEQUENCE: 660
MGSWYEFEQR LGAIEERLWA LGGSEAELAA FEDIIAYFEY QLQSYKGKGN PEVEALDEEA  60
WAIDDELWAY RHN                                                    73
```

```
SEQ ID NO: 661         moltype = AA  length = 73
FEATURE                Location/Qualifiers
REGION                 1..73
                       note = artificial construct
source                 1..73
                       mol_type = protein
                       organism = synthetic construct
SEQUENCE: 661
MGSWWEFEQR LDAIETRLWA LGGSEAELAY FEHIIADFED ELQIYKGKGN PEVEALGWEA  60
FAIDGELTAY RHN                                                     73

SEQ ID NO: 662         moltype = AA  length = 73
FEATURE                Location/Qualifiers
REGION                 1..73
                       note = artificial construct
source                 1..73
                       mol_type = protein
                       organism = synthetic construct
SEQUENCE: 662
MGSWFEFPYR LEAIEERLYA LGGSEAELAQ FEQFIAWFEM DLQDYKGKGN PEVEALWFEA  60
NAIVEELDAY RHN                                                     73

SEQ ID NO: 663         moltype = AA  length = 73
FEATURE                Location/Qualifiers
REGION                 1..73
                       note = artificial construct
source                 1..73
                       mol_type = protein
                       organism = synthetic construct
SEQUENCE: 663
MGSWVEFYDR LEAIEIRLWA LGGSEAELAD FESFIAHFED DLQAYKGKGN PEVEALMDEA  60
NAIVFELDAY RHN                                                     73

SEQ ID NO: 664         moltype = AA  length = 73
FEATURE                Location/Qualifiers
REGION                 1..73
                       note = artificial construct
source                 1..73
                       mol_type = protein
                       organism = synthetic construct
SEQUENCE: 664
MGSWVEFWDR LDAIEERLWA LGGSEAELAE FEFMIAMFEQ HLQEYKGKGN PEVEALIPEA  60
GAIDKELTAY RHN                                                     73

SEQ ID NO: 665         moltype = AA  length = 73
FEATURE                Location/Qualifiers
REGION                 1..73
                       note = artificial construct
source                 1..73
                       mol_type = protein
                       organism = synthetic construct
SEQUENCE: 665
MGSWDEFDAR LWAIEERLWA LGGSEAELAE FEFMIAAFED VLQEYKGKGN PEVEALMGEA  60
NAIVMELDAY RHN                                                     73

SEQ ID NO: 666         moltype = AA  length = 73
FEATURE                Location/Qualifiers
REGION                 1..73
                       note = artificial construct
source                 1..73
                       mol_type = protein
                       organism = synthetic construct
SEQUENCE: 666
MGSWYEFWRR LDAIEERLWA LGGSEAELAM FETDIAGFEW MLQLYKGKGN PEVEALEHEA  60
WAINSELDAY RHN                                                     73

SEQ ID NO: 667         moltype = AA  length = 73
FEATURE                Location/Qualifiers
REGION                 1..73
                       note = artificial construct
source                 1..73
                       mol_type = protein
                       organism = synthetic construct
SEQUENCE: 667
MGSWHEFIWR LDAIEERLWA LGGSEAELAW FETEIATFEA QLQDYKGKGN PEVEALEWEA  60
IAIAWELDAY RHN                                                     73

SEQ ID NO: 668         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 668
MGSWYEFYWR LEAIEERLWA LGGSEAELAE FEKAIATFED QLQTYKGKGN PEVEALETEA  60
LAIHAELEAY RHN                                                     73

SEQ ID NO: 669          moltype = AA  length = 73
FEATURE                 Location/Qualifiers
REGION                  1..73
                        note = artificial construct
source                  1..73
                        mol_type = protein
                        organism = synthetic construct
SEQUENCE: 669
MGSWFEFQWR LEAIEDRLWA LGGSEAELAE FETIIAGFEE QLQVYKGKGN PEVEALEEEA  60
MAIQTELHAY RHN                                                     73

SEQ ID NO: 670          moltype = AA  length = 73
FEATURE                 Location/Qualifiers
REGION                  1..73
                        note = artificial construct
source                  1..73
                        mol_type = protein
                        organism = synthetic construct
SEQUENCE: 670
MGSWWEFEDR LWAIEQRLDA LGGSEAELAV FENSIAKFED MLQVYKGKGN PEVEALHEEA  60
DAIIWELYAY RHN                                                     73

SEQ ID NO: 671          moltype = AA  length = 73
FEATURE                 Location/Qualifiers
REGION                  1..73
                        note = artificial construct
source                  1..73
                        mol_type = protein
                        organism = synthetic construct
SEQUENCE: 671
MGSWWEFEDR LWAIDRRLMA LGGSEAELAV FEQMIAHFEQ ILQVYKGKGN PEVEALHFEA  60
HAIGMELAAY RHN                                                     73

SEQ ID NO: 672          moltype = AA  length = 73
FEATURE                 Location/Qualifiers
REGION                  1..73
                        note = artificial construct
source                  1..73
                        mol_type = protein
                        organism = synthetic construct
SEQUENCE: 672
MGSWWEFLDR LEAIEYRLQA LGGSEAELAV FEWEIAMFED HLQGYKGKGN PEVEALHSEA  60
HAIISELSAY RHN                                                     73

SEQ ID NO: 673          moltype = AA  length = 73
FEATURE                 Location/Qualifiers
REGION                  1..73
                        note = artificial construct
source                  1..73
                        mol_type = protein
                        organism = synthetic construct
SEQUENCE: 673
MGSWAEFEDR LAAIERRLEA LGGSEAELAD FESSIAWFEP DLQYYKGKGN PEVEALMYEA  60
EAIFSELYAY RHN                                                     73

SEQ ID NO: 674          moltype = AA  length = 73
FEATURE                 Location/Qualifiers
REGION                  1..73
                        note = artificial construct
source                  1..73
                        mol_type = protein
                        organism = synthetic construct
SEQUENCE: 674
MGSWWEFYDR LTAIEARLWA LGGSEAELAD FEEGIADFEY DLQDYKGKGN PEVEALFWEA  60
WAIQSELTAY RHN                                                     73

SEQ ID NO: 675          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 675
MGSWYEFEDR LAAIEARLWA LGGSEAELAD FEEEIAYFEH GLQWYKGKGN PEVEALESEA  60
MAIIDELHAY RHN                                                     73

SEQ ID NO: 676          moltype = AA  length = 73
FEATURE                 Location/Qualifiers
REGION                  1..73
                        note = artificial construct
source                  1..73
                        mol_type = protein
                        organism = synthetic construct
SEQUENCE: 676
MGSWWEFSWR LEAIETRLDA LGGSEAELAF FEMDIAWFEQ DLQLYKGKGN PEVEALEEEA  60
YAIYEELEAY RHN                                                     73

SEQ ID NO: 677          moltype = AA  length = 73
FEATURE                 Location/Qualifiers
REGION                  1..73
                        note = artificial construct
source                  1..73
                        mol_type = protein
                        organism = synthetic construct
SEQUENCE: 677
MGSWEEFFFR LEAIDDRLYA LGGSEAELAL FEEVIAYFEQ DLQWYKGKGN PEVEALYVEA  60
YAIQEELYAY RHN                                                     73

SEQ ID NO: 678          moltype = AA  length = 73
FEATURE                 Location/Qualifiers
REGION                  1..73
                        note = artificial construct
source                  1..73
                        mol_type = protein
                        organism = synthetic construct
SEQUENCE: 678
MGSWFEFEER LNAISWRLHA LGGSEAELAY FEEDIAWFED DLQFYKGKGN PEVEALENEA  60
YAIWEELDAY RHN                                                     73

SEQ ID NO: 679          moltype = AA  length = 73
FEATURE                 Location/Qualifiers
REGION                  1..73
                        note = artificial construct
source                  1..73
                        mol_type = protein
                        organism = synthetic construct
SEQUENCE: 679
MGSWFEFEER LEAIIYRLWA LGGSEAELAM FEESIAWFES DLQQYKGKGN PEVEALEYEA  60
MAISKELKAY RHN                                                     73

SEQ ID NO: 680          moltype = AA  length = 73
FEATURE                 Location/Qualifiers
REGION                  1..73
                        note = artificial construct
source                  1..73
                        mol_type = protein
                        organism = synthetic construct
SEQUENCE: 680
MGSWAEFDDR LEAIEYRLHA LGGSEAELAW FEEGIAGFEH ALQSYKGKGN PEVEALETEA  60
GAINEELWAY RHN                                                     73

SEQ ID NO: 681          moltype = AA  length = 73
FEATURE                 Location/Qualifiers
REGION                  1..73
                        note = artificial construct
source                  1..73
                        mol_type = protein
                        organism = synthetic construct
SEQUENCE: 681
MGSWDEFEER LQAIEYRLWA LGGSEAELAW FEEVIAQFEY DLQKYKGKGN PEVEALSTEA  60
QAIQDELWAY RHN                                                     73

SEQ ID NO: 682          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 682
MGSWWEFTDR LDAIFDRLWA LGGSEAELAA FEESIAIFEQ DLQYYKGKGN PEVEALEYEA  60
NAIQYELEAY RHN                                                    73

SEQ ID NO: 683           moltype = AA  length = 73
FEATURE                  Location/Qualifiers
REGION                   1..73
                         note = artificial construct
source                   1..73
                         mol_type = protein
                         organism = synthetic construct
SEQUENCE: 683
MGSWWEFTDR LEAIEDRLWA LGGSEAELAH FEDSIAQFEQ ELQWYKGKGN PEVEALADEA  60
DAIESELHAY RHN                                                    73

SEQ ID NO: 684           moltype = AA  length = 73
FEATURE                  Location/Qualifiers
REGION                   1..73
                         note = artificial construct
source                   1..73
                         mol_type = protein
                         organism = synthetic construct
SEQUENCE: 684
MGSWVEFFWR LDAIEDRLWA LGGSEAELAN FEFEIADFEA WLQKYKGKGN PEVEALHSEA  60
DAIQLELRAY RHN                                                    73

SEQ ID NO: 685           moltype = AA  length = 73
FEATURE                  Location/Qualifiers
REGION                   1..73
                         note = artificial construct
source                   1..73
                         mol_type = protein
                         organism = synthetic construct
SEQUENCE: 685
MGSWVEFYNR LDAIENRLWA LGGSEAELAF FEELIAQFEF ALQDYKGKGN PEVEALEDEA  60
DAIWEELMAY RHN                                                    73

SEQ ID NO: 686           moltype = AA  length = 73
FEATURE                  Location/Qualifiers
REGION                   1..73
                         note = artificial construct
source                   1..73
                         mol_type = protein
                         organism = synthetic construct
SEQUENCE: 686
MGSWEEFYYR LHAIDNRLWA LGGSEAELAY FEWHIADFEL ELQDYKGKGN PEVEALSEEA  60
TAIFEELWAY RHN                                                    73

SEQ ID NO: 687           moltype = AA  length = 73
FEATURE                  Location/Qualifiers
REGION                   1..73
                         note = artificial construct
source                   1..73
                         mol_type = protein
                         organism = synthetic construct
SEQUENCE: 687
MGSWREFHDR LFAIDGRLWA LGGSEAELAN FEWDIADFEF ELQDYKGKGN PEVEALSWEA  60
DAIMQELGAY RHN                                                    73

SEQ ID NO: 688           moltype = AA  length = 73
FEATURE                  Location/Qualifiers
REGION                   1..73
                         note = artificial construct
source                   1..73
                         mol_type = protein
                         organism = synthetic construct
SEQUENCE: 688
MGSWEEFDER LWAISDRLWA LGGSEAELAY FEGEIAYFEQ NLQTYKGKGN PEVEALQTEA  60
LAIDTELWAY RHN                                                    73

SEQ ID NO: 689           moltype = AA  length = 73
FEATURE                  Location/Qualifiers
REGION                   1..73
                         note = artificial construct
source                   1..73
                         mol_type = protein
                         organism = synthetic construct
SEQUENCE: 689
```

```
MGSWEEFEQR LWAIDDRLWA LGGSEAELAF FEYEIAEFEM DLQWYKGKGN PEVEALFYEA  60
HAINEELWAY RHN                                                     73

SEQ ID NO: 690         moltype = AA  length = 73
FEATURE                Location/Qualifiers
REGION                 1..73
                       note = artificial construct
source                 1..73
                       mol_type = protein
                       organism = synthetic construct
SEQUENCE: 690
MGSWDEFHQR LAAIGDRLWA LGGSEAELAY FEWEIATFEW DLQVYKGKGN PEVEALYFEA  60
TAIDEELMAY RHN                                                     73

SEQ ID NO: 691         moltype = AA  length = 73
FEATURE                Location/Qualifiers
REGION                 1..73
                       note = artificial construct
source                 1..73
                       mol_type = protein
                       organism = synthetic construct
SEQUENCE: 691
MGSWVEFEYR LDAISDRLWA LGGSEAELAF FENEIASFES DLQFYKGKGN PEVEALMFEA  60
EAIDDELHAY RHN                                                     73

SEQ ID NO: 692         moltype = AA  length = 73
FEATURE                Location/Qualifiers
REGION                 1..73
                       note = artificial construct
source                 1..73
                       mol_type = protein
                       organism = synthetic construct
SEQUENCE: 692
MGSWDEFDTR LDAIFSRLYA LGGSEAELAM FEGEIAEFEG SLQHYKGKGN PEVEALDFEA  60
HAIDEELWAY RHN                                                     73

SEQ ID NO: 693         moltype = AA  length = 73
FEATURE                Location/Qualifiers
REGION                 1..73
                       note = artificial construct
source                 1..73
                       mol_type = protein
                       organism = synthetic construct
SEQUENCE: 693
MGSWHEFDDR LDAIMSRLDA LGGSEAELAT FEAEIATFEF VLQLYKGKGN PEVEALLAEA  60
YAIDWELEAY RHN                                                     73

SEQ ID NO: 694         moltype = AA  length = 73
FEATURE                Location/Qualifiers
REGION                 1..73
                       note = artificial construct
source                 1..73
                       mol_type = protein
                       organism = synthetic construct
SEQUENCE: 694
MGSWYEFFDR LDAIYDRLYA LGGSEAELAS FEAQIAEFEV ELQSYKGKGN PEVEALEWEA  60
WAIDEELYAY RHN                                                     73

SEQ ID NO: 695         moltype = AA  length = 73
FEATURE                Location/Qualifiers
REGION                 1..73
                       note = artificial construct
source                 1..73
                       mol_type = protein
                       organism = synthetic construct
SEQUENCE: 695
MGSWFEFLYR LDAIEDRLWA LGGSEAELAE FEQEIAKFES ELQSYKGKGN PEVEALEWEA  60
HAIDMELEAY RHN                                                     73

SEQ ID NO: 696         moltype = AA  length = 73
FEATURE                Location/Qualifiers
REGION                 1..73
                       note = artificial construct
source                 1..73
                       mol_type = protein
                       organism = synthetic construct
SEQUENCE: 696
MGSWLEFEDR LVAIDHRLFA LGGSEAELAE FEEEIALFES YLQDYKGKGN PEVEALNWEA  60
DAIHAELYAY RHN                                                     73
```

```
SEQ ID NO: 697          moltype = AA  length = 73
FEATURE                 Location/Qualifiers
REGION                  1..73
                        note = artificial construct
source                  1..73
                        mol_type = protein
                        organism = synthetic construct
SEQUENCE: 697
MGSWYEFESR LDAIVDRLWA LGGSEAELAE FEYEIAKFEW ELQDYKGKGN PEVEALNWEA  60
GAIEFELYAY RHN                                                     73

SEQ ID NO: 698          moltype = AA  length = 73
FEATURE                 Location/Qualifiers
REGION                  1..73
                        note = artificial construct
source                  1..73
                        mol_type = protein
                        organism = synthetic construct
SEQUENCE: 698
MGSWYEFEDR LDAILYRLLA LGGSEAELAW FERDIAFFES ELQWYKGKGN PEVEALEWEA  60
MAIDDELFAY RHN                                                     73

SEQ ID NO: 699          moltype = AA  length = 73
FEATURE                 Location/Qualifiers
REGION                  1..73
                        note = artificial construct
source                  1..73
                        mol_type = protein
                        organism = synthetic construct
SEQUENCE: 699
MGSWGEFMDR LEAIDYRLWA LGGSEAELAW FESDIAEFEQ ELQMYKGKGN PEVEALWDEA  60
MAIRDELFAY RHN                                                     73

SEQ ID NO: 700          moltype = AA  length = 73
FEATURE                 Location/Qualifiers
REGION                  1..73
                        note = artificial construct
source                  1..73
                        mol_type = protein
                        organism = synthetic construct
SEQUENCE: 700
MGSWEEFDDR LDAIEHRLWA LGGSEAELAD FEGSIAAFES WLQVYKGKGN PEVEALEAEA  60
EAIADELWAY RHN                                                     73

SEQ ID NO: 701          moltype = AA  length = 73
FEATURE                 Location/Qualifiers
REGION                  1..73
                        note = artificial construct
source                  1..73
                        mol_type = protein
                        organism = synthetic construct
SEQUENCE: 701
MGSWYEFADR LDAIMDRLVA LGGSEAELAY FEWEIAAFEE FLQMYKGKGN PEVEALDEEA  60
EAIKDELMAY RHN                                                     73

SEQ ID NO: 702          moltype = AA  length = 73
FEATURE                 Location/Qualifiers
REGION                  1..73
                        note = artificial construct
source                  1..73
                        mol_type = protein
                        organism = synthetic construct
SEQUENCE: 702
MGSWNEFWER LDAIEWRLFA LGGSEAELAF FELDIAWFEE ELQWYKGKGN PEVEALIFEA  60
HAITLELDAY RHN                                                     73

SEQ ID NO: 703          moltype = AA  length = 73
FEATURE                 Location/Qualifiers
REGION                  1..73
                        note = artificial construct
source                  1..73
                        mol_type = protein
                        organism = synthetic construct
SEQUENCE: 703
MGSWYEFDAR LDAIEERLYA LGGSEAELAA FEFEIAGFEE ALQWYKGKGN PEVEALLKEA  60
EAITDELYAY RHN                                                     73

SEQ ID NO: 704          moltype = AA  length = 73
```

```
FEATURE                Location/Qualifiers
REGION                 1..73
                       note = artificial construct
source                 1..73
                       mol_type = protein
                       organism = synthetic construct
SEQUENCE: 704
MGSWDEFSER LDAIWGRLEA LGGSEAELAT FEFHIAEFEH ELQYYKGKGN PEVEALQGEA  60
AAIINELYAY RHN                                                    73

SEQ ID NO: 705         moltype = AA  length = 73
FEATURE                Location/Qualifiers
REGION                 1..73
                       note = artificial construct
source                 1..73
                       mol_type = protein
                       organism = synthetic construct
SEQUENCE: 705
MGSWDEFWDR LDAIEDRLFA LGGSEAELAD FERVIAWFEN DLQEYKGKGN PEVEALDNEA  60
DAIRIELHAY RHN                                                    73

SEQ ID NO: 706         moltype = AA  length = 73
FEATURE                Location/Qualifiers
REGION                 1..73
                       note = artificial construct
source                 1..73
                       mol_type = protein
                       organism = synthetic construct
SEQUENCE: 706
MGSWDEFDDR LEAIVDRLFA LGGSEAELAM FEFEIAQFEH QLQYYKGKGN PEVEALRDEA  60
DAIWIELDAY RHN                                                    73

SEQ ID NO: 707         moltype = AA  length = 73
FEATURE                Location/Qualifiers
REGION                 1..73
                       note = artificial construct
source                 1..73
                       mol_type = protein
                       organism = synthetic construct
SEQUENCE: 707
MGSWEEFTIR LGAIYWRLFA LGGSEAELAN FEWFIAEFEY ELQPYKGKGN PEVEALVIEA  60
NAIDGELQAY RHN                                                    73

SEQ ID NO: 708         moltype = AA  length = 73
FEATURE                Location/Qualifiers
REGION                 1..73
                       note = artificial construct
source                 1..73
                       mol_type = protein
                       organism = synthetic construct
SEQUENCE: 708
MGSWFEFEWR LDAIENRLNA LGGSEAELAW FEYHIAAFED SLQHYKGKGN PEVEALEWEA  60
HAIQSELQAY RHN                                                    73

SEQ ID NO: 709         moltype = AA  length = 73
FEATURE                Location/Qualifiers
REGION                 1..73
                       note = artificial construct
source                 1..73
                       mol_type = protein
                       organism = synthetic construct
SEQUENCE: 709
MGSWYEFDDR LEAIWDRLGA LGGSEAELAA FEKEIAAFES ELQAYKGKGN PEVEWLRETA  60
ADIRAELQAY RHN                                                    73

SEQ ID NO: 710         moltype = AA  length = 73
FEATURE                Location/Qualifiers
REGION                 1..73
                       note = artificial construct
source                 1..73
                       mol_type = protein
                       organism = synthetic construct
SEQUENCE: 710
MGSWGEFWAR LEAIWIRLDA LGGSEAELAA FEKEIAAFES ELQAYKGKGN PEVEWLREEA  60
ADIRRSLQAY RHN                                                    73

SEQ ID NO: 711         moltype = AA  length = 73
FEATURE                Location/Qualifiers
REGION                 1..73
```

```
                       note = artificial construct
source                 1..73
                       mol_type = protein
                       organism = synthetic construct
SEQUENCE: 711
MGSWIEFEVR LDAIWDRLFA LGGSEAELAA FEKEIAAFES ELQAYKGKGN PEVEYLRDEA  60
ADIRQSLQAY RHN                                                     73

SEQ ID NO: 712         moltype = AA  length = 73
FEATURE                Location/Qualifiers
REGION                 1..73
                       note = artificial construct
source                 1..73
                       mol_type = protein
                       organism = synthetic construct
SEQUENCE: 712
MGSWTEFDRR LDAIWDRLFA LGGSEAELAA FEKEIAAFES ELQAYKGKGN PEVEWLREEA  60
ADIRDYLQAY RHN                                                     73

SEQ ID NO: 713         moltype = AA  length = 73
FEATURE                Location/Qualifiers
REGION                 1..73
                       note = artificial construct
source                 1..73
                       mol_type = protein
                       organism = synthetic construct
SEQUENCE: 713
MGSWTEFDMR LDAIWDRLFA LGGSEAELAA FEKEIAAFES ELQAYKGKGN PEVEELREEA  60
ATIRGVLQAY RHN                                                     73

SEQ ID NO: 714         moltype = AA  length = 73
FEATURE                Location/Qualifiers
REGION                 1..73
                       note = artificial construct
source                 1..73
                       mol_type = protein
                       organism = synthetic construct
SEQUENCE: 714
MGSWEEFHDR LMAIETRLWA LGGSEAELAA FEKEIAAFES ELQAYKGKGN PEVEWLRYEA  60
ADIRDYLQAY RHN                                                     73

SEQ ID NO: 715         moltype = AA  length = 73
FEATURE                Location/Qualifiers
REGION                 1..73
                       note = artificial construct
source                 1..73
                       mol_type = protein
                       organism = synthetic construct
SEQUENCE: 715
MGSWVEFRDR LDAIETRLWA LGGSEAELAA FEKEIAAFES ELQAYKGKGN PEVEWLRYEA  60
AEIRMVLQAY RHN                                                     73

SEQ ID NO: 716         moltype = AA  length = 73
FEATURE                Location/Qualifiers
REGION                 1..73
                       note = artificial construct
source                 1..73
                       mol_type = protein
                       organism = synthetic construct
SEQUENCE: 716
MGSWMEFIDR LDAIEHRLWA LGGSEAELAA FEKEIAAFES ELQAYKGKGN PEVEFLREEA  60
AEIRMYLQAY RHN                                                     73

SEQ ID NO: 717         moltype = AA  length = 73
FEATURE                Location/Qualifiers
REGION                 1..73
                       note = artificial construct
source                 1..73
                       mol_type = protein
                       organism = synthetic construct
SEQUENCE: 717
MGSWTEFVWR LDAIEWRLEA LGGSEAELAA FEKEIAAFES ELQAYKGKGN PEVEFLREEA  60
AEIRDWLQAY RHN                                                     73

SEQ ID NO: 718         moltype = AA  length = 73
FEATURE                Location/Qualifiers
REGION                 1..73
                       note = artificial construct
source                 1..73
```

```
                        mol_type = protein
                        organism = synthetic construct
SEQUENCE: 718
MGSWVEFYDR LYAIEVRLLA LGGSEAELAA FEKEIAAFES ELQAYKGKGN PEVEFLRQEA  60
AEIRDWLQAY RHN                                                     73

SEQ ID NO: 719          moltype = AA  length = 73
FEATURE                 Location/Qualifiers
REGION                  1..73
                        note = artificial construct
source                  1..73
                        mol_type = protein
                        organism = synthetic construct
SEQUENCE: 719
MGSWYEFYDR LDAIEWRLWA LGGSEAELAA FEKEIAAFES ELQAYKGKGN PEVEWLRDEA  60
AQIRDFLQAY RHN                                                     73

SEQ ID NO: 720          moltype = AA  length = 73
FEATURE                 Location/Qualifiers
REGION                  1..73
                        note = artificial construct
source                  1..73
                        mol_type = protein
                        organism = synthetic construct
SEQUENCE: 720
MGSWVEFYDR LDAIEHRLDA LGGSEAELAA FEKEIAAFES ELQAYKGKGN PEVEWLRDEA  60
AFIRDMLQAY RHN                                                     73

SEQ ID NO: 721          moltype = AA  length = 73
FEATURE                 Location/Qualifiers
REGION                  1..73
                        note = artificial construct
source                  1..73
                        mol_type = protein
                        organism = synthetic construct
SEQUENCE: 721
MGSWFEFVDR LTAIQVRLWA LGGSEAELAA FEKEIAAFES ELQAYKGKGN PEVEYLREEA  60
ALIRYSLQAY RHN                                                     73

SEQ ID NO: 722          moltype = AA  length = 73
FEATURE                 Location/Qualifiers
REGION                  1..73
                        note = artificial construct
source                  1..73
                        mol_type = protein
                        organism = synthetic construct
SEQUENCE: 722
MGSWFEFLDR LDAIEERLWA LGGSEAELAA FEKEIAAFES ELQAYKGKGN PEVEWLREEA  60
AVIRDSLQAY RHN                                                     73

SEQ ID NO: 723          moltype = AA  length = 73
FEATURE                 Location/Qualifiers
REGION                  1..73
                        note = artificial construct
source                  1..73
                        mol_type = protein
                        organism = synthetic construct
SEQUENCE: 723
MGSWYEFMVR LDAIEERLFA LGGSEAELAA FEKEIAAFES ELQAYKGKGN PEVEFLREEA  60
ASIRYHLQAY RHN                                                     73

SEQ ID NO: 724          moltype = AA  length = 73
FEATURE                 Location/Qualifiers
REGION                  1..73
                        note = artificial construct
source                  1..73
                        mol_type = protein
                        organism = synthetic construct
SEQUENCE: 724
MGSWYEFEDR LDAIQWRLWA LGGSEAELAA FEKEIAAFES ELQAYKGKGN PEVEFLRESA  60
ANIRQHLQAY RHN                                                     73

SEQ ID NO: 725          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 725
MGSWSEFEYR LFAIENRLDA LGGSEAELAA FEKEIAAFES ELQAYKGKGN PEVEFLREEA  60
AMIRQLLQAY RHN                                                     73

SEQ ID NO: 726         moltype = AA  length = 73
FEATURE                Location/Qualifiers
REGION                 1..73
                       note = artificial construct
source                 1..73
                       mol_type = protein
                       organism = synthetic construct
SEQUENCE: 726
MGSWVEFEYR LDAITERLLA LGGSEAELAA FEKEIAAFES ELQAYKGKGN PEVEILREEA  60
AFIRQWLQAY RHN                                                     73

SEQ ID NO: 727         moltype = AA  length = 73
FEATURE                Location/Qualifiers
REGION                 1..73
                       note = artificial construct
source                 1..73
                       mol_type = protein
                       organism = synthetic construct
SEQUENCE: 727
MGSWWEFLDR LDAIEMRLFA LGGSEAELAA FEKEIAAFES ELQAYKGKGN PEVEYLREEA  60
ALIRNMLQAY RHN                                                     73

SEQ ID NO: 728         moltype = AA  length = 73
FEATURE                Location/Qualifiers
REGION                 1..73
                       note = artificial construct
source                 1..73
                       mol_type = protein
                       organism = synthetic construct
SEQUENCE: 728
MGSWWEFEDR LDAIEYRLFA LGGSEAELAA FEKEIAAFES ELQAYKGKGN PEVEFLREEA  60
AFIRIFLQAY RHN                                                     73

SEQ ID NO: 729         moltype = AA  length = 73
FEATURE                Location/Qualifiers
REGION                 1..73
                       note = artificial construct
source                 1..73
                       mol_type = protein
                       organism = synthetic construct
SEQUENCE: 729
MGSWWEFESR LDAIFMRLTA LGGSEAELAA FEKEIAAFES ELQAYKGKGN PEVEDLREDA  60
AFIREFLQAY RHN                                                     73

SEQ ID NO: 730         moltype = AA  length = 73
FEATURE                Location/Qualifiers
REGION                 1..73
                       note = artificial construct
source                 1..73
                       mol_type = protein
                       organism = synthetic construct
SEQUENCE: 730
MGSWVEFWHR LDAIKARLNA LGGSEAELAA FEKEIAAFES ELQAYKGKGN PEVEDLRWYA  60
ADFRLILQAY RHN                                                     73

SEQ ID NO: 731         moltype = AA  length = 73
FEATURE                Location/Qualifiers
REGION                 1..73
                       note = artificial construct
source                 1..73
                       mol_type = protein
                       organism = synthetic construct
SEQUENCE: 731
MGSWYEFYNR LSAIYARLQA LGGSEAELAA FEKEIAAFES ELQAYKGKGN PEVEDLRWYA  60
ADIRYMLQAY RHN                                                     73

SEQ ID NO: 732         moltype = AA  length = 73
FEATURE                Location/Qualifiers
REGION                 1..73
                       note = artificial construct
source                 1..73
                       mol_type = protein
                       organism = synthetic construct
SEQUENCE: 732
MGSWYEFYDR LSAIYARLQA LGGSEAELAA FEKEIAAFES ELQAYKGKGN PEVEDLRWYA  60
```

```
ADIRYMLQAY RHN                                                    73

SEQ ID NO: 733          moltype = AA  length = 73
FEATURE                 Location/Qualifiers
REGION                  1..73
                        note = artificial construct
source                  1..73
                        mol_type = protein
                        organism = synthetic construct
SEQUENCE: 733
MGSWNEFYDR LSAIYFRLQA LGGSEAELAA FEKEIAAFES ELQAYKGKGN PEVEHLRWYA  60
ADIRMILQAY RHN                                                    73

SEQ ID NO: 734          moltype = AA  length = 73
FEATURE                 Location/Qualifiers
REGION                  1..73
                        note = artificial construct
source                  1..73
                        mol_type = protein
                        organism = synthetic construct
SEQUENCE: 734
MGSWNEFYDR LSAIYFRLQA LGGFEAELAA FEKEIAAFES ELQAYKGKGN PEVEHLRWYA  60
ADIRMILQAY RHN                                                    73

SEQ ID NO: 735          moltype = AA  length = 73
FEATURE                 Location/Qualifiers
REGION                  1..73
                        note = artificial construct
source                  1..73
                        mol_type = protein
                        organism = synthetic construct
SEQUENCE: 735
MGSWEEFYDR LGAIFARLHA LGGSEAELAA FEKEIAAFES ELQAYKGKGN PEVEDLRWYA  60
ADIRMILQAY RHN                                                    73

SEQ ID NO: 736          moltype = AA  length = 73
FEATURE                 Location/Qualifiers
REGION                  1..73
                        note = artificial construct
source                  1..73
                        mol_type = protein
                        organism = synthetic construct
SEQUENCE: 736
MGSWVEFYDR LHAIYFRLLA LGGSEAELAA FEKEIAAFES ELQAYKGKGN PEVEDLRWYA  60
ADIRLVLQAY RHN                                                    73

SEQ ID NO: 737          moltype = AA  length = 73
FEATURE                 Location/Qualifiers
REGION                  1..73
                        note = artificial construct
source                  1..73
                        mol_type = protein
                        organism = synthetic construct
SEQUENCE: 737
MGSWKEFDNR LYAIEDRLRA LGGSEAELAA FEKEIAAFES ELQAYKGKGN PEVEHLRWYA  60
ADIRMILQAY RHN                                                    73

SEQ ID NO: 738          moltype = AA  length = 73
FEATURE                 Location/Qualifiers
REGION                  1..73
                        note = artificial construct
source                  1..73
                        mol_type = protein
                        organism = synthetic construct
SEQUENCE: 738
MGSWVEFWDR LWAIEDRLWA LGGSEAELAA FEKEIAAFES ELQAYKGKGN PEVEHLRHYA  60
ADIRVWLQAY RHN                                                    73

SEQ ID NO: 739          moltype = AA  length = 73
FEATURE                 Location/Qualifiers
REGION                  1..73
                        note = artificial construct
source                  1..73
                        mol_type = protein
                        organism = synthetic construct
SEQUENCE: 739
MGSWYEFADR LWAIEDRLWA LGGSEAELAA FEKEIAAFES ELQAYKGKGN PEVEFLRYYA  60
ADIRWVLQAY RHN                                                    73
```

```
SEQ ID NO: 740         moltype = AA  length = 73
FEATURE                Location/Qualifiers
REGION                 1..73
                       note = artificial construct
source                 1..73
                       mol_type = protein
                       organism = synthetic construct
SEQUENCE: 740
MGSWYEFEER LYAIEDRLYA LGGSEAELAA FEKEIAAFES ELQAYKGKGN PEVEFLRQEA  60
ADIRLMLQAY RHN                                                     73

SEQ ID NO: 741         moltype = AA  length = 73
FEATURE                Location/Qualifiers
REGION                 1..73
                       note = artificial construct
source                 1..73
                       mol_type = protein
                       organism = synthetic construct
SEQUENCE: 741
MGSWTEFEWR LYAIEDRLMA LGGSEAELAA FEKEIAAFES ELQAYKGKGN PEVEFLRDEA  60
ADIRQYLQAY RHN                                                     73

SEQ ID NO: 742         moltype = AA  length = 73
FEATURE                Location/Qualifiers
REGION                 1..73
                       note = artificial construct
source                 1..73
                       mol_type = protein
                       organism = synthetic construct
SEQUENCE: 742
MGSWIEFESR LWAIEDRLLA LGGSEAELAA FEKEIAAFES ELQAYKGKGN PEVEFLRLEA  60
ADIREDLQAY RHN                                                     73

SEQ ID NO: 743         moltype = AA  length = 73
FEATURE                Location/Qualifiers
REGION                 1..73
                       note = artificial construct
source                 1..73
                       mol_type = protein
                       organism = synthetic construct
SEQUENCE: 743
MGSWFEFEDR LDAIWDRLWA LGGSEAELAA FEKEIAAFES ELQAYKGKGN PEVEFLRMDA  60
AMIRYILQAY RHN                                                     73

SEQ ID NO: 744         moltype = AA  length = 73
FEATURE                Location/Qualifiers
REGION                 1..73
                       note = artificial construct
source                 1..73
                       mol_type = protein
                       organism = synthetic construct
SEQUENCE: 744
MGSWEEFEDR LWAIEDRLWA LGGSEAELAA FEKEIAAFES ELQAYKGKGN PEVEILRYDA  60
AYIREILQAY RHN                                                     73

SEQ ID NO: 745         moltype = AA  length = 73
FEATURE                Location/Qualifiers
REGION                 1..73
                       note = artificial construct
source                 1..73
                       mol_type = protein
                       organism = synthetic construct
SEQUENCE: 745
MGSWIEFEDR LYAIEDRLWA LGGSEAELAA FEKEIAAFES ELQAYKGKGN PEVEFLRYEA  60
AEIRYWLQAY RHN                                                     73

SEQ ID NO: 746         moltype = AA  length = 73
FEATURE                Location/Qualifiers
REGION                 1..73
                       note = artificial construct
source                 1..73
                       mol_type = protein
                       organism = synthetic construct
SEQUENCE: 746
MGSWYEFWDR LEAIEDRLWA LGGSEAELAA FEKEIAAFES ELQAYKGKGN PEVEFLRYSA  60
AEIRYQLQAY RHN                                                     73

SEQ ID NO: 747         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 747
MGSWVEFESR LAAIEHRLWA LGGSEAELAA FEKEIAAFES ELQAYKGKGN PEVEELREYA  60
AEIRDWLQAY RHN                                                    73

SEQ ID NO: 748          moltype = AA  length = 73
FEATURE                 Location/Qualifiers
REGION                  1..73
                        note = artificial construct
source                  1..73
                        mol_type = protein
                        organism = synthetic construct
SEQUENCE: 748
MGSWWEFEHR LFAIEDRLWA LGGSEAELAA FEKEIAAFES ELQAYKGKGN PEVEFLRDYA  60
AEIRDYLQAY RHN                                                    73

SEQ ID NO: 749          moltype = AA  length = 73
FEATURE                 Location/Qualifiers
REGION                  1..73
                        note = artificial construct
source                  1..73
                        mol_type = protein
                        organism = synthetic construct
SEQUENCE: 749
MGSWYEFDSR LMAIEDRLWA LGGSEAELAA FEKEIAAFES ELQAYKGKGN PEVEYLRQEA  60
AEIRMILQAY RHN                                                    73

SEQ ID NO: 750          moltype = AA  length = 73
FEATURE                 Location/Qualifiers
REGION                  1..73
                        note = artificial construct
source                  1..73
                        mol_type = protein
                        organism = synthetic construct
SEQUENCE: 750
MGSWYEFEWR LMAIEDRLWA LGGSEAELAA FEKEIAAFES ELQAYKGKGN PEVEYLRHEA  60
AEIRDVLQAY RHN                                                    73

SEQ ID NO: 751          moltype = AA  length = 73
FEATURE                 Location/Qualifiers
REGION                  1..73
                        note = artificial construct
source                  1..73
                        mol_type = protein
                        organism = synthetic construct
SEQUENCE: 751
MGSWYEFYNR LDAIEDRLWA LGGSEAELAA FEKEIAAFES ELQAYKGKGN PEVEYLRQEA  60
ADIRGQLQAY RHN                                                    73

SEQ ID NO: 752          moltype = AA  length = 73
FEATURE                 Location/Qualifiers
REGION                  1..73
                        note = artificial construct
source                  1..73
                        mol_type = protein
                        organism = synthetic construct
SEQUENCE: 752
MGSWWEFHDR LEAIEDRLWA LGGSEAELAA FEKEIAAFES ELQAYKGKGN PEVEYLRIEA  60
ADIRRQLQAY RHN                                                    73

SEQ ID NO: 753          moltype = AA  length = 73
FEATURE                 Location/Qualifiers
REGION                  1..73
                        note = artificial construct
source                  1..73
                        mol_type = protein
                        organism = synthetic construct
SEQUENCE: 753
MGSWYEFWDR LEAIEERLWA LGGSEAELAA FEKEIAAFES ELQAYKGKGN PEVEYLRLEA  60
ADIRRILQAY RHN                                                    73

SEQ ID NO: 754          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 754
MGSWYEFEER LWAIEERLYA LGGSEAELAA FEKEIAAFES ELQAYKGKGN PEVEYLRYEA  60
AWIRDFLQAY RHN                                                    73

SEQ ID NO: 755          moltype = AA  length = 73
FEATURE                 Location/Qualifiers
REGION                  1..73
                        note = artificial construct
source                  1..73
                        mol_type = protein
                        organism = synthetic construct
SEQUENCE: 755
MGSWYEFENR LEAIEERLWA LGGSEAELAA FEKEIAAFES ELQAYKGKGN PEVEMLREEA  60
AFIRDWLQAY RHN                                                    73

SEQ ID NO: 756          moltype = AA  length = 73
FEATURE                 Location/Qualifiers
REGION                  1..73
                        note = artificial construct
source                  1..73
                        mol_type = protein
                        organism = synthetic construct
SEQUENCE: 756
MGSWYEFEYR LEAIEDRLWA LGGSEAELAA FEKEIAAFES ELQAYKGKGN PEVEYLREEA  60
AWIRVWLQAY RHN                                                    73

SEQ ID NO: 757          moltype = AA  length = 73
FEATURE                 Location/Qualifiers
REGION                  1..73
                        note = artificial construct
source                  1..73
                        mol_type = protein
                        organism = synthetic construct
SEQUENCE: 757
MGSWYEFENR LGAIGDRLWA LGGSEAELAA FEKEIAAFES ELQAYKGKGN PEVEWLRDEA  60
AYIRAVLQAY RHN                                                    73

SEQ ID NO: 758          moltype = AA  length = 73
FEATURE                 Location/Qualifiers
REGION                  1..73
                        note = artificial construct
source                  1..73
                        mol_type = protein
                        organism = synthetic construct
SEQUENCE: 758
MGSWYEFEHR LDAIYDRLWA LGGSEAELAA FEKEIAAFES ELQAYKGKGN PEVEWLREEA  60
AWIRLWLQAY RHN                                                    73

SEQ ID NO: 759          moltype = AA  length = 73
FEATURE                 Location/Qualifiers
REGION                  1..73
                        note = artificial construct
source                  1..73
                        mol_type = protein
                        organism = synthetic construct
SEQUENCE: 759
MGSWYEFEWR LDAIYDRLGA LGGSEAELAA FEKEIAAFES ELQAYKGKGN PEVEWLREDA  60
AEIRALLQAY RHN                                                    73

SEQ ID NO: 760          moltype = AA  length = 73
FEATURE                 Location/Qualifiers
REGION                  1..73
                        note = artificial construct
source                  1..73
                        mol_type = protein
                        organism = synthetic construct
SEQUENCE: 760
MGSWVEFENR LEAIENRLWA LGGSEAELAA FEKEIAAFES ELQAYKGKGN PEVEWLREDA  60
AQIRMMLQAY RHN                                                    73

SEQ ID NO: 761          moltype = AA  length = 73
FEATURE                 Location/Qualifiers
REGION                  1..73
                        note = artificial construct
source                  1..73
                        mol_type = protein
```

```
                         organism = synthetic construct
SEQUENCE: 761
MGSWYEFEER LEAIEDRLWA LGGSEAELAA FEKEIAAFES ELQAYKGKGN PEVEWLREQA  60
AFIRTMLQAY RHN                                                    73

SEQ ID NO: 762           moltype = AA  length = 73
FEATURE                  Location/Qualifiers
REGION                   1..73
                         note = artificial construct
source                   1..73
                         mol_type = protein
                         organism = synthetic construct
SEQUENCE: 762
MGSWFEFEWR LEAIFDRLYA LGGSEAELAA FEKEIAAFES ELQAYKGKGN PEVEVLRAEA  60
AEIRLRLQAY RHN                                                    73

SEQ ID NO: 763           moltype = AA  length = 73
FEATURE                  Location/Qualifiers
REGION                   1..73
                         note = artificial construct
source                   1..73
                         mol_type = protein
                         organism = synthetic construct
SEQUENCE: 763
MGSWWEFEDR LMAIYDRLYA LGGSEAELAA FEKEIAAFES ELQAYKGKGN PEVEYLRAEA  60
ALIRETLQAY RHN                                                    73

SEQ ID NO: 764           moltype = AA  length = 73
FEATURE                  Location/Qualifiers
REGION                   1..73
                         note = artificial construct
source                   1..73
                         mol_type = protein
                         organism = synthetic construct
SEQUENCE: 764
MGSWFEFEDR LYAIEDRLYA LGGSEAELAA FEKEIAAFES ELQAYKGKGN PEVEYLRWGA  60
ATIRDELQAY RHN                                                    73

SEQ ID NO: 765           moltype = AA  length = 73
FEATURE                  Location/Qualifiers
REGION                   1..73
                         note = artificial construct
source                   1..73
                         mol_type = protein
                         organism = synthetic construct
SEQUENCE: 765
MGSWIEFWDR LEAIEDRLWA LGGSEAELAA FEKEIAAFES ELQAYKGKGN PEVEELRDEA  60
AWIRDSLQAY RHN                                                    73

SEQ ID NO: 766           moltype = AA  length = 73
FEATURE                  Location/Qualifiers
REGION                   1..73
                         note = artificial construct
source                   1..73
                         mol_type = protein
                         organism = synthetic construct
SEQUENCE: 766
MGSWFEFWDR LDAIEDRLYA LGGSEAELAA FEKEIAAFES ELQAYKGKGN PEVEELRDEA  60
AWIRGTLQAY RHN                                                    73

SEQ ID NO: 767           moltype = AA  length = 73
FEATURE                  Location/Qualifiers
REGION                   1..73
                         note = artificial construct
source                   1..73
                         mol_type = protein
                         organism = synthetic construct
SEQUENCE: 767
MGSWEEFTDR LWAIEDRLYA LGGSEAELAA FEKEIAAFES ELQAYKGKGN PEVEWLRDEA  60
AFIRKSLQAY RHN                                                    73

SEQ ID NO: 768           moltype = AA  length = 73
FEATURE                  Location/Qualifiers
REGION                   1..73
                         note = artificial construct
source                   1..73
                         mol_type = protein
                         organism = synthetic construct
SEQUENCE: 768
```

```
MGSWVEFVDR LEAIEDRLFA LGGSEAELAA FEKEIAAFES ELQAYKGKGN PEVEFLRDQA  60
AYIRFMLQAY RHN                                                    73

SEQ ID NO: 769         moltype = AA  length = 73
FEATURE                Location/Qualifiers
REGION                 1..73
                       note = artificial construct
source                 1..73
                       mol_type = protein
                       organism = synthetic construct
SEQUENCE: 769
MGSWFEFVDR LEAIEMRLFA LGGSEAELAA FEKEIAAFES ELQAYKGKGN PEVELLRWRA  60
AMIRYDLQAY RHN                                                    73

SEQ ID NO: 770         moltype = AA  length = 73
FEATURE                Location/Qualifiers
REGION                 1..73
                       note = artificial construct
source                 1..73
                       mol_type = protein
                       organism = synthetic construct
SEQUENCE: 770
MGSWWEFEMR LEAIEDRLFA LGGSEAELAA FEKEIAAFES ELQAYKGKGN PEVESLRWEA  60
AFIRDILQAY RHN                                                    73

SEQ ID NO: 771         moltype = AA  length = 73
FEATURE                Location/Qualifiers
REGION                 1..73
                       note = artificial construct
source                 1..73
                       mol_type = protein
                       organism = synthetic construct
SEQUENCE: 771
MGSWFEFEIR LEAIEDRLFA LGGSEAELAA FEKEIAAFES ELQAYKGKGN PEVEFLRDEA  60
AEIRQVLQAY RHN                                                    73

SEQ ID NO: 772         moltype = AA  length = 73
FEATURE                Location/Qualifiers
REGION                 1..73
                       note = artificial construct
source                 1..73
                       mol_type = protein
                       organism = synthetic construct
SEQUENCE: 772
MGSWYEFYQR LEAIEDRLFA LGGSEAELAA FEKEIAAFES ELQAYKGKGN PEVEWLRDEA  60
AEIRVVLQAY RHN                                                    73

SEQ ID NO: 773         moltype = AA  length = 73
FEATURE                Location/Qualifiers
REGION                 1..73
                       note = artificial construct
source                 1..73
                       mol_type = protein
                       organism = synthetic construct
SEQUENCE: 773
MGSWIEFEDR LEAIEDRLFA LGGSEAELAA FEKEIAAFES ELQAYKGKGN PEVEWLRQEA  60
AEIRLMLQAY RHN                                                    73

SEQ ID NO: 774         moltype =   length =
SEQUENCE: 774
000

SEQ ID NO: 775         moltype =   length =
SEQUENCE: 775
000

SEQ ID NO: 776         moltype =   length =
SEQUENCE: 776
000

SEQ ID NO: 777         moltype =   length =
SEQUENCE: 777
000

SEQ ID NO: 778         moltype =   length =
SEQUENCE: 778
000

SEQ ID NO: 779         moltype =   length =
```

```
SEQUENCE: 779
000

SEQ ID NO: 780          moltype = AA  length = 73
FEATURE                 Location/Qualifiers
REGION                  1..73
                        note = artificial construct
source                  1..73
                        mol_type = protein
                        organism = synthetic construct
SEQUENCE: 780
MGSWVEFEAR LSAIYERLEA LGGSEAELAA FEKEIAAFES ELQAYKGKGN PEVEKLRRHA  60
AGIRSNLQAY RHN                                                    73

SEQ ID NO: 781          moltype = AA  length = 73
FEATURE                 Location/Qualifiers
REGION                  1..73
                        note = artificial construct
source                  1..73
                        mol_type = protein
                        organism = synthetic construct
SEQUENCE: 781
MGSWVEFFVR LDAIWERLEA LGGSEAELAA FEKEIAAFES ELQAYKGKGN PEVETLRFHA  60
AGIRQKLQAY RHN                                                    73

SEQ ID NO: 782          moltype = AA  length = 73
FEATURE                 Location/Qualifiers
REGION                  1..73
                        note = artificial construct
source                  1..73
                        mol_type = protein
                        organism = synthetic construct
SEQUENCE: 782
MGSWTEFNLR LDAIYERLEA LGGSEAELAA FEKEIAAFES ELQAYKGKGN PEVEALRWHA  60
AGIRQQLQAY RHN                                                    73

SEQ ID NO: 783          moltype = AA  length = 73
FEATURE                 Location/Qualifiers
REGION                  1..73
                        note = artificial construct
source                  1..73
                        mol_type = protein
                        organism = synthetic construct
SEQUENCE: 783
MGSWMEFYDR LDAIWVRLEA LGGSEAELAA FEKEIAAFES ELQAYKGKGN PEVEVLRFHA  60
AGIREQLQAY RHN                                                    73

SEQ ID NO: 784          moltype = AA  length = 73
FEATURE                 Location/Qualifiers
REGION                  1..73
                        note = artificial construct
source                  1..73
                        mol_type = protein
                        organism = synthetic construct
SEQUENCE: 784
MGSWHEFNGR LWAIYARLDA LGGSEAELAA FEKEIAAFES ELQAYKGKGN PEVETLRRHA  60
AGIRGILQAY RHN                                                    73

SEQ ID NO: 785          moltype = AA  length = 73
FEATURE                 Location/Qualifiers
REGION                  1..73
                        note = artificial construct
source                  1..73
                        mol_type = protein
                        organism = synthetic construct
SEQUENCE: 785
MGSWYEFVQR LHAINDRLSA LGGSEAELAA FEKEIAAFES ELQAYKGKGN PEVEVLRRHA  60
AGIRYTLQAY RHN                                                    73

SEQ ID NO: 786          moltype = AA  length = 73
FEATURE                 Location/Qualifiers
REGION                  1..73
                        note = artificial construct
source                  1..73
                        mol_type = protein
                        organism = synthetic construct
SEQUENCE: 786
MGSWAEFYQR LNAIWNRLEA LGGSEAELAA FEKEIAAFES ELQAYKGKGN PEVEVLRRHA  60
AGIRGQLQAY RHN                                                    73
```

```
SEQ ID NO: 787          moltype = AA  length = 73
FEATURE                 Location/Qualifiers
REGION                  1..73
                        note = artificial construct
source                  1..73
                        mol_type = protein
                        organism = synthetic construct
SEQUENCE: 787
MGSWVEFNER LHAIYLRLDA LGGSEAELAA FEKEIAAFES ELQAYKGKGN PEVETLRRHA  60
AGIRWQLQAY RHN                                                     73

SEQ ID NO: 788          moltype = AA  length = 73
FEATURE                 Location/Qualifiers
REGION                  1..73
                        note = artificial construct
source                  1..73
                        mol_type = protein
                        organism = synthetic construct
SEQUENCE: 788
MGSWNEFKLE LAFIKDWLEA LGGSEAELAN FEEAIAEFEA GLQGYKGKGN PEVEALRKEA  60
AAIRDELQAY RHN                                                     73

SEQ ID NO: 789          moltype = AA  length = 73
FEATURE                 Location/Qualifiers
REGION                  1..73
                        note = artificial construct
source                  1..73
                        mol_type = protein
                        organism = synthetic construct
SEQUENCE: 789
MGSWMEFEAR LEAIWDRLEA LGGSEAELAA FEKEIAAFES ELQAYKGKGN PEVESLRFHA  60
AGIRQHLQAY RHN                                                     73

SEQ ID NO: 790          moltype = AA  length = 73
FEATURE                 Location/Qualifiers
REGION                  1..73
                        note = artificial construct
source                  1..73
                        mol_type = protein
                        organism = synthetic construct
SEQUENCE: 790
MGSWVEFEDR LNAIWWRLEA LGGSEAELAA FEKEIAAFES ELQAYKGKGN PEVEKLRRHA  60
AGIRTQLQAY RHN                                                     73

SEQ ID NO: 791          moltype = AA  length = 73
FEATURE                 Location/Qualifiers
REGION                  1..73
                        note = artificial construct
source                  1..73
                        mol_type = protein
                        organism = synthetic construct
SEQUENCE: 791
MGSWHHFKMH LAGIKLQLEA LGGSEAELAE FEEWIADFEG ALQDYKGKGN PEVEALRKEA  60
AAIRDELQAY RHN                                                     73

SEQ ID NO: 792          moltype = AA  length = 73
FEATURE                 Location/Qualifiers
REGION                  1..73
                        note = artificial construct
source                  1..73
                        mol_type = protein
                        organism = synthetic construct
SEQUENCE: 792
MGSWAEFFAR LDAIWERLEA LGGSEAELAA FEKEIAAFES ELQAYKGKGN PEVETLRFHA  60
AGIRQKLQAY RHN                                                     73

SEQ ID NO: 793          moltype = AA  length = 73
FEATURE                 Location/Qualifiers
REGION                  1..73
                        note = artificial construct
source                  1..73
                        mol_type = protein
                        organism = synthetic construct
SEQUENCE: 793
MGSWAEFFAR LDAIWDRLEA LGGSEAELAA FEKEIAAFES ELQAYKGKGN PEVETLRFHA  60
AGIRQKLQAY RHN                                                     73

SEQ ID NO: 794          moltype = AA  length = 73
```

```
FEATURE                 Location/Qualifiers
REGION                  1..73
                        note = artificial construct
source                  1..73
                        mol_type = protein
                        organism = synthetic construct
SEQUENCE: 794
MGSWAEFFAR LDAIWERLEA LGGSEAELAA FEKEIAAFES ELQAYKGKGN PEVETLKFHA  60
AGIRQKLQAY RHN                                                     73

SEQ ID NO: 795          moltype = AA  length = 73
FEATURE                 Location/Qualifiers
REGION                  1..73
                        note = artificial construct
source                  1..73
                        mol_type = protein
                        organism = synthetic construct
SEQUENCE: 795
MGSWAEFFAR LDAIWDRLEA LGGSEAELAA FEKEIAAFES ELQAYKGKGN PEVETLKFHA  60
AGIRQKLQAY RHN                                                     73

SEQ ID NO: 796          moltype =   length =
SEQUENCE: 796
000

SEQ ID NO: 797          moltype =   length =
SEQUENCE: 797
000

SEQ ID NO: 798          moltype =   length =
SEQUENCE: 798
000

SEQ ID NO: 799          moltype =   length =
SEQUENCE: 799
000

SEQ ID NO: 800          moltype = AA  length = 73
FEATURE                 Location/Qualifiers
REGION                  1..73
                        note = artificial construct
source                  1..73
                        mol_type = protein
                        organism = synthetic construct
SEQUENCE: 800
MGSWHEFRWR LFAIWQRLHA LGGSEAELAA FEKEIAAFES ELQAYKGKGN PEVEWLRLDA  60
ALIRVMLQAY RHN                                                     73

SEQ ID NO: 801          moltype = AA  length = 73
FEATURE                 Location/Qualifiers
REGION                  1..73
                        note = artificial construct
source                  1..73
                        mol_type = protein
                        organism = synthetic construct
SEQUENCE: 801
MGSWAEFRWR LHAIWLKLGE LGGSEAELAA FEKEIAAFES ELQAYKGKGN PEVEWLREDA  60
EQIKYILQAY RHN                                                     73

SEQ ID NO: 802          moltype = AA  length = 73
FEATURE                 Location/Qualifiers
REGION                  1..73
                        note = artificial construct
source                  1..73
                        mol_type = protein
                        organism = synthetic construct
SEQUENCE: 802
MGSWAEFRWA LHAIWLKLGE LGGSEAELAA FEKEIAAFES ELQAYKGKGN PEVEWLREDA  60
EQIKYILQAY RHN                                                     73

SEQ ID NO: 803          moltype = AA  length = 73
FEATURE                 Location/Qualifiers
REGION                  1..73
                        note = artificial construct
source                  1..73
                        mol_type = protein
                        organism = synthetic construct
SEQUENCE: 803
MGSWAEFRWR LHAIWLKLGA LGGSEAELAA FEKEIAAFES ELQAYKGKGN PEVEWLRQDA  60
```

```
AQIKYILQAY RHN                                                    73

SEQ ID NO: 804          moltype = AA  length = 73
FEATURE                 Location/Qualifiers
REGION                  1..73
                        note = artificial construct
source                  1..73
                        mol_type = protein
                        organism = synthetic construct
SEQUENCE: 804
MGSWAEFRWR LHAIWLQLGA LGGSEAELAA FEKEIAAFES ELQAYKGKGN PEVEWLRQDA  60
AQIKYILQAY RHN                                                    73

SEQ ID NO: 805          moltype = AA  length = 73
FEATURE                 Location/Qualifiers
REGION                  1..73
                        note = artificial construct
source                  1..73
                        mol_type = protein
                        organism = synthetic construct
SEQUENCE: 805
MGSWAEFRWR LHAIWLRLGA LGGTEAELAA FEKEIAAFES ELQAYKGKGN PEVEWLRQDA  60
AQIKYILQAY RHN                                                    73

SEQ ID NO: 806          moltype = AA  length = 73
FEATURE                 Location/Qualifiers
REGION                  1..73
                        note = artificial construct
source                  1..73
                        mol_type = protein
                        organism = synthetic construct
SEQUENCE: 806
MGSWAEFRWR LHAIWLRLGA LGGSEAELAA FEKEIAAFES ELQAYKGKGN PEVEWLRQDA  60
AQIKYILQAY RHN                                                    73

SEQ ID NO: 807          moltype = AA  length = 73
FEATURE                 Location/Qualifiers
REGION                  1..73
                        note = artificial construct
source                  1..73
                        mol_type = protein
                        organism = synthetic construct
SEQUENCE: 807
MGSWAEFRWK LEAIWLRLGA LGGSEAELAA FEKEIAAFES ELQAYKGKGN PEVEWLRQDA  60
AQIKYILQAY RHN                                                    73

SEQ ID NO: 808          moltype = AA  length = 73
FEATURE                 Location/Qualifiers
REGION                  1..73
                        note = artificial construct
source                  1..73
                        mol_type = protein
                        organism = synthetic construct
SEQUENCE: 808
MGSWAEFRWK LGAIWLRLGA LGGSEAELAA FEKEIAAFES ELQAYKGKGN PEVEWLRQDA  60
AQIKYILQAY RHN                                                    73

SEQ ID NO: 809          moltype = AA  length = 73
FEATURE                 Location/Qualifiers
REGION                  1..73
                        note = artificial construct
source                  1..73
                        mol_type = protein
                        organism = synthetic construct
SEQUENCE: 809
MGSWYEFRWR LHAIWLRLGA LGGSEAELAA FEKEIAAFES ELQAYKGKGN PEVEWLRQDA  60
AQIRYILQAY RHN                                                    73

SEQ ID NO: 810          moltype = AA  length = 73
FEATURE                 Location/Qualifiers
REGION                  1..73
                        note = artificial construct
source                  1..73
                        mol_type = protein
                        organism = synthetic construct
SEQUENCE: 810
MGSWHEFLRR LLAIEMRLYA LGGSEAELAA FEKEIAAFES ELQAYKGKGN PEVEHLRVRA  60
ASIRQMLQAY RHN                                                    73
```

```
SEQ ID NO: 811         moltype = AA  length = 73
FEATURE                Location/Qualifiers
REGION                 1..73
                       note = artificial construct
source                 1..73
                       mol_type = protein
                       organism = synthetic construct
SEQUENCE: 811
MGSWWGFKVN LAWIKWKLEA LGGSEAELAY FELWIANFEH SLQEYKGKGN PEVEALRKEA  60
AAIRDELQAY RHN                                                     73

SEQ ID NO: 812         moltype = AA  length = 73
FEATURE                Location/Qualifiers
REGION                 1..73
                       note = artificial construct
source                 1..73
                       mol_type = protein
                       organism = synthetic construct
SEQUENCE: 812
MGSWVNFKTH LARIKVHLEA LGGSEAELAL FEHDIANFEQ VLQQYKGKGN PEVEALRKEA  60
AAIRDELQAY RHN                                                     73

SEQ ID NO: 813         moltype = AA  length = 73
FEATURE                Location/Qualifiers
REGION                 1..73
                       note = artificial construct
source                 1..73
                       mol_type = protein
                       organism = synthetic construct
SEQUENCE: 813
MGSWLVFKDE LAGIKNYLEA LGGSEAELAT FEQDIAWFEQ WLQNYKGKGN PEVEALRKEA  60
AAIRDELQAY RHN                                                     73

SEQ ID NO: 814         moltype = AA  length = 73
FEATURE                Location/Qualifiers
REGION                 1..73
                       note = artificial construct
source                 1..73
                       mol_type = protein
                       organism = synthetic construct
SEQUENCE: 814
MGSWKTFKIE LAGIKLELEA LGGSEAELAG FENAIAQFES SLQYYKGKGN PEVEALRKEA  60
AAIRDELQAY RHN                                                     73

SEQ ID NO: 815         moltype = AA  length = 73
FEATURE                Location/Qualifiers
REGION                 1..73
                       note = artificial construct
source                 1..73
                       mol_type = protein
                       organism = synthetic construct
SEQUENCE: 815
MGSWWEFKVR LSAIQYRLYA LGGSEAELAA FEKEIAAFES ELQAYKGKGN PEVEALREQA  60
ALIRTILQAY RHN                                                     73

SEQ ID NO: 816         moltype = AA  length = 73
FEATURE                Location/Qualifiers
REGION                 1..73
                       note = artificial construct
source                 1..73
                       mol_type = protein
                       organism = synthetic construct
SEQUENCE: 816
MGSWWEFHIR LHAINYRLAA LGGSEAELAA FEKEIAAFES ELQAYKGKGN PEVEALRELA  60
AKIRGDLQAY RHN                                                     73

SEQ ID NO: 817         moltype = AA  length = 73
FEATURE                Location/Qualifiers
REGION                 1..73
                       note = artificial construct
source                 1..73
                       mol_type = protein
                       organism = synthetic construct
SEQUENCE: 817
MGSWWEFQVR LRAIQYRLNA LGGSEAELAA FEKEIAAFES ELQAYKGKGN PEVEYLRGLA  60
AQIRFDLQAY RHN                                                     73

SEQ ID NO: 818         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 818
MGSWWEFKIR LYAIEYRLNA LGGSEAELAA FEKEIAAFES ELQAYKGKGN PEVEALRAKA  60
AQIRYNLQAY RHN                                                     73

SEQ ID NO: 819          moltype = AA  length = 73
FEATURE                 Location/Qualifiers
REGION                  1..73
                        note = artificial construct
source                  1..73
                        mol_type = protein
                        organism = synthetic construct
SEQUENCE: 819
MGSWFEFNIR LHAIEYRLKA LGGSEAELAA FEKEIAAFES ELQAYKGKGN PEVEELRNYA  60
ASIRKLLQAY RHN                                                     73

SEQ ID NO: 820          moltype = AA  length = 73
FEATURE                 Location/Qualifiers
REGION                  1..73
                        note = artificial construct
source                  1..73
                        mol_type = protein
                        organism = synthetic construct
SEQUENCE: 820
MGSWFEFEIR LRAIEYRLSA LGGSEAELAA FEKEIAAFES ELQAYKGKGN PEVEKLRELA  60
AEIRYALQAY RHN                                                     73

SEQ ID NO: 821          moltype = AA  length = 73
FEATURE                 Location/Qualifiers
REGION                  1..73
                        note = artificial construct
source                  1..73
                        mol_type = protein
                        organism = synthetic construct
SEQUENCE: 821
MGSWFEFKIR LYAIQYRLSA LGGSEAELAA FEKEIAAFES ELQAYKGKGN PEVEELRNLA  60
AEIRHSLQAY RHN                                                     73

SEQ ID NO: 822          moltype = AA  length = 73
FEATURE                 Location/Qualifiers
REGION                  1..73
                        note = artificial construct
source                  1..73
                        mol_type = protein
                        organism = synthetic construct
SEQUENCE: 822
MGSWWEFKVR LRAIEYRLSA LGGSEAELAA FEKEIAAFES ELQAYKGKGN PEVEELRVLA  60
ASIRIHLQAY RHN                                                     73

SEQ ID NO: 823          moltype = AA  length = 73
FEATURE                 Location/Qualifiers
REGION                  1..73
                        note = artificial construct
source                  1..73
                        mol_type = protein
                        organism = synthetic construct
SEQUENCE: 823
MGSWSEFWFR LHAILYRLQA LGGSEAELAA FEKEIAAFES ELQAYKGKGN PEVETLRDAA  60
AEIRVALQAY RHN                                                     73

SEQ ID NO: 824          moltype = AA  length = 73
FEATURE                 Location/Qualifiers
REGION                  1..73
                        note = artificial construct
source                  1..73
                        mol_type = protein
                        organism = synthetic construct
SEQUENCE: 824
MGSWIEFWVR LNAILYRLYA LGGSEAELAA FEKEIAAFES ELQAYKGKGN PEVEALRDSA  60
AEIRRWLQAY RHN                                                     73

SEQ ID NO: 825          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 825
MGSWVEFWIR LNAIKYRLLA LGGSEAELAA FEKEIAAFES ELQAYKGKGN PEVEKLRQDA  60
ADIRELLQAY RHN                                                     73

SEQ ID NO: 826          moltype = AA  length = 73
FEATURE                 Location/Qualifiers
REGION                  1..73
                        note = artificial construct
source                  1..73
                        mol_type = protein
                        organism = synthetic construct
SEQUENCE: 826
MGSWTEFWWR LSAIVYRLNA LGGSEAELAA FEKEIAAFES ELQAYKGKGN PEVEELRDMA  60
ADIRSLLQAY RHN                                                     73

SEQ ID NO: 827          moltype = AA  length = 73
FEATURE                 Location/Qualifiers
REGION                  1..73
                        note = artificial construct
source                  1..73
                        mol_type = protein
                        organism = synthetic construct
SEQUENCE: 827
MGSWWEFYLR LRAISYRLQA LGGSEAELAA FEKEIAAFES ELQAYKGKGN PEVEGLRQDA  60
AEIRKLLQAY RHN                                                     73

SEQ ID NO: 828          moltype = AA  length = 73
FEATURE                 Location/Qualifiers
REGION                  1..73
                        note = artificial construct
source                  1..73
                        mol_type = protein
                        organism = synthetic construct
SEQUENCE: 828
MGSWWEFHVR LRAIEYRLEA LGGSEAELAA FEKEIAAFES ELQAYKGKGN PEVEQLRLIA  60
ANIRHLLQAY RHN                                                     73

SEQ ID NO: 829          moltype = AA  length = 73
FEATURE                 Location/Qualifiers
REGION                  1..73
                        note = artificial construct
source                  1..73
                        mol_type = protein
                        organism = synthetic construct
SEQUENCE: 829
MGSWWEFHVR LKAIEYRLLA LGGSEAELAA FEKEIAAFES ELQAYKGKGN PEVEDLRYIA  60
ANIRQLLQAY RHN                                                     73

SEQ ID NO: 830          moltype = AA  length = 73
FEATURE                 Location/Qualifiers
REGION                  1..73
                        note = artificial construct
source                  1..73
                        mol_type = protein
                        organism = synthetic construct
SEQUENCE: 830
MGSWWEFKVR LKAIEYRLLA LGGSEAELAA FEKEIAAFES ELQAYKGKGN PEVEDLRYIA  60
ANIRQLLQAY RHN                                                     73

SEQ ID NO: 831          moltype = AA  length = 73
FEATURE                 Location/Qualifiers
REGION                  1..73
                        note = artificial construct
source                  1..73
                        mol_type = protein
                        organism = synthetic construct
SEQUENCE: 831
MGSWWEFQVR LAAIEYRLKA LGGSEAELAA FEKEIAAFES ELQAYKGKGN PEVENLRQLA  60
AHIRSVLQAY RHN                                                     73

SEQ ID NO: 832          moltype = AA  length = 73
FEATURE                 Location/Qualifiers
REGION                  1..73
                        note = artificial construct
source                  1..73
                        mol_type = protein
```

```
                        organism = synthetic construct
SEQUENCE: 832
MGSWWEFQVR LSAIEYRLTA LGGSEAELAA FEKEIAAFES ELQAYKGKGN PEVEELRQKA  60
ARIRSLLQAY RHN                                                     73

SEQ ID NO: 833          moltype = AA  length = 73
FEATURE                 Location/Qualifiers
REGION                  1..73
                        note = artificial construct
source                  1..73
                        mol_type = protein
                        organism = synthetic construct
SEQUENCE: 833
MGSWWEFNIR LHAIDYRLKA LGGSEAELAA FEKEIAAFES ELQAYKGKGN PEVELLREKA  60
AQIRAQLQAY RHN                                                     73

SEQ ID NO: 834          moltype = AA  length = 73
FEATURE                 Location/Qualifiers
REGION                  1..73
                        note = artificial construct
source                  1..73
                        mol_type = protein
                        organism = synthetic construct
SEQUENCE: 834
MGSWWEFRVR LEAIDYRLKA LGGSEAELAA FEKEIAAFES ELQAYKGKGN PEVEYLRMKA  60
ATIRAILQAY RHN                                                     73

SEQ ID NO: 835          moltype = AA  length = 73
FEATURE                 Location/Qualifiers
REGION                  1..73
                        note = artificial construct
source                  1..73
                        mol_type = protein
                        organism = synthetic construct
SEQUENCE: 835
MGSWYEFDIR LEAIKYRLSA LGGSEAELAA FEKEIAAFES ELQAYKGKGN PEVEYLRKKA  60
AVIRSMLQAY RHN                                                     73

SEQ ID NO: 836          moltype = AA  length = 73
FEATURE                 Location/Qualifiers
REGION                  1..73
                        note = artificial construct
source                  1..73
                        mol_type = protein
                        organism = synthetic construct
SEQUENCE: 836
MGSWWEFRIR LEAIWYRLHA LGGSEAELAA FEKEIAAFES ELQAYKGKGN PEVEDLRIFA  60
ANIRSKLQAY RHN                                                     73

SEQ ID NO: 837          moltype = AA  length = 73
FEATURE                 Location/Qualifiers
REGION                  1..73
                        note = artificial construct
source                  1..73
                        mol_type = protein
                        organism = synthetic construct
SEQUENCE: 837
MGSWWEFNVR LQAIKYRLSA LGGSEAELAA FEKEIAAFES ELQAYKGKGN PEVEDLRKTA  60
AHIRWQLQAY RHN                                                     73

SEQ ID NO: 838          moltype = AA  length = 73
FEATURE                 Location/Qualifiers
REGION                  1..73
                        note = artificial construct
source                  1..73
                        mol_type = protein
                        organism = synthetic construct
SEQUENCE: 838
MGSWWEFNVR LSAIRYRLLA LGGSEAELAA FEKEIAAFES ELQAYKGKGN PEVEDLRASA  60
AQIRAMLQAY RHN                                                     73

SEQ ID NO: 839          moltype = AA  length = 73
FEATURE                 Location/Qualifiers
REGION                  1..73
                        note = artificial construct
source                  1..73
                        mol_type = protein
                        organism = synthetic construct
SEQUENCE: 839
```

```
MGSWWEFNMR LSAIKYRLYA LGGSEAELAA FEKEIAAFES ELQAYKGKGN PEVEILRRLA  60
ADIRERLQAY RHN                                                      73

SEQ ID NO: 840         moltype = AA  length = 73
FEATURE                Location/Qualifiers
REGION                 1..73
                       note = artificial construct
source                 1..73
                       mol_type = protein
                       organism = synthetic construct
SEQUENCE: 840
MGSWWEFHIR LRAIKYRLYA LGGSEAELAA FEKEIAAFES ELQAYKGKGN PEVEDLRILA  60
AEIRAQLQAY RHN                                                      73

SEQ ID NO: 841         moltype = AA  length = 73
FEATURE                Location/Qualifiers
REGION                 1..73
                       note = artificial construct
source                 1..73
                       mol_type = protein
                       organism = synthetic construct
SEQUENCE: 841
MGSWVEFYER LDAIDRRLWA LGGSEAELAA FEKEIAAFES ELQAYKGKGN PEVEELRVHA  60
ASIRAWLQAY RHN                                                      73

SEQ ID NO: 842         moltype = AA  length = 73
FEATURE                Location/Qualifiers
REGION                 1..73
                       note = artificial construct
source                 1..73
                       mol_type = protein
                       organism = synthetic construct
SEQUENCE: 842
MGSWFEFYDR LNAIDARLWA LGGSEAELAA FEKEIAAFES ELQAYKGKGN PEVESLRAHA  60
AAIREWLQAY RHN                                                      73

SEQ ID NO: 843         moltype = AA  length = 73
FEATURE                Location/Qualifiers
REGION                 1..73
                       note = artificial construct
source                 1..73
                       mol_type = protein
                       organism = synthetic construct
SEQUENCE: 843
MGSWSEFYDR LNAIDARLWA LGGSEAELAA FEKEIAAFES ELQAYKGKGN PEVESLRVHA  60
AAIREWLQAY RHN                                                      73

SEQ ID NO: 844         moltype = AA  length = 73
FEATURE                Location/Qualifiers
REGION                 1..73
                       note = artificial construct
source                 1..73
                       mol_type = protein
                       organism = synthetic construct
SEQUENCE: 844
MGSWSEFYDR LNAIDARLWA LGGSEAELAA FEKEIAAFES ELQAYKGKGN PEVESLRAHA  60
AAIREWLQAY RHN                                                      73

SEQ ID NO: 845         moltype = AA  length = 73
FEATURE                Location/Qualifiers
REGION                 1..73
                       note = artificial construct
source                 1..73
                       mol_type = protein
                       organism = synthetic construct
SEQUENCE: 845
MGSWSEFYDR LNAIDARLWA LGGSEAELAA FEKEIAAFES ELQAYKGKGN PEVESLKAHA  60
AAIREWLQAY RHN                                                      73

SEQ ID NO: 846         moltype = AA  length = 73
FEATURE                Location/Qualifiers
REGION                 1..73
                       note = artificial construct
source                 1..73
                       mol_type = protein
                       organism = synthetic construct
SEQUENCE: 846
MGSWSEFYDR LNAIDARLWA LGGSEAELAA FEKEIAAFES ELQAYKGKGN PEVESLQAHA  60
AAIREWLQAY RHN                                                      73
```

```
SEQ ID NO: 847         moltype = AA  length = 73
FEATURE                Location/Qualifiers
REGION                 1..73
                       note = artificial construct
source                 1..73
                       mol_type = protein
                       organism = synthetic construct
SEQUENCE: 847
MGSWSEFYDR LNAIDARLWA LGGSEAELAA FEKEIAAFES ELQAYKGKGN PEVESLRAHA  60
AGIREWLQAY RHN                                                     73

SEQ ID NO: 848         moltype = AA  length = 73
FEATURE                Location/Qualifiers
REGION                 1..73
                       note = artificial construct
source                 1..73
                       mol_type = protein
                       organism = synthetic construct
SEQUENCE: 848
MGSWFEFYDR LNAIDARLWA LGGSEAELAA FEKEIAAFES ELQAYKGKGN PEVESLREHA  60
AHIREWLQAY RHN                                                     73

SEQ ID NO: 849         moltype = AA  length = 73
FEATURE                Location/Qualifiers
REGION                 1..73
                       note = artificial construct
source                 1..73
                       mol_type = protein
                       organism = synthetic construct
SEQUENCE: 849
MGSWFEFYDR LNAIDARLWA LGGSEAELAA FEKEIAAFES ELQAYKGKGN PEVESLREHA  60
AAIREWLQAY RHN                                                     73

SEQ ID NO: 850         moltype = AA  length = 73
FEATURE                Location/Qualifiers
REGION                 1..73
                       note = artificial construct
source                 1..73
                       mol_type = protein
                       organism = synthetic construct
SEQUENCE: 850
MGSWSEFYDR LNAIDARLWA LGGSEAELAA FEKEIAAFES ELQAYKGKGN PEVESLREHA  60
AAIREWLQAY RHN                                                     73

SEQ ID NO: 851         moltype = AA  length = 73
FEATURE                Location/Qualifiers
REGION                 1..73
                       note = artificial construct
source                 1..73
                       mol_type = protein
                       organism = synthetic construct
SEQUENCE: 851
MGSWHEFYDR LDAIYFRLWA LGGSEAELAA FEKEIAAFES ELQAYKGKGN PEVELLRLLA  60
AEIRKELQAY RHN                                                     73

SEQ ID NO: 852         moltype = AA  length = 73
FEATURE                Location/Qualifiers
REGION                 1..73
                       note = artificial construct
source                 1..73
                       mol_type = protein
                       organism = synthetic construct
SEQUENCE: 852
MGSWHEFITR LEAIDQRLWA LGGSEAELAA FEKEIAAFES ELQAYKGKGN PEVEYLRFWA  60
AEIRFILQAY RHN                                                     73

SEQ ID NO: 853         moltype = AA  length = 73
FEATURE                Location/Qualifiers
REGION                 1..73
                       note = artificial construct
source                 1..73
                       mol_type = protein
                       organism = synthetic construct
SEQUENCE: 853
MGSWMEFFDR LVAIDERLWA LGGSEAELAA FEKEIAAFES ELQAYKGKGN PEVEYLRMWA  60
AEIRFLLQAY RHN                                                     73

SEQ ID NO: 854         moltype = AA  length = 73
```

```
FEATURE                Location/Qualifiers
REGION                 1..73
                       note = artificial construct
source                 1..73
                       mol_type = protein
                       organism = synthetic construct
SEQUENCE: 854
MGSWVEFSGR LIAIDNRLWA LGGSEAELAA FEKEIAAFES ELQAYKGKGN PEVEYLRMWA  60
AEIRYILQAY RHN                                                     73

SEQ ID NO: 855         moltype = AA  length = 73
FEATURE                Location/Qualifiers
REGION                 1..73
                       note = artificial construct
source                 1..73
                       mol_type = protein
                       organism = synthetic construct
SEQUENCE: 855
MGSWVEFHHR LFAIDERLWA LGGSEAELAA FEKEIAAFES ELQAYKGKGN PEVEYLRMVA  60
AEIRYILQAY RHN                                                     73

SEQ ID NO: 856         moltype = AA  length = 73
FEATURE                Location/Qualifiers
REGION                 1..73
                       note = artificial construct
source                 1..73
                       mol_type = protein
                       organism = synthetic construct
SEQUENCE: 856
MGSWHEFMER LIAIDGRLWA LGGSEAELAA FEKEIAAFES ELQAYKGKGN PEVEYLRFVA  60
AFIRDVLQAY RHN                                                     73

SEQ ID NO: 857         moltype = AA  length = 73
FEATURE                Location/Qualifiers
REGION                 1..73
                       note = artificial construct
source                 1..73
                       mol_type = protein
                       organism = synthetic construct
SEQUENCE: 857
MGSWKEFIQR LDAIHYRLWA LGGSEAELAA FEKEIAAFES ELQAYKGKGN PEVEYLRFVA  60
AFIRFELQAY RHN                                                     73

SEQ ID NO: 858         moltype = AA  length = 73
FEATURE                Location/Qualifiers
REGION                 1..73
                       note = artificial construct
source                 1..73
                       mol_type = protein
                       organism = synthetic construct
SEQUENCE: 858
MGSWSEFIFR LDAIHSRLQA LGGSEAELAA FEKEIAAFES ELQAYKGKGN PEVEYLRFIA  60
AEIRLKLQAY RHN                                                     73

SEQ ID NO: 859         moltype = AA  length = 73
FEATURE                Location/Qualifiers
REGION                 1..73
                       note = artificial construct
source                 1..73
                       mol_type = protein
                       organism = synthetic construct
SEQUENCE: 859
MGSWFEFYDR LNAIDARLWA LGGSEAELAA FEKEIAAFES ELQAYKGKGN PEVENLRVHA  60
AAIREWLQAY RHN                                                     73

SEQ ID NO: 860         moltype = AA  length = 73
FEATURE                Location/Qualifiers
REGION                 1..73
                       note = artificial construct
source                 1..73
                       mol_type = protein
                       organism = synthetic construct
SEQUENCE: 860
MGSWLEFYDR LNAIDARLWA LGGSEAELAA FEKEIAAFES ELQAYKGKGN PEVENLRVHA  60
AAIREWLQAY RHN                                                     73

SEQ ID NO: 861         moltype = AA  length = 73
FEATURE                Location/Qualifiers
REGION                 1..73
```

```
                        note = artificial construct
source                  1..73
                        mol_type = protein
                        organism = synthetic construct
SEQUENCE: 861
MGSWFEFYHR LNAIDARLWA LGGSEAELAA FEKEIAAFES ELQAYKGKGN PEVENLRVHA  60
AAIREWLQAY RHN                                                     73

SEQ ID NO: 862          moltype = AA  length = 73
FEATURE                 Location/Qualifiers
REGION                  1..73
                        note = artificial construct
source                  1..73
                        mol_type = protein
                        organism = synthetic construct
SEQUENCE: 862
MGSWFEFYDR LNAIDSRLWA LGGSEAELAA FEKEIAAFES ELQAYKGKGN PEVENLRVHA  60
AAIREWLQAY RHN                                                     73

SEQ ID NO: 863          moltype = AA  length = 73
FEATURE                 Location/Qualifiers
REGION                  1..73
                        note = artificial construct
source                  1..73
                        mol_type = protein
                        organism = synthetic construct
SEQUENCE: 863
MGSWFEFYDR LNAIDARLWA LGGSEAELAA FEKEIAAFES ELQAYKGKGN PEVESLRVHA  60
AAIREWLQAY RHN                                                     73

SEQ ID NO: 864          moltype = AA  length = 73
FEATURE                 Location/Qualifiers
REGION                  1..73
                        note = artificial construct
source                  1..73
                        mol_type = protein
                        organism = synthetic construct
SEQUENCE: 864
MGSWFEFYDR LNAIDARLWA LGGSEAELAA FEKEIAAFES ELQAYKGKGN PEVENLRDHA  60
AAIREWLQAY RHN                                                     73

SEQ ID NO: 865          moltype = AA  length = 73
FEATURE                 Location/Qualifiers
REGION                  1..73
                        note = artificial construct
source                  1..73
                        mol_type = protein
                        organism = synthetic construct
SEQUENCE: 865
MGSWFEFYDR LNAIDARLWA LGGSEAELAA FEKEIAAFES ELQAYKGKGN PEVENLREHA  60
AAIREWLQAY RHN                                                     73

SEQ ID NO: 866          moltype = AA  length = 73
FEATURE                 Location/Qualifiers
REGION                  1..73
                        note = artificial construct
source                  1..73
                        mol_type = protein
                        organism = synthetic construct
SEQUENCE: 866
MGSWFEFYDR LNAIDARLWA LGGSEAELAA FEKEIAAFES ELQAYKGKGN PEVENLRVHA  60
AHIREWLQAY RHN                                                     73

SEQ ID NO: 867          moltype = AA  length = 73
FEATURE                 Location/Qualifiers
REGION                  1..73
                        note = artificial construct
source                  1..73
                        mol_type = protein
                        organism = synthetic construct
SEQUENCE: 867
MGSWLEFYHR LNAIDSRLWA LGGSEAELAA FEKEIAAFES ELQAYKGKGN PEVENLRVHA  60
AAIREWLQAY RHN                                                     73

SEQ ID NO: 868          moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 868
MGSWLEFYHR LNAIDSRLWA LGGSEAELAA FEKEIAAFES ELQAYKGKGN PEVESLRDHA  60
AHIREWLQAY RHN                                                    73

SEQ ID NO: 869          moltype = AA  length = 73
FEATURE                 Location/Qualifiers
REGION                  1..73
                        note = artificial construct
source                  1..73
                        mol_type = protein
                        organism = synthetic construct
SEQUENCE: 869
MGSWFEFYHR LNAIDSRLWA LGGSEAELAA FEKEIAAFES ELQAYKGKGN PEVESLRDHA  60
AHIREWLQAY RHN                                                    73

SEQ ID NO: 870          moltype = AA  length = 73
FEATURE                 Location/Qualifiers
REGION                  1..73
                        note = artificial construct
source                  1..73
                        mol_type = protein
                        organism = synthetic construct
SEQUENCE: 870
MGSWLEFYDR LNAIDSRLWA LGGSEAELAA FEKEIAAFES ELQAYKGKGN PEVESLRDHA  60
AHIREWLQAY RHN                                                    73

SEQ ID NO: 871          moltype = AA  length = 73
FEATURE                 Location/Qualifiers
REGION                  1..73
                        note = artificial construct
source                  1..73
                        mol_type = protein
                        organism = synthetic construct
SEQUENCE: 871
MGSWLEFYHR LNAIDARLWA LGGSEAELAA FEKEIAAFES ELQAYKGKGN PEVESLRDHA  60
AHIREWLQAY RHN                                                    73

SEQ ID NO: 872          moltype = AA  length = 73
FEATURE                 Location/Qualifiers
REGION                  1..73
                        note = artificial construct
source                  1..73
                        mol_type = protein
                        organism = synthetic construct
SEQUENCE: 872
MGSWLEFYHR LNAIDSRLWA LGGSEAELAA FEKEIAAFES ELQAYKGKGN PEVENLRDHA  60
AHIREWLQAY RHN                                                    73

SEQ ID NO: 873          moltype = AA  length = 73
FEATURE                 Location/Qualifiers
REGION                  1..73
                        note = artificial construct
source                  1..73
                        mol_type = protein
                        organism = synthetic construct
SEQUENCE: 873
MGSWLEFYHR LNAIDSRLWA LGGSEAELAA FEKEIAAFES ELQAYKGKGN PEVESLRVHA  60
AHIREWLQAY RHN                                                    73

SEQ ID NO: 874          moltype = AA  length = 73
FEATURE                 Location/Qualifiers
REGION                  1..73
                        note = artificial construct
source                  1..73
                        mol_type = protein
                        organism = synthetic construct
SEQUENCE: 874
MGSWLEFYHR LNAIDSRLWA LGGSEAELAA FEKEIAAFES ELQAYKGKGN PEVESLRDHA  60
AAIREWLQAY RHN                                                    73

SEQ ID NO: 875          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 875
MGSWFEFYDR LNAIDARLWA LGGSEAELAA FEKEIAAFES ELQAYKGKGN PEVESLRDHA  60
AHIREWLQAY RHN                                                     73

SEQ ID NO: 876          moltype = AA  length = 73
FEATURE                 Location/Qualifiers
REGION                  1..73
                        note = artificial construct
source                  1..73
                        mol_type = protein
                        organism = synthetic construct
SEQUENCE: 876
MGSWFEFYER LNAIDSRLWA LGGSEAELAA FEKEIAAFES ELQAYKGKGN PEVEKLRAHA  60
ASIRTWLQAY RHN                                                     73

SEQ ID NO: 877          moltype = AA  length = 73
FEATURE                 Location/Qualifiers
REGION                  1..73
                        note = artificial construct
source                  1..73
                        mol_type = protein
                        organism = synthetic construct
SEQUENCE: 877
MGSWIEFYWR LEAIDQRLWA LGGSEAELAA FEKEIAAFES ELQAYKGKGN PEVEDLRVHA  60
AAIRWWLQAY RHN                                                     73

SEQ ID NO: 878          moltype = AA  length = 73
FEATURE                 Location/Qualifiers
REGION                  1..73
                        note = artificial construct
source                  1..73
                        mol_type = protein
                        organism = synthetic construct
SEQUENCE: 878
MGSWSEFVKR LDAIDQRLWA LGGSEAELAA FEKEIAAFES ELQAYKGKGN PEVESLRVHA  60
AAIRAWLQAY RHN                                                     73

SEQ ID NO: 879          moltype = AA  length = 73
FEATURE                 Location/Qualifiers
REGION                  1..73
                        note = artificial construct
source                  1..73
                        mol_type = protein
                        organism = synthetic construct
SEQUENCE: 879
MGSWEEFYYR LEAIDARLFA LGGSEAELAA FEKEIAAFES ELQAYKGKGN PEVEELRVHA  60
AHIRDWLQAY RHN                                                     73

SEQ ID NO: 880          moltype = AA  length = 73
FEATURE                 Location/Qualifiers
REGION                  1..73
                        note = artificial construct
source                  1..73
                        mol_type = protein
                        organism = synthetic construct
SEQUENCE: 880
MGSWVEFHYR LQAIDARLWA LGGSEAELAA FEKEIAAFES ELQAYKGKGN PEVEELRVHA  60
AHIRKWLQAY RHN                                                     73

SEQ ID NO: 881          moltype = AA  length = 73
FEATURE                 Location/Qualifiers
REGION                  1..73
                        note = artificial construct
source                  1..73
                        mol_type = protein
                        organism = synthetic construct
SEQUENCE: 881
MGSWVEFVGR LNAIDARLWA LGGSEAELAA FEKEIAAFES ELQAYKGKGN PEVEELRHHA  60
AEIRNWLQAY RHN                                                     73

SEQ ID NO: 882          moltype = AA  length = 73
FEATURE                 Location/Qualifiers
REGION                  1..73
                        note = artificial construct
source                  1..73
                        mol_type = protein
                        organism = synthetic construct
SEQUENCE: 882
MGSWNEFMDR LNAIDNRLWA LGGSEAELAA FEKEIAAFES ELQAYKGKGN PEVENLRKQA  60
```

```
ASIRLWLQAY RHN                                                    73

SEQ ID NO: 883          moltype = AA  length = 73
FEATURE                 Location/Qualifiers
REGION                  1..73
                        note = artificial construct
source                  1..73
                        mol_type = protein
                        organism = synthetic construct
SEQUENCE: 883
MGSWNEFFQR LNAIDERLWA LGGSEAELAA FEKEIAAFES ELQAYKGKGN PEVEDLRQHA  60
ANIRWWLQAY RHN                                                    73

SEQ ID NO: 884          moltype = AA  length = 73
FEATURE                 Location/Qualifiers
REGION                  1..73
                        note = artificial construct
source                  1..73
                        mol_type = protein
                        organism = synthetic construct
SEQUENCE: 884
MGSWYEFVVR LFAIDERLWA LGGSEAELAA FEKEIAAFES ELQAYKGKGN PEVESLREHA  60
AHIRSWLQAY RHN                                                    73

SEQ ID NO: 885          moltype = AA  length = 73
FEATURE                 Location/Qualifiers
REGION                  1..73
                        note = artificial construct
source                  1..73
                        mol_type = protein
                        organism = synthetic construct
SEQUENCE: 885
MGSWYEFYLR LDAIDHRLWA LGGSEAELAA FEKEIAAFES ELQAYKGKGN PEVEMLREHA  60
AHIRKWLQAY RHN                                                    73

SEQ ID NO: 886          moltype = AA  length = 73
FEATURE                 Location/Qualifiers
REGION                  1..73
                        note = artificial construct
source                  1..73
                        mol_type = protein
                        organism = synthetic construct
SEQUENCE: 886
MGSWYEFRAR LLAIDERLWA LGGSEAELAA FEKEIAAFES ELQAYKGKGN PEVEHLREHA  60
AHIRNFLQAY RHN                                                    73

SEQ ID NO: 887          moltype = AA  length = 73
FEATURE                 Location/Qualifiers
REGION                  1..73
                        note = artificial construct
source                  1..73
                        mol_type = protein
                        organism = synthetic construct
SEQUENCE: 887
MGSWTEFWHR LEAIDSRLWA LGGSEAELAA FEKEIAAFES ELQAYKGKGN PEVESLREHA  60
AHIRVWLQAY RHN                                                    73

SEQ ID NO: 888          moltype = AA  length = 73
FEATURE                 Location/Qualifiers
REGION                  1..73
                        note = artificial construct
source                  1..73
                        mol_type = protein
                        organism = synthetic construct
SEQUENCE: 888
MGSWTEFQNR LNAIDHRLWA LGGSEAELAA FEKEIAAFES ELQAYKGKGN PEVESLREHA  60
AKIRVWLQAY RHN                                                    73

SEQ ID NO: 889          moltype = AA  length = 73
FEATURE                 Location/Qualifiers
REGION                  1..73
                        note = artificial construct
source                  1..73
                        mol_type = protein
                        organism = synthetic construct
SEQUENCE: 889
MGSWSEFFKR LEAIDRRLWA LGGSEAELAA FEKEIAAFES ELQAYKGKGN PEVEELREHA  60
AHIRVWLQAY RHN                                                    73
```

```
SEQ ID NO: 890          moltype = AA  length = 73
FEATURE                 Location/Qualifiers
REGION                  1..73
                        note = artificial construct
source                  1..73
                        mol_type = protein
                        organism = synthetic construct
SEQUENCE: 890
MGSWYEFQQR LEAIDTRLWA LGGSEAELAA FEKEIAAFES ELQAYKGKGN PEVEELREHA  60
AHIRHWLQAY RHN                                                     73

SEQ ID NO: 891          moltype = AA  length = 73
FEATURE                 Location/Qualifiers
REGION                  1..73
                        note = artificial construct
source                  1..73
                        mol_type = protein
                        organism = synthetic construct
SEQUENCE: 891
MGSWTEFEKR LHAIDYRLWA LGGSEAELAA FEKEIAAFES ELQAYKGKGN PEVEDLREHA  60
AAIRHWLQAY RHN                                                     73

SEQ ID NO: 892          moltype = AA  length = 73
FEATURE                 Location/Qualifiers
REGION                  1..73
                        note = artificial construct
source                  1..73
                        mol_type = protein
                        organism = synthetic construct
SEQUENCE: 892
MGSWTEFHQR LDAIDERLWA LGGSEAELAA FEKEIAAFES ELQAYKGKGN PEVEFLREHA  60
AKIRMWLQAY RHN                                                     73

SEQ ID NO: 893          moltype = AA  length = 73
FEATURE                 Location/Qualifiers
REGION                  1..73
                        note = artificial construct
source                  1..73
                        mol_type = protein
                        organism = synthetic construct
SEQUENCE: 893
MGSWLEFSQR LTAIDSRLWA LGGSEAELAA FEKEIAAFES ELQAYKGKGN PEVENLREHA  60
AKIRNWLQAY RHN                                                     73

SEQ ID NO: 894          moltype = AA  length = 73
FEATURE                 Location/Qualifiers
REGION                  1..73
                        note = artificial construct
source                  1..73
                        mol_type = protein
                        organism = synthetic construct
SEQUENCE: 894
MGSWTEFVNR LYAIDSRLWA LGGSEAELAA FEKEIAAFES ELQAYKGKGN PEVEGLRTHA  60
AKIRHWLQAY RHN                                                     73

SEQ ID NO: 895          moltype = AA  length = 73
FEATURE                 Location/Qualifiers
REGION                  1..73
                        note = artificial construct
source                  1..73
                        mol_type = protein
                        organism = synthetic construct
SEQUENCE: 895
MGSWMEFVDR LSAIDRRLWA LGGSEAELAA FEKEIAAFES ELQAYKGKGN PEVEVLREHA  60
ANIRQWLQAY RHN                                                     73

SEQ ID NO: 896          moltype = AA  length = 73
FEATURE                 Location/Qualifiers
REGION                  1..73
                        note = artificial construct
source                  1..73
                        mol_type = protein
                        organism = synthetic construct
SEQUENCE: 896
MGSWVEFVSR LYAIDFRLWA LGGSEAELAA FEKEIAAFES ELQAYKGKGN PEVEALREHA  60
AQIRDWLQAY RHN                                                     73

SEQ ID NO: 897          moltype = AA  length = 73
FEATURE                 Location/Qualifiers
```

```
REGION                  1..73
                        note = artificial construct
source                  1..73
                        mol_type = protein
                        organism = synthetic construct
SEQUENCE: 897
MGSWSEFHTR LDAIDTRLWA LGGSEAELAA FEKEIAAFES ELQAYKGKGN PEVEDLRRHA  60
AAIRFWLQAY RHN                                                     73

SEQ ID NO: 898          moltype = AA  length = 73
FEATURE                 Location/Qualifiers
REGION                  1..73
                        note = artificial construct
source                  1..73
                        mol_type = protein
                        organism = synthetic construct
SEQUENCE: 898
MGSWLEFHSR LDAIDTRLWA LGGSEAELAA FEKEIAAFES ELQAYKGKGN PEVEKLREHA  60
AAIRHYLQAY RHN                                                     73

SEQ ID NO: 899          moltype = AA  length = 73
FEATURE                 Location/Qualifiers
REGION                  1..73
                        note = artificial construct
source                  1..73
                        mol_type = protein
                        organism = synthetic construct
SEQUENCE: 899
MGSWTEFYQR LDAIDTRLWA LGGSEAELAA FEKEIAAFES ELQAYKGKGN PEVEGLRQQA  60
AQIRAWLQAY RHN                                                     73

SEQ ID NO: 900          moltype = AA  length = 73
FEATURE                 Location/Qualifiers
REGION                  1..73
                        note = artificial construct
source                  1..73
                        mol_type = protein
                        organism = synthetic construct
SEQUENCE: 900
MGSWAEFSDR LNAIDQRLWA LGGSEAELAA FEKEIAAFES ELQAYKGKGN PEVEILREHA  60
AEIRKFLQAY RHN                                                     73

SEQ ID NO: 901          moltype = AA  length = 73
FEATURE                 Location/Qualifiers
REGION                  1..73
                        note = artificial construct
source                  1..73
                        mol_type = protein
                        organism = synthetic construct
SEQUENCE: 901
MGSWMEFNHR LQAIDGRLWA LGGSEAELAA FEKEIAAFES ELQAYKGKGN PEVEMLREHA  60
AAIRAFLQAY RHN                                                     73

SEQ ID NO: 902          moltype = AA  length = 73
FEATURE                 Location/Qualifiers
REGION                  1..73
                        note = artificial construct
source                  1..73
                        mol_type = protein
                        organism = synthetic construct
SEQUENCE: 902
MGSWYEFYKR LEAIDNRLYA LGGSEAELAA FEKEIAAFES ELQAYKGKGN PEVEYLREHA  60
AAIRHWLQAY RHN                                                     73

SEQ ID NO: 903          moltype = AA  length = 73
FEATURE                 Location/Qualifiers
REGION                  1..73
                        note = artificial construct
source                  1..73
                        mol_type = protein
                        organism = synthetic construct
SEQUENCE: 903
MGSWYEFYYR LEAIDNRLIA LGGSEAELAA FEKEIAAFES ELQAYKGKGN PEVEVLREHA  60
AKIREWLQAY RHN                                                     73

SEQ ID NO: 904          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 904
MGSWYEFVSR LEAIDDRLYA LGGSEAELAA FEKEIAAFES ELQAYKGKGN PEVEMLRQHA  60
AAIRHWLQAY RHN                                                     73

SEQ ID NO: 905          moltype = AA  length = 73
FEATURE                 Location/Qualifiers
REGION                  1..73
                        note = artificial construct
source                  1..73
                        mol_type = protein
                        organism = synthetic construct
SEQUENCE: 905
MGSWYEFSHR LEAIEDRLFA LGGSEAELAA FEKEIAAFES ELQAYKGKGN PEVEPLREHA  60
AYIRHWLQAY RHN                                                     73

SEQ ID NO: 906          moltype = AA  length = 73
FEATURE                 Location/Qualifiers
REGION                  1..73
                        note = artificial construct
source                  1..73
                        mol_type = protein
                        organism = synthetic construct
SEQUENCE: 906
MGSWFEFFER LAAIEDRLWA LGGSEAELAA FEKEIAAFES ELQAYKGKGN PEVESLRVHA  60
AAIRAFLQAY RHN                                                     73

SEQ ID NO: 907          moltype = AA  length = 73
FEATURE                 Location/Qualifiers
REGION                  1..73
                        note = artificial construct
source                  1..73
                        mol_type = protein
                        organism = synthetic construct
SEQUENCE: 907
MGSWIEFKYR LDAIEWRLEA LGGSEAELAA FEKEIAAFES ELQAYKGKGN PEVESLRIHA  60
AAIRTWLQAY RHN                                                     73

SEQ ID NO: 908          moltype = AA  length = 73
FEATURE                 Location/Qualifiers
REGION                  1..73
                        note = artificial construct
source                  1..73
                        mol_type = protein
                        organism = synthetic construct
SEQUENCE: 908
MGSWYEFMYR LDAIEYRLFA LGGSEAELAA FEKEIAAFES ELQAYKGKGN PEVESLRIHA  60
AMIREWLQAY RHN                                                     73

SEQ ID NO: 909          moltype = AA  length = 73
FEATURE                 Location/Qualifiers
REGION                  1..73
                        note = artificial construct
source                  1..73
                        mol_type = protein
                        organism = synthetic construct
SEQUENCE: 909
MGSWVEFVTR LEAIEDRLFA LGGSEAELAA FEKEIAAFES ELQAYKGKGN PEVEHLRAHA  60
AHIRHWLQAY RHN                                                     73

SEQ ID NO: 910          moltype = AA  length = 73
FEATURE                 Location/Qualifiers
REGION                  1..73
                        note = artificial construct
source                  1..73
                        mol_type = protein
                        organism = synthetic construct
SEQUENCE: 910
MGSWYEFVIR LDAIEDRLFA LGGSEAELAA FEKEIAAFES ELQAYKGKGN PEVEHLRVHA  60
AHIRVWLQAY RHN                                                     73

SEQ ID NO: 911          moltype = AA  length = 73
FEATURE                 Location/Qualifiers
REGION                  1..73
                        note = artificial construct
source                  1..73
                        mol_type = protein
```

```
                       organism = synthetic construct
SEQUENCE: 911
MGSWVEFVER LDAIEFRLFA LGGSEAELAA FEKEIAAFES ELQAYKGKGN PEVEKLRNHA  60
AHIRSWLQAY RHN                                                    73

SEQ ID NO: 912         moltype = AA  length = 73
FEATURE                Location/Qualifiers
REGION                 1..73
                       note = artificial construct
source                 1..73
                       mol_type = protein
                       organism = synthetic construct
SEQUENCE: 912
MGSWSEFVHR LDAIEVRLFA LGGSEAELAA FEKEIAAFES ELQAYKGKGN PEVEELRYHA  60
AKIRSWLQAY RHN                                                    73

SEQ ID NO: 913         moltype = AA  length = 73
FEATURE                Location/Qualifiers
REGION                 1..73
                       note = artificial construct
source                 1..73
                       mol_type = protein
                       organism = synthetic construct
SEQUENCE: 913
MGSWSEFYYR LAAIESRLFA LGGSEAELAA FEKEIAAFES ELQAYKGKGN PEVERLREHA  60
AHIRRWLQAY RHN                                                    73

SEQ ID NO: 914         moltype = AA  length = 73
FEATURE                Location/Qualifiers
REGION                 1..73
                       note = artificial construct
source                 1..73
                       mol_type = protein
                       organism = synthetic construct
SEQUENCE: 914
MGSWYEFYLR LSAIEDRLFA LGGSEAELAA FEKEIAAFES ELQAYKGKGN PEVESLRVQA  60
AHIRTWLQAY RHN                                                    73

SEQ ID NO: 915         moltype = AA  length = 73
FEATURE                Location/Qualifiers
REGION                 1..73
                       note = artificial construct
source                 1..73
                       mol_type = protein
                       organism = synthetic construct
SEQUENCE: 915
MGSWYEFYDR LDAIEDRLFA LGGSEAELAA FEKEIAAFES ELQAYKGKGN PEVESLRDQA  60
AYIRTWLQAY RHN                                                    73

SEQ ID NO: 916         moltype = AA  length = 73
FEATURE                Location/Qualifiers
REGION                 1..73
                       note = artificial construct
source                 1..73
                       mol_type = protein
                       organism = synthetic construct
SEQUENCE: 916
MGSWHEFWVR LEAIESRLFA LGGSEAELAA FEKEIAAFES ELQAYKGKGN PEVESLRVQA  60
AHIRSWLQAY RHN                                                    73

SEQ ID NO: 917         moltype = AA  length = 73
FEATURE                Location/Qualifiers
REGION                 1..73
                       note = artificial construct
source                 1..73
                       mol_type = protein
                       organism = synthetic construct
SEQUENCE: 917
MGSWVEFYHR LEAIEQRLMA LGGSEAELAA FEKEIAAFES ELQAYKGKGN PEVESLREQA  60
AAIRSWLQAY RHN                                                    73

SEQ ID NO: 918         moltype = AA  length = 73
FEATURE                Location/Qualifiers
REGION                 1..73
                       note = artificial construct
source                 1..73
                       mol_type = protein
                       organism = synthetic construct
SEQUENCE: 918
```

```
MGSWVEFYER LNAIEYRLEA LGGSEAELAA FEKEIAAFES ELQAYKGKGN PEVESLREHA  60
AYIRQWLQAY RHN                                                     73

SEQ ID NO: 919         moltype = AA  length = 73
FEATURE                Location/Qualifiers
REGION                 1..73
                       note = artificial construct
source                 1..73
                       mol_type = protein
                       organism = synthetic construct
SEQUENCE: 919
MGSWVEFYHR LDAIFDRLDA LGGSEAELAA FEKEIAAFES ELQAYKGKGN PEVEELRANA  60
AGIRSWLQAY RHN                                                     73

SEQ ID NO: 920         moltype = AA  length = 73
FEATURE                Location/Qualifiers
REGION                 1..73
                       note = artificial construct
source                 1..73
                       mol_type = protein
                       organism = synthetic construct
SEQUENCE: 920
MGSWSEFTDR LFAIEDRLLA LGGSEAELAA FEKEIAAFES ELQAYKGKGN PEVEDLRMHA  60
ASIRLWLQAY RHN                                                     73

SEQ ID NO: 921         moltype = AA  length = 73
FEATURE                Location/Qualifiers
REGION                 1..73
                       note = artificial construct
source                 1..73
                       mol_type = protein
                       organism = synthetic construct
SEQUENCE: 921
MGSWHEFYDR LYAIWDRLDA LGGSEAELAA FEKEIAAFES ELQAYKGKGN PEVEGLRNAA  60
AVIRIFLQAY RHN                                                     73

SEQ ID NO: 922         moltype = AA  length = 73
FEATURE                Location/Qualifiers
REGION                 1..73
                       note = artificial construct
source                 1..73
                       mol_type = protein
                       organism = synthetic construct
SEQUENCE: 922
MGSWFEFSNR LYAIWHRLTA LGGSEAELAA FEKEIAAFES ELQAYKGKGN PEVESLRTQA  60
AFIRILLQAY RHN                                                     73

SEQ ID NO: 923         moltype = AA  length = 73
FEATURE                Location/Qualifiers
REGION                 1..73
                       note = artificial construct
source                 1..73
                       mol_type = protein
                       organism = synthetic construct
SEQUENCE: 923
MGSWFEFSDR LYAIWERLDA LGGSEAELAA FEKEIAAFES ELQAYKGKGN PEVESLRFQA  60
AFIRYQLQAY RHN                                                     73

SEQ ID NO: 924         moltype = AA  length = 73
FEATURE                Location/Qualifiers
REGION                 1..73
                       note = artificial construct
source                 1..73
                       mol_type = protein
                       organism = synthetic construct
SEQUENCE: 924
MGSWFEFEDR LFAIWTRLEA LGGSEAELAA FEKEIAAFES ELQAYKGKGN PEVESLRQSA  60
ASIRWLLQAY RHN                                                     73

SEQ ID NO: 925         moltype = AA  length = 73
FEATURE                Location/Qualifiers
REGION                 1..73
                       note = artificial construct
source                 1..73
                       mol_type = protein
                       organism = synthetic construct
SEQUENCE: 925
MGSWHEFSER LFAIWTRLEA LGGSEAELAA FEKEIAAFES ELQAYKGKGN PEVEALRQSA  60
AFIRVMLQAY RHN                                                     73
```

```
SEQ ID NO: 926         moltype = AA  length = 73
FEATURE                Location/Qualifiers
REGION                 1..73
                       note = artificial construct
source                 1..73
                       mol_type = protein
                       organism = synthetic construct
SEQUENCE: 926
MGSWGEFTVR LYAIDRRLDA LGGSEAELAA FEKEIAAFES ELQAYKGKGN PEVEELRRFA  60
AIIRAFLQAY RHN                                                     73

SEQ ID NO: 927         moltype = AA  length = 73
FEATURE                Location/Qualifiers
REGION                 1..73
                       note = artificial construct
source                 1..73
                       mol_type = protein
                       organism = synthetic construct
SEQUENCE: 927
MGSWYEFDHR LMAISFRLVA LGGSEAELAA FEKEIAAFES ELQAYKGKGN PEVETLRRRA  60
ANIRHLLQAY RHN                                                     73

SEQ ID NO: 928         moltype = AA  length = 73
FEATURE                Location/Qualifiers
REGION                 1..73
                       note = artificial construct
source                 1..73
                       mol_type = protein
                       organism = synthetic construct
SEQUENCE: 928
MGSWSIFKYH LADIKLLLEA LGGSEAELAY FEFLIADFEF TLQDYKGKGN PEVEALRKEA  60
AAIRDELQAY RHN                                                     73

SEQ ID NO: 929         moltype = AA  length = 73
FEATURE                Location/Qualifiers
REGION                 1..73
                       note = artificial construct
source                 1..73
                       mol_type = protein
                       organism = synthetic construct
SEQUENCE: 929
MGSWHHFKYF LADIKSILEA LGGSEAELAI FEVQIAYFED LLQSYKGKGN PEVEALRKEA  60
AAIRDELQAY RHN                                                     73

SEQ ID NO: 930         moltype = AA  length = 73
FEATURE                Location/Qualifiers
REGION                 1..73
                       note = artificial construct
source                 1..73
                       mol_type = protein
                       organism = synthetic construct
SEQUENCE: 930
MGSWLYFKYN LAVIKHWLEA LGGSEAELAI FEMSIADFEY ELQWYKGKGN PEVEALRKEA  60
AAIRDELQAY RHN                                                     73

SEQ ID NO: 931         moltype = AA  length = 73
FEATURE                Location/Qualifiers
REGION                 1..73
                       note = artificial construct
source                 1..73
                       mol_type = protein
                       organism = synthetic construct
SEQUENCE: 931
MGSWFYFKYE LAWIKHWLEA LGGSEAELAS FETHIAFFEH QLQYYKGKGN PEVEALRKEA  60
AAIRDELQAY RHN                                                     73

SEQ ID NO: 932         moltype = AA  length = 73
FEATURE                Location/Qualifiers
REGION                 1..73
                       note = artificial construct
source                 1..73
                       mol_type = protein
                       organism = synthetic construct
SEQUENCE: 932
MGSWADFKWT LAYIKHRLEA LGGSEAELAF FEMEIAYFEQ SLQNYKGKGN PEVEALRKEA  60
AAIRDELQAY RHN                                                     73

SEQ ID NO: 933         moltype = AA  length = 73
```

```
FEATURE                Location/Qualifiers
REGION                 1..73
                       note = artificial construct
source                 1..73
                       mol_type = protein
                       organism = synthetic construct
SEQUENCE: 933
MGSWAYFKGQ LAYIKSGLEA LGGSEAELAY FELRIAYFEH WLQNYKGKGN PEVEALRKEA  60
AAIRDELQAY RHN                                                    73

SEQ ID NO: 934         moltype = AA  length = 73
FEATURE                Location/Qualifiers
REGION                 1..73
                       note = artificial construct
source                 1..73
                       mol_type = protein
                       organism = synthetic construct
SEQUENCE: 934
MGSWENFKDT LAWIKEYLEA LGGSEAELAG FEHRIAIFEH YLQYYKGKGN PEVEALRKEA  60
AAIRDELQAY RHN                                                    73

SEQ ID NO: 935         moltype = AA  length = 73
FEATURE                Location/Qualifiers
REGION                 1..73
                       note = artificial construct
source                 1..73
                       mol_type = protein
                       organism = synthetic construct
SEQUENCE: 935
MGSWVLFKDY LADIKHYLEA LGGSEAELAN FEHLIANFEG DLQTYKGKGN PEVEALRKEA  60
AAIRDELQAY RHN                                                    73

SEQ ID NO: 936         moltype = AA  length = 73
FEATURE                Location/Qualifiers
REGION                 1..73
                       note = artificial construct
source                 1..73
                       mol_type = protein
                       organism = synthetic construct
SEQUENCE: 936
MGSWSLFKHR LANIKVYLEA LGGSEAELAD FETFIAYFEK DLQEYKGKGN PEVEALRKEA  60
AAIRDELQAY RHN                                                    73

SEQ ID NO: 937         moltype = AA  length = 73
FEATURE                Location/Qualifiers
REGION                 1..73
                       note = artificial construct
source                 1..73
                       mol_type = protein
                       organism = synthetic construct
SEQUENCE: 937
MGSWEHFKVE LAGIKAYLEA LGGSEAELAL FEWAIADFES ILQDYKGKGN PEVEALRKEA  60
AAIRDELQAY RHN                                                    73

SEQ ID NO: 938         moltype = AA  length = 73
FEATURE                Location/Qualifiers
REGION                 1..73
                       note = artificial construct
source                 1..73
                       mol_type = protein
                       organism = synthetic construct
SEQUENCE: 938
MGSWIYFKDE LAGIKKYLEA LGGSEAELAM FEVAIADFEA ILQKYKGKGN PEVEALRKEA  60
AAIRDELQAY RHN                                                    73

SEQ ID NO: 939         moltype = AA  length = 73
FEATURE                Location/Qualifiers
REGION                 1..73
                       note = artificial construct
source                 1..73
                       mol_type = protein
                       organism = synthetic construct
SEQUENCE: 939
MGSWVLFKQE LAWIKWLLEA LGGSEAELAA FEEQIARFEH DLQKYKGKGN PEVEALRKEA  60
AAIRDELQAY RHN                                                    73

SEQ ID NO: 940         moltype = AA  length = 73
FEATURE                Location/Qualifiers
REGION                 1..73
```

```
                         note = artificial construct
source                   1..73
                         mol_type = protein
                         organism = synthetic construct
SEQUENCE: 940
MGSWVLFKQE LAWIKWYLEA LGGSEAELAA FEWEIAAFEQ RLQIYKGKGN PEVEALRKEA  60
AAIRDELQAY RHN                                                     73

SEQ ID NO: 941           moltype = AA  length = 73
FEATURE                  Location/Qualifiers
REGION                   1..73
                         note = artificial construct
source                   1..73
                         mol_type = protein
                         organism = synthetic construct
SEQUENCE: 941
MGSWFLFKSE LAWIKWRLEA LGGSEAELAY FEYQIAEFEF WLQSYKGKGN PEVEALRKEA  60
AAIRDELQAY RHN                                                     73

SEQ ID NO: 942           moltype = AA  length = 73
FEATURE                  Location/Qualifiers
REGION                   1..73
                         note = artificial construct
source                   1..73
                         mol_type = protein
                         organism = synthetic construct
SEQUENCE: 942
MGSWLLFKSE LAWIKWYLEA LGGSEAELAE FEWNIAEFEK NLQKYKGKGN PEVEALRKEA  60
AAIRDELQAY RHN                                                     73

SEQ ID NO: 943           moltype = AA  length = 73
FEATURE                  Location/Qualifiers
REGION                   1..73
                         note = artificial construct
source                   1..73
                         mol_type = protein
                         organism = synthetic construct
SEQUENCE: 943
MGSWLLFKSD LAWIKWRLEA LGGSEAELAE FEESIAMFEH WLQEYKGKGN PEVEALRKEA  60
AAIRDELQAY RHN                                                     73

SEQ ID NO: 944           moltype = AA  length = 73
FEATURE                  Location/Qualifiers
REGION                   1..73
                         note = artificial construct
source                   1..73
                         mol_type = protein
                         organism = synthetic construct
SEQUENCE: 944
MGSWLYFKSD LAWIKWRLEA LGGSEAELAD FEEAIAEFEQ ALQIYKGKGN PEVEALRKEA  60
AAIRDELQAY RHN                                                     73

SEQ ID NO: 945           moltype = AA  length = 73
FEATURE                  Location/Qualifiers
REGION                   1..73
                         note = artificial construct
source                   1..73
                         mol_type = protein
                         organism = synthetic construct
SEQUENCE: 945
MGSWKLFKYE LAWIKWRLEA LGGSEAELAD FEASIAQFEK YLQTYKGKGN PEVEALRKEA  60
AAIRDELQAY RHN                                                     73

SEQ ID NO: 946           moltype = AA  length = 73
FEATURE                  Location/Qualifiers
REGION                   1..73
                         note = artificial construct
source                   1..73
                         mol_type = protein
                         organism = synthetic construct
SEQUENCE: 946
MGSWYLFKNE LAWIKWRLEA LGGSEAELAD FEMVIAMFED HLQEYKGKGN PEVEALRKEA  60
AAIRDELQAY RHN                                                     73

SEQ ID NO: 947           moltype = AA  length = 73
FEATURE                  Location/Qualifiers
REGION                   1..73
                         note = artificial construct
source                   1..73
```

```
                         mol_type = protein
                         organism = synthetic construct
SEQUENCE: 947
MGSWVYFKAH LAFIKWELEA LGGSEAELAN FESTIAEFEK YLQVYKGKGN PEVEALRKEA  60
AAIRDELQAY RHN                                                    73

SEQ ID NO: 948          moltype = AA  length = 73
FEATURE                 Location/Qualifiers
REGION                  1..73
                        note = artificial construct
source                  1..73
                        mol_type = protein
                        organism = synthetic construct
SEQUENCE: 948
MGSWMYFKSH LAWIKWELEA LGGSEAELAF FEDNIAQFEY WLQLYKGKGN PEVEALRKEA  60
AAIRDELQAY RHN                                                    73

SEQ ID NO: 949          moltype = AA  length = 73
FEATURE                 Location/Qualifiers
REGION                  1..73
                        note = artificial construct
source                  1..73
                        mol_type = protein
                        organism = synthetic construct
SEQUENCE: 949
MGSWTLFKWD LAFIKWQLEA LGGSEAELAW FEYEIAAFED SLQNYKGKGN PEVEALRKEA  60
AAIRDELQAY RHN                                                    73

SEQ ID NO: 950          moltype = AA  length = 73
FEATURE                 Location/Qualifiers
REGION                  1..73
                        note = artificial construct
source                  1..73
                        mol_type = protein
                        organism = synthetic construct
SEQUENCE: 950
MGSWILFKED LAFIKWQLEA LGGSEAELAW FETTIANFES DLQKYKGKGN PEVEALRKEA  60
AAIRDELQAY RHN                                                    73

SEQ ID NO: 951          moltype = AA  length = 73
FEATURE                 Location/Qualifiers
REGION                  1..73
                        note = artificial construct
source                  1..73
                        mol_type = protein
                        organism = synthetic construct
SEQUENCE: 951
MGSWYFFKSR LAYIKVYLEA LGGSEAELAG FEWEIAHFEE WLQRYKGKGN PEVEALRKEA  60
AAIRDELQAY RHN                                                    73

SEQ ID NO: 952          moltype = AA  length = 73
FEATURE                 Location/Qualifiers
REGION                  1..73
                        note = artificial construct
source                  1..73
                        mol_type = protein
                        organism = synthetic construct
SEQUENCE: 952
MGSWYIFKSE LAWIKWYLEA LGGSEAELAN FEVEIATFET WLQGYKGKGN PEVEALRKEA  60
AAIRDELQAY RHN                                                    73

SEQ ID NO: 953          moltype = AA  length = 73
FEATURE                 Location/Qualifiers
REGION                  1..73
                        note = artificial construct
source                  1..73
                        mol_type = protein
                        organism = synthetic construct
SEQUENCE: 953
MGSWYIFKQE LASIKLSLEA LGGSEAELAH FEAEIAWFEW WLQWYKGKGN PEVEALRKEA  60
AAIRDELQAY RHN                                                    73

SEQ ID NO: 954          moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 954
MGSWVRFKTE LAYIKESLEA LGGSEAELAM FESEIAIFEH SLQTYKGKGN PEVEALRKEA  60
AAIRDELQAY RHN                                                    73

SEQ ID NO: 955         moltype = AA  length = 73
FEATURE                Location/Qualifiers
REGION                 1..73
                       note = artificial construct
source                 1..73
                       mol_type = protein
                       organism = synthetic construct
SEQUENCE: 955
MGSWYLFKTE LAAIKYRLEA LGGSEAELAS FEYEIAWFEH ILQFYKGKGN PEVEALRKEA  60
AAIRDELQAY RHN                                                    73

SEQ ID NO: 956         moltype = AA  length = 73
FEATURE                Location/Qualifiers
REGION                 1..73
                       note = artificial construct
source                 1..73
                       mol_type = protein
                       organism = synthetic construct
SEQUENCE: 956
MGSWYWFKYE LAEIKWHLEA LGGSEAELAH FEHSIAVFES QLQQYKGKGN PEVEALRKEA  60
AAIRDELQAY RHN                                                    73

SEQ ID NO: 957         moltype = AA  length = 73
FEATURE                Location/Qualifiers
REGION                 1..73
                       note = artificial construct
source                 1..73
                       mol_type = protein
                       organism = synthetic construct
SEQUENCE: 957
MGSWWVFKKT LAEIKWTLEA LGGSEAELAY FEAEIAFFEF ILQQYKGKGN PEVEALRKEA  60
AAIRDELQAY RHN                                                    73

SEQ ID NO: 958         moltype = AA  length = 73
FEATURE                Location/Qualifiers
REGION                 1..73
                       note = artificial construct
source                 1..73
                       mol_type = protein
                       organism = synthetic construct
SEQUENCE: 958
MGSWVYFKDH LAEIKSQLEA LGGSEAELAL FEYDIAWFEF ILQYYKGKGN PEVEALRKEA  60
AAIRDELQAY RHN                                                    73

SEQ ID NO: 959         moltype = AA  length = 73
FEATURE                Location/Qualifiers
REGION                 1..73
                       note = artificial construct
source                 1..73
                       mol_type = protein
                       organism = synthetic construct
SEQUENCE: 959
MGSWVYFKHR LAEIKDQLEA LGGSEAELAE FETDIAWFEW MLQYYKGKGN PEVEALRKEA  60
AAIRDELQAY RHN                                                    73

SEQ ID NO: 960         moltype = AA  length = 73
FEATURE                Location/Qualifiers
REGION                 1..73
                       note = artificial construct
source                 1..73
                       mol_type = protein
                       organism = synthetic construct
SEQUENCE: 960
MGSWIIFKTD LARIKNYLEA LGGSEAELAT FERDIAWFEF MLQIYKGKGN PEVEALRKEA  60
AAIRDELQAY RHN                                                    73

SEQ ID NO: 961         moltype = AA  length = 73
FEATURE                Location/Qualifiers
REGION                 1..73
                       note = artificial construct
source                 1..73
                       mol_type = protein
                       organism = synthetic construct
SEQUENCE: 961
MGSWMHFKQD LAEIKGYLEA LGGSEAELAI FEMDIAWFEY MLQYYKGKGN PEVEALRKEA  60
```

```
AAIRDELQAY RHN                                              73

SEQ ID NO: 962          moltype = AA  length = 73
FEATURE                 Location/Qualifiers
REGION                  1..73
                        note = artificial construct
source                  1..73
                        mol_type = protein
                        organism = synthetic construct
SEQUENCE: 962
MGSWQIFKQD LAAIKDYLEA LGGSEAELAI FEFDIAWFEH MLQWYKGKGN PEVEALRKEA  60
AAIRDELQAY RHN                                              73

SEQ ID NO: 963          moltype = AA  length = 73
FEATURE                 Location/Qualifiers
REGION                  1..73
                        note = artificial construct
source                  1..73
                        mol_type = protein
                        organism = synthetic construct
SEQUENCE: 963
MGSWLAFKED LAHIKSILEA LGGSEAELAE FEHDIAWFEY MLQYYKGKGN PEVEALRKEA  60
AAIRDELQAY RHN                                              73

SEQ ID NO: 964          moltype = AA  length = 73
FEATURE                 Location/Qualifiers
REGION                  1..73
                        note = artificial construct
source                  1..73
                        mol_type = protein
                        organism = synthetic construct
SEQUENCE: 964
MGSWFVFKED LAGIKFILEA LGGSEAELAM FETDIAWFEY MLQYYKGKGN PEVEALRKEA  60
AAIRDELQAY RHN                                              73

SEQ ID NO: 965          moltype = AA  length = 73
FEATURE                 Location/Qualifiers
REGION                  1..73
                        note = artificial construct
source                  1..73
                        mol_type = protein
                        organism = synthetic construct
SEQUENCE: 965
MGSWTHFKED LAHIKDRLEA LGGSEAELAA FELDIAWFEF MLQYYKGKGN PEVEALRKEA  60
AAIRDELQAY RHN                                              73

SEQ ID NO: 966          moltype = AA  length = 73
FEATURE                 Location/Qualifiers
REGION                  1..73
                        note = artificial construct
source                  1..73
                        mol_type = protein
                        organism = synthetic construct
SEQUENCE: 966
MGSWYYFKER LAAIKDRLEA LGGSEAELAI FEADIAWFEF MLQYYKGKGN PEVEALRKEA  60
AAIRDELQAY RHN                                              73

SEQ ID NO: 967          moltype = AA  length = 73
FEATURE                 Location/Qualifiers
REGION                  1..73
                        note = artificial construct
source                  1..73
                        mol_type = protein
                        organism = synthetic construct
SEQUENCE: 967
MGSWYTFKGS LAEIKNRLEA LGGSEAELAM FESDIAWFEF MLQFYKGKGN PEVEALRKEA  60
AAIRDELQAY RHN                                              73

SEQ ID NO: 968          moltype = AA  length = 73
FEATURE                 Location/Qualifiers
REGION                  1..73
                        note = artificial construct
source                  1..73
                        mol_type = protein
                        organism = synthetic construct
SEQUENCE: 968
MGSWFTFKDD LAQIKNRLEA LGGSEAELAN FEMSIAWFEF MLQYYKGKGN PEVEALRKEA  60
AAIRDELQAY RHN                                              73
```

```
SEQ ID NO: 969         moltype = AA  length = 73
FEATURE                Location/Qualifiers
REGION                 1..73
                       note = artificial construct
source                 1..73
                       mol_type = protein
                       organism = synthetic construct
SEQUENCE: 969
MGSWVLFKQD LAMIKQRLEA LGGSEAELAM FEYDIAWFEH MLQYYKGKGN PEVEALRKEA  60
AAIRDELQAY RHN                                                     73

SEQ ID NO: 970         moltype = AA  length = 73
FEATURE                Location/Qualifiers
REGION                 1..73
                       note = artificial construct
source                 1..73
                       mol_type = protein
                       organism = synthetic construct
SEQUENCE: 970
MGSWVEFKRD LANIKQRLEA LGGSEAELAQ FEMQIAWFEH TLQYYKGKGN PEVEALRKEA  60
AAIRDELQAY RHN                                                     73

SEQ ID NO: 971         moltype = AA  length = 73
FEATURE                Location/Qualifiers
REGION                 1..73
                       note = artificial construct
source                 1..73
                       mol_type = protein
                       organism = synthetic construct
SEQUENCE: 971
MGSWSYFKED LANIKSSLEA LGGSEAELAW FESSIAWFEH TLQYYKGKGN PEVEALRKEA  60
AAIRDELQAY RHN                                                     73

SEQ ID NO: 972         moltype = AA  length = 73
FEATURE                Location/Qualifiers
REGION                 1..73
                       note = artificial construct
source                 1..73
                       mol_type = protein
                       organism = synthetic construct
SEQUENCE: 972
MGSWSIFKQD LADIKDSLEA LGGSEAELAM FEMDIAWFEH TLQYYKGKGN PEVEALRKEA  60
AAIRDELQAY RHN                                                     73

SEQ ID NO: 973         moltype = AA  length = 73
FEATURE                Location/Qualifiers
REGION                 1..73
                       note = artificial construct
source                 1..73
                       mol_type = protein
                       organism = synthetic construct
SEQUENCE: 973
MGSWEIFKDD LASIKKVLEA LGGSEAELAL FESDIAWFEL MLQYYKGKGN PEVEALRKEA  60
AAIRDELQAY RHN                                                     73

SEQ ID NO: 974         moltype = AA  length = 73
FEATURE                Location/Qualifiers
REGION                 1..73
                       note = artificial construct
source                 1..73
                       mol_type = protein
                       organism = synthetic construct
SEQUENCE: 974
MGSWSIFKDD LAVIKERLEA LGGSEAELAH FEQDIAWFEH LLQYYKGKGN PEVEALRKEA  60
AAIRDELQAY RHN                                                     73

SEQ ID NO: 975         moltype = AA  length = 73
FEATURE                Location/Qualifiers
REGION                 1..73
                       note = artificial construct
source                 1..73
                       mol_type = protein
                       organism = synthetic construct
SEQUENCE: 975
MGSWSVFKDD LAQIKDRLEA LGGSEAELAQ FELDIAWFEY VLQFYKGKGN PEVEALRKEA  60
AAIRDELQAY RHN                                                     73

SEQ ID NO: 976         moltype = AA  length = 73
FEATURE                Location/Qualifiers
```

```
REGION                  1..73
                        note = artificial construct
source                  1..73
                        mol_type = protein
                        organism = synthetic construct
SEQUENCE: 976
MGSWAVFKDS LAHIKDVLEA LGGSEAELAL FEMDIAWFEY VLQDYKGKGN PEVEALRKEA  60
AAIRDELQAY RHN                                                     73

SEQ ID NO: 977          moltype = AA  length = 73
FEATURE                 Location/Qualifiers
REGION                  1..73
                        note = artificial construct
source                  1..73
                        mol_type = protein
                        organism = synthetic construct
SEQUENCE: 977
MGSWIAFKDH LAIIKQRLEA LGGSEAELAR FEFEIAWFEW MLQYYKGKGN PEVEALRKEA  60
AAIRDELQAY RHN                                                     73

SEQ ID NO: 978          moltype = AA  length = 73
FEATURE                 Location/Qualifiers
REGION                  1..73
                        note = artificial construct
source                  1..73
                        mol_type = protein
                        organism = synthetic construct
SEQUENCE: 978
MGSWIHFKND LAVIKDELEA LGGSEAELAR FEIMIAWFED ALQWYKGKGN PEVEALRKEA  60
AAIRDELQAY RHN                                                     73

SEQ ID NO: 979          moltype = AA  length = 73
FEATURE                 Location/Qualifiers
REGION                  1..73
                        note = artificial construct
source                  1..73
                        mol_type = protein
                        organism = synthetic construct
SEQUENCE: 979
MGSWMVFKQD LAEIKANLEA LGGSEAELAD FEFAIAWFEY ELQWYKGKGN PEVEALRKEA  60
AAIRDELQAY RHN                                                     73

SEQ ID NO: 980          moltype = AA  length = 73
FEATURE                 Location/Qualifiers
REGION                  1..73
                        note = artificial construct
source                  1..73
                        mol_type = protein
                        organism = synthetic construct
SEQUENCE: 980
MGSWKNFKLE LALIKSKLEA LGGSEAELAQ FEADIAFFEW SLQWYKGKGN PEVEALRKEA  60
AAIRDELQAY RHN                                                     73

SEQ ID NO: 981          moltype = AA  length = 73
FEATURE                 Location/Qualifiers
REGION                  1..73
                        note = artificial construct
source                  1..73
                        mol_type = protein
                        organism = synthetic construct
SEQUENCE: 981
MGSWHSFKQD LAYIKYLLEA LGGSEAELAQ FEELIAFFEY YLQTYKGKGN PEVEALRKEA  60
AAIRDELQAY RHN                                                     73

SEQ ID NO: 982          moltype = AA  length = 73
FEATURE                 Location/Qualifiers
REGION                  1..73
                        note = artificial construct
source                  1..73
                        mol_type = protein
                        organism = synthetic construct
SEQUENCE: 982
MGSWVVFKSS LAQIKILLEA LGGSEAELAI FEVKIAHFEQ ELQEYKGKGN PEVEALRKEA  60
AAIRDELQAY RHN                                                     73

SEQ ID NO: 983          moltype = AA  length = 73
FEATURE                 Location/Qualifiers
REGION                  1..73
                        note = artificial construct
```

```
source                  1..73
                        mol_type = protein
                        organism = synthetic construct
SEQUENCE: 983
MGSWDQFKNS LASIKRVLEA LGGSEAELAI FEVKIAHFEH FLQQYKGKGN PEVEALRKEA  60
AAIRDELQAY RHN                                                    73

SEQ ID NO: 984          moltype = AA  length = 73
FEATURE                 Location/Qualifiers
REGION                  1..73
                        note = artificial construct
source                  1..73
                        mol_type = protein
                        organism = synthetic construct
SEQUENCE: 984
MGSWNNFKSS LASIKQVLEA LGGSEAELAV FELQIAHFER ELQYYKGKGN PEVEALRKEA  60
AAIRDELQAY RHN                                                    73

SEQ ID NO: 985          moltype = AA  length = 73
FEATURE                 Location/Qualifiers
REGION                  1..73
                        note = artificial construct
source                  1..73
                        mol_type = protein
                        organism = synthetic construct
SEQUENCE: 985
MGSWVEFGHR LWAIDQRLYA LGGSEAELAA FEKEIAAFES ELQAYKGKGN PEVEKLRQRA  60
AFIRFRLQAY RHN                                                    73

SEQ ID NO: 986          moltype = AA  length = 73
FEATURE                 Location/Qualifiers
REGION                  1..73
                        note = artificial construct
source                  1..73
                        mol_type = protein
                        organism = synthetic construct
SEQUENCE: 986
MGSWVEFANR LWAIDQRLFA LGGSEAELAA FEKEIAAFES ELQAYKGKGN PEVEHLRDQA  60
AFIRHKLQAY RHN                                                    73

SEQ ID NO: 987          moltype = AA  length = 73
FEATURE                 Location/Qualifiers
REGION                  1..73
                        note = artificial construct
source                  1..73
                        mol_type = protein
                        organism = synthetic construct
SEQUENCE: 987
MGSWYEFRHR LWAIDQRLYA LGGSEAELAA FEKEIAAFES ELQAYKGKGN PEVEGLREAA  60
AFIRAKLQAY RHN                                                    73

SEQ ID NO: 988          moltype = AA  length = 73
FEATURE                 Location/Qualifiers
REGION                  1..73
                        note = artificial construct
source                  1..73
                        mol_type = protein
                        organism = synthetic construct
SEQUENCE: 988
MGSWYEFSMR LWAIDQRLYA LGGSEAELAA FEKEIAAFES ELQAYKGKGN PEVEALRAKA  60
AYIRWKLQAY RHN                                                    73

SEQ ID NO: 989          moltype = AA  length = 73
FEATURE                 Location/Qualifiers
REGION                  1..73
                        note = artificial construct
source                  1..73
                        mol_type = protein
                        organism = synthetic construct
SEQUENCE: 989
MGSWYEFGHR LWAIDQRLYA LGGSEAELAA FEKEIAAFES ELQAYKGKGN PEVEYLRETA  60
AHIRTRLQAY RHN                                                    73

SEQ ID NO: 990          moltype = AA  length = 73
FEATURE                 Location/Qualifiers
REGION                  1..73
                        note = artificial construct
source                  1..73
                        mol_type = protein
```

```
                       organism = synthetic construct
SEQUENCE: 990
MGSWYEFHYR LHAIDQRLYA LGGSEAELAA FEKEIAAFES ELQAYKGKGN PEVEELRIKA  60
AFIRDRLQAY RHN                                                     73

SEQ ID NO: 991         moltype = AA  length = 73
FEATURE                Location/Qualifiers
REGION                 1..73
                       note = artificial construct
source                 1..73
                       mol_type = protein
                       organism = synthetic construct
SEQUENCE: 991
MGSWAEFKQR LAAIKTRLEA LGGSEAELAA FLGEIWAFEM ELAAYKGKGN PEVEALGREA  60
AAIRMELQAY RHN                                                     73

SEQ ID NO: 992         moltype = AA  length = 73
FEATURE                Location/Qualifiers
REGION                 1..73
                       note = artificial construct
source                 1..73
                       mol_type = protein
                       organism = synthetic construct
SEQUENCE: 992
MGSWYEFDLR LHAIYDRLVA LGGSEAELAA FEKEIAAFES ELQAYKGKGN PEVEILRDNA  60
AYIRQMLQAY RHN                                                     73

SEQ ID NO: 993         moltype = AA  length = 73
FEATURE                Location/Qualifiers
REGION                 1..73
                       note = artificial construct
source                 1..73
                       mol_type = protein
                       organism = synthetic construct
SEQUENCE: 993
MGSWTEFTYR LSAIEWRLWA LGGSEAELAW FEQKIAFFED FLQYYKGKGN PEVEALKHEA  60
GAILNELMAY RHN                                                     73

SEQ ID NO: 994         moltype = AA  length = 73
FEATURE                Location/Qualifiers
REGION                 1..73
                       note = artificial construct
source                 1..73
                       mol_type = protein
                       organism = synthetic construct
SEQUENCE: 994
MGSWAEFDHR LHAIRERLHA LGGSEAELAA FEKEIAAFES ELQAYKGKGN PEVEILRGNA  60
AYIRALLQAY RHN                                                     73

SEQ ID NO: 995         moltype = AA  length = 73
FEATURE                Location/Qualifiers
REGION                 1..73
                       note = artificial construct
source                 1..73
                       mol_type = protein
                       organism = synthetic construct
SEQUENCE: 995
MGSWTEFVGR LAAIEFRLWA LGGSEAELAW FEAHIAFFED YLQWYKGKGN PEVEALREEA  60
GAIMEELKAY RHN                                                     73

SEQ ID NO: 996         moltype = AA  length = 73
FEATURE                Location/Qualifiers
REGION                 1..73
                       note = artificial construct
source                 1..73
                       mol_type = protein
                       organism = synthetic construct
SEQUENCE: 996
MGSWTEFYSR LEAIWVRLQA LGGSEAELAM FEDRIAHFEW FLQQYKGKGN PEVEALHEEA  60
IAIRKELAAY RHN                                                     73

SEQ ID NO: 997         moltype = AA  length = 73
FEATURE                Location/Qualifiers
REGION                 1..73
                       note = artificial construct
source                 1..73
                       mol_type = protein
                       organism = synthetic construct
SEQUENCE: 997
```

```
MGSWHEFHDR LQAIHERLYA LGGSEAELAA FEKEIAAFES ELQAYKGKGN PEVESLRIAA  60
AHIRQVLQAY RHN                                                     73

SEQ ID NO: 998         moltype = AA  length = 73
FEATURE                Location/Qualifiers
REGION                 1..73
                       note = artificial construct
source                 1..73
                       mol_type = protein
                       organism = synthetic construct
SEQUENCE: 998
MGSWNYFKDH LAWIKNSLEA LGGSEAELAH FETAIASFER QLQEYKGKGN PEVEALRKEA  60
AAIRDELQAY RHN                                                     73

SEQ ID NO: 999         moltype = AA  length = 73
FEATURE                Location/Qualifiers
REGION                 1..73
                       note = artificial construct
source                 1..73
                       mol_type = protein
                       organism = synthetic construct
SEQUENCE: 999
MGSWLYFKEH LAHIKAWLEA LGGSEAELAH FELAIADFEY HLQEYKGKGN PEVEALRKEA  60
AAIRDELQAY RHN                                                     73

SEQ ID NO: 1000        moltype = AA  length = 73
FEATURE                Location/Qualifiers
REGION                 1..73
                       note = artificial construct
source                 1..73
                       mol_type = protein
                       organism = synthetic construct
SEQUENCE: 1000
MGSWVYFKEH LAWIKTELEA LGGSEAELAH FEHSIADFEM SLQFYKGKGN PEVEALRKEA  60
AAIRDELQAY RHN                                                     73

SEQ ID NO: 1001        moltype = AA  length = 73
FEATURE                Location/Qualifiers
REGION                 1..73
                       note = artificial construct
source                 1..73
                       mol_type = protein
                       organism = synthetic construct
SEQUENCE: 1001
MGSWFYFKQH LAWIKSYLEA LGGSEAELAH FERAIAAFEQ HLQMYKGKGN PEVEALRKEA  60
AAIRDELQAY RHN                                                     73

SEQ ID NO: 1002        moltype = AA  length = 73
FEATURE                Location/Qualifiers
REGION                 1..73
                       note = artificial construct
source                 1..73
                       mol_type = protein
                       organism = synthetic construct
SEQUENCE: 1002
MGSWHYFKDH LAEIKGLLEA LGGSEAELAH FEMAIADFEH NLQYYKGKGN PEVEALRKEA  60
AAIRDELQAY RHN                                                     73

SEQ ID NO: 1003        moltype = AA  length = 73
FEATURE                Location/Qualifiers
REGION                 1..73
                       note = artificial construct
source                 1..73
                       mol_type = protein
                       organism = synthetic construct
SEQUENCE: 1003
MGSWHYFKGH LAEIKNHLEA LGGSEAELAH FERAIAAFER SLQWYKGKGN PEVEALRKEA  60
AAIRDELQAY RHN                                                     73

SEQ ID NO: 1004        moltype = AA  length = 73
FEATURE                Location/Qualifiers
REGION                 1..73
                       note = artificial construct
source                 1..73
                       mol_type = protein
                       organism = synthetic construct
SEQUENCE: 1004
MGSWIYFKEH LAYIKKELEA LGGSEAELAH FESAIAVFES TLQYYKGKGN PEVEALRKEA  60
AAIRDELQAY RHN                                                     73
```

SEQ ID NO: 1005 moltype = AA length = 73
FEATURE Location/Qualifiers
REGION 1..73
note = artificial construct
source 1..73
mol_type = protein
organism = synthetic construct
SEQUENCE: 1005
MGSWTYFKEH LAEIKYMLEA LGGSEAELAH FEVAIADFEK MLQYYKGKGN PEVEALRKEA 60
AAIRDELQAY RHN 73

SEQ ID NO: 1006 moltype = AA length = 73
FEATURE Location/Qualifiers
REGION 1..73
note = artificial construct
source 1..73
mol_type = protein
organism = synthetic construct
SEQUENCE: 1006
MGSWWLFKDH LAEIKTALEA LGGSEAELAH FEMAIAAFEK QLQYYKGKGN PEVEALRKEA 60
AAIRDELQAY RHN 73

SEQ ID NO: 1007 moltype = AA length = 73
FEATURE Location/Qualifiers
REGION 1..73
note = artificial construct
source 1..73
mol_type = protein
organism = synthetic construct
SEQUENCE: 1007
MGSWSEFYNR LDAIESRLLA LGGSEAELAL FEIQIARFEK VLQAYKGKGN PEVEALRGEA 60
RAIFAELYAY RHN 73

SEQ ID NO: 1008 moltype = AA length = 73
FEATURE Location/Qualifiers
REGION 1..73
note = artificial construct
source 1..73
mol_type = protein
organism = synthetic construct
SEQUENCE: 1008
MGSWYEFYNR LYAIEIRLYA LGGSEAELAA FEKEIAAFES ELQAYKGKGN PEVERLRVRA 60
AKIRVILQAY RHN 73

SEQ ID NO: 1009 moltype = AA length = 73
FEATURE Location/Qualifiers
REGION 1..73
note = artificial construct
source 1..73
mol_type = protein
organism = synthetic construct
SEQUENCE: 1009
MGSWLWFKIF LAEIKYFLEA LGGSEAELAA FDFEIHAFHV ELFAYKGKGN PEVEVLREVA 60
AEIRWDLQAY RHN 73

SEQ ID NO: 1010 moltype = AA length = 73
FEATURE Location/Qualifiers
REGION 1..73
note = artificial construct
source 1..73
mol_type = protein
organism = synthetic construct
SEQUENCE: 1010
MGSWTEFQSR LDAIHSRLRA LGGSEAELAA FEKEIAAFES ELQAYKGKGN PEVELLRDDA 60
AFIRHFLQAY RHN 73

SEQ ID NO: 1011 moltype = AA length = 73
FEATURE Location/Qualifiers
REGION 1..73
note = artificial construct
source 1..73
mol_type = protein
organism = synthetic construct
SEQUENCE: 1011
MGSWQEFDDR LNAIKARLQA LGGSEAELAA FEKEIAAFES ELQAYKGKGN PEVEDLRDDA 60
AFIRRFLQAY RHN 73

SEQ ID NO: 1012 moltype = AA length = 73

```
FEATURE                Location/Qualifiers
REGION                 1..73
                       note = artificial construct
source                 1..73
                       mol_type = protein
                       organism = synthetic construct
SEQUENCE: 1012
MGSWYEFQNR LHAIHERLNA LGGSEAELAA FEKEIAAFES ELQAYKGKGN PEVELLRDDA  60
AFIRHFLQAY RHN                                                     73

SEQ ID NO: 1013        moltype = AA  length = 73
FEATURE                Location/Qualifiers
REGION                 1..73
                       note = artificial construct
source                 1..73
                       mol_type = protein
                       organism = synthetic construct
SEQUENCE: 1013
MGSWFEFQDR LTAINERLSA LGGSEAELAA FEKEIAAFES ELQAYKGKGN PEVETLRSDA  60
AFIRRFLQAY RHN                                                     73

SEQ ID NO: 1014        moltype = AA  length = 73
FEATURE                Location/Qualifiers
REGION                 1..73
                       note = artificial construct
source                 1..73
                       mol_type = protein
                       organism = synthetic construct
SEQUENCE: 1014
MGSWYEFESR LDAIHERLHA LGGSEAELAA FEKEIAAFES ELQAYKGKGN PEVENLRGDA  60
AFIRHFLQAY RHN                                                     73

SEQ ID NO: 1015        moltype = AA  length = 73
FEATURE                Location/Qualifiers
REGION                 1..73
                       note = artificial construct
source                 1..73
                       mol_type = protein
                       organism = synthetic construct
SEQUENCE: 1015
MGSWYEFNHR LDAISKRLNA LGGSEAELAA FEKEIAAFES ELQAYKGKGN PEVEELRGDA  60
AFIRHFLQAY RHN                                                     73

SEQ ID NO: 1016        moltype = AA  length = 73
FEATURE                Location/Qualifiers
REGION                 1..73
                       note = artificial construct
source                 1..73
                       mol_type = protein
                       organism = synthetic construct
SEQUENCE: 1016
MGSWFEFENR LHAIVHRLGA LGGSEAELAA FEKEIAAFES ELQAYKGKGN PEVETLRADA  60
AFIRHYLQAY RHN                                                     73

SEQ ID NO: 1017        moltype = AA  length = 73
FEATURE                Location/Qualifiers
REGION                 1..73
                       note = artificial construct
source                 1..73
                       mol_type = protein
                       organism = synthetic construct
SEQUENCE: 1017
MGSWVVFKVD LATIKYILEA LGGSEAELAE FEGEIAGFEY SLQFYKGKGN PEVEALRKEA  60
AAIRDELQAY RHN                                                     73

SEQ ID NO: 1018        moltype = AA  length = 73
FEATURE                Location/Qualifiers
REGION                 1..73
                       note = artificial construct
source                 1..73
                       mol_type = protein
                       organism = synthetic construct
SEQUENCE: 1018
MGSWTIFKEW LAFIKTDLEA LGGSEAELAF FEGWIASFEM ELQKYKGKGN PEVEALRKEA  60
AAIRDELQAY RHN                                                     73

SEQ ID NO: 1019        moltype = AA  length = 73
FEATURE                Location/Qualifiers
REGION                 1..73
```

```
                         note = artificial construct
source                   1..73
                         mol_type = protein
                         organism = synthetic construct
SEQUENCE: 1019
MGSWVMFKWL LADIKSHLEA LGGSEAELAF FEGFIAAFET HLQVYKGKGN PEVEALRKEA  60
AAIRDELQAY RHN                                                     73

SEQ ID NO: 1020          moltype = AA  length = 73
FEATURE                  Location/Qualifiers
REGION                   1..73
                         note = artificial construct
source                   1..73
                         mol_type = protein
                         organism = synthetic construct
SEQUENCE: 1020
MGSWYAFKDY LADIKGWLEA LGGSEAELAF FEIFIARFEL ELQAYKGKGN PEVEALRKEA  60
AAIRDELQAY RHN                                                     73

SEQ ID NO: 1021          moltype = AA  length = 73
FEATURE                  Location/Qualifiers
REGION                   1..73
                         note = artificial construct
source                   1..73
                         mol_type = protein
                         organism = synthetic construct
SEQUENCE: 1021
MGSWAEFKQR LAAIKTRLEA LGGSEAELAA FEKEIAAFES ELQAYKGKGN PEVEALRKEA  60
AAIRDELQAY RHN                                                     73

SEQ ID NO: 1022          moltype =   length =
SEQUENCE: 1022
000

SEQ ID NO: 1023          moltype =   length =
SEQUENCE: 1023
000

SEQ ID NO: 1024          moltype =   length =
SEQUENCE: 1024
000

SEQ ID NO: 1025          moltype =   length =
SEQUENCE: 1025
000

SEQ ID NO: 1026          moltype =   length =
SEQUENCE: 1026
000

SEQ ID NO: 1027          moltype =   length =
SEQUENCE: 1027
000

SEQ ID NO: 1028          moltype =   length =
SEQUENCE: 1028
000

SEQ ID NO: 1029          moltype =   length =
SEQUENCE: 1029
000

SEQ ID NO: 1030          moltype = AA  length = 73
FEATURE                  Location/Qualifiers
REGION                   1..73
                         note = artificial construct
source                   1..73
                         mol_type = protein
                         organism = synthetic construct
SEQUENCE: 1030
MGSWEEFELR LNAIEERLYA LGGSEAELAY FEYVIADFEG NLQRYKGKGN PEVEALYFEA  60
DAIFEELVAY RHN                                                     73

SEQ ID NO: 1031          moltype = AA  length = 73
FEATURE                  Location/Qualifiers
REGION                   1..73
                         note = artificial construct
source                   1..73
                         mol_type = protein
```

```
                         organism = synthetic construct
SEQUENCE: 1031
MGSWFEFNHR LWAIFERLMA LGGSEAELAA FEKEIAAFES ELQAYKGKGN PEVEYLRAMA  60
AVIRYHLQAY RHN                                                     73

SEQ ID NO: 1032          moltype = AA  length = 73
FEATURE                  Location/Qualifiers
REGION                   1..73
                         note = artificial construct
source                   1..73
                         mol_type = protein
                         organism = synthetic construct
SEQUENCE: 1032
MGSWEEFDGR LFAIEQRLQA LGGSEAELAA FEKEIAAFES ELQAYKGKGN PEVEVLRWFA  60
AGIRDFLQAY RHN                                                     73

SEQ ID NO: 1033          moltype = AA  length = 73
FEATURE                  Location/Qualifiers
REGION                   1..73
                         note = artificial construct
source                   1..73
                         mol_type = protein
                         organism = synthetic construct
SEQUENCE: 1033
MGSWAEFYHR LYAIETRLSA LGGSEAELAA FEKEIAAFES ELQAYKGKGN PEVEYLRHWA  60
AWIRTYLQAY RHN                                                     73

SEQ ID NO: 1034          moltype = AA  length = 73
FEATURE                  Location/Qualifiers
REGION                   1..73
                         note = artificial construct
source                   1..73
                         mol_type = protein
                         organism = synthetic construct
SEQUENCE: 1034
MGSWVEFSDR LYAIEERLWA LGGSEAELAA FEKEIAAFES ELQAYKGKGN PEVEELRELA  60
AIIRHSLQAY RHN                                                     73

SEQ ID NO: 1035          moltype = AA  length = 73
FEATURE                  Location/Qualifiers
REGION                   1..73
                         note = artificial construct
source                   1..73
                         mol_type = protein
                         organism = synthetic construct
SEQUENCE: 1035
MGSWWEFEGR LYAIEERLTA LGGSEAELAA FEKEIAAFES ELQAYKGKGN PEVEYLREWA  60
AWIRQMLQAY RHN                                                     73

SEQ ID NO: 1036          moltype = AA  length = 73
FEATURE                  Location/Qualifiers
REGION                   1..73
                         note = artificial construct
source                   1..73
                         mol_type = protein
                         organism = synthetic construct
SEQUENCE: 1036
MGSWWEFEHR LYAIEERLVA LGGSEAELAA FEKEIAAFES ELQAYKGKGN PEVEYLRNWA  60
AYIRMALQAY RHN                                                     73

SEQ ID NO: 1037          moltype = AA  length = 73
FEATURE                  Location/Qualifiers
REGION                   1..73
                         note = artificial construct
source                   1..73
                         mol_type = protein
                         organism = synthetic construct
SEQUENCE: 1037
MGSWWEFEAR LYAIEFRLSA LGGSEAELAA FEKEIAAFES ELQAYKGKGN PEVEYLRSWA  60
AYIRTSLQAY RHN                                                     73

SEQ ID NO: 1038          moltype = AA  length = 73
FEATURE                  Location/Qualifiers
REGION                   1..73
                         note = artificial construct
source                   1..73
                         mol_type = protein
                         organism = synthetic construct
SEQUENCE: 1038
```

```
MGSWWEFEAR LWAIESRLKA LGGSEAELAA FEKEIAAFES ELQAYKGKGN PEVEYLRHWA  60
AYIRVILQAY RHN                                                     73

SEQ ID NO: 1039        moltype = AA  length = 73
FEATURE                Location/Qualifiers
REGION                 1..73
                       note = artificial construct
source                 1..73
                       mol_type = protein
                       organism = synthetic construct
SEQUENCE: 1039
MGSWWEFEAR LYAIEFRLSA LGGSEAELAA FEKEIAAFES ELQAYKGKGN PEVEYLRSWA  60
AYIRTSLQAY RHN                                                     73

SEQ ID NO: 1040        moltype = AA  length = 73
FEATURE                Location/Qualifiers
REGION                 1..73
                       note = artificial construct
source                 1..73
                       mol_type = protein
                       organism = synthetic construct
SEQUENCE: 1040
MGSWEEFYHR LDAIELRLYA LGGSEAELAA FEKEIAAFES ELQAYKGKGN PEVEYLRWYA  60
AEIREILQAY RHN                                                     73

SEQ ID NO: 1041        moltype = AA  length = 73
FEATURE                Location/Qualifiers
REGION                 1..73
                       note = artificial construct
source                 1..73
                       mol_type = protein
                       organism = synthetic construct
SEQUENCE: 1041
MGSWYEFYER LDAIDTRLWA LGGSEAELAA FEKEIAAFES ELQAYKGKGN PEVEFLREYA  60
AEIRHFLQAY RHN                                                     73

SEQ ID NO: 1042        moltype = AA  length = 73
FEATURE                Location/Qualifiers
REGION                 1..73
                       note = artificial construct
source                 1..73
                       mol_type = protein
                       organism = synthetic construct
SEQUENCE: 1042
MGSWNEFFDR LDAILYRLDA LGGSEAELAA FEKEIAAFES ELQAYKGKGN PEVEYLRFVA  60
ADIRSWLQAY RHN                                                     73

SEQ ID NO: 1043        moltype = AA  length = 73
FEATURE                Location/Qualifiers
REGION                 1..73
                       note = artificial construct
source                 1..73
                       mol_type = protein
                       organism = synthetic construct
SEQUENCE: 1043
MGSWIEFDDR LLAIMDRLWA LGGSEAELAA FEKEIAAFES ELQAYKGKGN PEVEDLRDVA  60
ADIRHYLQAY RHN                                                     73

SEQ ID NO: 1044        moltype = AA  length = 73
FEATURE                Location/Qualifiers
REGION                 1..73
                       note = artificial construct
source                 1..73
                       mol_type = protein
                       organism = synthetic construct
SEQUENCE: 1044
MGSWYEFWER LDAITFRLYA LGGSEAELAA FEKEIAAFES ELQAYKGKGN PEVEDLRTWA  60
ADIRAILQAY RHN                                                     73

SEQ ID NO: 1045        moltype = AA  length = 73
FEATURE                Location/Qualifiers
REGION                 1..73
                       note = artificial construct
source                 1..73
                       mol_type = protein
                       organism = synthetic construct
SEQUENCE: 1045
MGSWEEFYIR LDAIMERLWA LGGSEAELAA FEKEIAAFES ELQAYKGKGN PEVEDLRYAA  60
ADIRHFLQAY RHN                                                     73
```

SEQ ID NO: 1046 moltype = AA length = 73
FEATURE Location/Qualifiers
REGION 1..73
note = artificial construct
source 1..73
mol_type = protein
organism = synthetic construct
SEQUENCE: 1046
MGSWIEFEER LYAIETRLLA LGGSEAELAA FEKEIAAFES ELQAYKGKGN PEVEFLRVVA 60
ADIREWLQAY RHN 73

SEQ ID NO: 1047 moltype = AA length = 73
FEATURE Location/Qualifiers
REGION 1..73
note = artificial construct
source 1..73
mol_type = protein
organism = synthetic construct
SEQUENCE: 1047
MGSWIEFEHR LSAINDRLYA LGGSEAELAA FEKEIAAFES ELQAYKGKGN PEVEDLREWA 60
ADIRSLLQAY RHN 73

SEQ ID NO: 1048 moltype = AA length = 73
FEATURE Location/Qualifiers
REGION 1..73
note = artificial construct
source 1..73
mol_type = protein
organism = synthetic construct
SEQUENCE: 1048
MGSWFEFEMR LDAIMARLWA LGGSEAELAA FEKEIAAFES ELQAYKGKGN PEVEDLRYAA 60
ADIRDYLQAY RHN 73

SEQ ID NO: 1049 moltype = AA length = 73
FEATURE Location/Qualifiers
REGION 1..73
note = artificial construct
source 1..73
mol_type = protein
organism = synthetic construct
SEQUENCE: 1049
MGSWYEFVYR LDAIYDRLWA LGGSEAELAA FEKEIAAFES ELQAYKGKGN PEVEDLRYAA 60
ADIRDFLQAY RHN 73

SEQ ID NO: 1050 moltype = AA length = 73
FEATURE Location/Qualifiers
REGION 1..73
note = artificial construct
source 1..73
mol_type = protein
organism = synthetic construct
SEQUENCE: 1050
MGSWVEFEDR LDAILERLWA LGGSEAELAA FEKEIAAFES ELQAYKGKGN PEVEDLRELA 60
ADIRDFLQAY RHN 73

SEQ ID NO: 1051 moltype = AA length = 73
FEATURE Location/Qualifiers
REGION 1..73
note = artificial construct
source 1..73
mol_type = protein
organism = synthetic construct
SEQUENCE: 1051
MGSWFEFEER LIAIEERLFA LGGSEAELAA FEKEIAAFES ELQAYKGKGN PEVEYLRWIA 60
ADIRDVLQAY RHN 73

SEQ ID NO: 1052 moltype = AA length = 73
FEATURE Location/Qualifiers
REGION 1..73
note = artificial construct
source 1..73
mol_type = protein
organism = synthetic construct
SEQUENCE: 1052
MGSWIEFADR LDAILDRLDA LGGSEAELAA FEKEIAAFES ELQAYKGKGN PEVEWLREIA 60
ADIRAYLQAY RHN 73

SEQ ID NO: 1053 moltype = AA length = 73

```
FEATURE                Location/Qualifiers
REGION                 1..73
                       note = artificial construct
source                 1..73
                       mol_type = protein
                       organism = synthetic construct
SEQUENCE: 1053
MGSWLEFEYR LDAILDRLFA LGGSEAELAA FEKEIAAFES ELQAYKGKGN PEVEDLREVA  60
ADIRMLLQAY RHN                                                     73

SEQ ID NO: 1054        moltype = AA  length = 73
FEATURE                Location/Qualifiers
REGION                 1..73
                       note = artificial construct
source                 1..73
                       mol_type = protein
                       organism = synthetic construct
SEQUENCE: 1054
MGSWYEFHDR LDAITNRLYA LGGSEAELAA FEKEIAAFES ELQAYKGKGN PEVEDLRDWA  60
ADIRVWLQAY RHN                                                     73

SEQ ID NO: 1055        moltype = AA  length = 73
FEATURE                Location/Qualifiers
REGION                 1..73
                       note = artificial construct
source                 1..73
                       mol_type = protein
                       organism = synthetic construct
SEQUENCE: 1055
MGSWQEFEQR LDAINWRLWA LGGSEAELAA FEKEIAAFES ELQAYKGKGN PEVEELREWA  60
ADIRIFLQAY RHN                                                     73

SEQ ID NO: 1056        moltype = AA  length = 73
FEATURE                Location/Qualifiers
REGION                 1..73
                       note = artificial construct
source                 1..73
                       mol_type = protein
                       organism = synthetic construct
SEQUENCE: 1056
MGSWYEFYSR LDAIDSRLYA LGGSEAELAA FEKEIAAFES ELQAYKGKGN PEVEFLRDYA  60
AEIRRYLQAY RHN                                                     73

SEQ ID NO: 1057        moltype = AA  length = 73
FEATURE                Location/Qualifiers
REGION                 1..73
                       note = artificial construct
source                 1..73
                       mol_type = protein
                       organism = synthetic construct
SEQUENCE: 1057
MGSWEEFHDR LEAISDRLWA LGGSEAELAA FEKEIAAFES ELQAYKGKGN PEVEDLRDWA  60
ADIRFYLQAY RHN                                                     73

SEQ ID NO: 1058        moltype = AA  length = 73
FEATURE                Location/Qualifiers
REGION                 1..73
                       note = artificial construct
source                 1..73
                       mol_type = protein
                       organism = synthetic construct
SEQUENCE: 1058
MGSWWEFDER LYAIEDRLFA LGGSEAELAA FEKEIAAFES ELQAYKGKGN PEVEWLRIVA  60
ADIREILQAY RHN                                                     73

SEQ ID NO: 1059        moltype = AA  length = 73
FEATURE                Location/Qualifiers
REGION                 1..73
                       note = artificial construct
source                 1..73
                       mol_type = protein
                       organism = synthetic construct
SEQUENCE: 1059
MGSWEEFEYR LMAIEVRLWA LGGSEAELAA FEKEIAAFES ELQAYKGKGN PEVEVLREIA  60
ADIRQILQAY RHN                                                     73

SEQ ID NO: 1060        moltype = AA  length = 73
FEATURE                Location/Qualifiers
REGION                 1..73
```

```
                        note = artificial construct
source                  1..73
                        mol_type = protein
                        organism = synthetic construct
SEQUENCE: 1060
MGSWVVFKQR LAYIKDLLEA LGGSEAELAY FEMSIAFFEE DLQVYKGKGN PEVEALRKEA  60
AAIRDELQAY RHN                                                     73

SEQ ID NO: 1061         moltype = AA  length = 73
FEATURE                 Location/Qualifiers
REGION                  1..73
                        note = artificial construct
source                  1..73
                        mol_type = protein
                        organism = synthetic construct
SEQUENCE: 1061
MGSWYEFKND LAWIKVHLEA LGGSEAELAY FEFRIAHFEN ALQYYKGKGN PEVEALRKEA  60
AAIRDELQAY RHN                                                     73

SEQ ID NO: 1062         moltype = AA  length = 73
FEATURE                 Location/Qualifiers
REGION                  1..73
                        note = artificial construct
source                  1..73
                        mol_type = protein
                        organism = synthetic construct
SEQUENCE: 1062
MGSWVEFYNR LWAIDHRLHA LGGSEAELAA FEKEIAAFES ELQAYKGKGN PEVEVLRYHA  60
ASIRVTLQAY RHN                                                     73

SEQ ID NO: 1063         moltype = AA  length = 73
FEATURE                 Location/Qualifiers
REGION                  1..73
                        note = artificial construct
source                  1..73
                        mol_type = protein
                        organism = synthetic construct
SEQUENCE: 1063
MGSWSEFYDR LHAIHHRLYA LGGSEAELAA FEKEIAAFES ELQAYKGKGN PEVEALRDTA  60
AFIRTRLQAY RHN                                                     73

SEQ ID NO: 1064         moltype = AA  length = 73
FEATURE                 Location/Qualifiers
REGION                  1..73
                        note = artificial construct
source                  1..73
                        mol_type = protein
                        organism = synthetic construct
SEQUENCE: 1064
MGSWKEFHFR LHAIEHRLIA LGGSEAELAA FEKEIAAFES ELQAYKGKGN PEVEFLRAKA  60
ANIRTHLQAY RHN                                                     73

SEQ ID NO: 1065         moltype = AA  length = 73
FEATURE                 Location/Qualifiers
REGION                  1..73
                        note = artificial construct
source                  1..73
                        mol_type = protein
                        organism = synthetic construct
SEQUENCE: 1065
MGSWFEFHGR LHAIYGRLSA LGGSEAELAA FEKEIAAFES ELQAYKGKGN PEVEHLRAHA  60
AHIRDHLQAY RHN                                                     73

SEQ ID NO: 1066         moltype = AA  length = 73
FEATURE                 Location/Qualifiers
REGION                  1..73
                        note = artificial construct
source                  1..73
                        mol_type = protein
                        organism = synthetic construct
SEQUENCE: 1066
MGSWYEFADR LHAIHQRLYA LGGSEAELAA FEKEIAAFES ELQAYKGKGN PEVEALRMTA  60
AFIRSRLQAY RHN                                                     73

SEQ ID NO: 1067         moltype = AA  length = 73
FEATURE                 Location/Qualifiers
REGION                  1..73
                        note = artificial construct
source                  1..73
```

```
                        mol_type = protein
                        organism = synthetic construct
SEQUENCE: 1067
MGSWNEFYNR LHAIHQRLYA LGGSEAELAA FEKEIAAFES ELQAYKGKGN PEVESLRQTA  60
AYIRDRLQAY RHN                                                     73

SEQ ID NO: 1068         moltype = AA  length = 73
FEATURE                 Location/Qualifiers
REGION                  1..73
                        note = artificial construct
source                  1..73
                        mol_type = protein
                        organism = synthetic construct
SEQUENCE: 1068
MGSWNEFADR LHAIHQRLYA LGGSEAELAA FEKEIAAFES ELQAYKGKGN PEVESLRMTA  60
AFIRSRLQAY RHN                                                     73

SEQ ID NO: 1069         moltype = AA  length = 73
FEATURE                 Location/Qualifiers
REGION                  1..73
                        note = artificial construct
source                  1..73
                        mol_type = protein
                        organism = synthetic construct
SEQUENCE: 1069
MGSWTEFSYR LGAIQSRLHA LGGSEAELAA FEKEIAAFES ELQAYKGKGN PEVEHLRYNA  60
AKIRHFLQAY RHN                                                     73

SEQ ID NO: 1070         moltype = AA  length = 73
FEATURE                 Location/Qualifiers
REGION                  1..73
                        note = artificial construct
source                  1..73
                        mol_type = protein
                        organism = synthetic construct
SEQUENCE: 1070
MGSWQEFTTR LEAIYHRLRA LGGSEAELAN FEGFIAEFEG NLQMYKGKGN PEVEALVHEA  60
YAIMEELHAY RHN                                                     73

SEQ ID NO: 1071         moltype = AA  length = 73
FEATURE                 Location/Qualifiers
REGION                  1..73
                        note = artificial construct
source                  1..73
                        mol_type = protein
                        organism = synthetic construct
SEQUENCE: 1071
MGSWVEFFDR LKAIHDRLEA LGGSEAELAH FEKLIAHFEH RLQNYKGKGN PEVEALEKEA  60
DAILYELAAY RHN                                                     73

SEQ ID NO: 1072         moltype = AA  length = 73
FEATURE                 Location/Qualifiers
REGION                  1..73
                        note = artificial construct
source                  1..73
                        mol_type = protein
                        organism = synthetic construct
SEQUENCE: 1072
MGSWYYFKHH LAWIKMELEA LGGSEAELAH FESSIASFER DLQQYKGKGN PEVEALRKEA  60
AAIRDELQAY RHN                                                     73

SEQ ID NO: 1073         moltype = AA  length = 73
FEATURE                 Location/Qualifiers
REGION                  1..73
                        note = artificial construct
source                  1..73
                        mol_type = protein
                        organism = synthetic construct
SEQUENCE: 1073
MGSWVEFHIR LHAIQYRLYA LGGSEAELAA FEKEIAAFES ELQAYKGKGN PEVEELRHWA  60
AFIRLQLQAY RHN                                                     73

SEQ ID NO: 1074         moltype = AA  length = 73
FEATURE                 Location/Qualifiers
REGION                  1..73
                        note = artificial construct
source                  1..73
                        mol_type = protein
                        organism = synthetic construct
```

```
SEQUENCE: 1074
MGSWNEFHDR LNAIHARLHA LGGSEAELAA FEKEIAAFES ELQAYKGKGN PEVENLRDDA  60
AFIRRFLQAY RHN                                                     73

SEQ ID NO: 1075        moltype = AA  length = 73
FEATURE                Location/Qualifiers
REGION                 1..73
                       note = artificial construct
source                 1..73
                       mol_type = protein
                       organism = synthetic construct
SEQUENCE: 1075
MGSWYEFTVR LEAIHERLKA LGGSEAELAA FEKEIAAFES ELQAYKGKGN PEVEILRDDA  60
AFIRRFLQAY RHN                                                     73

SEQ ID NO: 1076        moltype = AA  length = 73
FEATURE                Location/Qualifiers
REGION                 1..73
                       note = artificial construct
source                 1..73
                       mol_type = protein
                       organism = synthetic construct
SEQUENCE: 1076
MGSWKEFDDR LNAIKARLQA LGGSEAELAA FEKEIAAFES ELQAYKGKGN PEVEDLRDDA  60
AFIRRFLQAY RHN                                                     73

SEQ ID NO: 1077        moltype = AA  length = 73
FEATURE                Location/Qualifiers
REGION                 1..73
                       note = artificial construct
source                 1..73
                       mol_type = protein
                       organism = synthetic construct
SEQUENCE: 1077
MGSWYEFDDR LNAIHDRLQA LGGSEAELAA FEKEIAAFES ELQAYKGKGN PEVEDLRDDA  60
AFIRRFLQAY RHN                                                     73

SEQ ID NO: 1078        moltype = AA  length = 73
FEATURE                Location/Qualifiers
REGION                 1..73
                       note = artificial construct
source                 1..73
                       mol_type = protein
                       organism = synthetic construct
SEQUENCE: 1078
MGSWNEFKNR LDAIHKRLNA LGGSEAELAA FEKEIAAFES ELQAYKGKGN PEVENLRDDA  60
AFIRHFLQAY RHN                                                     73

SEQ ID NO: 1079        moltype = AA  length = 73
FEATURE                Location/Qualifiers
REGION                 1..73
                       note = artificial construct
source                 1..73
                       mol_type = protein
                       organism = synthetic construct
SEQUENCE: 1079
MGSWTEFEQR LEAIHNRLQA LGGSEAELAA FEKEIAAFES ELQAYKGKGN PEVEELRNDA  60
AFIRHFLQAY RHN                                                     73

SEQ ID NO: 1080        moltype =   length =
SEQUENCE: 1080
000

SEQ ID NO: 1081        moltype = AA  length = 163
FEATURE                Location/Qualifiers
source                 1..163
                       mol_type = protein
                       organism = Homo sapiens
SEQUENCE: 1081
LQDPCSNCPA GTFCDNNRNQ ICSPCPPNSF SSAGGQRTCD ICRQCKGVFR TRKECSSTSN  60
AECDCTPGFH CLGAGCSMCE QDCKQGQELT KKGCKDCCFG TFNDQKRGIC RPWTNCSLDG  120
KSVLVNGTKE RDVVCGPSPA DLSPGASSVT PPAPAREPGH SPQ                    163

SEQ ID NO: 1082        moltype = AA  length = 170
FEATURE                Location/Qualifiers
REGION                 1..170
                       note = artificial construct
source                 1..170
                       mol_type = protein
```

```
                         organism = synthetic construct
SEQUENCE: 1082
DEMGSWDEFG RRLYAIEWRL YALGGSEAEL AAFEKEIAAF ESELQAYKGK GNPEVEKLRE  60
IAAVIRSNLQ AYRHNGGGGS GGGGSGGGGS GMLQMAGQCS QNEYFDSLLH ACIPCQLRCS  120
SNTPPLTCQR YCNASVTNSV KGTNAGGGGS GGGGSGGGGS HHHHHHHHHH            170

SEQ ID NO: 1083          moltype = AA  length = 175
FEATURE                  Location/Qualifiers
REGION                   1..175
                         note = artificial construct
source                   1..175
                         mol_type = protein
                         organism = synthetic construct
SEQUENCE: 1083
DEGGGGSMGS WAEFKQRLAA IKTRLQALGG SEAELAAFEK EIAAFESELQ AYKGKGNPEV  60
EALRKEAAAI RDELQAYRHN GGGGSGGGGS GGGGSGMLQM AGQCSQNEYF DSLLHACIPC  120
QLRCSSNTPP LTCQRYCNAS VTNSVKGTNA GGGGSGGGGS GGGGSHHHHH HHHHH       175

SEQ ID NO: 1084          moltype = AA  length = 343
FEATURE                  Location/Qualifiers
REGION                   1..343
                         note = artificial construct
source                   1..343
                         mol_type = protein
                         organism = synthetic construct
SEQUENCE: 1084
DEHHHHHHHH HHKLENLYFQ GGGGGSMGSW DEFGRRLYAI EWRLYALGGS EAELAAFEKE  60
IAAFESELQA YKGKGNPEVE KLREIAAVIR SNLQAYRHNG GGGSGGGGSG GGGSLEKCFQ  120
TENPLECQDK GEEELQKYIQ ESQALAKRSC GLFQKLGEYY LQNAFLVAYT KKAPQLTSSE  180
LMAITRKMAA TAATCCQLSE DKLLACGEGA ADIIIGHLCI RHEMTPVNPG VGQCCTSSYA  240
NRRPCFSSLV VDETYVPPAF SDDKFIFHKD LCQAQGVALQ TMKQEFLINL VKQKPQITEE  300
QLEAVIADFS GLLEKCCQGQ EQEVCFAEEG QKLISKTRAA LGV                   343

SEQ ID NO: 1085          moltype = AA  length = 343
FEATURE                  Location/Qualifiers
REGION                   1..343
                         note = artificial construct
source                   1..343
                         mol_type = protein
                         organism = synthetic construct
SEQUENCE: 1085
DEHHHHHHHH HHKLENLYFQ GGGGGSMGSW SEFWVRLGAI RERLDALGGS EAELAAFEKE  60
IAAFESELQA YKGKGNPEVE KLRYTAATIR RFLQAYRHNG GGGSGGGGSG GGGSLEKCFQ  120
TENPLECQDK GEEELQKYIQ ESQALAKRSC GLFQKLGEYY LQNAFLVAYT KKAPQLTSSE  180
LMAITRKMAA TAATCCQLSE DKLLACGEGA ADIIIGHLCI RHEMTPVNPG VGQCCTSSYA  240
NRRPCFSSLV VDETYVPPAF SDDKFIFHKD LCQAQGVALQ TMKQEFLINL VKQKPQITEE  300
QLEAVIADFS GLLEKCCQGQ EQEVCFAEEG QKLISKTRAA LGV                   343

SEQ ID NO: 1086          moltype = AA  length = 343
FEATURE                  Location/Qualifiers
REGION                   1..343
                         note = artificial construct
source                   1..343
                         mol_type = protein
                         organism = synthetic construct
SEQUENCE: 1086
DEHHHHHHHH HHKLENLYFQ GGGGGSMGSW AEFKQRLAAI KTRLEALGGS EAELAAFEKE  60
IAAFESELQA YKGKGNPEVE ALRKEAAAIR DELQAYRHNG GGGSGGGGSG GGGSLEKCFQ  120
TENPLECQDK GEEELQKYIQ ESQALAKRSC GLFQKLGEYY LQNAFLVAYT KKAPQLTSSE  180
LMAITRKMAA TAATCCQLSE DKLLACGEGA ADIIIGHLCI RHEMTPVNPG VGQCCTSSYA  240
NRRPCFSSLV VDETYVPPAF SDDKFIFHKD LCQAQGVALQ TMKQEFLINL VKQKPQITEE  300
QLEAVIADFS GLLEKCCQGQ EQEVCFAEEG QKLISKTRAA LGV                   343

SEQ ID NO: 1087          moltype = AA  length = 438
FEATURE                  Location/Qualifiers
REGION                   1..438
                         note = artificial construct
source                   1..438
                         mol_type = protein
                         organism = synthetic construct
SEQUENCE: 1087
DEGGGGSMGS WDEFGRRLYA IEWQLYALGG TEAELAAFEK EIAAFESELQ AYKGKGNPEV  60
EKLREIAAVI RENLQAYRHN GGGGSGGGGS GGGGSGLEKC FQTENPLECQ DKGEEELQKY  120
IQESQALAKR SCGLFQKLGE YYLQNAFLVA YTKKAPQLTS SELMAITRKM AATAATCCQL  180
SEDKLLACGE GAADIIIGHL CIRHEMTPVN PGVGQCCTSS YANRRPCFSS LVVDETYVPP  240
AFSDDKFIFH KDLCQAQGVA LQTMKQEFLI NLVKQKPQIT EEQLEAVIAD FSGLLEKCCQ  300
GQEQEVCFAE EGQKLISKTR AALGVGGGGS GGGGSGGGGS MGSWDEFGRR LYAIEWQLYA  360
LGGTEAELAA FEKEIAAFES ELQAYKGKGN PEVEKLREIA AVIRENLQAY RHNGGGGSGG  420
GGSGGGGSHH HHHHHHHH                                                438
```

```
SEQ ID NO: 1088        moltype = AA  length = 438
FEATURE                Location/Qualifiers
REGION                 1..438
                       note = artificial construct
source                 1..438
                       mol_type = protein
                       organism = synthetic construct
SEQUENCE: 1088
DEGGGGSMGS WSEFWVRLGA IRERLDALGG SEAELAAFEK EIAAFESELQ AYKGKGNPEV  60
EKLRYTAATI RRFLQAYRHN GGGGSGGGGS GGGGSGLEKC FQTENPLECQ DKGEEELQKY  120
IQESQALAKR SCGLFQKLGE YYLQNAFLVA YTKKAPQLTS SELMAITRKM AATAATCCQL  180
SEDKLLACGE GAADIIIGHL CIRHEMTPVN PGVGQCCTSS YANRRPCFSS LVVDETYVPP  240
AFSDDKFIFH KDLCQAQGVA LQTMKQEFLI NLVKQKPQIT EEQLEAVIAD FSGLLEKCCQ  300
GQEQEVCFAE EGQKLISKTR AALGVGGGGS GGGGSGGGGS MGSWSEFWVR LGAIRERLDA  360
LGGSEAELAA FEKEIAAFES ELQAYKGKGN PEVEKLRYTA ATIRRFLQAY RHNGGGGSGG  420
GGSGGGGSHH HHHHHHHH                                                438

SEQ ID NO: 1089        moltype = AA  length = 338
FEATURE                Location/Qualifiers
REGION                 1..338
                       note = artificial construct
source                 1..338
                       mol_type = protein
                       organism = synthetic construct
SEQUENCE: 1089
MAFLWLLSCW ALLGTTFGDY KDDDDKGGGG SGGGGSMGSW AEFKQRLAAI KTRLEALGGS  60
EAELAAFEKE IAAFESELQA YKGKGNPEVE ALRKEAAAIR DELQAYRHNG QAGSGTTTPA  120
PRPPTPAPTI ASQPLSLRPE ACRPAAGGAV HTRGLDFACD IYIWAPLAGT CGVLLLSLVI  180
TLYCKRGRKK LLYIFKQPFM RPVQTTQEED GCSCRFPEEE EGGCELRVKF SRSADAPAYK  240
QGQNQLYNEL NLGRREEYDV LDKRRGRDPE MGGKPRRKNP QEGLYNELQK DKMAEAYSEI  300
GMKGERRRGK GHDGLYQGLS TATKDTYDAL HMQALPPR                          338

SEQ ID NO: 1090        moltype = AA  length = 343
FEATURE                Location/Qualifiers
REGION                 1..343
                       note = artificial construct
source                 1..343
                       mol_type = protein
                       organism = synthetic construct
SEQUENCE: 1090
MAFLWLLSCW ALLGTTFGDY KDDDDKGGGG SGGGGSMGSW DEFGRRLYAI EWRLYALGGS  60
EAELAAFEKE IAAFESELQA YKGKGNPEVE KLREIAAVIR SNLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 1091        moltype = AA  length = 343
FEATURE                Location/Qualifiers
REGION                 1..343
                       note = artificial construct
source                 1..343
                       mol_type = protein
                       organism = synthetic construct
SEQUENCE: 1091
MAFLWLLSCW ALLGTTFGDY KDDDDKGGGG SGGGGSMGSW SEFWVRLGAI RERLDALGGS  60
EAELAAFEKE IAAFESELQA YKGKGNPEVE KLRYTAATIR RFLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 1092        moltype = AA  length = 343
FEATURE                Location/Qualifiers
REGION                 1..343
                       note = artificial construct
source                 1..343
                       mol_type = protein
                       organism = synthetic construct
SEQUENCE: 1092
MAFLWLLSCW ALLGTTFGDY KDDDDKGGGG SGGGGSMGSW FEFYDRLNAI DARLWALGGS  60
EAELAAFEKE IAAFESELQA YKGKGNPEVE NLRVHAAAIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 1093        moltype = AA  length = 343
```

```
FEATURE                Location/Qualifiers
REGION                 1..343
                       note = artificial construct
source                 1..343
                       mol_type = protein
                       organism = synthetic construct
SEQUENCE: 1093
MAFLWLLSCW ALLGTTFGDY KDDDDKGGGG SGGGGSMGSW LEFYHRLNAI DSRLWALGGS  60
EAELAAFEKE IAAFESELQA YKGKGNPEVE SLRDHAAHIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 1094        moltype =   length =
SEQUENCE: 1094
000

SEQ ID NO: 1095        moltype =   length =
SEQUENCE: 1095
000

SEQ ID NO: 1096        moltype =   length =
SEQUENCE: 1096
000

SEQ ID NO: 1097        moltype =   length =
SEQUENCE: 1097
000

SEQ ID NO: 1098        moltype =   length =
SEQUENCE: 1098
000

SEQ ID NO: 1099        moltype = AA  length = 5
FEATURE                Location/Qualifiers
REGION                 1..5
                       note = artificial construct
source                 1..5
                       mol_type = protein
                       organism = synthetic construct
SEQUENCE: 1099
GGGGG                                                              5

SEQ ID NO: 1100        moltype = AA  length = 8
FEATURE                Location/Qualifiers
REGION                 1..8
                       note = artificial construct
source                 1..8
                       mol_type = protein
                       organism = synthetic construct
SEQUENCE: 1100
GGGGGGGG                                                           8

SEQ ID NO: 1101        moltype = AA  length = 25
FEATURE                Location/Qualifiers
source                 1..25
                       mol_type = protein
                       organism = Homo sapiens
SEQUENCE: 1101
MTMYLWLKLL AFGFAFLDTE VFVTG                                        25

SEQ ID NO: 1102        moltype = AA  length = 1306
FEATURE                Location/Qualifiers
source                 1..1306
                       mol_type = protein
                       organism = Homo sapiens
SEQUENCE: 1102
MTMYLWLKLL AFGFAFLDTE VFVTGQSPTP SPTGLTTAKM PSVPLSSDPL PTHTTAFSPA  60
STFERENDFS ETTTSLSPDN TSTQVSPDSL DNASAFNTTG VSSVQTPHLP THADSQTPSA  120
GTDTQTFSGS AANAKLNPTP GSNAISDVPG ERSTASTFPT DPVSPLTTTL SLAHHSSAAL  180
PARTSNTTIT ANTSDAYLNA SETTTLSPSG SAVISTTTIA TTPSKPTCDE KYANITVDYL  240
YNKETKLFTA KLNVNENVEC GNNTCTNNEV HNLTECKNAS VSISHNSCTA PDKTLILDVP  300
PGVEKFQLHD CTQVEKADTT ICLKWKNIET FTCDTQNITY RFQCGNMIFD NKEIKLENLE  360
PEHEYKCDSE ILYNNHKFTN ASKIIKTDFG SPGEPQIIFC RSEAAHQGVI TWNPPQRSFH  420
NFTLCYIKET EKDCLNLDKN LIKYDLQNLK PYTKYVLSLH AYIIAKVQRN GSAAMCHFTT  480
KSAPPSQVWN MTVSMTSDNS MHVKCRPPRD RNGPHERYHL EVEAGNTLVR NESHKNCDFR  540
VKDLQYSTDY TFKAYFHNGD YPGEPFILHH STSYNSKALI AFLAFLIIVT SIALLVVLYK  600
IYDLHKKRSC NLDEQQELVE RDDEKQLMNV EPIHADILLE TYKRKIADEG RLFLAEFQSI  660
```

```
PRVFSKFPIK EARKPFNQNK NRYVDILPYD YNRVELSEIN GDAGSNYINA SYIDGFKEPR  720
KYIAAQGPRD ETVDDFWRMI WEQKATVIVM VTRCEEGNRN KCAEYWPSME EGTRAFGDVV  780
VKINQHKRCP DYIIQKLNIV NKKEKATGRE VTHIQFTSWP DHGVPEDPHL LLKLRRRVNA  840
FSNFFSGPIV VHCSAGVGRT GTYIGIDAML EGLEAENKVD VYGYVVKLRR QRCLMVQVEA  900
QYILIHQALV EYNQFGETEV NLSELHPYLH NMKKRDPPSE PSPLEAEFQR LPSYRSWRTQ  960
HIGNQEENKS KNRNSNVIPY DYNRVPLKHE LEMSKESEHD SDESSDDDSD SEEPSKYINA  1020
SFIMSYWKPE VMIAAQGPLK ETIGDFWQMI FQRKVKVIVM LTELKHGDQE ICAQYWGEGK  1080
QTYGDIEVDL KDTDKSSTYT LRVFELRHSK RKDSRTVYQY QYTNWSVEQL PAEPKELISM  1140
IQVVKQKLPQ KNSSEGNKHH KSTPLLIHCR DGSQQTGIFC ALLNLLESAE TEEVVDIFQV  1200
VKALRKARPG MVSTFEQYQF LYDVIASTYP AQNGQVKKNN HQEDKIEFDN EVDKVKQDAN  1260
CVNPLGAPEK LPEAKEQAEG SEPTSGTEGP EHSVNGPASP ALNQGS                1306

SEQ ID NO: 1103        moltype = AA  length = 1145
FEATURE                Location/Qualifiers
source                 1..1145
                       mol_type = protein
                       organism = Homo sapiens
SEQUENCE: 1103
MTMYLWLKLL AFGFAFLDTE VFVTGQSPTP SPTDAYLNAS ETTTLSPSGS AVISTTTIAT  60
TPSKPTCDEK YANITVDYLY NKETKLFTAK LNVNENVECG NNTCTNNEVH NLTECKNASV  120
SISHNSCTAP DKTLILDVPP GVEKFQLHDC TQVEKADTTI CLKWKNIETF TCDTQNITYR  180
FQCGNMIFDN KEIKLENLEP EHEYKCDSEI LYNNHKFTNA SKIIKTDFGS PGEPQIIFCR  240
SEAAHQGVIT WNPPQRSFHN FTLCYIKETE KDCLNLDKNL IKYDLQNLKP YTKYVLSLHA  300
YIIAKVQRNG SAAMCHFTTK SAPPSQVWNM TVSMTSDNSM HVKCRPPRDR NGPHERYHLE  360
VEAGNTLVRN ESHKNCDFRV KDLQYSTDYT FKAYFHNGDY PGEPFILHHS TSYNSKALIA  420
FLAFLIIVTS IALLVVLYKI YDLHKKRSCN LDEQQELVER DDEKQLMNVE PIHADILLET  480
YKRKIADEGR LFLAEFQSIP RVFSKFPIKE ARKPFNQNKN RYVDILPYDY NRVELSEING  540
DAGSNYINAS YIDGFKEPRK YIAAQGPRDE TVDDFWRMIW EQKATVIVMV TRCEEGNRNK  600
CAEYWPSMEE GTRAFGDVVV KINQHKRCPD YIIQKLNIVN KKEKATGREV THIQFTSWPD  660
HGVPEDPHLL LKLRRRVNAF SNFFSGPIVV HCSAGVGRTG TYIGIDAMLE GLEAENKVDV  720
YGYVVKLRRQ RCLMVQVEAQ YILIHQALVE YNQFGETEVN LSELHPYLHN MKKRDPPSEP  780
SPLEAEFQRL PSYRSWRTQH IGNQEENKSK NRNSNVIPYD YNRVPLKHEL EMSKESEHDS  840
DESSDDDSDS EEPSKYINAS FIMSYWKPEV MIAAQGPLKE TIGDFWQMIF QRKVKVIVML  900
TELKHGDQEI CAQYWGEGKQ TYGDIEVDLK DTDKSSTYTL RVFELRHSKR KDSRTVYQYQ  960
YTNWSVEQLP AEPKELISMI QVVKQKLPQK NSSEGNKHHK STPLLIHCRD GSQQTGIFCA  1020
LLNLLESAET EEVVDIFQVV KALRKARPGM VSTFEQYQFL YDVIASTYPA QNGQVKKNNH  1080
QEDKIEFDNE VDKVKQDANC VNPLGAPEKL PEAKEQAEGS EPTSGTEGPE HSVNGPASPA  1140
LNQGS                                                             1145

SEQ ID NO: 1104        moltype = AA  length = 1310
FEATURE                Location/Qualifiers
source                 1..1310
                       mol_type = protein
                       organism = Macaca mulatta
SEQUENCE: 1104
MTMCLWLKLL AFVFAFLDTE VFVTGQGSTL SPTGRRTTKM PSVPLSSDPL PTHTTAFSPA  60
SISERENDFS ETTPSLSSDN TSTHVSPDSL DNASAFNTTG VSSALTPHLP THADSQTPST  120
GTDTQTPSGS AANTTLSPTP RSNDISDVPG ERSTASTFPT DPISPLATTL IPARNSSAAL  180
PARTSNTTIT ANTSVSYLNA SETTTPSPSG STVISTPTIA TTTSKPTCAE KYATIPVDYL  240
YNNKTKLFTA KLNVNENVEC TNNNHTHNIC TNNEVLNLPE CKEMNVFVSH NSCTDRHKEL  300
KLDVPPEVEK FQLDDCTPDV EANTTICLKW KIIETFACDK SKITYRFQCG NKTYNKEGIY  360
LENLEPEYEY KCDSEILYNN HKYINITKLI KTDFGIPGQP QNVVCRHEDA HQGVITWNPP  420
QRSFHNFTLC YVSKTAKKCL SLDKHLTTYH LQNLKPYTNY SLSLHAYIIA KVQRNGTAAT  480
CNFTTESAPP SQVQNMIVST SDNSMRVKCE GPRDVNGPTG LYHLEVEAGN TLVRNLSQSK  540
CDFSVNNLQY STYYNLKAYY HNGKYSGEPV ILRESTSYNS KALIAFLAFL IIVTSIALLV  600
VLYKIYDLHK KRSCNLDEQQ ELVERDDEKQ LMNVEPIHAD ILLETYKRKI ADEGRLFLAE  660
FQSIPRVFSK FPIKEARKPF NQNKNRYVDI LPYDYNRVEL SEINGDAGSN YINASYIDGF  720
KEPRKYIAAQ GPRDETVDDF WRMIWEQKAT VIVMVTRCEE GNRNKCAEYW PSMEEGTRAF  780
GDVVVKINQH KRCPDYIIQK LNIVNKKEKA TGREVTHIQF TSWPDHGVPE DPHLLLKLRR  840
RVNAFSNFFS GPIVVHCSAG VGRTGTYIGI DAMLEGLEAE NKVDVYGYVV KLRRQRCLMV  900
QVEAQYILIH QALVEYNQFG ETEVNLSELH PYLHNMKKRD PPSEPSPLEA EFQRLPSYRS  960
WRTQHIGNQE ENKNKNRNSN VIPYDYNRVP LKHELEMSKE SDHDSDESSD DDSDSEEPSK  1020
YINASFIMSY WKPEVMIAAQ GPLKETIGDF WQMIFQRKVK VIVMLTELKH GDQEICAQYW  1080
GEGKQTYGDI EVDMKDTNKS STYTLRVFEL RHSKRKDSRT VYQYQYTNWS VEQLPAEPKE  1140
LVSLIQVLKE KLPQKNSSEG NKHHKSTPLL IHCRDGSQQT GIFCALLNLL ESAETEEVVD  1200
IFQVVKALRK ARPGMVSTFE QYQFLYDIIA STYPAQNGQV KKNNHQEDKI EFDNEVDKVK  1260
QDANCVNPLG ATEKLPEAKE QATGSEPTSG TEGPEHSVNG PASPALNQGS            1310

SEQ ID NO: 1105        moltype = AA  length = 1310
FEATURE                Location/Qualifiers
source                 1..1310
                       mol_type = protein
                       organism = Macaca fascicularis
SEQUENCE: 1105
MTMCLWLKLL AFVFAFLDTE VFVTGQGSTL SPTGRRTTKM PSVPLSSDPL PTHTTAFSPA  60
SISERENDFS ETTPSLSSDN TSTQVSPDSL DNASAFNTTG VSSALTPHLP THADSQTPST  120
GTDTQTPSGS AANTTLSPTP RSNDISDVPG ERSTASTFPT DPISPLATTL IPARNSSAAL  180
PARTSNTTIT ANTSVSYLNA SETTTPSPSG STVISTPTIA TTTSKPTCAE KYATIPVDYL  240
YNNKTKLFTA KLNVNENVEC TNNNHTHNIC TNNEVLNLPE CKEMNVFVSH NSCTDRHKEL  300
```

```
KLDVPPEVEK FQLDDCTPDV EANTTICLKW KIIETFACDK SKITYRFQCG NKTYNKEGIY  360
LENLEPEYEY KCDSEILYNN HKYINITKLI KTDFGIPGQP QNVVCRHEDA HQGVITWNPP  420
QRSFHNFTLC YVNKPAKKCL ILDKHLTTYH LQNLKPYTNY SLSLHAYIIA KVQRNGTAAT  480
CNFTTESAPP SQVQNMIVST SDNSMHVKCE VPRDVNGPTG LYHLEVEAGN TLVRNLSQSK  540
CDFSVNNLQY STYYNLKAYY HNGKYSGEPV ILRESTSYNS KALIAFLAFL IIVTSIALLV  600
VLYKIYDLHK KRSCNLDEQQ ELVERDDEKQ LMNVEPIHAD ILLETYKRKI ADEGRLFLAE  660
FQSIPRVFSK FPIKEARKPF NQNKNRYVDI LPYDYNRVEL SEINGDAGSN YINASYIDGF  720
KEPRKYIAAQ GPRDETVDDF WRMIWEQKAT VIVMVTRCEE GNRNKCAEYW PSMEEGTRAF  780
GDIVVKINQH KRCPDYIIQK LNIVNKKEKA TGREVTHIQF TSWPDHGVPE DPHLLLKLRR  840
RVNAFSNFFS GPIVVHCSAG VGRTGTYIGI DAMLEGLEAE NKVDVYGYVV KLRRQRCLMV  900
QVEAQYILIH QALVEYNQFG ETEVNLSELH PYLHNMKKRD PPSEPSPLEA EFQRLPSYRS  960
WRTQHIGNQE ENKNKNRNSN VIPYDYNRVP LKHELEMSKE SDHDSDESSD DDSDSEEPSK  1020
YINASFIMSY WKPEVMIAAQ GPLKETIGDF WQMIFQRKVK VIVMLTELKH GDQEICAQYW  1080
GEGKQTYGDI EVDMKDTNKS STYTLRVFEL RHSKRKDSRT VYQYQYTNWS VEQLPAEPKE  1140
LVSLIQVLKE KLPQKNFSEG NKHHKSTPLL IHCRDGSQQT GIFCALLNLL ESAETEEVVD  1200
IFQVVKALRK ARPGMVSTFE QYQFLYDIIA STYPAQNGQV KKNNHQEDKI EFDNEVDKVK  1260
QDANCVNPLG ATEKLPEAKE QATGSEPTSG TEGPEHSVNG PASPALNQGS             1310

SEQ ID NO: 1106        moltype = AA  length = 552
FEATURE                Location/Qualifiers
source                 1..552
                       mol_type = protein
                       organism = Homo sapiens
SEQUENCE: 1106
QSPTPSPTGL TTAKMPSVPL SSDPLPTHTT AFSPASTFER ENDFSETTTS LSPDNTSTQV  60
SPDSLDNASA FNTTGVSSVQ TPHLPTHADS QTPSAGTDTQ TFSGSAANAK LNPTPGSNAI  120
SDVPGERSTA STFPTDPVSP LTTTLSLAHH SSAALPARTS NTTITANTSD AYLNASETTT  180
LSPSGSAVIS TTTIATTPSK PTCDEKYANI TVDYLYNKET KLFTAKLNVN ENVECGNNTC  240
TNNEVHNLTE CKNASVSISH NSCTAPDKTL ILDVPPGVEK FQLHDCTQVE KADTTICLKW  300
KNIETFTCDT QNITYRFQCG NMIFDNKEIK LENLEPEHEY KCDSEILYNN HKFTNASKII  360
KTDFGSPGEP QIIFCRSEAA HQGVITWNPP QRSFHNFTLC YIKETEKDCL NLDKNLIKYD  420
LQNLKPYTKY VLSLHAYIIA KVQRNGSAAM CHFTTKSAPP SQVWNMTVSM TSDNSMHVKC  480
RPPRDRNGPH ERYHLEVEAG NTLVRNESHK NCDFRVKDLQ YSTDYTFKAY FHNGDYPGEP  540
FILHHSTSYN SK                                                     552

SEQ ID NO: 1107        moltype = AA  length = 391
FEATURE                Location/Qualifiers
source                 1..391
                       mol_type = protein
                       organism = Homo sapiens
SEQUENCE: 1107
QSPTPSPTDA YLNASETTTL SPSGSAVIST TTIATTPSKP TCDEKYANIT VDYLYNKETK  60
LFTAKLNVNE NVECGNNTCT NNEVHNLTEC KNASVSISHN SCTAPDKTLI LDVPPGVEKF  120
QLHDCTQVEK ADTTICLKWK NIETFTCDTQ NITYRFQCGN MIFDNKEIKL ENLEPEHEYK  180
CDSEILYNNH KFTNASKIIK TDFGSPGEPQ IIFCRSEAAH QGVITWNPPQ RSFHNFTLCY  240
IKETEKDCLN LDKNLIKYDL QNLKPYTKYV LSLHAYIIAK VQRNGSAAMC HFTTKSAPPS  300
QVWNMTVSMT SDNSMHVKCR PPRDRNGPHE RYHLEVEAGN TLVRNESHKN CDFRVKDLQY  360
STDYTFKAYF HNGDYPGEPF ILHHSTSYNS K                                391

SEQ ID NO: 1108        moltype = AA  length = 457
FEATURE                Location/Qualifiers
source                 1..457
                       mol_type = protein
                       organism = Homo sapiens
SEQUENCE: 1108
QSPTPSPTGL TTAKMPSVPL SSDPLPTHTT AFSPASTFER ENDFSETTTS LSPDNTSTQV  60
SPDSLDNASA FNTTDAYLNA SETTTLSPSG SAVISTTTIA TTPSKPTCDE KYANITVDYL  120
YNKETKLFTA KLNVNENVEC GNNTCTNNEV HNLTECKNAS VSISHNSCTA PDKTLILDVP  180
PGVEKFQLHD CTQVEKADTT ICLKWKNIET FTCDTQNITY RFQCGNMIFD NKEIKLENLE  240
PEHEYKCDSE ILYNNHKFTN ASKIIKTDFG SPGEPQIIFC RSEAAHQGVI TWNPPQRSFH  300
NFTLCYIKET EKDCLNLDKN LIKYDLQNLK PYTKYVLSLH AYIIAKVQRN GSAAMCHFTT  360
KSAPPSQVWN MTVSMTSDNS MHVKCRPPRD RNGPHERYHL EVEAGNTLVR NESHKNCDFR  420
VKDLQYSTDY TFKAYFHNGD YPGEPFILHH STSYNSK                          457

SEQ ID NO: 1109        moltype = AA  length = 438
FEATURE                Location/Qualifiers
source                 1..438
                       mol_type = protein
                       organism = Homo sapiens
SEQUENCE: 1109
QSPTPSPTGV SSVQTPHLPT HADSQTPSAG TDTQTFSGSA ANAKLNPTPG SNAISDAYLN  60
ASETTTLSPS GSAVISTTTI ATTPSKPTCD EKYANITVDY LYNKETKLFT AKLNVNENVE  120
CGNNTCTNNE VHNLTECKNA SVSISHNSCT APDKTLILDV PPGVEKFQLH DCTQVEKADT  180
TICLKWKNIE TFTCDTQNIT YRFQCGNMIF DNKEIKLENL EPEHEYKCDS EILYNNHKFT  240
NASKIIKTDF GSPGEPQIIF CRSEAAHQGV ITWNPPQRSF HNFTLCYIKE TEKDCLNLDK  300
NLIKYDLQNL KPYTKYVLSL HAYIIAKVQR NGSAAMCHFT TKSAPPSQVW NMTVSMTSDN  360
SMHVKCRPPR DRNGPHERYH LEVEAGNTLV RNESHKNCDF RVKDLQYSTD YTFKAYFHNG  420
DYPGEPFILH HSTSYNSK                                               438
```

```
SEQ ID NO: 1110        moltype = AA  length = 504
FEATURE                Location/Qualifiers
source                 1..504
                       mol_type = protein
                       organism = Homo sapiens
SEQUENCE: 1110
QSPTPSPTGL TTAKMPSVPL SSDPLPTHTT AFSPASTFER ENDFSETTTS LSPDNTSTQV  60
SPDSLDNASA FNTTGVSSVQ TPHLPTHADS QTPSAGTDTQ TFSGSAANAK LNPTPGSNAI  120
SDAYLNASET TTLSPSGSAV ISTTTIATTP SKPTCDEKYA NITVDYLYNK ETKLFTAKLN  180
VNENVECGNN TCTNNEVHNL TECKNASVSI SHNSCTAPDK TLILDVPPGV EKFQLHDCTQ  240
VEKADTTICL KWKNIETFTC DTQNITYRFQ CGNMIFDNKE IKLENLEPEH EYKCDSEILY  300
NNHKFTNASK IIKTDFGSPG EPQIIFCRSE AAHQGVITWN PPQRSFHNFT LCYIKETEKD  360
CLNLDKNLIK YDLQNLKPYT KYVLSLHAYI IAKVQRNGSA AMCHFTTKSA PPSQVWNMTV  420
SMTSDNSMHV KCRPPRDRNG PHERYHLEVE AGNTLVRNES HKNCDFRVKD LQYSTDYTFK  480
AYFHNGDYPG EPFILHHSTS YNSK                                        504

SEQ ID NO: 1111        moltype = AA  length = 505
FEATURE                Location/Qualifiers
source                 1..505
                       mol_type = protein
                       organism = Homo sapiens
SEQUENCE: 1111
QSPTPSPTGL TTAKMPSVPL SSDPLPTHTT AFSPASTFER ENDFSETTTS LSPDNTSTQV  60
SPDSLDNASA FNTTDVPGER STASTFPTDP VSPLTTTLSL AHHSSAALPA RTSNTTITAN  120
TSDAYLNASE TTTLSPSGSA VISTTTIATT PSKPTCDEKY ANITVDYLYN KETKLFTAKL  180
NVNENVECGN NTCTNNEVHN LTECKNASVS ISHNSCTAPD KTLILDVPPG VEKFQLHDCT  240
QVEKADTTIC LKWKNIETFT CDTQNITYRF QCGNMIFDNK EIKLENLEPE HEYKCDSEIL  300
YNNHKFTNAS KIIKTDFGSP GEPQIIFCRS EAAHQGVITW NPPQRSFHNF TLCYIKETEK  360
DCLNLDKNLI KYDLQNLKPY TKYVLSLHAY IIAKVQRNGS AAMCHFTTKS APPSQVWNMT  420
VSMTSDNSMH VKCRPPRDRN GPHERYHLEV EAGNTLVRNE SHKNCDFRVK DLQYSTDYTF  480
KAYFHNGDYP GEPFILHHST SYNSK                                       505

SEQ ID NO: 1112        moltype = AA  length = 486
FEATURE                Location/Qualifiers
source                 1..486
                       mol_type = protein
                       organism = Homo sapiens
SEQUENCE: 1112
QSPTPSPTGV SSVQTPHLPT HADSQTPSAG TDTQTFSGSA ANAKLNPTPG SNAISDVPGE  60
RSTASTFPTD PVSPLTTTLS LAHHSSAALP ARTSNTTITA NTSDAYLNAS ETTTLSPSGS  120
AVISTTTIAT TPSKPTCDEK YANITVDYLY NKETKLFTAK LNVNENVECG NNTCTNNEVH  180
NLTECKNASV SISHNSCTAP DKTLILDVPP GVEKFQLHDC TQVEKADTTI CLKWKNIETF  240
TCDTQNITYR FQCGNMIFDN KEIKLENLEP EHEYKCDSEI LYNNHKFTNA SKIIKTDFGS  300
PGEPQIIFCR SEAAHQGVIT WNPPQRSFHN FTLCYIKETE KDCLNLDKNL IKYDLQNLKP  360
YTKYVLSLHA YIIAKVQRNG SAAMCHFTTK SAPPSQVWNM TVSMTSDNSM HVKCRPPRDR  420
NGPHERYHLE VEAGNTLVRN ESHKNCDFRV KDLQYSTDYT FKAYFHNGDY PGEPFILHHS  480
TSYNSK                                                            486

SEQ ID NO: 1113        moltype = AA  length = 766
FEATURE                Location/Qualifiers
source                 1..766
                       mol_type = protein
                       organism = Homo sapiens
SEQUENCE: 1113
MKTPWKVLLG LLGAAALVTI ITVPVVLLNK GTDDATADSR KTYTLTDYLK NTYRLKLYSL  60
RWISDHEYLY KQENNILVFN AEYGNSSVFL ENSTFDEFGH SINDYSISPD GQFILLEYNY  120
VKQWRHSYTA SYDIYDLNKR QLITEERIPN NTQWVTWSPV GHKLAYVWNN DIYVKIEPNL  180
PSYRITWTGK EDIIYNGITD WVYEEEVFSA YSALWWSPNG TFLAYAQFND TEVPLIEYSF  240
YSDESLQYPK TVRVPYPKAG AVNPTVKFFV VNTDSLSSVT NATSIQITAP ASMLIGDHYL  300
CDVTWATQER ISLQWLRRIQ NYSVMDICDY DESSGRWNCL VARQHIEMST TGWVGRFRPS  360
EPHFTLDGNS FYKIISNEEG YRHICYFQID KKDCTFITKG TWEVIGIEAL TSDYLYYISN  420
EYKGMPGGRN LYKIQLSDYT KVTCLSCELN PERCQYYSVS FSKEAKYYQL RCSGPGLPLY  480
TLHSSVNDKG LRVLEDNSAL DKMLQNVQMP SKKLDFIILN ETKFWYQMIL PPHFDKSKKY  540
PLLLDVYAGP CSQKADTVFR LNWATYLAST ENIIVASFDG RGSGYQGDKI MHAINRRLGT  600
FEVEDQIEAA RQFSKMGFVD NKRIAIWGWS YGGYVTSMVL GSGSGVFKCG IAVAPVSRWE  660
YYDSVYTERY MGLPTPEDNL DHYRNSTVMS RAENFKQVEY LLIHGTADDN VHFQQSAQIS  720
KALVDVGVDF QAMWYTDEDH GIASSTAHQH IYTHMSHFIK QCFSLP                766

SEQ ID NO: 1114        moltype = AA  length = 595
FEATURE                Location/Qualifiers
source                 1..595
                       mol_type = protein
                       organism = Homo sapiens
SEQUENCE: 1114
MRVLLAALGL LFLGALRAFP QDRPFEDTCH GNPSHYYDKA VRRCCYRCPM GLFPTQQCPQ  60
RPTDCRKQCE PDYYLDEADR CTACVTCSRD DLVEKTPCAW NSSRVCECRP GMFCSTSAVN  120
SCARCFFHSV CPAGMIVKFP GTAQKNTVCE PASPGVSPAC ASPENCKEPS SGTIPQAKPT  180
PVSPATSSAS TMPVRGGTRL AQEAASKLTR APDSPSSVGR PSSDPGLSPT QPCPEGSGDC  240
RKQCEPDYYL DEAGRCTACV SCSRDDLVEK TPCAWNSSRT CECRPGMICA TSATNSCARC  300
```

```
VPYPICAAET VTKPQDMAEK DTTFEAPPLG TQPDCNPTPE NGEAPASTSP TQSLLVDSQA  360
SKTLPIPTSA PVALSSTGKP VLDAGPVLFW VILVLVVVVG SSAFLLCHRR ACRKRIRQKL  420
HLCYPVQTSQ PKLELVDSRP RRSSTQLRSG ASVTEPVAEE RGLMSQPLME TCHSVGAAYL  480
ESLPLQDASP AGGPSSPRDL PEPRVSTEHT NNKIEKIYIM KADTVIVGTV KAELPEGRGL  540
AGPAEPELEE ELEADHTPHY PEQETEPPLG SCSDVMLSVE EEGKEDPLPT AASGK       595

SEQ ID NO: 1115        moltype = AA  length = 364
FEATURE                Location/Qualifiers
source                 1..364
                       mol_type = protein
                       organism = Homo sapiens
SEQUENCE: 1115
MPLLLLLPLL WAGALAMDPN FWLQVQESVT VQEGLCVLVP CTFFHPIPYY DKNSPVHGYW  60
FREGAIISRD SPVATNKLDQ EVQEETQGRF RLLGDPSRNN CSLSIVDARR RDNGSYFFRM  120
ERGSTKYSYK SPQLSVHVTD LTHRPKILIP GTLEPGHSKN LTCSVSWACE QGTPPIFSWL  180
SAAPTSLGPR TTHSSVLIIT PRPQDHGTNL TCQVKFAGAG VTTERTIQLN VTYVPQNPTT  240
GIFPGDGSGK QETRAGVVHG AIGGAGVTAL LALCLCLIFF IVKTHRRKAA RTAVGRNDTH  300
PTTGSASPKH QKKSKLHGPT ETSSCSGAAP TVEMDEELHY ASLNFHGMNP SKDTSTEYSE  360
VRTQ                                                              364

SEQ ID NO: 1116        moltype = AA  length = 300
FEATURE                Location/Qualifiers
source                 1..300
                       mol_type = protein
                       organism = Homo sapiens
SEQUENCE: 1116
MANCEFSPVS GDKPCCRLSR RAQLCLGVSI LVLILVVVLA VVVPRWRQQW SGPGTTKRFP  60
ETVLARCVKY TEIHPEMRHV DCQSVWDAFK GAFISKHPCN ITEEDYQPLM KLGTQTVPCN  120
KILLWSRIKD LAHQFTQVQR DMFTLEDTLL GYLADDLTWC GEFNTSKINY QSCPDWRKDC  180
SNNPVSVFWK TVSRRFAEAA CDVVHVMLNG SRSKIFDKNS TFGSVEVHNL QPEKVQTLEA  240
WVIHGGREDS RDLCQDPTIK ELESIISKRN IQFSCKNIYR PDKFLQCVKN PEDSSCTSEI  300

SEQ ID NO: 1117        moltype = AA  length = 229
FEATURE                Location/Qualifiers
REGION                 1..229
                       note = artificial construct
source                 1..229
                       mol_type = protein
                       organism = synthetic construct
SEQUENCE: 1117
LEKCFQTENP LECQDKGEEE LQKYIQESQA LAKRSCGLFQ KLGEYYLQNA FLVAYTKKAP  60
QLTSSELMAI TRKMAATAAT CCQLSEDKLL ACGEGAADII IGHLCIRHEM TPVNPGVGQC  120
CTSSYANRRP CFSSLVVDET YVPPAFSDDK FIFHKDLCQA QGVALQTMKQ EFLINLVKQK  180
PQITEEQLEA VIADFSGLLE KCCQGQEQEV CFAEEGPKLI SKTRAALGV             229

SEQ ID NO: 1118        moltype = AA  length = 204
FEATURE                Location/Qualifiers
REGION                 1..204
                       note = artificial construct
source                 1..204
                       mol_type = protein
                       organism = synthetic construct
SEQUENCE: 1118
QESQALAKRS CGLFQKLGEY YLQNAFLVAY TKKAPQLTSS ELMAITRKMA ATAATCCQLS  60
EDKLLACGEG AADIIIGHLC IRHEMTPVNP GVGQCCTSSY ANRRPCFSSL VVDETYVPPA  120
FSDDKFIFHK DLCQAQGVAL QTMKQEFLIN LVKQKPQITE EQLEAVIADF SGLLEKCCQG  180
QEQEVCFAEE GQKLISKTRA ALGV                                        204

SEQ ID NO: 1119        moltype = AA  length = 204
FEATURE                Location/Qualifiers
REGION                 1..204
                       note = artificial construct
source                 1..204
                       mol_type = protein
                       organism = synthetic construct
SEQUENCE: 1119
QESQALAKRS CGLFQKLGEY YLQNAFLVAY TKKAPQLTSS ELMAITRKMA ATAATCCQLS  60
EDKLLACGEG AADIIIGHLC IRHEMTPVNP GVGQCCTSSY ANRRPCFSSL VVDETYVPPA  120
FSDDKFIFHK DLCQAQGVAL QTMKQEFLIN LVKQKPQITE EQLEAVIADF SGLLEKCCQG  180
QEQEVCFAEE GPKLISKTRA ALGV                                        204

SEQ ID NO: 1120        moltype = AA  length = 207
FEATURE                Location/Qualifiers
REGION                 1..207
                       note = artificial construct
source                 1..207
                       mol_type = protein
                       organism = synthetic construct
SEQUENCE: 1120
```

```
KYIQESQALA KRSCGLFQKL GEYYLQNAFL VAYTKKAPQL TSSELMAITR KMAATAATCC  60
QLSEDKLLAC GEGAADIIIG HLCIRHEMTP VNPGVGQCCT SSYANRRPCF SSLVVDETYV  120
PPAFSDDKFI FHKDLCQAQG VALQTMKQEF LINLVKQKPQ ITEEQLEAVI ADFSGLLEKC  180
CQGQEQEVCF AEEGQKLISK TRAALGV                                      207

SEQ ID NO: 1121        moltype = AA  length = 207
FEATURE                Location/Qualifiers
REGION                 1..207
                       note = artificial construct
source                 1..207
                       mol_type = protein
                       organism = synthetic construct
SEQUENCE: 1121
KYIQESQALA KRSCGLFQKL GEYYLQNAFL VAYTKKAPQL TSSELMAITR KMAATAATCC  60
QLSEDKLLAC GEGAADIIIG HLCIRHEMTP VNPGVGQCCT SSYANRRPCF SSLVVDETYV  120
PPAFSDDKFI FHKDLCQAQG VALQTMKQEF LINLVKQKPQ ITEEQLEAVI ADFSGLLEKC  180
CQGQEQEVCF AEEGPKLISK TRAALGV                                      207

SEQ ID NO: 1122        moltype = AA  length = 213
FEATURE                Location/Qualifiers
REGION                 1..213
                       note = artificial construct
source                 1..213
                       mol_type = protein
                       organism = synthetic construct
SEQUENCE: 1122
GEEELQKYIQ ESQALAKRSC GLFQKLGEYY LQNAFLVAYT KKAPQLTSSE LMAITRKMAA  60
TAATCCQLSE DKLLACGEGA ADIIIGHLCI RHEMTPVNPG VGQCCTSSYA NRRPCFSSLV  120
VDETYVPPAF SDDKFIFHKD LCQAQGVALQ TMKQEFLINL VKQKPQITEE QLEAVIADFS  180
GLLEKCCQGQ EQEVCFAEEG QKLISKTRAA LGV                               213

SEQ ID NO: 1123        moltype = AA  length = 213
FEATURE                Location/Qualifiers
REGION                 1..213
                       note = artificial construct
source                 1..213
                       mol_type = protein
                       organism = synthetic construct
SEQUENCE: 1123
GEEELQKYIQ ESQALAKRSC GLFQKLGEYY LQNAFLVAYT KKAPQLTSSE LMAITRKMAA  60
TAATCCQLSE DKLLACGEGA ADIIIGHLCI RHEMTPVNPG VGQCCTSSYA NRRPCFSSLV  120
VDETYVPPAF SDDKFIFHKD LCQAQGVALQ TMKQEFLINL VKQKPQITEE QLEAVIADFS  180
GLLEKCCQGQ EQEVCFAEEG PKLISKTRAA LGV                               213

SEQ ID NO: 1124        moltype = AA  length = 350
FEATURE                Location/Qualifiers
REGION                 1..350
                       note = artificial construct
source                 1..350
                       mol_type = protein
                       organism = synthetic construct
SEQUENCE: 1124
DEGGGGSMGS WSEFWARLGA IRERLDALGG SEAELAAFEK EIAAFESELQ AYKGKGNPEV  60
EKLRYTAGTI KRFLQAYRHN GGGGDGGGGS GGGGSGLEKC FQTENPLECQ DKGEEELQKY  120
IQESQALAKR SCGLFQKLGE YYLQNAFLVA YTKKAPQLTS SELMAITRKM AATAATCCQL  180
SEDKLLACGE GAADIIIGHL CIRHEMTPVN PGVGQCCTSS YANRRPCFSS LVVDETYVPP  240
AFSDDKFIFH KDLCQAQGVA LQTMKQEFLI NLVKQKPQIT EEQLEAVIAD FSGLLEKCCQ  300
GQEQEVCFAE EGQKLISKTR AALGVGGGGS GGGGSGGGGS HHHHHHHHHH             350

SEQ ID NO: 1125        moltype = AA  length = 345
FEATURE                Location/Qualifiers
REGION                 1..345
                       note = artificial construct
source                 1..345
                       mol_type = protein
                       organism = synthetic construct
SEQUENCE: 1125
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GLEKCFQTEN PLECQDKGEE ELQKYIQESQ  120
ALAKRSCGLF QKLGEYYLQN AFLVAYTKKA PQLTSSELMA ITRKMAATAA TCCQLSEDKL  180
LACGEGAADI IIGHLCIRHE MTPVNPGVGQ CCTSSYANRR PCFSSLVVDE TYVPPAFSDD  240
KFIFHKDLCQ AQGVALQTMK QEFLINLVKQ KPQITEEQLE AVIADFSGLL EKCCQGQEQE  300
VCFAEEGQKL ISKTRAALGV GGGGSGGGGS GGGGSHHHHH HHHHH                  345

SEQ ID NO: 1126        moltype = AA  length = 320
FEATURE                Location/Qualifiers
REGION                 1..320
                       note = artificial construct
source                 1..320
```

```
                      mol_type = protein
                      organism = synthetic construct
SEQUENCE: 1126
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GQESQALAKR SCGLFQKLGE YYLQNAFLVA  120
YTKKAPQLTS SELMAITRKM AATAATCCQL SEDKLLACGE GAADIIIGHL CIRHEMTPVN  180
PGVGQCCTSS YANRRPCFSS LVVDETYVPP AFSDDKFIFH KDLCQAQGVA LQTMKQEFLI  240
NLVKQKPQIT EEQLEAVIAD FSGLLEKCCQ GQEQEVCFAE EGQKLISKTR AALGVGGGGS  300
GGGGSGGGGS HHHHHHHHHH                                           320

SEQ ID NO: 1127       moltype = AA  length = 323
FEATURE               Location/Qualifiers
REGION                1..323
                      note = artificial construct
source                1..323
                      mol_type = protein
                      organism = synthetic construct
SEQUENCE: 1127
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GKYIQESQAL AKRSCGLFQK LGEYYLQNAF  120
LVAYTKKAPQ LTSSELMAIT RKMAATAATC CQLSEDKLLA CGEGAADIII GHLCIRHEMT  180
PVNPGVGQCC TSSYANRRPC FSSLVVDETY VPPAFSDDKF IFHKDLCQAQ GVALQTMKQE  240
FLINLVKQKP QITEEQLEAV IADFSGLLEK CCQGQEQEVC FAEEGQKLIS KTRAALGVGG  300
GGSGGGGSGG GGSHHHHHHH HHH                                       323

SEQ ID NO: 1128       moltype = AA  length = 329
FEATURE               Location/Qualifiers
REGION                1..329
                      note = artificial construct
source                1..329
                      mol_type = protein
                      organism = synthetic construct
SEQUENCE: 1128
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GGEEELQKYI QESQALAKRS CGLFQKLGEY  120
YLQNAFLVAY TKKAPQLTSS ELMAITRKMA ATAATCCQLS EDKLLACGEG AADIIIGHLC  180
IRHEMTPVNP GVGQCCTSSY ANRRPCFSSL VVDETYVPPA FSDDKFIFHK DLCQAQGVAL  240
QTMKQEFLIN LVKQKPQITE EQLEAVIADF SGLLEKCCQG QEQEVCFAEE GQKLISKTRA  300
ALGVGGGGSG GGGSGGGGSH HHHHHHHH                                  329

SEQ ID NO: 1129       moltype = AA  length = 438
FEATURE               Location/Qualifiers
REGION                1..438
                      note = artificial construct
source                1..438
                      mol_type = protein
                      organism = synthetic construct
SEQUENCE: 1129
DEGGGGSMGS WSEFWARLGA IRERLDALGG SEAELAAFEK EIAAFESELQ AYKGKGNPEV  60
EKLRYTAGTI KRFLQAYRHN GGGGDGGGGS GGGGSGLEKC FQTENPLECQ DKGEEELQKY  120
IQESQALAKR SCGLFQKLGE YYLQNAFLVA YTKKAPQLTS SELMAITRKM AATAATCCQL  180
SEDKLLACGE GAADIIIGHL CIRHEMTPVN PGVGQCCTSS YANRRPCFSS LVVDETYVPP  240
AFSDDKFIFH KDLCQAQGVA LQTMKQEFLI NLVKQKPQIT EEQLEAVIAD FSGLLEKCCQ  300
GQEQEVCFAE EGQKLISKTR AALGVGGGGS GGGGSGGGGS MGSWSEFWAR LGAIRERLDA  360
LGGSEAELAA FEKEIAAFES ELQAYKGKGN PEVEKLRYTA GTIKRFLQAY RHNGGGGDGG  420
GGSGGGGSHH HHHHHHHH                                             438

SEQ ID NO: 1130       moltype = AA  length = 408
FEATURE               Location/Qualifiers
REGION                1..408
                      note = artificial construct
source                1..408
                      mol_type = protein
                      organism = synthetic construct
SEQUENCE: 1130
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GQESQALAKR SCGLFQKLGE YYLQNAFLVA  120
YTKKAPQLTS SELMAITRKM AATAATCCQL SEDKLLACGE GAADIIIGHL CIRHEMTPVN  180
PGVGQCCTSS YANRRPCFSS LVVDETYVPP AFSDDKFIFH KDLCQAQGVA LQTMKQEFLI  240
NLVKQKPQIT EEQLEAVIAD FSGLLEKCCQ GQEQEVCFAE EGPKLISKTR AALGVGGGGS  300
GGGGSGGGGS MGSWSEFWAR LGAIRERLDA LGGSEAELAA FEKEIAAFES ELQAYKGKGN  360
PEVEKLRYTA GTIKRFLQAY RHNGGGGSGG GGSGGGGSHH HHHHHHHH            408

SEQ ID NO: 1131       moltype = AA  length = 320
FEATURE               Location/Qualifiers
REGION                1..320
                      note = artificial construct
source                1..320
                      mol_type = protein
```

```
                      organism = synthetic construct
SEQUENCE: 1131
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GQESQALAKR SCGLFQKLGE YYLQNAFLVA  120
YTKKAPQLTS SELMAITRKM AATAATCCQL SEDKLLACGE GAADIIIGHL CIRHEMTPVN  180
PGVGQCCTSS YANRRPCFSS LVVDETYVPP AFSDDKFIFH KDLCQAQGVA LQTMKQEFLI  240
NLVKQKPQIT EEQLEAVIAD FSGLLEKCCQ GQEQEVCFAE EGPKLISKTR AALGVGGGGS  300
GGGGSGGGGS HHHHHHHHHH                                            320

SEQ ID NO: 1132       moltype = AA  length = 408
FEATURE               Location/Qualifiers
REGION                1..408
                      note = artificial construct
source                1..408
                      mol_type = protein
                      organism = synthetic construct
SEQUENCE: 1132
DEMGSWSEFW ARLGAIRERL DALGGSEAEL AAFEKEIAAF ESELQAYKGK GNPEVEKLRY  60
TAGTIKRFLQ AYRHNGGGGD GGGGSGGGGS GQESQALAKR SCGLFQKLGE YYLQNAFLVA  120
YTKKAPQLTS SELMAITRKM AATAATCCQL SEDKLLACGE GAADIIIGHL CIRHEMTPVN  180
PGVGQCCTSS YANRRPCFSS LVVDETYVPP AFSDDKFIFH KDLCQAQGVA LQTMKQEFLI  240
NLVKQKPQIT EEQLEAVIAD FSGLLEKCCQ GQEQEVCFAE EGQKLISKTR AALGVGGGGS  300
GGGGSGGGGS MGSWSEFWAR LGAIRERLDA LGGSEAELAA FEKEIAAFES ELQAYKGKGN  360
PEVEKLRYTA GTIKRFLQAY RHNGGGGSGG GGSGGGGSHH HHHHHHHH              408

SEQ ID NO: 1133       moltype = AA  length = 343
FEATURE               Location/Qualifiers
REGION                1..343
                      note = artificial construct
source                1..343
                      mol_type = protein
                      organism = synthetic construct
SEQUENCE: 1133
MAFLWLLSCW ALLGTTFGDY KDDDDKGGGG SGGGGSMGSW FEFYDRLNAI DARLWALGGS  60
EAELAAFEKE IAAFESELQA YKGKGNPEVE SLRVHAAAIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                   343

SEQ ID NO: 1134       moltype = AA  length = 343
FEATURE               Location/Qualifiers
REGION                1..343
                      note = artificial construct
source                1..343
                      mol_type = protein
                      organism = synthetic construct
SEQUENCE: 1134
MAFLWLLSCW ALLGTTFGDY KDDDDKGGGG SGGGGSMGSW SEFYDRLNAI DARLWALGGS  60
EAELAAFEKE IAAFESELQA YKGKGNPEVE SLRVHAAAIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                   343

SEQ ID NO: 1135       moltype = AA  length = 343
FEATURE               Location/Qualifiers
REGION                1..343
                      note = artificial construct
source                1..343
                      mol_type = protein
                      organism = synthetic construct
SEQUENCE: 1135
MAFLWLLSCW ALLGTTFGDY KDDDDKGGGG SGGGGSMGSW FEFYDRLNAI DARLWALGGS  60
EAELAAFEKE IAAFESELQA YKGKGNPEVE SLREHAAAIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                   343

SEQ ID NO: 1136       moltype = AA  length = 343
FEATURE               Location/Qualifiers
REGION                1..343
                      note = artificial construct
source                1..343
                      mol_type = protein
                      organism = synthetic construct
SEQUENCE: 1136
MAFLWLLSCW ALLGTTFGDY KDDDDKGGGG SGGGGSMGSW SEFYDRLNAI DARLWALGGS  60
```

```
EAELAAFEKE IAAFESELQA YKGKGNPEVE SLREHAAAIR EWLQAYRHNG GGGSGGGGSG  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYKQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 1137        moltype = AA  length = 22
FEATURE                Location/Qualifiers
source                 1..22
                       mol_type = protein
                       organism = Homo sapiens
SEQUENCE: 1137
MAGSPTCLTL IYILWQLTGS AA                                           22

SEQ ID NO: 1138        moltype = AA  length = 226
FEATURE                Location/Qualifiers
source                 1..226
                       mol_type = protein
                       organism = Homo sapiens
SEQUENCE: 1138
MAGSPTCLTL IYILWQLTGS AASGPVKELV GSVGGAVTFP LKSKVKQVDS IVWTFNTTPL  60
VTIQPEGGTI IVTQNRNRER VDFPDGGYSL KLSKLKKNDS GIYYVGIYSS SLQQPSTQEY  120
VLHVYEHLSK PKVTMGLQSN KNGTCVTNLT CCMEHGEEDV IYTWKALGQA ANESHNGSIL  180
PISWRWGESD MTFICVARNP VSRNFSSPIL ARKLCEGAAD DPDSSM                 226

SEQ ID NO: 1139        moltype = AA  length = 335
FEATURE                Location/Qualifiers
source                 1..335
                       mol_type = protein
                       organism = Homo sapiens
SEQUENCE: 1139
MAGSPTCLTL IYILWQLTGS AASGPVKELV GSVGGAVTFP LKSKVKQVDS IVWTFNTTPL  60
VTIQPEGGTI IVTQNRNRER VDFPDGGYSL KLSKLKKNDS GIYYVGIYSS SLQQPSTQEY  120
VLHVYEHLSK PKVTMGLQSN KNGTCVTNLT CCMEHGEEDV IYTWKALGQA ANESHNGSIL  180
PISWRWGESD MTFICVARNP VSRNFSSPIL ARKLCEGAAD DPDSSMVLLC LLLVPLLLSL  240
FVLGLFLWFL KRERQEEYIE EKKRVDICRE TPNICPHSGE NTEYDTIPHT NRTILKEDPA  300
NTVYSTVEIP KKMENPHSLL TMPDTPRLFA YENVI                             335

SEQ ID NO: 1140        moltype =   length =
SEQUENCE: 1140
000

SEQ ID NO: 1141        moltype = AA  length = 491
FEATURE                Location/Qualifiers
REGION                 1..491
                       note = artificial construct
source                 1..491
                       mol_type = protein
                       organism = synthetic construct
SEQUENCE: 1141
QVQLVESGGG LVQPGGSLKL SCAASGFDFS RYWMSWVRQA PGKGLEWIGE INPTSSTINF  60
TPSLKDKVFI SRDNAKNTLY LQMSKVRSED TALYYCARGN YYRYGDAMDY WGQGTSVTVS  120
GGGGSGGGGS AGGGSDIVLT QSPASLAVSL GQRATISCRA SKSVSTSGYS YLHWYQQKPG  180
QPPKLLIYLA SNLESGVPAR FSGSGSGTDF TLNIHPVEEE DAATYYCQHS RELPFTFGSG  240
TKLEIKGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG V                                                       491

SEQ ID NO: 1142        moltype = AA  length = 491
FEATURE                Location/Qualifiers
REGION                 1..491
                       note = artificial construct
source                 1..491
                       mol_type = protein
                       organism = synthetic construct
SEQUENCE: 1142
DIVLTQSPAS LAVSLGQRAT ISCRASKSVS TSGYSYLHWY QQKPGQPPKL LIYLASNLES  60
GVPARFSGSG SGTDFTLNIH PVEEEDAATY YCQHSRELPF TFGSGTKLEI KGGGGSGGGG  120
SAGGGSQVQL VESGGGLVQP GGSLKLSCAA SGFDFSRYWM SWVRQAPGKG LEWIGEINPT  180
SSTINFTPSL KDKVFISRDN AKNTLYLQMS KVRSEDTALY YCARGNYYRY GDAMDYWGQG  240
TSVTVSGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG V                                                       491

SEQ ID NO: 1143        moltype = AA  length = 491
```

```
FEATURE                 Location/Qualifiers
REGION                  1..491
                        note = artificial construct
source                  1..491
                        mol_type = protein
                        organism = synthetic construct
SEQUENCE: 1143
LEKCFQTENP LECQDKGEEE LQKYIQESQA LAKRSCGLFQ KLGEYYLQNA FLVAYTKKAP  60
QLTSSELMAI TRKMAATAAT CCQLSEDKLL ACGEGAADII IGHLCIRHEM TPVNPGVGQC  120
CTSSYANRRP CFSSLVVDET YVPPAFSDDK FIFHKDLCQA QGVALQTMKQ EFLINLVKQK  180
PQITEEQLEA VIADFSGLLE KCCQGQEQEV CFAEEGQKLI SKTRAALGVG GGGSGGGGSG  240
GGGSGQVQLV ESGGGLVQPG GSLKLSCAAS GFDFSRYWMS WVRQAPGKGL EWIGEINPTS  300
STINFTPSLK DKVFISRDNA KNTLYLQMSK VRSEDTALYY CARGNYYRYG DAMDYWGQGT  360
SVTVSGGGGS GGGGSAGGGS DIVLTQSPAS LAVSLGQRAT ISCRASKSVS TSGYSYLHWY  420
QQKPGQPPKL LIYLASNLES GVPARFSGSG SGTDFTLNIH PVEEEDAATY YCQHSRELPF  480
TFGSGTKLEI K                                                       491

SEQ ID NO: 1144         moltype = AA  length = 491
FEATURE                 Location/Qualifiers
REGION                  1..491
                        note = artificial construct
source                  1..491
                        mol_type = protein
                        organism = synthetic construct
SEQUENCE: 1144
LEKCFQTENP LECQDKGEEE LQKYIQESQA LAKRSCGLFQ KLGEYYLQNA FLVAYTKKAP  60
QLTSSELMAI TRKMAATAAT CCQLSEDKLL ACGEGAADII IGHLCIRHEM TPVNPGVGQC  120
CTSSYANRRP CFSSLVVDET YVPPAFSDDK FIFHKDLCQA QGVALQTMKQ EFLINLVKQK  180
PQITEEQLEA VIADFSGLLE KCCQGQEQEV CFAEEGQKLI SKTRAALGVG GGGSGGGGSG  240
GGGSGDIVLT QSPASLAVSL GQRATISCRA SKSVSTSGYS YLHWYQQKPG QPPKLLIYLA  300
SNLESGVPAR FSGSGSGTDF TLNIHPVEEE DAATYYCQHS RELPFTFGSG TKLEIKGGGG  360
SGGGGSAGGG SQVQLVESGG GLVQPGGSLK LSCAASGFDF SRYWMSWVRQ APGKGLEWIG  420
EINPTSSTIN FTPSLKDKVF ISRDNAKNTL YLQMSKVRSE DTALYYCARG NYYRYGDAMD  480
YWGQGTSVTV S                                                       491

SEQ ID NO: 1145         moltype = AA  length = 753
FEATURE                 Location/Qualifiers
REGION                  1..753
                        note = artificial construct
source                  1..753
                        mol_type = protein
                        organism = synthetic construct
SEQUENCE: 1145
DIVLTQSPAS LAVSLGQRAT ISCRASKSVS TSGYSYLHWY QQKPGQPPKL LIYLASNLES  60
GVPARFSGSG SGTDFTLNIH PVEEEDAATY YCQHSRELPF TFGSGTKLEI KGGGGSGGGG  120
SAGGGSQVQL VESGGGLVQP GGSLKLSCAA SGFDFSRYWM SWVRQAPGKG LEWIGEINPT  180
SSTINFTPSL KDKVFISRDN AKNTLYLQMS KVRSEDTALY YCARGNYYRY GDAMDYWGQG  240
TSVTVSGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG VGGGGSGGGG SGGGGSGDIV LTQSPASLAV SLGQRATISC RASKSVSTSG  540
YSYLHWYQQK PGQPPKLLIY LASNLESGVP ARFSGSGSGT DFTLNIHPVE EEDAATYYCQ  600
HSRELPFTFG SGTKLEIKGG GGSGGGGSAG GGSQVQLVES GGGLVQPGGS LKLSCAASGF  660
DFSRYWMSWV RQAPGKGLEW IGEINPTSST INFTPSLKDK VFISRDNAKN TLYLQMSKVR  720
SEDTALYYCA RGNYYRYGDA MDYWGQGTSV TVS                               753

SEQ ID NO: 1146         moltype = AA  length = 753
FEATURE                 Location/Qualifiers
REGION                  1..753
                        note = artificial construct
source                  1..753
                        mol_type = protein
                        organism = synthetic construct
SEQUENCE: 1146
QVQLVESGGG LVQPGGSLKL SCAASGFDFS RYWMSWVRQA PGKGLEWIGE INPTSSTINF  60
TPSLKDKVFI SRDNAKNTLY LQMSKVRSED TALYYCARGN YYRYGDAMDY WGQGTSVTVS  120
GGGGSGGGGS AGGGSDIVLT QSPASLAVSL GQRATISCRA SKSVSTSGYS YLHWYQQKPG  180
QPPKLLIYLA SNLESGVPAR FSGSGSGTDF TLNIHPVEEE DAATYYCQHS RELPFTFGSG  240
TKLEIKGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG VGGGGSGGGG SGGGGSGQVQ LVESGGGLVQ PGGSLKLSCA ASGFDFSRYW  540
MSWVRQAPGK GLEWIGEINP TSSTINFTPS LKDKVFISRD NAKNTLYLQM SKVRSEDTAL  600
YYCARGNYYR YGDAMDYWGQ GTSVTVSGGG GSGGGGSAGG GSDIVLTQSP ASLAVSLGQR  660
ATISCRASKS VSTSGYSYLH WYQQKPGQPP KLLIYLASNL ESGVPARFSG SGSGTDFTLN  720
IHPVEEEDAA TYYCQHSREL PFTFGSGTKL EIK                               753
```

```
SEQ ID NO: 1147        moltype = AA  length = 753
FEATURE                Location/Qualifiers
REGION                 1..753
                       note = artificial construct
source                 1..753
                       mol_type = protein
                       organism = synthetic construct
SEQUENCE: 1147
DIVLTQSPAS LAVSLGQRAT ISCRASKSVS TSGYSYLHWY QQKPGQPPKL LIYLASNLES  60
GVPARFSGSG SGTDFTLNIH PVEEEDAATY YCQHSRELPF TFGSGTKLEI KGGGGSGGGG  120
SAGGGSQVQL VESGGGLVQP GGSLKLSCAA SGFDFSRYWM SWVRQAPGKG LEWIGEINPT  180
SSTINFTPSL KDKVFISRDN AKNTLYLQMS KVRSEDTALY YCARGNYYRY GDAMDYWGQG  240
TSVTVSGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG VGGGGSGGGG SGGGGSGQVQ LVESGGGLVQ PGGSLKLSCA ASGFDFSRYW  540
MSWVRQAPGK GLEWIGEINP TSSTINFTPS LKDKVFISRD NAKNTLYLQM SKVRSEDTAL  600
YYCARGNYYR YGDAMDYWGQ GTSVTVSGGG GSGGGGSAGG GSDIVLTQSP ASLAVSLGQR  660
ATISCRASKS VSTSGYSYLH WYQQKPGQPP KLLIYLASNL ESGVPARFSG SGSGTDFTLN  720
IHPVEEEDAA TYYCQHSREL PFTFGSGTKL EIK                              753

SEQ ID NO: 1148        moltype = AA  length = 753
FEATURE                Location/Qualifiers
REGION                 1..753
                       note = artificial construct
source                 1..753
                       mol_type = protein
                       organism = synthetic construct
SEQUENCE: 1148
QVQLVESGGG LVQPGGSLKL SCAASGFDFS RYWMSWVRQA PGKGLEWIGE INPTSSTINF  60
TPSLKDKVFI SRDNAKNTLY LQMSKVRSED TALYYCARGN YYRYGDAMDY WGQGTSVTVS  120
GGGGSGGGGS AGGGSDIVLT QSPASLAVSL GQRATISCRA SKSVSTSGYS YLHWYQQKPG  180
QPPKLLIYLA SNLESGVPAR FSGSGSGTDF TLNIHPVEEE DAATYYCQHS RELPFTFGSG  240
TKLEIKGGGG SGGGGSGGGG SGLEKCFQTE NPLECQDKGE EELQKYIQES QALAKRSCGL  300
FQKLGEYYLQ NAFLVAYTKK APQLTSSELM AITRKMAATA ATCCQLSEDK LLACGEGAAD  360
IIIGHLCIRH EMTPVNPGVG QCCTSSYANR RPCFSSLVVD ETYVPPAFSD DKFIFHKDLC  420
QAQGVALQTM KQEFLINLVK QKPQITEEQL EAVIADFSGL LEKCCQGQEQ EVCFAEEGQK  480
LISKTRAALG VGGGGSGGGG SGGGGSGDIV LTQSPASLAV SLGQRATISC RASKSVSTSG  540
YSYLHWYQQK PGQPPKLLIY LASNLESGVP ARFSGSGSGT DFTLNIHPVE EEDAATYYCQ  600
HSRELPFTFG SGTKLEIKGG GGSGGGGSAG GGSQVQLVES GGGLVQPGGS LKLSCAASGF  660
DFSRYWMSWV RQAPGKGLEW IGEINPTSST INFTPSLKDK VFISRDNAKN TLYLQMSKVR  720
SEDTALYYCA RGNYYRYGDA MDYWGQGTSV TVS                              753

SEQ ID NO: 1149        moltype =   length =
SEQUENCE: 1149
000

SEQ ID NO: 1150        moltype = AA  length = 432
FEATURE                Location/Qualifiers
REGION                 1..432
                       note = artificial construct
source                 1..432
                       mol_type = protein
                       organism = synthetic construct
SEQUENCE: 1150
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWVE FNERLHAIYL RLDALGGSEA  360
ELAAFEKEIA AFESELQAYK GKGNPEVETL RRHAAGIRWQ LQAYRHNGGG GSGGGGSGGG  420
GSHHHHHHHH HH                                                     432

SEQ ID NO: 1151        moltype = AA  length = 432
FEATURE                Location/Qualifiers
REGION                 1..432
                       note = artificial construct
source                 1..432
                       mol_type = protein
                       organism = synthetic construct
SEQUENCE: 1151
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWVE FEARLSAIYE RLEALGGSEA  360
```

```
ELAAFEKEIA AFESELQAYK GKGNPEVEKL RRHAAGIRSN LQAYRHNGGG GSGGGGSGGG  420
GSHHHHHHHH HH                                                     432

SEQ ID NO: 1152        moltype = AA  length = 432
FEATURE                Location/Qualifiers
REGION                 1..432
                       note = artificial construct
source                 1..432
                       mol_type = protein
                       organism = synthetic construct
SEQUENCE: 1152
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKKQP QITEEQLEAV IADFSGLLEK CCQGQEQEVC  300
FAEEGQKLIS KTRAALGVGG GGSGGGGSGG GGSGMGSWVE FFVRLDAIWE RLEALGGSEA  360
ELAAFEKEIA AFESELQAYK GKGNPEVETL RFHAAGIRQK LQAYRHNGGG GSGGGGSGGG  420
GSHHHHHHHH HH                                                     432

SEQ ID NO: 1153        moltype = AA  length = 432
FEATURE                Location/Qualifiers
REGION                 1..432
                       note = artificial construct
source                 1..432
                       mol_type = protein
                       organism = synthetic construct
SEQUENCE: 1153
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKKQP QITEEQLEAV IADFSGLLEK CCQGQEQEVC  300
FAEEGQKLIS KTRAALGVGG GGSGGGGSGG GGSGMGSWNE FKLELAFIKD WLEALGGSEA  360
ELANFEEAIA EFEAGLQGYK GKGNPEVEAL RKEAAAIRDE LQAYRHNGGG GSGGGGSGGG  420
GSHHHHHHHH HH                                                     432

SEQ ID NO: 1154        moltype = AA  length = 432
FEATURE                Location/Qualifiers
REGION                 1..432
                       note = artificial construct
source                 1..432
                       mol_type = protein
                       organism = synthetic construct
SEQUENCE: 1154
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKKQP QITEEQLEAV IADFSGLLEK CCQGQEQEVC  300
FAEEGQKLIS KTRAALGVGG GGSGGGGSGG GGSGMGSWME FEARLEAIWD RLEALGGSEA  360
ELAAFEKEIA AFESELQAYK GKGNPEVESL RFHAAGIRQH LQAYRHNGGG GSGGGGSGGG  420
GSHHHHHHHH HH                                                     432

SEQ ID NO: 1155        moltype = AA  length = 432
FEATURE                Location/Qualifiers
REGION                 1..432
                       note = artificial construct
source                 1..432
                       mol_type = protein
                       organism = synthetic construct
SEQUENCE: 1155
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKKQP QITEEQLEAV IADFSGLLEK CCQGQEQEVC  300
FAEEGQKLIS KTRAALGVGG GGSGGGGSGG GGSGMGSWHH FKMHLAGIKL QLEALGGSEA  360
ELAEFEEWIA DFEGALQDYK GKGNPEVEAL RKEAAAIRDE LQAYRHNGGG GSGGGGSGGG  420
GSHHHHHHHH HH                                                     432

SEQ ID NO: 1156        moltype = AA  length = 432
FEATURE                Location/Qualifiers
REGION                 1..432
                       note = artificial construct
source                 1..432
                       mol_type = protein
                       organism = synthetic construct
SEQUENCE: 1156
```

-continued

```
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWAE FKQRLAAIKT RLEALGGSEA  360
ELAAFEKEIA AFESELQAYK GKGNPEVEAL RKEAAAIRDE LQAYRHNGGG GSGGGGSGGG  420
GSHHHHHHHH HH                                                     432

SEQ ID NO: 1157        moltype = AA  length = 432
FEATURE                Location/Qualifiers
REGION                 1..432
                       note = artificial construct
source                 1..432
                       mol_type = protein
                       organism = synthetic construct
SEQUENCE: 1157
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWAE FRWRLHAIWL QLGALGGSEA  360
ELAAFEKEIA AFESELQAYK GKGNPEVEWL RQDAAQIKYI LQAYRHNGGG GSGGGGSGGG  420
GSHHHHHHHH HH                                                     432

SEQ ID NO: 1158        moltype = AA  length = 432
FEATURE                Location/Qualifiers
REGION                 1..432
                       note = artificial construct
source                 1..432
                       mol_type = protein
                       organism = synthetic construct
SEQUENCE: 1158
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWKT FKIELAGIKL ELEALGGSEA  360
ELAGFENAIA QFESSLQYYK GKGNPEVEAL RKEAAAIRDE LQAYRHNGGG GSGGGGSGGG  420
GSHHHHHHHH HH                                                     432

SEQ ID NO: 1159        moltype = AA  length = 432
FEATURE                Location/Qualifiers
REGION                 1..432
                       note = artificial construct
source                 1..432
                       mol_type = protein
                       organism = synthetic construct
SEQUENCE: 1159
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWHE FLRRLLAIEM RLYALGGSEA  360
ELAAFEKEIA AFESELQAYK GKGNPEVEHL RVRAASIRQM LQAYRHNGGG GSGGGGSGGG  420
GSHHHHHHHH HH                                                     432

SEQ ID NO: 1160        moltype = AA  length = 432
FEATURE                Location/Qualifiers
REGION                 1..432
                       note = artificial construct
source                 1..432
                       mol_type = protein
                       organism = synthetic construct
SEQUENCE: 1160
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWWE FRVRLEAIDY RLKALGGSEA  360
ELAAFEKEIA AFESELQAYK GKGNPEVEYL RMKAATIRAI LQAYRHNGGG GSGGGGSGGG  420
GSHHHHHHHH HH                                                     432

SEQ ID NO: 1161        moltype = AA  length = 432
FEATURE                Location/Qualifiers
```

-continued

```
REGION                  1..432
                        note = artificial construct
source                  1..432
                        mol_type = protein
                        organism = synthetic construct
SEQUENCE: 1161
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWYE FRWRLHAIWL RLGALGGSEA  360
ELAAFEKEIA AFESELQAYK GKGNPEVEWL RQDAAQIRYI LQAYRHNGGG GSGGGGSGGG  420
GSHHHHHHHH HH                                                      432

SEQ ID NO: 1162         moltype = AA  length = 432
FEATURE                 Location/Qualifiers
REGION                  1..432
                        note = artificial construct
source                  1..432
                        mol_type = protein
                        organism = synthetic construct
SEQUENCE: 1162
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWWE FNIRLHAIDY RLKALGGSEA  360
ELAAFEKEIA AFESELQAYK GKGNPEVELL REKAAQIRAQ LQAYRHNGGG GSGGGGSGGG  420
GSHHHHHHHH HH                                                      432

SEQ ID NO: 1163         moltype = AA  length = 432
FEATURE                 Location/Qualifiers
REGION                  1..432
                        note = artificial construct
source                  1..432
                        mol_type = protein
                        organism = synthetic construct
SEQUENCE: 1163
MGSWAEFKQR LAAIKTRLEA LGGSEAELAA FEKEIAAFES ELQAYKGKGN PEVEALRKEA  60
AAIRDELQAY RHNGGGGSGG GGSGGGGSGL EKCFQTENPL ECQDKGEEEL QKYIQESQAL  120
AKRSCGLFQK LGEYYLQNAF LVAYTKKAPQ LTSSELMAIT RKMAATAATC CQLSEDKLLA  180
CGEGAADIII GHLCIRHEMT PVNPGVGQCC TSSYANRRPC FSSLVVDETY VPPAFSDDKF  240
IFHKDLCQAQ GVALQTMKQE FLINLVKQKP QITEEQLEAV IADFSGLLEK CCQGQEQEVC  300
FAEEGQKLIS KTRAALGVGG GGSGGGGSGG GGSGMGSWWE FNMRLSAIKY RLYALGGSEA  360
ELAAFEKEIA AFESELQAYK GKGNPEVEIL RRLAADIRER LQAYRHNGGG GSGGGGSGGG  420
GSHHHHHHHH HH                                                      432
```